US012630562B2

(12) United States Patent
Corbin et al.

(10) Patent No.: US 12,630,562 B2
(45) Date of Patent: May 19, 2026

(54) PIPERIDYLUREA COMPOUNDS AND METHODS OF USE THEREOF

(71) Applicant: Arcus Biosciences, Inc., Hayward, CA (US)

(72) Inventors: Joshua R. Corbin, Hayward, CA (US); Sandeep Dhanju, Fremont, CA (US); Corinne Nicole Foley, San Carlos, CA (US); Jeremy Fournier, San Mateo, CA (US); Padmanabha V. Kattamuri, Fremont, CA (US); Manjunath Lamani, Dublin, CA (US); Manmohan Reddy Leleti, Dublin, CA (US); Pradeep Nareddy, Fremont, CA (US); Ehesan Ul Sharif, Castro Valley, CA (US); Joice Thomas, San Ramon, CA (US); Monika Yadav, Fremont, CA (US)

(73) Assignee: Arcus Biosciences, Inc., Hayward, CA (US)

(*) Notice: Subject to any disclaimer, the term of this patent is extended or adjusted under 35 U.S.C. 154(b) by 0 days.

(21) Appl. No.: 19/290,944

(22) Filed: Aug. 5, 2025

(65) Prior Publication Data

US 2026/0042777 A1 Feb. 12, 2026

Related U.S. Application Data

(60) Provisional application No. 63/842,513, filed on Jul. 11, 2025, provisional application No. 63/755,602, filed on Feb. 7, 2025, provisional application No. 63/688,773, filed on Aug. 29, 2024, provisional application No. 63/680,550, filed on Aug. 7, 2024.

(51) Int. Cl.

| | |
|---|---|
| ***C07D 498/08*** | (2006.01) |
| ***A61K 31/4545*** | (2006.01) |
| ***A61K 31/497*** | (2006.01) |
| ***A61K 31/506*** | (2006.01) |
| ***A61K 31/5377*** | (2006.01) |
| ***A61K 31/5386*** | (2006.01) |
| ***C07D 401/14*** | (2006.01) |
| ***C07D 405/14*** | (2006.01) |
| ***C07D 413/14*** | (2006.01) |
| ***C07D 417/14*** | (2006.01) |
| ***C07D 451/14*** | (2006.01) |
| ***C07D 471/04*** | (2006.01) |
| ***C07D 471/08*** | (2006.01) |
| ***C07D 487/04*** | (2006.01) |
| ***C07D 513/04*** | (2006.01) |

(52) U.S. Cl.

CPC ........ *C07D 498/08* (2013.01); *A61K 31/4545* (2013.01); *A61K 31/497* (2013.01); *A61K 31/506* (2013.01); *A61K 31/5377* (2013.01); *A61K 31/5386* (2013.01); *C07D 401/14* (2013.01); *C07D 405/14* (2013.01); *C07D 413/14* (2013.01); *C07D 417/14* (2013.01); *C07D 451/14* (2013.01); *C07D 471/04* (2013.01); *C07D 471/08* (2013.01); *C07D 487/04* (2013.01); *C07D 513/04* (2013.01)

(58) Field of Classification Search

CPC .. C07D 498/08; C07D 401/14; C07D 405/14; C07D 413/14; C07D 417/14; C07D 451/14; C07D 471/04; C07D 471/08; C07D 487/04; C07D 513/04; A61K 31/4545; A61K 31/497; A61K 31/506; A61K 31/5377; A61K 31/5386

See application file for complete search history.

(56) References Cited

U.S. PATENT DOCUMENTS

| | | | |
|---|---|---|---|
| 2025/0154174 | A1 | 5/2025 | Nguyen et al. |
| 2025/0206734 | A1 | 6/2025 | Das et al. |

FOREIGN PATENT DOCUMENTS

| | | | | |
|---|---|---|---|---|
| WO | WO-2010144647 | A1 * | 12/2010 | .............. A61P 37/06 |
| WO | WO-2016118632 | A1 * | 7/2016 | .............. A61P 17/04 |
| WO | WO-2016196776 | A2 * | 12/2016 | .............. A61P 19/10 |
| WO | WO-2020/223255 | A1 | 11/2020 | |
| WO | WO-2021/092240 | A1 | 5/2021 | |

(Continued)

OTHER PUBLICATIONS

Hamamura-Yasuno et al., "Determination of Key Residues in MRGPRX2 to Enhance Pseudo-Allergic Reactions Induced by Fluoroquinolones," Sci. Rep. 22(1):6650, 9 pages (Apr. 22, 2022).

(Continued)

*Primary Examiner* — George W Kosturko

(74) *Attorney, Agent, or Firm* — Foley & Lardner LLP; Zhengzheng Yao

(57) ABSTRACT

Disclosed herein are compounds having a structure according to Formula II, and compositions containing those compounds. Methods of preparing the compounds, and methods of using the compounds for the treatment of diseases, disorders, or conditions are also described.

(Formula II)

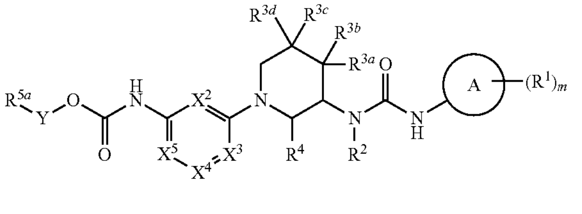

29 Claims, No Drawings

(56) References Cited

FOREIGN PATENT DOCUMENTS

| | | | | |
|---|---|---|---|---|
| WO | WO-2021/092262 A1 | 5/2021 | | |
| WO | WO-2021/092264 A1 | 5/2021 | | |
| WO | WO-2022/067094 A1 | 3/2022 | | |
| WO | WO-2022/073905 A1 | 4/2022 | | |
| WO | WO-2022/087083 A1 | 4/2022 | | |
| WO | WO-2022073904 A1 * | 4/2022 | ........... | C07D 413/14 |
| WO | WO-2022/111473 A1 | 6/2022 | | |
| WO | WO-2022/125636 A1 | 6/2022 | | |
| WO | WO-2022/140520 A1 | 6/2022 | | |
| WO | WO-2022/152852 A1 | 7/2022 | | |
| WO | WO-2022/152853 A1 | 7/2022 | | |
| WO | WO-2022/192370 A1 | 9/2022 | | |
| WO | WO-2023/039448 A1 | 3/2023 | | |
| WO | WO-2023/122267 A2 | 6/2023 | | |
| WO | WO-2023/192901 A1 | 10/2023 | | |
| WO | WO-2024/035627 A1 | 2/2024 | | |
| WO | WO-2024/226914 A2 | 10/2024 | | |
| WO | WO-2025/042730 A1 | 2/2025 | | |
| WO | WO-2025/042736 A1 | 2/2025 | | |
| WO | WO-2025/076455 A1 | 4/2025 | | |
| WO | WO-2025/160430 A1 | 7/2025 | | |

OTHER PUBLICATIONS

Iio et al., “Synthesis of Unnatural Morphinan Compounds to Induce Itch-Like Behaviors in Mice: Towards the Development of MRGPRX2 Selective Ligands,” Bioorg. Med. Chem. Lett. 56:128485, 5 pages (Jan. 15, 2022).

Lansu et al., “In Silico Design of Novel Probes for the Atypical Opioid Receptor MRGPR X2,” Nat. Chem. Biol. 13(5):529-536 (May 2017).

Lu et al., “Synthesis and Evaluation of New Potential Anti-Pseudo-Allergic Agents,” Bioorg. Med. Chem. Lett. 59:128575, 5 pages (Mar. 1, 2022).

Sabnis, Ram W., “Novel MRGX2 Antagonists for Treating Diseases,” ACS Med. Chem. Lett. 13:1006-1007 (Jun. 21, 2002).

Wang et al., “Convenient Diaryl Ureas as Promising Anti-pseudo-allergic Agents,” J. Med. Chem. 65(15):10626-10637 (Aug. 11, 2022).

International Search Report and Written Opinion on PCT/US2025/040710 Dtd Oct. 17, 2025, 13 pages.

* cited by examiner

PIPERIDYLUREA COMPOUNDS AND METHODS OF USE THEREOF

CROSS-REFERENCES TO RELATED APPLICATIONS

This application claims the benefit of priority under 35 U.S.C. § 119(e) to U.S. Provisional Application Ser. No. 63/680,550, filed Aug. 7, 2024, U.S. Provisional Application Ser. No. 63/688,773, filed Aug. 29, 2024, U.S. Provisional Application Ser. No. 63/755,602, filed Feb. 7, 2025, and U.S. Provisional Application Ser. No. 63/842,513, filed Jul. 11, 2025, the entire disclosure of each of which is incorporated by reference herein.

BACKGROUND

The following discussion is provided to aid the reader in understanding the disclosure and is not admitted to describe or constitute prior art thereto.

Mast cells are most prominent in organs that are exposed to the environment such as the skin, gut, and lung. Mast cells are characterized by granules containing proinflammatory and immunomodulatory mediators. Upon activation, degranulation occurs, releasing these proinflammatory and immunomodulatory mediators into the surrounding tissues, generally in response to a perceived pathogen (e.g., parasitic, bacterial and viral infections, allergens, toxins, etc.). Classically mast cells are activated by immunoglobulin E (IgE) antibodies, secreting a wide range of substances with local and systemic effects to induce an immune response to protect the body from pathogens, and to aid in wound healing, and tissue repair. However, misfunctioning mast cells underlie the etiology of many allergic and chronic inflammatory diseases and are implicated in a broad spectrum of conditions.

Mas-related G-protein coupled receptor X2 (MRGPRX2) mediates IgE independent activation of mast cells providing an alternative route for mast cell degranulation and the release of inflammatory mediators independent of the IgE pathway. For certain diseases, especially inflammatory, allergic and immune diseases, MRGPRX2 activation may play a central role in the onset and progression of the disease. Accordingly, MRGPRX2 antagonists may provide a therapeutic approach for mast cell-driven diseases.

SUMMARY

In one aspect, this disclosure is directed to a compound having a structure according to Formula II:

(Formula II)

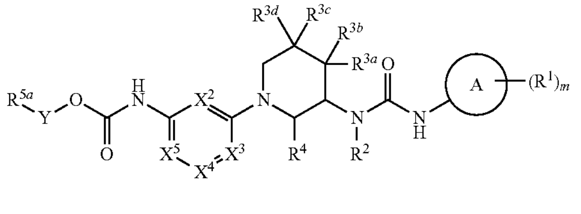

or a pharmaceutically acceptable salt thereof, wherein:

A is phenyl or 5- to 10-membered heteroaryl having 1-4 ring heteroatoms independently selected from N, O, and S;

$X^2$ is $CR^7$ or N; wherein $R^7$, if present, is H, halogen, $C_1$-$C_3$ alkyl, or —$NH_2$;

$X^3$ is $CR^8$ or N; wherein $R^8$, if present, is H, halogen, $C_1$-$C_3$ alkyl, or —$NH_2$;

$X^4$ is $CR^9$; and $X^5$ is $CR^{10}$; wherein $R^9$ and $R^{10}$ are independently H, halogen, $C_1$-$C_3$ alkyl, or —$NH_2$;

m is 0, 1, 2, or 3;

$R^1$ is halogen, $C_1$-$C_6$ alkyl, $C_1$-$C_6$ haloalkyl, $C_3$-$C_6$ cycloalkyl, phenyl, 4- to 9-membered heterocycloalkyl, 5- to 10-membered heteroaryl, —O—$R^{1a}$, or -Q-$R^{1b}$; wherein the 4- to 9-membered heterocycloalkyl has 1-2 ring heteroatoms or heteroatom groups independently selected from N, O, S, and $S(O)_2$; and the 5- to 10-membered heteroaryl has 1-4 ring heteroatoms independently selected from N, O, and S; the phenyl is unsubstituted or substituted with 1 or 2 substituents independently selected from halogen, —CN, $C_1$-$C_3$ alkyl, and $C_1$-$C_3$ haloalkyl; and the 5- to 10-membered heteroaryl is unsubstituted or substituted with $C_1$-$C_6$ alkyl (e.g., unsubstituted or substituted with one $C_1$-$C_6$ alkyl);

Q is $C_1$-$C_6$ alkylene, $C_1$-$C_6$ haloalkylene, or $C_3$-$C_6$ cycloalkylene;

$R^{1a}$ is $C_1$-$C_6$ alkyl, $C_3$-$C_6$ cycloalkyl, —($C_1$-$C_6$ alkylene)-($C_3$-$C_6$ cycloalkyl), —($C_1$-$C_6$ alkylene)-(4 to 9-membered heterocycloalkyl), or phenyl; wherein the 4- to 9-membered heterocycloalkyl has 1-2 ring heteroatoms or heteroatom groups independently selected from N, O, S, and $S(O)_2$; and wherein $R^{1a}$ is unsubstituted or substituted with 1-3 halogens; and $R^{1b}$ is $C_1$-$C_6$ alkoxy, $C_3$-$C_6$ cycloalkyl, or phenyl; wherein $R^{1b}$ is unsubstituted or substituted with 1-3 halogens;

$R^2$ is H or $C_1$-$C_3$ alkyl;

$R^{3a}$, $R^{3b}$, $R^{3c}$, $R^{3d}$ are each independently H, halogen, or $C_1$-$C_6$ alkyl; and $R^4$ is H, $C_1$-$C_6$ alkyl, $C_1$-$C_6$ haloalkyl, $C_1$-$C_6$ alkoxy, —($C_1$-$C_4$ alkylene)-($C_1$-$C_3$ alkoxy), or $C_1$-$C_6$ hydroxyalkyl; or $R^{3c}$ and $R^4$ together form a $C_1$-$C_2$ alkylene group; Y is absent or $C_1$-$C_6$ alkylene;

$R^{5a}$ is $C_1$-$C_6$ alkyl, $C_3$-$C_8$ cycloalkyl, phenyl, 5- to 10-membered heteroaryl, or 4- to 10-membered heterocycloalkyl; wherein the 5- to 10-membered heteroaryl has 1-4 ring heteroatoms independently selected from N, O, and S; the 4- to 10-membered heterocycloalkyl has 1-3 ring heteroatoms or ring heteroatom groups independently selected from N, O, S, and $S(O)_2$; and $R^{5a}$ is unsubstituted or substituted with 1-4 $R^{5d}$;

each $R^{5d}$ when present is independently selected from oxo, halogen, —OH, —$NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —($C_1$-$C_6$ alkylene)-(4- to 10-membered heterocycloalkyl), —($C_1$-$C_4$ alkylene)-C(O)N$(CH_3)_2$, —$S(O)_2$—($C_1$-$C_3$ alkyl), —C(O)—($C_1$-$C_4$ alkyl), —C(O)—($C_1$-$C_4$ hydroxyalkyl), —C(O)O—($C_1$-$C_4$ alkyl), —C(O)OH, —C(O)$NH_2$, 4- to 10-membered heterocycloalkyl, and phenyl; and each of the 4- to 10-membered heterocycloalkyl independently has 1-3 ring heteroatoms or ring heteroatom groups independently selected from N, O, S, and $S(O)_2$ and is independently unsubstituted or substituted with 1 or 2 substituents independently selected from OH, halo, and $C_1$-$C_6$ alkyl; and the $C_3$-$C_8$ cycloalkyl is unsubstituted or substituted with OH; or two $R^{5d}$ are taken together with the atoms to which they are attached to form phenyl, 5- or 6-membered heteroaryl, or 4- to 6-membered heterocycloalkyl; wherein the 5- or 6-membered heteroaryl has 1-2 ring heteroatoms independently selected from N, O, and S; the 4- to 6-membered heterocycloalkyl has 1-3 ring heteroatoms or ring heteroatom groups independently selected from N, O, S, and $S(O)_2$; and the 4- to 6-membered heterocycloalkyl is unsubstituted or substituted with $C_1$-$C_6$ alkyl; and $R^{5b}$ and $R^{5c}$ are independently selected from H, $C_1$-$C_3$ alkyl, —C(O)—($C_1$-$C_4$ alkyl), 4- to 9-membered heterocycloalkyl; wherein the 4- to 9-membered heterocycloalkyl has 1-3 ring heteroatoms or ring heteroatom groups independently selected from N, O, S, and $S(O)_2$.

In another aspect, this disclosure is directed to methods of antagonizing MRGPRX2 in a subject comprising administering to the subject an effective amount of a compound described herein.

In yet another aspect, this disclosure provides methods for treating a disease, disorder, or condition mediated at least in part by MRGPRX2 in a subject, comprising administering to the subject a therapeutically effective amount of a compound described herein. Diseases, disorders, and conditions mediated by MRGPRX2 may include e.g., an allergic disease, disorder, or condition; an inflammatory disease, disorder, or condition; a neuroinflammatory disease, disorder, or condition; a neurological disease, disorder, or condition; an immune related disease, disorder, or condition; an autoimmune related disease, disorder, or condition; a dermatological disease, disorder, or condition; a respiratory disease, disorder, or condition; a metabolic disease, disorder, or condition; a cardiovascular disease, disorder, or condition; a fibrotic disease, disorder, or condition; or cancer.

Certain aspects of the present disclosure further comprise the administration of one or more additional therapeutic agents as set forth herein below.

DETAILED DESCRIPTION OF THE DISCLOSURE

Before the present disclosure is further described, it is to be understood that the disclosure is not limited to the particular embodiments set forth herein, and it is also to be understood that the terminology used herein is for the purpose of describing particular embodiments only, and is not intended to be limiting.

Definitions

Unless otherwise defined, all terms of art, notations and other scientific terms or terminology used herein are intended to have the meanings commonly understood by those of skill in the art to which this disclosure pertains.

The term "about" as used herein has its original meaning of approximately and is to provide literal support for the exact number that it precedes, as well as a number that is near to or approximately the number that the term precedes. In general, the term "about" refers to the usual error range for the respective value readily known to the skilled person in this technical field. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "alkyl", by itself or as part of another substituent, means, unless otherwise stated, a saturated monovalent hydrocarbon radical, having, in some embodiments, one to eight (e.g., $C_1$-$C_8$alkyl), or one to six (e.g., $C_1$-$C_6$ alkyl), or one to three (e.g., $C_1$-$C_3$ alkyl) carbon atoms, respectively. The term "alkyl" encompasses straight and branched-chain hydrocarbon groups. Examples of alkyl groups include, but are not limited to, methyl (Me), ethyl (Et), n-propyl, isopropyl, n-butyl, t-butyl, isobutyl, sec-butyl, isopentyl, tert-pentyl, n-pentyl, isohexyl, n-hexyl, n-heptyl, 4-isopropylheptane, n-octyl, and the like. In some embodiments, the alkyl groups are $C_1$-$C_4$ alkyl groups (e.g., methyl, ethyl, isopropyl, or t-butyl). In some embodiments, the alkyl groups are $C_1$-$C_3$ alkyl groups (e.g., methyl, ethyl, n-propyl, or isopropyl).

The term "alkylene" refers to a straight or branched, saturated, hydrocarbon radical having, in some embodiments, one to six (e.g., $C_1$-$C_6$ alkylene), one to four (e.g., $C_1$-$C_4$ alkylene), one to three (e.g., $C_1$-$C_3$ alkylene), or one to two (e.g., $C_1$-$C_2$ alkylene) carbon atoms, and linking at least two other groups, i.e., a divalent hydrocarbon radical. The two moieties linked to the alkylene can be attached to the same carbon atom (i.e., geminal), or different carbon atoms of the alkylene group. For instance, a straight chain alkylene can be the bivalent radical of —$(CH_2)$n-, where n is 1, 2, 3, 4, 5 or 6 (i.e., a $C_1$-$C_6$ alkylene). Representative alkylene groups include, but are not limited to, methylene, ethylene, propylene, isopropylene, butylene, isobutylene, secbutylene, pentylene, hexylene and the like. In some embodiments, the alkylene groups are $C_1$-$C_2$ alkylene groups (e.g., methylene, or ethylene). In some embodiments, the alkylene groups are $C_1$-$C_3$ alkylene groups (e.g., methylene, ethylene, propylene, or isopropylene). In some embodiments, the alkylene groups are $C_1$-$C_6$ alkylene groups (e.g., methylene, ethylene, propylene, isopropylene, butylene, isobutylene, secbutylene, pentylene, hexylene, and the like).

As used herein, the term "alkoxy" refers to an alkyl group, as defined herein, that is attached to the remainder of the molecule via an oxygen atom (e.g., —O—$C_1$-$C_{12}$ alkyl, —O—$C_1$-$C_8$ alkyl, —O—$C_1$-$C_6$ alkyl, or —O—$C_1$-$C_3$ alkyl). Non-limiting examples of alkoxy groups include methoxy, ethoxy, n-propoxy, iso-propoxy, n-butoxy, sec-butoxy, n-pentoxy, n-hexoxy, and the like. In some embodiments, the alkoxy groups are $C_1$-$C_3$ alkoxy groups (e.g., methoxy, ethoxy, n-propoxy, or iso-propoxy).

The term "cycloalkyl" refers to a monocyclic, bicyclic or polycyclic hydrocarbon ring system having, in some embodiments, 3 to 14 carbon atoms (e.g., $C_3$-$C_{14}$ cycloalkyl), or 3 to 10 carbon atoms (e.g., $C_3$-$C_{10}$ cycloalkyl), or 3 to 8 carbon atoms (e.g., $C_3$-$C_8$ cycloalkyl), or 3 to 6 carbon atoms (e.g., $C_3$-$C_6$ cycloalkyl) or 3 to 4 carbon atoms (e.g., $C_3$-$C_4$ cycloalkyl). Cycloalkyl groups can be saturated or characterized by one or more points of unsaturation (i.e., carbon-carbon double and/or triple bonds), provided that the points of unsaturation do not result in an aromatic system. Examples of monocyclic cycloalkyl groups include, but are not limited to, cyclopropyl, cyclobutyl, cyclopentyl, cyclohexyl, cyclohexenyl, cycloheptyl, cycloheptenyl, cycloheptadienyl, cyclooctyl, cyclooctenyl, cyclooctadienyl and the like. The rings of bicyclic and polycyclic cycloalkyl groups can be fused, bridged, or spirocyclic. Non-limiting examples of bicyclic, spirocyclic and polycyclic cycloalkyl groups include bicyclo[1.1.1]pentane, bicyclo[2.2.1]heptane, bicyclo[2.2.2]octane, adamantyl, indanyl, spiro[5.5]undecane, spiro[2.2]pentane, spiro[2.2]pentadiene, spiro[2.3]hexane, spiro[2.5]octane, spiro[2.2]pentadiene, and the like. In some embodiments, the cycloalkyl groups of the present disclosure are monocyclic $C_3$-$C_6$ cycloalkyl moieties (e.g., cyclopropyl, cyclobutyl, cyclopentyl, or cyclohexyl).

The term “cycloalkylene” refers to a cycloalkyl group as defined herein that links at least two other moieties, i.e., a divalent cycloalkyl group. The two moieties linked to the cycloalkylene group can be attached to the same carbon atom, or different carbon atoms of the cycloalkylene group. Examples of cycloalkyl groups include, but are not limited to, cyclopropylene, cyclobutylene, cyclopentylene, cyclohexylene, cyclohexenylene, and the like. In some embodiments, the cycloalkylene groups are $C_3$-$C_4$ cycloalkylene moieties (e.g., cyclopropylene, or cyclobutylene).

The term “heterocycloalkyl” refers to a non-aromatic monocyclic, bicyclic or polycyclic cycloalkyl ring having, in some embodiments, 3 to 14 members (e.g., 3- to 14-membered heterocycle), or 3 to 10 members (e.g., 3- to 10-membered heterocycle), or 3 to 8 members (e.g., 3- to 8-membered heterocycle), or 3 to 6 members (e.g., 3- to 6-membered heterocycle), or 5 to 6 members (e.g., 5- to 6-membered heterocycle), and having from one to five, one to four, one to three, one to two or one heteroatom or heteroatom group(s) independently selected from nitrogen (N), oxygen (O), sulfur (S), sulfoxide (S(O)), and sulfone ($S(O)_2$). Heterocycloalkyl groups are saturated or characterized by one or more points of unsaturation (e.g., one or more carbon-carbon double bonds, carbon-carbon triple bonds, carbon-nitrogen double bonds, and/or nitrogen-nitrogen double bonds), provided that the points of unsaturation do not result in an aromatic system. The rings of bicyclic and polycyclic heterocycloalkyl groups can be fused, bridged, or spirocyclic. Non-limiting examples of heterocycloalkyl groups include aziridine, oxirane, thiirane, azetidine, pyrrolidine, imidazolidine, pyrazolidine, dioxolane, phthalimide, piperidine, 1,4-dioxane, morpholine, thiomorpholine, thiomorpholine-S-oxide, thiomorpholine-S,S-oxide, piperazine, 3,4,5,6-tetrahydropyridazine, tetrahydropyran, pyran, decahydroisoquinoline, 3-pyrroline, thiopyran, tetrahydrofuran, tetrahydrothiophene, tetrahydro-1,1-dioxido-2H-thiopyran, quinuclidine, 1,4-oxazepane, oxazolidine, 1,3-oxazinane, indolizidine, azabicyclo[2.1.1]hexane, 3-azabicyclo[3.1.0]hexane, 2-azabicyclo[3.1.0]hexane, 3-oxabicyclo[3.1.0]hexane, 2-azabicyclo[3.1.1]heptane, 2-azabicyclo[4.1.0]heptane, 2-oxa-5-azabicyclo[2.2.1]heptane, 2-azabicyclo[2.2.1]heptane, 2,5-diazabicyclo[2.2.1]heptane, 6-oxa-3-azabicyclo[3.1.1]heptane, 3-oxa-6-azabicyclo[3.1.1]heptane, 2,5-diazabicyclo[2.2.1]heptane, 2-thia-6-azaspiro[3.3]heptane 2,2-dioxide, 2,6-diazaspiro[3.3]heptane, 2-azaspiro[3.3]heptane, 1-oxaspiro[3.3]heptane, 4-azaspiro[2.4]heptane, 5-azaspiro[2.4]heptane, 7-oxabicyclo[2.2.1]heptane, 1-azabicyclo[2.2.2]octane, 1,4-diazabicyclo[2.2.2]octane, 6-azaspiro[3.4]octane, 6-azaspiro[2.5]octane, 4-oxa-7-azaspiro[2.5]octane, 3-oxa-8-azabicyclo[3.2.1]octane, octahydrocyclopenta[c]pyrrolole, 7-azaspiro[3.5]nonane, and the like. A heterocycloalkyl group can be attached to the remainder of the molecule through a ring carbon atom, or a ring heteroatom, when chemically permissible. In some embodiments, the heterocycloalkyl groups of the present disclosure are monocyclic or bicyclic 5- to 9-membered heterocycloalkyl moieties having one or two ring heteroatoms independently selected from N and O (e.g., oxazolidine, piperidine, piperazine, morpholine, pyrrolidine, tetrahydrofuran, tetrahydropyran, 1,4-dioxane, 1,4-oxazepane, indolizidine, quinuclidine, 7-azaspiro[3.5]nonane, 2-azabicyclo[2.2.1]heptane, and the like).

The term “aryl” refers to an aromatic ring system containing one ring, or two or three rings fused together, and having, in some embodiments, six to fourteen (i.e., $C_6$-$C_{14}$ aryl), or six to ten (i.e., $C_6$-$C_{10}$ aryl), or six (i.e., $C_6$ aryl) carbon atoms. Non-limiting examples of aryl groups include phenyl, naphthyl and anthracenyl. In some embodiments, aryl groups are phenyl.

The term “heteroaryl” refers to monocyclic or fused bicyclic aromatic groups (or rings) having, in some embodiments, from 5 to 14 (i.e., 5- to 14-membered heteroaryl), or from 5 to 10 (i.e., 5- to 10-membered heteroaryl), or from 5 to 6 (i.e., 5- to 6-membered heteroaryl) members (i.e., ring vertices), and containing from one to five, one to four, one to three, one to two or one heteroatom independently selected from nitrogen (N), oxygen (O), and sulfur (S). A heteroaryl group can be attached to the remainder of the molecule through a carbon atom or a heteroatom of the heteroaryl group, when chemically permissible. Non-limiting examples of heteroaryl groups include isoquinolinyl, pyridyl, pyridazinyl, pyrazinyl, pyrimidinyl, triazinyl, purinyl, thienopyridinyl, thienopyrimidinyl, pyrazolopyrimidinyl, imidazopyridines, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. In some embodiments, the heteroaryl groups of the present disclosure are monocyclic 5- to 10-membered heteroaryl moieties having 1-3 heteroatoms independently selected from N, O, and S (e.g., isoquinolinyl, pyridinyl, pyrimidinyl, pyridazinyl, pyrazinyl, triazolyl, imidazolyl, pyrazolyl, oxazolyl, oxadiazolyl, thiadiazole, or thiazolyl). In some embodiments, the heteroaryl groups of the present disclosure are monocyclic 5- to 6-membered heteroaryl moieties having 1-2 ring heteroatoms independently selected from N and S (e.g., pyridinyl, pyrimidinyl, pyridazinyl, pyrazinyl, imidazolyl, thiazolyl, thiadiazolyl, or pyrazolyl).

As used herein, a wavy line, “~”, that intersects a single, double or triple bond in any chemical structure depicted herein, represents that the point of attachment of the single, double, or triple bond to the remainder of the molecule is through either one of the atoms that make up the single, double or triple bond. Additionally, a bond extending from a substituent to the center of a ring (e.g., a phenyl ring) is meant to indicate attachment of that substituent to the ring at any of the available ring vertices, i.e., such that attachment of the substituent to the ring results in a chemically stable arrangement.

The terms “halo” or “halogen,” by itself or as part of another substituent, means, unless otherwise stated, a fluorine, chlorine, bromine, or iodine atom. The term “haloalkyl” refers to an alkyl group as defined herein, that are substituted with one or more halogen(s) (e.g., 1-3 halogen(s)). For example, the term “$C_1$-$C_4$ haloalkyl” is meant to include trifluoromethyl, difluoromethyl, 2,2,2-trifluoroethyl, 4-chlorobutyl, 3-bromopropyl, and the like. Additionally, exemplary $C_1$-$C_3$ haloalkoxy groups include, but are not limited to, difluoromethoxy ($—OCF_2H$), difluoroethoxy ($—OCH_2CF_2H$), and the like. The term “haloalkylene” refers to an alkylene group as defined herein that is substituted by one or more (e.g., 1-3) halogen atoms.

The term “hydroxyalkyl” refers to an alkyl group, as defined herein, that is substituted with one or more hydroxyl groups (e.g., 1-3 hydroxyl groups). Exemplary hydroxyalkyl groups include methanol, ethanol, 1,2-propanediol, 1,2-hexanediol, glycerol, and the like.

The compounds of the present disclosure can be present in their neutral form, or as a pharmaceutically acceptable salt, isomer, polymorph or solvate thereof, and may be present in a crystalline form, amorphous form or mixtures thereof.

As referred to herein, "pharmaceutically acceptable salt" is meant to include salts of the compounds according to this disclosure that are prepared with suitably nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain suitably basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure may contain both basic and acidic functionalities that allow the compounds to be converted into either base or acid addition salts.

The neutral forms of the compounds may be regenerated by contacting the salt with a base or acid and isolating the parent compound.

This disclosure also contemplates isomers of the compounds described herein (e.g., stereoisomers, and atropisomers). For example, certain compounds of the present disclosure possess asymmetric carbon atoms (chiral centers); or hindered rotation about a single bond; the racemates, diastereomers, enantiomers, and atropisomers (e.g., $R_a$, $S_a$, P and M isomers) of which are all intended to be encompassed within the scope of the present disclosure. Stereoisomeric forms may be defined, in terms of absolute stereochemistry, as (R) or (S), and/or depicted uses dashes and/or wedges. When a stereochemical depiction (e.g., using dashes, ~, and/or wedges, M) is shown in a chemical structure, or a stereochemical assignment (e.g., using (R) and (S) notation) is made in a chemical name, it is meant to indicate that the depicted isomer is present and substantially free of one or more other isomer(s) (e.g., enantiomers and diastereomers, when present). "Substantially free of" other isomer(s) indicates at least an 70/30 ratio of the indicated isomer to the other isomer(s), more preferably 80/20, 90/10, or 95/5 or more. In some embodiments, the indicated isomer will be present in an amount of at least 99%. A chemical bond to an asymmetric carbon that is depicted as a solid line ( —— ) or a wavy line ( ∿∿ ) In indicates that all possible stereoisomers (e.g., enantiomers, diastereomers, racemic mixtures, etc.) are included. In such instances, the compound may be present as a racemic mixture, scalemic mixture, or a mixture of diastereomers.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere herein. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. In some embodiments, the compounds according to this disclosure are characterized by one or more deuterium atoms. Exemplary deuterated groups include $CD_3$, and the like.

The compounds according to this disclosure may also be in a prodrug form. A "prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The terms "treat", "treating", treatment" and the like refer to a course of action that eliminates, reduces, suppresses, mitigates, ameliorates, or prevents the worsening of, either temporarily or permanently, a disease, disorder or condition to which the term applies, or at least one of the symptoms associated therewith. Treatment includes alleviation of symptoms, diminishment of extent of disease, inhibiting (e.g., arresting the development or further development of the disease, disorder or condition or clinical symptoms association therewith) an active disease, delaying or slowing of disease progression, improving the quality of life, and/or prolonging survival of a subject as compared to expected survival if not receiving treatment or as compared to a published standard of care therapy for a particular disease.

The term "in need of treatment" as used herein refers to a judgment made by a physician or similar professional that a subject requires or will benefit from treatment. This judgment is made based on a variety of factors that are in the realm of the physician's expertise, which may include a positive diagnosis of a disease, disorder or condition.

The terms "prevent", "preventing", "prevention", "prophylaxis" and the like refer to a course of action initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state. Prevention also refers to a course of action initiated in a subject after the subject has been treated for a disease, disorder, condition or a symptom associated therewith in order to prevent relapse of that disease, disorder, condition or symptom. In one or more embodiments, the preventative course of action is taken based on anticipation of a condition or event, for example exposure of an agonist to MRGPX2 (e.g., a peptide agonist (e.g., cortistatin-14, substance P, and somatostatin) or a non-peptide agonist (e.g., compound 48/80)). In one embodiment, prevention refers to the prevention, suppression, inhibition or reduction of an allergic, immune, or autoimmune response in a subject suffering from an allergic, inflammatory, neuroinflammatory, neurological, immune, autoimmune, dermatological, respiratory, metabolic, cardiovascular or fibrotic disease, disorder, or condition.

The term "in need of prevention" as used herein refers to a judgment made by a physician or other caregiver that a subject requires or will benefit from preventative care. This judgment is made based on a variety of factors that are in the realm of a physician's or caregiver's expertise.

"Substantially pure" indicates that a component (e.g., a compound according to this disclosure) makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

The terms "antagonist of MRGPRX2" and "MRGPRX2 antagonist" may be used interchangeably and refer to the ability of a molecule to decrease the activation of MRGPRX2 either directly or indirectly, thereby decreasing activation of mast cells, mast cell degranulation, or neuronal activity.

Compounds described herein may have advantageous profiles. For example, the compounds of the examples may be selective over other MRGPRX family members. In one embodiment, the compounds described herein have a greater than 2000-fold selectivity over MRGPRX1 and/or MRGPRX4.

Compounds of the Disclosure

In one aspect, this disclosure is directed to a compound having a structure of Formula II:

(Formula II)

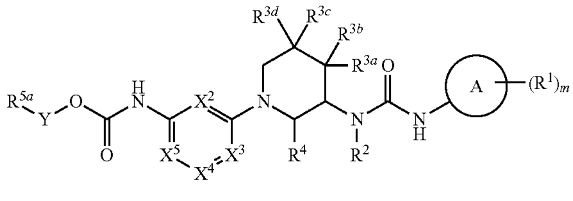

or a pharmaceutically acceptable salt thereof, wherein:

A is phenyl or 5- to 10-membered heteroaryl having 1-4 ring heteroatoms independently selected from N, O, and S;

$X^2$ is $CR^7$ or N; wherein $R^7$, if present, is H, halogen, $C_1$-$C_3$ alkyl, or —$NH_2$;

$X^3$ is $CR^I$ or N; wherein $R^8$, if present, is H, halogen, $C_1$-$C_3$ alkyl, or —$NH_2$;

$X^4$ is $CR^9$; and $X^5$ is $CR^{10}$; wherein $R^9$ and $R^{10}$ are independently H, halogen, $C_1$-$C_3$ alkyl, or —$NH_2$;

m is 0, 1, 2, or 3;

$R^1$ is halogen, $C_1$-$C_6$ alkyl, $C_1$-$C_6$ haloalkyl, $C_3$-$C_6$ cycloalkyl, phenyl, 4- to 9-membered heterocycloalkyl, 5- to 10-membered heteroaryl, —O—$R^{1a}$, or -Q-$R^{1b}$; wherein the 4- to 9-membered heterocycloalkyl has 1-2 ring heteroatoms or heteroatom groups independently selected from N, O, S, and $S(O)_2$; and the 5- to 10-membered heteroaryl has 1-4 ring heteroatoms independently selected from N, O, and S; the phenyl is unsubstituted or substituted with 1 or 2 substituents independently selected from halogen, —CN, $C_1$-$C_3$ alkyl, and $C_1$-$C_3$ haloalkyl; and the 5- to 10-membered heteroaryl is unsubstituted or substituted with $C_1$-$C_6$ alkyl (e.g., unsubstituted or substituted with one $C_1$-$C_6$ alkyl);

Q is $C_1$-$C_6$ alkylene, $C_1$-$C_6$ haloalkylene, or $C_3$-$C_6$ cycloalkylene;

$R^{1a}$ is $C_1$-$C_6$ alkyl, $C_3$-$C_6$ cycloalkyl, —($C_1$-$C_6$ alkylene)-($C_3$-$C_6$ cycloalkyl), —($C_1$-$C_6$ alkylene)-(4 to 9-membered heterocycloalkyl), or phenyl; wherein the 4- to 9-membered heterocycloalkyl has 1-2 ring heteroatoms or heteroatom groups independently selected from N, O, S, and $S(O)_2$; and wherein $R^{1a}$ is unsubstituted or substituted with 1-3 halogens; and $R^{1b}$ is $C_1$-$C_6$ alkoxy, $C_3$-$C_6$ cycloalkyl, or phenyl; wherein $R^{1b}$ is unsubstituted or substituted with 1-3 halogens;

$R^2$ is H or $C_1$-$C_3$ alkyl;

$R^{3a}$, $R^{3b}$, $R^{3c}$, $R^{3d}$ are each independently H, halogen, or $C_1$-$C_6$ alkyl; and $R^4$ is H, $C_1$-$C_6$ alkyl, $C_1$-$C_6$ haloalkyl, $C_1$-$C_6$ alkoxy, —($C_1$-$C_4$ alkylene)-($C_1$-$C_3$ alkoxy), or $C_1$-$C_6$ hydroxyalkyl; or $R^{3c}$ and $R^4$ together form a $C_1$-$C_2$ alkylene group;

Y is absent or $C_1$-$C_6$ alkylene;

$R^{5a}$ is $C_1$-$C_6$ alkyl, $C_3$-$C_8$ cycloalkyl, phenyl, 5- to 10-membered heteroaryl, or 4- to 10-membered heterocycloalkyl; wherein the 5- to 10-membered heteroaryl has 1-4 ring heteroatoms independently selected from N, O, and S; the 4- to 10-membered heterocycloalkyl has 1-3 ring heteroatoms or ring heteroatom groups independently selected from N, O, S, and $S(O)_2$; and $R^{5a}$ is unsubstituted or substituted with 1-4 $R^{5d}$;

each $R^{5d}$ when present is independently selected from oxo, halogen, —OH, —$NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —($C_1$-$C_6$ alkylene)-(4- to 10-membered heterocycloalkyl), —($C_1$-$C_4$ alkylene)-C(O)N$(CH_3)_2$, —$S(O)_2$—($C_1$-$C_3$ alkyl), —C(O)—($C_1$-$C_4$ alkyl), —C(O)—($C_1$-$C_4$ hydroxyalkyl), —C(O)O—($C_1$-$C_4$ alkyl), —C(O)OH, —C(O)$NH_2$, 4- to 10-membered heterocycloalkyl, and phenyl; and each of the 4- to 10-membered heterocycloalkyl independently has 1-3 ring heteroatoms or ring heteroatom groups independently selected from N, O, S, and $S(O)_2$ and is independently unsubstituted or substituted with 1 or 2 substituents independently selected from OH, halo, and $C_1$-$C_6$ alkyl; and the $C_3$-$C_8$ cycloalkyl is unsubstituted or substituted with OH; or two $R^{5d}$ are taken together with the atoms to which they are attached to form phenyl, 5- or 6-membered heteroaryl, or 4- to 6-membered heterocycloalkyl; wherein the 5- or 6-membered heteroaryl has 1-2 ring heteroatoms independently selected from N, O, and S; the 4- to 6-membered heterocycloalkyl has 1-3 ring heteroatoms or ring heteroatom groups independently selected from N, O, S, and $S(O)_2$; and the 4- to 6-membered heterocycloalkyl is unsubstituted or substituted with $C_1$-$C_6$ alkyl; and $R^{5b}$ and $R^{5c}$ are independently selected from H, $C_1$-$C_3$ alkyl, —C(O)—($C_1$-$C_4$ alkyl), 4- to 9-membered heterocycloalkyl; wherein the 4- to 9-membered heterocycloalkyl has 1-3 ring heteroatoms or ring heteroatom groups independently selected from N, O, S, and $S(O)_2$.

In some embodiments, A is pyrazinyl, pyridinyl, pyridazinyl, isoquinolinyl, 1,3,4-thiadiazolyl, or thiazolyl. In some embodiments, A is pyrazinyl. In some embodiments, A is pyridinyl. In some embodiments, A is pyridazinyl. In some embodiments, A is isoquinolinyl. In some embodiments, A is 1,3,4-thiadiazolyl. In some embodiments, A is thiazolyl. In some embodiments, A is pyrazinyl or pyridinyl. In some embodiments, A is

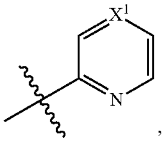

, wherein $X^1$ is $CX^{1a}$ or N; and $X^{1a}$ is H, halo, $C_1$-$C_6$ alkyl, $C_1$-$C_6$ haloalkyl, $C_1$-$C_6$ alkoxy, or $C_3$-$C_8$ cycloalkyl; and A is unsubstituted or substituted with 1 to 3 $R^1$. In some embodiments, A is

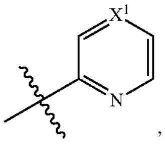

, wherein $X^1$ is CH or N; and A is unsubstituted or substituted with 1 to 3 $R^1$. In some embodiments,

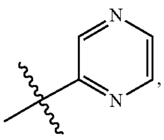

,

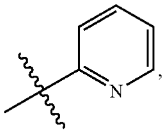

,

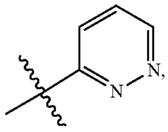

,

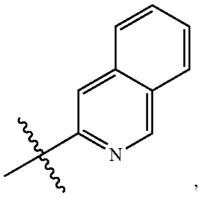

,

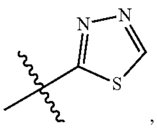

, or

-continued

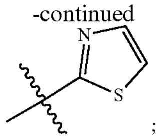

;

and A is unsubstituted or substituted with 1 to 3 $R^1$. In some embodiments, A is

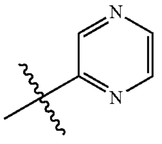

or

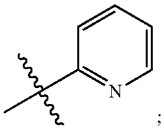

;

and A is unsubstituted or substituted with 1 to 3 $R^1$. In some embodiments, A is

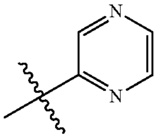

;

and A is unsubstituted or substituted with 1 to 3 $R^1$.

In some embodiments, when A is substituted with 2 or 3 $R^1$, the 2 or 3 $R^1$ can be the same or different. In some embodiments, A is substituted with 2 different R's. In some embodiments, each $R^1$ is independently halogen, $C_1$-$C_6$ alkyl, $C_1$-$C_6$ haloalkyl, $C_3$-$C_6$ cycloalkyl, phenyl, 4- to 9-membered heterocycloalkyl, 5- to 10-membered heteroaryl, —O—$R^{1a}$, or -Q-$R^{5b}$; wherein the phenyl is unsubstituted or substituted with 1 or 2 substituents independently selected from halogen, —CN, $C_1$-$C_3$ alkyl, and $C_1$-$C_3$ haloalkyl (e.g., 1 or 2 substituents independently selected from halogen and $C_1$-$C_3$ alkyl); the 4- to 9-membered heterocycloalkyl has 1-2 ring heteroatoms or heteroatom groups independently selected from N, O, S, and $S(O)_2$; the 5- to 10-membered heteroaryl has 1-4 ring heteroatoms independently selected from N, O, and S; and the 5- to 10-membered heteroaryl is unsubstituted or substituted with $C_1$-$C_6$ alkyl (e.g., unsubstituted or substituted with one $C_1$-$C_6$ alkyl). In some embodiments, Q is $C_1$-$C_6$ alkylene, $C_1$-$C_6$ haloalkylene, or $C_3$-$C_6$ cycloalkylene. In some embodiments, $R^{1a}$ is $C_1$-$C_6$ alkyl, $C_3$-$C_6$ cycloalkyl, —($C_1$-$C_6$ alkylene)-($C_3$-$C_6$ cycloalkyl), —($C_1$-$C_6$ alkylene)-(4- to 9-membered heterocycloalkyl), or phenyl; wherein the 4- to 9-membered heterocycloalkyl has 1-2 ring heteroatoms or heteroatom groups independently selected from N, O, S, and $S(O)_2$; and wherein $R^{1a}$ is unsubstituted or substituted with 1-3 halogens; and each $R^{1b}$ is independently $C_1$-$C_6$ alkoxy, $C_3$-$C_6$ cycloalkyl, or phenyl; wherein $R^{1b}$ is unsubstituted or substituted with 1-3 halogens.

In some embodiments, A is

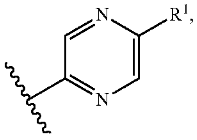

,

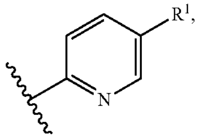

,

-continued
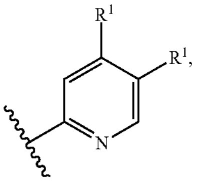
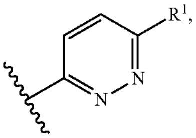
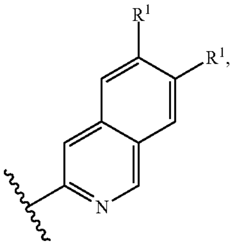
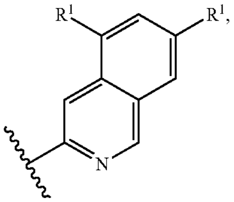
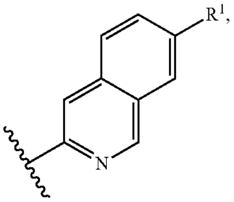
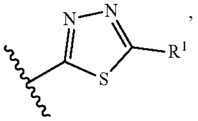
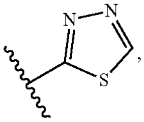
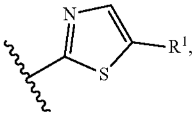
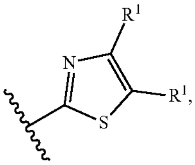
or
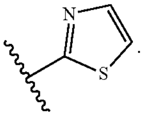
In some embodiments, A is
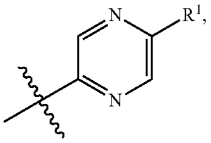
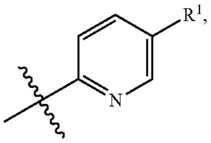
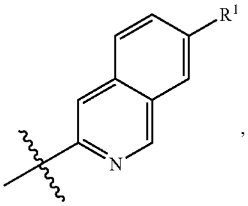
, or
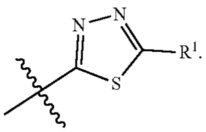
In some embodiments, A is
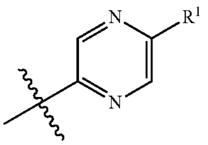
or
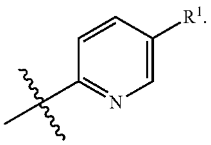
In some embodiments, A is
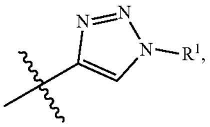
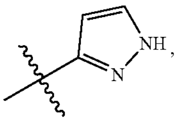
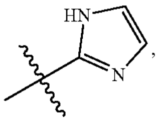
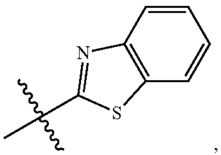
,
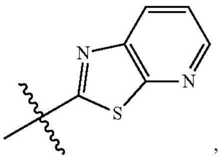
,
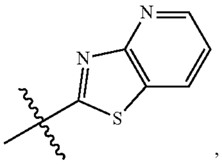
,
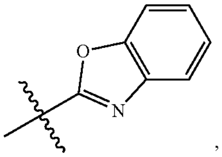
, or
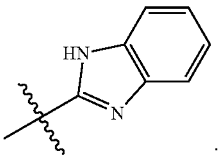
In some embodiments, A is
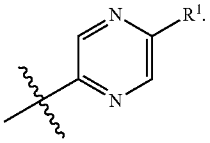
In some embodiments, A is
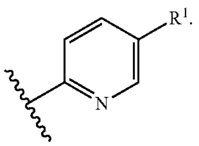
In some embodiments, A is
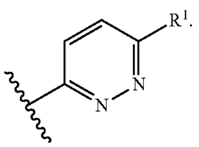
In some embodiments, A is
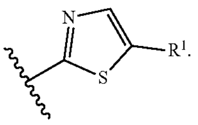

In some embodiments, A is
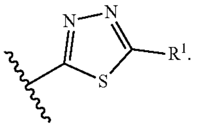
In some embodiments, A is
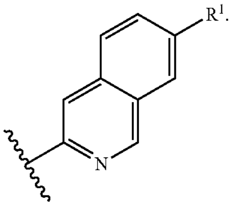
In some embodiments, A is
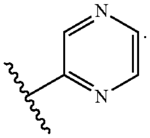 [SMILES: *c1cnccn1]
In some embodiments, A is
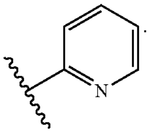 [SMILES: *c1ccccn1]
In some embodiments, A is
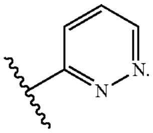 [SMILES: *c1cccnn1]
In some embodiments, A is
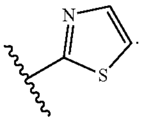
In some embodiments, A is
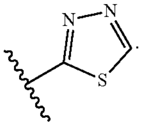
In some embodiments, A is
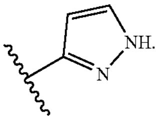 [SMILES: *c1cc[nH]n1]
In some embodiments, A is
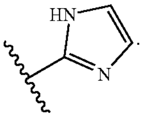 [SMILES: *c1ncc[nH]1]
In some embodiments, A is
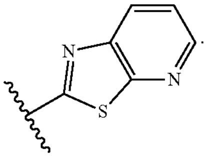 [SMILES: *c1nc2cccnc2s1]
In some embodiments, A is
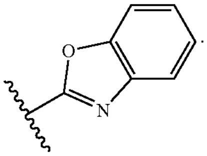 [SMILES: *c1nc2ccccc2o1]
In some embodiments, A is
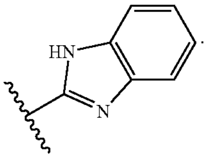 [SMILES: *c1nc2ccccc2[nH]1]
In some embodiments, A is
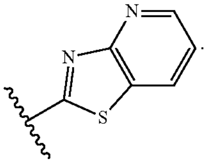 [SMILES: *c1nc2ncccc2s1]

In some embodiments, $X^2$ is N. In some embodiments, $X^2$ is $CR^7$. In some embodiments, $X^2$ is CH. In some embodiments, $X^2$ is $CR^7$, wherein $R^7$ is halogen. In some embodiments, $X^2$ is $CR^7$, wherein $R^7$ is $C_1$-$C_3$ alkyl. In some embodiments, $X^2$ is $CR^7$, wherein $R^7$ is —$NH_2$. In some embodiments, $X^2$ is CH or N.

In some embodiments, $X^3$ is N. In some embodiments, $X^3$ is $CR^8$. In some embodiments, $X^3$ is CH. In some embodiments, $X^3$ is $CR^8$, wherein $R^8$ is halogen. In some embodiments, $X^3$ is $CR^8$, wherein $R^1$ is $C_1$-$C_3$ alkyl. In some embodiments, $X^3$ is $CR^8$, wherein $R^1$ is —$NH_2$. In some embodiments, $X^3$ is CH or N.

In some embodiments, $X^4$ is CH. In some embodiments, $X^4$ is $CR^9$, wherein $R^9$ is halogen. In some embodiments, $X^4$ is $CR^9$, wherein $R^9$ is $C_1$-$C_3$ alkyl. In some embodiments, $X^4$ is $CR^9$, wherein $R^9$ is —$NH_2$.

In some embodiments, $X^5$ is CH. In some embodiments, $X^5$ is $CR^{10}$, wherein $R^{10}$ is halogen. In some embodiments, $X^5$ is $CR^{10}$, wherein $R^{10}$ is $C_1$-$C_3$ alkyl. In some embodiments, $X^5$ is $CR^{10}$, wherein $R^{10}$ is —$NH_2$.

In some embodiments, $X^2$ is CH or N; $X^3$ is N; and $X^4$ and $X^5$ are each independently CH.

In some embodiments, m is 0. In some embodiments, m is 1. In some embodiments, m is 2. In some embodiments, m is 3. In some embodiments, m is 0, 1, or 2. In some embodiments, m is 0 or 1.

In some embodiments, $R^1$ is halogen. In some embodiments, $R^1$ is $C_1$-$C_6$ alkyl. In some embodiments, $R^1$ is $C_1$-$C_6$ haloalkyl. In some embodiments, $R^1$ is $C_3$-$C_6$ cycloalkyl.

In some embodiments, $R^1$ is -Q-$R^{1b}$. In some embodiments, $R^1$ is -Q-$R^{1b}$, wherein Q is $C_1$-$C_6$ alkylene, $C_1$-$C_6$ haloalkylene, or $C_3$-$C_6$ cycloalkylene; $R^{1b}$ is $C_1$-$C_6$ alkoxy, $C_3$-$C_6$ cycloalkyl, or phenyl; and $R^{1b}$ is unsubstituted or substituted with 1-3 halogens. In some embodiments, $R^1$ is —$CH_2$—$R^{1b}$, wherein $R^{1b}$ is $C_1$-$C_6$ alkoxy, $C_3$-$C_6$ cycloalkyl, or phenyl; and $R^{1b}$ is unsubstituted or substituted with 1-3 halogens. In some embodiments, $R^1$ is —$CH_2$—$R^{1b}$, wherein $R^{1b}$ is phenyl that is unsubstituted or substituted with 1-3 halogens. In some embodiments, $R^1$ is —$CH_2$—$R^{1b}$, wherein $R^{1b}$ is $C_1$-$C_6$ alkoxy that is unsubstituted or substituted with 1-3 halogens. In some embodiments, $R^1$ is

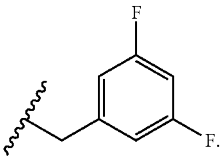 [SMILES: *Cc1cc(F)cc(F)c1]

In some embodiments, $R^1$ is

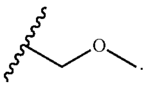 [SMILES: *COC]

In some embodiments, $R^1$ is phenyl, wherein the phenyl is unsubstituted or substituted with 1 or 2 substituents independently selected from halogen, —CN, $C_1$-$C_3$ alkyl, and $C_1$-$C_3$ haloalkyl. In some embodiments, $R^1$ is phenyl, wherein the phenyl is unsubstituted or substituted with 1 or 2 substituents independently selected from halogen.

In some embodiments, $R^1$ is 4- to 9-membered heterocycloalkyl, wherein the 4- to 9-membered heterocycloalkyl has 1-2 ring heteroatoms or heteroatom groups independently selected from N, O, S, and $S(O)_2$.

In some embodiments, $R^1$ is 5- to 10-membered heteroaryl, wherein the 5- to 10-membered heteroaryl has 1-4 ring heteroatoms independently selected from N, O, and S; and the 5- to 10-membered heteroaryl is unsubstituted or substituted with $C_1$-$C_6$ alkyl (e.g., unsubstituted or substituted with one $C_1$-$C_6$ alkyl). In some embodiments, the 5- to 10-membered heteroaryl is unsubstituted.

In some embodiments, $R^1$ is —O—$R^{1a}$. In some embodiments, $R^1$ is —O—$R^{1a}$, wherein $R^{1a}$ is $C_1$-$C_6$ alkyl (e.g., ethyl), and $R^{1a}$ is unsubstituted or substituted with 1-3 halogens. In some embodiments, $R^1$ is —O—$C_1$-$C_6$ alkyl (e.g., —OEt). In some embodiments, $R^1$ is —O—$R^{1a}$, wherein $R^{1a}$ is —$C_3$-$C_6$ cycloalkyl, and $R^{1a}$ is unsubstituted or substituted with 1-3 halogens. In some embodiments, $R^1$ is —O—$R^{1a}$, wherein $R^{1a}$ is —($C_1$-$C_6$ alkylene)-($C_3$-$C_6$ cycloalkyl), and $R^{1a}$ is unsubstituted or substituted with 1-3 halogens. In some embodiments, $R^1$ is —O—$R^{1a}$, wherein $R^{1a}$ is —($C_1$-$C_6$ alkylene)-(4- to 9-membered heterocycloalkyl), wherein the 4- to 9-membered heterocycloalkyl has 1-2 ring heteroatoms or heteroatom groups independently selected from N, O, S, and $S(O)_2$, and $R^{1a}$ is unsubstituted or substituted with 1-3 halogens. In some embodiments, $R^1$ is —O—$R^{1a}$, wherein $R^{1a}$ is $C_1$-$C_6$ alkyl, $C_3$-$C_6$ cycloalkyl, or phenyl; wherein $R^{1a}$ is unsubstituted or substituted with 1-3 halogens.

In some embodiments, $R^{1a}$ is $C_1$-$C_6$ alkyl, $C_3$-$C_6$ cycloalkyl, or phenyl; wherein $R^{1a}$ is unsubstituted or substituted with 1-3 halogens. In some embodiments, $R^{1a}$ is $C_1$-$C_6$ alkyl, wherein $R^{1a}$ is unsubstituted or substituted with 1-3 halogens. In some embodiments, $R^{1a}$ is $C_1$-$C_6$ alkyl. In some embodiments, $R^{1a}$ is $C_3$-$C_6$ cycloalkyl, wherein $R^{1a}$ is unsubstituted or substituted with 1-3 halogens. In some embodiments, $R^{1a}$ is phenyl, wherein $R^{1a}$ is unsubstituted or substituted with 1-3 halogens.

In some embodiments, $R^1$ is halogen, $C_1$-$C_6$ alkyl, $C_3$-$C_6$ cycloalkyl, phenyl, —($C_1$-$C_6$ alkylene)-$C_1$-$C_6$ alkoxy, or —O—$R^{1a}$.

In some embodiments, $R^1$ is methyl, ethyl, F, methoxy, ethoxy,

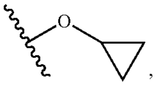,
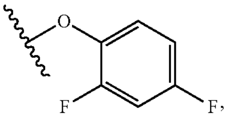,
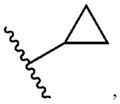,
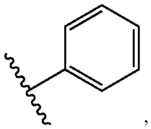, or
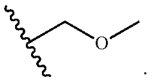.

In some embodiments, $R^1$ is ethyl, F, ethoxy,

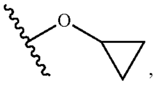,
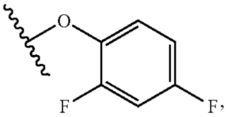,
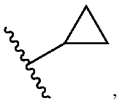,
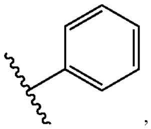, or
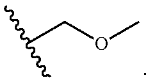.

In some embodiments, R is Cl,

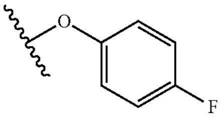, 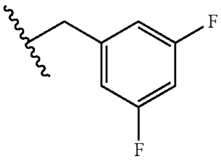, 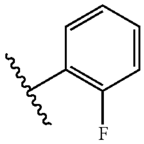, 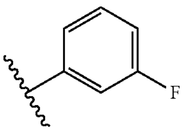, 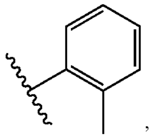, 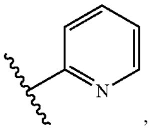, or 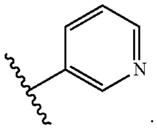.

In some embodiments, $R^2$ is $C_1$-$C_3$ alkyl. In some embodiments, $R^2$ is methyl. In some embodiments, $R^2$ is H. In some embodiments, $R^2$ is methyl or H.

In some embodiments, $R^{3a}$ and $R^{3b}$ are H. In some embodiments, $R^{3a}$ and $R^{3b}$ are halogen. In some embodiments, $R^{3a}$ and $R^{3b}$ are F. In some embodiments, $R^{3a}$ and $R^{3b}$ are independently H or F. In some embodiments, $R^{3a}$ is halogen and $R^{3b}$ is H. In some embodiments, $R^{3a}$ is F and $R^{3b}$ is H.

In some embodiments, $R^{3c}$ and $R^{3d}$ are H. In some embodiments, $R^{3c}$ and $R^{3d}$ are halogen. In some embodiments, $R^{3c}$ and $R^{3d}$ are F. In some embodiments, $R^{3c}$ and $R^{3d}$ are independently H or F. In some embodiments, $R^{3c}$ is halogen and $R^{3d}$ is H. In some embodiments, $R^{3c}$ is F and $R^{3d}$ is H.

In some embodiments, $R^{3a}$ and $R^{3b}$ are each independently H or halogen; and $R^{3c}$ and $R^{3d}$ are H. In some embodiments, $R^{3a}$ and $R^{3b}$ are halogen; and $R^{3c}$ and $R^{3d}$ are H. In some embodiments, $R^{3a}$ and $R^{3b}$ are F, and $R^{3c}$ and $R^{3d}$ are H. In some embodiments, $R^{3a}$ is F, and $R^{3b}$, $R^{3c}$, and $R^{3d}$ are H. In some embodiments, $R^{3a}$, $R^{3b}$, $R^{3c}$, and $R^{3d}$ are H.

In some embodiments, $R^4$ is H or $C_1$-$C_6$ alkyl. In some embodiments, $R^4$ is H. In some embodiments, $R^4$ is $C_1$-$C_6$ alkyl. In some embodiments, $R^4$ is $C_1$-$C_6$ haloalkyl. In some embodiments, $R^4$ is $C_1$-$C_6$ alkoxy. In some embodiments, $R^4$ is $C_1$-$C_6$ hydroxyalkyl. In some embodiments, $R^4$ is H, methyl, or ethyl.

In some embodiments, Y is absent. In some embodiments, Y is $C_1$-$C_6$ alkylene.

In some embodiments, $R^{5a}$ is $C_1$-$C_6$ alkyl; wherein $R^{5a}$ is unsubstituted or substituted with 1-4 $R^{5d}$. In some embodiments, $R^{5a}$ is $C_3$-$C_8$ cycloalkyl; wherein $R^{5a}$ is unsubstituted or substituted with 1-4 $R^{5d}$. In some embodiments, $R^{5a}$ is phenyl; wherein $R^{5a}$ is unsubstituted or substituted with 1-4 $R^{5d}$. In some embodiments, $R^{5a}$ is 5- to 10-membered heteroaryl; wherein the 5- to 10-membered heteroaryl has 1-4 ring heteroatoms independently selected from N, O, and S; and $R^{5a}$ is unsubstituted or substituted with 1-4 $R^{5d}$. In some embodiments, $R^{5a}$ is 4- to 10-membered heterocycloalkyl; wherein the 4- to 10-membered heterocycloalkyl has 1-3 ring heteroatoms or ring heteroatom groups independently selected from N, O, S, and $S(O)_2$; and $R^{5a}$ is unsubstituted or substituted with 1-4 $R^{5d}$.

In some embodiments, $R^{5a}$ is $C_1$-$C_6$ alkyl, $C_3$-$C_8$ cycloalkyl, 5- to 6-membered heteroaryl, or 5- to 9-membered heterocycloalkyl; wherein the 5- to 6-membered heteroaryl has 1 or 2 nitrogen ring heteroatoms; the 5- to 9-membered heterocycloalkyl has 1 or 2 ring heteroatoms independently selected from N and O; and $R^{5a}$ is unsubstituted or substituted with 1-3 $R^{5d}$; each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5d}$ is —C(O)—($C_1$-$C_4$ alkyl). In some embodiments, $R^{5d}$ is 4- to 10-membered heterocycloalkyl, wherein the 4- to 10-membered heterocycloalkyl has 1-3 ring heteroatoms or ring heteroatom groups independently selected from N, O, S, and $S(O)_2$. In particular embodiments, $R^{5d}$ is 4- to 6-membered heterocycloalkyl with one N as a ring heteroatom.

In some embodiments, $R^{5a}$ is 5- to 6-membered heteroaryl or 5- to 9-membered heterocycloalkyl; wherein the 5- to 6-membered heteroaryl has 1 or 2 nitrogen ring heteroatoms; the 5- to 9-membered heterocycloalkyl has 1 or 2 ring heteroatoms independently selected from N and O; and $R^{5a}$ is unsubstituted or substituted with 1-2 $R^{5d}$; and each $R^{5d}$ when present is independently selected from oxo, halogen, —OH, and $C_1$-$C_6$ alkyl.

In some embodiments, Y is $C_1$-$C_6$ alkylene; and $R^{5a}$ is 5- to 6-membered heteroaryl or 5 to 9-membered heterocycloalkyl; wherein the 5- to 6-membered heteroaryl has 1 or 2 nitrogen ring heteroatoms; the 5- to 9-membered heterocycloalkyl has 1 or 2 ring heteroatoms independently selected from N and O; and $R^{5a}$ is unsubstituted or substituted with 1-2 $R^{5d}$; and each $R^{5d}$ when present is independently selected from oxo, halogen, —OH, and $C_1$-$C_6$ alkyl. In some embodiments, —Y—$R^{5a}$ is

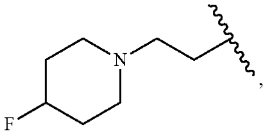, 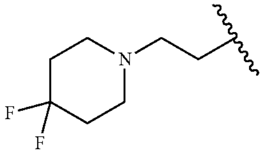,

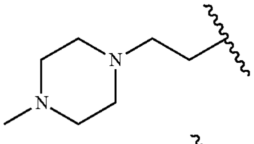, 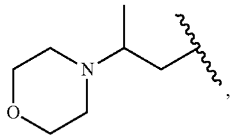,

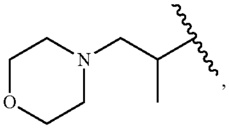, 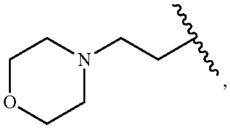,

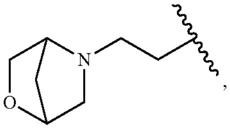, 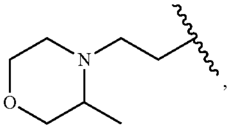,

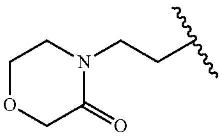, 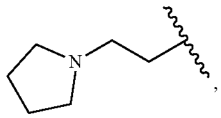,

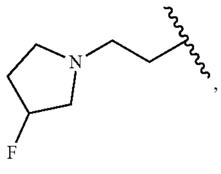, 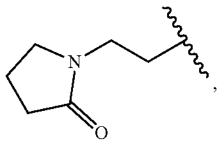,

-continued

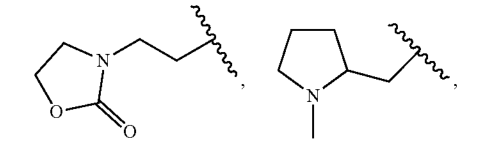

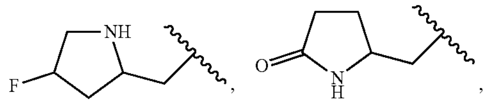

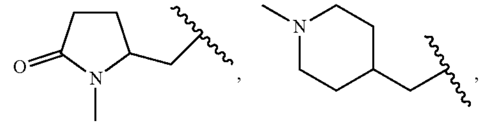

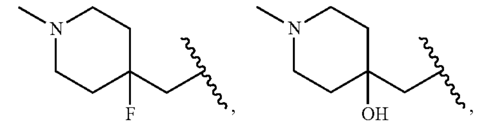

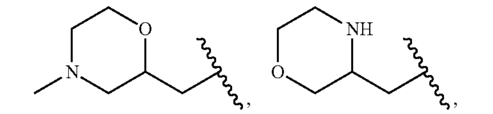

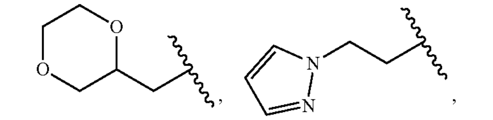

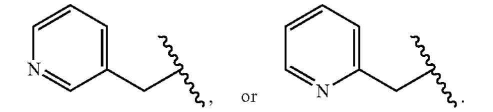

In some embodiments, —Y—$R^{5a}$ is

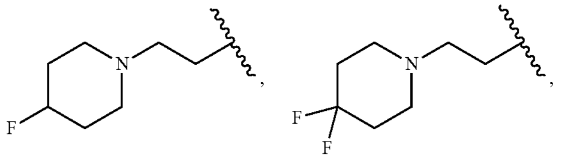

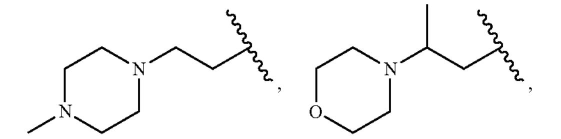

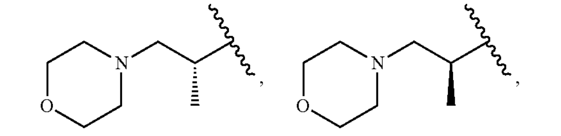

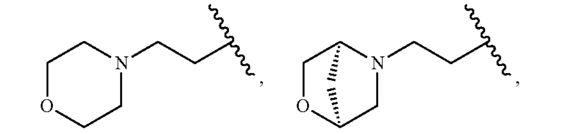

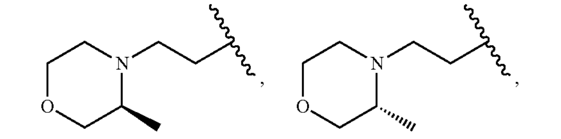

-continued

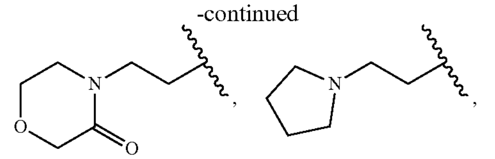

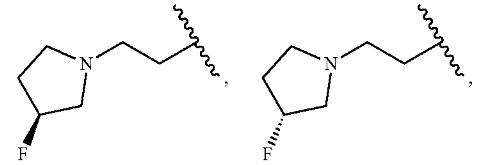

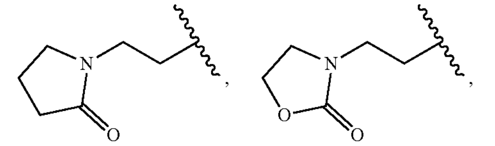

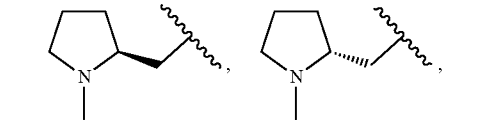

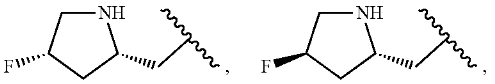

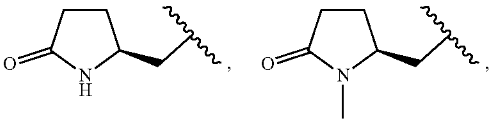

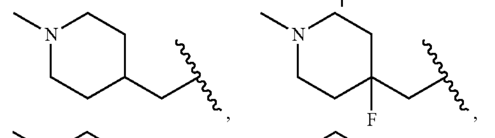

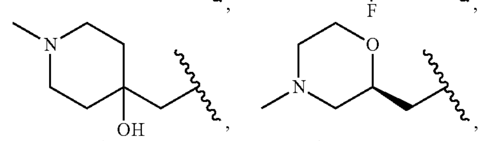

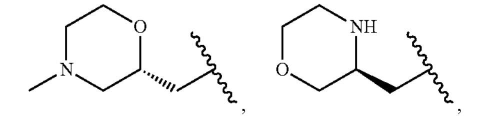

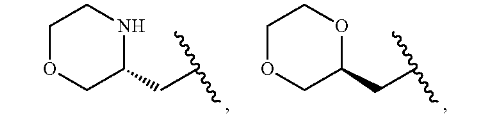

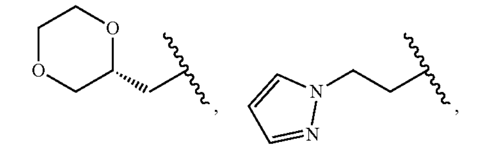

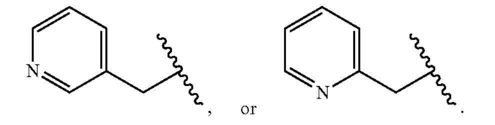

In some embodiments, Y is $C_1$-$C_6$ alkylene; and $R^{5a}$ is 5- to 9-membered heterocycloalkyl; wherein the 5- to 9-membered heterocycloalkyl has 1 or 2 ring heteroatoms independently selected from N and O; and $R^{5a}$ is unsubstituted or substituted with 1-2 $R^{5d}$; and each $R^{5d}$ when present is independently selected from oxo, halogen, —OH, and $C_1$-$C_6$ alkyl. In some embodiments, —Y—$R^{5a}$ is

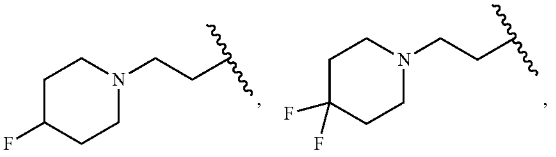,
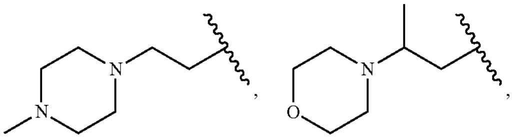,
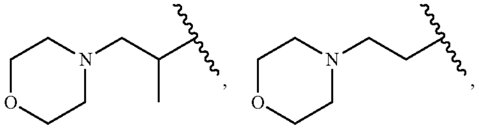,
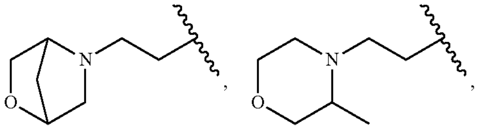,
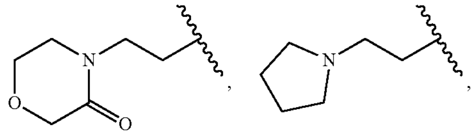,
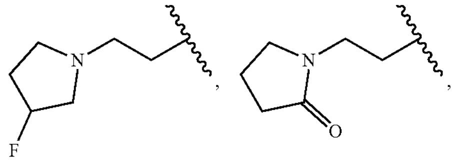,
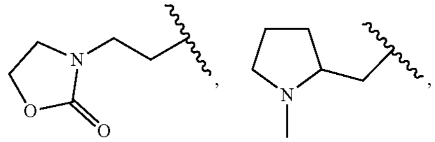,
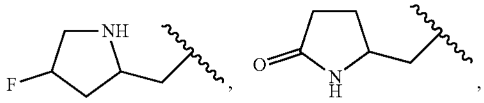,
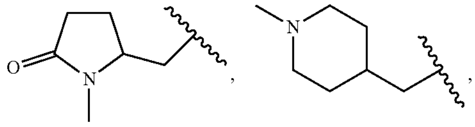,
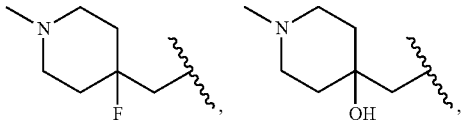,
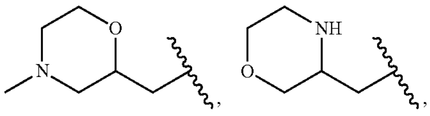, or
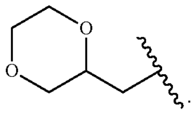.
In some embodiments, —Y—$R^{5a}$ is
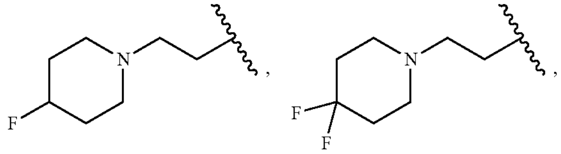,
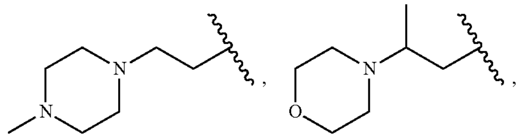,
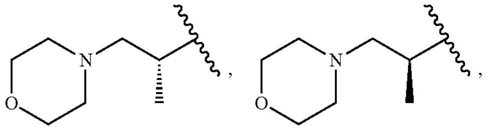,
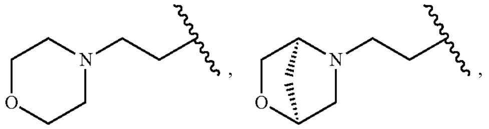,
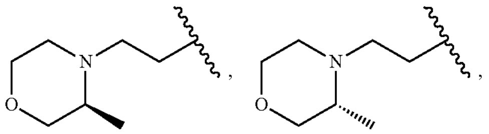,
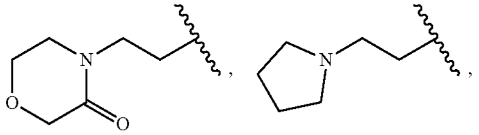,
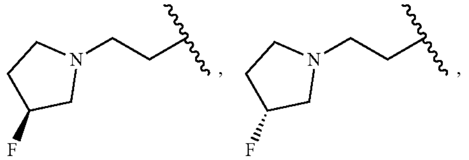,
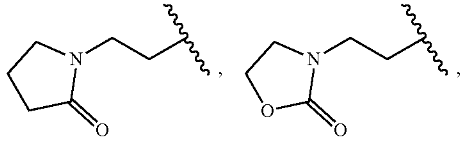,
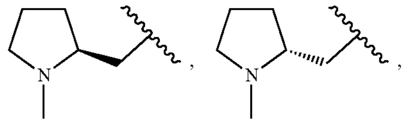,
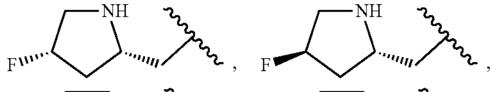,
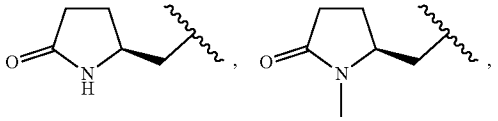,
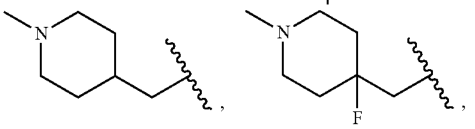,
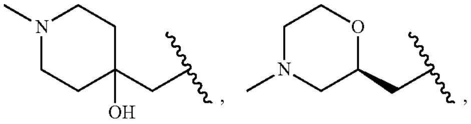, -continued

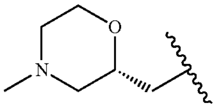, 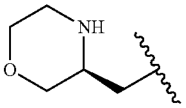, 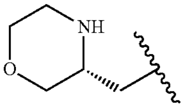, 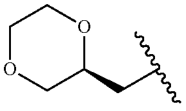, or 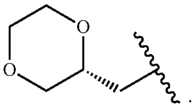.

In some embodiments, —Y—$R^{5a}$ is

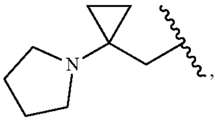, 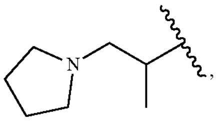, 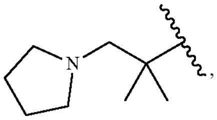, 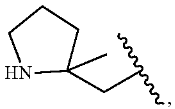, 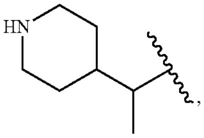, 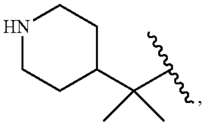, 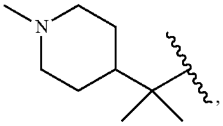, 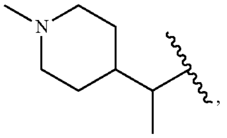 or 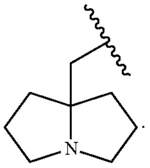.

In some embodiments, —Y—$R^{5a}$ is

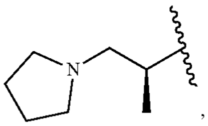, 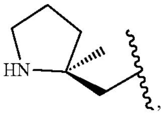, 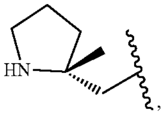, 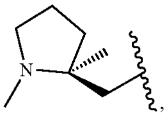, 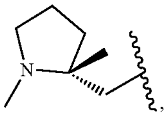, 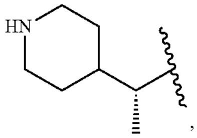, 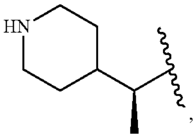, 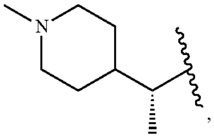, -continued

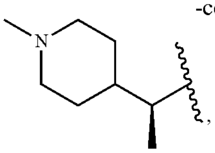, 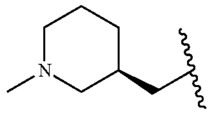, or 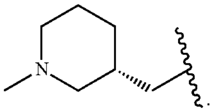.

In some embodiments, Y is $C_1$-$C_6$ alkylene; and $R^{5a}$ is 5- to 6-membered heteroaryl; wherein the 5- to 6-membered heteroaryl has 1 or 2 nitrogen ring heteroatoms; and $R^{5a}$ is unsubstituted or substituted with 1-2 $R^{5d}$; and each $R^{5d}$ when present is independently selected from oxo, halogen, —OH, and $C_1$-$C_6$ alkyl. In some embodiments, Y is $C_1$-$C_6$ alkylene; and $R^{5a}$ is 5- to 6-membered heteroaryl; wherein the 5- to 6-membered heteroaryl has 1 or 2 nitrogen ring heteroatoms. In some embodiments, —Y—$R^{5a}$ is

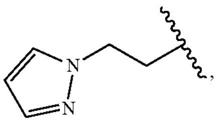, 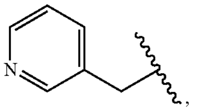, or 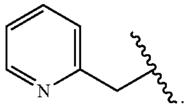.

In some embodiments, $R^{5a}$ is $C_1$-$C_6$ alkyl, $C_3$-$C_8$ cycloalkyl, or 5- to 9-membered heterocycloalkyl; wherein the 5- to 9-membered heterocycloalkyl has 1 ring heteroatom independently selected from N and O; and $R^{5a}$ is unsubstituted or substituted with 1-3 $R^{5d}$; each $R^{5d}$ when present is independently selected from halogen, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5d}$ is —C(O)—($C_1$-$C_4$ alkyl). In some embodiments, $R^{5d}$ is 4- to 10-membered heterocycloalkyl, wherein the 4- to 10-membered heterocycloalkyl has 1-3 ring heteroatoms or ring heteroatom groups independently selected from N, O, S, and $S(O)_2$. In particular embodiments, $R^{5d}$ is 4- to 6-membered heterocycloalkyl with one N as a ring heteroatom.

In some embodiments, Y is absent; and $R^{5a}$ is $C_1$-$C_6$ alkyl, $C_3$-$C_8$ cycloalkyl, or 5- to 9-membered heterocycloalkyl; wherein the 5- to 9-membered heterocycloalkyl has 1 ring heteroatom independently selected from N and O; and $R^{5a}$ is unsubstituted or substituted with 1-3 $R^{5d}$; each $R^{5d}$ when present is independently selected from halogen, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5d}$ is —C(O)—($C_1$-$C_4$ alkyl). In some embodiments, $R^{5d}$ is 4- to 10-membered heterocycloalkyl, wherein the 4- to 10-membered heterocycloalkyl has 1-3 ring heteroatoms or ring heteroatom groups independently selected from N, O, S, and $S(O)_2$. In particular embodiments, $R^{5d}$ is 4- to 6-membered heterocycloalkyl with one N as a ring heteroatom. In some embodiments, —Y—$R^{5a}$ is methyl, ethyl, isopropyl,
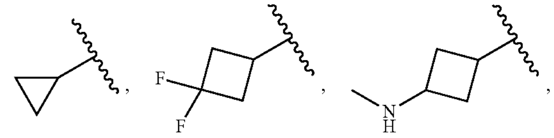
, , ,
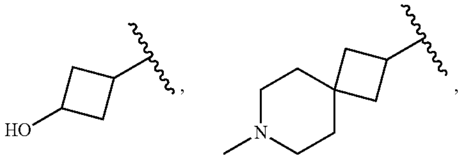
, ,
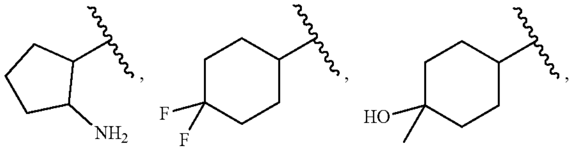
, , ,
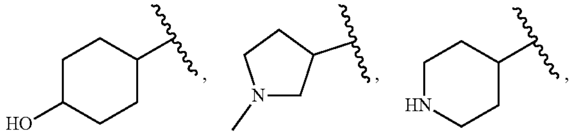
, , ,
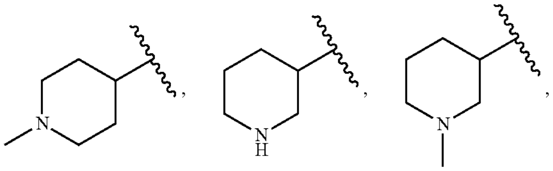
, , ,
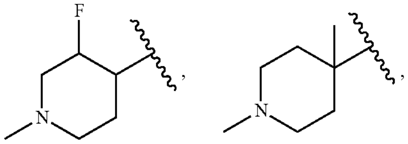
, ,
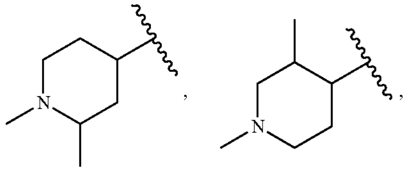
, ,
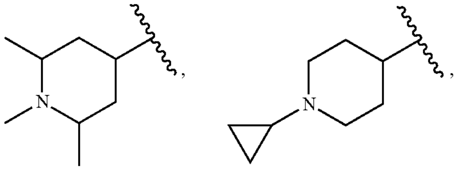
, ,
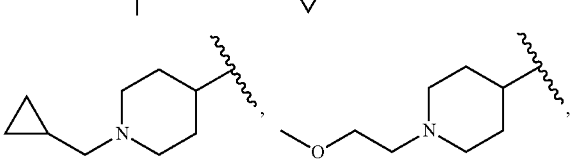
, ,
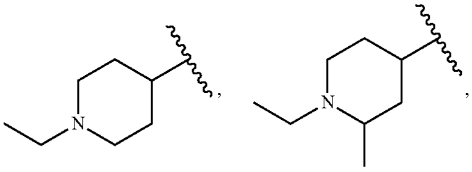
, ,
-continued
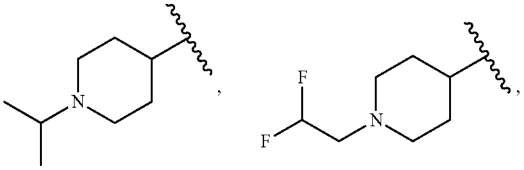
, ,
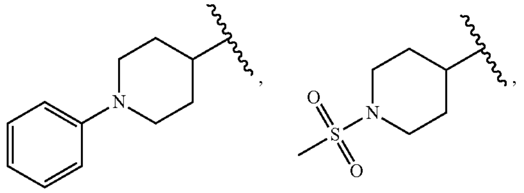
, ,
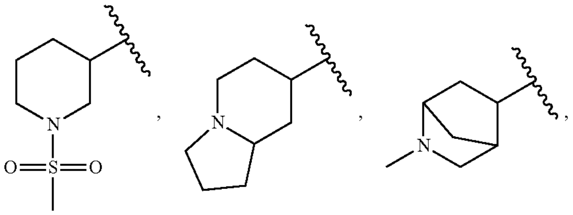
, , ,
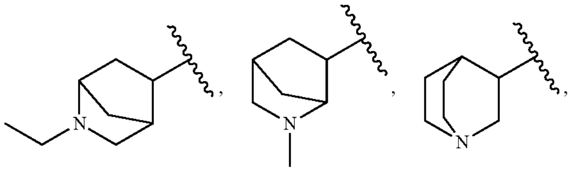
, , ,
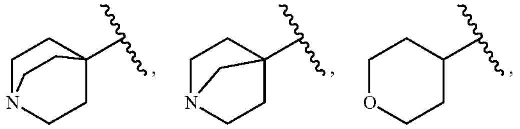
, , , or
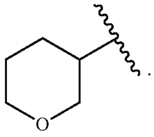
.
In some embodiments, —Y—$R^{5a}$ is methyl, ethyl, isopropyl,
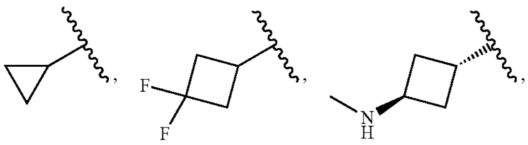
, , ,
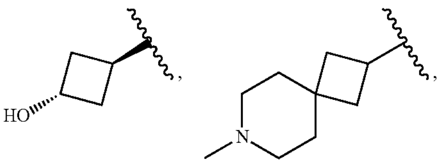
, ,
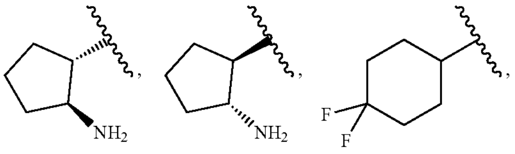
, , , -continued
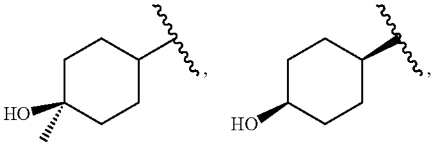
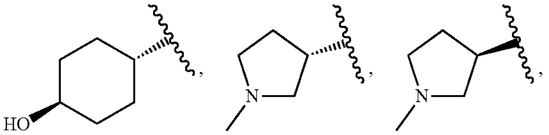
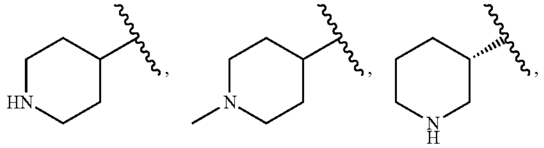
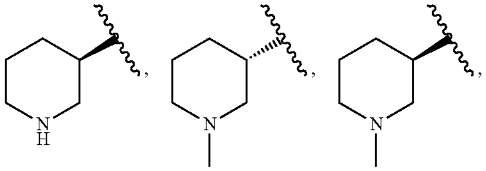
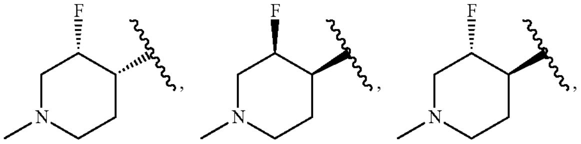
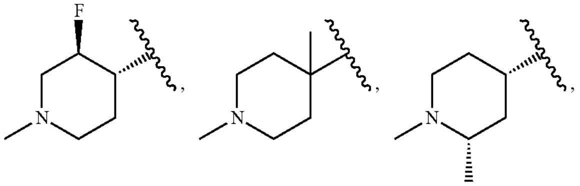
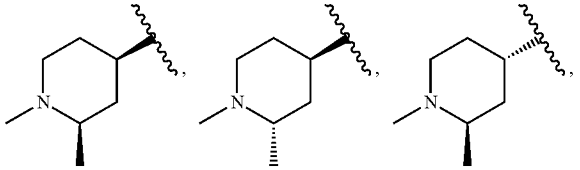
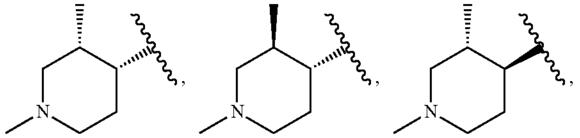
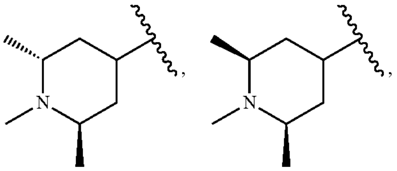
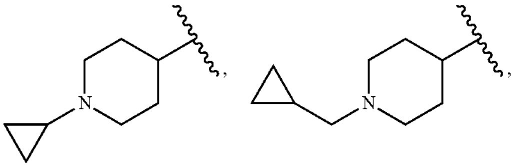
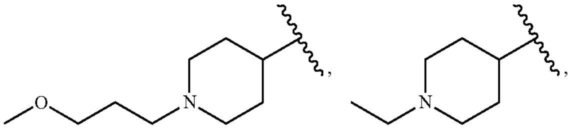
-continued
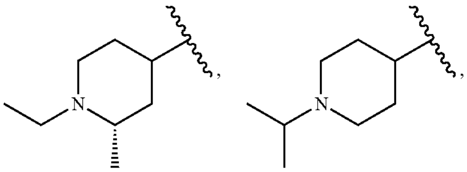
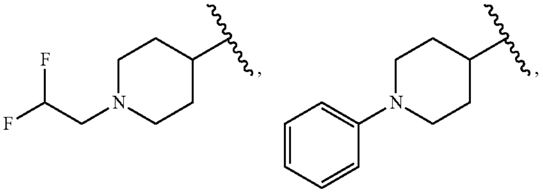
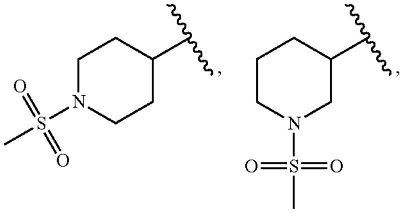
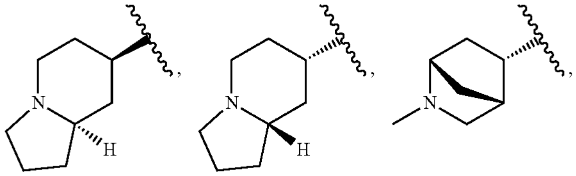
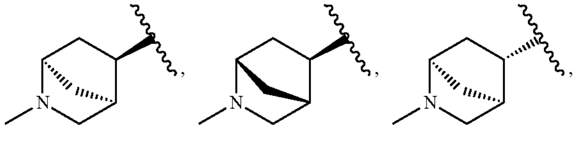
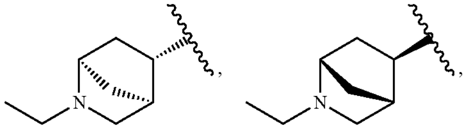
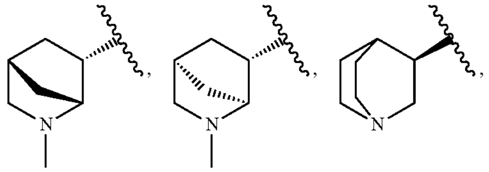
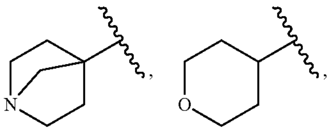
or
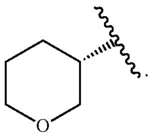
In some embodiments, —Y—$R^{5a}$ is
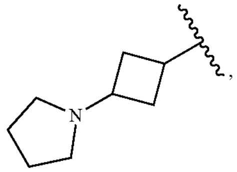

-continued

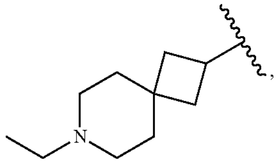,

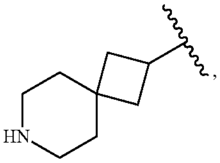, 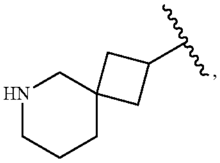,

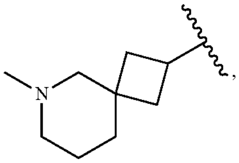, 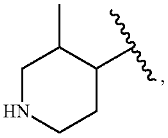,

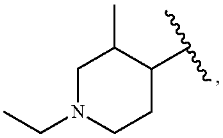, 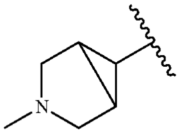, or

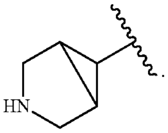.

In some embodiments, —Y—$R^{5a}$ is

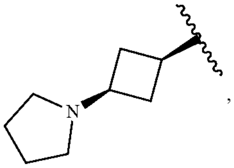, 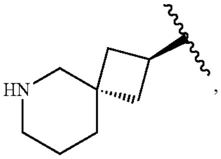,

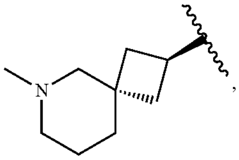, 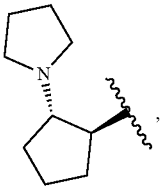,

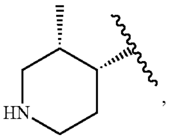, 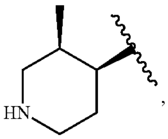, 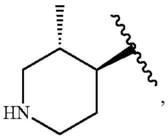,

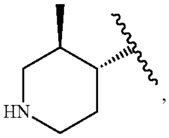, 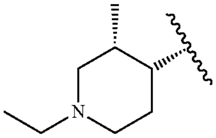,

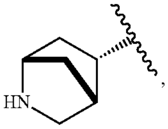, 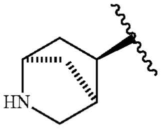, 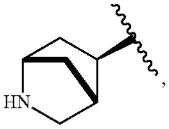,

-continued

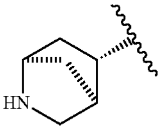, 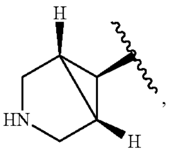, 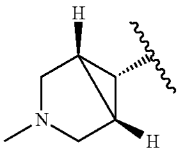,

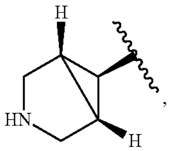, or 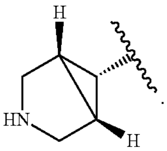.

In some embodiments, Y is absent; and $R^{5a}$ is $C_1$-$C_6$ alkyl. In some embodiments, —Y—$R^{5a}$ is methyl, ethyl, or isopropyl.

In some embodiments, Y is absent; and $R^{5a}$ is $C_3$-$C_8$ cycloalkyl; and $R^{5a}$ is unsubstituted or substituted with 1-3 $R^{5d}$; each $R^{5d}$ when present is independently selected from halogen, —OH, —$NR^{5b}R^{5c}$ $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5d}$ is —C(O)—($C_1$-$C_4$ alkyl). In some embodiments, $R^{5d}$ is 4- to 10-membered heterocycloalkyl, wherein the 4- to 10-membered heterocycloalkyl has 1-3 ring heteroatoms or ring heteroatom groups independently selected from N, O, S, and $S(O)_2$. In particular embodiments, $R^{5d}$ is 4- to 6-membered heterocycloalkyl with one N as a ring heteroatom. In some embodiments, Y is absent; and $R^{5a}$ is $C_3$-$C_8$ cycloalkyl; and $R^{5a}$ is unsubstituted or substituted with 1-3 $R^{5d}$; each $R^{5d}$ when present is independently selected from halogen, —OH, —$NR^{5b}R^{5c}$, and $C_1$-$C_6$ alkyl; and $R^{5b}$ and $R^{5c}$ are independently selected from H and $C_1$-$C_3$ alkyl. In some embodiments, —Y—$R^{5a}$ is

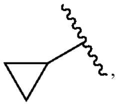, 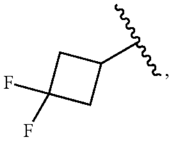,

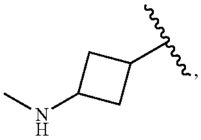, 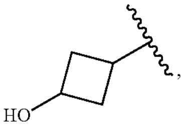,

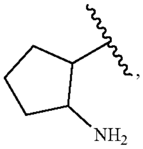, 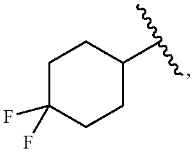,

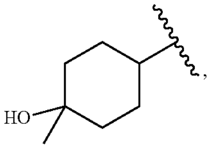, or 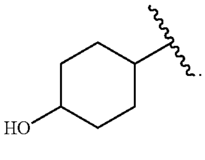.

In some embodiments, —Y—$R^{5a}$ is

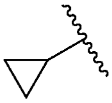, 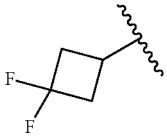, 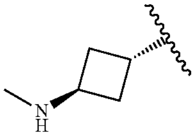,

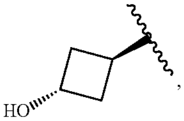, 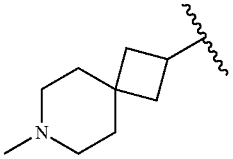,

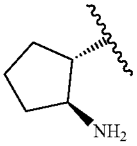, 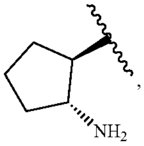, 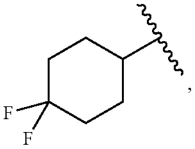,

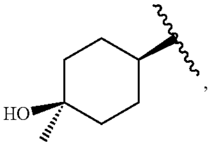, 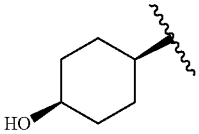, or

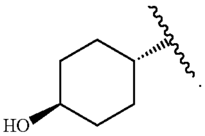.

In some embodiments, —Y—$R^{5a}$ is or

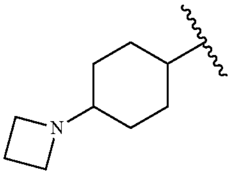, 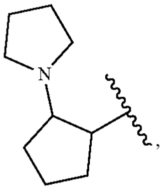, or

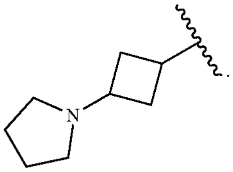.

In some embodiments, —Y—$R^{5a}$ is

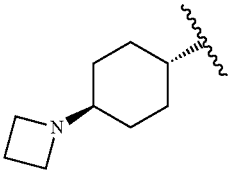, 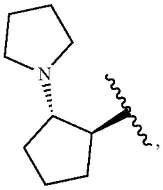, or

-continued

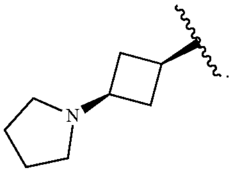.

In some embodiments, Y is absent; and $R^{5a}$ is 5- to 9-membered heterocycloalkyl; wherein the 5- to 9-membered heterocycloalkyl has 1 ring heteroatom independently selected from N and O; and $R^{5a}$ is unsubstituted or substituted with 1-3 $R^{5d}$; each $R^{5d}$ when present is independently selected from halogen, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, each $R^{5d}$ when present is independently selected from —C(O)—($C_1$-$C_4$ alkyl), —C(O)—($C_1$-$C_4$ hydroxyalkyl), and 4- to 10-membered heterocycloalkyl having 1-3 ring heteroatoms independently selected from N, O, and S. In some embodiments, —Y—$R^{5a}$ is

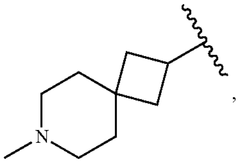, 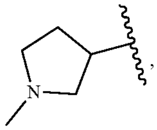,

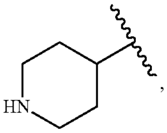, 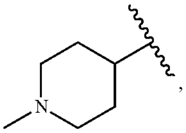, 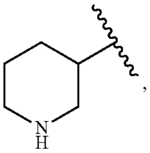,

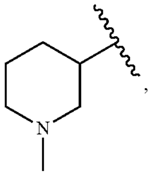, 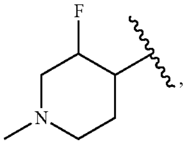, 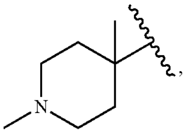,

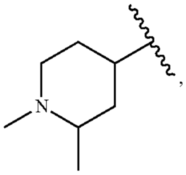, 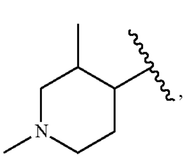, 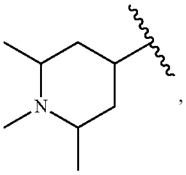,

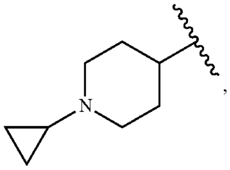, 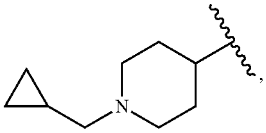,

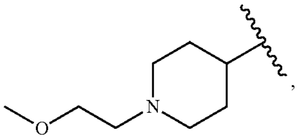, 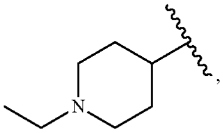,

-continued
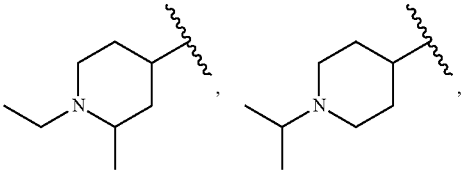
, ,
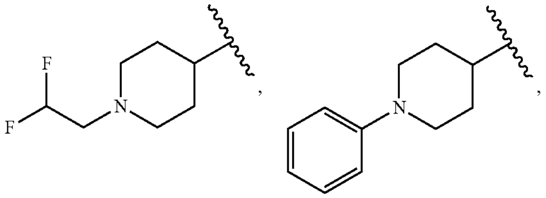
, ,
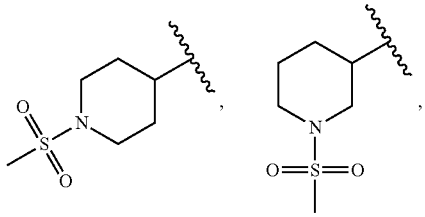
, ,
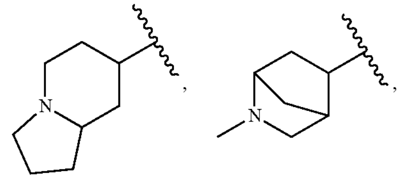
, ,
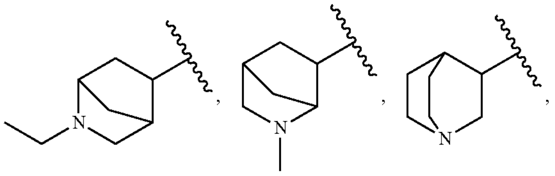
, , ,
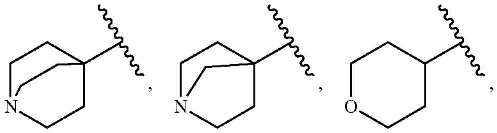
, , , or
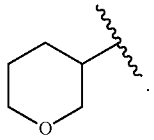
.
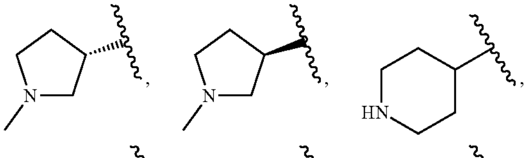
, , ,
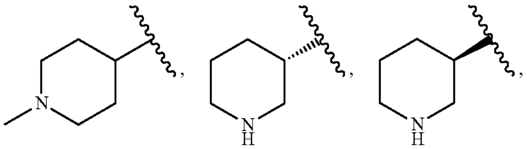
, , ,
-continued
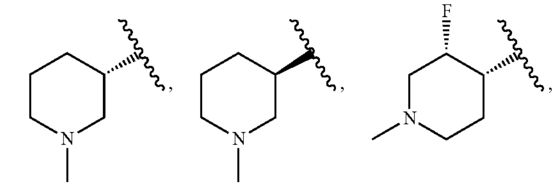
, , ,
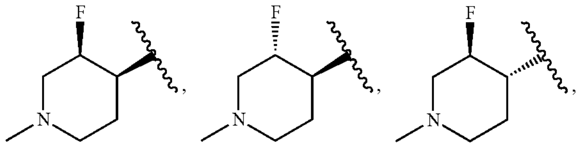
, , ,
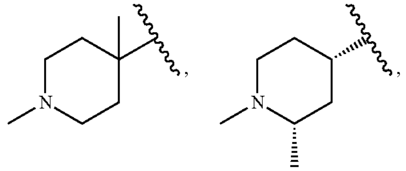
, ,
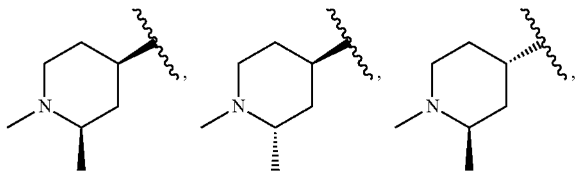
, , ,
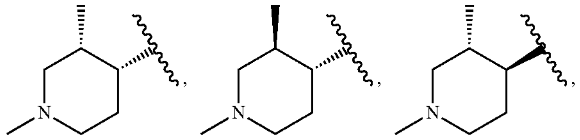
, , ,
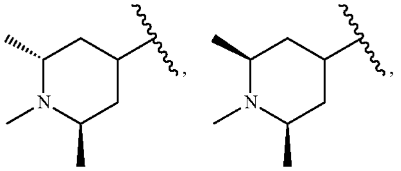
, ,
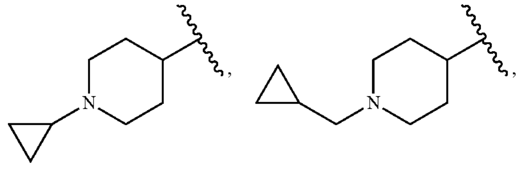
, ,
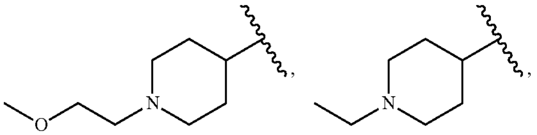
, ,
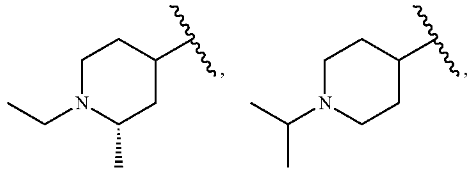
, ,
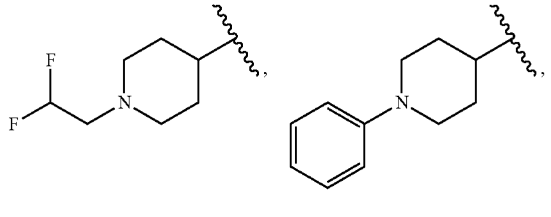
, , -continued
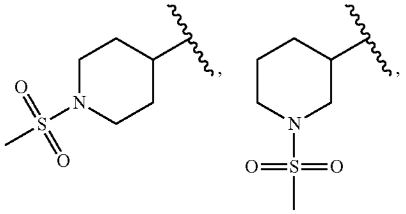
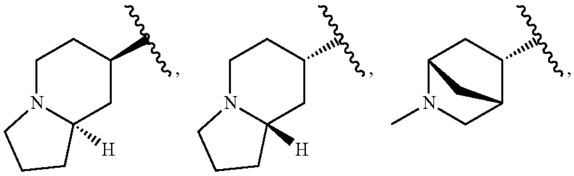
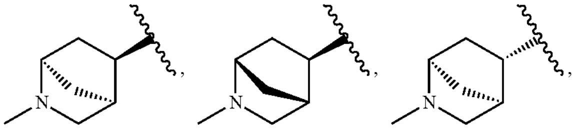
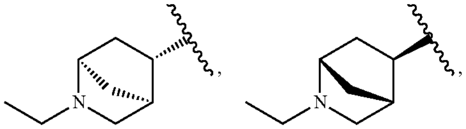
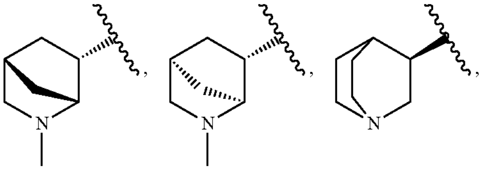
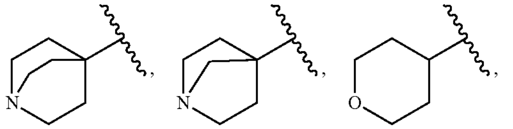
or
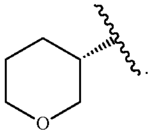
In some embodiments, —Y—$R^{5a}$ is
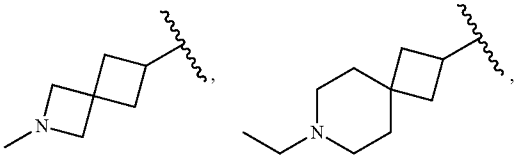
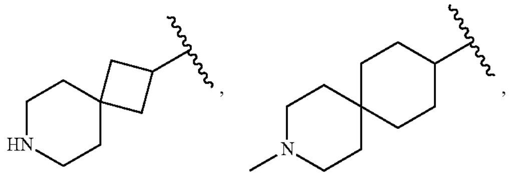
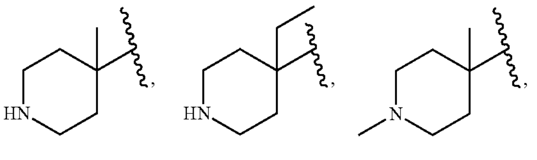
-continued
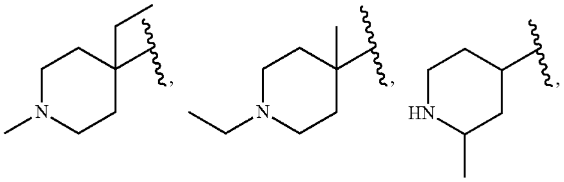
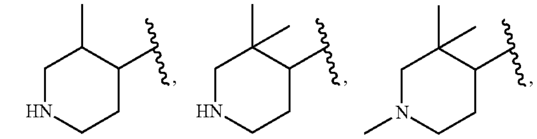
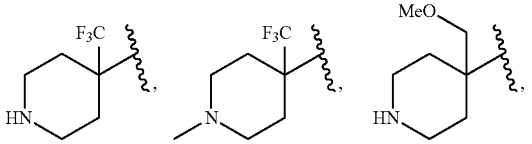
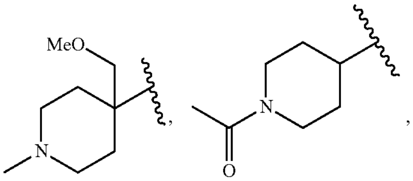
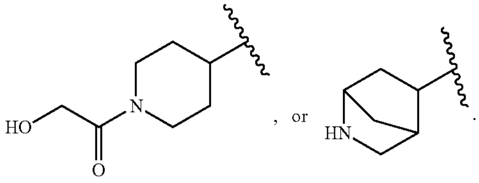
In some embodiments, —Y—$R^{5a}$ is
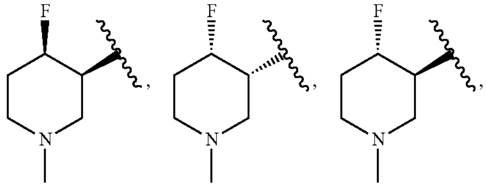
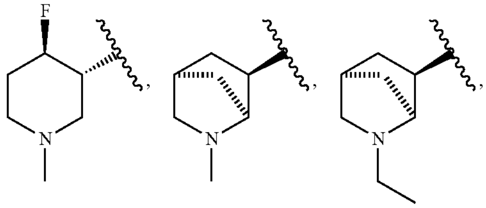
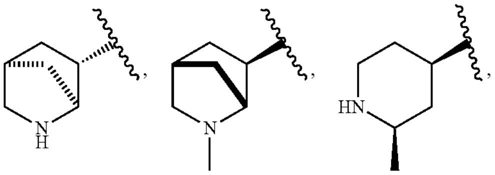
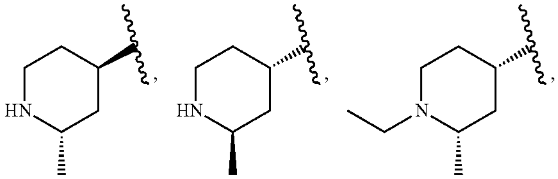

-continued

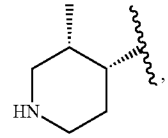, 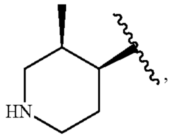, 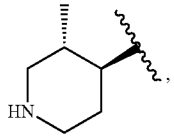, 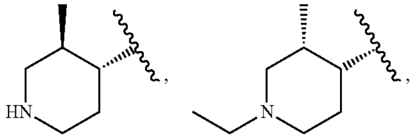, 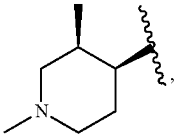, 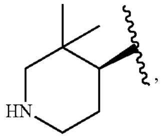, 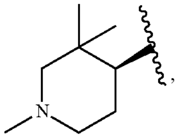, 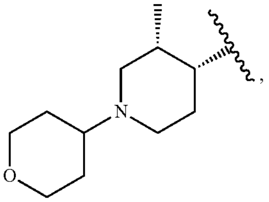, 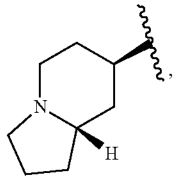, 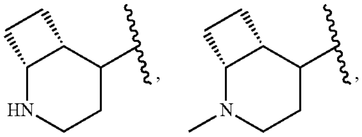, 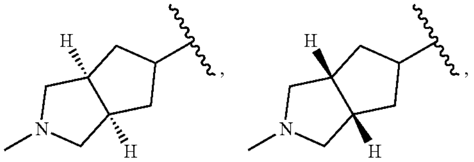, 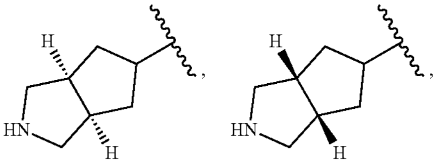, 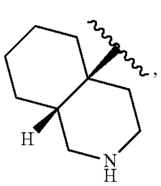, 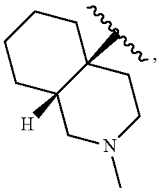, 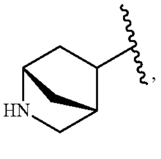, 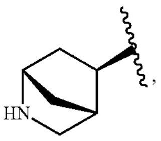, 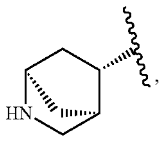, 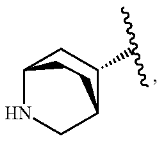, 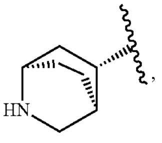, 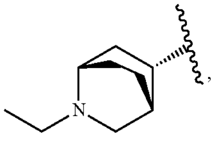, 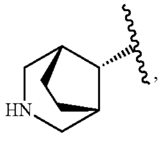, 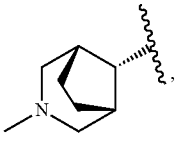, 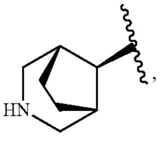, 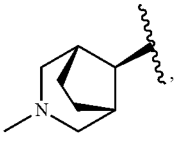, -continued

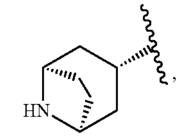, 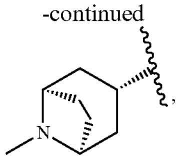, 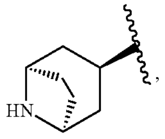, 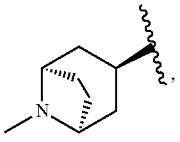, 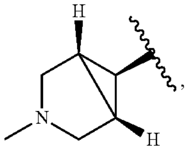, 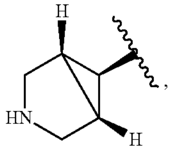, 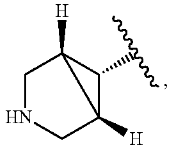, 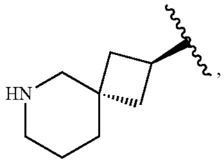, 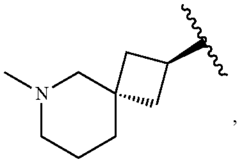, 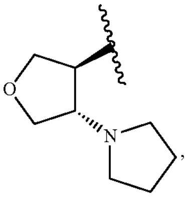, 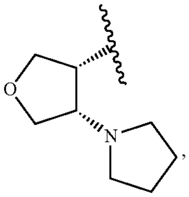, or 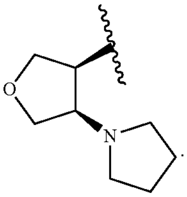.

In some embodiments, Y is absent; and $R^{5a}$ is

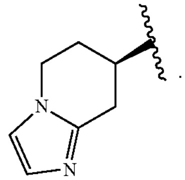 [SMILES: *[C@@H]1CCn2ccnc2C1].

In some embodiments, $R^{5a}$ is 5- to 9-membered heterocycloalkyl; wherein the 5- to 9-membered heterocycloalkyl has 1 or 2 ring heteroatoms independently selected from N and O; and $R^{5a}$ is unsubstituted or substituted with 1-3 $R^{5d}$; each $R^{5d}$ when present is independently selected from oxo, halogen, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5d}$ is $C_1$-$C_6$ alkyl. In some embodiments, —Y—$R^{5a}$ is

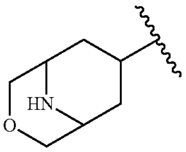 or 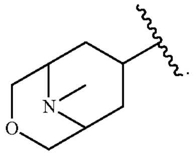.

In some embodiments, —Y—$R^{5a}$ is

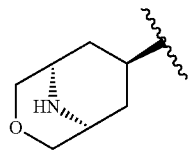 or 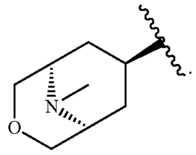.

In some embodiments, —Y—$R^{5a}$ is

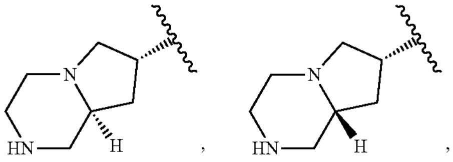,

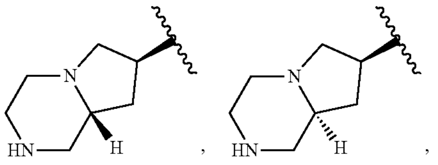,

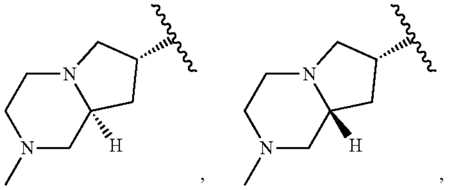,

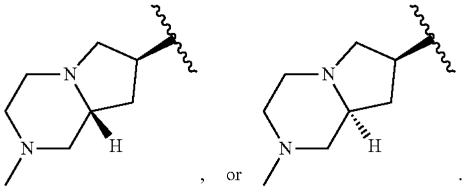 , or .

In some embodiments, $R^{5a}$ is methyl, ethyl, isopropyl, cyclopropyl, cyclobutyl, cyclopentyl, cyclohexyl, pyrrolidinyl, oxazolidinyl, piperidinyl, quinuclidinyl, morpholinyl, 2-azabicyclo[2.2.1]heptanyl, 1-azabicyclo[2.2.1]heptanyl, 2-oxa-5-azabicyclo[2.2.1]heptanyl, octahydroindolizinyl, 7-azaspiro[3.5]nonanyl, dioxanyl, piperazinyl, tetrahydropyranyl, pyrazolyl, or pyridinyl; and $R^{5a}$ is unsubstituted or substituted with 1-3 $R^{5d}$; each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5d}$ is —C(O)—($C_1$-$C_4$ alkyl).

In some embodiments, $R^{5a}$ is methyl, ethyl, isopropyl,

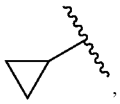, 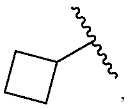, 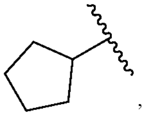,

-continued

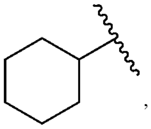, 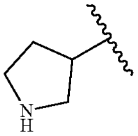, 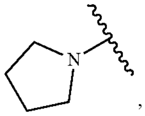,

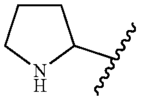, 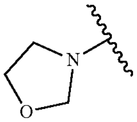, 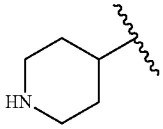,

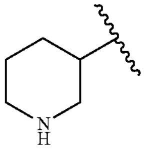, 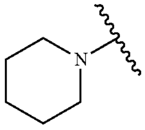, 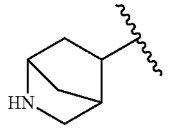,

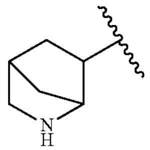, 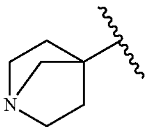, 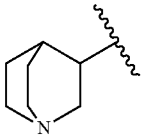,

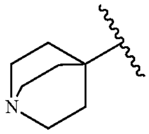, 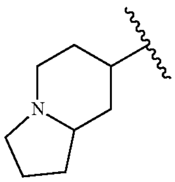,

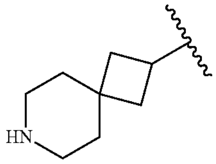, 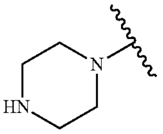,

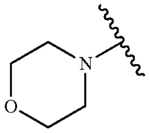, 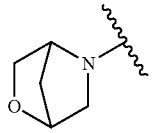, 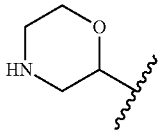,

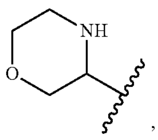, 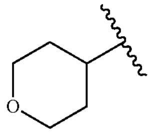, 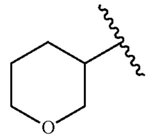,

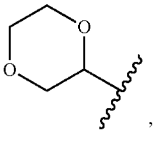, 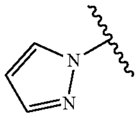, 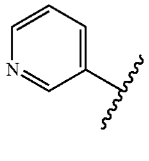, or

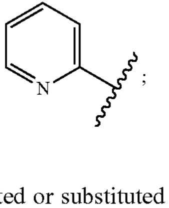;

and $R^{5a}$ is unsubstituted or substituted with 1-3 $R^{5d}$;

each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl.

In some embodiments, —Y—$R^{5a}$ is methyl, ethyl, isopropyl,
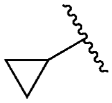, 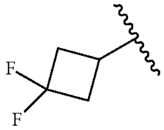,
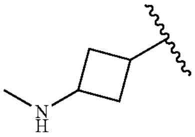, 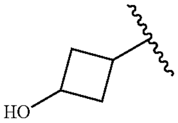,
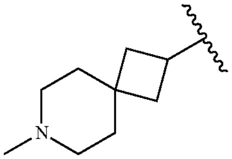, 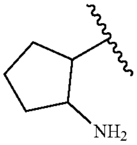,
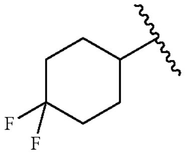, 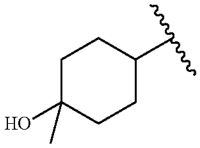,
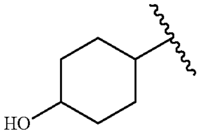, 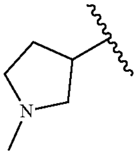,
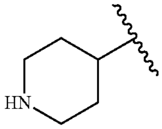, 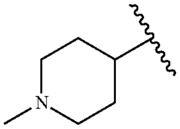,
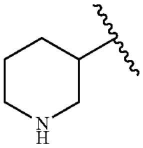, 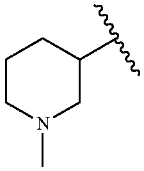,
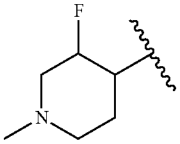, 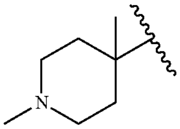,
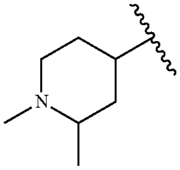, 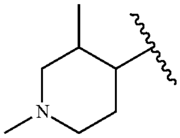,
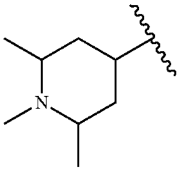, 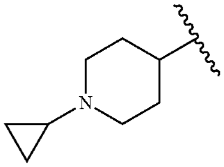,
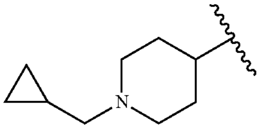,
-continued
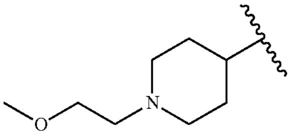,
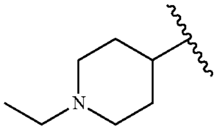, 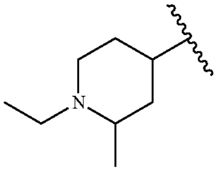,
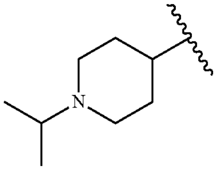, 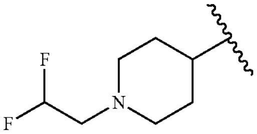,
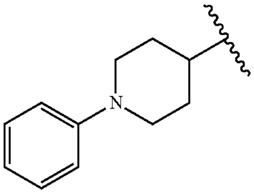, 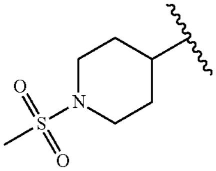,
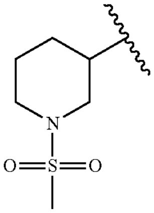, 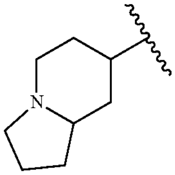,
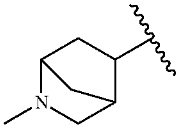, 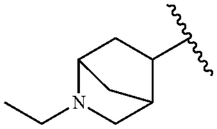,
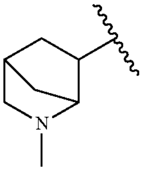, 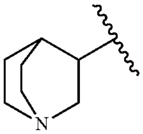, 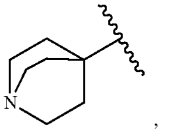,
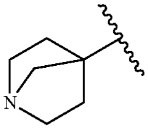, 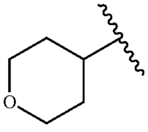, 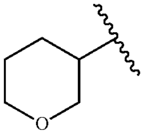,
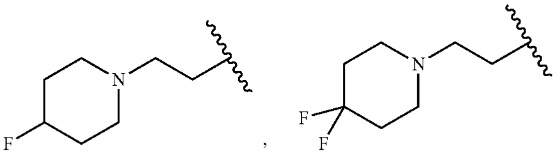,
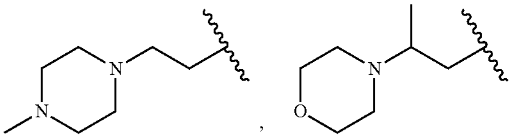, -continued
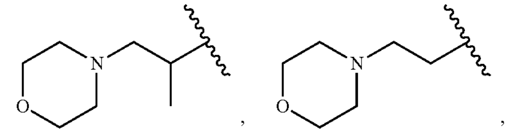
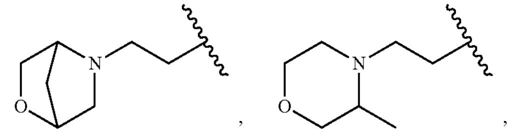
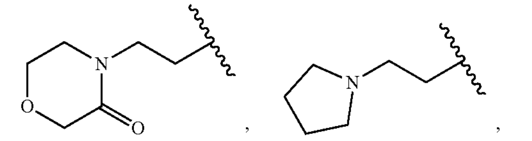
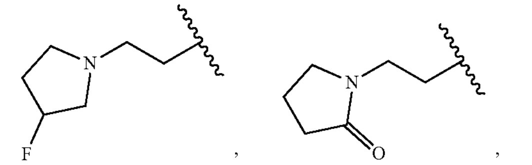
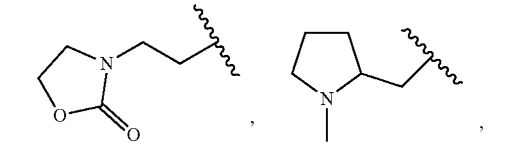
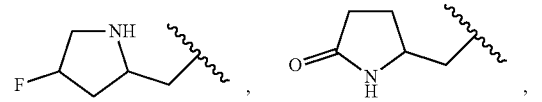
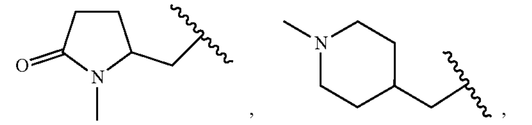
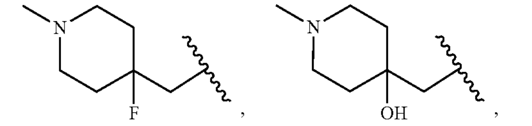
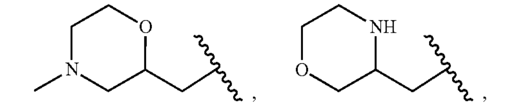
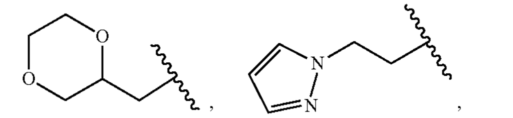
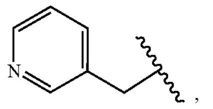 or 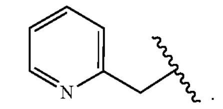
In some embodiments, —Y—$R^{5a}$ is methyl, ethyl, isopropyl,
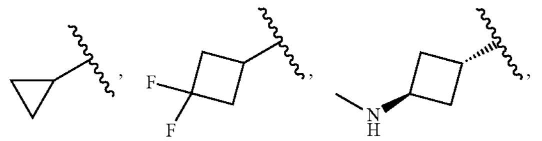
-continued
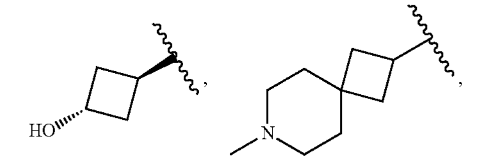
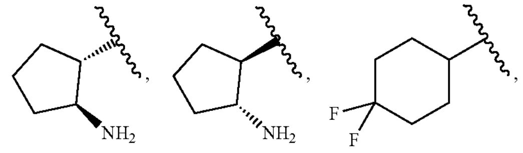
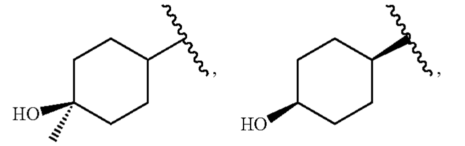
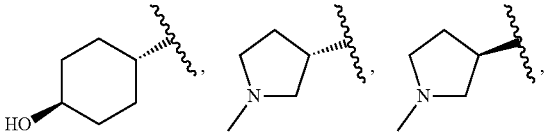
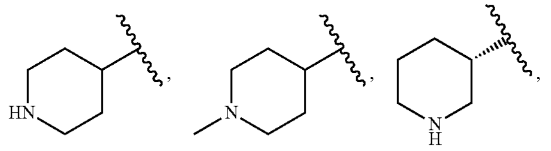
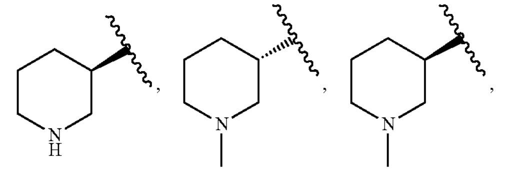
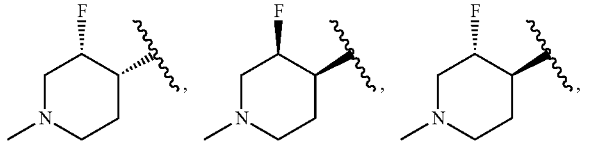
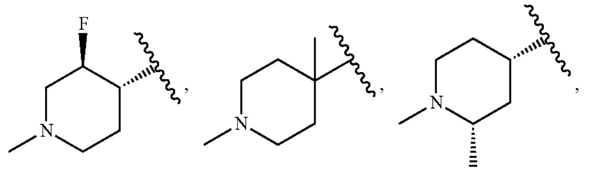
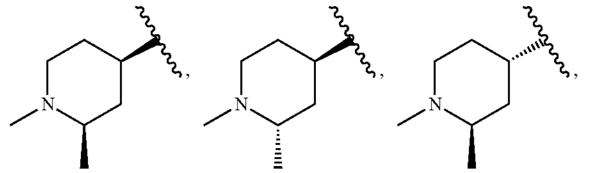
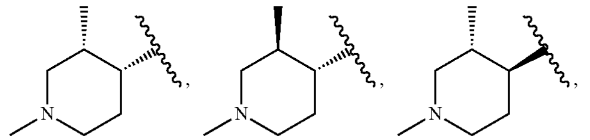
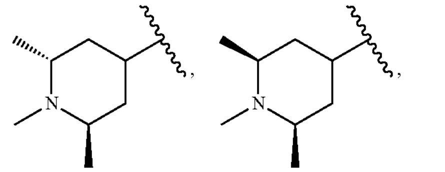

-continued
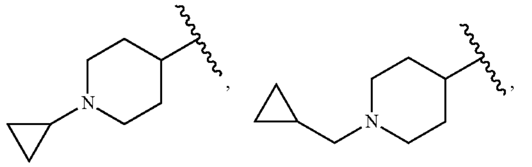
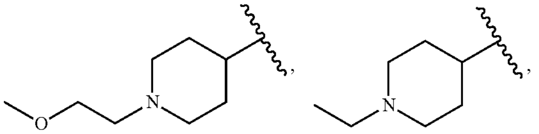
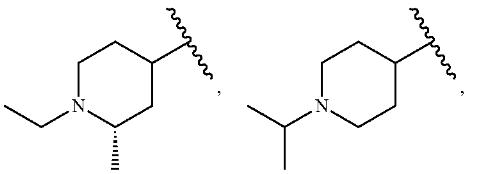
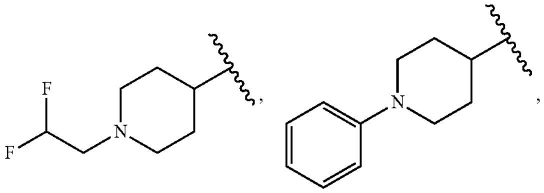
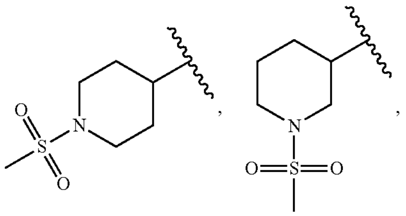
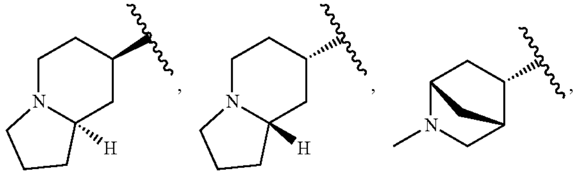
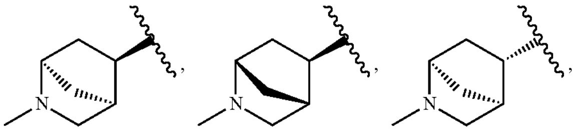
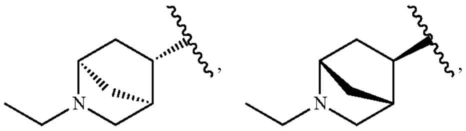
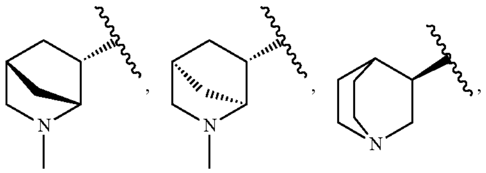
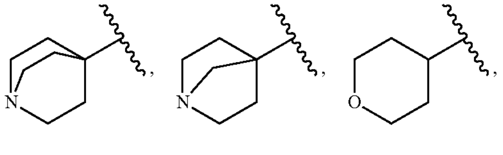
-continued
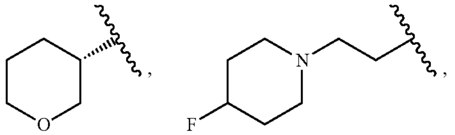
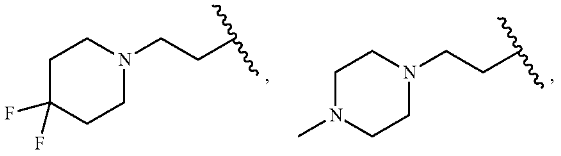
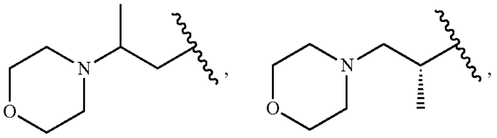
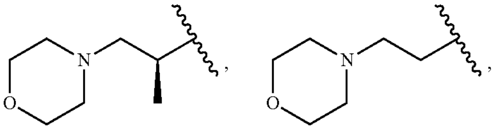
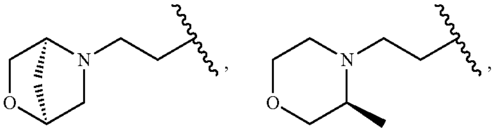
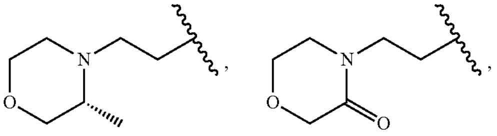
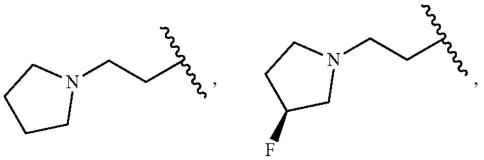
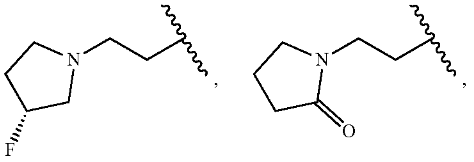
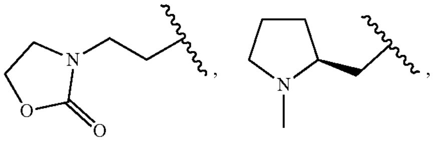
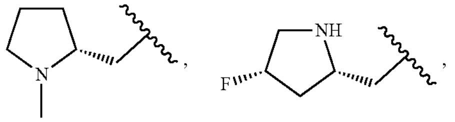
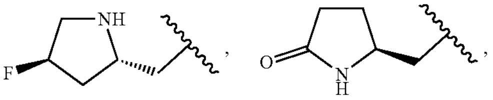
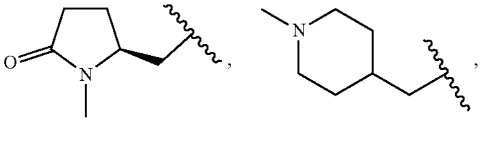

-continued

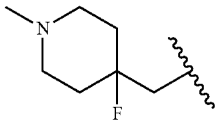, 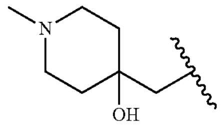,

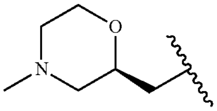, 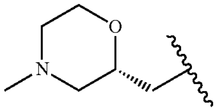,

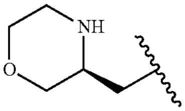, 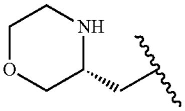,

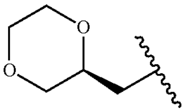, 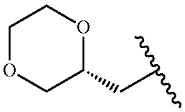,

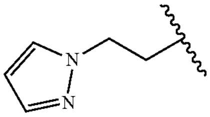, 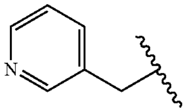, or

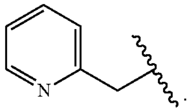.

In some embodiments, —Y—$R^{5a}$ is

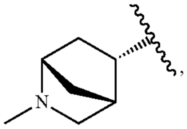, 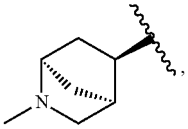,

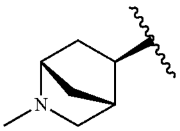, 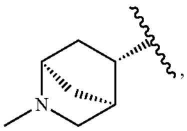,

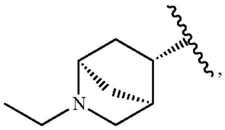, 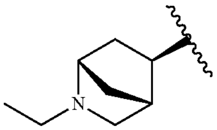,

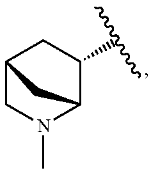, 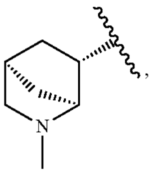, 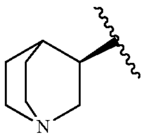,

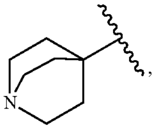, or 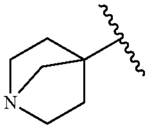.

In some embodiments, the compound has a structure according to Formula II-1:

(Formula II-1)

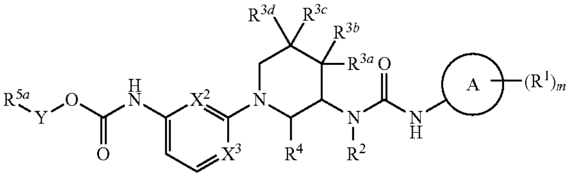

wherein:

A is 5- to 10-membered heteroaryl having 1-4 ring heteroatoms independently selected from N, O, and S;

$X^2$ is CH or N;

$X^3$ is CH or N;

m is 0 or 1;

$R^1$ is halogen, $C_1$-$C_6$ alkyl, $C_3$-$C_6$ cycloalkyl, phenyl, —($C_1$-$C_6$ alkylene)-$C_1$-$C_6$ alkoxy, —O—$R^{1a}$, or -Q-$R^{1b}$; wherein the phenyl is unsubstituted or substituted with 1 or 2 substituents independently selected from halogen, —CN, $C_1$-$C_3$ alkyl, and $C_1$-$C_3$ haloalkyl (e.g., $R^1$ is halogen, $C_1$-$C_6$ alkyl, $C_3$-$C_6$ cycloalkyl, phenyl, —($C_1$-$C_6$ alkylene)-$C_1$-$C_6$ alkoxy, —O—$R^{1a}$, or -Q-$R^{1b}$);

$R^{1a}$ is $C_1$-$C_6$ alkyl, $C_3$-$C_6$ cycloalkyl, or phenyl; and $R^{1a}$ is unsubstituted or substituted with 1-3 halogens;

Q is $C_1$-$C_6$ alkylene; and $R^{1b}$ is phenyl; wherein $R^{1b}$ is unsubstituted or substituted with 1-3 halogens;

$R^2$ is H or $C_1$-$C_3$ alkyl;

$R^{3a}$, $R^{3b}$, $R^{3c}$, $R^{3d}$ are each independently H, halogen, or $C_1$-$C_6$ alkyl;

$R^4$ is H, $C_1$-$C_6$ alkyl, $C_1$-$C_6$ haloalkyl, $C_1$-$C_6$ alkoxy, or $C_1$-$C_6$ hydroxyalkyl;

Y is absent or $C_1$-$C_6$ alkylene;

$R^{5a}$ is $C_1$-$C_6$ alkyl, $C_3$-$C_8$ cycloalkyl, phenyl, 5- to 10-membered heteroaryl, or 4- to 10-membered heterocycloalkyl; wherein the 5- to 10-membered heteroaryl has 1-4 ring heteroatoms independently selected from N, O, and S; the 4- to 10-membered heterocycloalkyl has 1-3 ring heteroatoms or ring heteroatom groups independently selected from N, O, S, and $S(O)_2$; and $R^{5a}$ is unsubstituted or substituted with 1-4 $R^{5d}$;

each $R^{5d}$ when present is independently selected from oxo, halo, —OH, —$NR^{5b}R^{5c}$, $C_1$-$C_6$ alkyl, $C_1$-$C_6$ haloalkyl, $C_1$-$C_6$ alkoxy, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), and phenyl; and $R^{5b}$ and $R^{5c}$ are independently selected from H and $C_1$-$C_3$ alkyl.

In some embodiments, the compound has a structure selected from the group consisting of:

(Formula IIa)

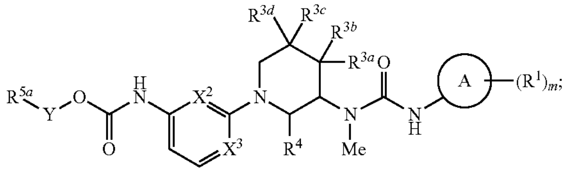

-continued (Formula IIb)

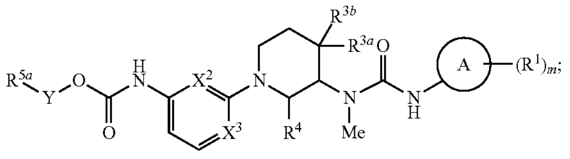

(Formula IIc)

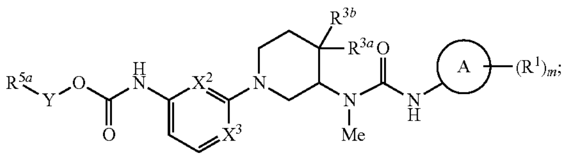

(Formula IId)

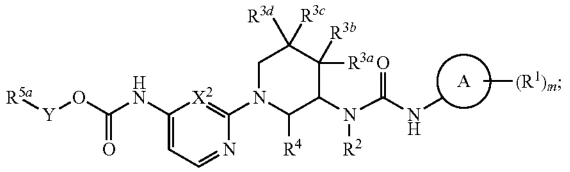

(Formula IIe)

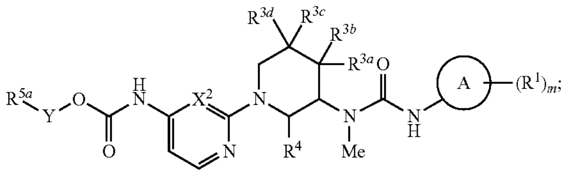

(Formula IIf)

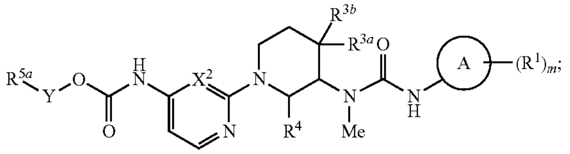

(Formula IIg)

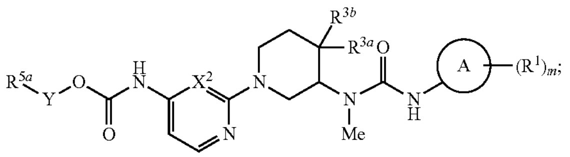

(Formula IIh)

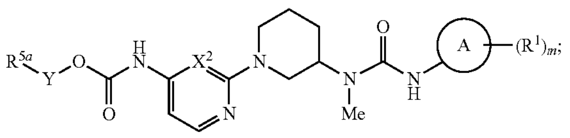

(Formula IIi)

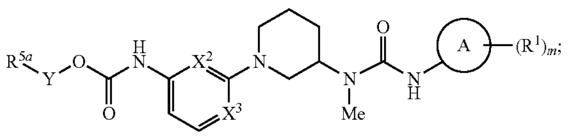

-continued (Formula IIk)

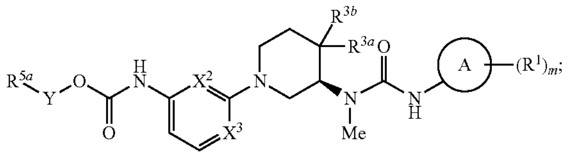

(Formula IIm)

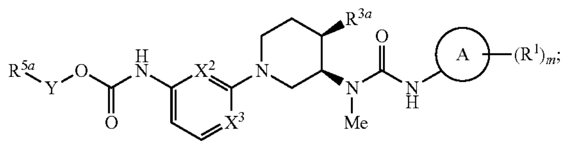

and (Formula IIn)

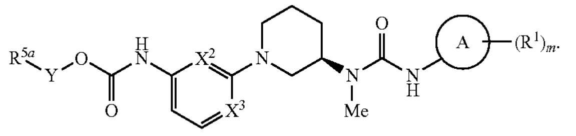

In some embodiments, the compound has a structure according to Formula IIa:

(Formula IIa)

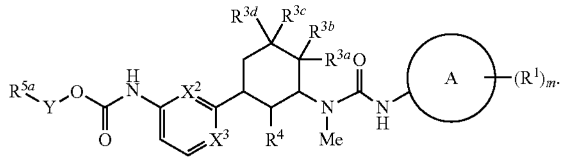

In some embodiments, the compound has a structure according to Formula IIb:

(Formula IIb)

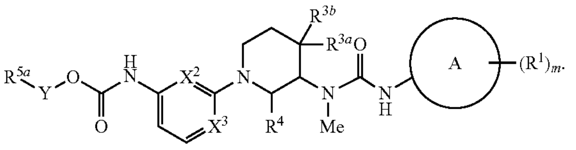

In some embodiments, the compound has a structure according to Formula IIc:

(Formula IIc)

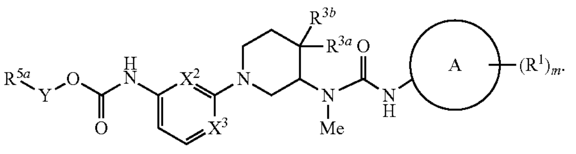

In some embodiments, the compound has a structure according to Formula IId:

(Formula IId)

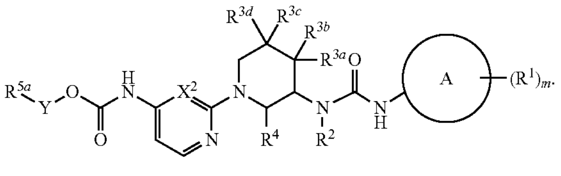

In some embodiments, the compound has a structure according to Formula IIe:

(Formula IIe)

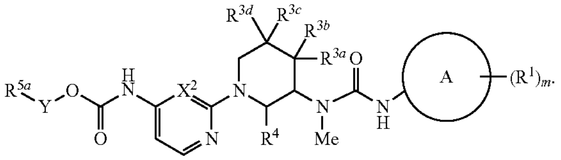

In some embodiments, the compound has a structure according to Formula IIf:

(Formula IIf)

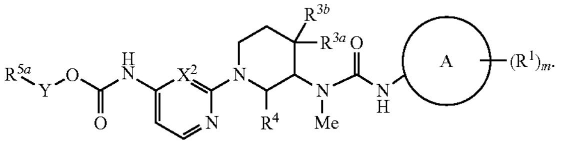

In some embodiments, the compound has a structure according to Formula IIg:

(Formula IIg)

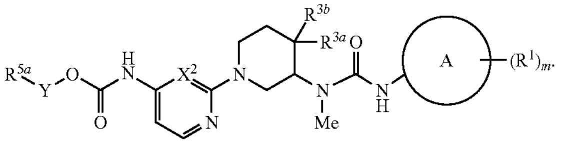

In some embodiments, the compound has a structure according to Formula IIh:

(Formula IIh)

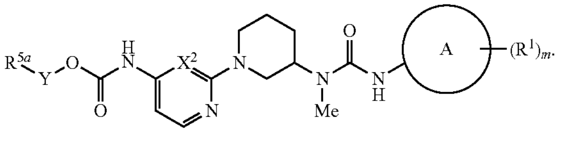

In some embodiments, the compound has a structure according to Formula IIi:

(Formula IIi)

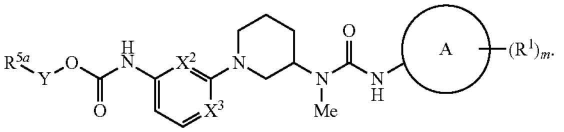

In some embodiments, the compound has a structure according to Formula IIk:

(Formula IIk)

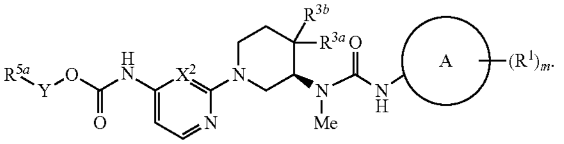

In some embodiments, the compound has a structure according to Formula IIm:

(Formula IIm)

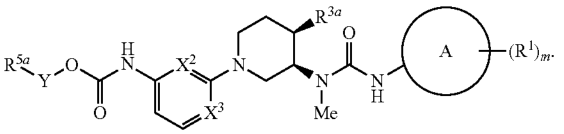

In some embodiments, the compound has a structure according to Formula IIn:

(Formula IIn)

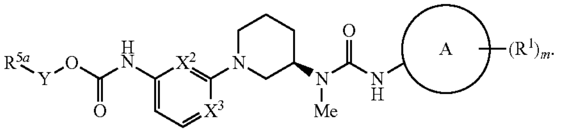

In any of the formulas described herein, in some embodiments, $R^1$, if present, is halogen, $C_1$-$C_6$ alkyl, $C_3$-$C_6$ cycloalkyl, phenyl, —($C_1$-$C_6$ alkylene)-$C_1$-$C_6$ alkoxy, or —O—$R^{1a}$; wherein the phenyl is unsubstituted or substituted with 1 or 2 substituents independently selected from halogen, —CN, $C_1$-$C_3$ alkyl, and $C_1$-$C_3$ haloalkyl (e.g., the phenyl is unsubstituted or substituted with 1 or 2 substituents independently selected from halogen and $C_1$-$C_3$ alkyl); $R^{1a}$, if present, is $C_1$-$C_6$ alkyl, $C_3$-$C_6$ cycloalkyl, or phenyl; and $R^{1a}$ is unsubstituted or substituted with 1-2 halogens.

In any of the formulas described herein, in some embodiments, $R^{3a}$ and $R^{3b}$, if present, are each independently H, halogen (e.g., F or Cl), or $C_1$-$C_6$ alkyl. In some embodiments, $R^{3a}$ and $R^{3b}$, if present, are each independently H or halogen (e.g., F or Cl). In some embodiments, $R^{3a}$ and $R^3$, if present, are each independently H or F. In some embodiments, $R^{3a}$ and $R^{3b}$, if present, are each H. In particular embodiments, $R^{3a}$ and $R^{3b}$, if present, are each halogen (e.g., F or Cl). In some embodiments, $R^{3a}$ and $R^{3b}$, if present, are each F. In some embodiments, $R^{3a}$ is H and $R^{3b}$ is F, if present.

In any of the formulas described herein, in some embodiments, Y is absent or $C_1$-$C_6$ alkylene.

In any of the formulas described herein, in some embodiments, $R^{5a}$ is $C_1$-$C_6$ alkyl, $C_3$-$C_8$ cycloalkyl, 5- to 6-membered heteroaryl, or 5- to 9-membered heterocycloalkyl; wherein the 5- to 6-membered heteroaryl has 1 or 2 nitrogen ring heteroatoms; the 5- to 9-membered heterocycloalkyl has 1 or 2 ring heteroatoms independently selected from N and O; and $R^{5a}$ is unsubstituted or substituted with 1-2 $R^{5d}$; each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —C(O)—($C_1$-$C_4$ alkyl), —$S(O)_2$—($C_1$-$C_3$ alkyl), and phenyl; and $R^{5b}$ and $R^{5c}$ are independently selected from H and $C_1$-$C_3$ alkyl.

In any of the formulas described herein, in some embodiments, $R^{5a}$ is a 5- to 9-membered heterocycloalkyl having one N as a ring heteroatom; and $R^{5a}$ is unsubstituted or substituted with 1-2 $R^{5d}$; each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —C(O)—($C_1$-$C_4$ alkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5a}$ is an unsubstituted or substituted bridged piperidine. In some embodiments, $R^{5a}$ is a bridged piperidine substituted with 1-2 $C_1$-$C_6$ alkyl.

In some embodiments, the compound has a structure according to Formula IIj:

(Formula IIj)

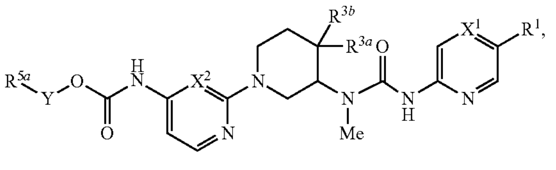

wherein:

$X^1$ is CH or N;

$X^2$ is CH or N;

$R^1$ is halogen, $C_1$-$C_6$ alkyl, $C_3$-$C_6$ cycloalkyl, phenyl, —($C_1$-$C_6$ alkylene)-$C_1$-$C_6$ alkoxy, or —O—$R^{1a}$; wherein $R^{1a}$ is $C_1$-$C_6$ alkyl, $C_3$-$C_6$ cycloalkyl, or phenyl; and $R^{1a}$ is unsubstituted or substituted with 1-2 halogens;

$R^{3a}$ and $R^{3b}$ are each independently H, halogen (e.g., F or Cl), or $C_1$-$C_6$ alkyl;

Y is absent or $C_1$-$C_6$ alkylene;

$R^{5a}$ is $C_1$-$C_6$ alkyl, $C_3$-$C_8$ cycloalkyl, 5- to 6-membered heteroaryl, or 5- to 9-membered heterocycloalkyl; wherein the 5- to 6-membered heteroaryl has 1 or 2 nitrogen ring heteroatoms; the 5- to 9-membered heterocycloalkyl has 1 or 2 ring heteroatoms independently selected from N and O; and $R^{5a}$ is unsubstituted or substituted with 1-2 $R^{5d}$;

each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl.

In some embodiments of Formula IIj, $X^1$ is CH or N. In some embodiments of Formula IIj, $X^1$ is CH and $X^2$ is CH. In some embodiments of Formula IIj, $X^1$ is N and $X^2$ is N. In some embodiments of Formula IIj, $X^1$ is N and $X^2$ is CH. In some embodiments of Formula IIj, $X^1$ is CH and X2 is N.

In some embodiments, the compound has a structure according to Formula IIj-1:

(Formula IIj-1)

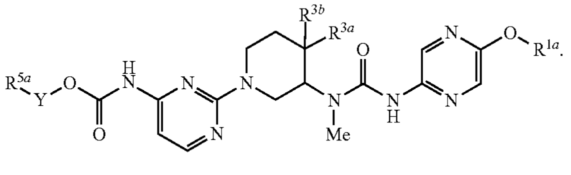

In some embodiments of Formulas IIj or IIj-1, $R^{3a}$ and $R^{3b}$ are each H. In particular embodiments, $R^{3a}$ is H and $R^{3b}$ is F.

In some embodiments, the compound has a structure according to Formula IIj-2:

(Formula IIj-2)

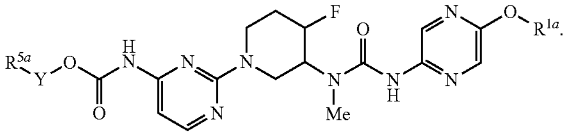

In some embodiments of Formula IIj-2, $R^{1a}$ is ethyl.

In some embodiments, the compound has a structure according to Formula IIj-3a:

(Formula IIj-3a)

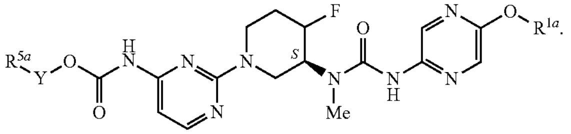

In some embodiments, the compound has a structure according to Formula IIj-3b:

(Formula IIj-3b)

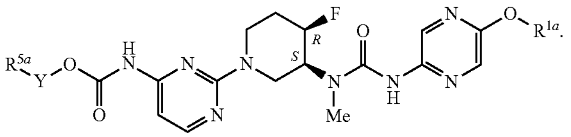

In some embodiments of Formula IIj-1, Formula IIj-2, Formula IIj-3a, and Formula IIj-3b, $R^{1a}$ is $C_1$-$C_6$ alkyl; and $R^{11}$ is unsubstituted or substituted with 1-2 halogens. In particular embodiments of Formula IIj-1, Formula IIj-2, Formula 3a, and Formula I-j-3b, $R^{1a}$ is ethyl. In some embodiments of Formula IIj-1, Formula IIj-2, Formula IIj-3a, and Formula IIj-3b, $R^{5a}$ is a 5- to 9-membered heterocycloalkyl having one N as a ring heteroatom; and $R^{5a}$ is unsubstituted or substituted with 1-2 $R^{5d}$; each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —C(O)—($C_1$-$C_4$ alkyl), —$S(O)_2$—($C_1$-$C_3$ alkyl), and phenyl; and $R^{5b}$ and $R^{5c}$ are independently selected from H and $C_1$-$C_3$ alkyl. In some embodiments, $R^{5a}$ is an unsubstituted or substituted bridged piperidine. In some embodiments, $R^{5a}$ is a bridged piperidine substituted with 1-2 $C_1$-$C_6$ alkyl.

In some embodiments, the compound has a structure according to Formula IIj-4:

(Formula IIj-4)

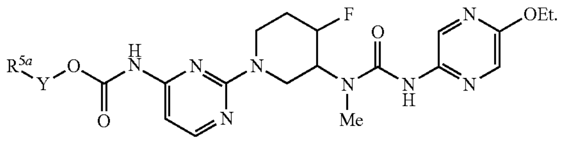

In some embodiments, the compound has a structure according to Formula IIo:

(Formula IIo)

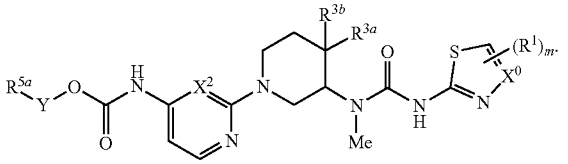

In some embodiments of Formula IIo, $X^0$ is C, CH, or N. In some embodiments of Formula IIo, $X^0$ is CH or N. In some embodiments of Formula IIo, m is 0. In some embodiments of Formula IIo, m is 1. In some embodiments of Formula IIo, $X^0$ is CH or N and m is 0 or 1. In some embodiments of Formula IIo, when m is 1, $X^0$ is C and $R^1$ is attached to $X^0$, such as

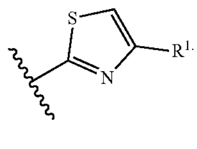

In some embodiments of Formula IIo, $X^0$ is CH and $X^2$ is CH. In some embodiments of Formula IIo, $X^0$ is N and $X^2$ is N. In some embodiments of Formula IIo, $X^0$ is N and $X^2$ is CH. In some embodiments of Formula IIo, $X^0$ is CH and $X^2$ is N.

In some embodiments, the compound has a structure according to Formula IIo-1:

(Formula IIo-1)

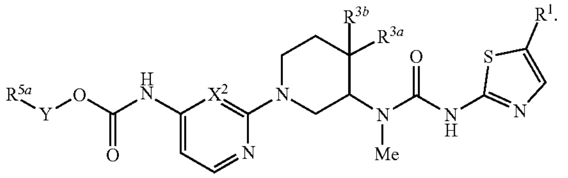

In some embodiments of Formulas IIo and IIo-1, $R^{3a}$ is H and $R^{3b}$ is F. In some embodiments of Formulas IIo and IIo-1, $R^1$ is halogen or $C_1$-$C_6$ alkyl. In some embodiments, $R^1$ is halogen, e.g., F or $C_1$. In some embodiments, $R^1$ is $C_1$-$C_6$ alkyl, e.g., methyl or ethyl.

In some embodiments, the compound has a structure according to Formula IIo-2:

(Formula IIo-2)

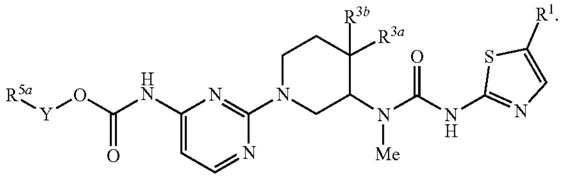

In some embodiments, the compound has a structure according to Formula IIo-3:

(Formula IIo-3)

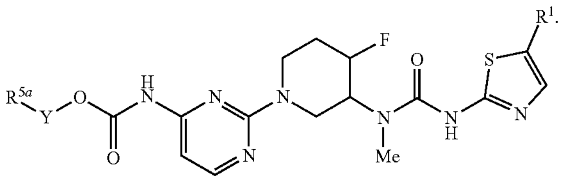

In some embodiments of Formula IIo, Formula IIo-1, Formula IIo-2, and Formula IIo-3, $R^1$ is halogen or $C_1$-$C_6$ alkyl. In particular embodiments, $R^1$ is halogen (e.g., F or Cl). In particular embodiments, $R^1$ is $C_1$-$C_6$ alkyl (e.g., methyl). In particular embodiments, $R^1$ is $C_3$-$C_6$ cycloalkyl (e.g., $C_3$ cycloalkyl). In particular embodiments, $R^1$ is phenyl and phenyl is unsubstituted or substituted with one $C_1$-$C_3$ alkyl (e.g., methyl). In particular embodiments, $R^1$ is —($C_1$-$C_6$ alkylene)-$C_1$-$C_6$ alkoxy (e.g., —($CH_2$)—OMe).

In some embodiments, the compound has a structure according to Formula IIo-4a:

(Formula IIo-4a)

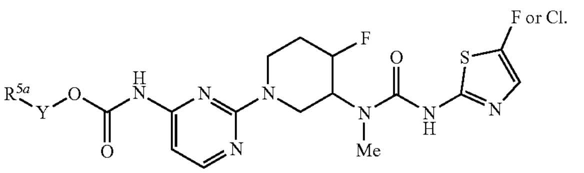

In some embodiments, the compound has a structure according to Formula IIo-4b:

(Formula IIo-4b)

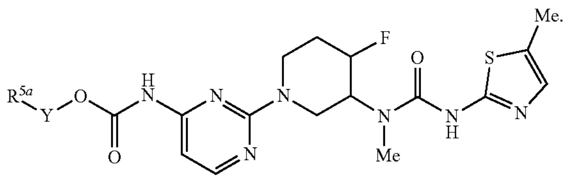

In some embodiments, the compound has a structure according to Formula IIp:

(Formula IIp)

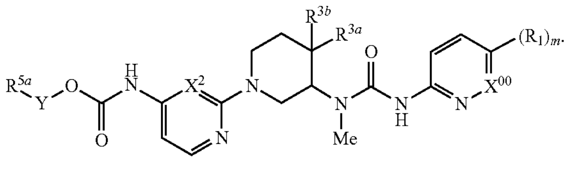

In some embodiments of Formula IIp, $X^{00}$ is CH or N. In some embodiments, $X^2$ is CH or N. In some embodiments of Formula IIp, $X^{00}$ is CH and $X^2$ is CH. In some embodiments of Formula IIp, $X^{00}$ is N and $X^2$ is N. In some embodiments of Formula IIp, $X^{00}$ is N and $X^2$ is CH. In some embodiments of Formula IIp, $X^{00}$ is CH and $X^2$ is N. In some embodiments of Formula IIp, m is 0. In some embodiments of Formula IIp, m is 1. In some embodiments of Formula IIp, $X^{00}$ is CH or N and m is 0 or 1. In some embodiments of Formula IIp, $R^1$ is $C_3$-$C_6$ cycloalkyl (e.g., $C_3$ cycloalkyl). In particular embodiments, $R^1$ is —O—($C_1$-$C_6$ alkyl) (e.g., —OEt).

In some embodiments, the compound has a structure according to Formula IIp-1a:

(Formula IIp-1a)

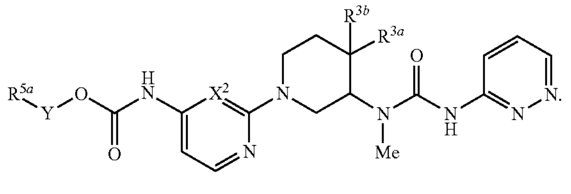

In some embodiments, the compound has a structure according to Formula IIp-1b:

(Formula IIp-1b)

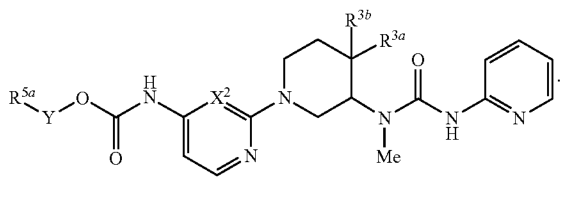

In some embodiments of Formulas IIp-1a and IIp-1b, $X^2$ is CH. In some embodiments of Formulas IIp-1a and IIp-1b, $X^2$ is N.

In some embodiments, the compound has a structure according to Formula IIp-2a:

(Formula IIp-2a)

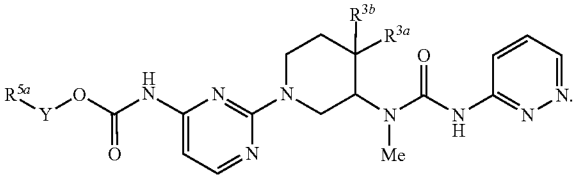

In some embodiments, the compound has a structure according to Formula IIp-2b:

(Formula IIp-2b)

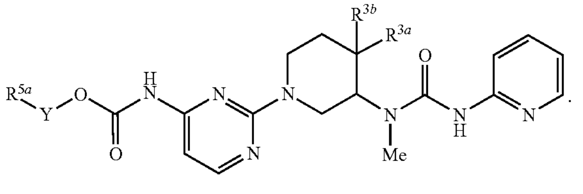

In some embodiments of any one of Formulas IIp, IIp-1a, IIp-1b, IIp-2a, and IIp-2b, $R^{3a}$ and $R^{3b}$ are each independently H or F.

In another aspect, this disclosure is directed to a compound having a structure according to Formula I:

(Formula I)

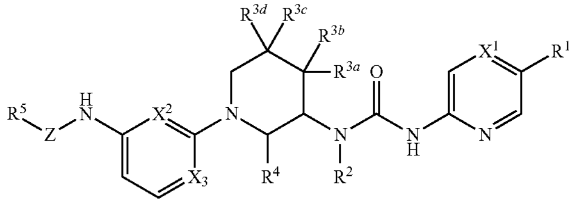

or a pharmaceutically acceptable salt thereof, wherein:

$X^1$ is $CX^{1a}$ or N; wherein:

$X^{1a}$ is H, halo, $C_1$-$C_6$ alkyl, $C_1$-$C_6$ haloalkyl, $C_1$-$C_6$ alkoxy, or $C_3$-$C_8$ cycloalkyl;

$X^2$ is CH or N;

$X^3$ is CH or N;

Z is —C(O)—, —OC(O)—, or —$S(O)_2$—;

$R^1$ is H, halo, $C_1$-$C_6$ alkyl, $C_1$-$C_6$ haloalkyl, $C_3$-$C_6$ cycloalkyl, —O—$R^{1a}$, or -Q-$R^{1b}$; wherein:

Q is $C_1$-$C_6$ alkylene, $C_1$-$C_6$ haloalkylene, or $C_3$-$C_6$ cycloalkylene;

$R^{1a}$ is $C_1$-$C_6$ alkyl, $C_3$-$C_6$ cycloalkyl, —($C_1$-$C_6$ alkylene)-($C_3$-$C_6$ cycloalkyl), or —($C_1$-$C_6$ alkylene)-(4- to 9-membered heterocycloalkyl), wherein the 4- to 9-membered heterocycloalkyl has 1-2 ring heteroatoms or heteroatom groups independently selected from N, O, S, and $S(O)_2$; and wherein $R^{1a}$ is unsubstituted or substituted with 1-3 halo; and $R^{1b}$ is $C_1$-$C_6$ alkoxy, or $C_3$-$C_6$ cycloalkyl; wherein $R^{1b}$ is unsubstituted or substituted with 1-3 halo;

$R^2$ is H or $C_1$-$C_3$ alkyl;

$R^{3a}$, $R^{3b}$, $R^{3c}$, $R^{3d}$ are each independently H, halo, or $C_1$-$C_6$ alkyl;

$R^4$ is H, $C_1$-$C_6$ alkyl, $C_1$-$C_6$ haloalkyl, $C_1$-$C_6$ alkoxy, or $C_1$-$C_6$ hydroxyalkyl;

$R^5$ is —Y—$R^{5a}$; wherein:

Y is absent or $C_1$-$C_6$ alkylene;

$R^{5a}$ is $C_1$-$C_6$ alkyl, $C_1$-$C_6$ alkoxy, $C_3$-$C_8$ cycloalkyl, phenyl, 5- to 10-membered heteroaryl, or 4- to 10-membered heterocycloalkyl; and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl; wherein the 5- to 10-membered heteroaryl has 1-4 ring heteroatoms independently selected from N, O, and S; and the 4- to 10-membered heterocycloalkyl has 1-3 ring heteroatoms or ring heteroatom groups independently selected from N, O, S, and $S(O)_2$; and $R^{5b}$ and $R^{5c}$ are independently selected from H and $C_1$-$C_3$ alkyl.

In some embodiments of a compound having a structure according to Formula I, $X^1$ is N. In some embodiments of a compound having a structure according to Formula I, $X^1$ is $CX^{1a}$. In some embodiments of a compound having a structure according to Formula I, $X^1$ is CH. In some embodiments of a compound having a structure according to Formula I, $X^1$ is $CX^{1a}$, wherein Xia is halo. In some embodiments of a compound having a structure according to Formula I, $X^1$ is $CX^{1a}$, wherein $X^{1a}$ is $C_1$-$C_6$ alkyl. In some embodiments of a compound having a structure according to Formula I, $X^1$ is $CX^{1a}$, wherein $X^{1a}$ is $C_1$-$C_6$ haloalkyl. In some embodiments of a compound having a structure according to Formula I, $X^1$ is $CX^{1a}$, wherein $X^{1a}$ is $C_1$-$C_6$ alkoxy. In some embodiments of a compound having a structure according to Formula I, $X^1$ is $CX^{1a}$, wherein $X^{1a}$ is $C_3$-$C_8$ cycloalkyl.

In some embodiments of a compound having a structure according to Formula I, $X^2$ is CH. In some embodiments of a compound having a structure according to Formula I, $X^2$ is N.

In some embodiments of a compound having a structure according to Formula I, $X^3$ is N.

In some embodiments of a compound having a structure according to Formula I, $X^3$ is CH.

In some embodiments of a compound having a structure according to Formula I, Z is —C(O)—. In some embodiments of a compound having a structure according to Formula I, Z is —OC(O)—. In some embodiments of a compound having a structure according to Formula I, Z is —$S(O)_2$—.

In some embodiments of a compound having a structure according to Formula I, $R^1$ is H.

In some embodiments of a compound having a structure according to Formula I, $R^1$ is halo. In some embodiments of a compound having a structure according to Formula I, $R^1$ is $C_1$-$C_6$ alkyl.

In some embodiments of a compound having a structure according to Formula I, $R^1$ is $C_1$-$C_6$ haloalkyl. In some embodiments of a compound having a structure according to Formula I, $R^1$ is $C_3$-$C_6$ cycloalkyl.

In some embodiments of a compound having a structure according to Formula I, $R^1$ is —O—$R^{1a}$. In some embodiments of a compound having a structure according to Formula I, $R^1$ is —O—$R^{1a}$, wherein $R^{1a}$ is $C_1$-$C_6$ alkyl, and $R^{1a}$ is unsubstituted or substituted with 1-3 halo. In some embodiments of a compound having a structure according to Formula I, $R^1$ is —O—$C_1$-$C_6$ alkyl. In some embodiments of a compound having a structure according to Formula I, $R^1$ is —O—$R^{1a}$, wherein $R^{1a}$ is —$C_3$-$C_6$ cycloalkyl, and $R^{1a}$ is unsubstituted or substituted with 1-3 halo. In some embodiments of a compound having a structure according to Formula I, $R^1$ is —O—$R^{1a}$, wherein $R^{1a}$ is —($C_1$-$C_6$ alkylene)-($C_3$-$C_6$ cycloalkyl), and $R^{1a}$ is unsubstituted or substituted with 1-3 halo. In some embodiments of a compound having a structure according to Formula I, $R^1$ is —O—$R^{1a}$, wherein $R^{1a}$ is —($C_1$-$C_6$ alkylene)-(4- to 9-membered heterocycloalkyl), wherein the 4- to 9-membered heterocycloalkyl has 1-2 ring heteroatoms or heteroatom groups independently selected from N, O, S, and $S(O)_2$, and $R^{1a}$ is unsubstituted or substituted with 1-3 halo.

In some embodiments of a compound having a structure according to Formula I, $R^1$ is -Q-$R^{1b}$. In some embodiments of a compound having a structure according to Formula I, $R^1$ is -Q-$R^{1b}$, and Q is $C_1$-$C_6$ alkylene. In some embodiments of a compound having a structure according to Formula I, $R^1$ is -Q-$R^{1b}$, Q is $C_1$-$C_6$ alkylene, and $R^{1b}$ is $C_1$-$C_6$ alkoxy, wherein $R^{1b}$ is unsubstituted or substituted with 1-3 halo. In some embodiments of a compound having a structure according to Formula I, $R^1$ is -Q-$R^{1b}$, Q is $C_1$-$C_6$ alkylene, and $R^{1b}$ is $C_3$-$C_6$ cycloalkyl, wherein $R^{1b}$ is unsubstituted or substituted with 1-3 halo.

In some embodiments of a compound having a structure according to Formula I, $R^1$ is -Q-$R^{1b}$, and Q is $C_1$-$C_6$ haloalkylene. In some embodiments of a compound having a structure according to Formula I, $R^1$ is -Q-$R^{1b}$, Q is $C_1$-$C_6$ haloalkylene, and $R^{1b}$ is $C_1$-$C_6$ alkoxy, wherein $R^{1b}$ is unsubstituted or substituted with 1-3 halo. In some embodiments of a compound having a structure according to Formula I, $R^1$ is -Q-$R^{1b}$, Q is $C_1$-$C_6$ haloalkylene, and $R^{1b}$ is $C_3$-$C_6$ cycloalkyl, wherein $R^{1b}$ is unsubstituted or substituted with 1-3 halo.

In some embodiments of a compound having a structure according to Formula I, $R^1$ is -Q-$R^{1b}$, and Q is $C_3$-$C_6$ cycloalkylene. In some embodiments of a compound having a structure according to Formula I, $R^1$ is -Q-$R^{1b}$, Q is $C_3$-$C_6$ cycloalkylene, and $R^{1b}$ is $C_1$-$C_6$ alkoxy, wherein $R^{1b}$ is unsubstituted or substituted with 1-3 halo. In some embodiments of a compound having a structure according to Formula I, $R^1$ is -Q-$R^{1b}$, Q is $C_3$-$C_6$ cycloalkylene, and $R^{1b}$ is $C_3$-$C_6$ cycloalkyl, wherein $R^{1b}$ is unsubstituted or substituted with 1-3 halo.

In some embodiments of a compound having a structure according to Formula I, $R^1$ is H, halo, $C_1$-$C_6$ alkyl, $C_1$-$C_6$ haloalkyl, $C_3$-$C_6$ cycloalkyl, —O—$R^{1a}$, or Q-$R^{1b}$; wherein Q is $C_1$-$C_6$ alkylene, $C_1$-$C_6$ haloalkylene, or $C_3$-$C_6$ cycloalkylene;

$R^{1a}$ is $C_1$-$C_6$ alkyl, $C_3$-$C_6$ cycloalkyl, —($C_1$-$C_6$ alkylene)-($C_3$-$C_6$ cycloalkyl), or —($C_1$-$C_6$ alkylene)-(4- to 9-membered heterocycloalkyl), wherein the 4- to 9-membered heterocycloalkyl has 1-2 ring heteroatoms independently selected from N and O; and wherein $R^{1a}$ is unsubstituted or substituted with 1-3 halo; and $R^{1b}$ is $C_1$-$C_6$ alkoxy; wherein $R^{1b}$ is unsubstituted or substituted with 1-3 halo.

In some embodiments of a compound having a structure according to Formula I, $R^1$ is $C_3$-$C_6$ cycloalkyl, —O—$R^{1a}$, or Q-$R^{1b}$;

Q is $C_1$-$C_6$ alkylene;

$R^{1a}$ is $C_1$-$C_6$ alkyl, $C_3$-$C_6$ cycloalkyl, or —($C_1$-$C_6$ alkylene)-($C_3$-$C_6$ cycloalkyl), wherein $R^{1a}$ is unsubstituted or substituted with 1-3 halo; and $R^{1b}$ is $C_1$-$C_6$ alkoxy; wherein $R^{1b}$ is unsubstituted or substituted with 1-3 halo.

In some embodiments of a compound having a structure according to Formula I, $R^1$ is $C_3$-$C_6$ cycloalkyl or —O—$R^{1a}$; and $R^{1a}$ is $C_1$-$C_6$ alkyl or —($C_1$-$C_6$ alkylene)-($C_3$-$C_6$ cycloalkyl).

In some embodiments of a compound having a structure according to Formula I, $R^1$ is H, methyl, ethyl, $C_1$, methoxy, ethoxy,

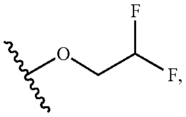 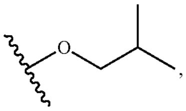, 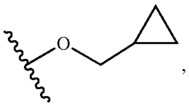, 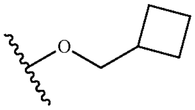, 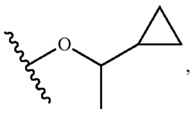, 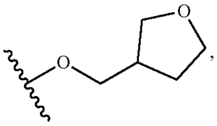, 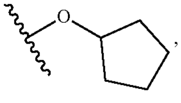, 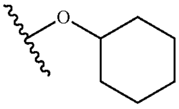, or 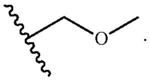.

In some embodiments of a compound having a structure according to Formula I, $R^2$ is $C_1$-$C_3$ alkyl. In some embodiments of a compound having a structure according to Formula I, $R^2$ is methyl. In some embodiments of a compound having a structure according to Formula I, $R^2$ is H. In some embodiments of a compound having a structure according to Formula I, $R^2$ is methyl or H.

In some embodiments of a compound having a structure according to Formula I, $R^{3a}$ and $R^{3b}$ are halo. In some embodiments of a compound having a structure according to Formula I, $R^{3a}$ and $R^{3b}$ are F. In some embodiments of a compound having a structure according to Formula I, $R^{3a}$ is halo and $R^{3b}$ is H. In some embodiments of a compound having a structure according to Formula I, $R^{3a}$ is F and $R^{3b}$ is H.

In some embodiments of a compound having a structure according to Formula I, $R^{3a}$ and $R^{3b}$ are each independently H or halo; and $R^{3c}$ and $R^{3d}$ are H. In some embodiments of a compound having a structure according to Formula I, $R^{3a}$ and $R^{3b}$ are halo; and $R^{3c}$ and $R^{3d}$ are H. In some embodiments of a compound having a structure according to Formula I, $R^{3a}$ and $R^{3b}$ are F, and $R^{3c}$ and $R^{3d}$ are H. In some embodiments of a compound having a structure according to Formula I, $R^{3a}$ is F, and $R^{3b}$, $R^{3c}$, and $R^{3d}$ are H. In some embodiments of a compound having a structure according to Formula I, $R^{3a}$, $R^{3b}$, $R^{3c}$, and $R^{3d}$ are H.

In some embodiments of a compound having a structure according to Formula I, $R^4$ is H or $C_1$-$C_6$ alkyl. In some embodiments of a compound having a structure according to Formula I, $R^4$ is H. In some embodiments of a compound having a structure according to Formula I, $R^4$ is $C_1$-$C_6$ alkyl. In some embodiments of a compound having a structure according to Formula I, $R^4$ is $C_1$-$C_6$ haloalkyl. In some embodiments of a compound having a structure according to Formula I, $R^4$ is $C_1$-$C_6$ alkoxy. In some embodiments of a compound having a structure according to Formula I, $R^4$ is $C_1$-$C_6$ hydroxyalkyl. In some embodiments of a compound having a structure according to Formula I, $R^4$ is H, methyl, or ethyl.

In some embodiments of a compound having a structure according to Formula I, $R^5$ is —Y—$R^{1a}$, and Y is absent. In some embodiments of a compound having a structure according to Formula I, $R^5$ is —Y—$R^{1a}$, and Y is $C_1$-$C_6$ alkylene.

In some embodiments of a compound having a structure according to Formula I, $R^5$ is —Y—$R^{5a}$; Y is absent; $R^{5a}$ is $C_1$-$C_6$ alkyl, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl. In some embodiments of a compound having a structure according to Formula I, $R^5$ is —Y—$R^{5a}$; Y is absent; $R^{5a}$ is $C_1$-$C_6$ alkyl, and $R^{5a}$ is unsubstituted or substituted with 1-2 substituents independently selected from OH, $NR^{5b}R^{5c}$, and $C_1$-$C_6$ alkoxy. In some embodiments of a compound having a structure according to Formula I, $R^5$ is —$CH_3$, —$CH_2CH_3$, —$CH_2CH(CH_3)_2$,

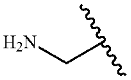, 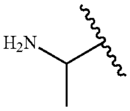, 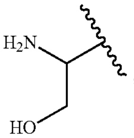, 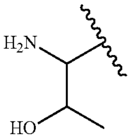, 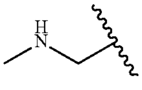, 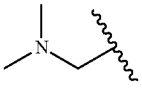, 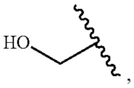, 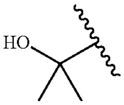, or 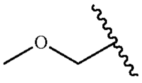.

In some embodiments of a compound having a structure according to Formula I, R is —CH3, —$CH_2CH_3$, —$CH_2CH(CH_3)_2$,

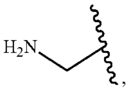, 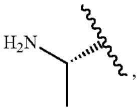, 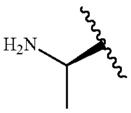, 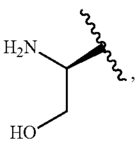, 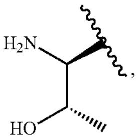, 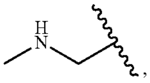, 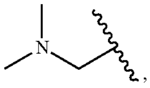, 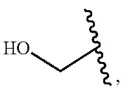, 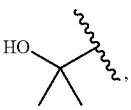, or 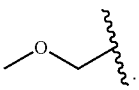.

In some embodiments of a compound having a structure according to Formula I, $R^5$ is —Y—$R^{5a}$; Y is absent or $C_1$-$C_6$ alkylene; $R^{5a}$ is $C_1$-$C_6$ alkoxy, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl. In some embodiments of a compound having a structure according to Formula I, $R^5$ is —Y—$R^{5a}$; Y is absent; $R^{5a}$ is $C_1$-$C_6$ alkoxy, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl. In some embodiments of a compound having a structure according to Formula I, $R^5$ is —Y—$R^{5a}$; Y is —$C_1$-$C_6$ alkylene; $R^{5a}$ is $C_1$-$C_6$ alkoxy, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl.

In some embodiments of a compound having a structure according to Formula I, $R^5$ is —Y—$R^{5a}$; Y is absent or $C_1$-$C_6$ alkylene; $R^{5a}$ is $C_3$-$C_8$ cycloalkyl, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl. In some embodiments of a compound having a structure according to Formula I, $R^5$ is —Y—$R^{5a}$; Y is absent; $R^{5a}$ is $C_3$-$C_8$ cycloalkyl, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$—Cs alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl. In some embodiments of a compound having a structure according to Formula I, $R^5$ is —Y—$R^{5a}$; Y is absent; $R^{5a}$ is $C_3$-$C_8$ cycloalkyl, and $R^{5a}$ is unsubstituted or substituted with 1-4 substituents independently selected from halo, OH, $NR^{5b}R^{5c}$, $C_1$-$C_6$ alkyl, and $C_1$-$C_6$ alkoxy. In some embodiments of a compound having a structure according to Formula I, $R^5$ is —Y—$R^{5a}$; Y is $C_1$-$C_6$ alkylene; $R^{5a}$ is $C_3$-$C_8$ cycloalkyl, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —C(O)$NH_2$, and phenyl. In some embodiments of a compound having a structure according to Formula I, $R^5$ is

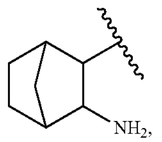 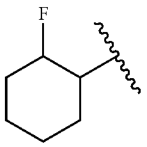 , 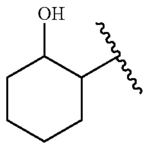 ,

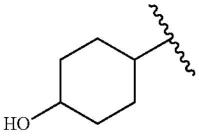 , 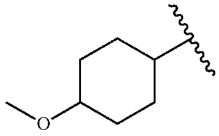 ,

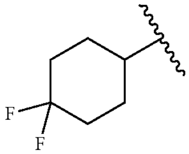 , 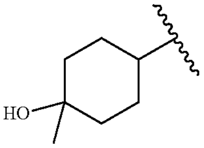 ,

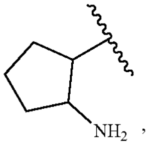 , 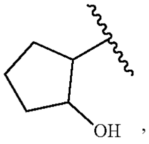 , 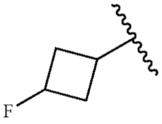 ,

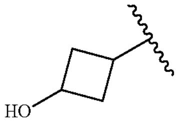 , 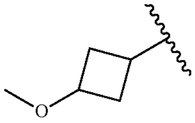 , 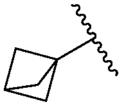 ,

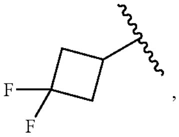 , 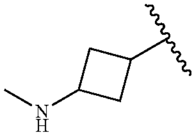 , 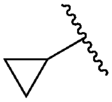 , or

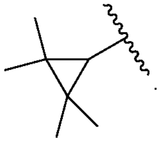 .

In some embodiments of a compound having a structure according to Formula I, $R^5$ is

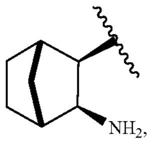 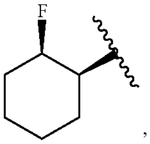 , 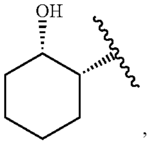 ,

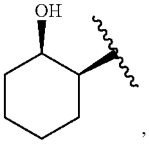 , 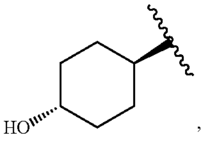 , 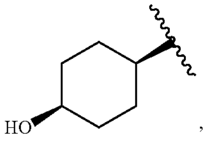 ,

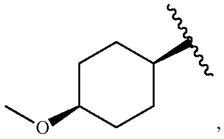 , 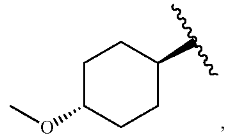 ,

-continued

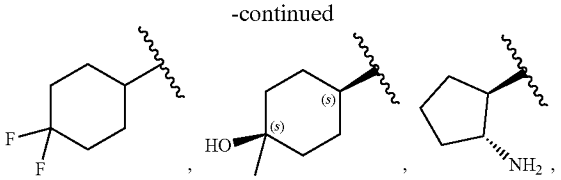

,  ,  ,

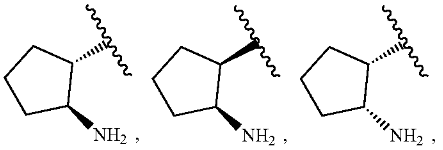

,  ,  ,

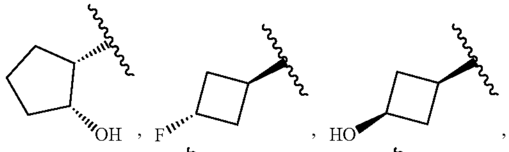

,  ,  ,

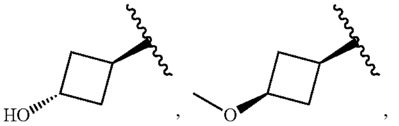

,  ,

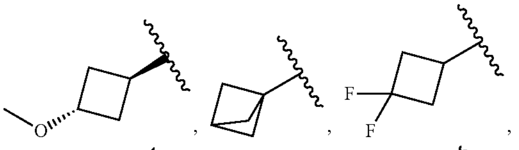

,  ,  ,

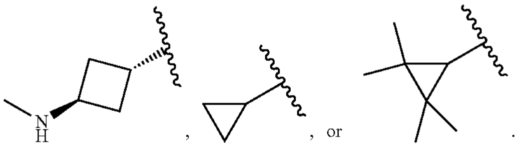

,  , or  .

In some embodiments of a compound having a structure according to Formula I, $R^5$ is —Y—$R^{5a}$; Y is absent or $C_1$-$C_6$ alkylene; $R^{5a}$ is phenyl, and $R^{5a}$ is unsubstituted or substituted with 1-4 substituents independently selected from halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is —Y—$R^{5a}$; Y is absent; $R^{5a}$ is phenyl, and $R^{5a}$ is unsubstituted or substituted with 1-4 substituents independently selected from halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is —Y—$R^{5a}$; Y is absent; $R^{5a}$ is phenyl, and $R^{5a}$ is unsubstituted or substituted with 1-2 substituents independently selected from halo, $C_1$-$C_6$ alkyl, and $C_1$-$C_6$ alkoxy. In some embodiments of a compound having a structure according to Formula I, $R^5$ is —Y—$R^{5a}$; Y is $C_1$-$C_6$ alkylene; $R^{5a}$ is phenyl, and $R^{5a}$ is unsubstituted or substituted with 1-4 substituents independently selected from halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$—Cs alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is —Y—$R^{5a}$; Y is $C_1$-$C_6$ alkylene; $R^{5a}$ is phenyl, and $R^{5a}$ is unsubstituted or substituted with halo. In some embodiments of a compound having a structure according to Formula I, $R^5$ is

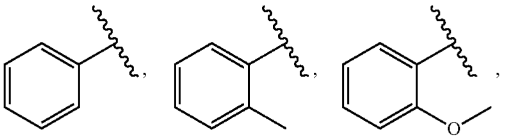

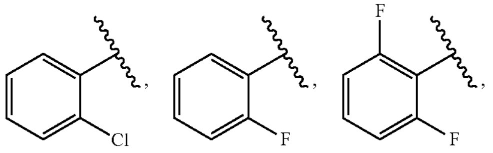

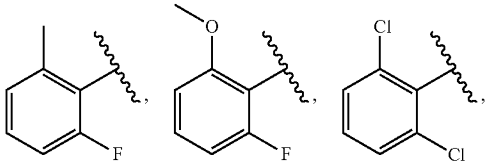

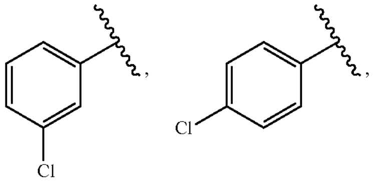

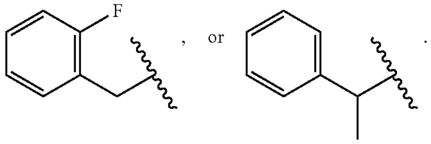

, or  .

In some embodiments of a compound having a structure according to Formula I, $R^5$

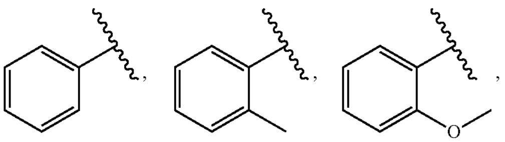

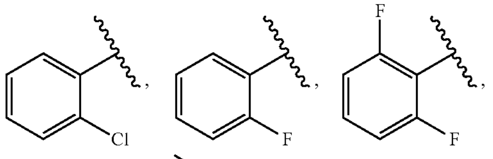

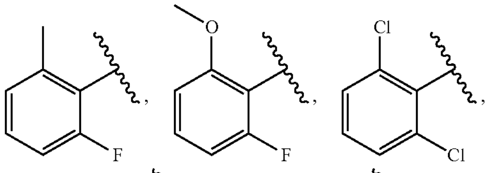

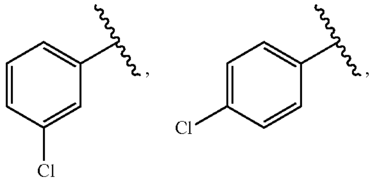

-continued

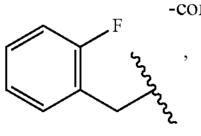

, or

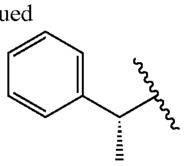

.

In some embodiments of a compound having a structure according to Formula I, $R^5$ is —Y—$R^{5a}$; Y is absent or $C_1$-$C_6$ alkylene; $R^{5a}$ is 5- to 10-membered heteroaryl, wherein the 5- to 10-membered heteroaryl has 1-4 ring heteroatoms independently selected from N, O, and S, and $R^{5a}$ is unsubstituted or substituted with 1-4 substituents independently selected from halo, OH, $NR^{5b}R^{5c}$ $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is —Y—$R^{5a}$; Y is absent; $R^{5a}$ is 5- to 10-membered heteroaryl, wherein the 5- to 10-membered heteroaryl has 1-4 ring heteroatoms independently selected from N, O, and S, and $R^{5a}$ is unsubstituted or substituted with 1-4 substituents independently selected from halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is —Y—$R^{5a}$; Y is $C_1$-$C_6$ alkylene; $R^{5a}$ is 5- to 10-membered heteroaryl, wherein the 5- to 10-membered heteroaryl has 1-4 ring heteroatoms independently selected from N, O, and S, and $R^{5a}$ is unsubstituted or substituted with 1-4 substituents independently selected from halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is

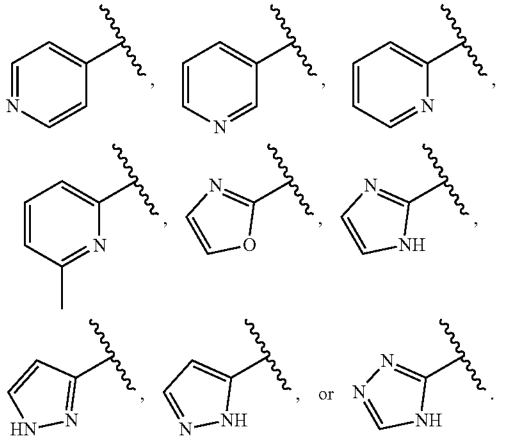

In some embodiments of a compound having a structure according to Formula I, $R^5$ is —Y—$R^{5a}$; Y is absent or $C_1$-$C_6$ alkylene; $R^{5a}$ is a 4- to 10-membered heterocycloalkyl having 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$ $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl.

In some embodiments of a compound having a structure according to Formula I, $R^5$ is —Y—$R^{5a}$; Y is absent; $R^{5a}$ is a 4- to 10-membered heterocycloalkyl having 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is

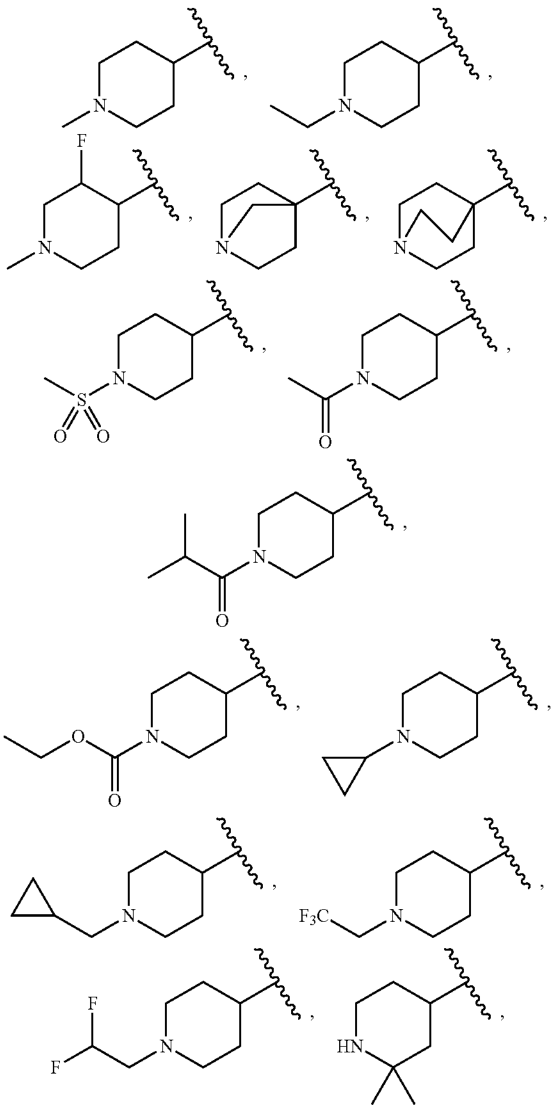

-continued
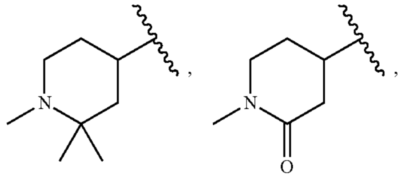
, ,
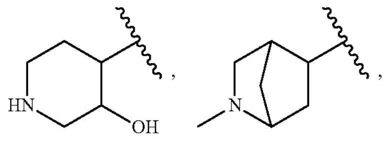
, ,
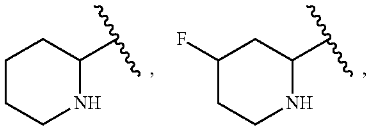
, ,
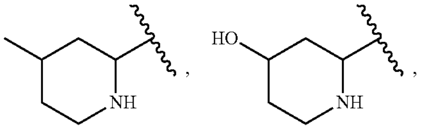
, ,
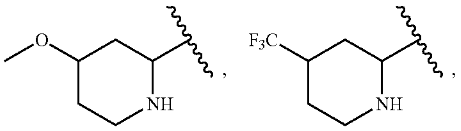
, ,
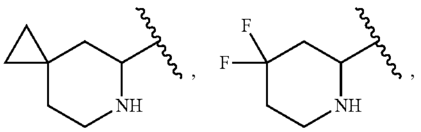
, ,
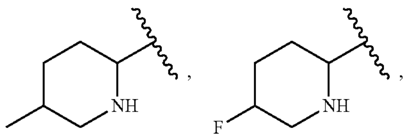
, ,
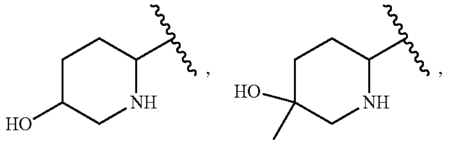
, ,
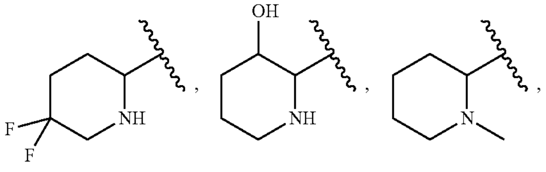
, , ,
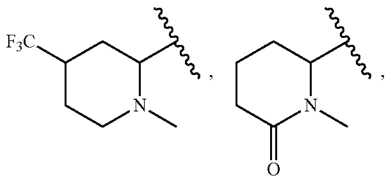
, ,
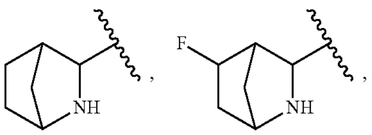
, ,
-continued
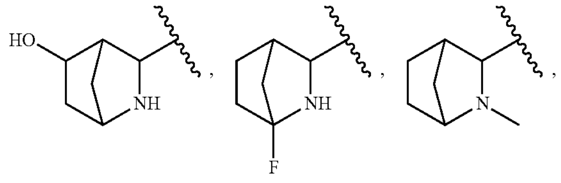
, , ,
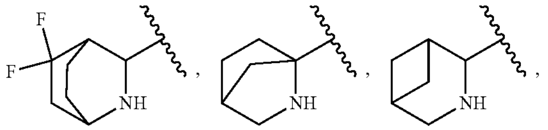
, , ,
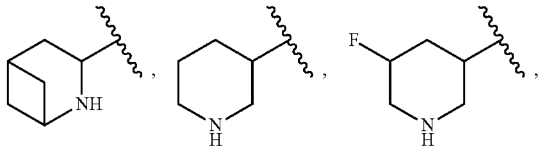
, , ,
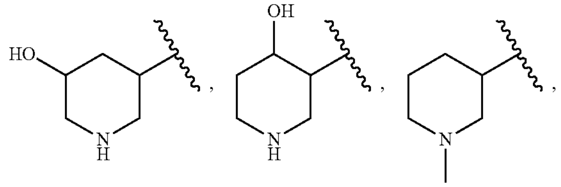
, , ,
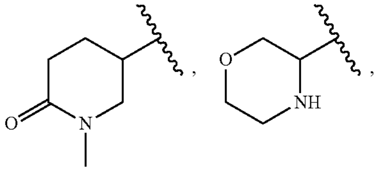
, ,
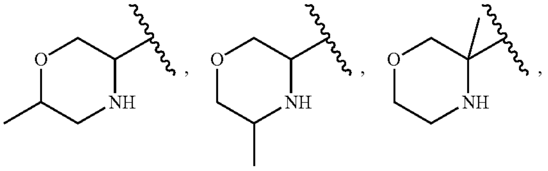
, , ,
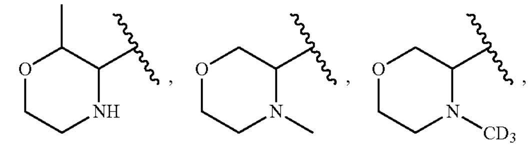
, , ,
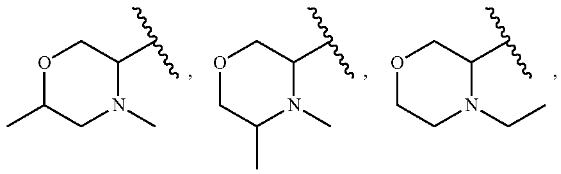
, , ,
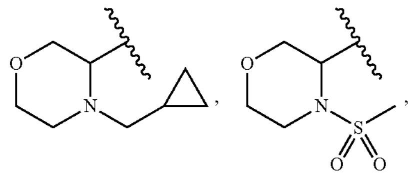
, ,
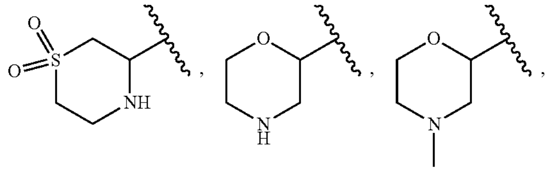
, , , -continued
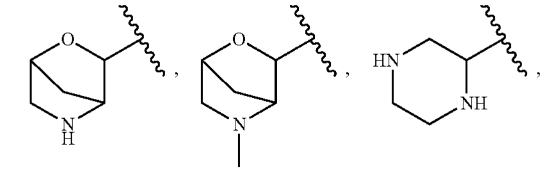
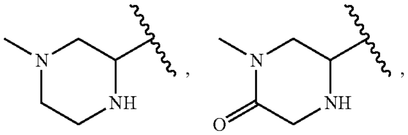
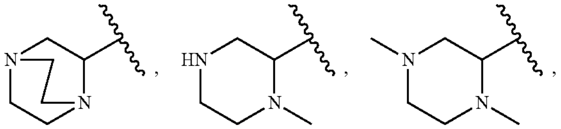
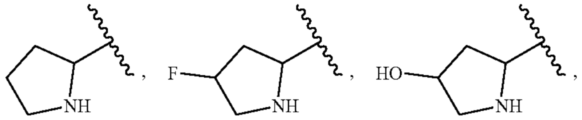
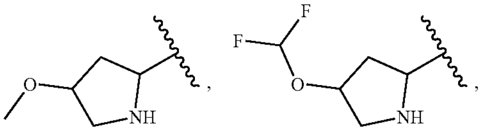
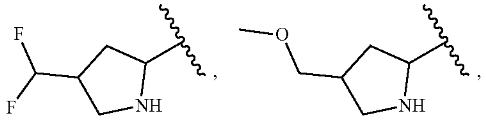
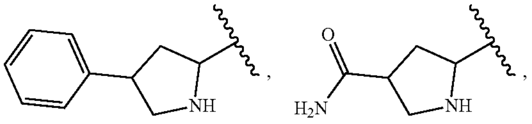
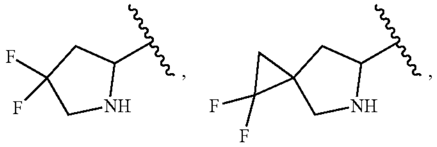
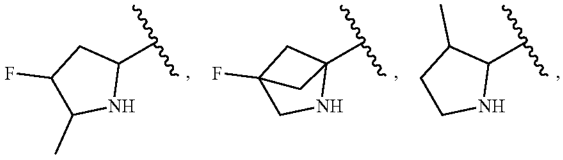
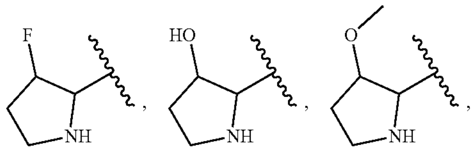
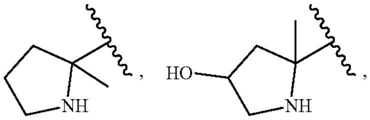
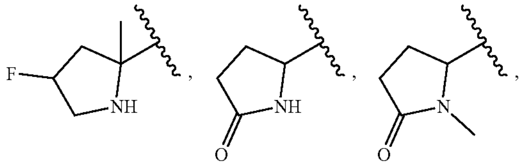
-continued
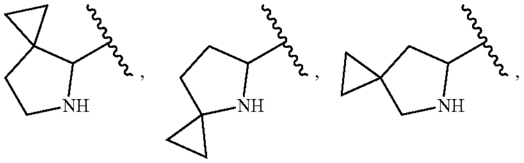
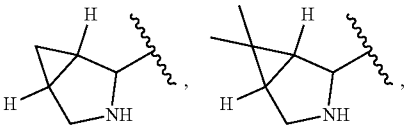
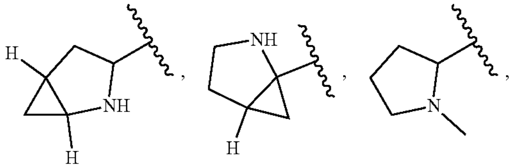
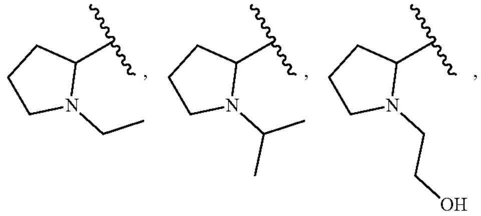
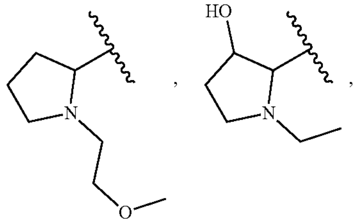
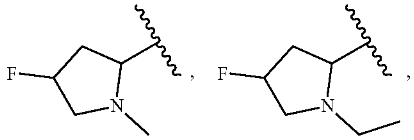
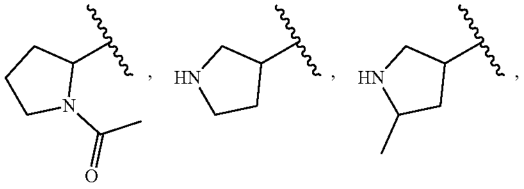
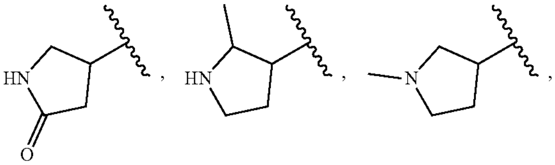
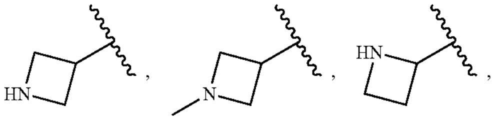
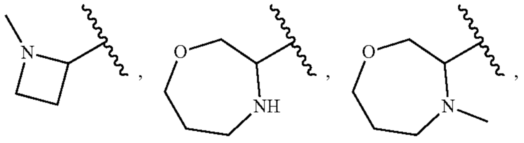

-continued
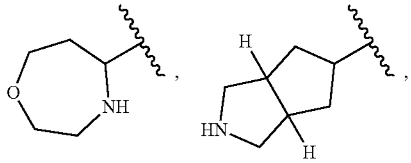
, ,
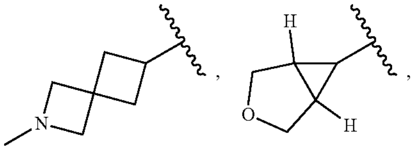
, ,
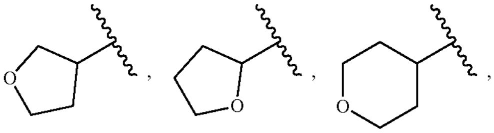
, , ,
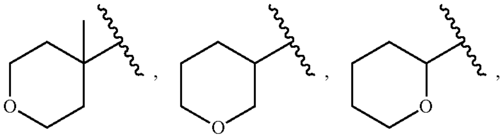
, , ,
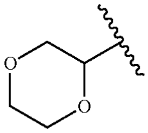
, or
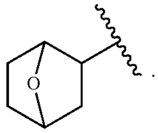
.
In some embodiments of a compound having a structure according to Formula I $R^5$ is
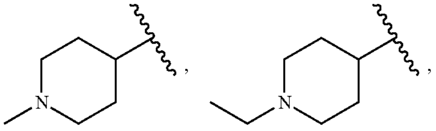
, ,
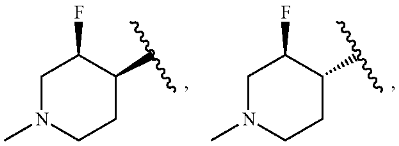
, ,
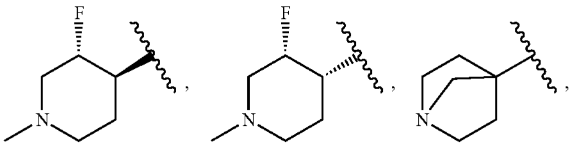
, , ,
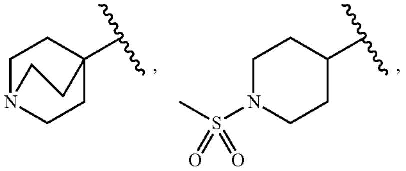
, ,
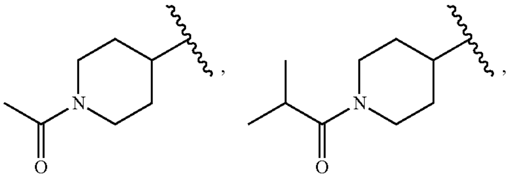
, ,
-continued
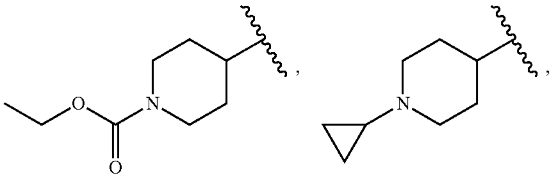
, ,
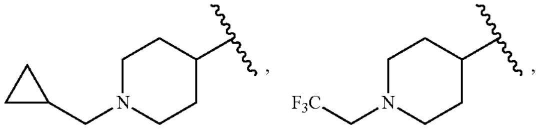
, ,
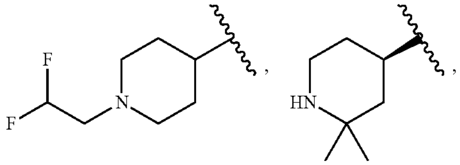
, ,
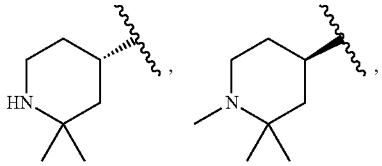
, ,
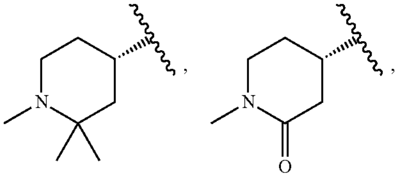
, ,
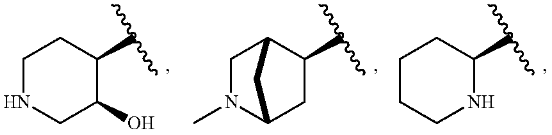
, , ,
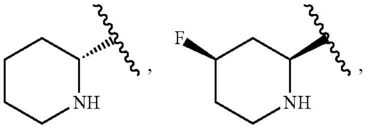
, ,
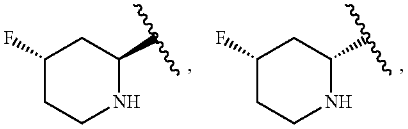
, ,
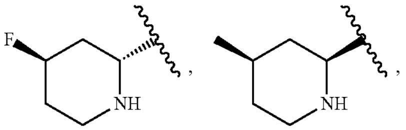
, ,
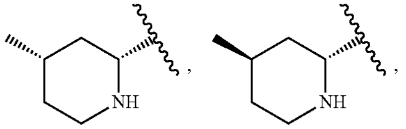
, ,
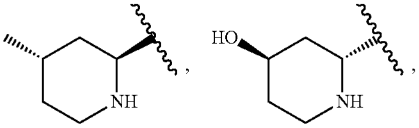
, , -continued
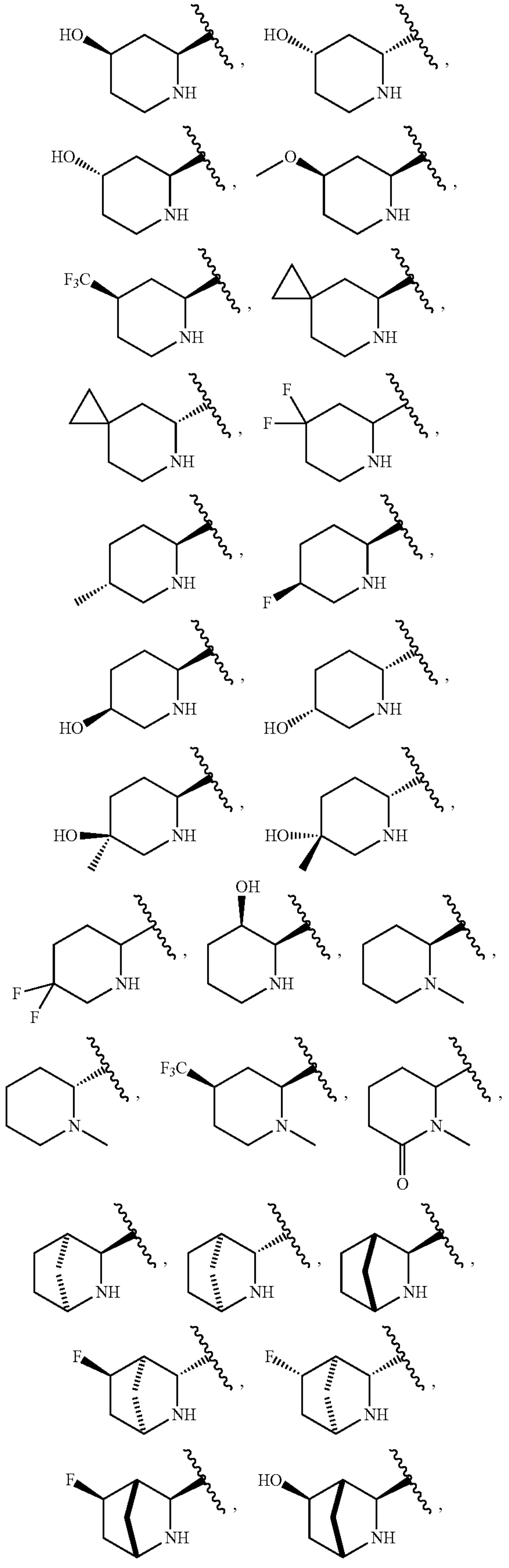
-continued
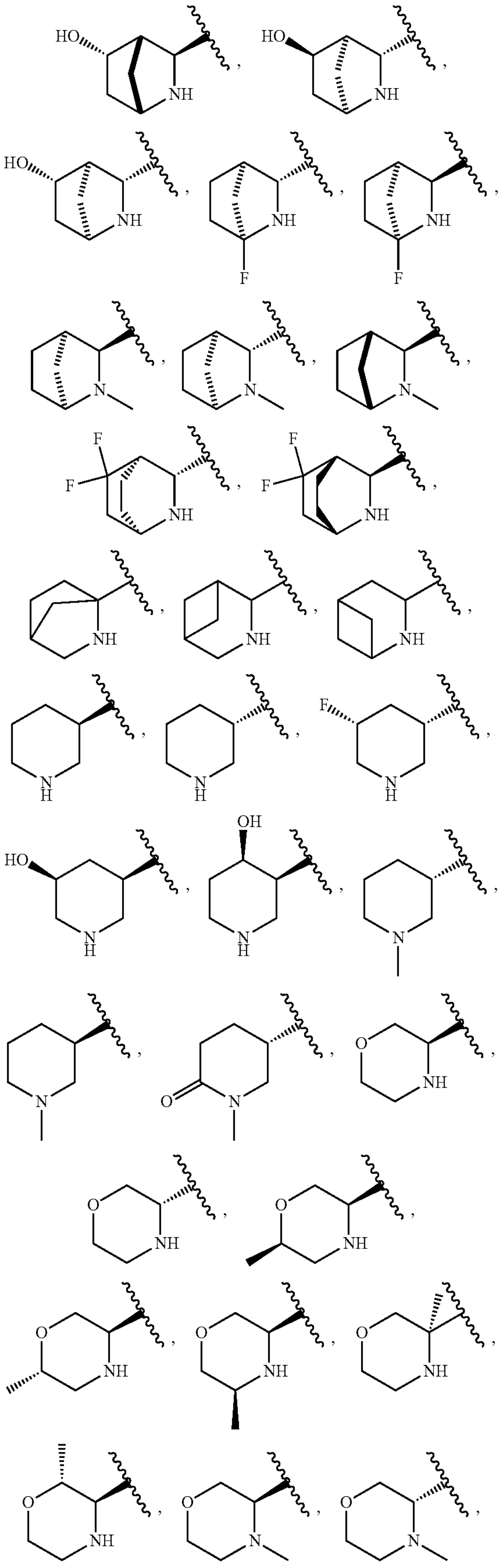

-continued
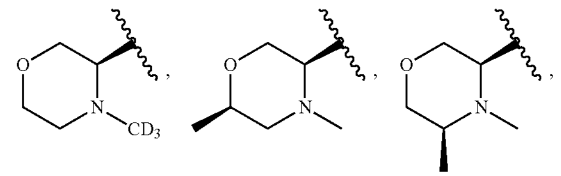
, , ,
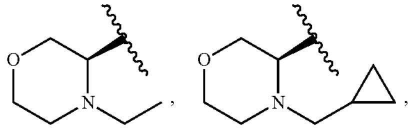
, ,
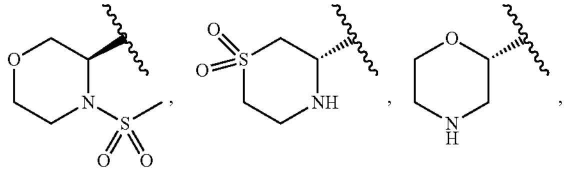
, , ,
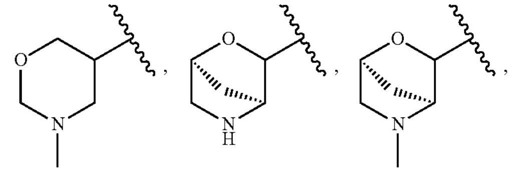
, , ,
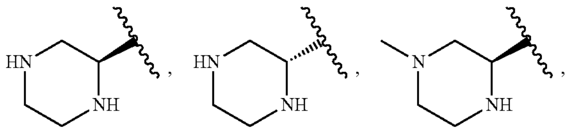
, , ,
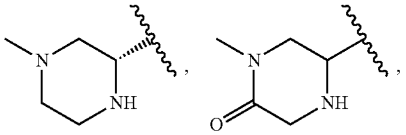
, ,
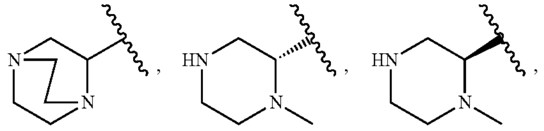
, , ,
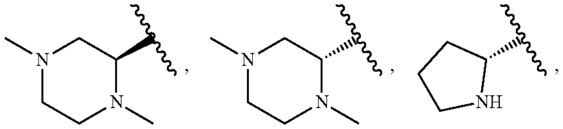
, , ,
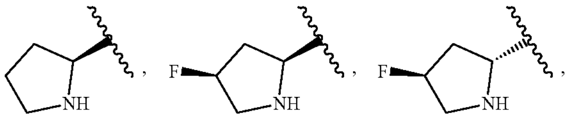
, , ,
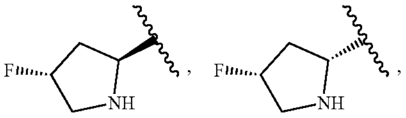
, ,
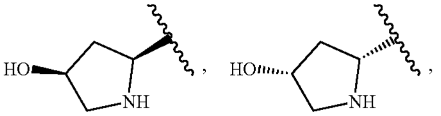
, ,
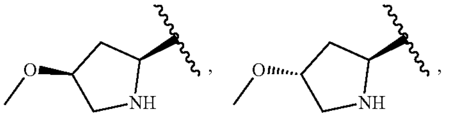
, ,
-continued
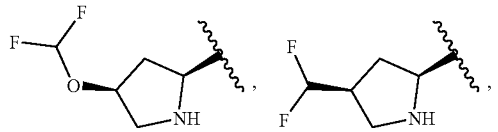
, ,
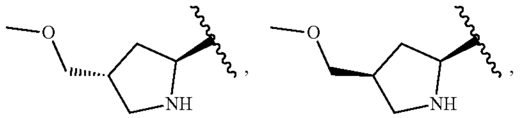
, ,
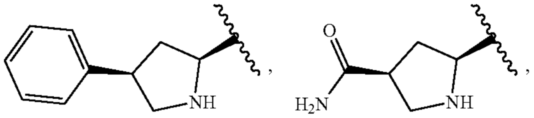
, ,
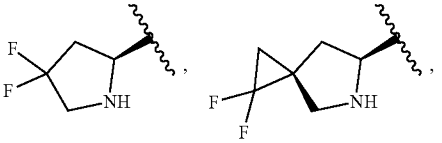
, ,
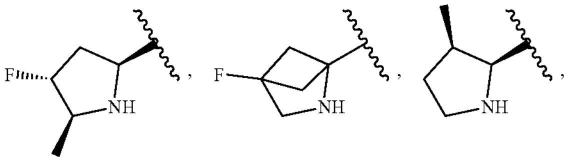
, , ,
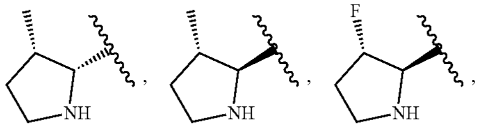
, , ,
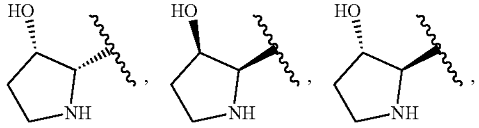
, , ,
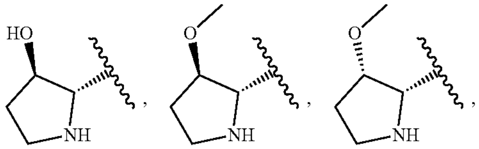
, , ,
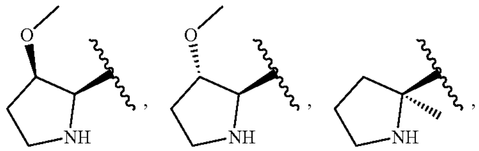
, , ,
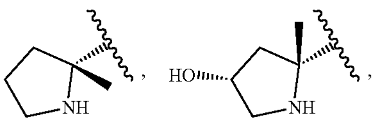
, ,
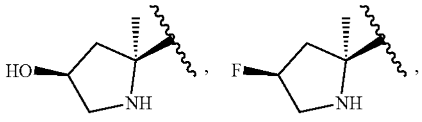
, ,
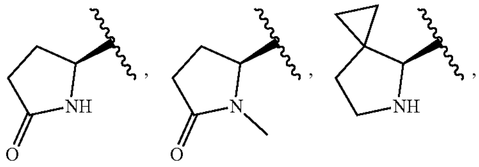
, , , -continued

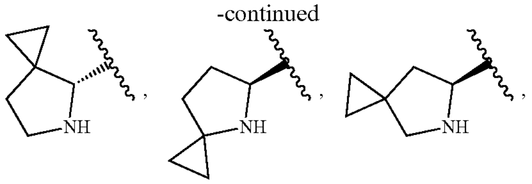

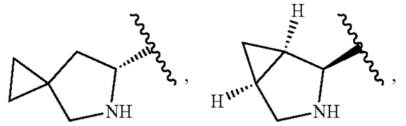

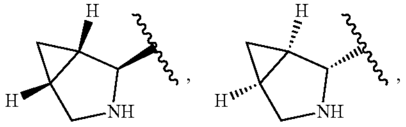

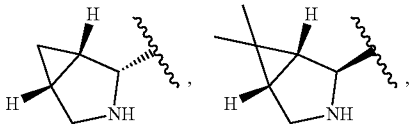

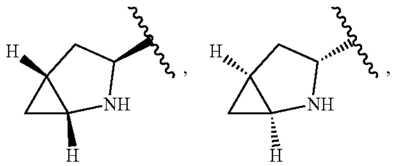

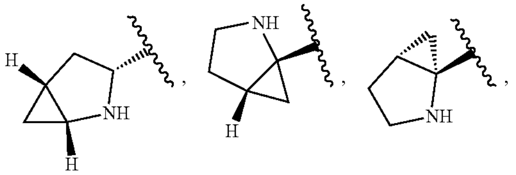

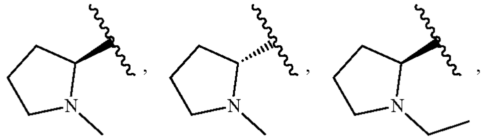

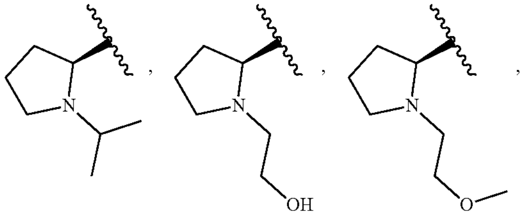

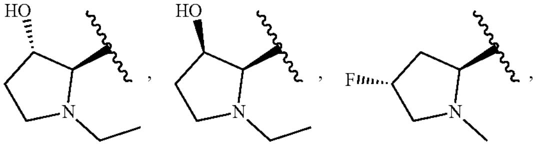

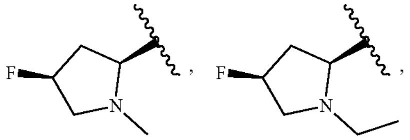

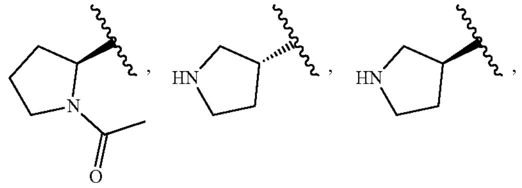

-continued

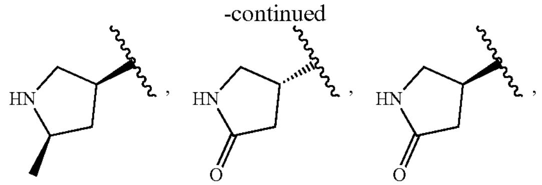

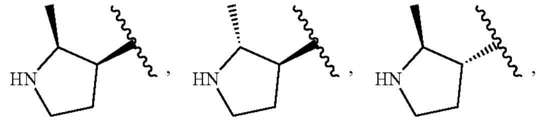

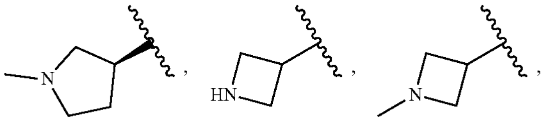

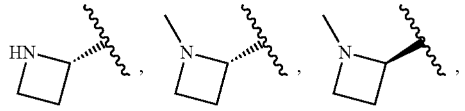

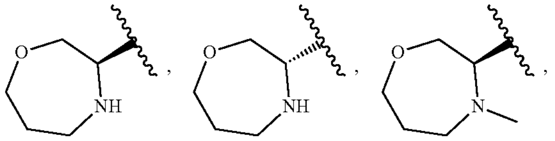

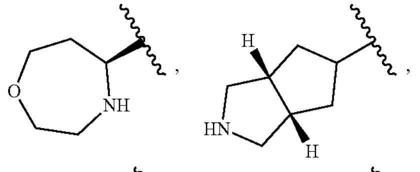

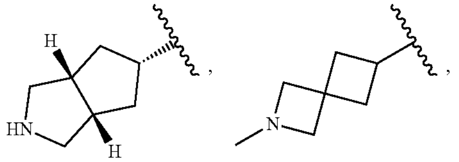

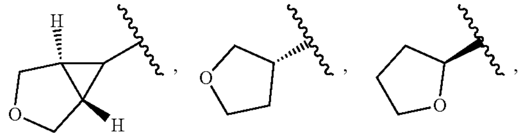

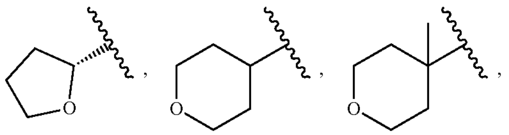

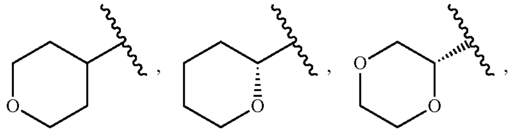

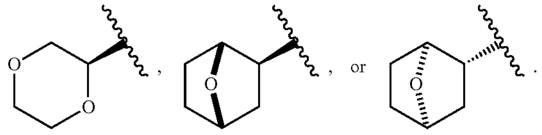

In some embodiments of a compound having a structure according to Formula I, $R^5$ is —Y—$R^{5a}$; Y is $C_1$-$C_6$ alkylene; $R^{5a}$ is a 4- to 10-membered heterocycloalkyl having 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$ $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl. In some embodiments of a compound having a structure according to Formula I, $R^5$ is —Y—$R^{5a}$; Y is $C_1$-$C_6$ alkylene; $R^{5a}$ is a 4- to 10-membered heterocycloalkyl having 1-3 ring heteroatoms or ring heteroatom groups independently selected from N, O, S, and $S(O)_2$, and $R^{5a}$ is unsubstituted or substituted with 1-4 substituents independently selected from oxo, halo, and $C_1$-$C_6$ alkyl. In some embodiments of a compound having a structure according to Formula I, $R^5$ is

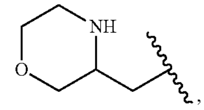,
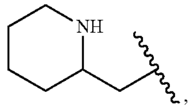,
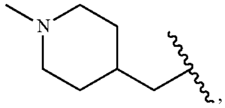,
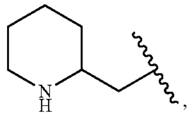,
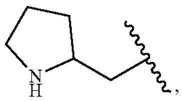,
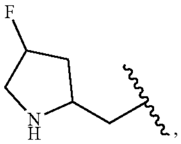,
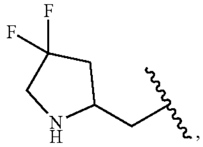,
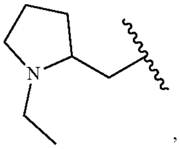,
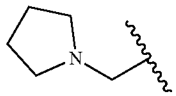,
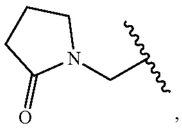,
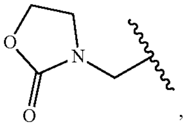,
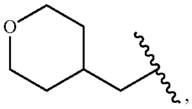, or
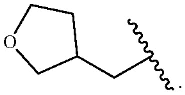.

In some embodiments of a compound having a structure according to Formula I, $R^5$ is

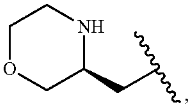,
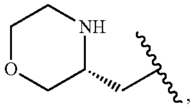,
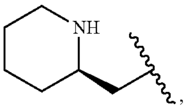,
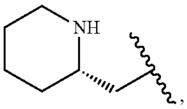,
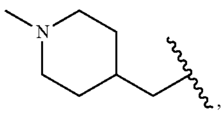,
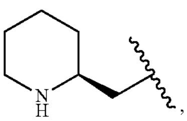,

-continued

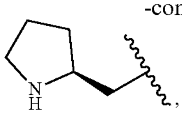,
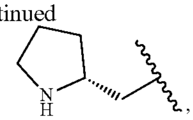,
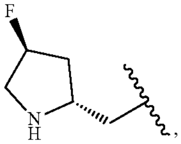,
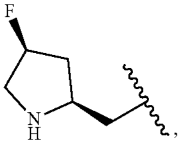,
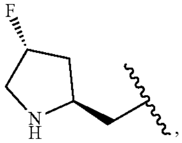,
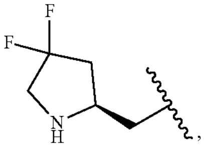,
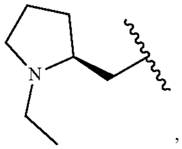,
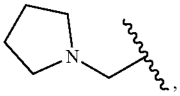,
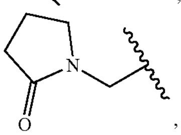,
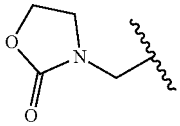,
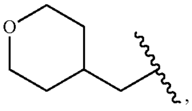,
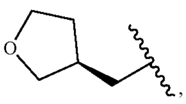, or
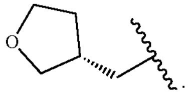.

In some embodiments of a compound having a structure according to Formula I, $R^5$ is —Y—$R^{5a}$; Y is absent; and $R^{5a}$ is $C_1$-$C_6$ alkyl, $C_3$-$C_8$ cycloalkyl, phenyl, 5- to 10-membered heteroaryl, or 4- to 10-membered heterocycloalkyl, wherein the 5- to 10-membered heteroaryl has 1-4 ring heteroatoms independently selected from N, O, and S; and the 4- to 10-membered heterocycloalkyl has 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl.

In some embodiments of a compound having a structure according to Formula I, $R^5$ is —Y—$R^{5a}$; Y is absent; and $R^{5a}$ is $C_1$-$C_6$ alkyl, $C_3$-$C_8$ cycloalkyl, phenyl, 5- to 6-membered heteroaryl, or 4- to 10-membered heterocycloalkyl, wherein the 5- to 6-membered heteroaryl has 1-4 ring heteroatoms independently selected from N, O, and S; and the 4- to 10-membered heterocycloalkyl has 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl.

In some embodiments of a compound having a structure according to Formula I, $R^{5a}$ is —$C_1$-$C_3$-alkyl, phenyl, pyridinyl, oxazolyl, imidazolyl, pyrazolyl, 1,2,4-triazolyl, cyclopropyl, cyclobutyl, cyclopentyl, cyclohexyl, bicyclo[1.1.1]pentyl, bicyclo[2.2.1]heptyl, azetidinyl, pyrrolidinyl, azabicyclo[2.1.1]hexyl, tetrahydrofuranyl, tetrahydropyranyl, 7-oxabicyclo[2.2.1]heptyl, 1,4-diazabicyclo[2.2.2]octyl, piperazinyl, piperidinyl, 1-azabicyclo[2.2.1]heptyl, 2-azabicyclo[2.2.1]heptyl, 6-azaspiro[2.5]octyl, 2-azabicyclo[3.1.1]heptyl, 1,3-oxazinanyl, morpholinyl, 2-oxa-5-azabicyclo[2.2.1]heptyl, 1-azabicyclo[2.2.2]octyl, 1,4-dioxanyl, 3-azabicyclo[3.1.0]hexyl, 2-azabicyclo[3.1.0]hexyl, 4-azaspiro[2.4]heptyl, 5-azaspiro[2.4]heptyl, 3-oxabicyclo[3.1.0]hexyl, octahydrocyclopenta[c]pyrrolyl, oxazolidinyl, or thiomorpholinyl dioxide; and $R^{5a}$ is unsubstituted or substituted with 1-4 substituents independently selected from oxo, halo, OH, $C_1$-$C_6$ alkyl, $C_1$-$C_6$ alkoxy, $NR^{5b}R^{5c}$, —($C_1$-$C_5$ alkylene)-($C_3$-$C_8$ cycloalkyl), —$S(O)_2$—($C_1$-$C_3$ alkyl), $C_1$-$C_3$ haloalkoxy, $C_1$-$C_6$ haloalkyl, phenyl, —($C_1$-$C_4$ alkylene)-($C_1$-$C_3$ alkoxy), —C(O)—($C_1$-$C_4$ alkyl), —C(O)O—($C_1$-$C_4$ alkyl), $C_3$-$C_8$ cycloalkyl, $C_1$-$C_4$ hydroxyalkyl, and —$C(O)NH_2$; and $R^{5b}$ and $R^{5c}$ are independently selected from H and $C_1$-$C_3$ alkyl.

In some embodiments of a compound having a structure according to Formula I, $R^{5a}$ is methyl, ethyl, n-propyl, isopropyl, phenyl,

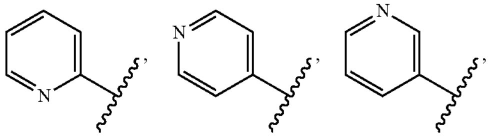
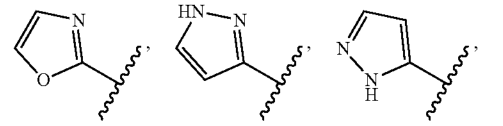
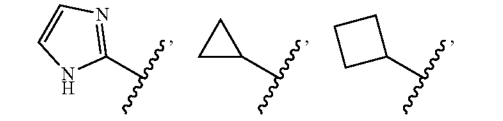
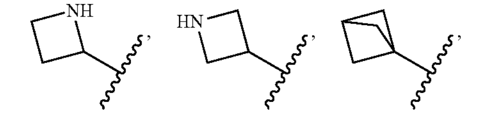
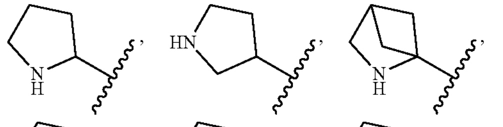
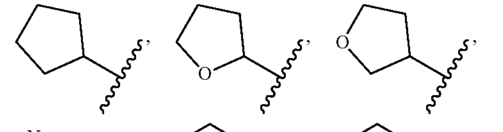
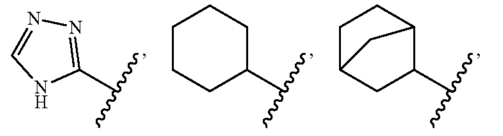
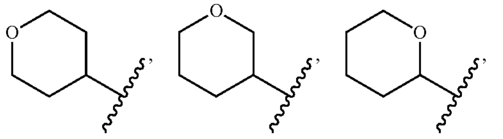

-continued

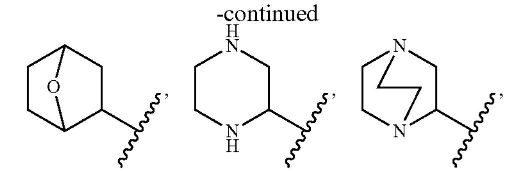
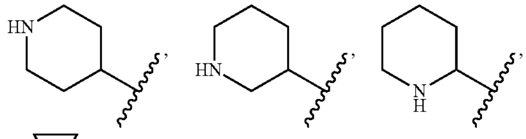
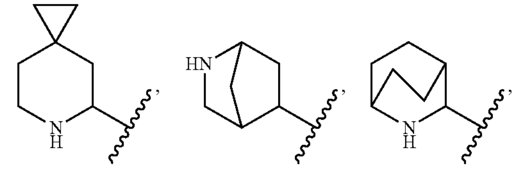
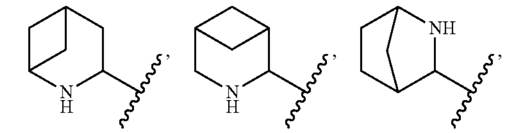
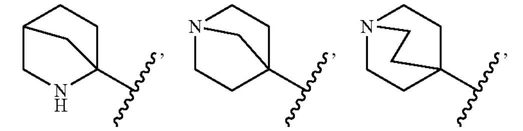
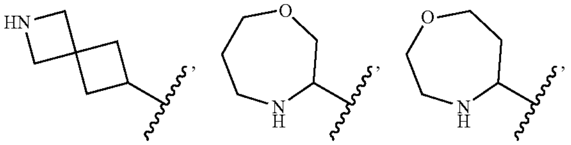
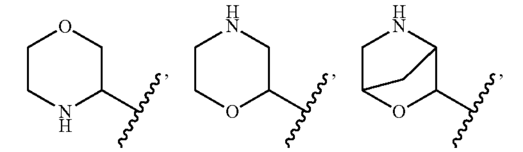
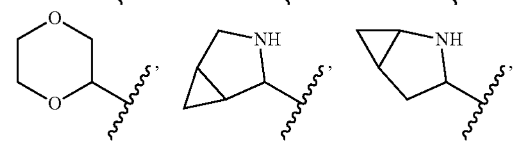
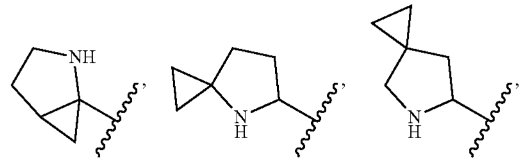
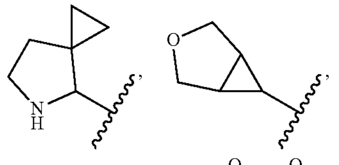
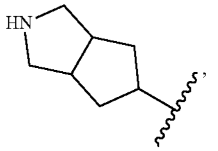
or
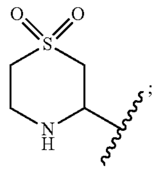

and $R^{5a}$ is unsubstituted or substituted with 1-4 substituents independently selected from oxo, halo, OH, $C_1$-$C_6$ alkyl, $C_1$-$C_6$ alkoxy, $NR^{5b}R^{5c}$, —($C_1$-$C_5$ alkylene)-($C_3$-$C_8$ cycloalkyl), —$S(O)_2$—($C_1$-$C_3$ alkyl), $C_1$-$C_3$ haloalkoxy, $C_1$-$C_6$ haloalkyl, phenyl, —($C_1$-$C_4$ alkylene)-($C_1$-$C_3$ alkoxy), —C(O)—($C_1$-$C_4$ alkyl), —C(O)O—($C_1$-$C_4$ alkyl), $C_3$-$C_8$ cycloalkyl, $C_1$-$C_4$ hydroxyalkyl, and —$C(O)NH_2$; and $R^{5b}$ and $R^{5c}$ are independently selected from H and $C_1$-$C_3$ alkyl.

In some embodiments of a compound having a structure according to Formula I, $R^5$ is Y—$R^{5a}$; Y is absent; and $R^{5a}$ is $C_1$-$C_6$ alkyl or 4- to 10-membered heterocycloalkyl; and $R^{5a}$ is unsubstituted or substituted with 1-2 substituents independently selected from OH, $NR^{5b}R^{5c}$, or $C_1$-$C_6$ alkyl; wherein the 4- to 10-membered heterocycloalkyl has 1-3 ring heteroatoms or ring heteroatom groups independently selected from N and O; and $R^{1b}$ and $R^{5c}$ are independently selected from H and $C_1$-$C_3$ alkyl.

In some embodiments of a compound having a structure according to Formula I, $R^5$ is Y—$R^{5a}$, wherein Y is $C_1$-$C_6$ alkylene; and $R^{5a}$ is phenyl or 4- to 6 membered heterocycloalkyl having 1-2 ring heteroatoms independently selected from N and O; wherein $R^{5a}$ is unsubstituted or substituted with 1-4 substituents independently selected from oxo, halo, OH, $NR^{5b}R^{o}$, $C_1$-$C_6$ alkoxy, and $C_1$-$C_6$ alkyl; and $R^{5b}$ and $R^{5c}$ are independently selected from H and $C_1$-$C_3$ alkyl.

In some embodiments of a compound having a structure according to Formula I, $R^{5a}$ is phenyl, piperidinyl, pyrrolidinyl, oxazolidinyl, tetrahydrofuranyl, tetrahydropyranyl, or morpholinyl, wherein $R^{5a}$ is unsubstituted or substituted with 1-4 substituents independently selected from oxo, halo, OH, $NR^{5b}R^{5c}$, $C_1$-$C_6$ alkoxy, and $C_1$-$C_6$ alkyl; and $R^{5b}$ and $R^{5c}$ are independently selected from H and $C_1$-$C_3$ alkyl.

In some embodiments of a compound having a structure according to Formula I, $R^{5a}$ is phenyl,

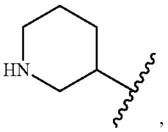, 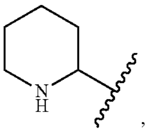, 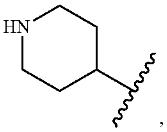,
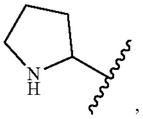, 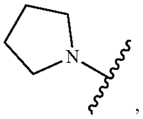, 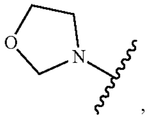,
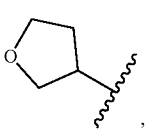, 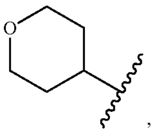, or 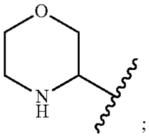;

and $R^{5a}$ is unsubstituted or substituted with 1-4 substituents independently selected from oxo, halo, OH, $NR^{5b}R^{5c}$, $C_1$-$C_6$ alkoxy, and $C_1$-$C_6$ alkyl; and wherein $R^{5b}$ and $R^{5c}$ are independently selected from H and $C_1$-$C_3$ alkyl. In some embodiments of a compound having a structure according to Formula I, $R^{5a}$ is phenyl,

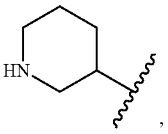, 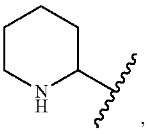, 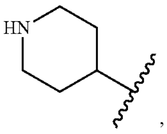,
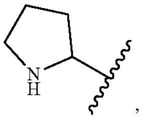, 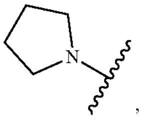, 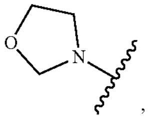,

-continued

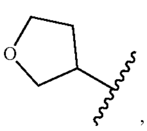, 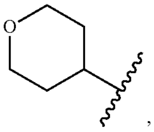, or 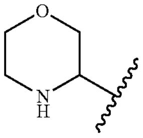;

and $R^{5a}$ is unsubstituted or substituted with 1-4 substituents independently selected from oxo, halo, and $C_1$-$C_6$ alkyl; and wherein $R^{5b}$ and $R^{5c}$ are independently selected from H and $C_1$-$C_3$ alkyl.

In some embodiments of a compound having a structure according to Formula I, $R^5$ is

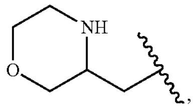, 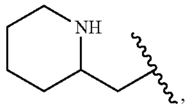,
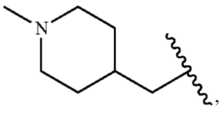, 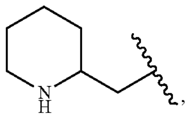,
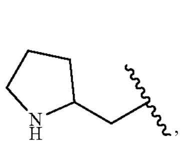, 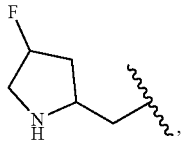,
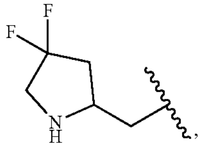, 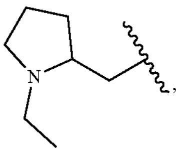,
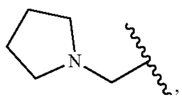, 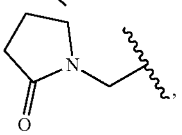,
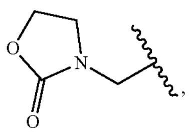, 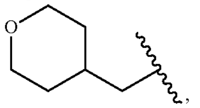,
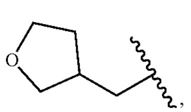, 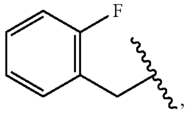, or
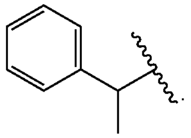.

In some embodiments of a compound having a structure according to Formula I, $R^5$ is

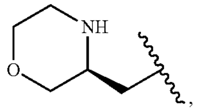, 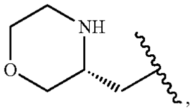,

-continued
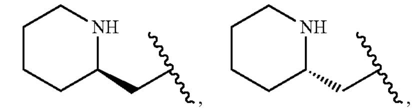
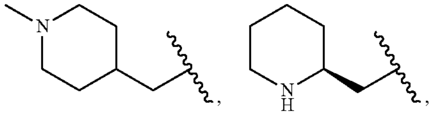
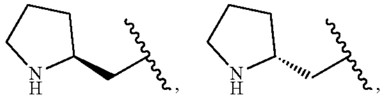
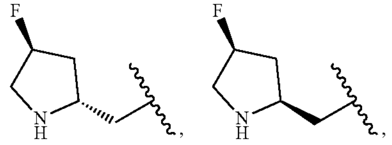
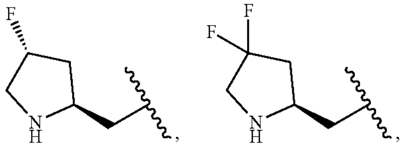
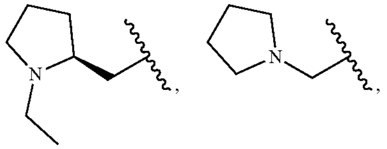
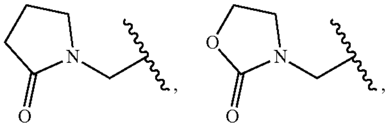
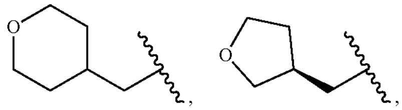
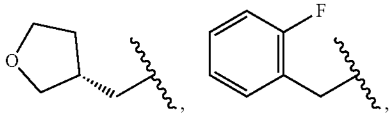
or
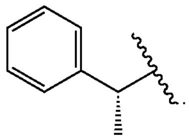
In some embodiments of a compound having a structure according to Formula I, $R^5$ is $—CH_3$, $—CH_2CH_3$, $—CH_2CH(CH_3)_2$,
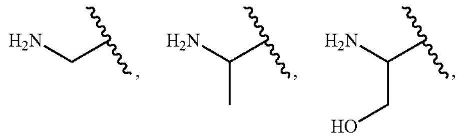
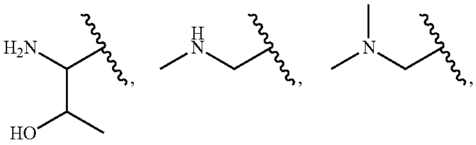
-continued
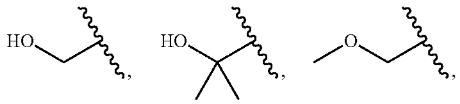
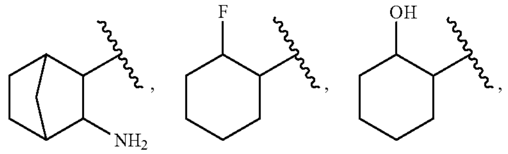
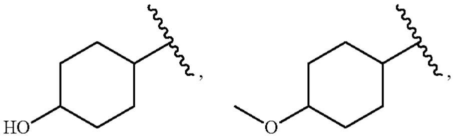
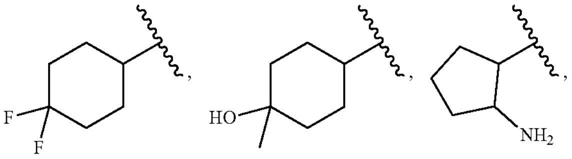
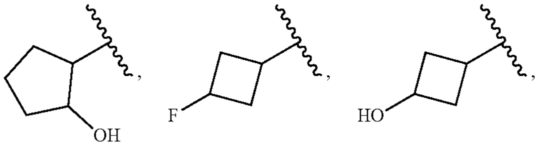
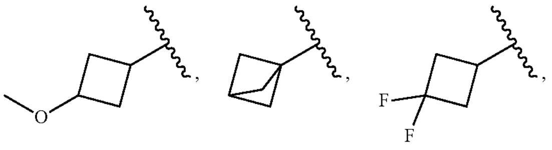
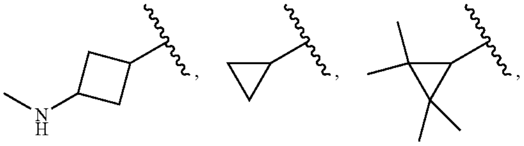
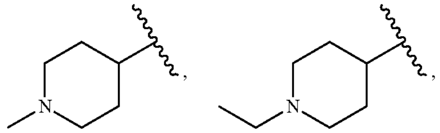
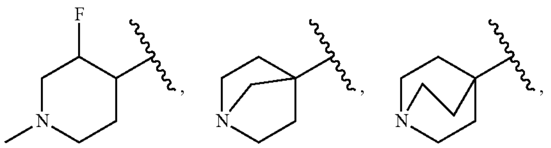
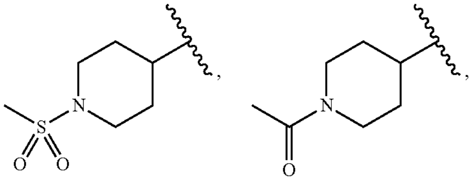
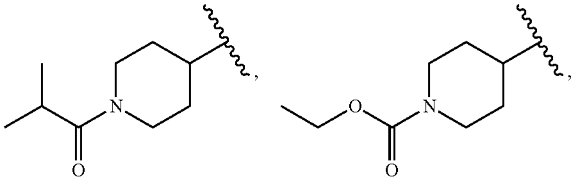

-continued
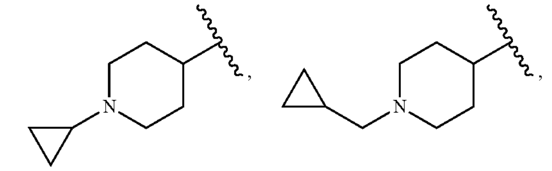
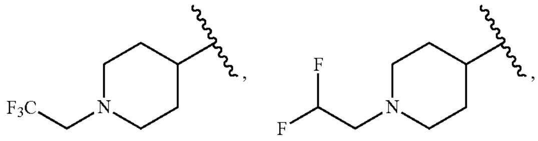
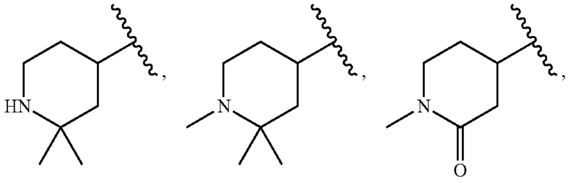
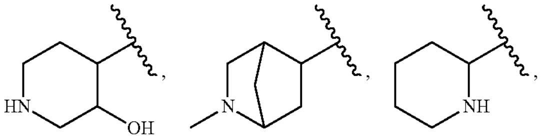
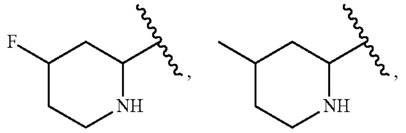
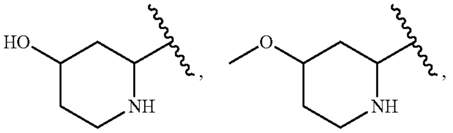
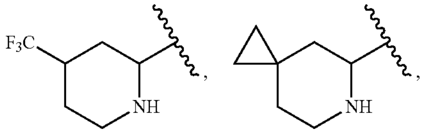
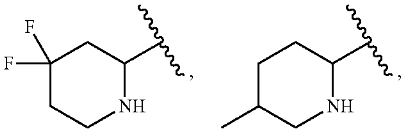
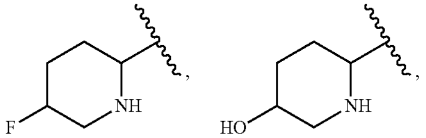
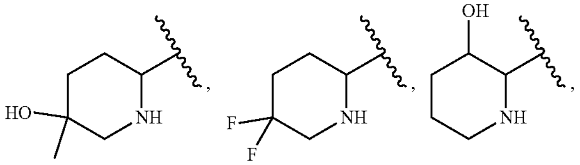
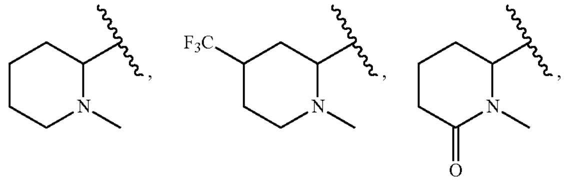
-continued
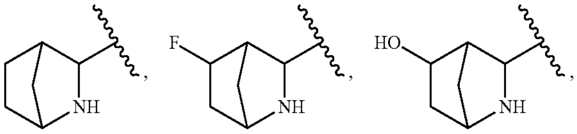
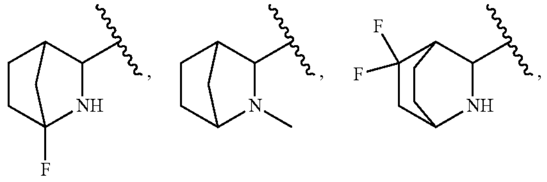
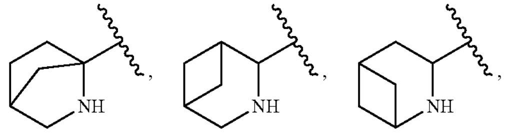
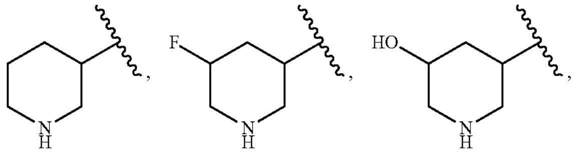
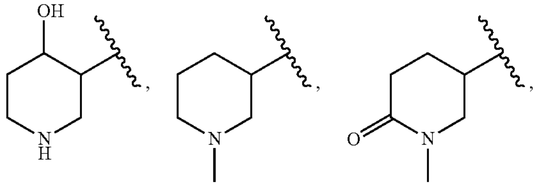
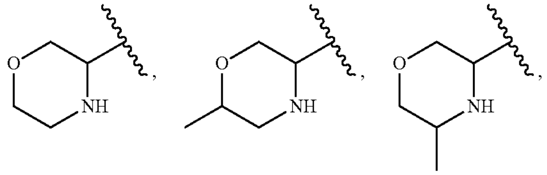
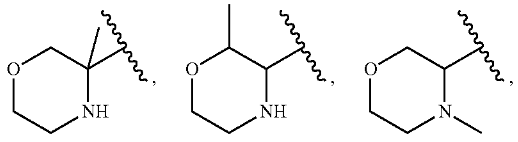
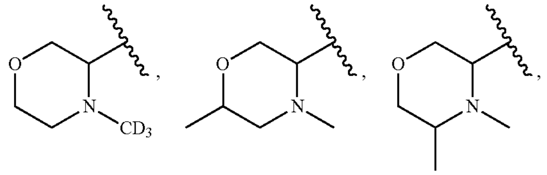
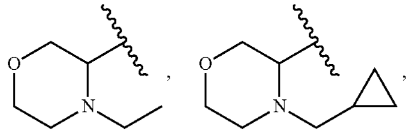
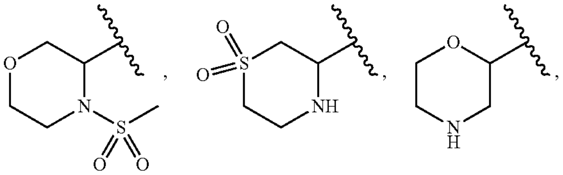

-continued
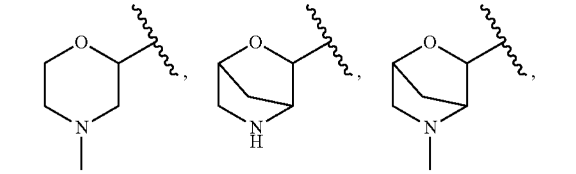
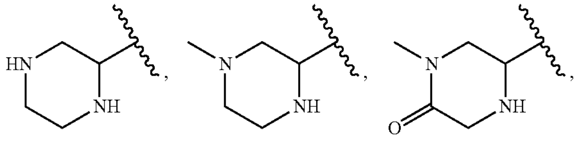
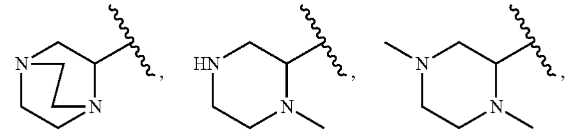
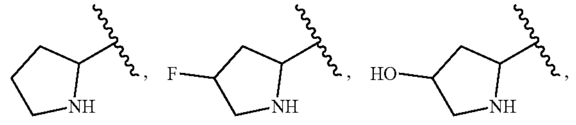
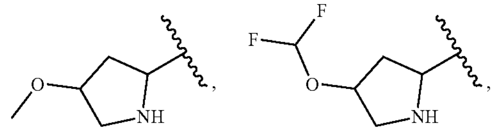
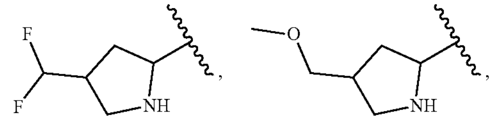
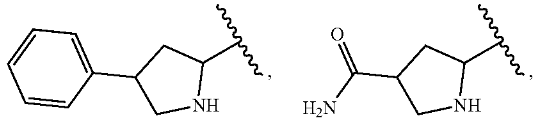
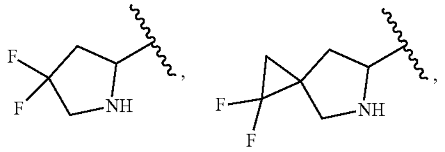
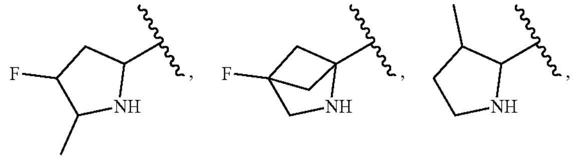
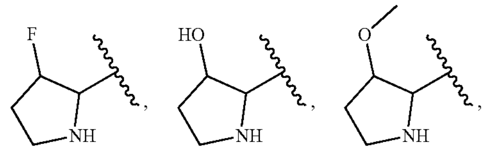
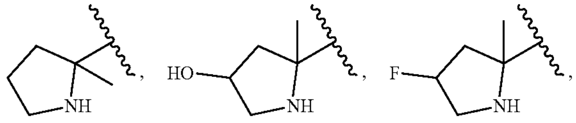
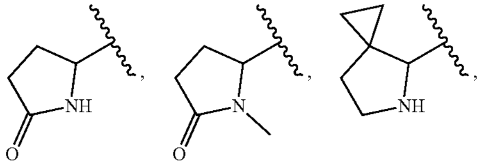
-continued
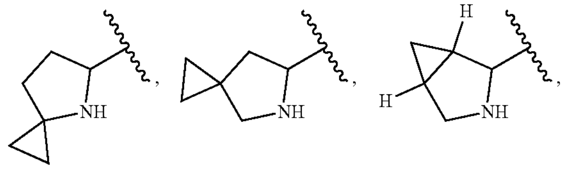
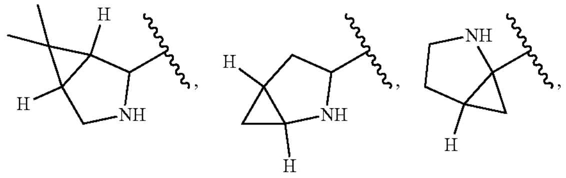
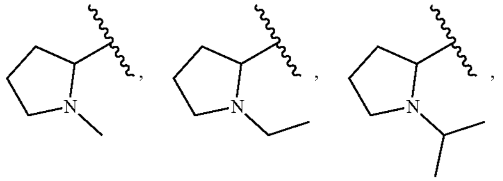
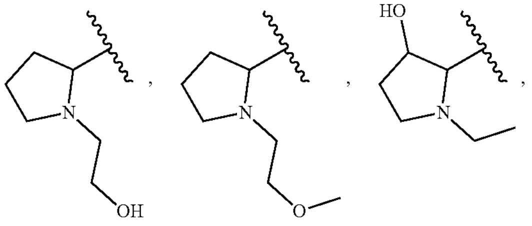
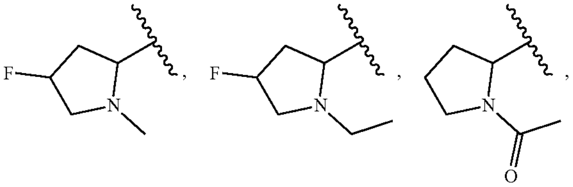
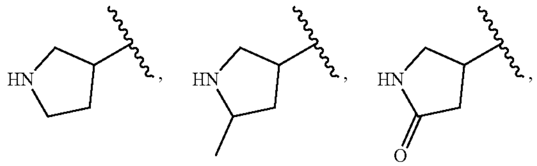
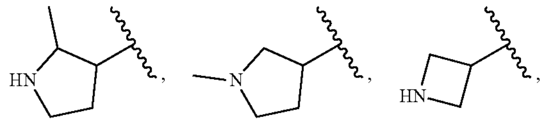
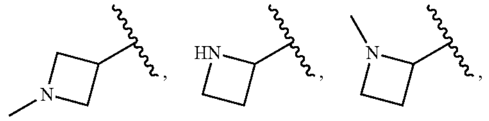
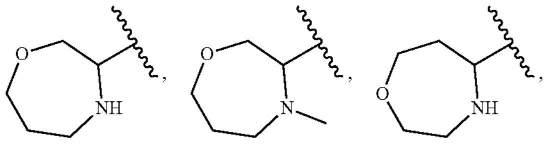
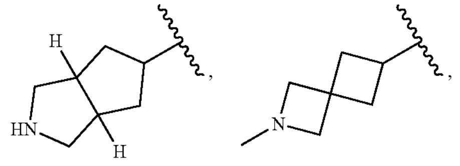

-continued
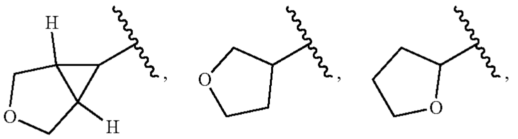
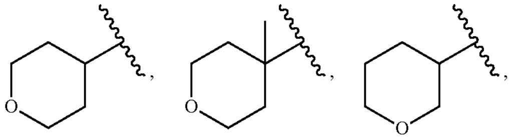
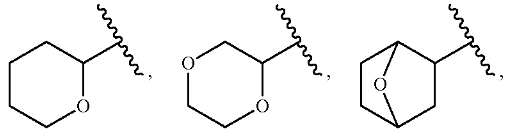
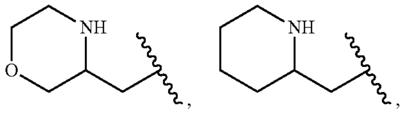
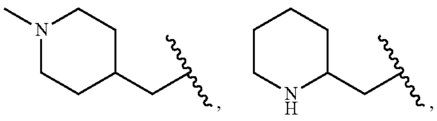
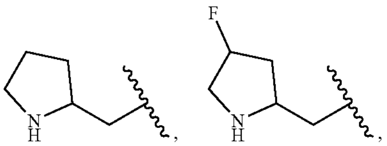
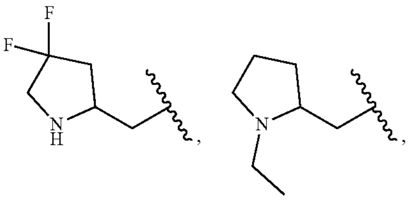
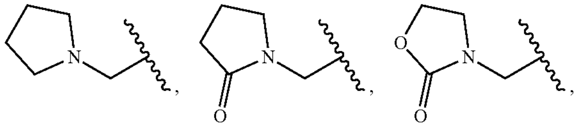
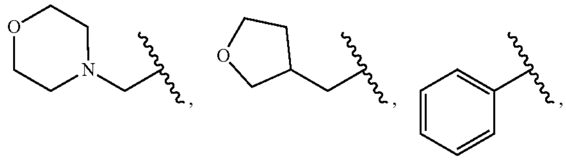
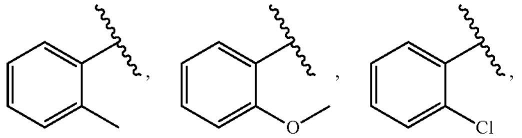
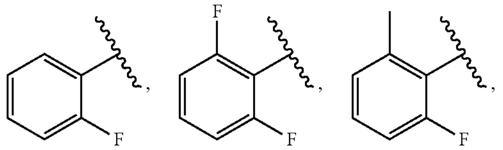
-continued
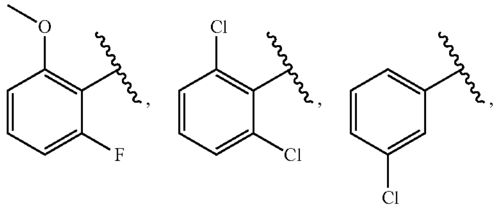
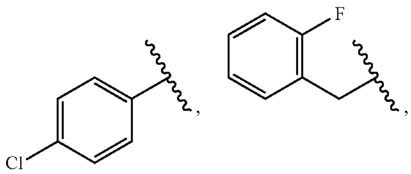
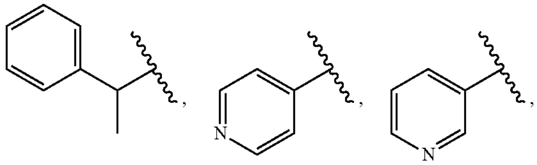
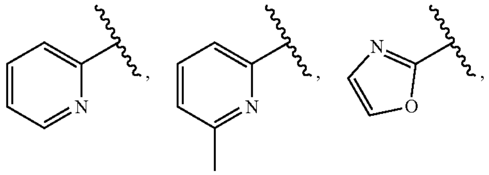
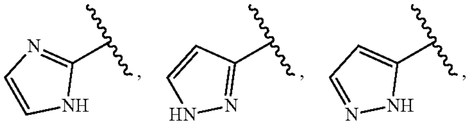
or
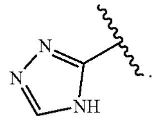
In some embodiments of a compound having a structure according to Formula I, $R^5$ is —$CH_3$, —$CH_2CH_3$, —$CH_2CH(CH_3)_2$,
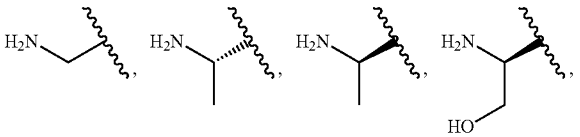
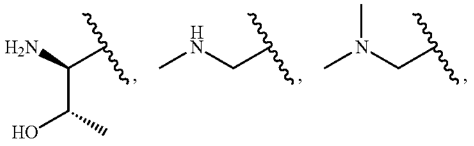
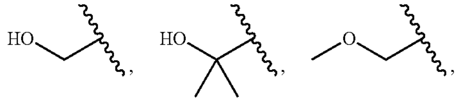
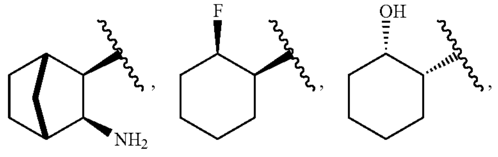

-continued
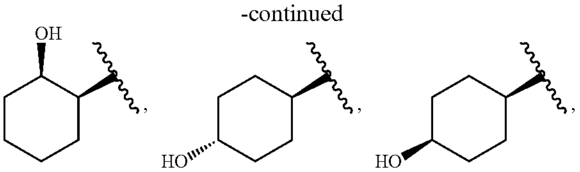
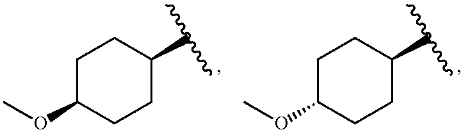
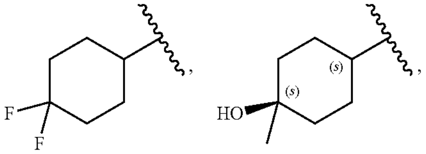
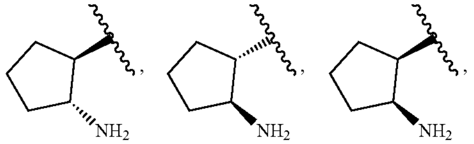
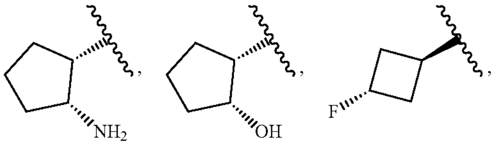
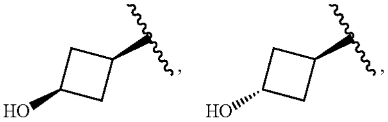
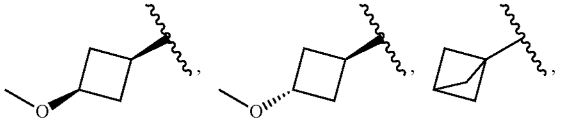
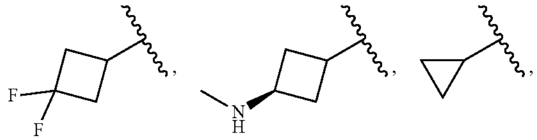
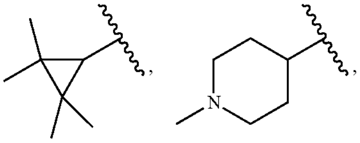
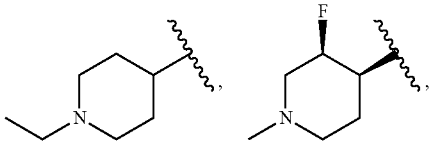
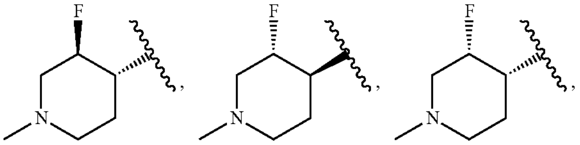
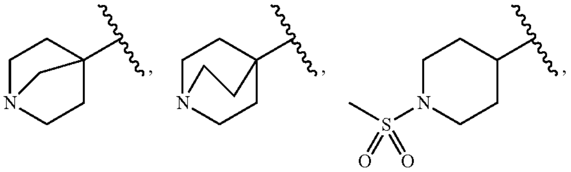
-continued
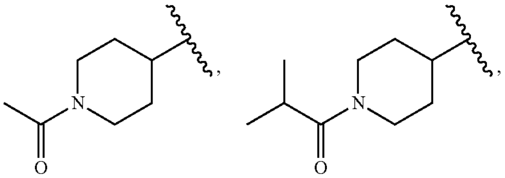
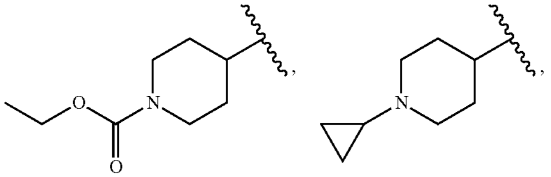
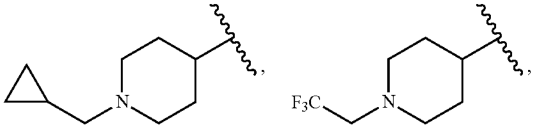
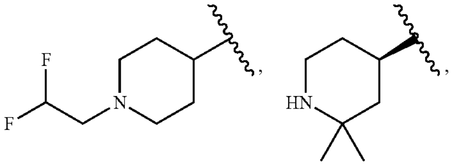
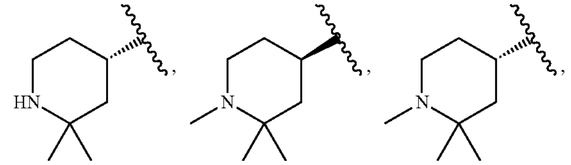
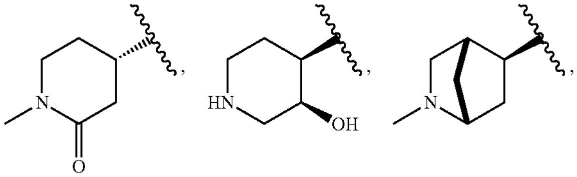
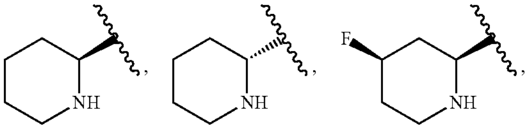
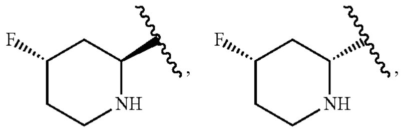
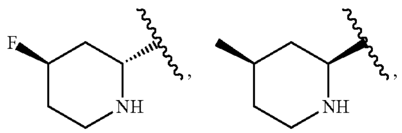
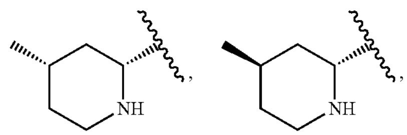
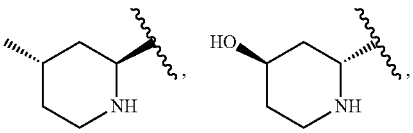

-continued
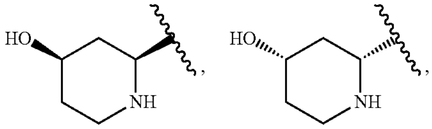
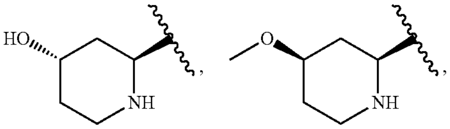
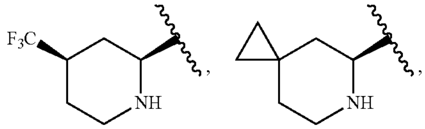
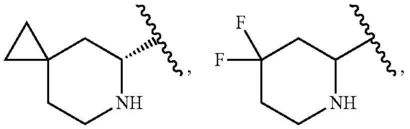
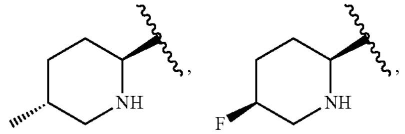
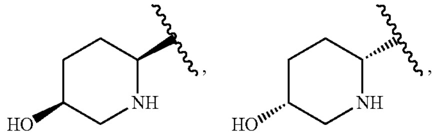
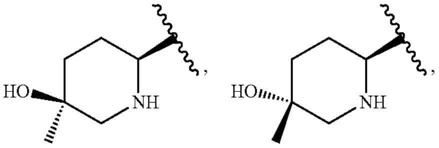
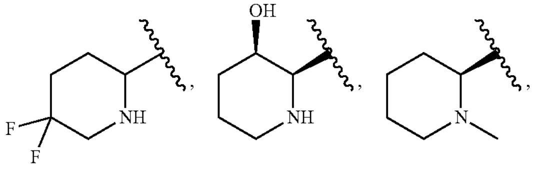
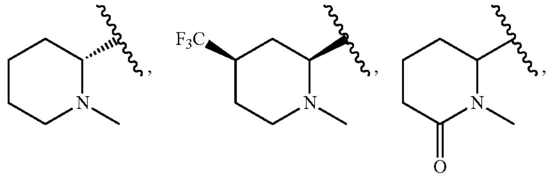
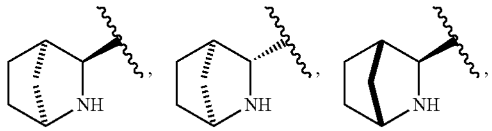
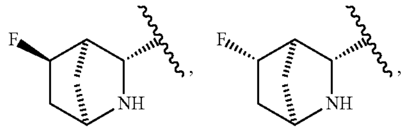
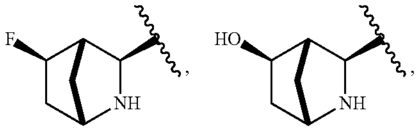
-continued
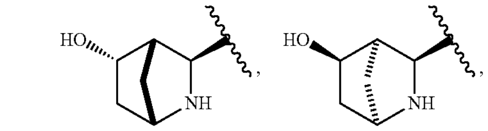
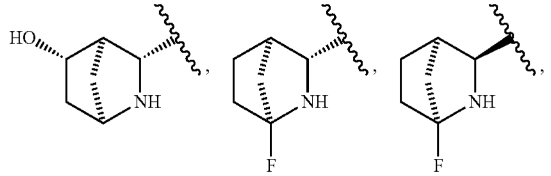
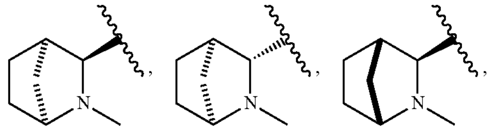
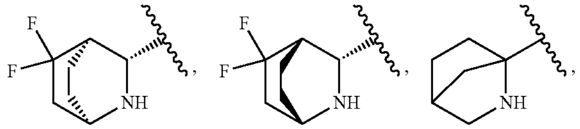
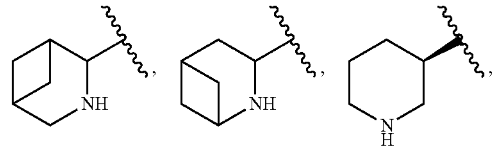
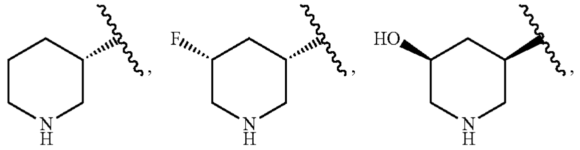
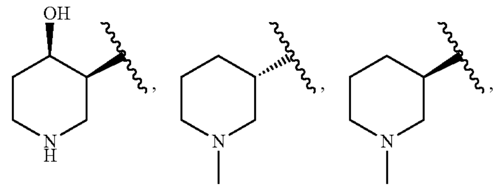
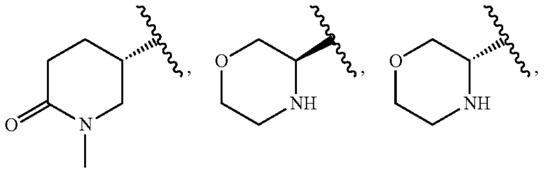
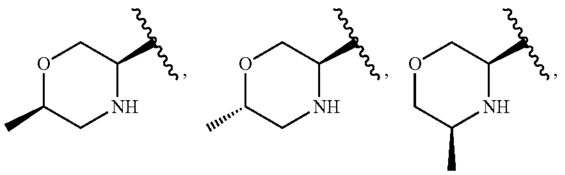
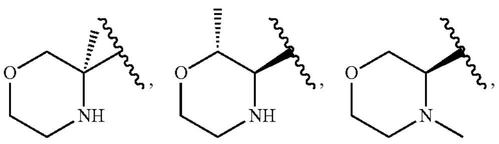
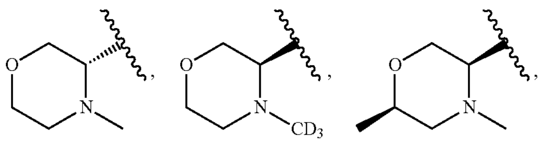

-continued
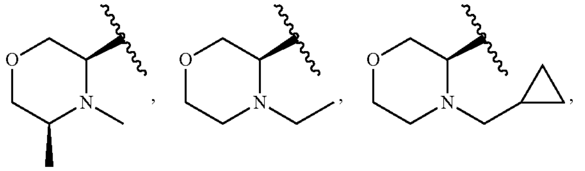
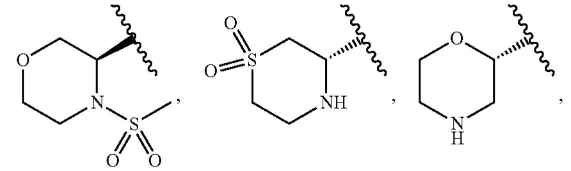
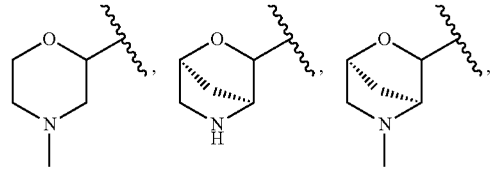
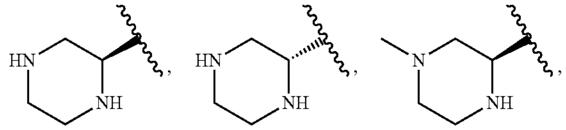
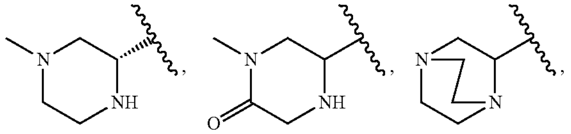
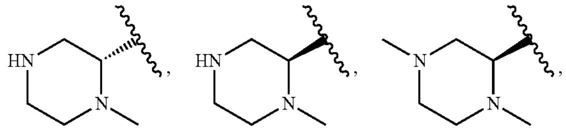
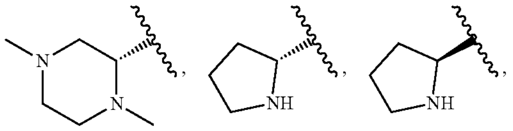
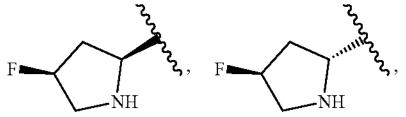
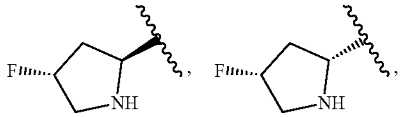
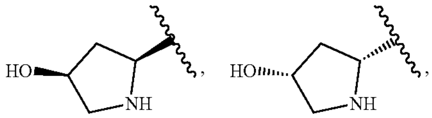
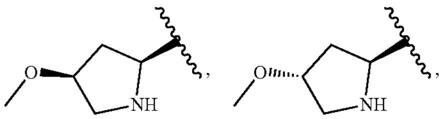
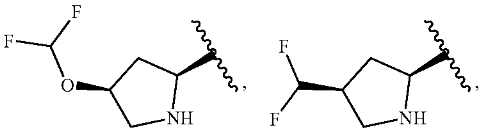
-continued
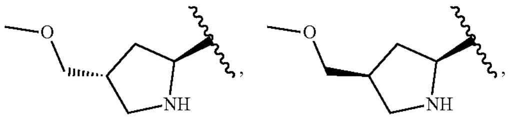
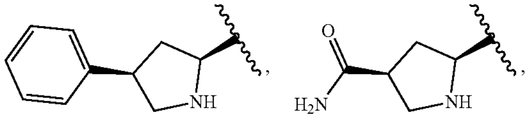
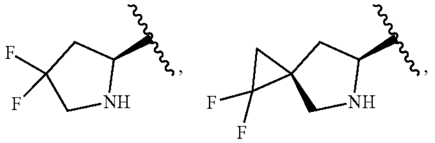
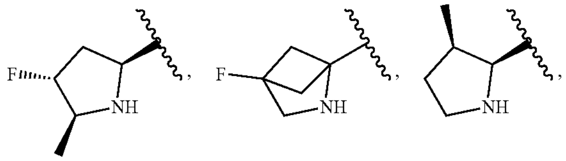
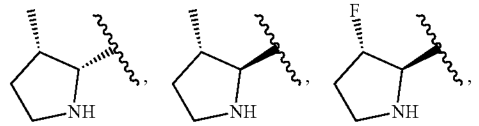
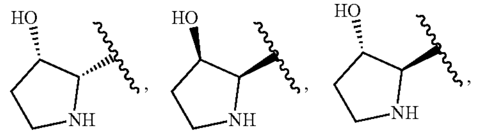
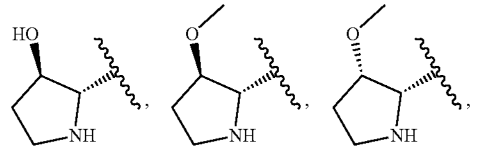
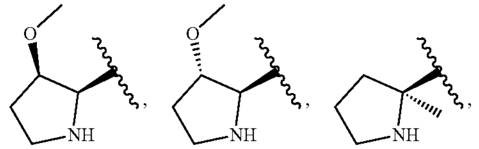
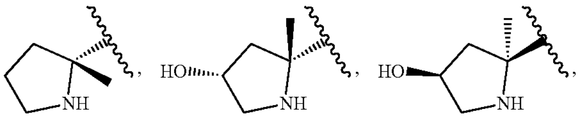
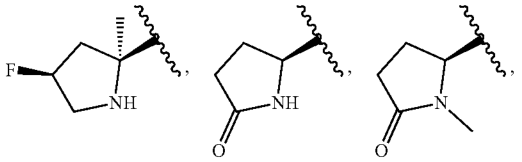
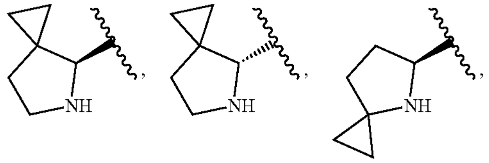
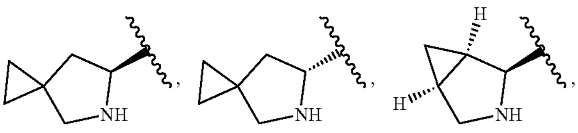

-continued
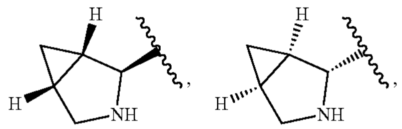
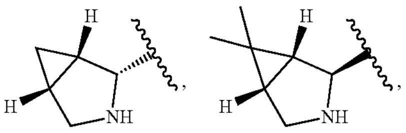
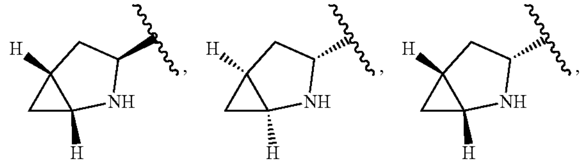
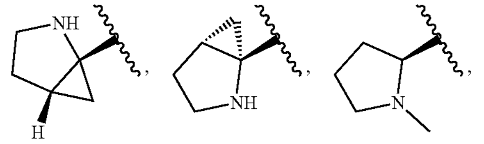
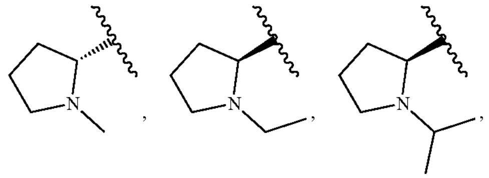
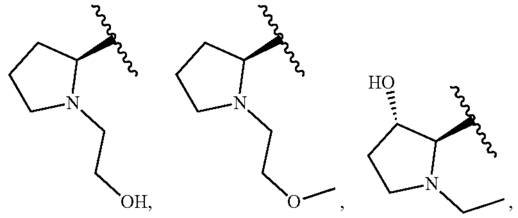
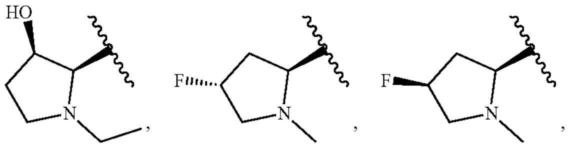
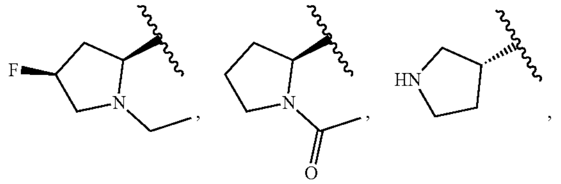
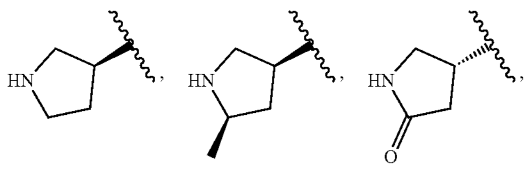
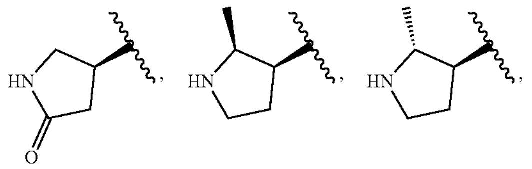
-continued
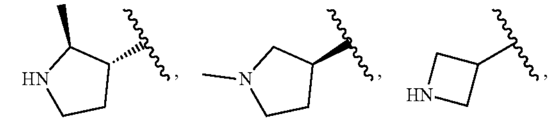
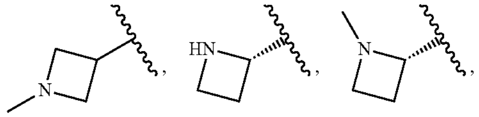
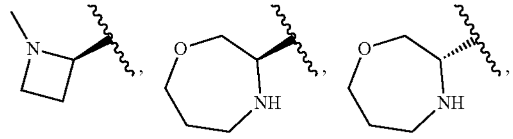
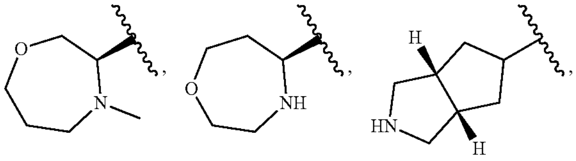
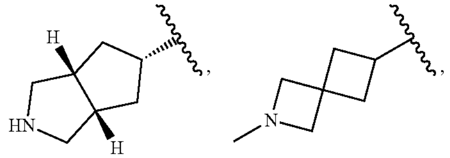
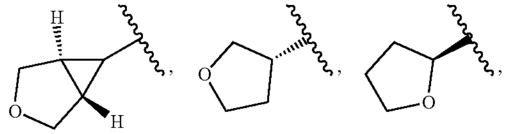
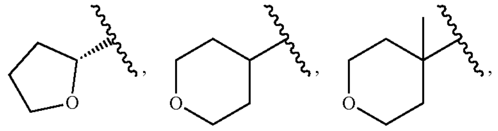
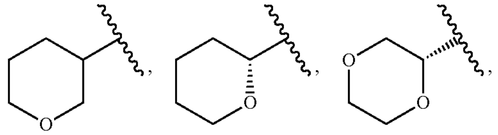
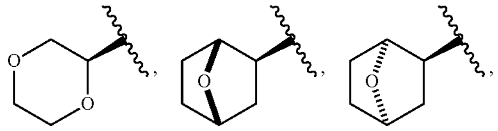
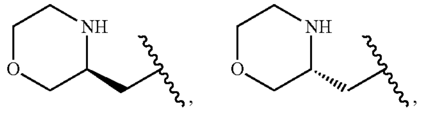
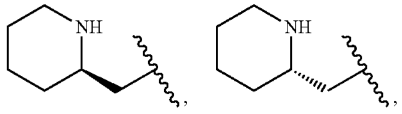
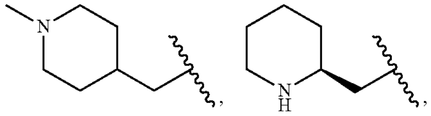
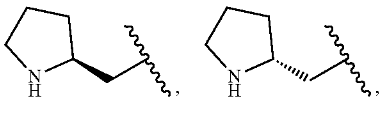

-continued
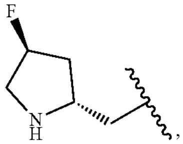, 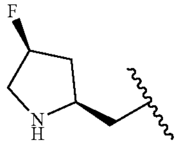, 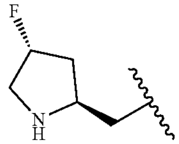,
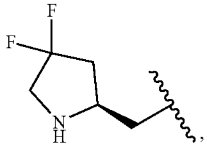, 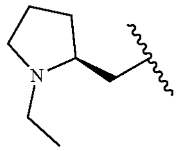,
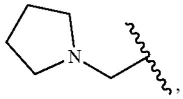, 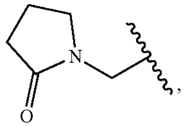, 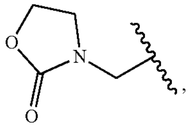,
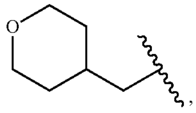, 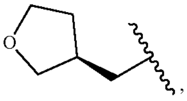,
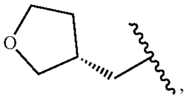, 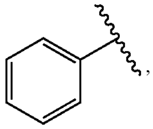,
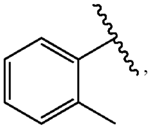, 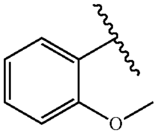, 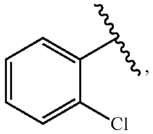,
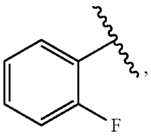, 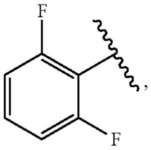, 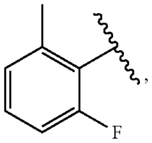,
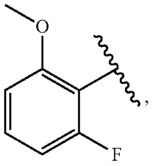, 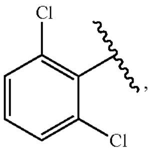, 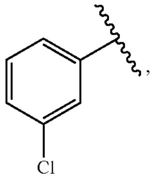,
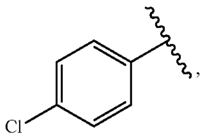, 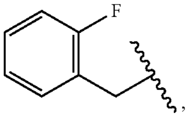,
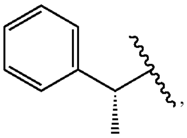, 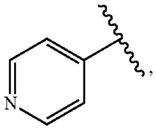, 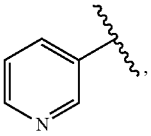,
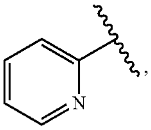, 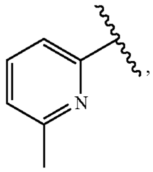, 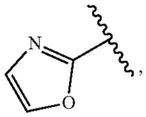,
-continued
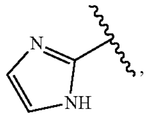, 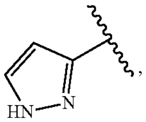, 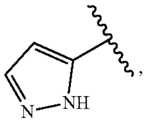, or
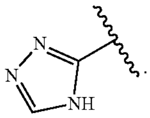.
In some embodiments, the compound has a structure selected from the group consisting of:
(Formula Ia)
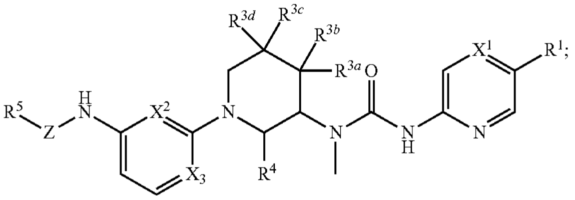
(Formula Ib)
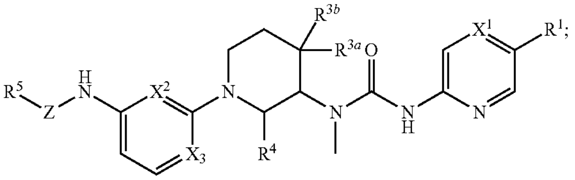
(Formula Ic)
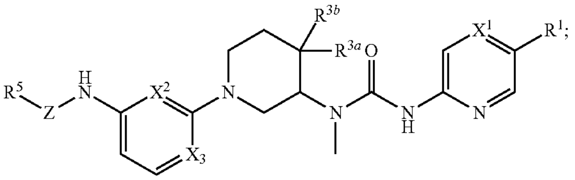
(Formula Id)
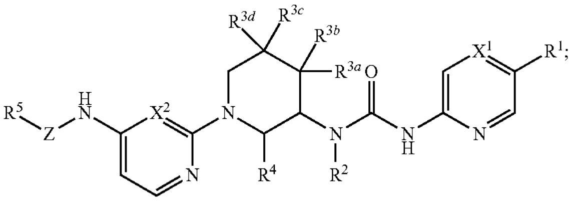
(Formula Ie)
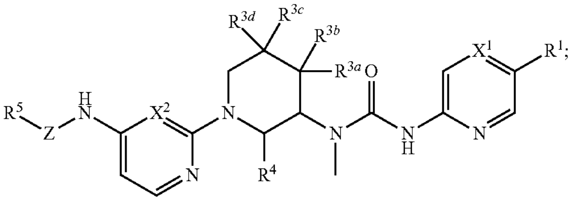

-continued (Formula If)

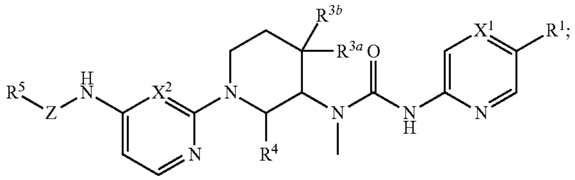

(Formula Ig)

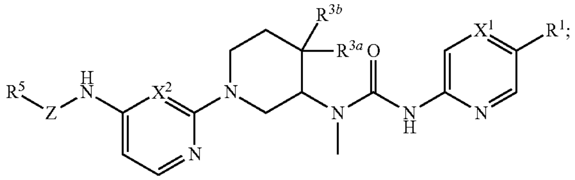

(Formula Ih)

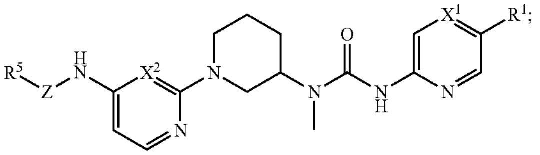

and (Formula Ii)

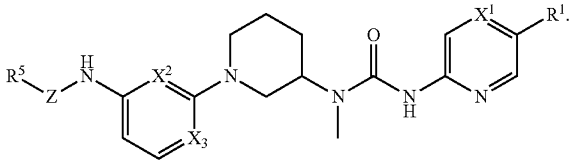

In some embodiments, the compound has a structure of Formula Ia:

(Formula Ia)

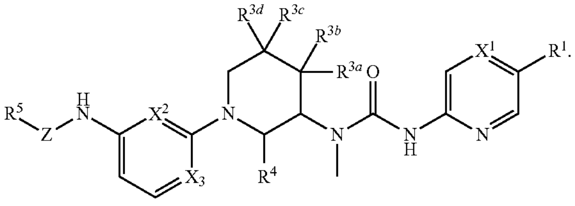

In some embodiments, the compound has a structure of Formula Ib:

(Formula Ib)

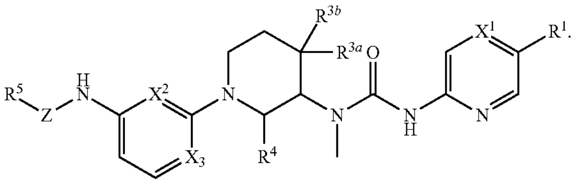

In some embodiments, the compound has a structure of Formula Ic:

(Formula Ic)

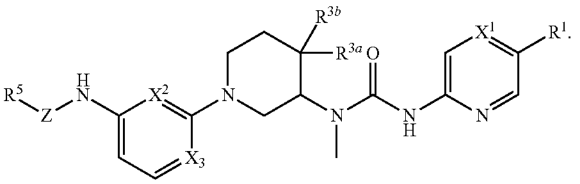

In some embodiments, the compound has a structure of Formula Id:

(Formula Id)

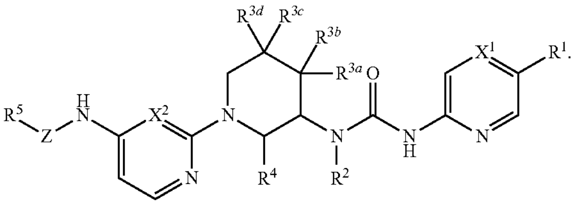

In some embodiments, the compound has a structure of Formula Ie:

(Formula Ia)

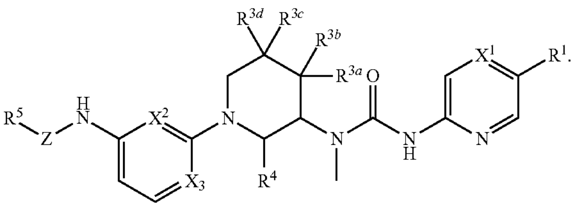

In some embodiments, the compound has a structure of Formula If:

(Formula If)

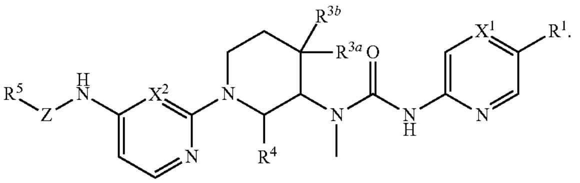

In some embodiments, the compound has a structure of Formula Ig:

(Formula Ig)

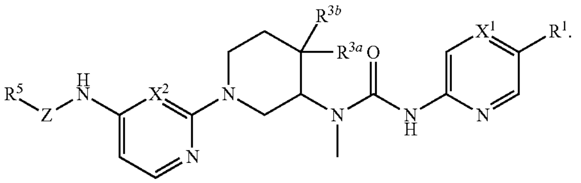

In some embodiments, the compound has a structure of Formula Ih:

(Formula Ih)

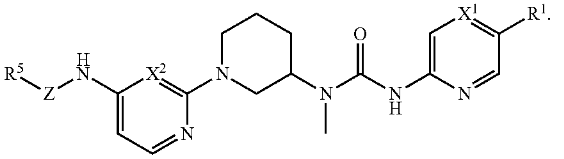

In some embodiments, the compound has a structure of Formula II:

(Formula Ii)

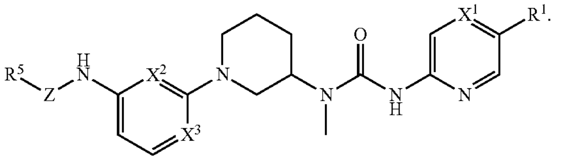

In some embodiments, the compound has a structure according to Formula Ij:

(Formula Ij)

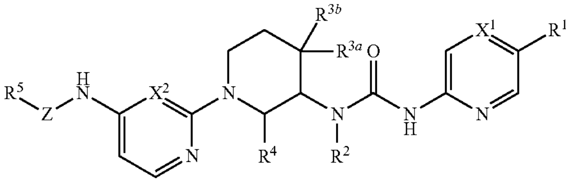

wherein:

$X^1$ is CH or N;

$X^2$ is CH or N;

Z is —C(O)—, —OC(O)—, or —$S(O)_2$—;

$R^1$ is $C_3$-$C_6$ cycloalkyl or —O—$R^{1a}$, wherein $R^{5a}$ is $C_1$-$C_6$ alkyl or —($C_1$-$C_6$ alkylene)-($C_3$-$C_6$ cycloalkyl);

$R^2$ is $C_1$-$C_3$ alkyl;

$R^{3a}$ and $R^{3b}$ are each independently H or halo;

$R^4$ is H or $C_1$-$C_6$ alkyl; and $R^5$ is —Y—$R^{5a}$, wherein Y is absent; and $R^{5a}$ is $C_1$-$C_6$ alkyl or 4- to 9-membered heterocycloalkyl; and $R^{5a}$ is unsubstituted or substituted with 1-2 substituents independently selected from OH, $NR^{5b}R^{5c}$, or $C_1$-$C_6$ alkyl; wherein the 4- to 10-membered heterocycloalkyl has 1-2 ring heteroatoms or ring heteroatom groups independently selected from N or O; and $R^{5b}$ and $R^{5c}$ are independently selected from H and $C_1$-$C_3$ alkyl.

In one or more embodiments, the compound, or pharmaceutically acceptable salt or solvate thereof, according to this disclosure is selected from the compounds provided in Table 1. In one or more embodiments, the compound according to this disclosure is selected from the compounds provided in Table 1.

TABLE 1

| Ex. No. | Structure |
|---|---|
| 1 | 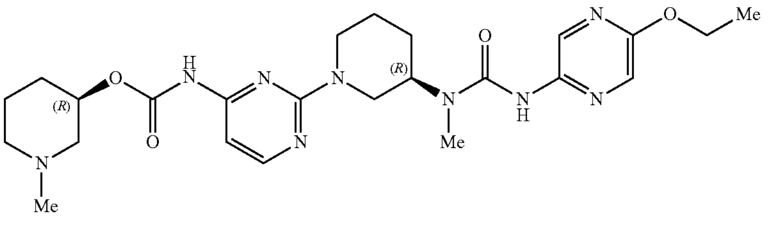 |
| 2 | 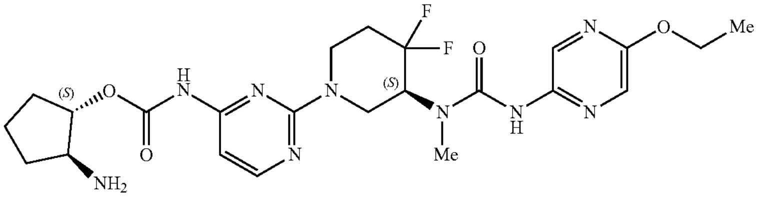 |

In one or more embodiments, the compound, or pharmaceutically acceptable salt or solvate thereof, according to this disclosure is selected from the compounds provided in Table 2A. In one or more embodiments, the compound according to this disclosure is selected from the compounds provided in Table 2A.
TABLE 2A
| Ex. No. | Structure |
| --- | --- |
| 3 | 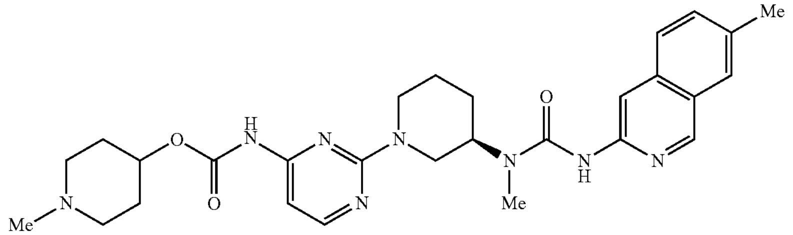 [SMILES: Cc1ccc2cc(NC(=O)N(C)[C@@H]3CCCN(c4nccc(NC(=O)OC5CCN(C)CC5)n4)C3)ncc2c1] |
| 4 | 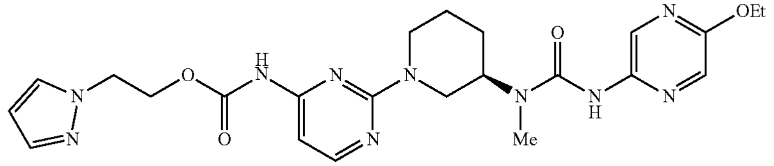 [SMILES: CCOc1cnc(NC(=O)N(C)[C@@H]2CCCN(c3nccc(NC(=O)OCCn4cccn4)n3)C2)cn1] |
| 5 | 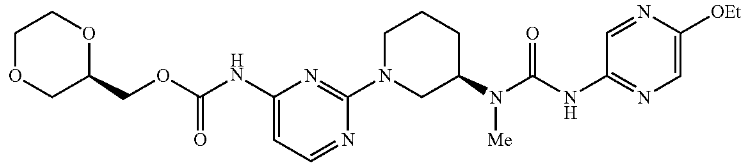 [SMILES: CCOc1cnc(NC(=O)N(C)[C@@H]2CCCN(c3nccc(NC(=O)OC[C@H]4COCCO4)n3)C2)cn1] |
| 6 | 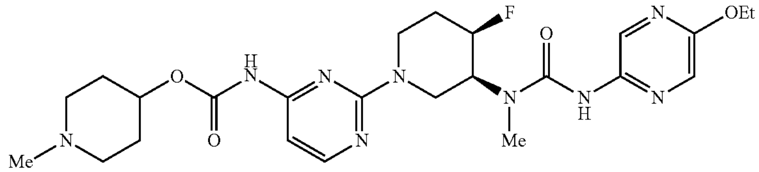 [SMILES: CCOc1cnc(NC(=O)N(C)[C@H]2CN(c3nccc(NC(=O)OC4CCN(C)CC4)n3)CC[C@H]2F)cn1] |
| 7 | 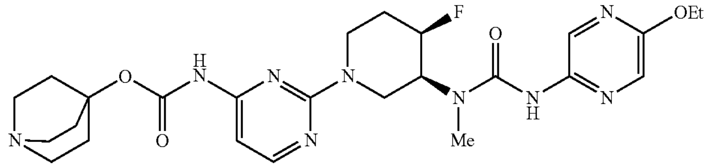 [SMILES: CCOc1cnc(NC(=O)N(C)[C@H]2CN(c3nccc(NC(=O)OC45CCN(CC4)CC5)n3)CC[C@H]2F)cn1] |
| 8 | 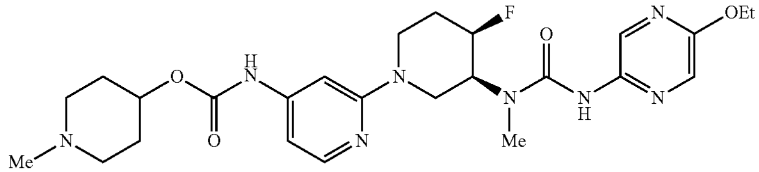 [SMILES: CCOc1cnc(NC(=O)N(C)[C@H]2CN(c3cc(NC(=O)OC4CCN(C)CC4)ccn3)CC[C@H]2F)cn1] |
| 9 | 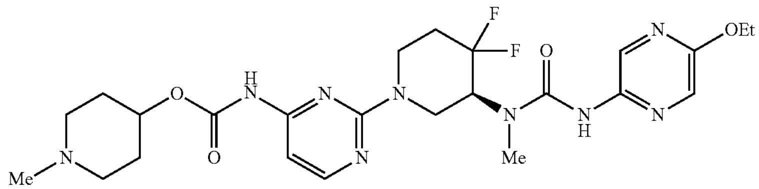 [SMILES: CCOc1cnc(NC(=O)N(C)[C@H]2CN(c3nccc(NC(=O)OC4CCN(C)CC4)n3)CCC2(F)F)cn1] |

TABLE 2A-continued
| Ex. No. | Structure |
|---|---|
| 10 | 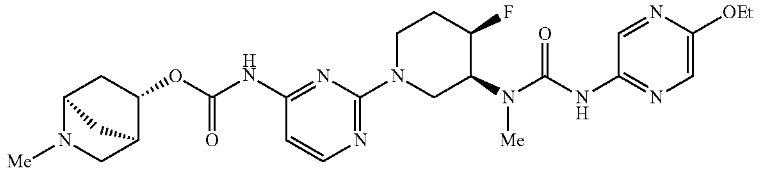 [SMILES: CCOc1cnc(NC(=O)N(C)[C@H]2CN(c3nccc(NC(=O)O[C@H]4C[C@H]5C[C@@H]4CN5C)n3)CC[C@H]2F)cn1] |
| 11 | 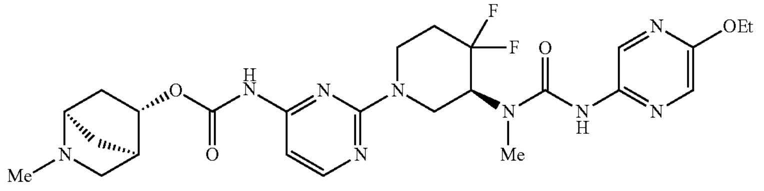 [SMILES: CCOc1cnc(NC(=O)N(C)[C@H]2CN(c3nccc(NC(=O)O[C@H]4C[C@H]5C[C@@H]4CN5C)n3)CCC2(F)F)cn1] |
| 12 | 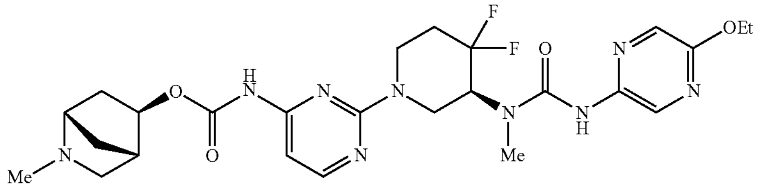 [SMILES: CCOc1cnc(NC(=O)N(C)[C@H]2CN(c3nccc(NC(=O)O[C@@H]4C[C@@H]5C[C@H]4CN5C)n3)CCC2(F)F)cn1] |
| 13 | 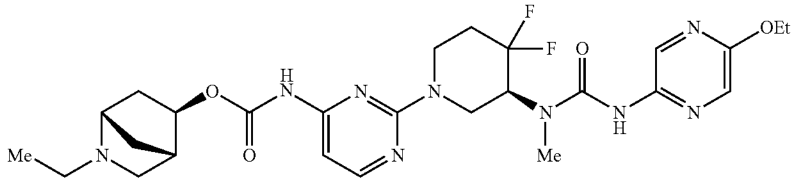 [SMILES: CCOc1cnc(NC(=O)N(C)[C@H]2CN(c3nccc(NC(=O)O[C@@H]4C[C@@H]5C[C@H]4CN5CC)n3)CCC2(F)F)cn1] |
| 14 | 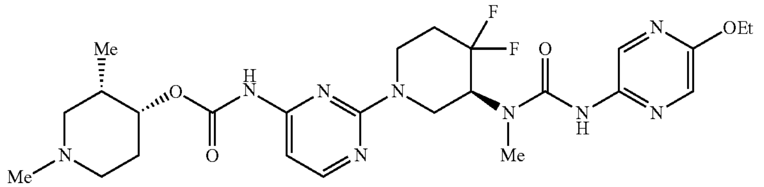 [SMILES: CCOc1cnc(NC(=O)N(C)[C@H]2CN(c3nccc(NC(=O)O[C@@H]4CCN(C)C[C@@H]4C)n3)CCC2(F)F)cn1] |
| 15 | 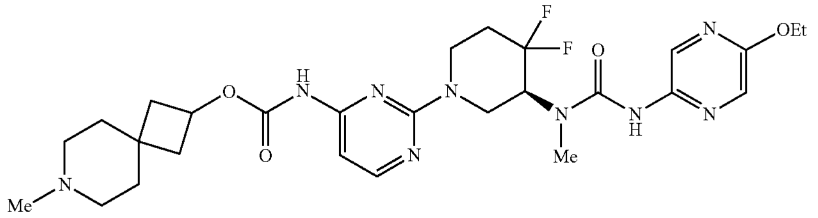 [SMILES: CCOc1cnc(NC(=O)N(C)[C@H]2CN(c3nccc(NC(=O)OC4CC5(CCN(C)CC5)C4)n3)CCC2(F)F)cn1] |
| 16 | 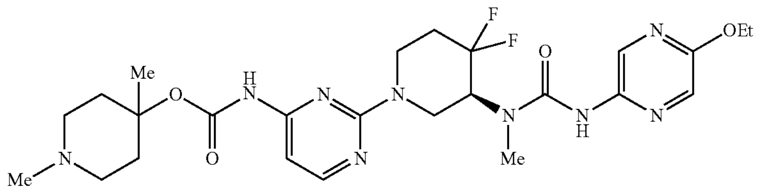 [SMILES: CCOc1cnc(NC(=O)N(C)[C@H]2CN(c3nccc(NC(=O)OC4(C)CCN(C)CC4)n3)CCC2(F)F)cn1] |
| 17 | 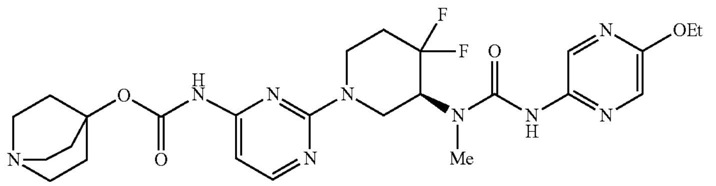 [SMILES: CCOc1cnc(NC(=O)N(C)[C@H]2CN(c3nccc(NC(=O)OC45CCN(CC4)CC5)n3)CCC2(F)F)cn1] |

TABLE 2A-continued
| Ex. No. | Structure |
| --- | --- |
| 18 | 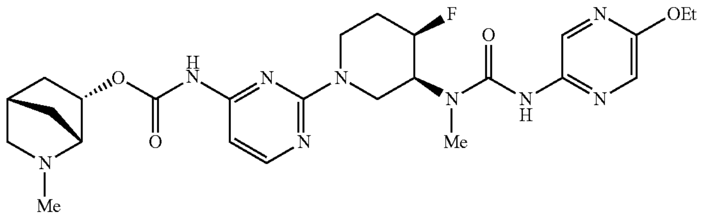 [SMILES: CCOc1cnc(NC(=O)N(C)[C@H]2CN(c3nccc(NC(=O)O[C@H]4C[C@@H]5C[C@H]4N(C)C5)n3)CC[C@H]2F)cn1] |
| 19 | 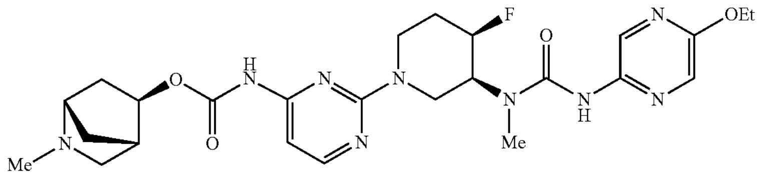 [SMILES: CCOc1cnc(NC(=O)N(C)[C@H]2CN(c3nccc(NC(=O)O[C@@H]4C[C@@H]5C[C@H]4CN5C)n3)CC[C@H]2F)cn1] |
| 20 | 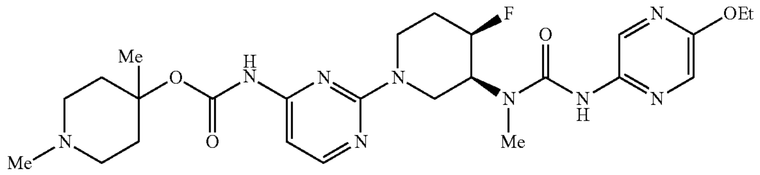 [SMILES: CCOc1cnc(NC(=O)N(C)[C@H]2CN(c3nccc(NC(=O)OC4(C)CCN(C)CC4)n3)CC[C@H]2F)cn1] |
| 21 | 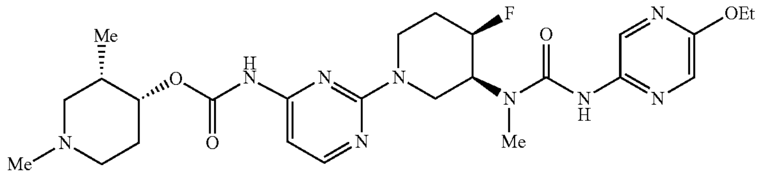 [SMILES: CCOc1cnc(NC(=O)N(C)[C@H]2CN(c3nccc(NC(=O)O[C@@H]4CCN(C)C[C@@H]4C)n3)CC[C@H]2F)cn1] |
| 22 | 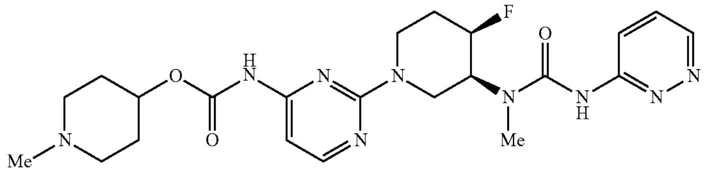 [SMILES: CN1CCC(OC(=O)Nc2ccnc(N3CC[C@@H](F)[C@@H](N(C)C(=O)Nc4cccnn4)C3)n2)CC1] |
| 23 | 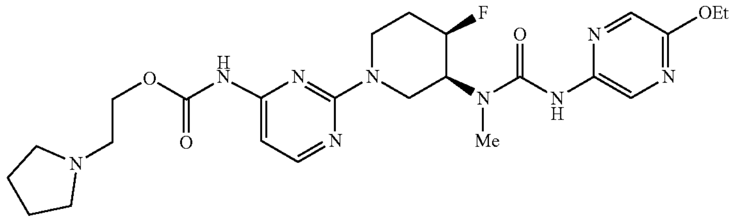 [SMILES: CCOc1cnc(NC(=O)N(C)[C@H]2CN(c3nccc(NC(=O)OCCN4CCCC4)n3)CC[C@H]2F)cn1] |
| 24 | 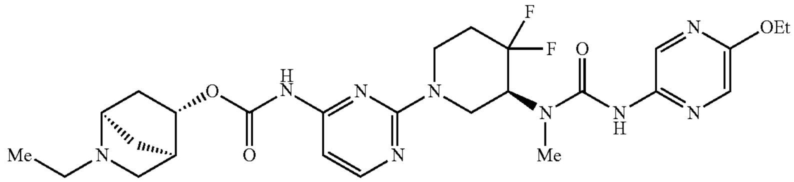 [SMILES: CCOc1cnc(NC(=O)N(C)[C@H]2CN(c3nccc(NC(=O)O[C@H]4C[C@H]5C[C@@H]4CN5CC)n3)CCC2(F)F)cn1] |
| 25 | 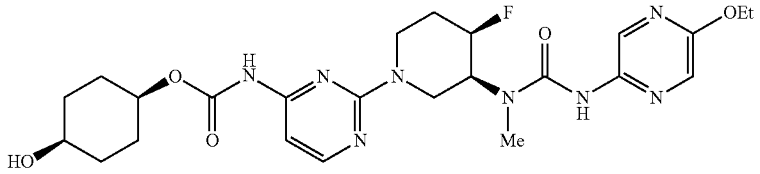 [SMILES: CCOc1cnc(NC(=O)N(C)[C@H]2CN(c3nccc(NC(=O)O[C@H]4CC[C@@H](O)CC4)n3)CC[C@H]2F)cn1] |

TABLE 2A-continued
| Ex. No. | Structure |
|---|---|
| 26 | 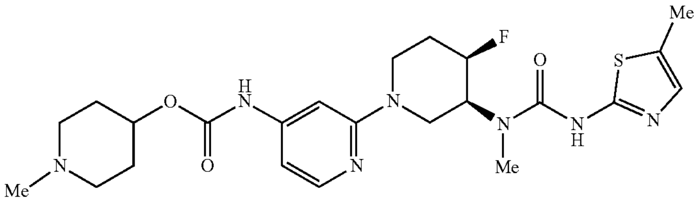 [SMILES: Cc1cnc(NC(=O)N(C)[C@H]2CN(c3cc(NC(=O)OC4CCN(C)CC4)ccn3)CC[C@H]2F)s1] |
| 27 | 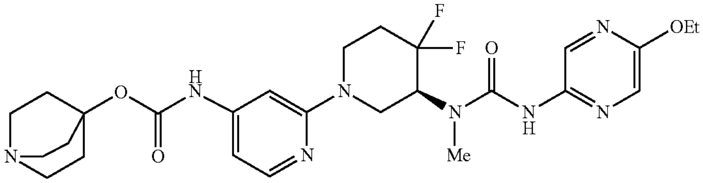 [SMILES: CCOc1cnc(NC(=O)N(C)[C@H]2CN(c3cc(NC(=O)OC45CCN(CC4)CC5)ccn3)CCC2(F)F)cn1] |
| 28 | 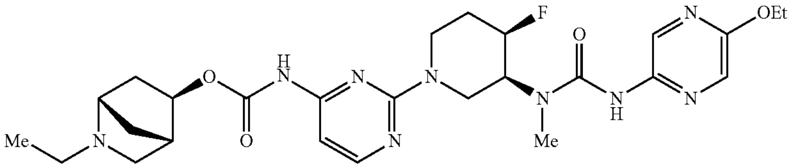 [SMILES: CCOc1cnc(NC(=O)N(C)[C@H]2CN(c3nccc(NC(=O)O[C@@H]4C[C@@H]5C[C@H]4CN5CC)n3)CC[C@H]2F)cn1] |
TABLE 2B
| Ex. No. | Structure |
|---|---|
| 29 | 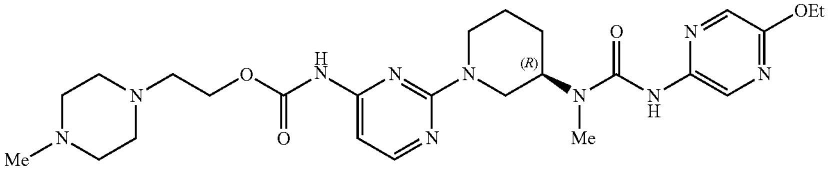 |
| 30 | 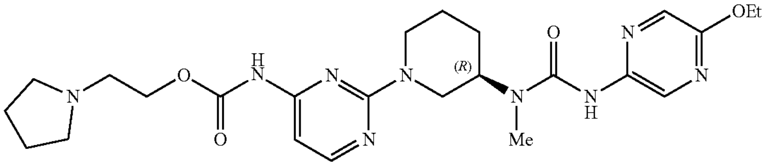 |
| 31 | 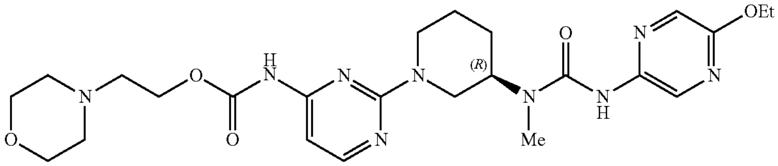 |
| 32 | 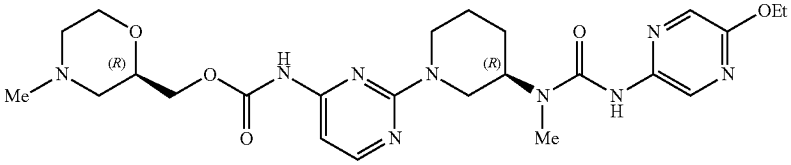 |

TABLE 2B-continued
| Ex. No. | Structure |
|---|---|
| 33 | 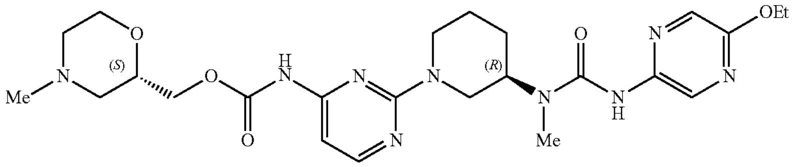 |
| 34 | 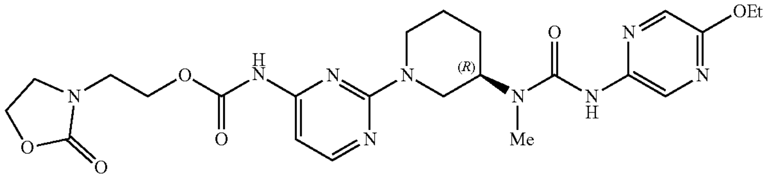 |
| 35 | 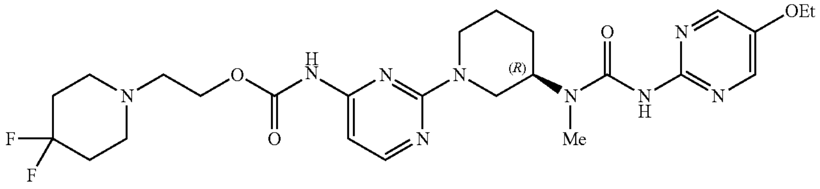 |
| 36 | 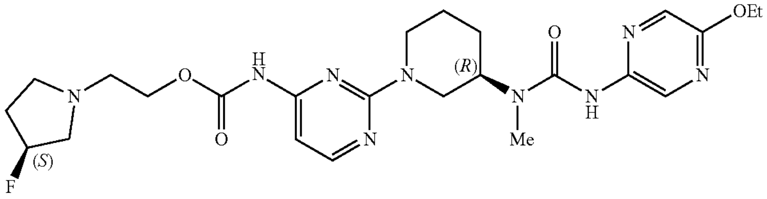 |
| 37 | 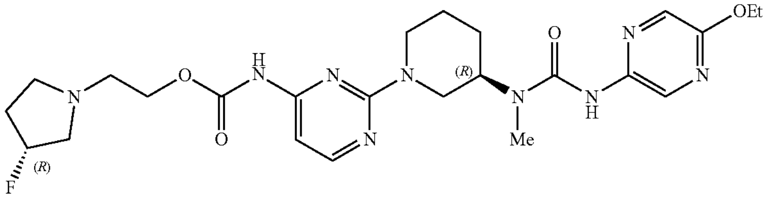 |
| 38 | 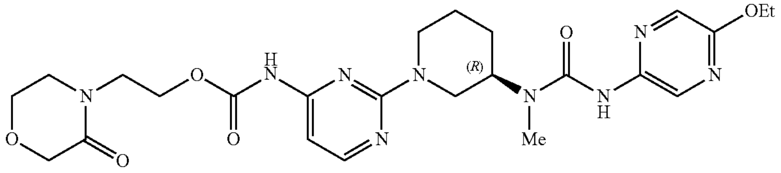 |
| 39 | 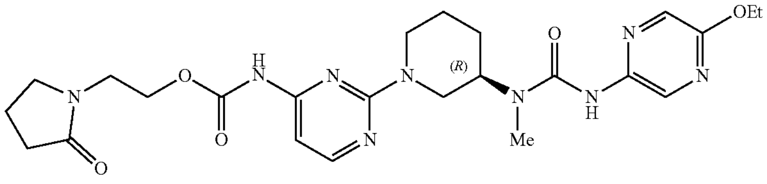 |
| 40 | 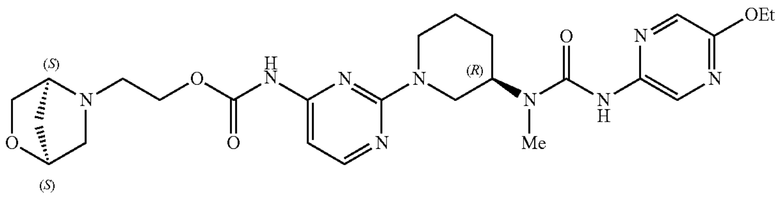 |

TABLE 2B-continued
| Ex. No. | Structure |
|---|---|
| 41 | 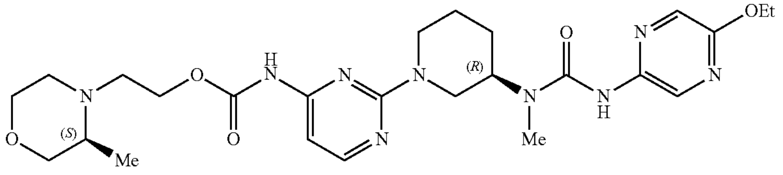 |
| 42 | 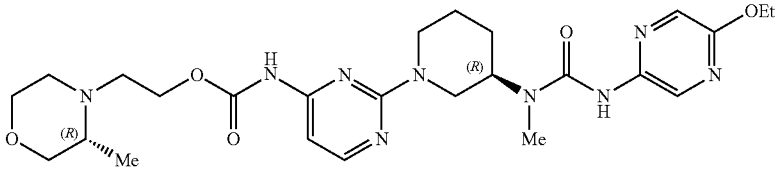 |
| 43 | 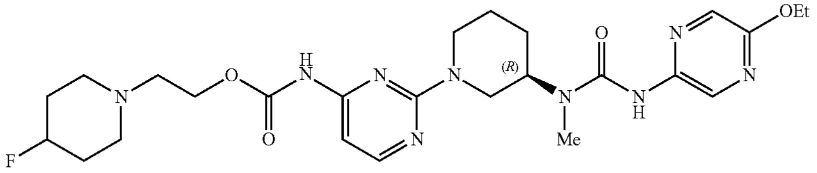 |
| 44 | 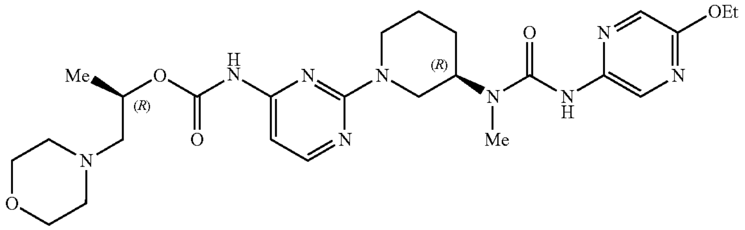 |
| 45 | 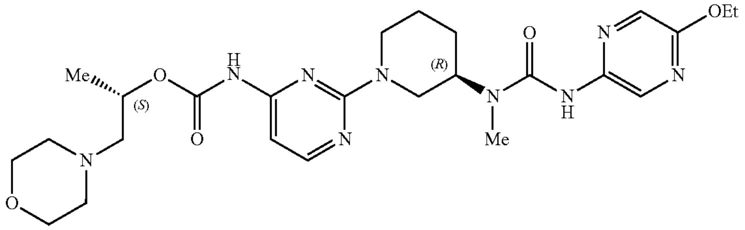 |
| 46 | 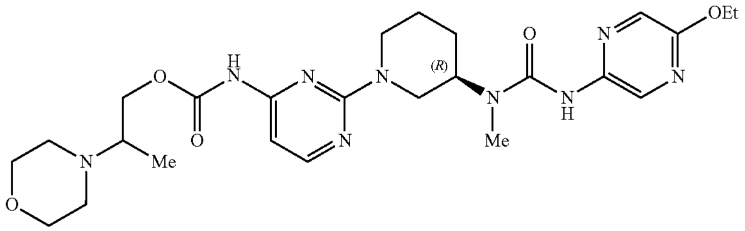 |
| 47 | 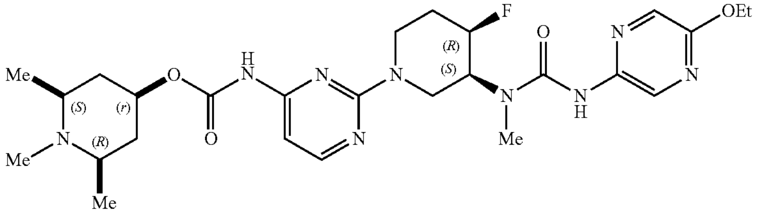 |

TABLE 2B-continued
| Ex. No. | Structure |
|---|---|
| 48 | 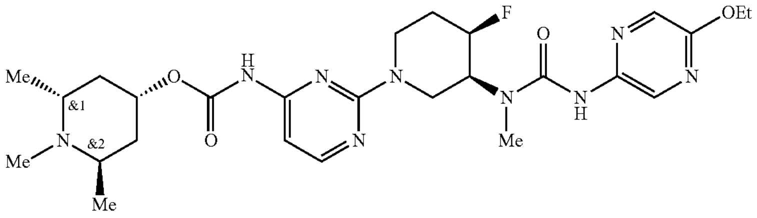 |
| 49 | 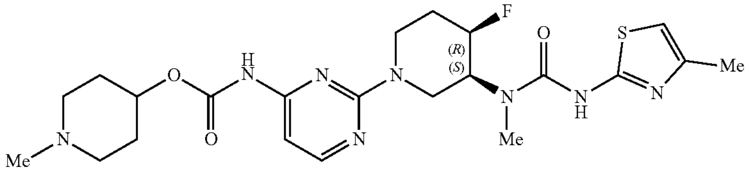 |
| 50 | 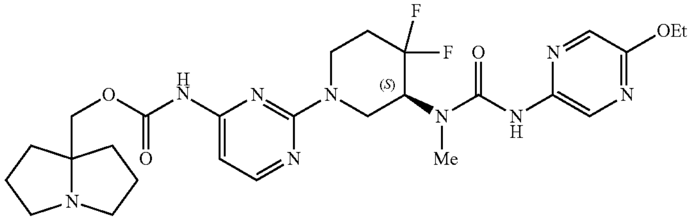 |
| 51 | 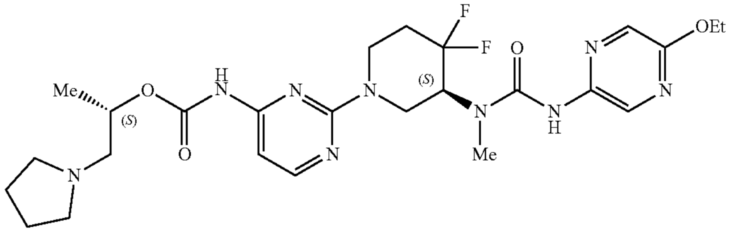 |
| 52 | 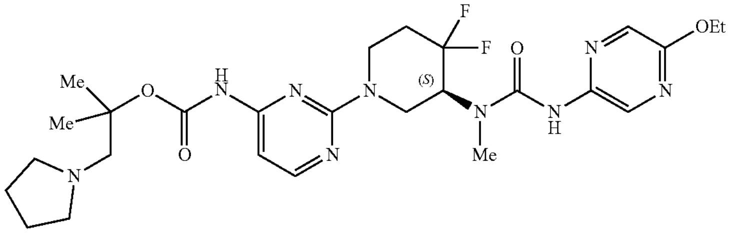 |
| 53 | 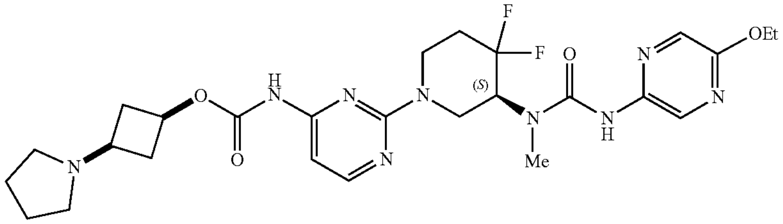 |
| 54 | 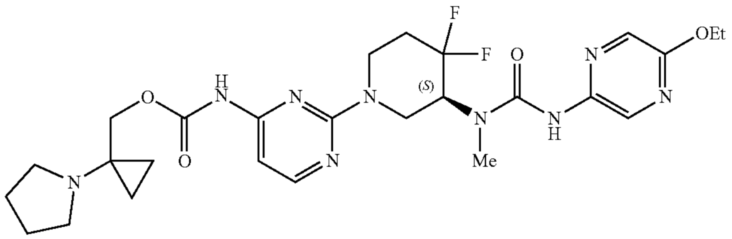 |

TABLE 2B-continued
| Ex. No. | Structure |
|---|---|
| 55 | 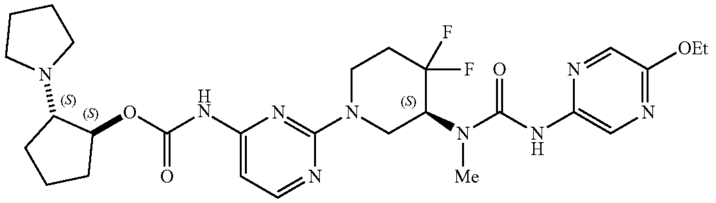 |
| 56 | 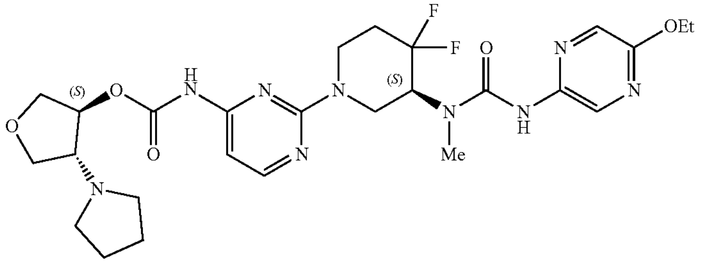 |
| 57 | 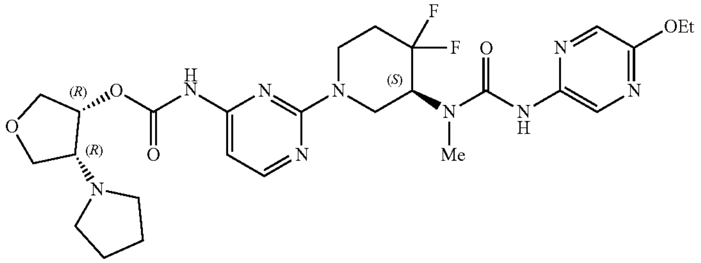 |
| 58 | 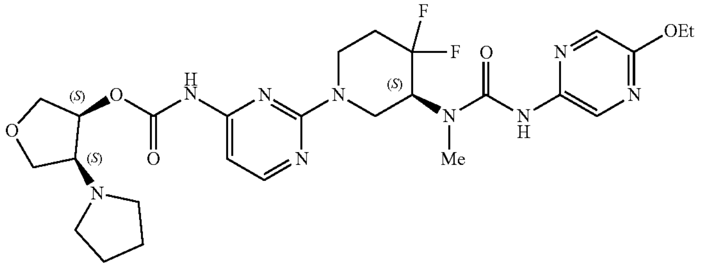 |
| 59 | 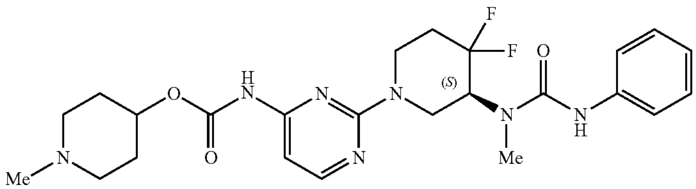 |
| 60 | 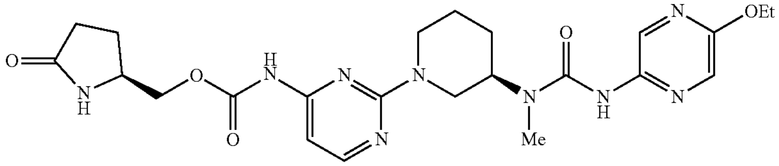 [SMILES: CCOc1cnc(NC(=O)N(C)[C@@H]2CCCN(c3nccc(NC(=O)OC[C@@H]4CCC(=O)N4)n3)C2)cn1] |

TABLE 2B-continued
| Ex. No. | Structure |
|---|---|
| 61 | 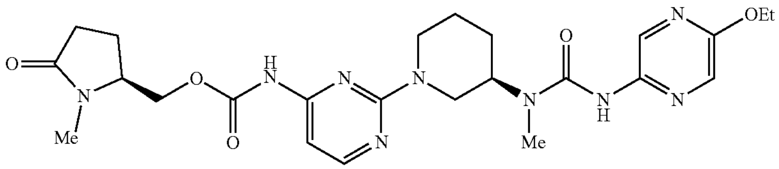 [SMILES: CCOc1cnc(NC(=O)N(C)[C@@H]2CCCN(c3nccc(NC(=O)OC[C@@H]4CCC(=O)N4C)n3)C2)cn1] |
| 62 | 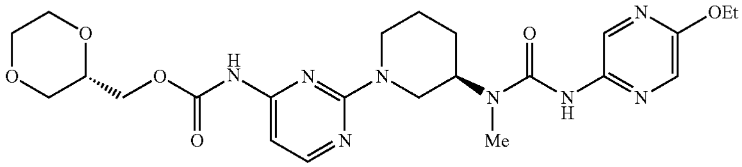 [SMILES: CCOc1cnc(NC(=O)N(C)[C@@H]2CCCN(c3nccc(NC(=O)OC[C@@H]4COCCO4)n3)C2)cn1] |
| 63 | 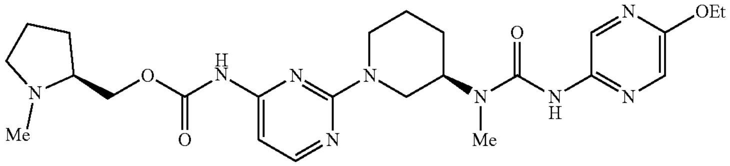 [SMILES: CCOc1cnc(NC(=O)N(C)[C@@H]2CCCN(c3nccc(NC(=O)OC[C@@H]4CCCN4C)n3)C2)cn1] |
| 64 | 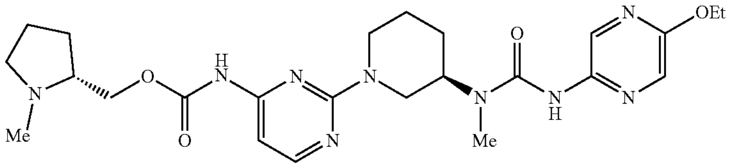 [SMILES: CCOc1cnc(NC(=O)N(C)[C@@H]2CCCN(c3nccc(NC(=O)OC[C@H]4CCCN4C)n3)C2)cn1] |
| 65 | 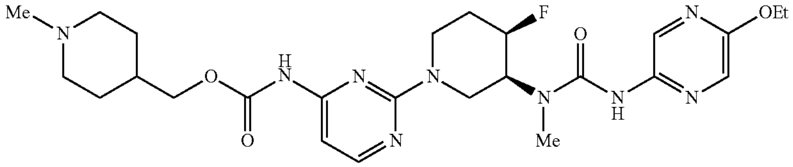 [SMILES: CCOc1cnc(NC(=O)N(C)[C@H]2CN(c3nccc(NC(=O)OCC4CCN(C)CC4)n3)CC[C@H]2F)cn1] |
| 66 | 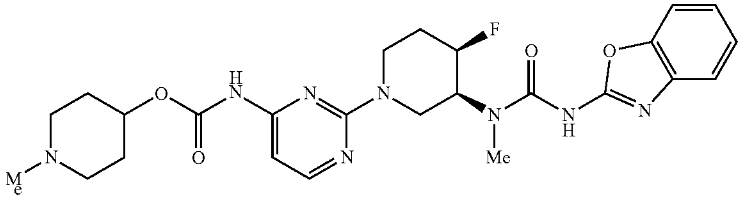 [SMILES: CN1CCC(OC(=O)Nc2ccnc(N3CC[C@@H](F)[C@@H](N(C)C(=O)Nc4nc5ccccc5o4)C3)n2)CC1] |
| 67 | 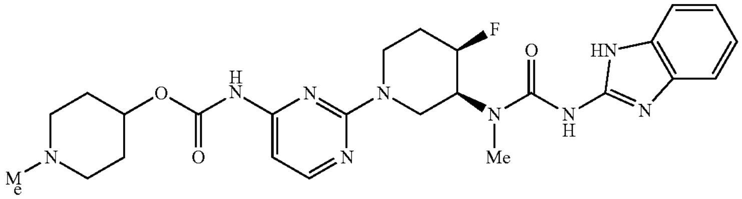 [SMILES: CN1CCC(OC(=O)Nc2ccnc(N3CC[C@@H](F)[C@@H](N(C)C(=O)Nc4nc5ccccc5[nH]4)C3)n2)CC1] |
| 68 | 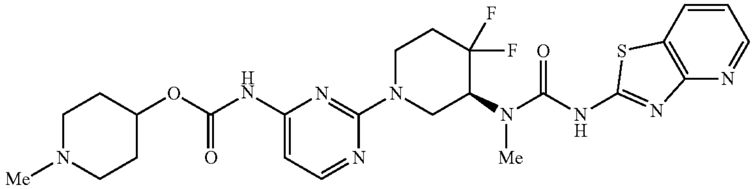 [SMILES: CN1CCC(OC(=O)Nc2ccnc(N3CCC(F)(F)[C@@H](N(C)C(=O)Nc4nc5ncccc5s4)C3)n2)CC1] |

TABLE 2B-continued
| Ex. No. | Structure |
| --- | --- |
| 69 | 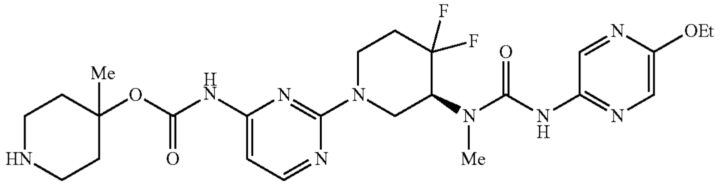 [SMILES: CCOc1cnc(NC(=O)N(C)[C@H]2CN(c3nccc(NC(=O)OC4(C)CCNCC4)n3)CCC2(F)F)cn1] |
| 70 | 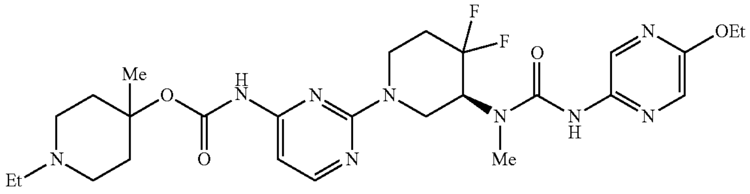 [SMILES: CCOc1cnc(NC(=O)N(C)[C@H]2CN(c3nccc(NC(=O)OC4(C)CCN(CC)CC4)n3)CCC2(F)F)cn1] |
| 71 | 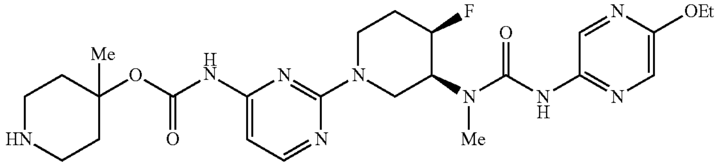 [SMILES: CCOc1cnc(NC(=O)N(C)[C@H]2CN(c3nccc(NC(=O)OC4(C)CCNCC4)n3)CC[C@H]2F)cn1] |
| 72 | 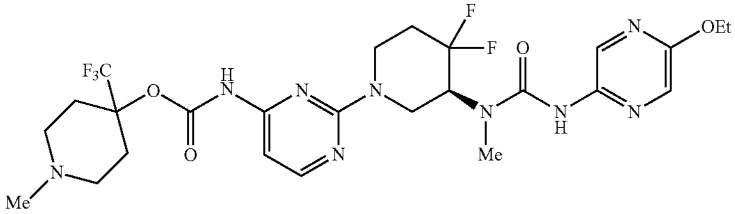 [SMILES: CCOc1cnc(NC(=O)N(C)[C@H]2CN(c3nccc(NC(=O)OC4(C(F)(F)F)CCN(C)CC4)n3)CCC2(F)F)cn1] |
| 73 | 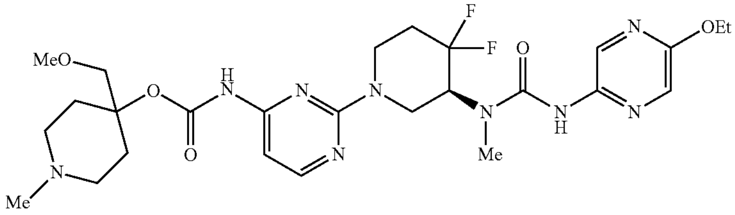 [SMILES: CCOc1cnc(NC(=O)N(C)[C@H]2CN(c3nccc(NC(=O)OC4(COC)CCN(C)CC4)n3)CCC2(F)F)cn1] |
| 74 | 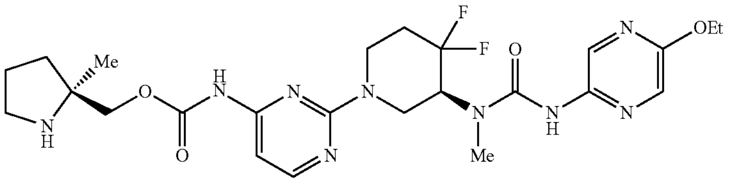 [SMILES: CCOc1cnc(NC(=O)N(C)[C@H]2CN(c3nccc(NC(=O)OC[C@]4(C)CCCN4)n3)CCC2(F)F)cn1] |
| 75 | 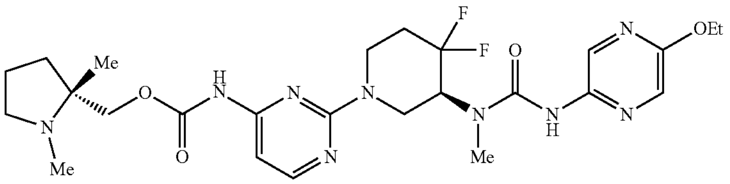 [SMILES: CCOc1cnc(NC(=O)N(C)[C@H]2CN(c3nccc(NC(=O)OC[C@@]4(C)CCCN4C)n3)CCC2(F)F)cn1] |

TABLE 2B-continued
| Ex. No. | Structure |
|---|---|
| 76 | 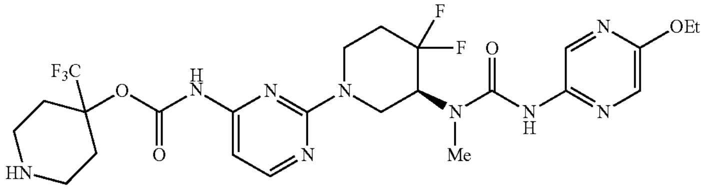 [SMILES: CCOc1cnc(NC(=O)N(C)[C@H]2CN(c3nccc(NC(=O)OC4(C(F)(F)F)CCNCC4)n3)CCC2(F)F)cn1] |
| 77 | 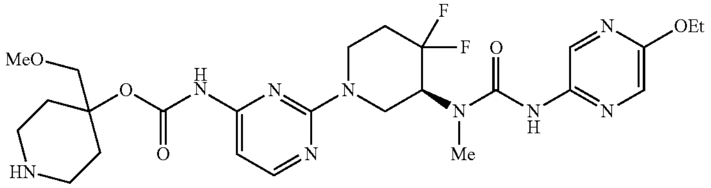 [SMILES: CCOc1cnc(NC(=O)N(C)[C@H]2CN(c3nccc(NC(=O)OC4(COC)CCNCC4)n3)CCC2(F)F)cn1] |
| 78 | 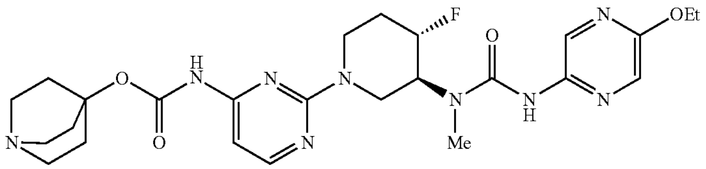 [SMILES: CCOc1cnc(NC(=O)N(C)[C@H]2CN(c3nccc(NC(=O)OC45CCN(CC4)CC5)n3)CC[C@@H]2F)cn1] |
| 79 | 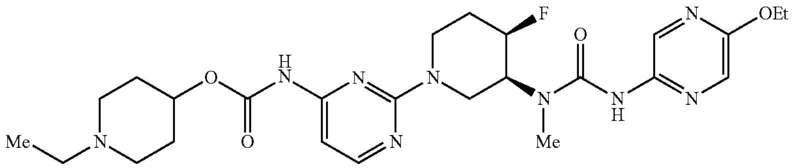 [SMILES: CCOc1cnc(NC(=O)N(C)[C@H]2CN(c3nccc(NC(=O)OC4CCN(CC)CC4)n3)CC[C@H]2F)cn1] |
| 80 | 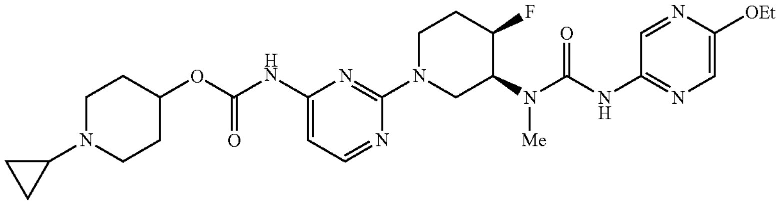 [SMILES: CCOc1cnc(NC(=O)N(C)[C@H]2CN(c3nccc(NC(=O)OC4CCN(C5CC5)CC4)n3)CC[C@H]2F)cn1] |
| 81 | 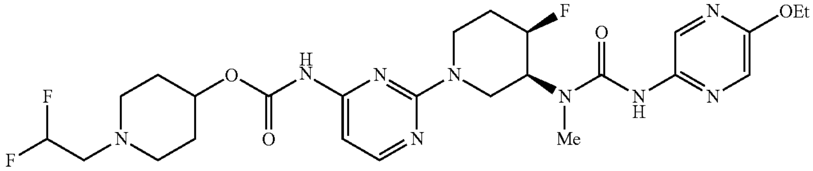 [SMILES: CCOc1cnc(NC(=O)N(C)[C@H]2CN(c3nccc(NC(=O)OC4CCN(CC(F)F)CC4)n3)CC[C@H]2F)cn1] |
| 82 | 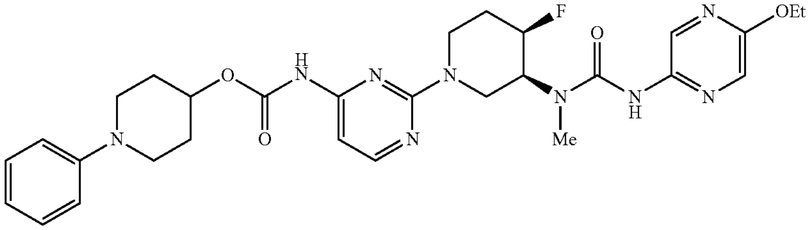 [SMILES: CCOc1cnc(NC(=O)N(C)[C@H]2CN(c3nccc(NC(=O)OC4CCN(c5ccccc5)CC4)n3)CC[C@H]2F)cn1] |
| 83 | 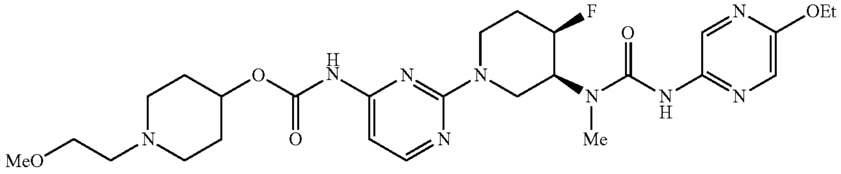 [SMILES: CCOc1cnc(NC(=O)N(C)[C@H]2CN(c3nccc(NC(=O)OC4CCN(CCOC)CC4)n3)CC[C@H]2F)cn1] |

TABLE 2B-continued
| Ex. No. | Structure |
|---|---|
| 84 | 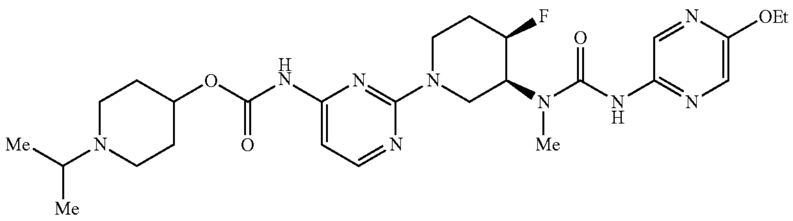 [SMILES: CCOc1cnc(NC(=O)N(C)[C@H]2CN(c3nccc(NC(=O)OC4CCN(C(C)C)CC4)n3)CC[C@H]2F)cn1] |
| 85 | 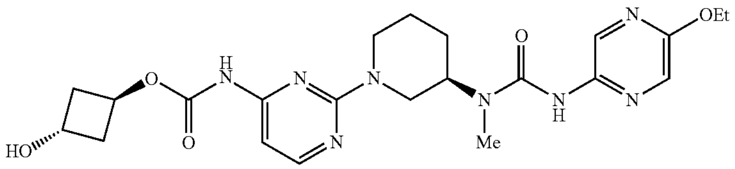 [SMILES: CCOc1cnc(NC(=O)N(C)[C@@H]2CCCN(c3nccc(NC(=O)O[C@H]4C[C@H](O)C4)n3)C2)cn1] |
| 86 | 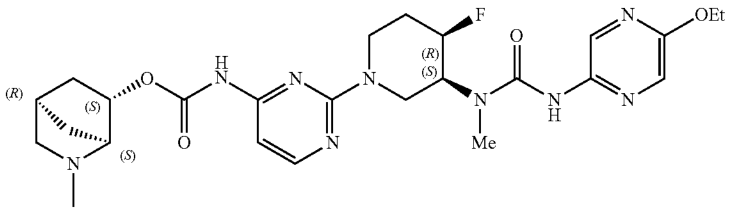 |
| 87 | 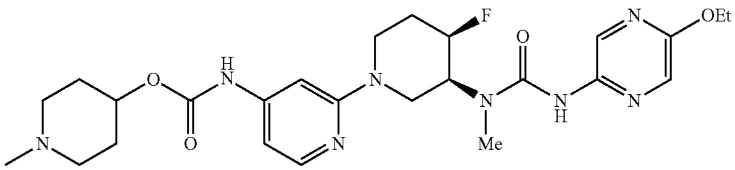 [SMILES: CCOc1cnc(NC(=O)N(C)[C@H]2CN(c3cc(NC(=O)OC4CCN(C)CC4)ccn3)CC[C@H]2F)cn1] |
| 88 | 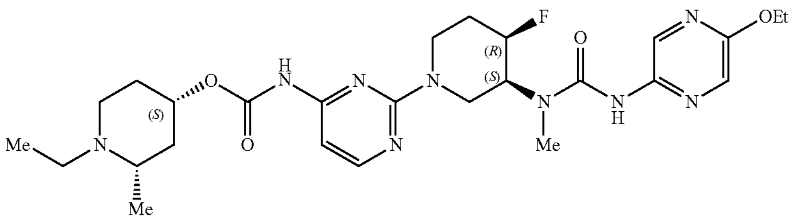 |
| 89 | 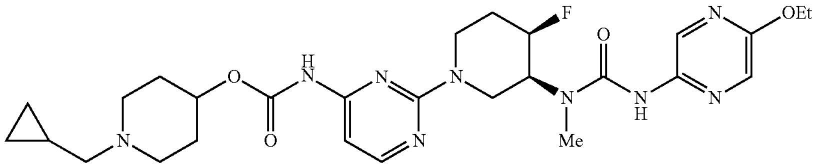 [SMILES: CCOc1cnc(NC(=O)N(C)[C@H]2CN(c3nccc(NC(=O)OC4CCN(CC5CC5)CC4)n3)CC[C@H]2F)cn1] |
| 90 | 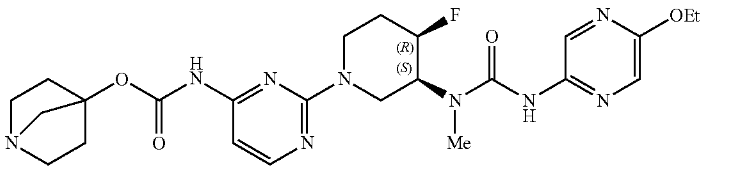 |

TABLE 2B-continued
| Ex. No. | Structure |
|---|---|
| 91 | 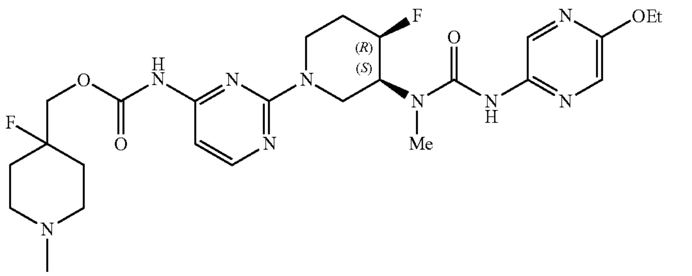 |
| 92 | 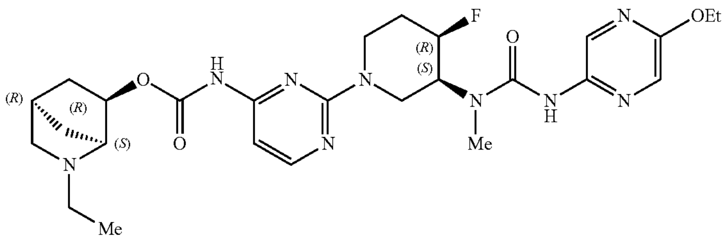 |
| 93 | 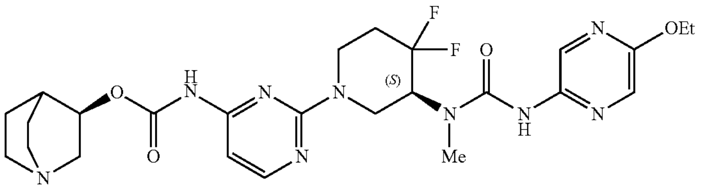 |
| 94 | 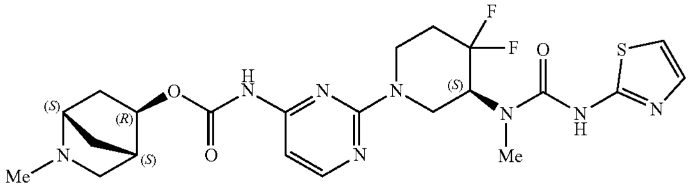 |
| 95 | 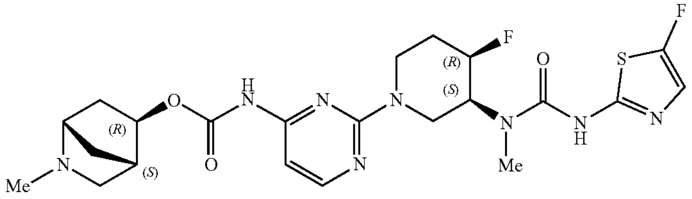 |
| 96 | 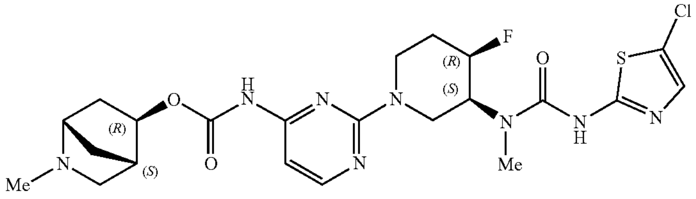 |
| 97 | 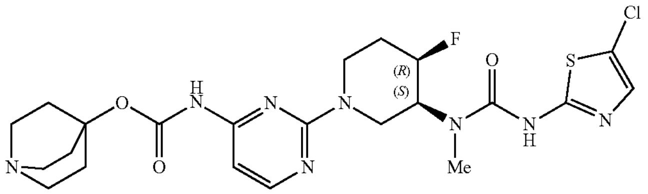 |

TABLE 2B-continued
| Ex. No. | Structure |
|---|---|
| 98 | 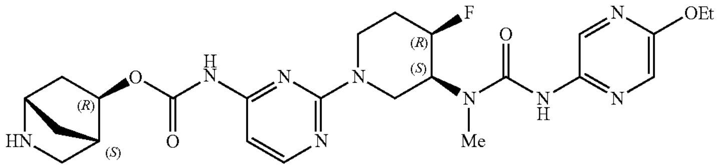 |
| 99 | 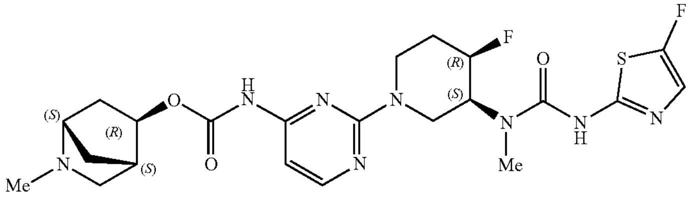 |
| 100 | 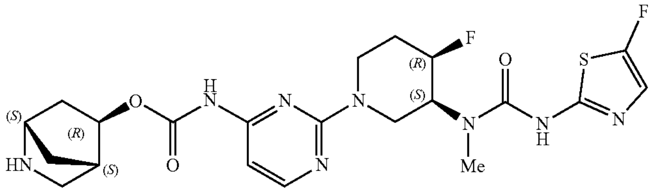 |
| 101 | 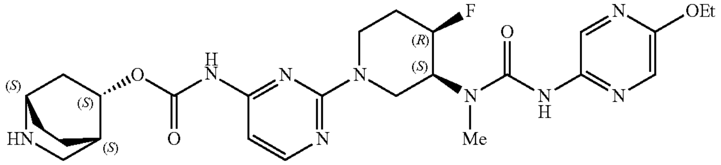 |
| 102 | 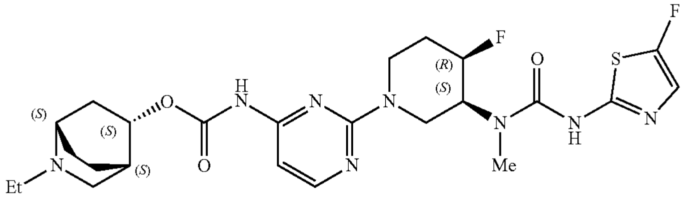 |
| 103 | 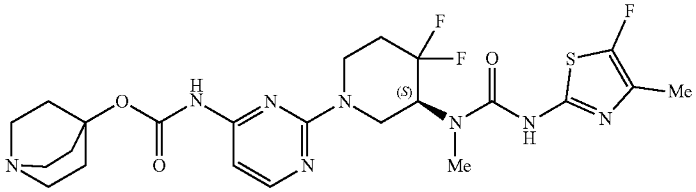 |
| 104 | 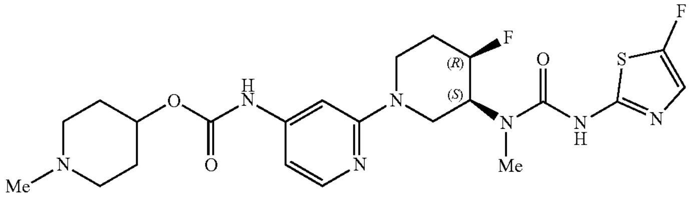 |
| 105 | 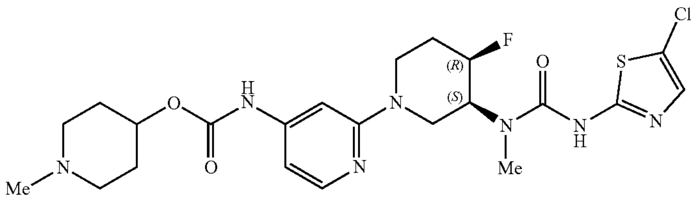 |

TABLE 2B-continued
| Ex. No. | Structure |
|---|---|
| 106 | 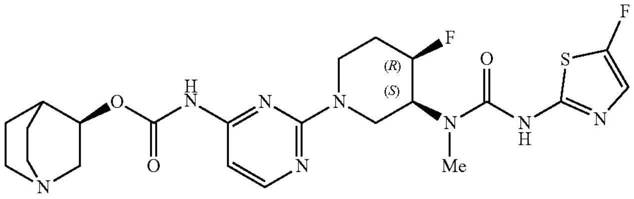 |
| 107 | 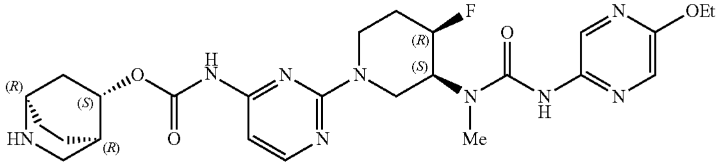 |
| 108 | 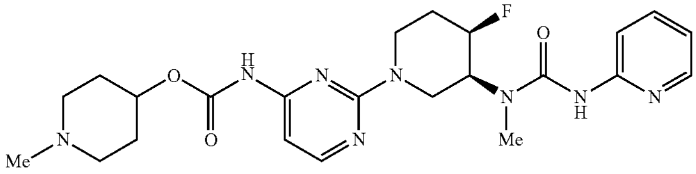 [SMILES: CN1CCC(OC(=O)Nc2ccnc(N3CC[C@@H](F)[C@@H](N(C)C(=O)Nc4ccccn4)C3)n2)CC1] |
| 109 | 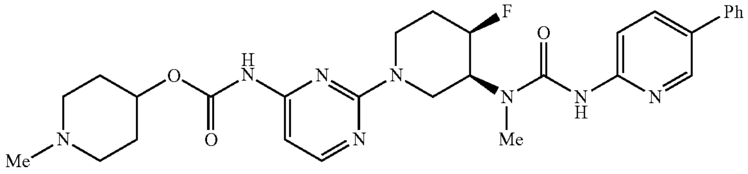 [SMILES: CN1CCC(OC(=O)Nc2ccnc(N3CC[C@@H](F)[C@@H](N(C)C(=O)Nc4ccc(-c5ccccc5)cn4)C3)n2)CC1] |
| 110 | 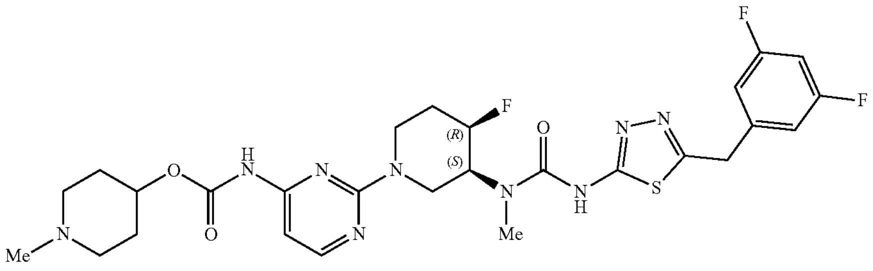 |
| 111 | 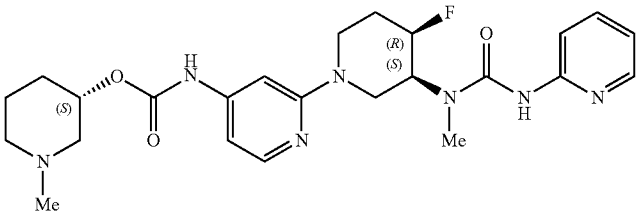 |
| 112 | 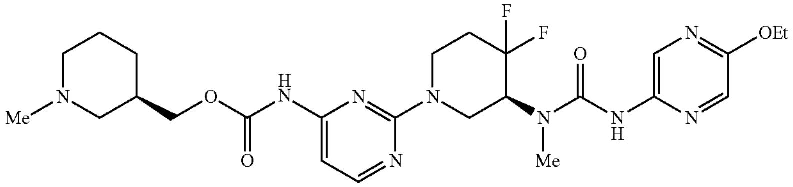 [SMILES: CCOc1cnc(NC(=O)N(C)[C@H]2CN(c3nccc(NC(=O)OC[C@@H]4CCCN(C)C4)n3)CCC2(F)F)cn1] |

TABLE 2B-continued
| Ex. No. | Structure |
| --- | --- |
| 113 | 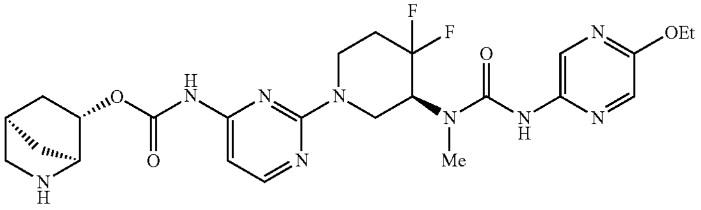 [SMILES: CCOc1cnc(NC(=O)N(C)[C@H]2CN(c3nccc(NC(=O)O[C@H]4C[C@@H]5CN[C@H]4C5)n3)CCC2(F)F)cn1] |
| 114 | 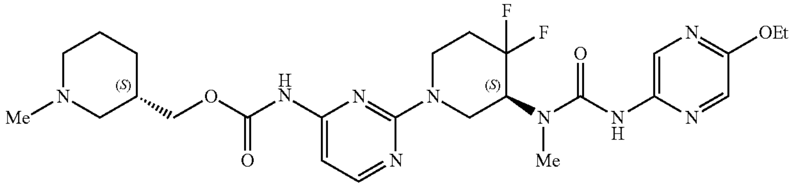 |
| 115 | 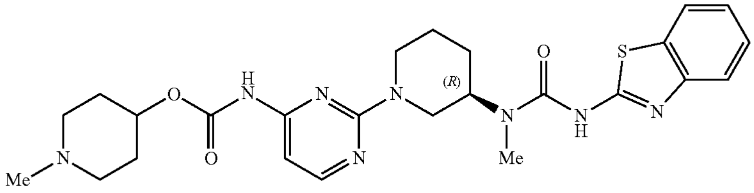 |
| 116 | 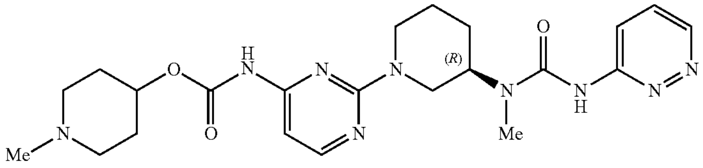 |
| 117 | 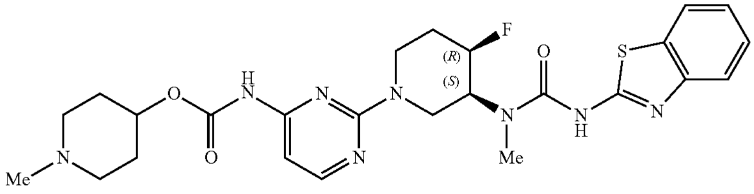 |
| 118 | 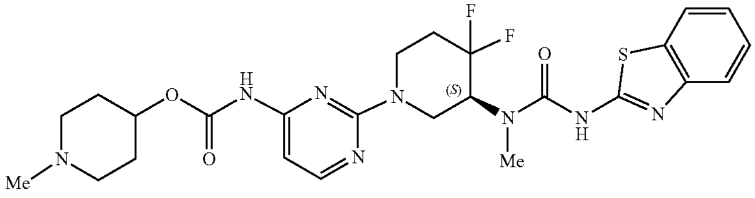 |
| 119 | 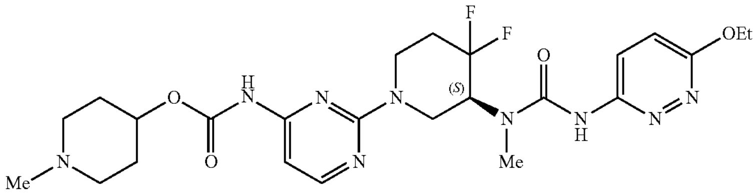 |

TABLE 2B-continued
| Ex. No. | Structure |
|---|---|
| 120 | 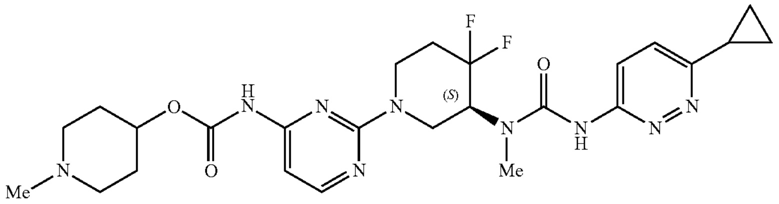 |
| 121A | 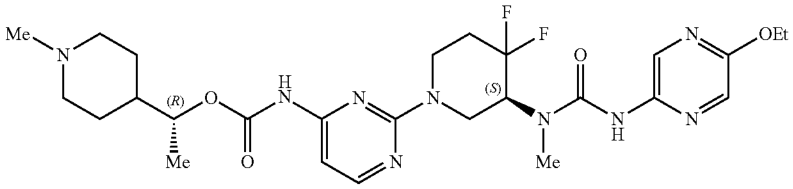 |
| 121B | 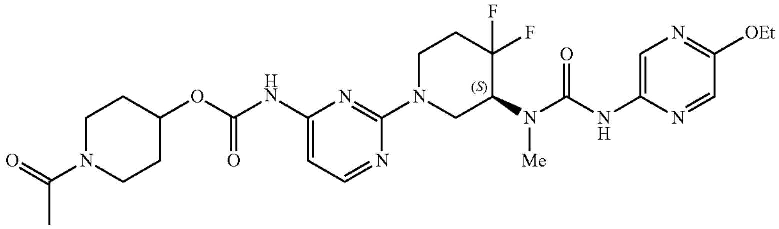 |
| 122 | 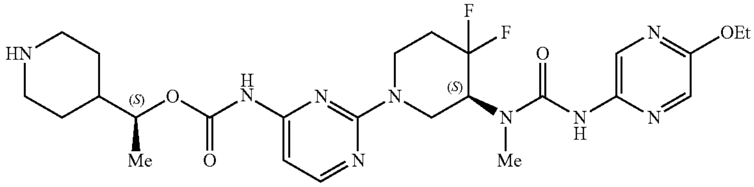 |
| 123 | 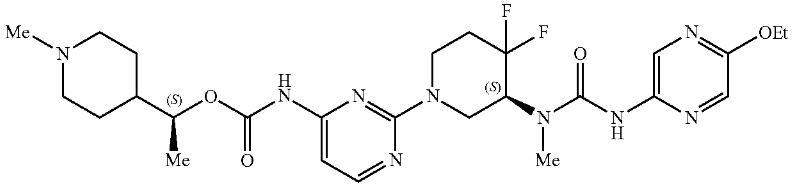 |
| 124 | 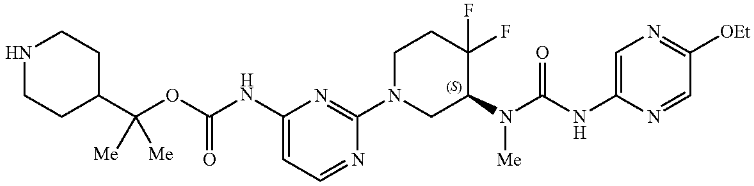 |
| 125 | 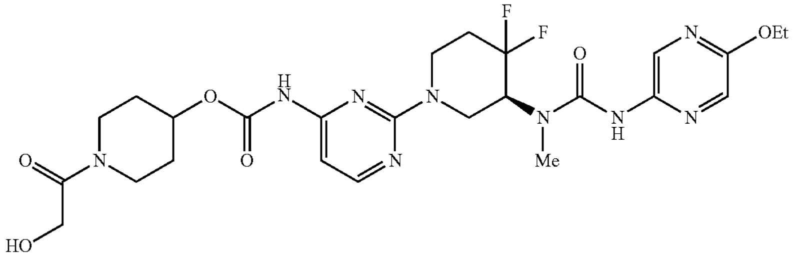 [SMILES: CCOc1cnc(NC(=O)N(C)[C@H]2CN(c3nccc(NC(=O)OC4CCN(C(=O)CO)CC4)n3)CCC2(F)F)cn1] |

TABLE 2B-continued
| Ex. No. | Structure |
|---|---|
| 126 | 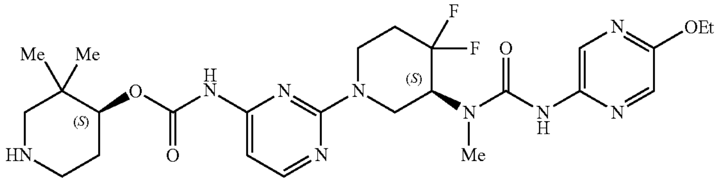 |
| 127 | 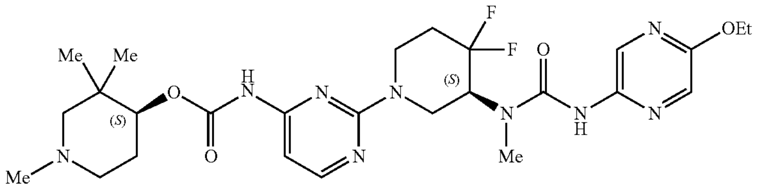 |
| 128 | 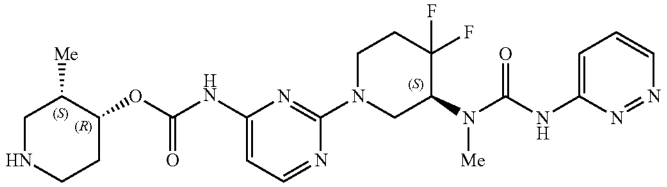 |
| 129 | 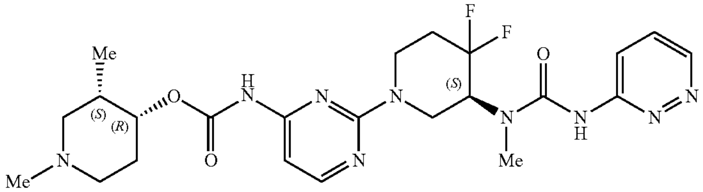 |
| 130 | 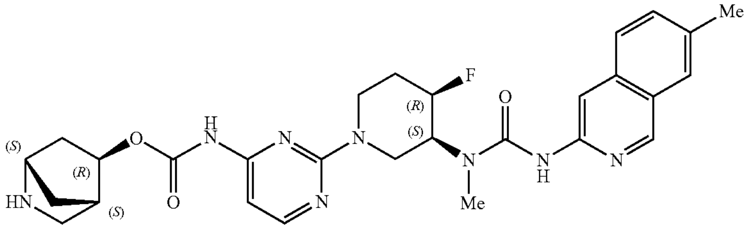 |
| 131 | 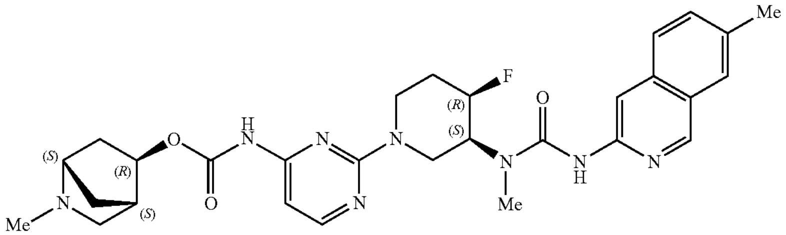 |
| 132 | 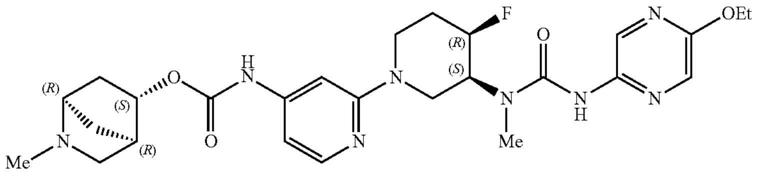 |

TABLE 2B-continued
| Ex. No. | Structure |
|---|---|
| 133 | 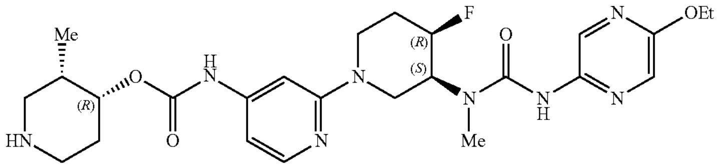 |
| 134 | 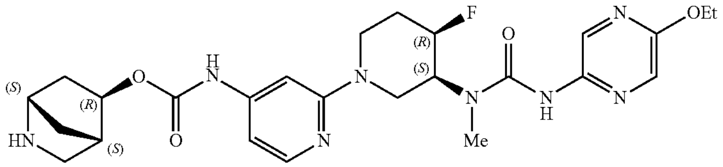 |
| 135 | 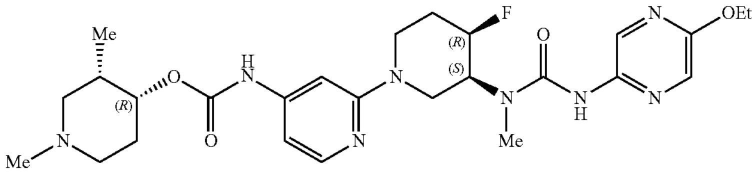 |
| 136 | 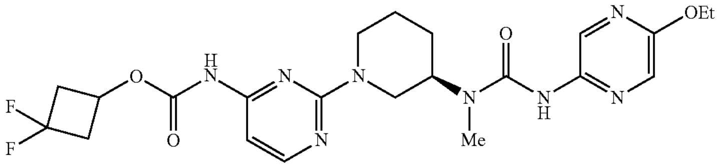 [SMILES: CCOc1cnc(NC(=O)N(C)[C@@H]2CCCN(c3nccc(NC(=O)OC4CC(F)(F)C4)n3)C2)cn1] |
| 137 | 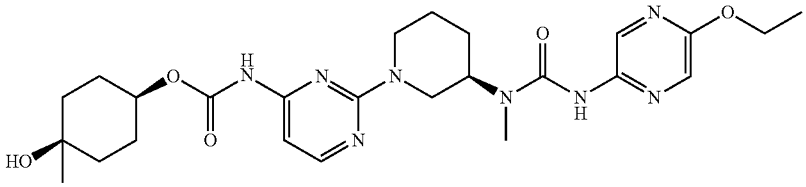 [SMILES: CCOc1cnc(NC(=O)N(C)[C@@H]2CCCN(c3nccc(NC(=O)O[C@H]4CC[C@@](C)(O)CC4)n3)C2)cn1] |
| 138 | 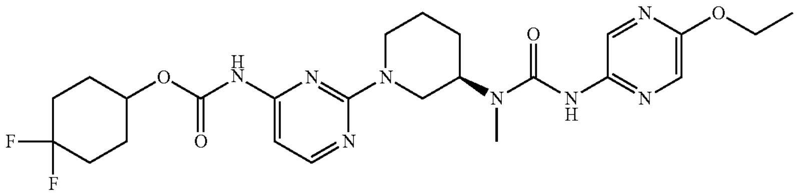 [SMILES: CCOc1cnc(NC(=O)N(C)[C@@H]2CCCN(c3nccc(NC(=O)OC4CCC(F)(F)CC4)n3)C2)cn1] |
| 139 | 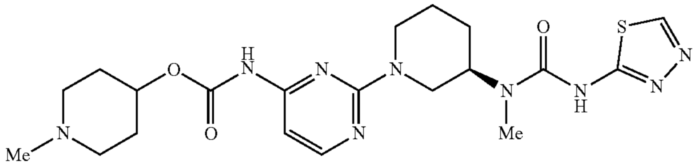 [SMILES: CN1CCC(OC(=O)Nc2ccnc(N3CCC[C@@H](N(C)C(=O)Nc4nncs4)C3)n2)CC1] |
| 140 | 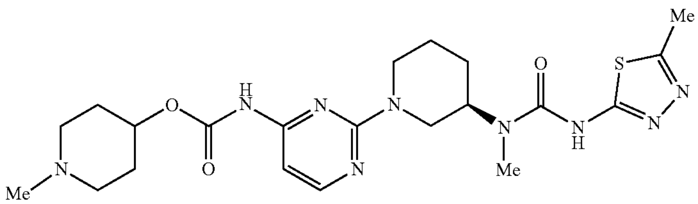 [SMILES: Cc1nnc(NC(=O)N(C)[C@@H]2CCCN(c3nccc(NC(=O)OC4CCN(C)CC4)n3)C2)s1] |

TABLE 2B-continued
| Ex. No. | Structure |
|---|---|
| 141 | 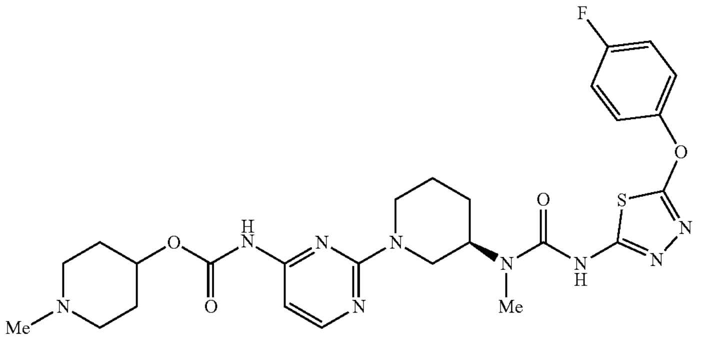 [SMILES: CN1CCC(OC(=O)Nc2ccnc(N3CCC[C@@H](N(C)C(=O)Nc4nnc(Oc5ccc(F)cc5)s4)C3)n2)CC1] |
| 142 | 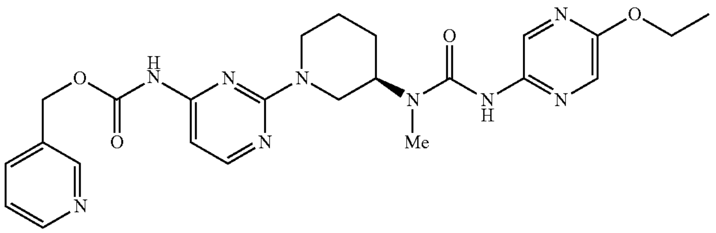 [SMILES: CCOc1cnc(NC(=O)N(C)[C@@H]2CCCN(c3nccc(NC(=O)OCc4cccnc4)n3)C2)cn1] |
| 143 | 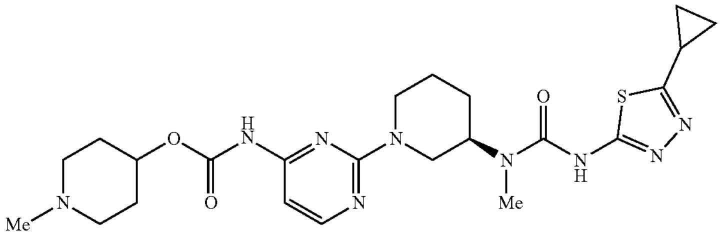 [SMILES: CN1CCC(OC(=O)Nc2ccnc(N3CCC[C@@H](N(C)C(=O)Nc4nnc(C5CC5)s4)C3)n2)CC1] |
| 144 | 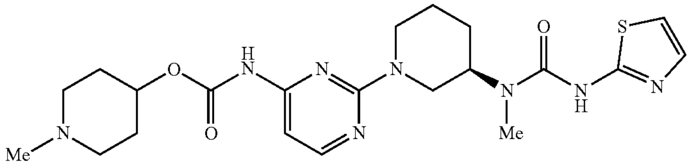 [SMILES: CN1CCC(OC(=O)Nc2ccnc(N3CCC[C@@H](N(C)C(=O)Nc4nccs4)C3)n2)CC1] |
| 145 | 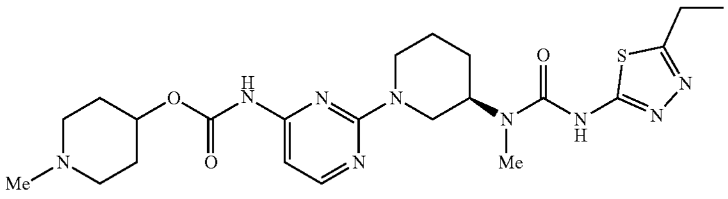 [SMILES: CCc1nnc(NC(=O)N(C)[C@@H]2CCCN(c3nccc(NC(=O)OC4CCN(C)CC4)n3)C2)s1] |
| 146 | 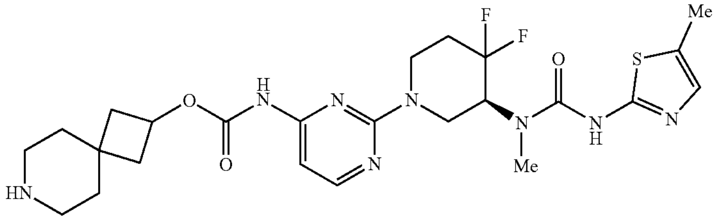 [SMILES: Cc1cnc(NC(=O)N(C)[C@H]2CN(c3nccc(NC(=O)OC4CC5(CCNCC5)C4)n3)CCC2(F)F)s1] |

TABLE 2B-continued
| Ex. No. | Structure |
|---|---|
| 147 | 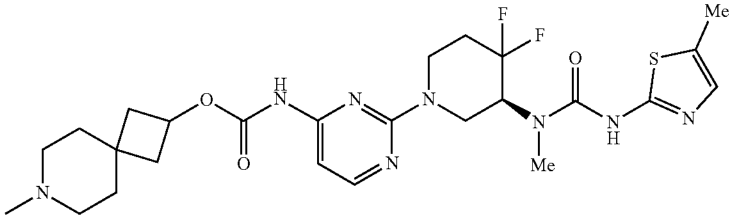 [SMILES: Cc1cnc(NC(=O)N(C)[C@H]2CN(c3nccc(NC(=O)OC4CC5(CCN(C)CC5)C4)n3)CCC2(F)F)s1] |
| 148 | 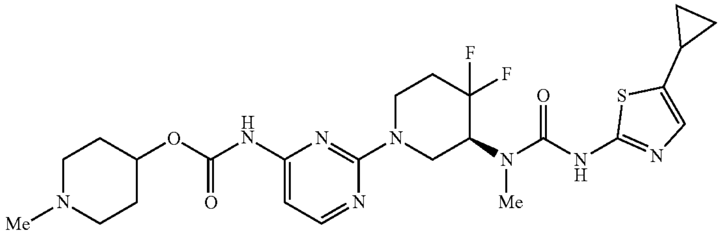 [SMILES: CN1CCC(OC(=O)Nc2ccnc(N3CCC(F)(F)[C@@H](N(C)C(=O)Nc4ncc(C5CC5)s4)C3)n2)CC1] |
| 149 | 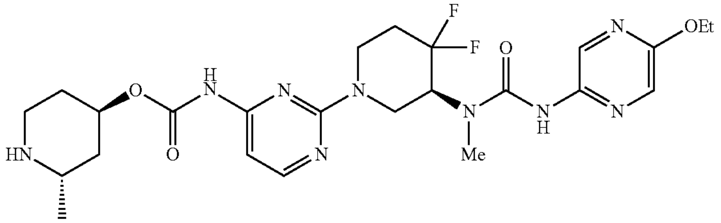 [SMILES: CCOc1cnc(NC(=O)N(C)[C@H]2CN(c3nccc(NC(=O)O[C@@H]4CCN[C@@H](C)C4)n3)CCC2(F)F)cn1] |
| 150 | 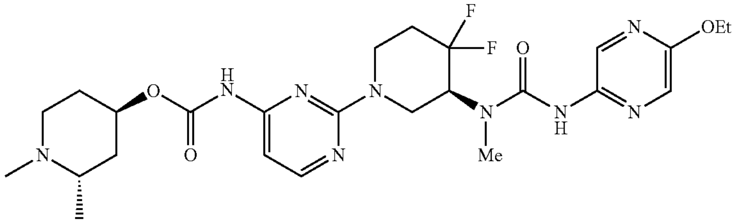 [SMILES: CCOc1cnc(NC(=O)N(C)[C@H]2CN(c3nccc(NC(=O)O[C@@H]4CCN(C)[C@@H](C)C4)n3)CCC2(F)F)cn1] |
| 151 | 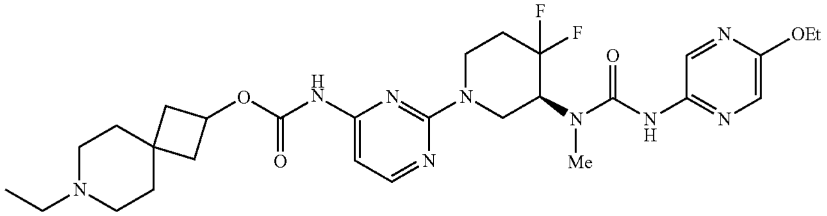 [SMILES: CCOc1cnc(NC(=O)N(C)[C@H]2CN(c3nccc(NC(=O)OC4CC5(CCN(CC)CC5)C4)n3)CCC2(F)F)cn1] |
| 152 | 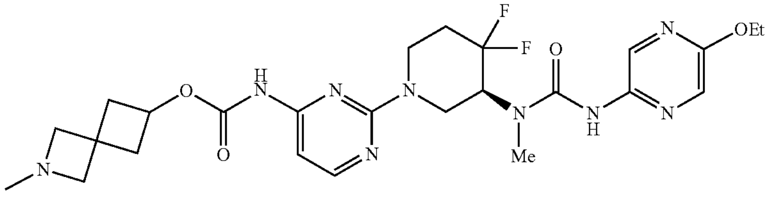 [SMILES: CCOc1cnc(NC(=O)N(C)[C@H]2CN(c3nccc(NC(=O)OC4CC5(C4)CN(C)C5)n3)CCC2(F)F)cn1] |

TABLE 2B-continued
| Ex. No. | Structure |
|---|---|
| 153 | 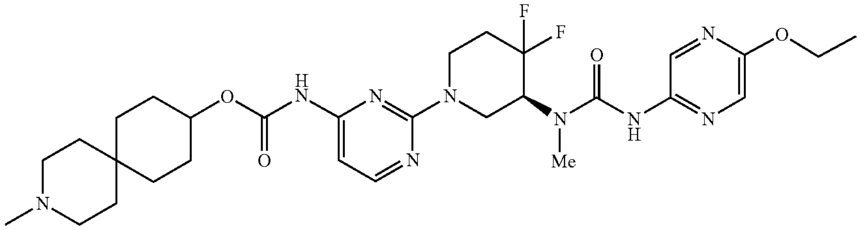 [SMILES: CCOc1cnc(NC(=O)N(C)[C@H]2CN(c3nccc(NC(=O)OC4CCC5(CC4)CCN(C)CC5)n3)CCC2(F)F)cn1] |
| 154 | 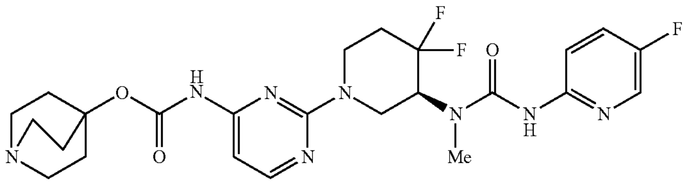 [SMILES: CN(C(=O)Nc1ccc(F)cn1)[C@H]1CN(c2nccc(NC(=O)OC34CCN(CC3)CC4)n2)CCC1(F)F] |
| 155 | 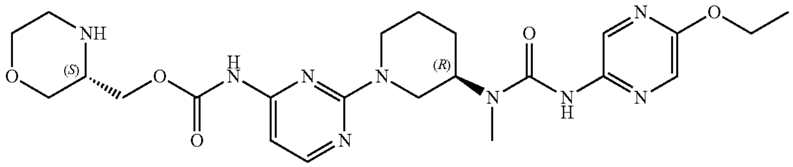 |
| 156 | 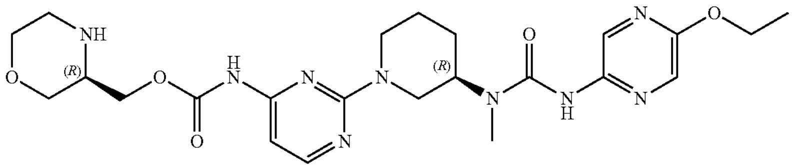 |
| 157 | 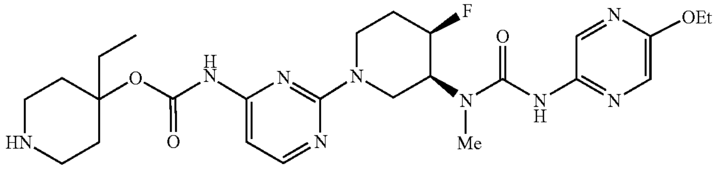 [SMILES: CCOc1cnc(NC(=O)N(C)[C@H]2CN(c3nccc(NC(=O)OC4(CC)CCNCC4)n3)CC[C@H]2F)cn1] |
| 158 | 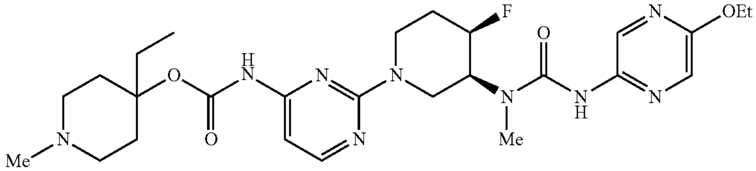 [SMILES: CCOc1cnc(NC(=O)N(C)[C@H]2CN(c3nccc(NC(=O)OC4(CC)CCN(C)CC4)n3)CC[C@H]2F)cn1] |
| 159 | 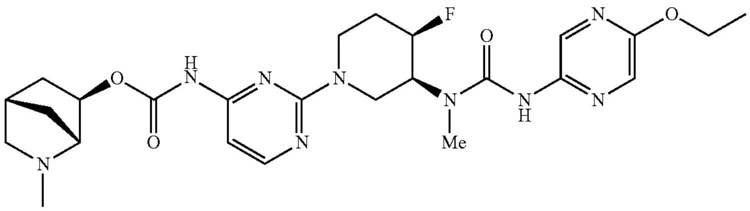 [SMILES: CCOc1cnc(NC(=O)N(C)[C@H]2CN(c3nccc(NC(=O)O[C@@H]4C[C@@H]5C[C@H]4N(C)C5)n3)CC[C@H]2F)cn1] |
| 160 | 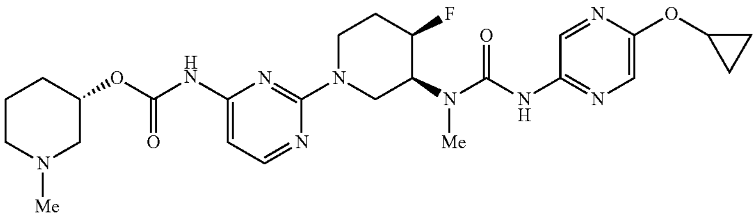 [SMILES: CN1CCC[C@H](OC(=O)Nc2ccnc(N3CC[C@@H](F)[C@@H](N(C)C(=O)Nc4cnc(OC5CC5)cn4)C3)n2)C1] |

TABLE 2B-continued
| Ex. No. | Structure |
| --- | --- |
| 161 | 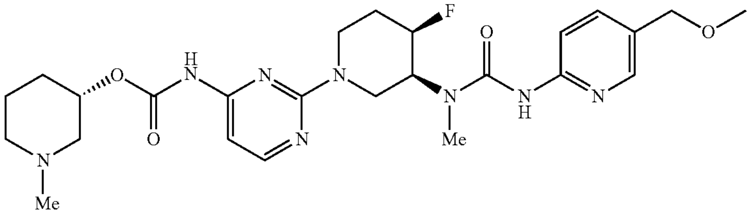 [SMILES: COCc1ccc(NC(=O)N(C)[C@H]2CN(c3nccc(NC(=O)O[C@H]4CCCN(C)C4)n3)CC[C@H]2F)nc1] |
| 162 | 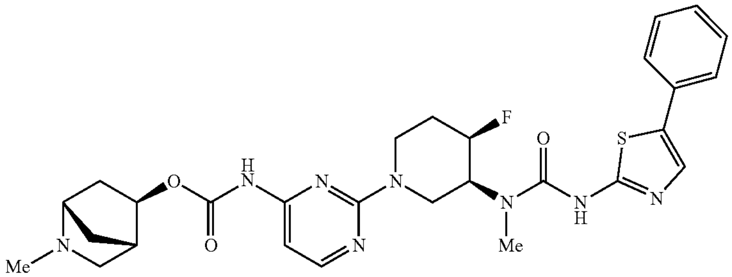 [SMILES: CN1C[C@@H]2C[C@H]1C[C@H]2OC(=O)Nc1ccnc(N2CC[C@@H](F)[C@@H](N(C)C(=O)Nc3ncc(-c4ccccc4)s3)C2)n1] |
| 163 | 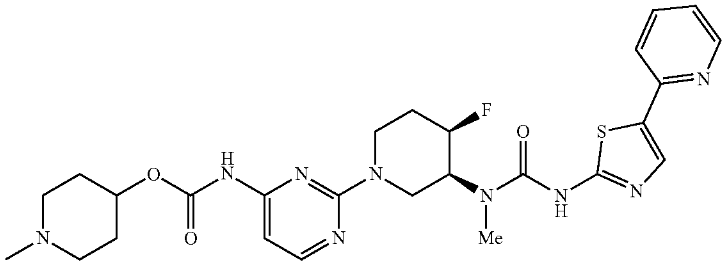 [SMILES: CN1CCC(OC(=O)Nc2ccnc(N3CC[C@@H](F)[C@@H](N(C)C(=O)Nc4ncc(-c5ccccn5)s4)C3)n2)CC1] |
| 164 | 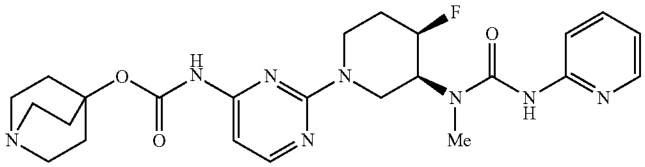 [SMILES: CN(C(=O)Nc1ccccn1)[C@H]1CN(c2nccc(NC(=O)OC34CCN(CC3)CC4)n2)CC[C@H]1F] |
| 165 | 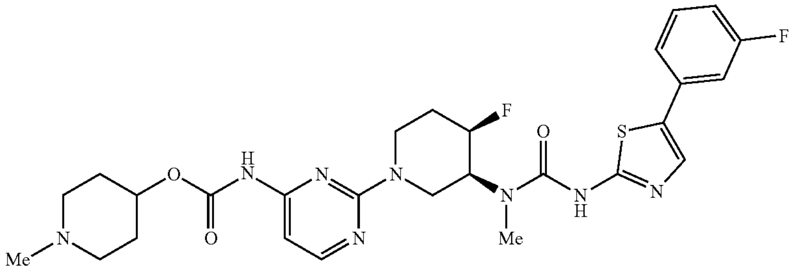 [SMILES: CN1CCC(OC(=O)Nc2ccnc(N3CC[C@@H](F)[C@@H](N(C)C(=O)Nc4ncc(-c5cccc(F)c5)s4)C3)n2)CC1] |
| 166 | 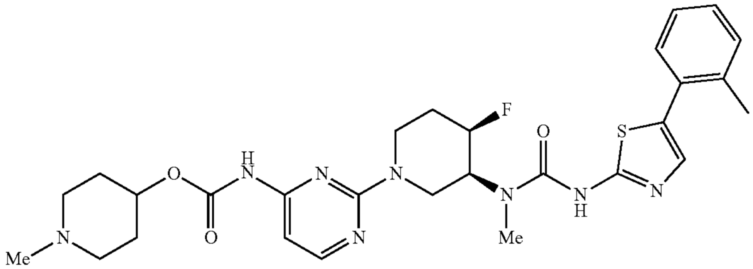 [SMILES: Cc1ccccc1-c1cnc(NC(=O)N(C)[C@H]2CN(c3nccc(NC(=O)OC4CCN(C)CC4)n3)CC[C@H]2F)s1] |

TABLE 2B-continued
| Ex. No. | Structure |
|---|---|
| 167 | 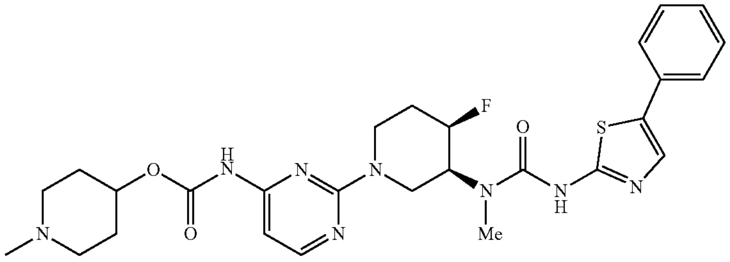 [SMILES: CN1CCC(OC(=O)Nc2ccnc(N3CC[C@@H](F)[C@@H](N(C)C(=O)Nc4ncc(-c5ccccc5)s4)C3)n2)CC1] |
| 168 | 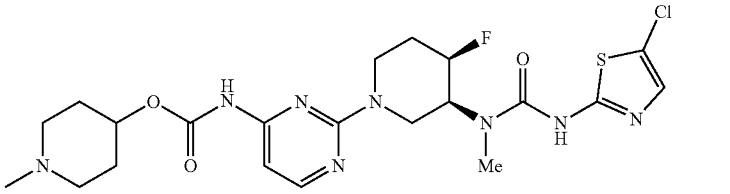 [SMILES: CN1CCC(OC(=O)Nc2ccnc(N3CC[C@@H](F)[C@@H](N(C)C(=O)Nc4ncc(Cl)s4)C3)n2)CC1] |
| 169 | 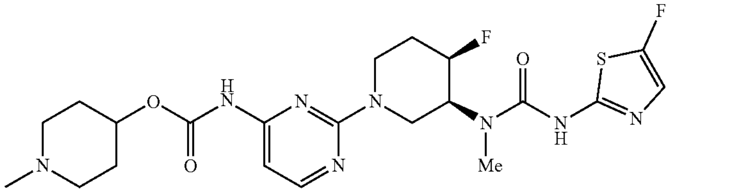 [SMILES: CN1CCC(OC(=O)Nc2ccnc(N3CC[C@@H](F)[C@@H](N(C)C(=O)Nc4ncc(F)s4)C3)n2)CC1] |
| 170 | 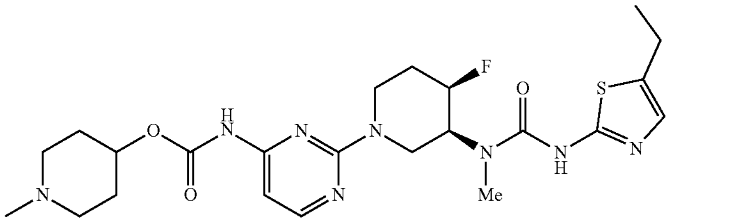 [SMILES: CCc1cnc(NC(=O)N(C)[C@H]2CN(c3nccc(NC(=O)OC4CCN(C)CC4)n3)CC[C@H]2F)s1] |
| 171 | 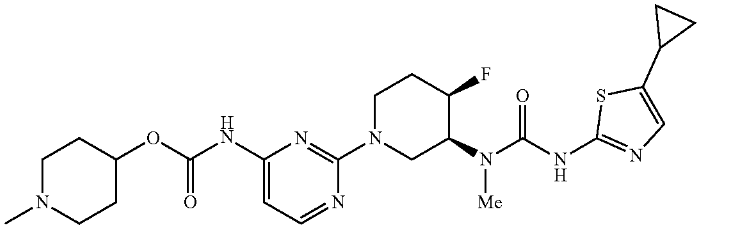 [SMILES: CN1CCC(OC(=O)Nc2ccnc(N3CC[C@@H](F)[C@@H](N(C)C(=O)Nc4ncc(C5CC5)s4)C3)n2)CC1] |
| 172 | 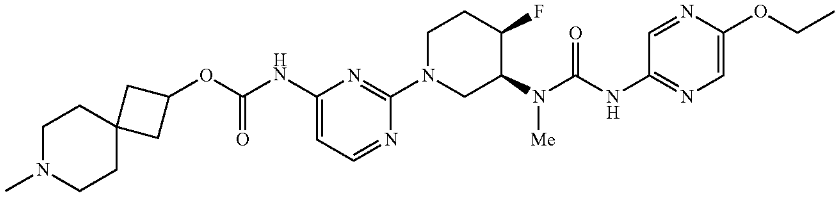 [SMILES: CCOc1cnc(NC(=O)N(C)[C@H]2CN(c3nccc(NC(=O)OC4CC5(CCN(C)CC5)C4)n3)CC[C@H]2F)cn1] |
| 173 | 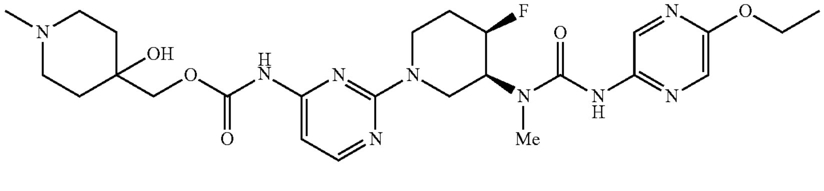 [SMILES: CCOc1cnc(NC(=O)N(C)[C@H]2CN(c3nccc(NC(=O)OCC4(O)CCN(C)CC4)n3)CC[C@H]2F)cn1] |

TABLE 2B-continued
| Ex. No. | Structure |
|---|---|
| 174 | 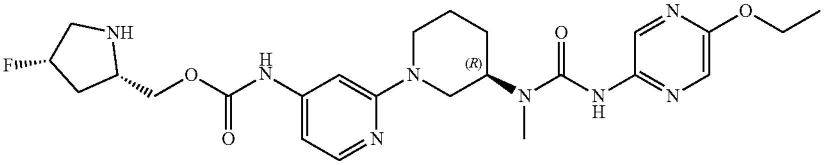 |
| 175 | 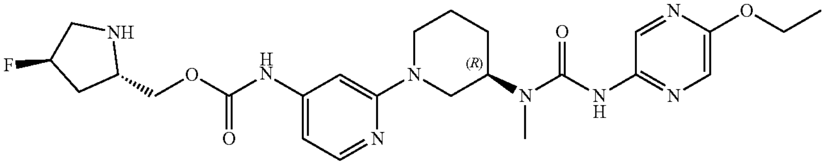 |
| 176 | 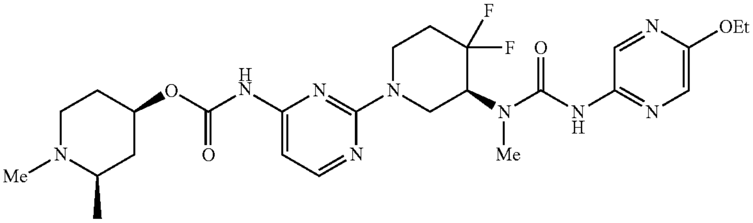 [SMILES: CCOc1cnc(NC(=O)N(C)[C@H]2CN(c3nccc(NC(=O)O[C@@H]4CCN(C)[C@H](C)C4)n3)CCC2(F)F)cn1] |
| 177 | 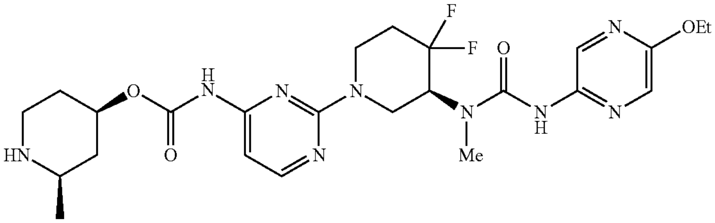 [SMILES: CCOc1cnc(NC(=O)N(C)[C@H]2CN(c3nccc(NC(=O)O[C@@H]4CCN[C@H](C)C4)n3)CCC2(F)F)cn1] |
| 178 | 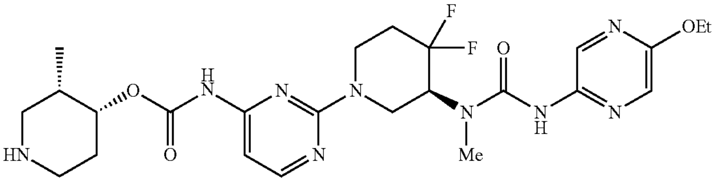 [SMILES: CCOc1cnc(NC(=O)N(C)[C@H]2CN(c3nccc(NC(=O)O[C@@H]4CCNC[C@@H]4C)n3)CCC2(F)F)cn1] |
| 179 | 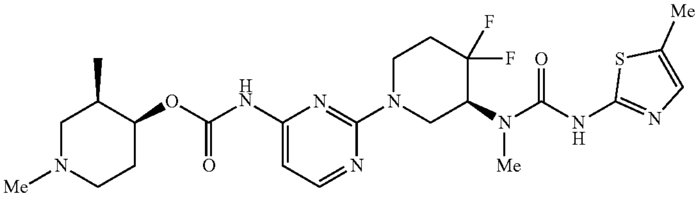 [SMILES: Cc1cnc(NC(=O)N(C)[C@H]2CN(c3nccc(NC(=O)O[C@H]4CCN(C)C[C@H]4C)n3)CCC2(F)F)s1] |
| 180 | 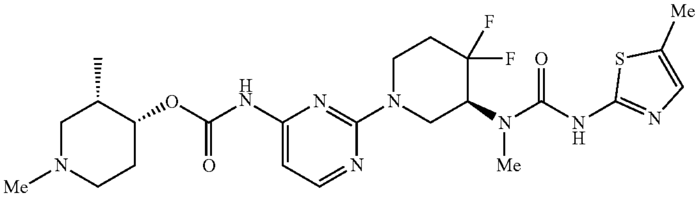 [SMILES: Cc1cnc(NC(=O)N(C)[C@H]2CN(c3nccc(NC(=O)O[C@@H]4CCN(C)C[C@@H]4C)n3)CCC2(F)F)s1] |

TABLE 2B-continued
| Ex. No. | Structure |
| --- | --- |
| 181 | 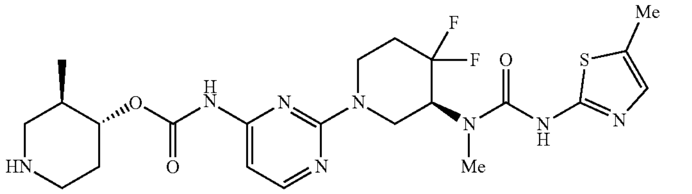 [SMILES: Cc1cnc(NC(=O)N(C)[C@H]2CN(c3nccc(NC(=O)O[C@@H]4CCNC[C@H]4C)n3)CCC2(F)F)s1] |
| 182 | 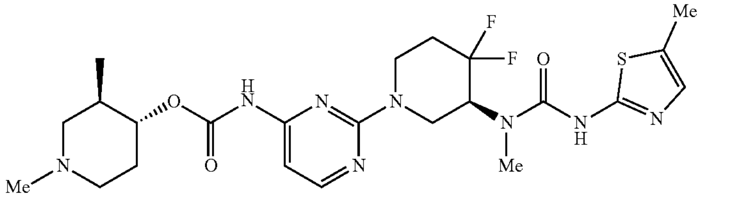 [SMILES: Cc1cnc(NC(=O)N(C)[C@H]2CN(c3nccc(NC(=O)O[C@@H]4CCN(C)C[C@H]4C)n3)CCC2(F)F)s1] |
| 183 | 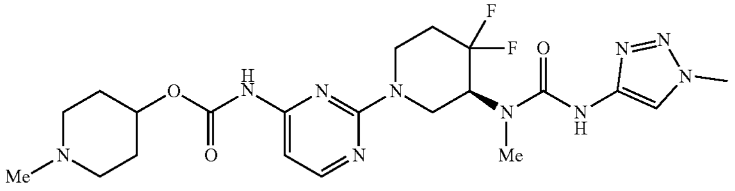 [SMILES: CN1CCC(OC(=O)Nc2ccnc(N3CCC(F)(F)[C@@H](N(C)C(=O)Nc4cn(C)nn4)C3)n2)CC1] |
| 184 | 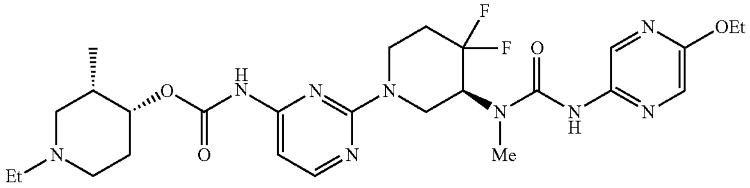 [SMILES: CCOc1cnc(NC(=O)N(C)[C@H]2CN(c3nccc(NC(=O)O[C@@H]4CCN(CC)C[C@@H]4C)n3)CCC2(F)F)cn1] |
| 185 | 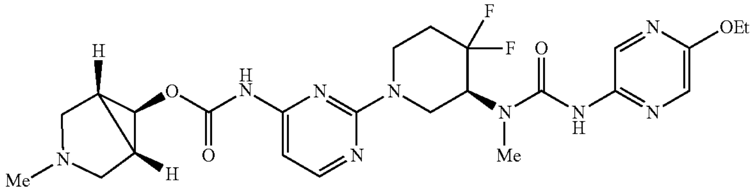 [SMILES: CCOc1cnc(NC(=O)N(C)[C@H]2CN(c3nccc(NC(=O)O[C@H]4[C@@H]5CN(C)C[C@@H]54)n3)CCC2(F)F)cn1] |
| 186 | 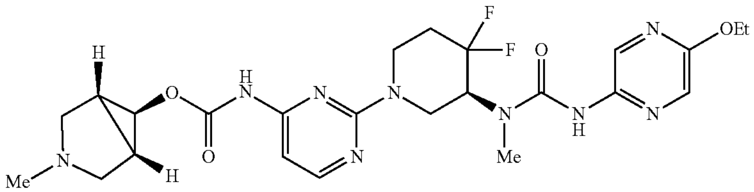 [SMILES: CCOc1cnc(NC(=O)N(C)[C@H]2CN(c3nccc(NC(=O)O[C@H]4[C@@H]5CN(C)C[C@@H]54)n3)CCC2(F)F)cn1] |
| 187 | 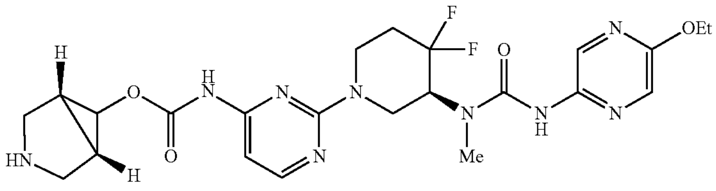 [SMILES: CCOc1cnc(NC(=O)N(C)[C@H]2CN(c3nccc(NC(=O)OC4[C@H]5CNC[C@@H]45)n3)CCC2(F)F)cn1] |

TABLE 2B-continued
| Ex. No. | Structure |
| --- | --- |
| 188 | 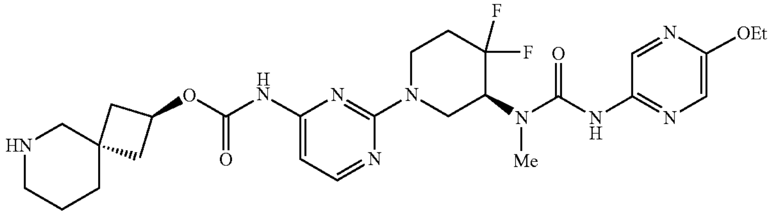 [SMILES: CCOc1cnc(NC(=O)N(C)[C@H]2CN(c3nccc(NC(=O)O[C@H]4C[C@@]5(CCCNC5)C4)n3)CCC2(F)F)cn1] |
| 189 | 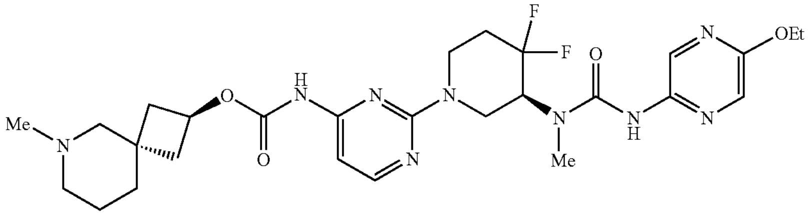 [SMILES: CCOc1cnc(NC(=O)N(C)[C@H]2CN(c3nccc(NC(=O)O[C@H]4C[C@@]5(CCCN(C)C5)C4)n3)CCC2(F)F)cn1] |
| 190 | 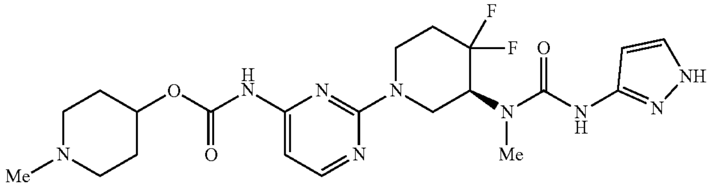 [SMILES: CN1CCC(OC(=O)Nc2ccnc(N3CCC(F)(F)[C@@H](N(C)C(=O)Nc4cc[nH]n4)C3)n2)CC1] |
| 191 | 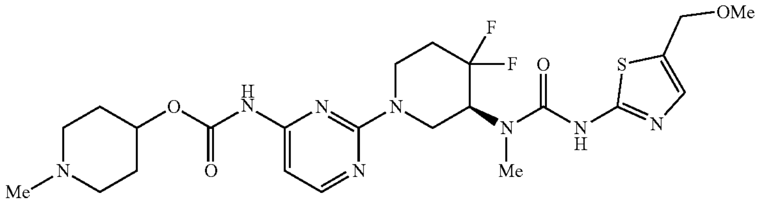 [SMILES: COCc1cnc(NC(=O)N(C)[C@H]2CN(c3nccc(NC(=O)OC4CCN(C)CC4)n3)CCC2(F)F)s1] |
| 192 | 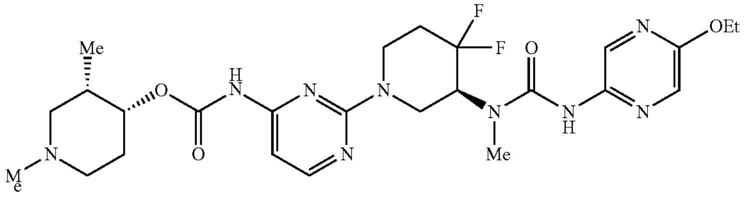 [SMILES: CCOc1cnc(NC(=O)N(C)[C@H]2CN(c3nccc(NC(=O)O[C@@H]4CCN(C)C[C@@H]4C)n3)CCC2(F)F)cn1] |
| 193 | 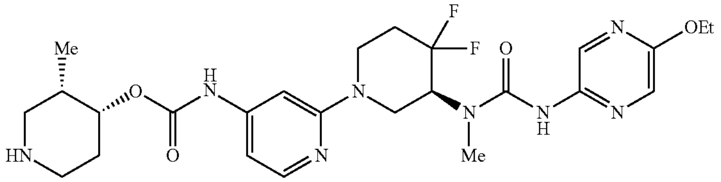 [SMILES: CCOc1cnc(NC(=O)N(C)[C@H]2CN(c3cc(NC(=O)O[C@@H]4CCNC[C@@H]4C)ccn3)CCC2(F)F)cn1] |
| 194 | 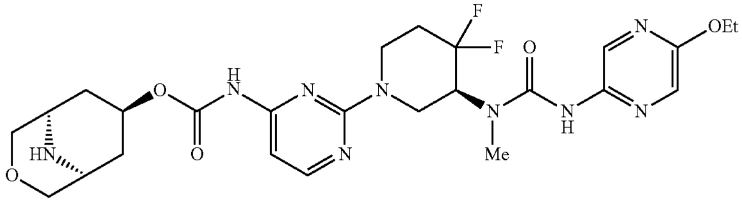 [SMILES: CCOc1cnc(NC(=O)N(C)[C@H]2CN(c3nccc(NC(=O)O[C@H]4C[C@H]5COC[C@@H](C4)N5)n3)CCC2(F)F)cn1] |

TABLE 2B-continued
| Ex. No. | Structure |
| --- | --- |
| 195 | 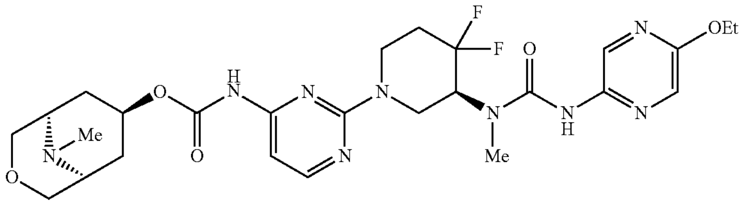 [SMILES: CCOc1cnc(NC(=O)N(C)[C@H]2CN(c3nccc(NC(=O)O[C@H]4C[C@H]5COC[C@@H](C4)N5C)n3)CCC2(F)F)cn1] |
| 196 | 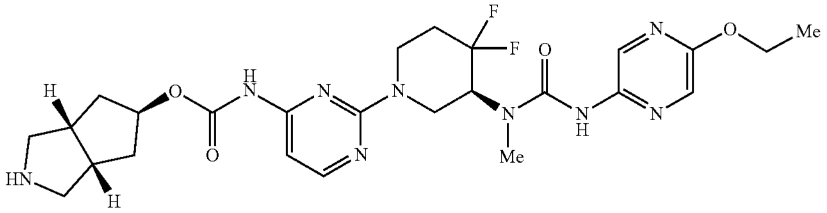 [SMILES: CCOc1cnc(NC(=O)N(C)[C@H]2CN(c3nccc(NC(=O)O[C@@H]4C[C@H]5CNC[C@H]5C4)n3)CCC2(F)F)cn1] |
| 197 | 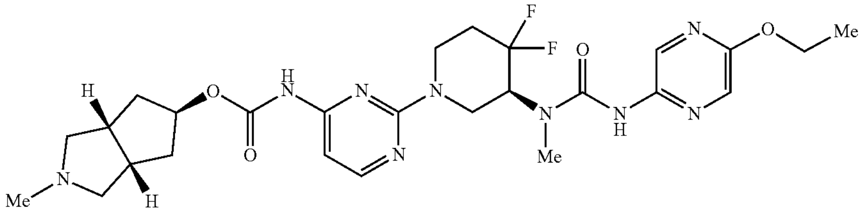 [SMILES: CCOc1cnc(NC(=O)N(C)[C@H]2CN(c3nccc(NC(=O)O[C@H]4C[C@@H]5CN(C)C[C@@H]5C4)n3)CCC2(F)F)cn1] |
| 198 | 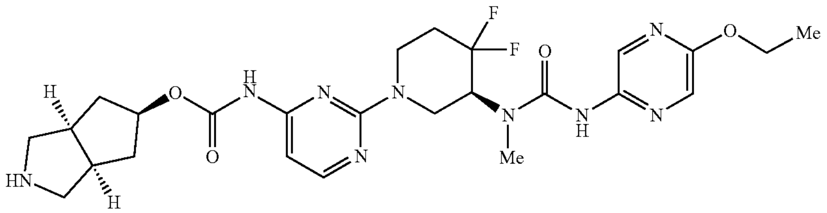 [SMILES: CCOc1cnc(NC(=O)N(C)[C@H]2CN(c3nccc(NC(=O)O[C@H]4C[C@H]5CNC[C@H]5C4)n3)CCC2(F)F)cn1] |
| 199 | 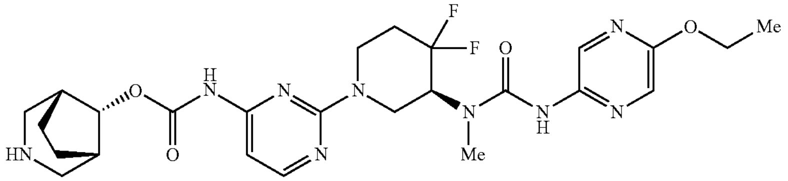 [SMILES: CCOc1cnc(NC(=O)N(C)[C@H]2CN(c3nccc(NC(=O)O[C@H]4[C@@H]5CC[C@H]4CNC5)n3)CCC2(F)F)cn1] |
| 200 | 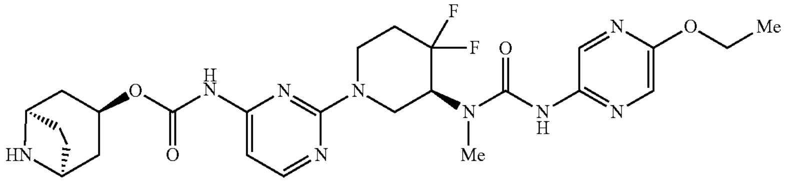 [SMILES: CCOc1cnc(NC(=O)N(C)[C@H]2CN(c3nccc(NC(=O)O[C@@H]4C[C@H]5CC[C@@H](C4)N5)n3)CCC2(F)F)cn1] |
| 201 | 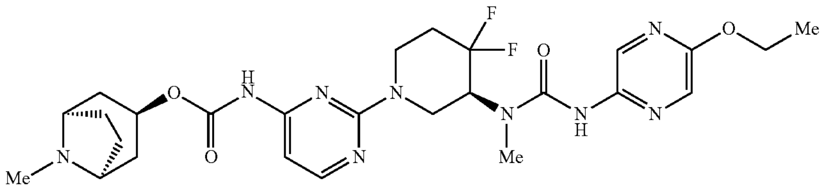 [SMILES: CCOc1cnc(NC(=O)N(C)[C@H]2CN(c3nccc(NC(=O)O[C@@H]4C[C@H]5CC[C@@H](C4)N5C)n3)CCC2(F)F)cn1] |

TABLE 2B-continued
| Ex. No. | Structure |
| --- | --- |
| 202 | 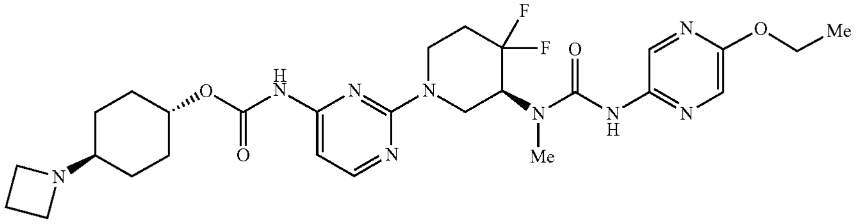 [SMILES: CCOc1cnc(NC(=O)N(C)[C@H]2CN(c3nccc(NC(=O)O[C@H]4CC[C@H](N5CCC5)CC4)n3)CCC2(F)F)cn1] |
| 203 | 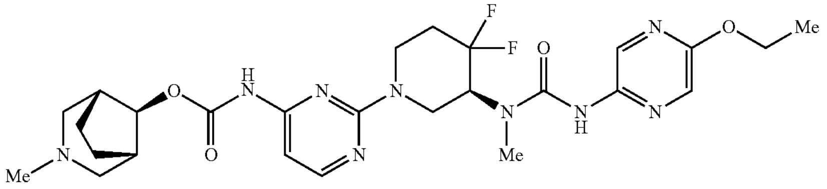 [SMILES: CCOc1cnc(NC(=O)N(C)[C@H]2CN(c3nccc(NC(=O)O[C@@H]4[C@@H]5CC[C@H]4CN(C)C5)n3)CCC2(F)F)cn1] |
| 204 | 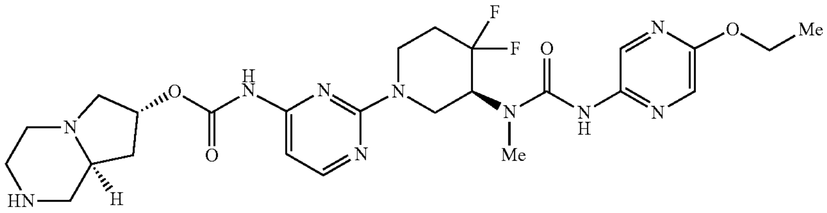 [SMILES: CCOc1cnc(NC(=O)N(C)[C@H]2CN(c3nccc(NC(=O)O[C@@H]4C[C@H]5CNCCN5C4)n3)CCC2(F)F)cn1] |
| 205 | 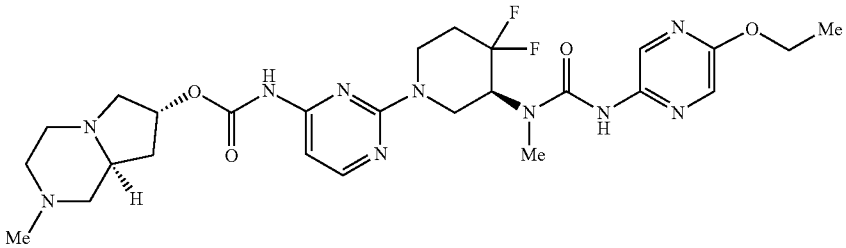 [SMILES: CCOc1cnc(NC(=O)N(C)[C@H]2CN(c3nccc(NC(=O)O[C@@H]4C[C@H]5CN(C)CCN5C4)n3)CCC2(F)F)cn1] |
| 206 | 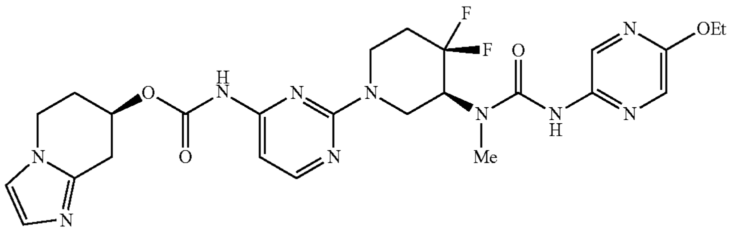 |
| 207 | 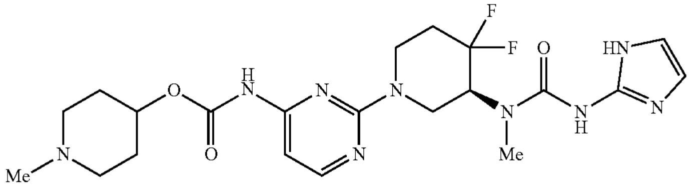 [SMILES: CN1CCC(OC(=O)Nc2ccnc(N3CCC(F)(F)[C@@H](N(C)C(=O)Nc4ncc[nH]4)C3)n2)CC1] |
| 208 | 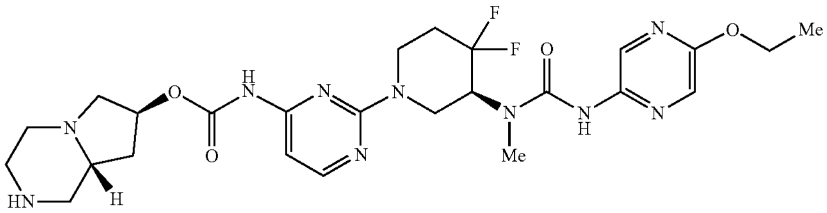 [SMILES: CCOc1cnc(NC(=O)N(C)[C@H]2CN(c3nccc(NC(=O)O[C@H]4C[C@@H]5CNCCN5C4)n3)CCC2(F)F)cn1] |

TABLE 2B-continued
| Ex. No. | Structure |
|---|---|
| 209 | 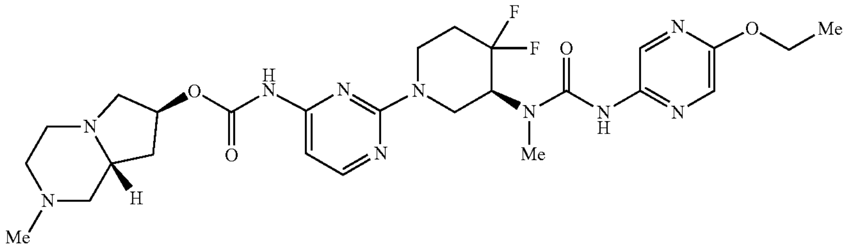 [SMILES: CCOc1cnc(NC(=O)N(C)[C@H]2CN(c3nccc(NC(=O)O[C@H]4C[C@@H]5CN(C)CCN5C4)n3)CCC2(F)F)cn1] |
| 210 | 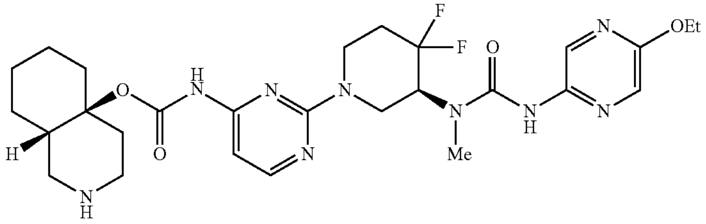 [SMILES: CCOc1cnc(NC(=O)N(C)[C@H]2CN(c3nccc(NC(=O)O[C@]45CCCC[C@H]4CNCC5)n3)CCC2(F)F)cn1] |
| 211 | 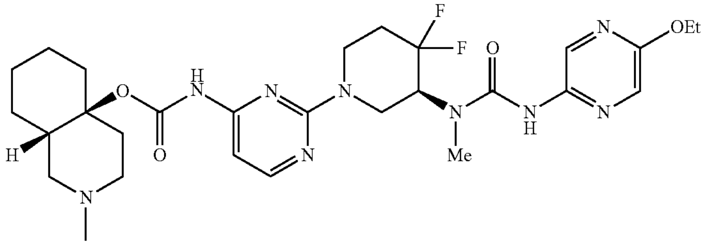 [SMILES: CCOc1cnc(NC(=O)N(C)[C@H]2CN(c3nccc(NC(=O)O[C@]45CCCC[C@H]4CN(C)CC5)n3)CCC2(F)F)cn1] |
| 212 | 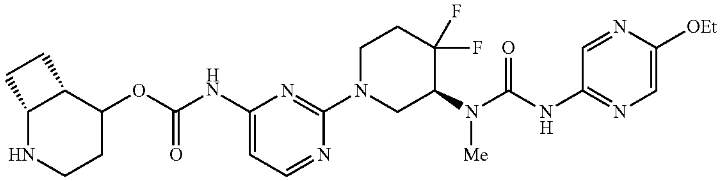 [SMILES: CCOc1cnc(NC(=O)N(C)[C@H]2CN(c3nccc(NC(=O)OC4CCN[C@@H]5CC[C@H]45)n3)CCC2(F)F)cn1] |
| 213 | 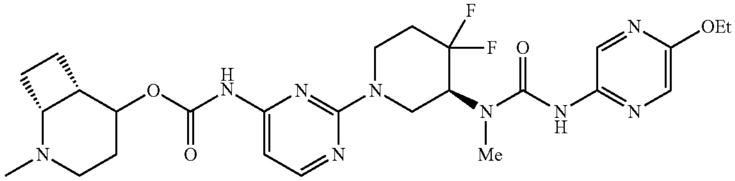 [SMILES: CCOc1cnc(NC(=O)N(C)[C@H]2CN(c3nccc(NC(=O)OC4CCN(C)[C@@H]5CC[C@H]45)n3)CCC2(F)F)cn1] |
| 214 | 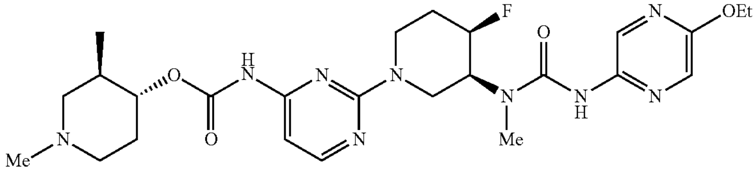 [SMILES: CCOc1cnc(NC(=O)N(C)[C@H]2CN(c3nccc(NC(=O)O[C@@H]4CCN(C)C[C@H]4C)n3)CC[C@H]2F)cn1] |
| 215 | 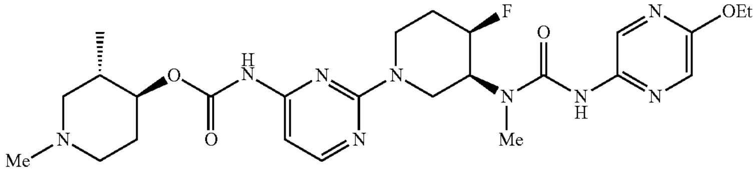 [SMILES: CCOc1cnc(NC(=O)N(C)[C@H]2CN(c3nccc(NC(=O)O[C@H]4CCN(C)C[C@@H]4C)n3)CC[C@H]2F)cn1]

TABLE 2B-continued
| Ex. No. | Structure |
| --- | --- |
| 216 | 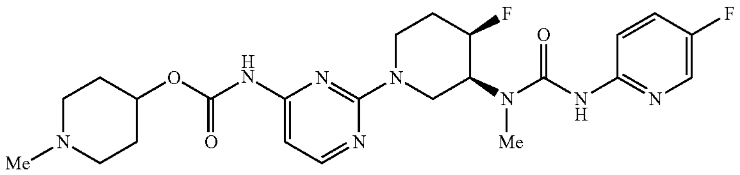 [SMILES: CN1CCC(OC(=O)Nc2ccnc(N3CC[C@@H](F)[C@@H](N(C)C(=O)Nc4ccc(F)cn4)C3)n2)CC1] |
| 217 | 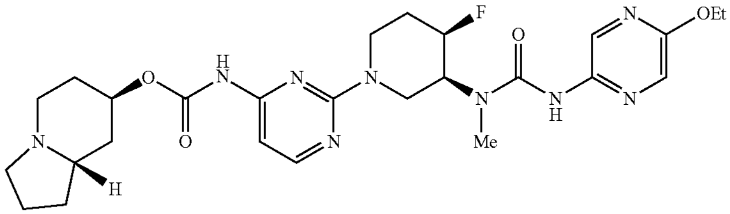 [SMILES: CCOc1cnc(NC(=O)N(C)[C@H]2CN(c3nccc(NC(=O)O[C@@H]4CCN5CCC[C@H]5C4)n3)CC[C@H]2F)cn1] |
| 218 | 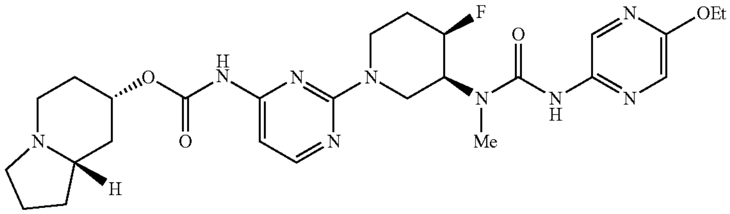 [SMILES: CCOc1cnc(NC(=O)N(C)[C@H]2CN(c3nccc(NC(=O)O[C@H]4CCN5CCC[C@H]5C4)n3)CC[C@H]2F)cn1] |
| 219 | 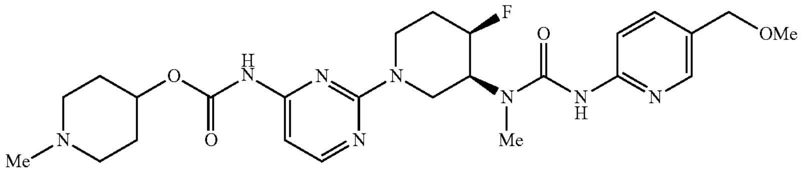 [SMILES: COCc1ccc(NC(=O)N(C)[C@H]2CN(c3nccc(NC(=O)OC4CCN(C)CC4)n3)CC[C@H]2F)nc1] |
| 220 | 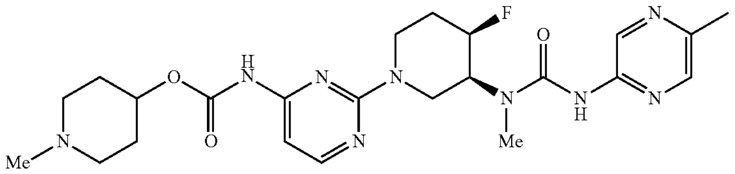 [SMILES: Cc1cnc(NC(=O)N(C)[C@H]2CN(c3nccc(NC(=O)OC4CCN(C)CC4)n3)CC[C@H]2F)cn1] |
| 221 | 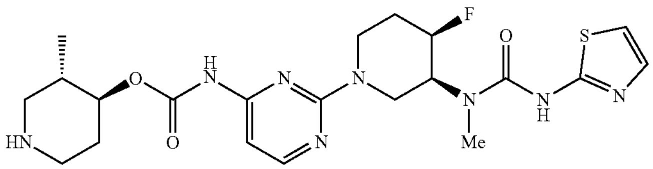 [SMILES: C[C@H]1CNCC[C@@H]1OC(=O)Nc1ccnc(N2CC[C@@H](F)[C@@H](N(C)C(=O)Nc3nccs3)C2)n1] |
| 222 | 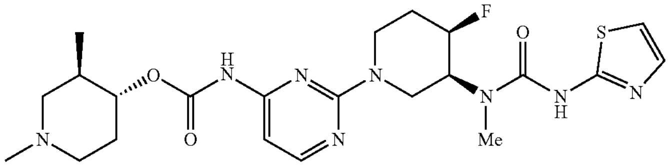 [SMILES: C[C@@H]1CN(C)CC[C@H]1OC(=O)Nc1ccnc(N2CC[C@@H](F)[C@@H](N(C)C(=O)Nc3nccs3)C2)n1] |
| 223 | 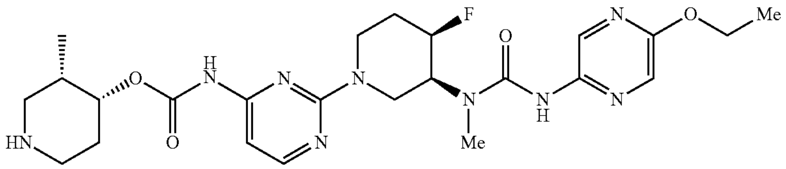 [SMILES: CCOc1cnc(NC(=O)N(C)[C@H]2CN(c3nccc(NC(=O)O[C@@H]4CCNC[C@@H]4C)n3)CC[C@H]2F)cn1] |

TABLE 2B-continued
| Ex. No. | Structure |
|---|---|
| 224 | 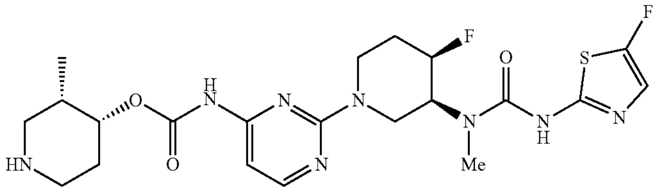 [SMILES: C[C@H]1CNCC[C@H]1OC(=O)Nc1ccnc(N2CC[C@@H](F)[C@@H](N(C)C(=O)Nc3ncc(F)s3)C2)n1] |
| 225 | 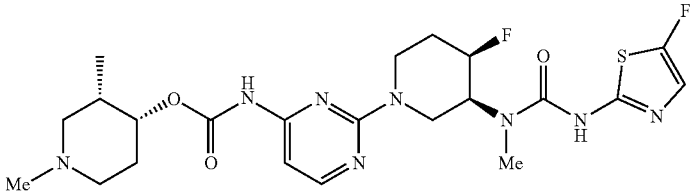 [SMILES: C[C@H]1CN(C)CC[C@H]1OC(=O)Nc1ccnc(N2CC[C@@H](F)[C@@H](N(C)C(=O)Nc3ncc(F)s3)C2)n1] |
| 226 | 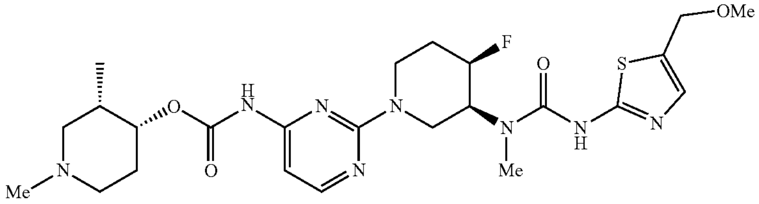 [SMILES: COCc1cnc(NC(=O)N(C)[C@H]2CN(c3nccc(NC(=O)O[C@@H]4CCN(C)C[C@@H]4C)n3)CC[C@H]2F)s1] |
| 227 | 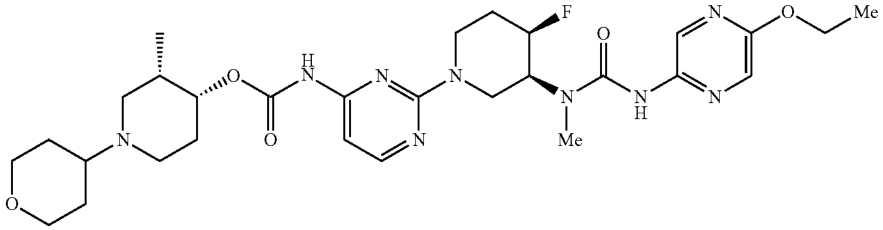 [SMILES: CCOc1cnc(NC(=O)N(C)[C@H]2CN(c3nccc(NC(=O)O[C@@H]4CCN(C5CCOCC5)C[C@@H]4C)n3)CC[C@H]2F)cn1] |
| 228 | 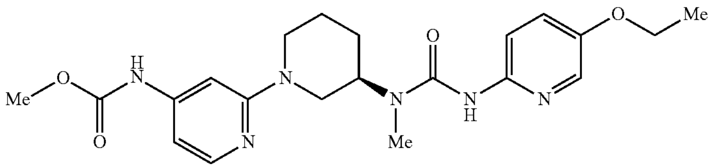 [SMILES: CCOc1ccc(NC(=O)N(C)[C@@H]2CCCN(c3cc(NC(=O)OC)ccn3)C2)nc1] |
| 229 | 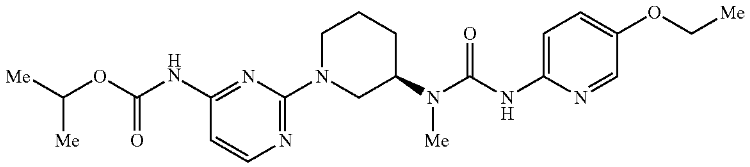 [SMILES: CCOc1ccc(NC(=O)N(C)[C@@H]2CCCN(c3nccc(NC(=O)OC(C)C)n3)C2)nc1] |
| 230 | 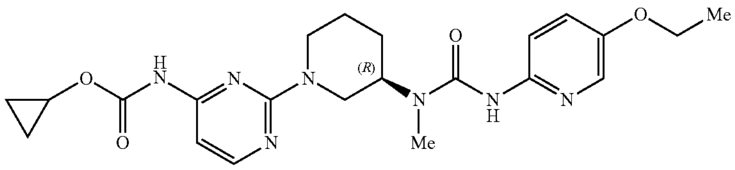 |
| 231 | 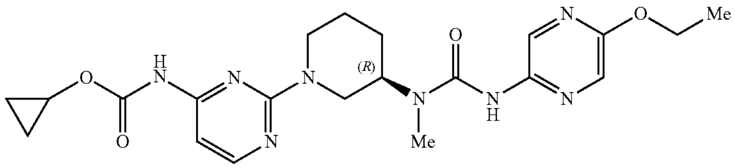 |

TABLE 2B-continued
| Ex. No. | Structure |
|---|---|
| 232 | 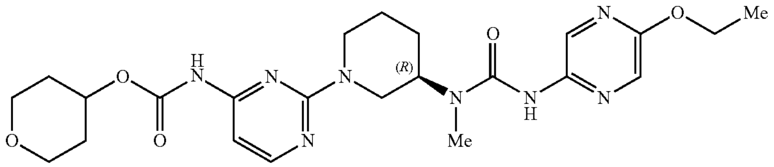 |
| 233 | 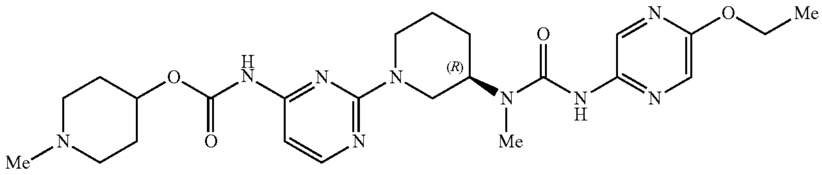 |
| 234 | 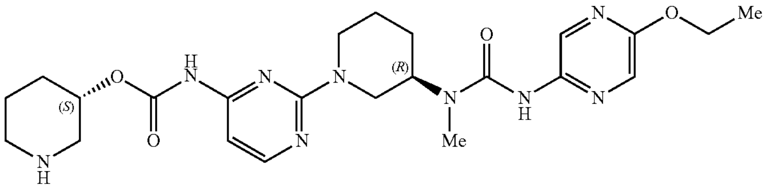 |
| 235 | 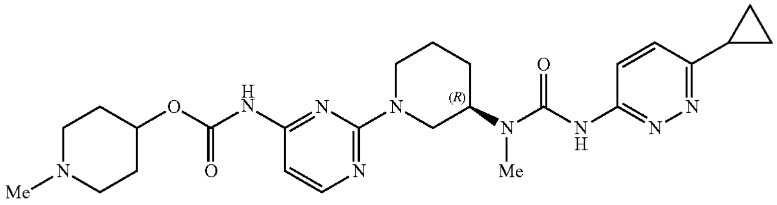 |
| 236 | 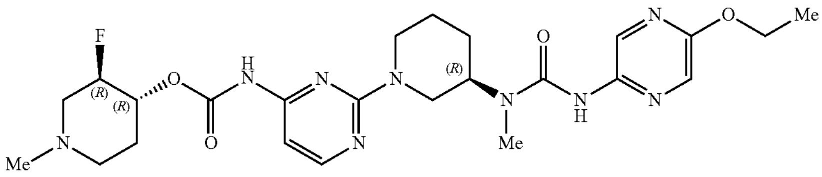 |
| 237 | 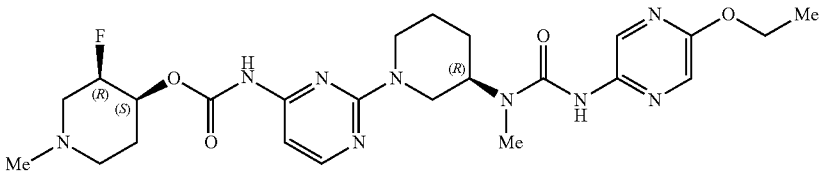 |
| 238 | 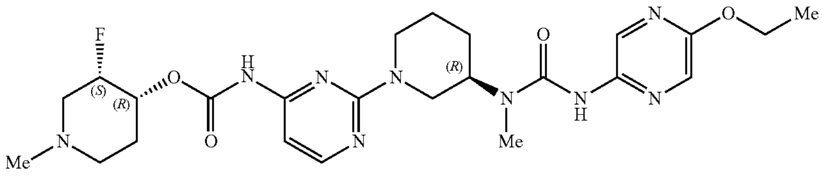 |
| 239 | 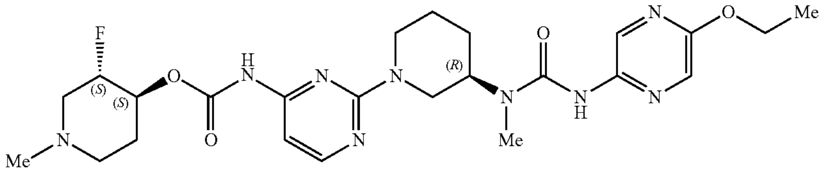 |

TABLE 2B-continued
| Ex. No. | Structure |
|---|---|
| 240 | 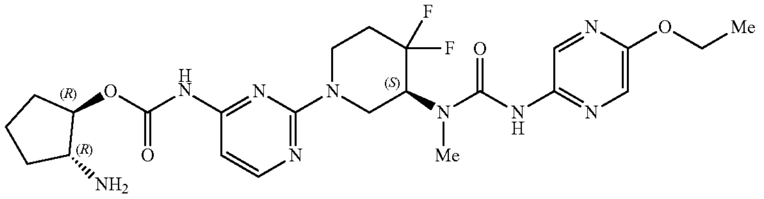 |
| 241 | 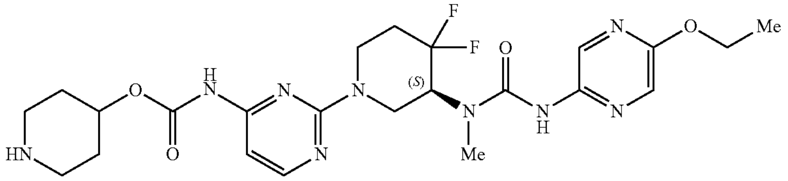 |
| 242 | 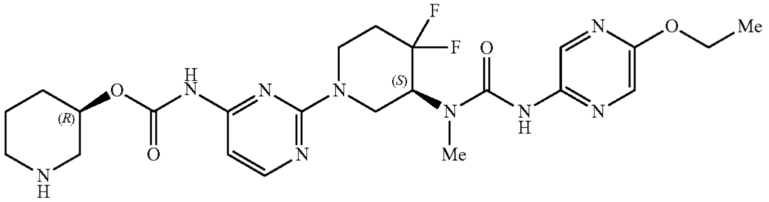 |
| 243 | 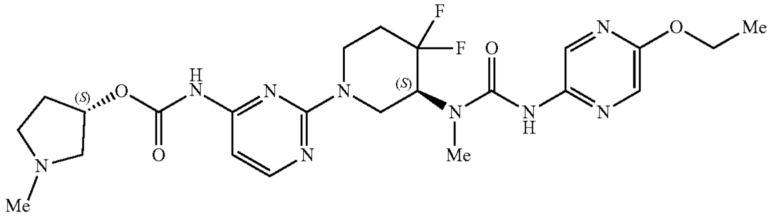 |
| 244 | 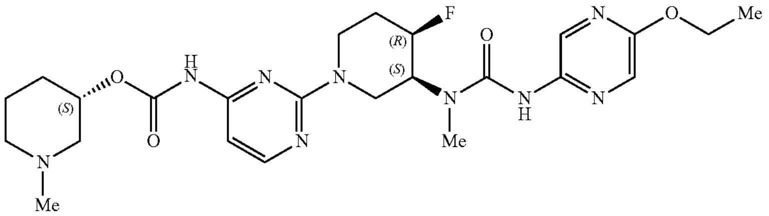 |
| 245 | 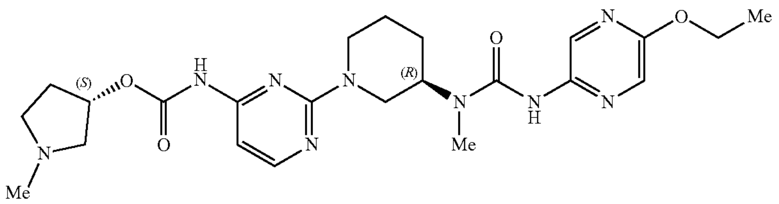 |
| 246 | 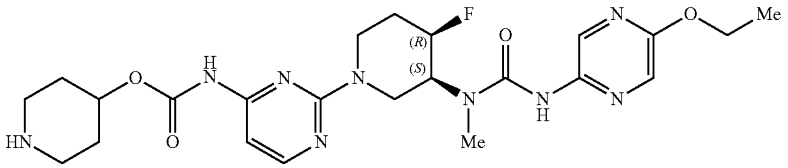 |

TABLE 2B-continued
| Ex. No. | Structure |
| --- | --- |
| 247 | 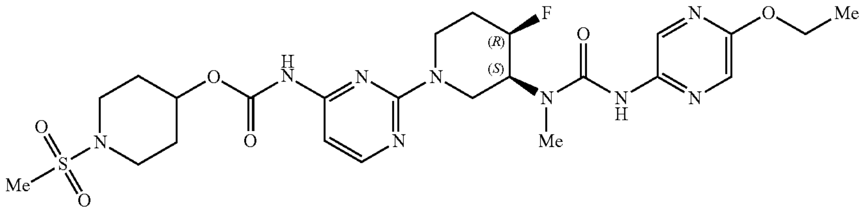 |
| 248 | 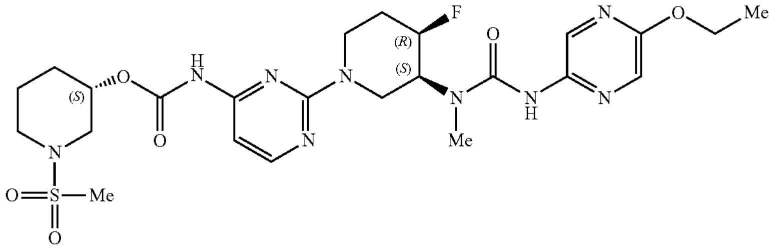 |
| 249 | 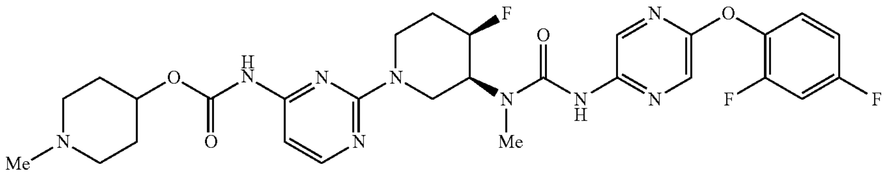 [SMILES: CN1CCC(OC(=O)Nc2ccnc(N3CC[C@@H](F)[C@@H](N(C)C(=O)Nc4cnc(Oc5ccc(F)cc5F)cn4)C3)n2)CC1] |
| 250 | 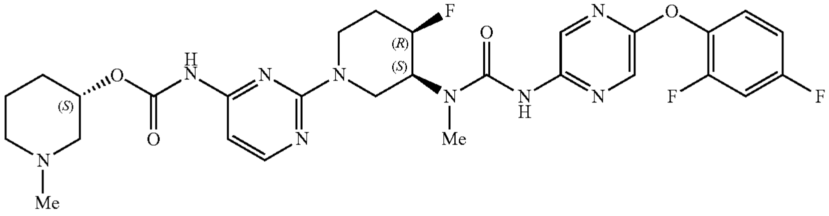 |
| 251 | 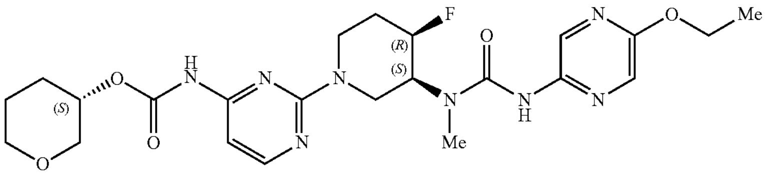 |
| 252 | 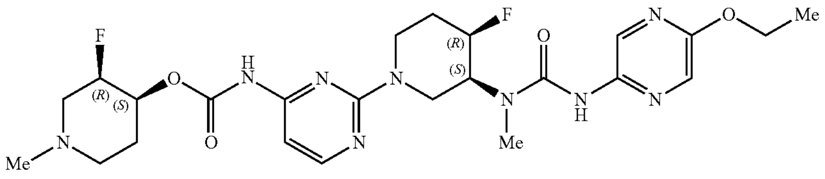 |
| 253 | 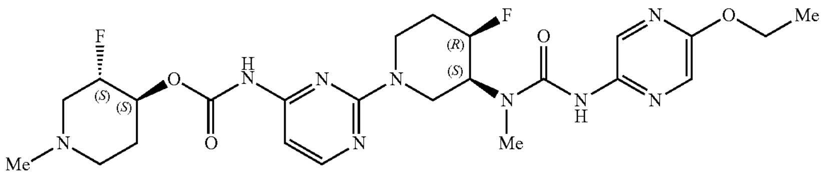 |

TABLE 2B-continued
| Ex. No. | Structure |
|---|---|
| 254 | 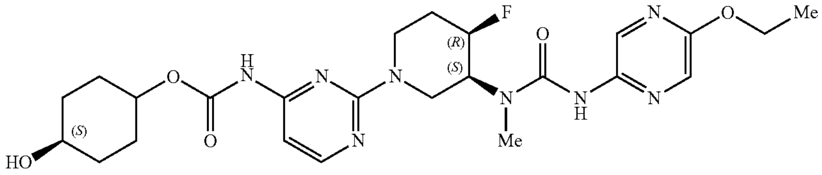 |
| 255 | 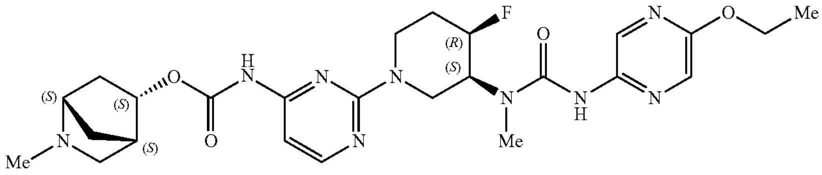 |
| 256 | 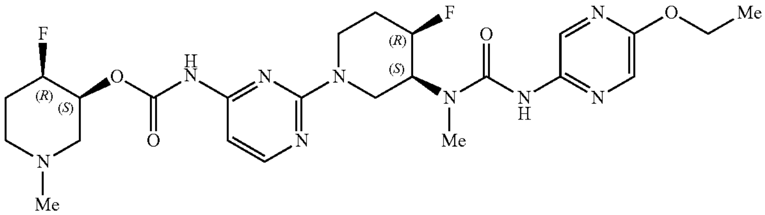 |
| 257 | 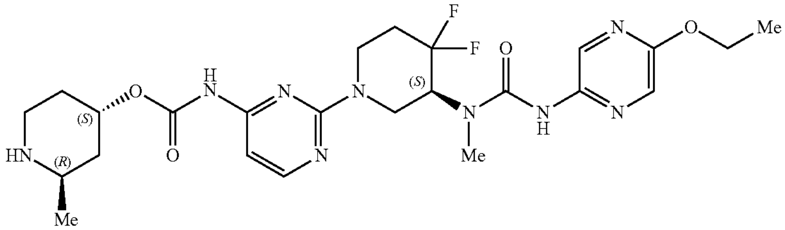 |
| 258 | 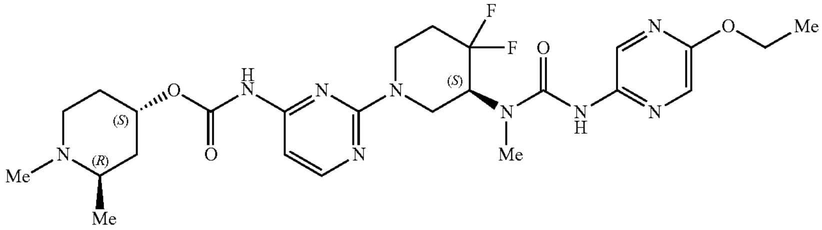 |
| 259 | 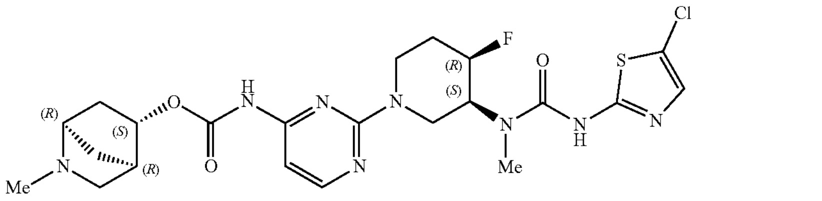 |
| 260 | 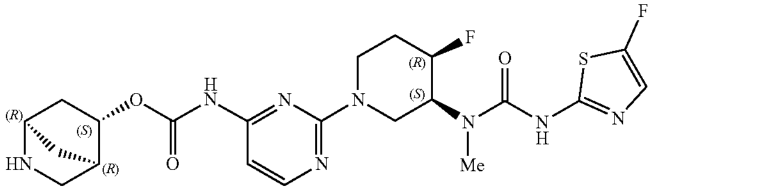 |

TABLE 2B-continued
| Ex. No. | Structure |
| --- | --- |
| 261 | 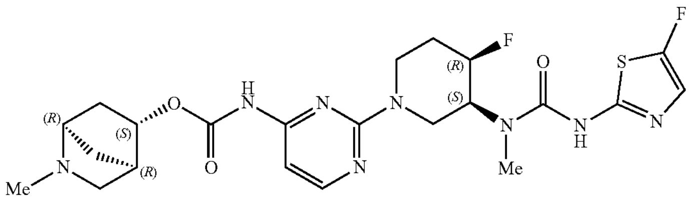 |
| 262 | 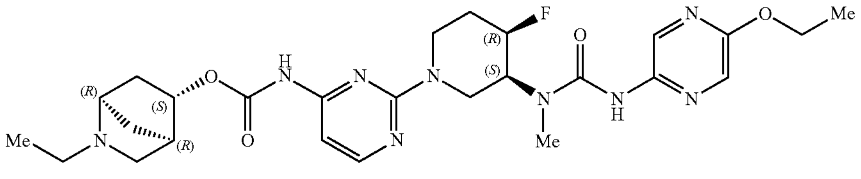 |
| 263 | 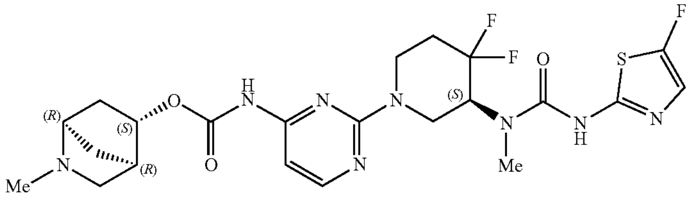 |
| 264 | 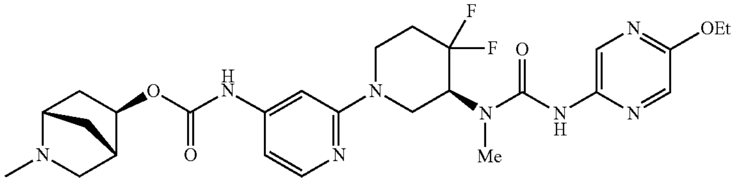 [SMILES: CCOc1cnc(NC(=O)N(C)[C@H]2CN(c3cc(NC(=O)O[C@@H]4C[C@@H]5C[C@H]4CN5C)ccn3)CCC2(F)F)cn1] |
| 265 | 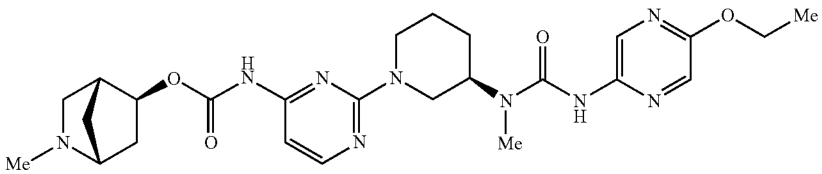 [SMILES: CCOc1cnc(NC(=O)N(C)[C@@H]2CCCN(c3nccc(NC(=O)O[C@H]4C[C@H]5C[C@@H]4CN5C)n3)C2)cn1] |
| 266 | 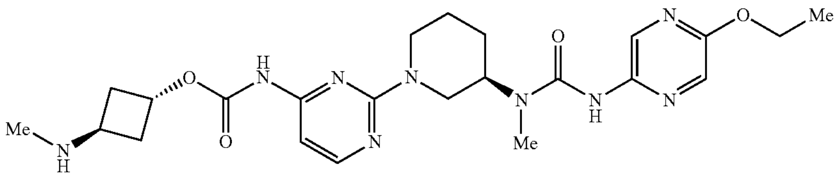 [SMILES: CCOc1cnc(NC(=O)N(C)[C@@H]2CCCN(c3nccc(NC(=O)O[C@H]4C[C@H](NC)C4)n3)C2)cn1] |
| 267 | 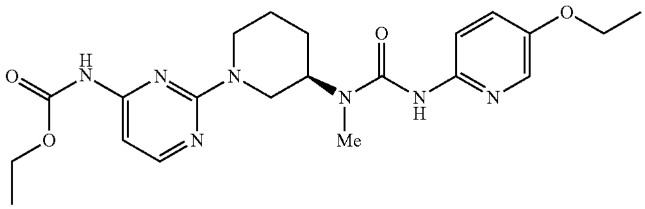 [SMILES: CCOC(=O)Nc1ccnc(N2CCC[C@@H](N(C)C(=O)Nc3ccc(OCC)cn3)C2)n1] |
| 268 | 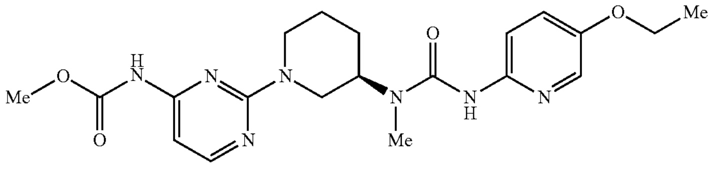 [SMILES: CCOc1ccc(NC(=O)N(C)[C@@H]2CCCN(c3nccc(NC(=O)OC)n3)C2)nc1] |

TABLE 2B-continued
| Ex. No. | Structure |
|---|---|
| 269 | 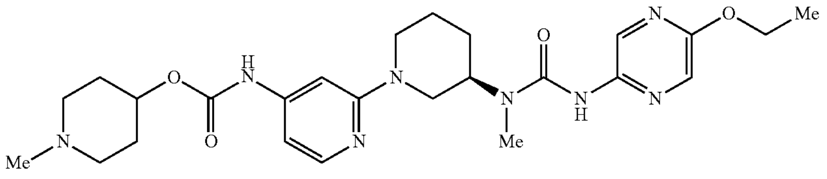 [SMILES: CCOc1cnc(NC(=O)N(C)[C@@H]2CCCN(c3cc(NC(=O)OC4CCN(C)CC4)ccn3)C2)cn1] |
| 270 | 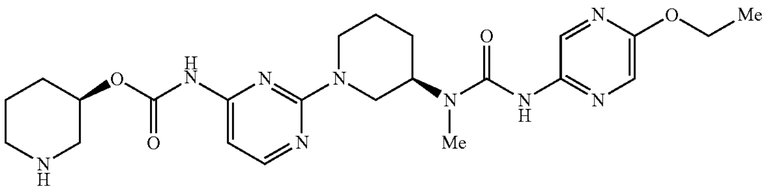 [SMILES: CCOc1cnc(NC(=O)N(C)[C@@H]2CCCN(c3nccc(NC(=O)O[C@@H]4CCCNC4)n3)C2)cn1] |
| 271 | 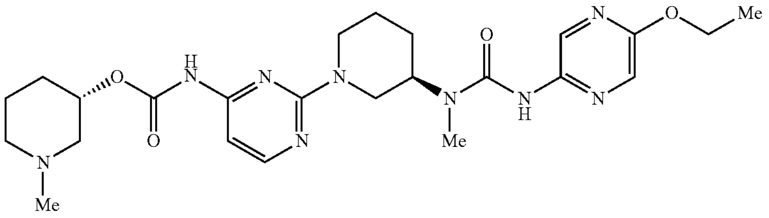 [SMILES: CCOc1cnc(NC(=O)N(C)[C@@H]2CCCN(c3nccc(NC(=O)O[C@H]4CCCN(C)C4)n3)C2)cn1] |
| 272 | 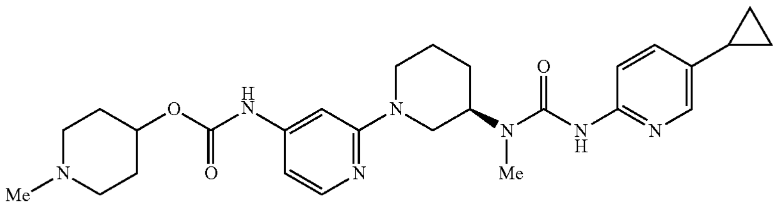 [SMILES: CN1CCC(OC(=O)Nc2ccnc(N3CCC[C@@H](N(C)C(=O)Nc4ccc(C5CC5)cn4)C3)c2)CC1] |
| 273 | 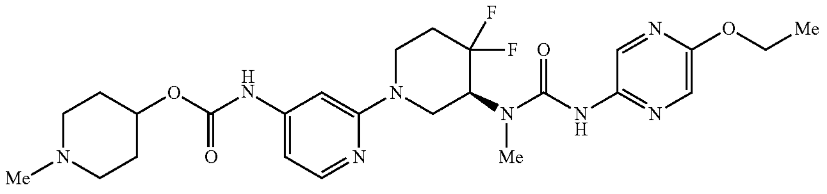 [SMILES: CCOc1cnc(NC(=O)N(C)[C@H]2CN(c3cc(NC(=O)OC4CCN(C)CC4)ccn3)CCC2(F)F)cn1] |
| 274 | 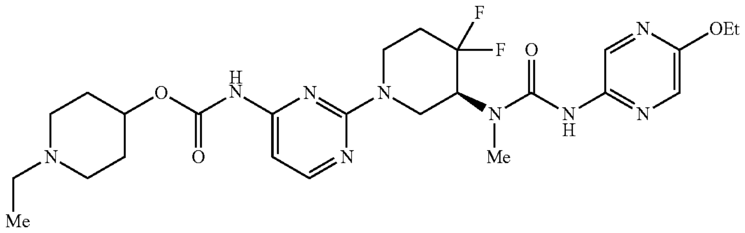 [SMILES: CCOc1cnc(NC(=O)N(C)[C@H]2CN(c3nccc(NC(=O)OC4CCN(CC)CC4)n3)CCC2(F)F)cn1] |
| 275 | 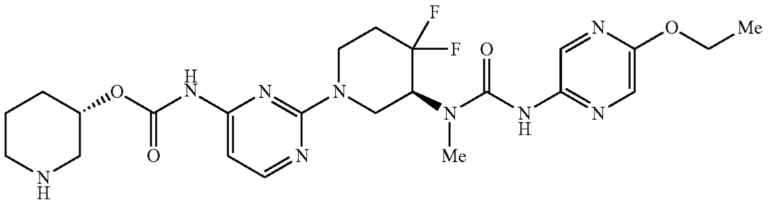 [SMILES: CCOc1cnc(NC(=O)N(C)[C@H]2CN(c3nccc(NC(=O)O[C@H]4CCCNC4)n3)CCC2(F)F)cn1] |

TABLE 2B-continued
| Ex. No. | Structure |
|---|---|
| 276 | 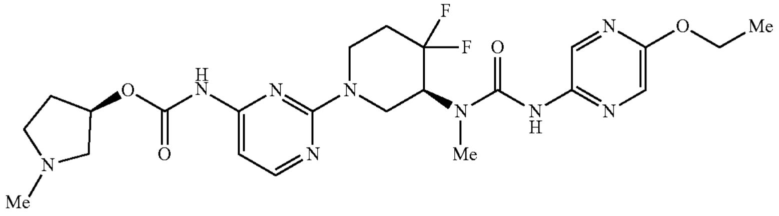 [SMILES: CCOc1cnc(NC(=O)N(C)[C@H]2CN(c3nccc(NC(=O)O[C@@H]4CCN(C)C4)n3)CCC2(F)F)cn1] |
| 277 | 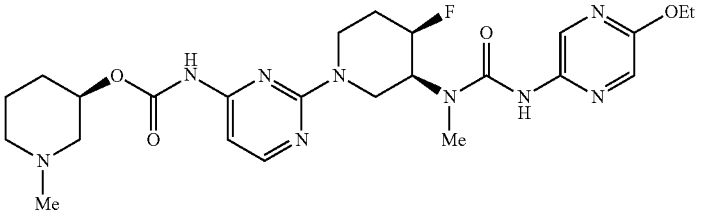 [SMILES: CCOc1cnc(NC(=O)N(C)[C@H]2CN(c3nccc(NC(=O)O[C@@H]4CCCN(C)C4)n3)CC[C@H]2F)cn1] |
| 278 | 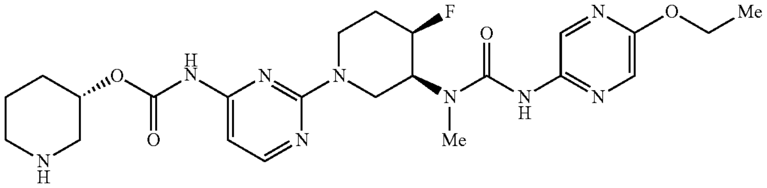 [SMILES: CCOc1cnc(NC(=O)N(C)[C@H]2CN(c3nccc(NC(=O)O[C@H]4CCCNC4)n3)CC[C@H]2F)cn1] |
| 279 | 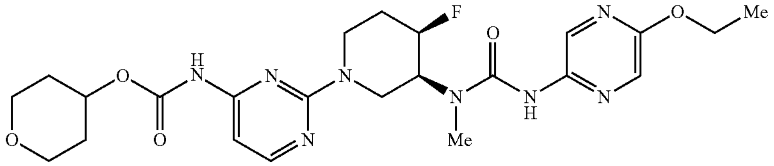 [SMILES: CCOc1cnc(NC(=O)N(C)[C@H]2CN(c3nccc(NC(=O)OC4CCOCC4)n3)CC[C@H]2F)cn1] |
| 280 | 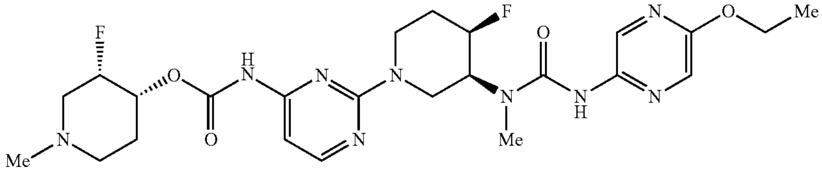 [SMILES: CCOc1cnc(NC(=O)N(C)[C@H]2CN(c3nccc(NC(=O)O[C@@H]4CCN(C)C[C@@H]4F)n3)CC[C@H]2F)cn1] |
| 281 | 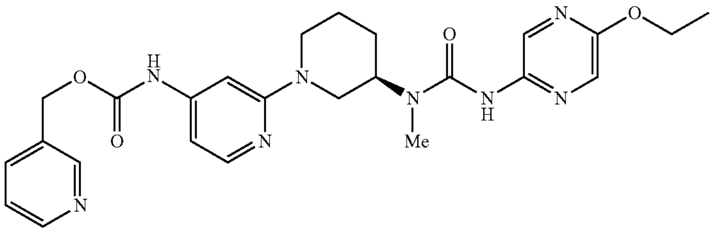 [SMILES: CCOc1cnc(NC(=O)N(C)[C@@H]2CCCN(c3cc(NC(=O)OCc4cccnc4)ccn3)C2)cn1] |
| 282 | 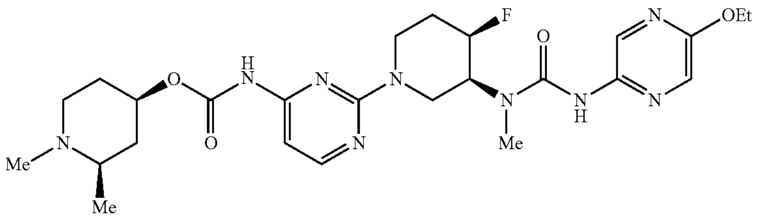 [SMILES: CCOc1cnc(NC(=O)N(C)[C@H]2CN(c3nccc(NC(=O)O[C@@H]4CCN(C)[C@H](C)C4)n3)CC[C@H]2F)cn1] |

TABLE 2B-continued
| Ex. No. | Structure |
|---|---|
| 283 | 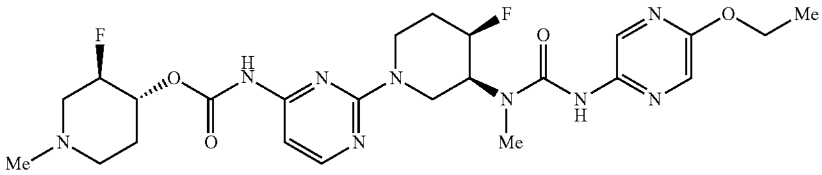 [SMILES: CCOc1cnc(NC(=O)N(C)[C@H]2CN(c3nccc(NC(=O)O[C@@H]4CCN(C)C[C@H]4F)n3)CC[C@H]2F)cn1] |
| 284 | 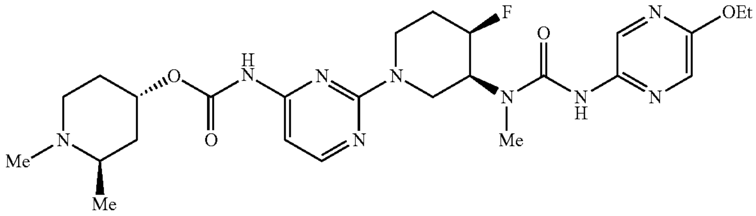 [SMILES: CCOc1cnc(NC(=O)N(C)[C@H]2CN(c3nccc(NC(=O)O[C@H]4CCN(C)[C@H](C)C4)n3)CC[C@H]2F)cn1] |
| 285 | 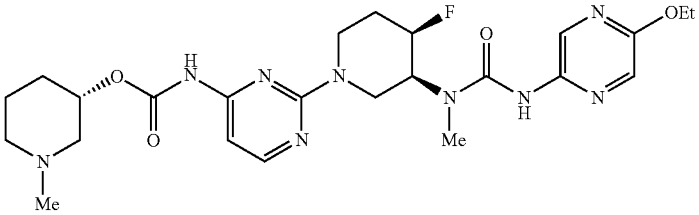 [SMILES: CCOc1cnc(NC(=O)N(C)[C@H]2CN(c3nccc(NC(=O)O[C@H]4CCCN(C)C4)n3)CC[C@H]2F)cn1] |
| 286 | 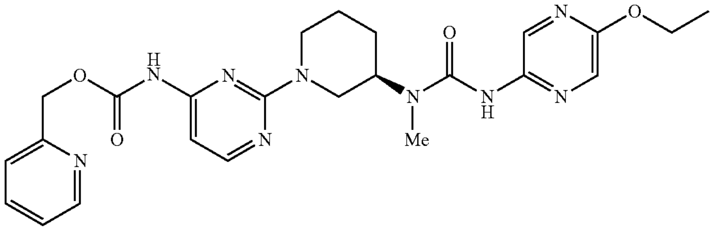 [SMILES: CCOc1cnc(NC(=O)N(C)[C@@H]2CCCN(c3nccc(NC(=O)OCc4ccccn4)n3)C2)cn1] |
| 287 | 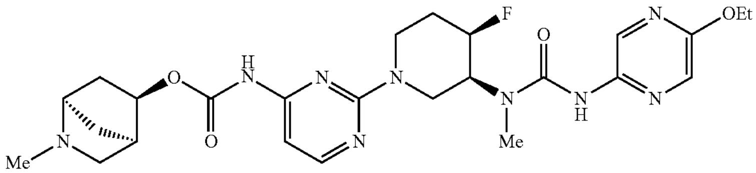 [SMILES: CCOc1cnc(NC(=O)N(C)[C@H]2CN(c3nccc(NC(=O)O[C@@H]4C[C@H]5C[C@@H]4CN5C)n3)CC[C@H]2F)cn1] |
| 288 | 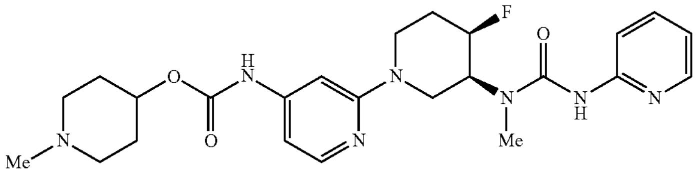 [SMILES: CN1CCC(OC(=O)Nc2ccnc(N3CC[C@@H](F)[C@@H](N(C)C(=O)Nc4ccccn4)C3)c2)CC1] |
| 289 | 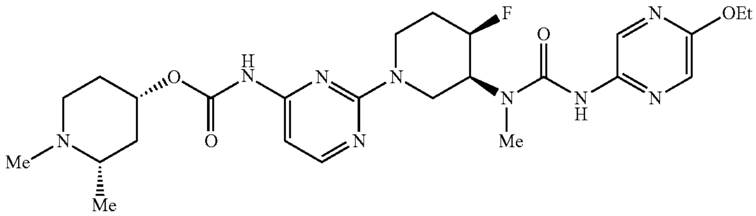 [SMILES: CCOc1cnc(NC(=O)N(C)[C@H]2CN(c3nccc(NC(=O)O[C@H]4CCN(C)[C@@H](C)C4)n3)CC[C@H]2F)cn1] |

TABLE 2B-continued
| Ex. No. | Structure |
| --- | --- |
| 290 | 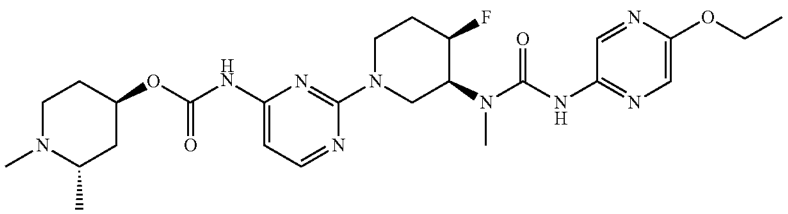 [SMILES: CCOc1cnc(NC(=O)N(C)[C@H]2CN(c3nccc(NC(=O)O[C@@H]4CCN(C)[C@@H](C)C4)n3)CC[C@H]2F)cn1] |
| 291 | 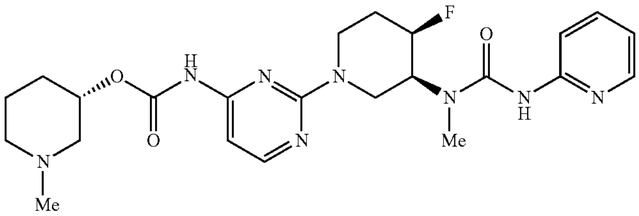 [SMILES: CN1CCC[C@H](OC(=O)Nc2ccnc(N3CC[C@@H](F)[C@@H](N(C)C(=O)Nc4ccccn4)C3)n2)C1] |
| 292 | 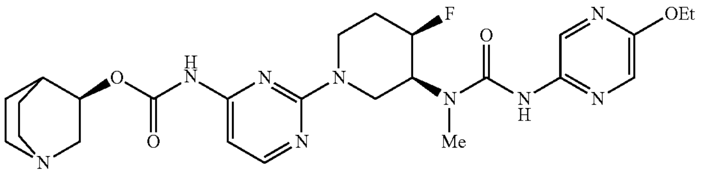 [SMILES: CCOc1cnc(NC(=O)N(C)[C@H]2CN(c3nccc(NC(=O)O[C@H]4CN5CCC4CC5)n3)CC[C@H]2F)cn1] |
| 293 | 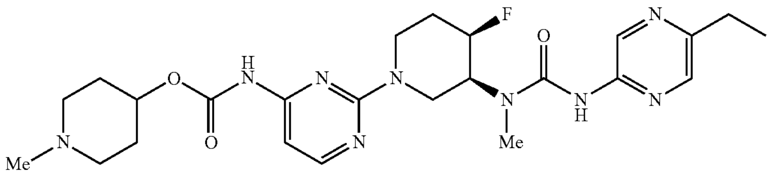 [SMILES: CCc1cnc(NC(=O)N(C)[C@H]2CN(c3nccc(NC(=O)OC4CCN(C)CC4)n3)CC[C@H]2F)cn1] |
| 294 | 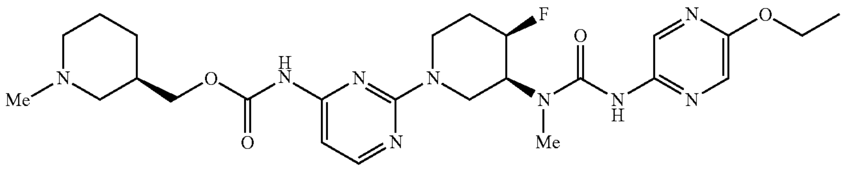 [SMILES: CCOc1cnc(NC(=O)N(C)[C@H]2CN(c3nccc(NC(=O)OC[C@@H]4CCCN(C)C4)n3)CC[C@H]2F)cn1] |
| 295 | 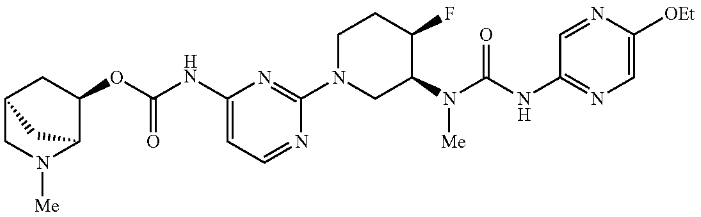 [SMILES: CCOc1cnc(NC(=O)N(C)[C@H]2CN(c3nccc(NC(=O)O[C@@H]4C[C@H]5C[C@@H]4N(C)C5)n3)CC[C@H]2F)cn1] |
| 296 | 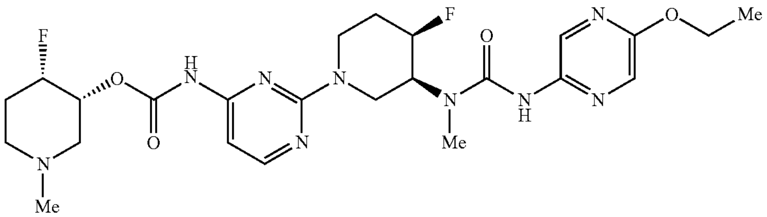 [SMILES: CCOc1cnc(NC(=O)N(C)[C@H]2CN(c3nccc(NC(=O)O[C@@H]4CN(C)CC[C@@H]4F)n3)CC[C@H]2F)cn1] |

TABLE 2B-continued
| Ex. No. | Structure |
|---|---|
| 297 | 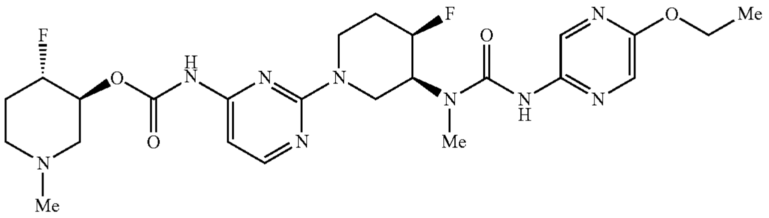 [SMILES: CCOc1cnc(NC(=O)N(C)[C@H]2CN(c3nccc(NC(=O)O[C@H]4CN(C)CC[C@@H]4F)n3)CC[C@H]2F)cn1] |
| 298 | 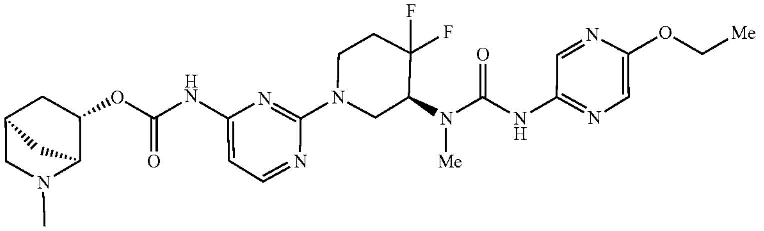 [SMILES: CCOc1cnc(NC(=O)N(C)[C@H]2CN(c3nccc(NC(=O)O[C@H]4C[C@H]5C[C@@H]4N(C)C5)n3)CCC2(F)F)cn1] |
| 299 | 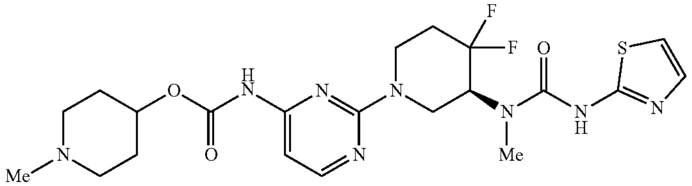 [SMILES: CN1CCC(OC(=O)Nc2ccnc(N3CCC(F)(F)[C@@H](N(C)C(=O)Nc4nccs4)C3)n2)CC1] |
| 300 | 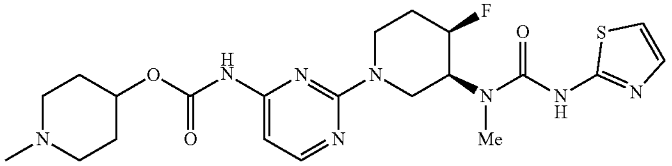 [SMILES: CN1CCC(OC(=O)Nc2ccnc(N3CC[C@@H](F)[C@@H](N(C)C(=O)Nc4nccs4)C3)n2)CC1] |
| 301 | 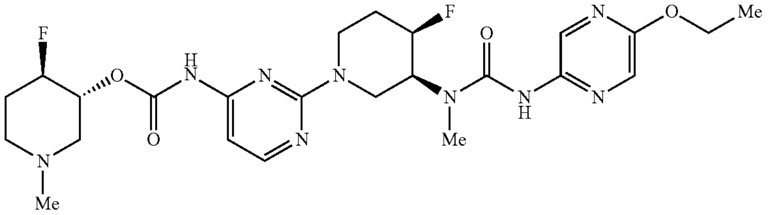 [SMILES: CCOc1cnc(NC(=O)N(C)[C@H]2CN(c3nccc(NC(=O)O[C@@H]4CN(C)CC[C@H]4F)n3)CC[C@H]2F)cn1] |
| 302 | 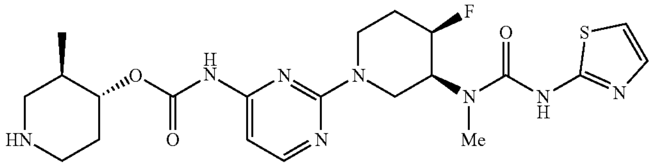 [SMILES: C[C@@H]1CNCC[C@H]1OC(=O)Nc1ccnc(N2CC[C@@H](F)[C@@H](N(C)C(=O)Nc3nccs3)C2)n1] |
| 303 | 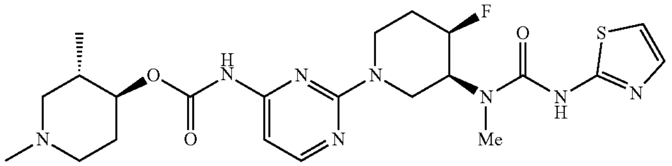 [SMILES: C[C@H]1CN(C)CC[C@@H]1OC(=O)Nc1ccnc(N2CC[C@@H](F)[C@@H](N(C)C(=O)Nc3nccs3)C2)n1] |

TABLE 2B-continued
| Ex. No. | Structure |
|---|---|
| 304 | 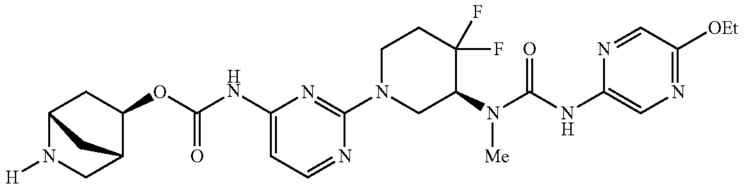 [SMILES: CCOc1cnc(NC(=O)N(C)[C@H]2CN(c3nccc(NC(=O)O[C@@H]4C[C@@H]5C[C@H]4CN5)n3)CCC2(F)F)cn1] |
| 305 | 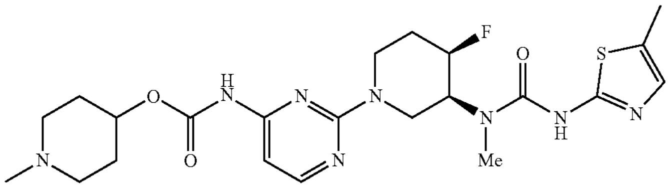 [SMILES: Cc1cnc(NC(=O)N(C)[C@H]2CN(c3nccc(NC(=O)OC4CCN(C)CC4)n3)CC[C@H]2F)s1] |
| 306 | 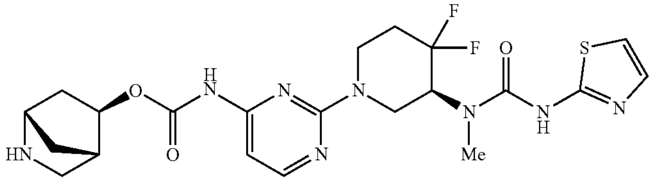 [SMILES: CN(C(=O)Nc1nccs1)[C@H]1CN(c2nccc(NC(=O)O[C@@H]3C[C@@H]4C[C@H]3CN4)n2)CCC1(F)F] |
| 307 | 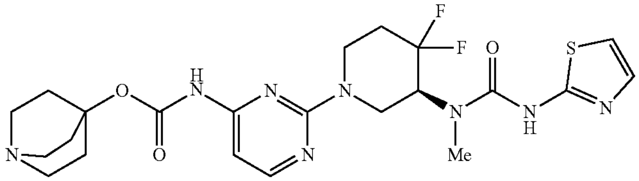 [SMILES: CN(C(=O)Nc1nccs1)[C@H]1CN(c2nccc(NC(=O)OC34CCN(CC3)CC4)n2)CCC1(F)F] |
| 308 | 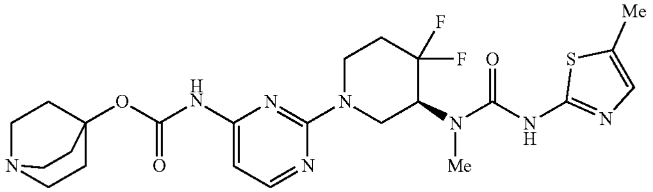 [SMILES: Cc1cnc(NC(=O)N(C)[C@H]2CN(c3nccc(NC(=O)OC45CCN(CC4)CC5)n3)CCC2(F)F)s1] |
| 309 | 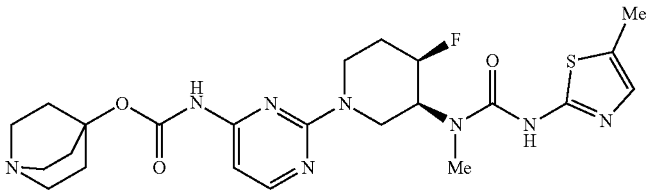 [SMILES: Cc1cnc(NC(=O)N(C)[C@H]2CN(c3nccc(NC(=O)OC45CCN(CC4)CC5)n3)CC[C@H]2F)s1] |
| 310 | 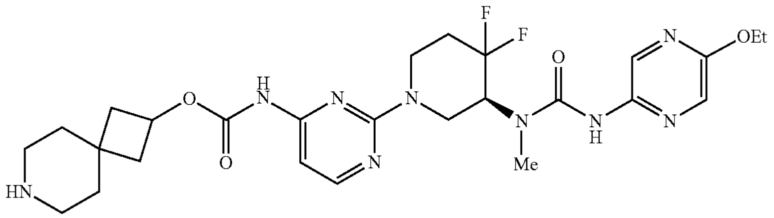 [SMILES: CCOc1cnc(NC(=O)N(C)[C@H]2CN(c3nccc(NC(=O)OC4CC5(CCNCC5)C4)n3)CCC2(F)F)cn1] |

TABLE 2B-continued
| Ex. No. | Structure |
|---|---|
| 311 | 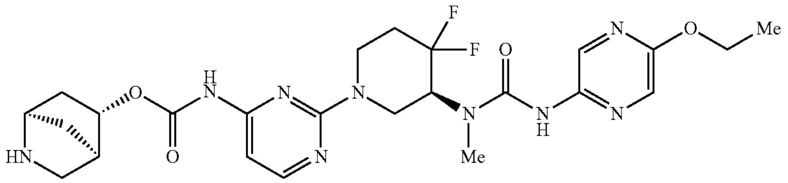 [SMILES: CCOc1cnc(NC(=O)N(C)[C@H]2CN(c3nccc(NC(=O)O[C@H]4C[C@H]5C[C@@H]4CN5)n3)CCC2(F)F)cn1] |
| 312 | 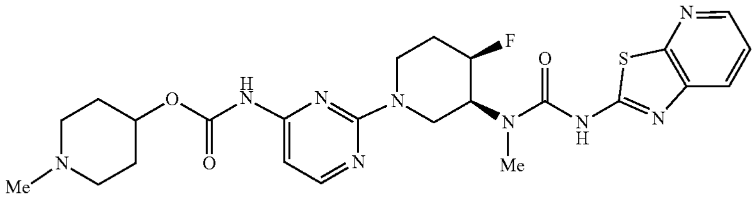 [SMILES: CN1CCC(OC(=O)Nc2ccnc(N3CC[C@@H](F)[C@@H](N(C)C(=O)Nc4nc5cccnc5s4)C3)n2)CC1] |
| 313 | 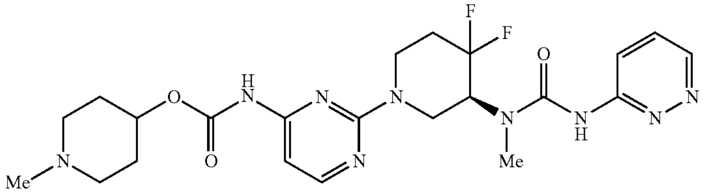 [SMILES: CN1CCC(OC(=O)Nc2ccnc(N3CCC(F)(F)[C@@H](N(C)C(=O)Nc4cccnn4)C3)n2)CC1] |
| 314 | 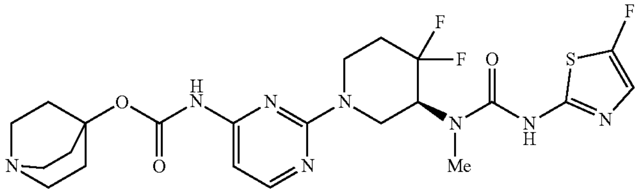 [SMILES: CN(C(=O)Nc1ncc(F)s1)[C@H]1CN(c2nccc(NC(=O)OC34CCN(CC3)CC4)n2)CCC1(F)F] |
| 315 | 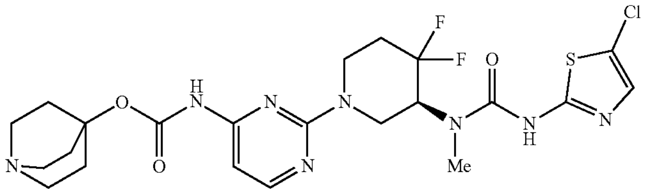 [SMILES: CN(C(=O)Nc1ncc(Cl)s1)[C@H]1CN(c2nccc(NC(=O)OC34CCN(CC3)CC4)n2)CCC1(F)F] |
| 316 | 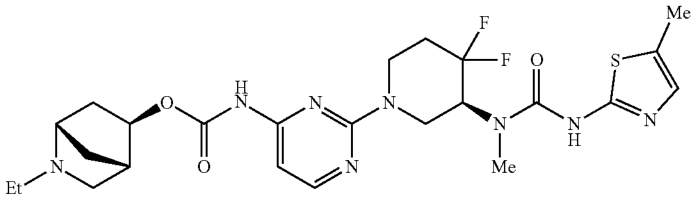 [SMILES: CCN1C[C@@H]2C[C@H]1C[C@H]2OC(=O)Nc1ccnc(N2CCC(F)(F)[C@@H](N(C)C(=O)Nc3ncc(C)s3)C2)n1] |
| 317 | 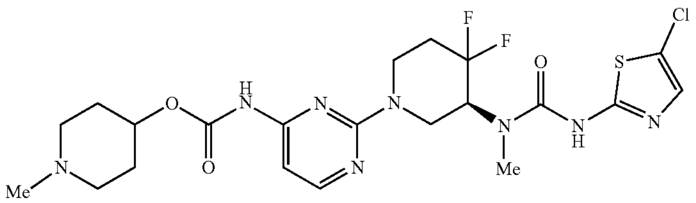 [SMILES: CN1CCC(OC(=O)Nc2ccnc(N3CCC(F)(F)[C@@H](N(C)C(=O)Nc4ncc(Cl)s4)C3)n2)CC1] |

TABLE 2B-continued
| Ex. No. | Structure |
|---|---|
| 318 | 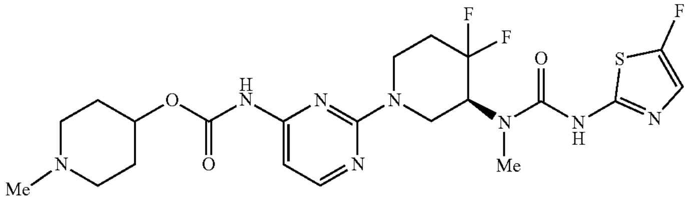 [SMILES: CN1CCC(OC(=O)Nc2ccnc(N3CCC(F)(F)[C@@H](N(C)C(=O)Nc4ncc(F)s4)C3)n2)CC1] |
| 319 | 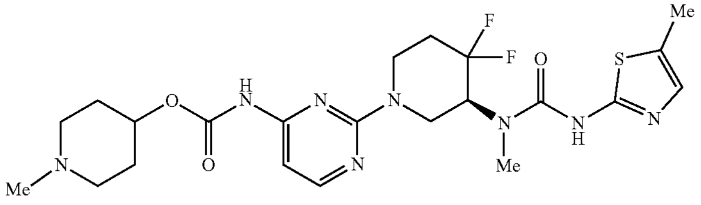 [SMILES: Cc1cnc(NC(=O)N(C)[C@H]2CN(c3nccc(NC(=O)OC4CCN(C)CC4)n3)CCC2(F)F)s1] |
| 320 | 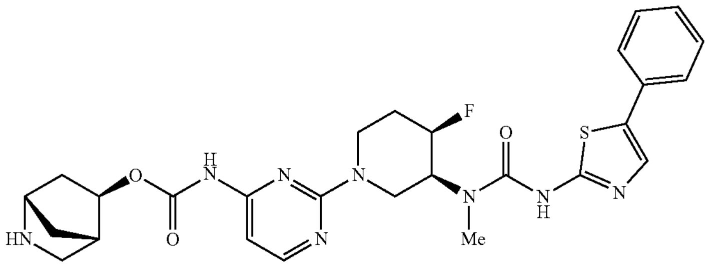 [SMILES: CN(C(=O)Nc1ncc(-c2ccccc2)s1)[C@H]1CN(c2nccc(NC(=O)O[C@@H]3C[C@@H]4C[C@H]3CN4)n2)CC[C@H]1F] |
| 321 | 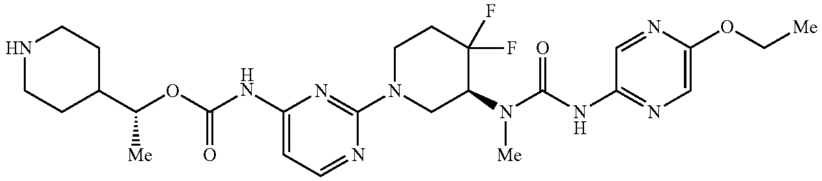 [SMILES: CCOc1cnc(NC(=O)N(C)[C@H]2CN(c3nccc(NC(=O)O[C@H](C)C4CCNCC4)n3)CCC2(F)F)cn1] |
| 322 | 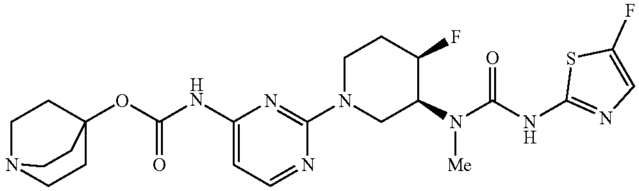 [SMILES: CN(C(=O)Nc1ncc(F)s1)[C@H]1CN(c2nccc(NC(=O)OC34CCN(CC3)CC4)n2)CC[C@H]1F] |
| 323 | 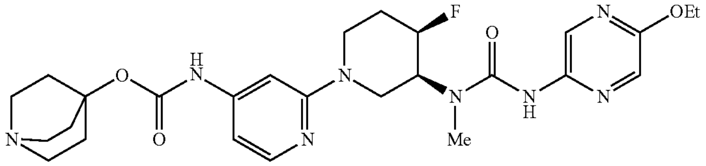 [SMILES: CCOc1cnc(NC(=O)N(C)[C@H]2CN(c3cc(NC(=O)OC45CCN(CC4)CC5)ccn3)CC[C@H]2F)cn1] |
| 324 | 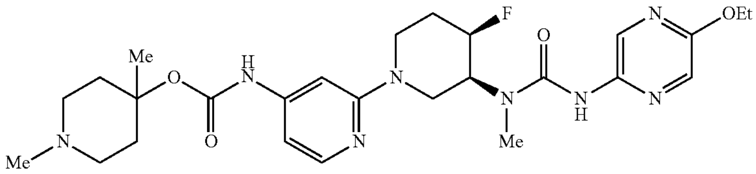 [SMILES: CCOc1cnc(NC(=O)N(C)[C@H]2CN(c3cc(NC(=O)OC4(C)CCN(C)CC4)ccn3)CC[C@H]2F)cn1] |

TABLE 2B-continued
| Ex. No. | Structure |
|---|---|
| 325 | 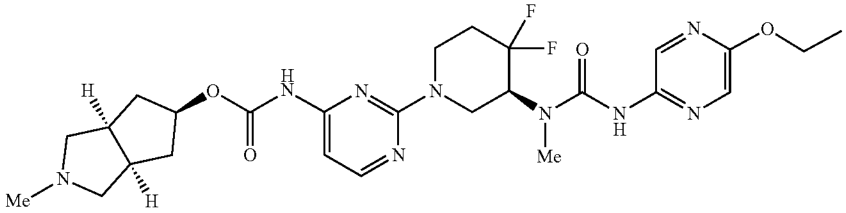 [SMILES: CCOc1cnc(NC(=O)N(C)[C@H]2CN(c3nccc(NC(=O)O[C@@H]4C[C@@H]5CN(C)C[C@@H]5C4)n3)CCC2(F)F)cn1] |
| 326 | 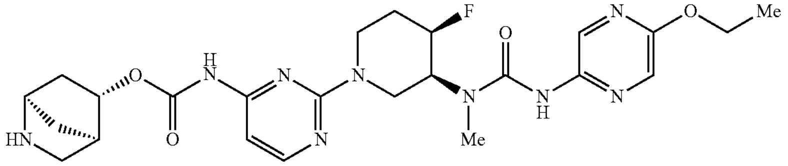 [SMILES: CCOc1cnc(NC(=O)N(C)[C@H]2CN(c3nccc(NC(=O)O[C@H]4C[C@H]5C[C@@H]4CN5)n3)CC[C@H]2F)cn1] |
| 327 | 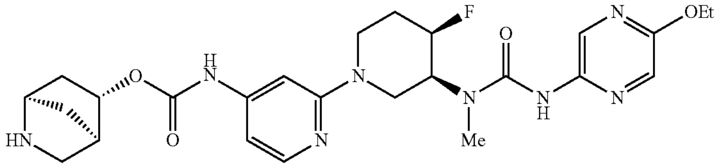 [SMILES: CCOc1cnc(NC(=O)N(C)[C@H]2CN(c3cc(NC(=O)O[C@H]4C[C@H]5C[C@@H]4CN5)ccn3)CC[C@H]2F)cn1] |
| 328 | 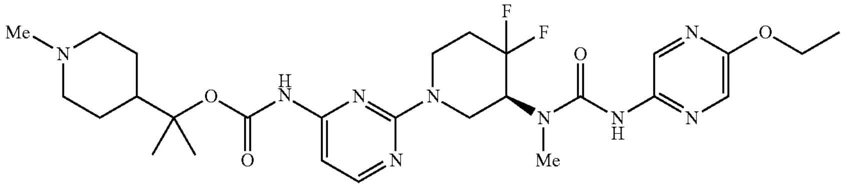 [SMILES: CCOc1cnc(NC(=O)N(C)[C@H]2CN(c3nccc(NC(=O)OC(C)(C)C4CCN(C)CC4)n3)CCC2(F)F)cn1] |
| 329 | 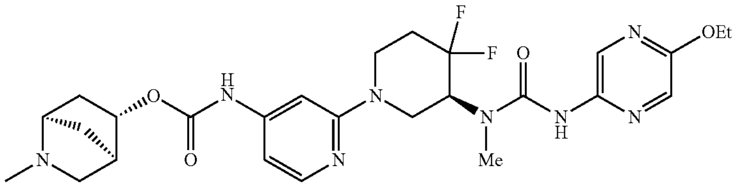 [SMILES: CCOc1cnc(NC(=O)N(C)[C@H]2CN(c3cc(NC(=O)O[C@H]4C[C@H]5C[C@@H]4CN5C)ccn3)CCC2(F)F)cn1] |
| 330 | 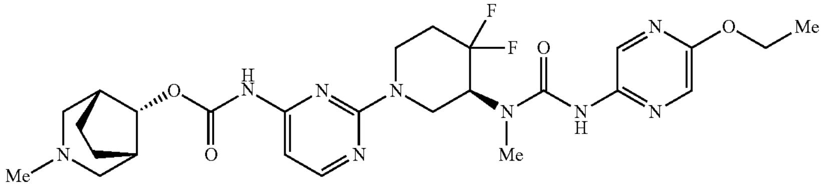 [SMILES: CCOc1cnc(NC(=O)N(C)[C@H]2CN(c3nccc(NC(=O)O[C@H]4[C@@H]5CC[C@H]4CN(C)C5)n3)CCC2(F)F)cn1] |
| 331 | 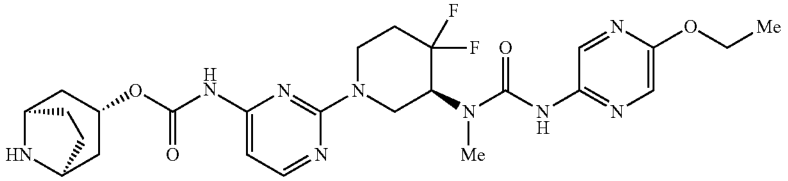 [SMILES: CCOc1cnc(NC(=O)N(C)[C@H]2CN(c3nccc(NC(=O)O[C@H]4C[C@H]5CC[C@@H](C4)N5)n3)CCC2(F)F)cn1] |
| 332 | 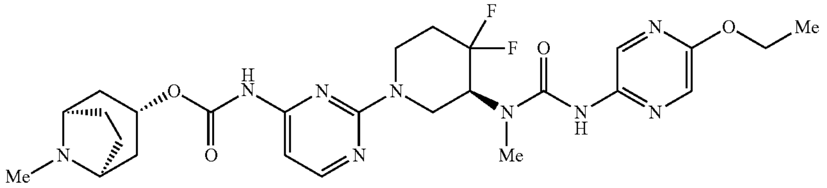 [SMILES: CCOc1cnc(NC(=O)N(C)[C@H]2CN(c3nccc(NC(=O)O[C@H]4C[C@H]5CC[C@@H](C4)N5C)n3)CCC2(F)F)cn1] |

TABLE 2B-continued
| Ex. No. | Structure |
|---|---|
| 333 | 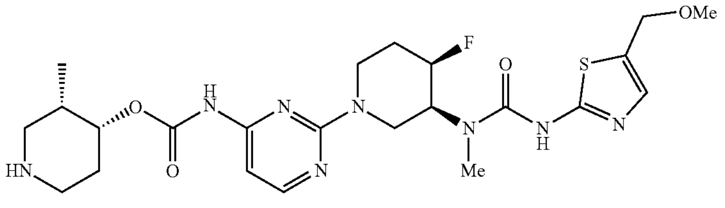 [SMILES: COCc1cnc(NC(=O)N(C)[C@H]2CN(c3nccc(NC(=O)O[C@@H]4CCNC[C@@H]4C)n3)CC[C@H]2F)s1] |
| 334 | 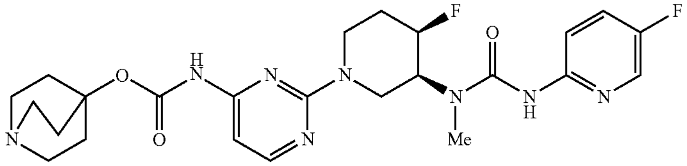 [SMILES: CN(C(=O)Nc1ccc(F)cn1)[C@H]1CN(c2nccc(NC(=O)OC34CCN(CC3)CC4)n2)CC[C@H]1F] |
| 335 | 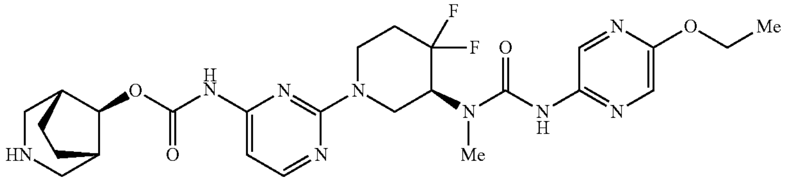 [SMILES: CCOc1cnc(NC(=O)N(C)[C@H]2CN(c3nccc(NC(=O)O[C@@H]4[C@@H]5CC[C@H]4CNC5)n3)CCC2(F)F)cn1] |
| 336 | 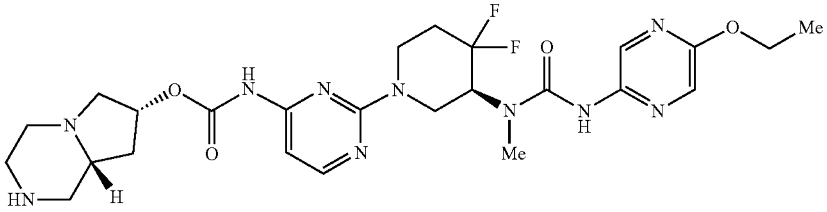 [SMILES: CCOc1cnc(NC(=O)N(C)[C@H]2CN(c3nccc(NC(=O)O[C@@H]4C[C@@H]5CNCCN5C4)n3)CCC2(F)F)cn1] |
| 337 | 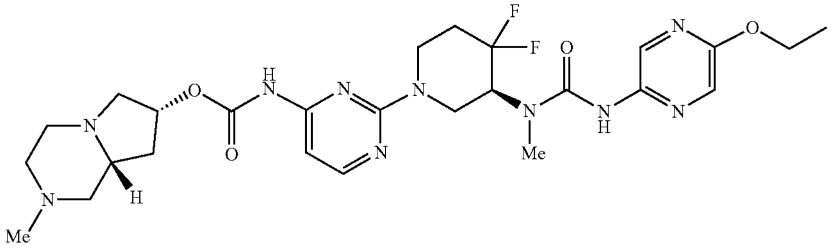 [SMILES: CCOc1cnc(NC(=O)N(C)[C@H]2CN(c3nccc(NC(=O)O[C@@H]4C[C@@H]5CN(C)CCN5C4)n3)CCC2(F)F)cn1] |
| 338 | 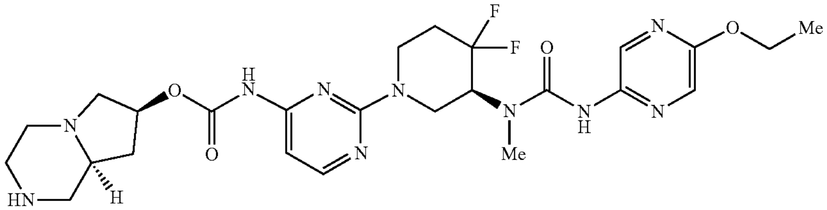 [SMILES: CCOc1cnc(NC(=O)N(C)[C@H]2CN(c3nccc(NC(=O)O[C@H]4C[C@H]5CNCCN5C4)n3)CCC2(F)F)cn1] |
| 339 | 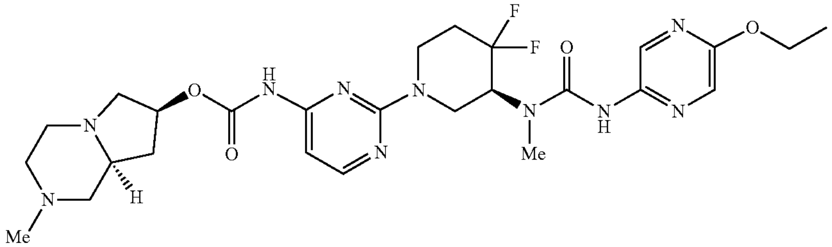 [SMILES: CCOc1cnc(NC(=O)N(C)[C@H]2CN(c3nccc(NC(=O)O[C@H]4C[C@H]5CN(C)CCN5C4)n3)CCC2(F)F)cn1] |

TABLE 2B-continued
| Ex. No. | Structure |
|---|---|
| 340 | 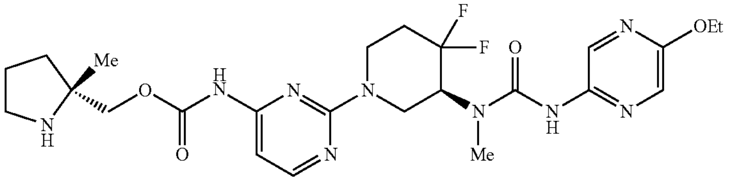 [SMILES: CCOc1cnc(NC(=O)N(C)[C@H]2CN(c3nccc(NC(=O)OC[C@@]4(C)CCCN4)n3)CCC2(F)F)cn1] |
| 341 | 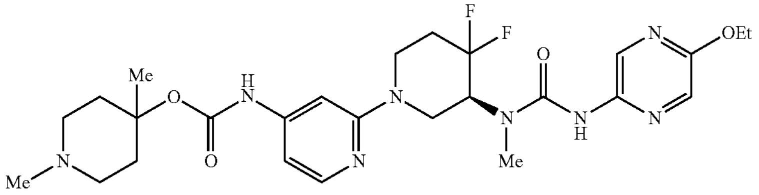 [SMILES: CCOc1cnc(NC(=O)N(C)[C@H]2CN(c3cc(NC(=O)OC4(C)CCN(C)CC4)ccn3)CCC2(F)F)cn1] |
| 342 | 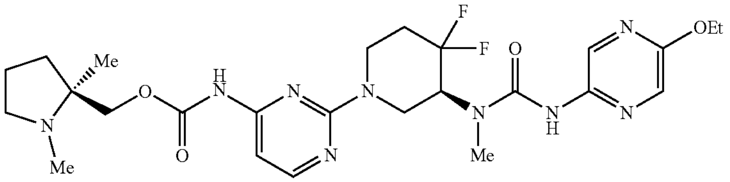 [SMILES: CCOc1cnc(NC(=O)N(C)[C@H]2CN(c3nccc(NC(=O)OC[C@]4(C)CCCN4C)n3)CCC2(F)F)cn1] |
| 343 | 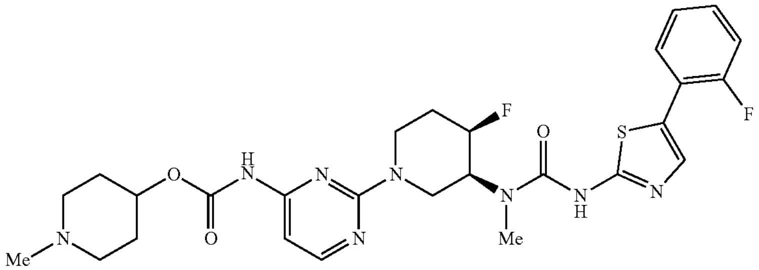 [SMILES: CN1CCC(OC(=O)Nc2ccnc(N3CC[C@@H](F)[C@@H](N(C)C(=O)Nc4ncc(-c5ccccc5F)s4)C3)n2)CC1] |
| 344 | 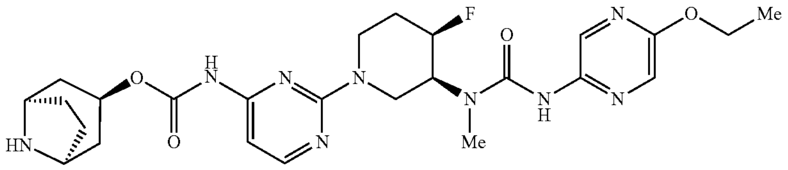 [SMILES: CCOc1cnc(NC(=O)N(C)[C@H]2CN(c3nccc(NC(=O)O[C@@H]4C[C@H]5CC[C@@H](C4)N5)n3)CC[C@H]2F)cn1] |
| 345 | 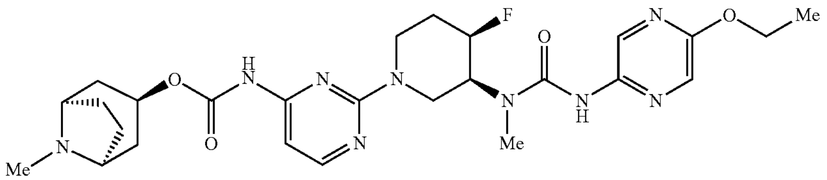 [SMILES: CCOc1cnc(NC(=O)N(C)[C@H]2CN(c3nccc(NC(=O)O[C@@H]4C[C@H]5CC[C@@H](C4)N5C)n3)CC[C@H]2F)cn1] |
| 346 | 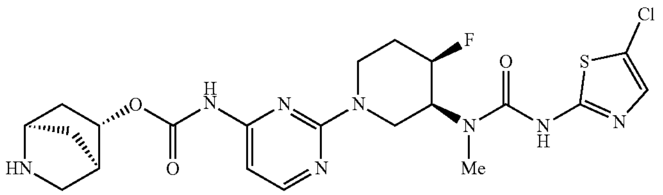 [SMILES: CN(C(=O)Nc1ncc(Cl)s1)[C@H]1CN(c2nccc(NC(=O)O[C@H]3C[C@H]4C[C@@H]3CN4)n2)CC[C@H]1F] |

TABLE 2B-continued
| Ex. No. | Structure |
| --- | --- |
| 347 | 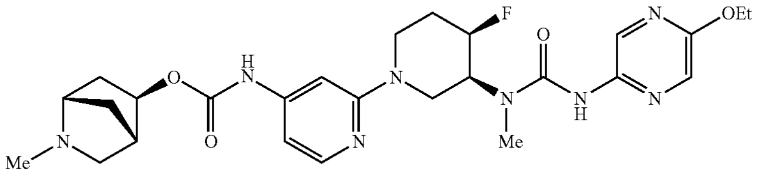 [SMILES: CCOc1cnc(NC(=O)N(C)[C@H]2CN(c3cc(NC(=O)O[C@@H]4C[C@@H]5C[C@H]4CN5C)ccn3)CC[C@H]2F)cn1] |
| 348 | 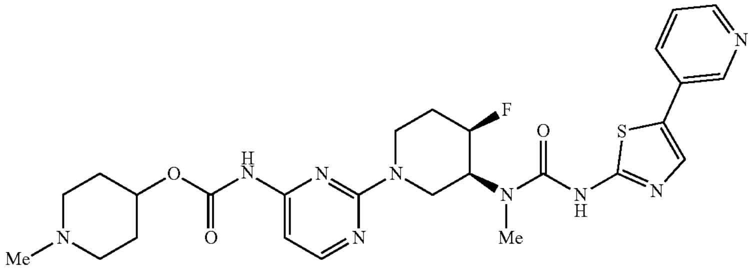 [SMILES: CN1CCC(OC(=O)Nc2ccnc(N3CC[C@@H](F)[C@@H](N(C)C(=O)Nc4ncc(-c5cccnc5)s4)C3)n2)CC1] |
| 349 | 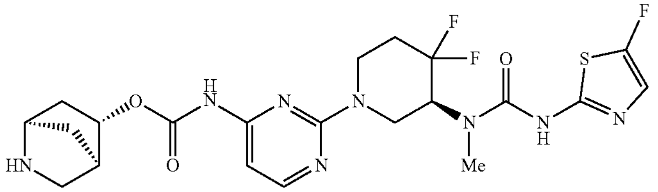 [SMILES: CN(C(=O)Nc1ncc(F)s1)[C@H]1CN(c2nccc(NC(=O)O[C@H]3C[C@H]4C[C@@H]3CN4)n2)CCC1(F)F] |
| 350 | 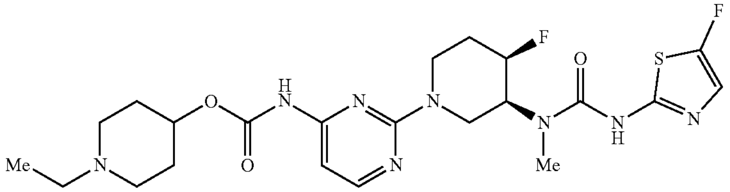 [SMILES: CCN1CCC(OC(=O)Nc2ccnc(N3CC[C@@H](F)[C@@H](N(C)C(=O)Nc4ncc(F)s4)C3)n2)CC1] |
| 351 | 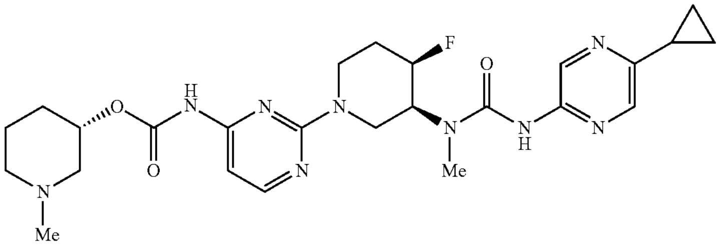 [SMILES: CN1CCC[C@H](OC(=O)Nc2ccnc(N3CC[C@@H](F)[C@@H](N(C)C(=O)Nc4cnc(C5CC5)cn4)C3)n2)C1] |
| 352 | 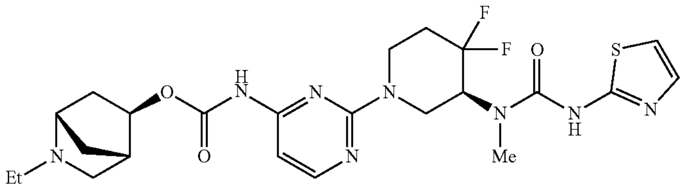 [SMILES: CCN1C[C@@H]2C[C@H]1C[C@H]2OC(=O)Nc1ccnc(N2CCC(F)(F)[C@@H](N(C)C(=O)Nc3nccs3)C2)n1] |

In one or more embodiments, the compound, or pharmaceutically acceptable salt or solvate thereof, according to this disclosure is selected from the compounds provided in Table A. In one or more embodiments, the compound according to this disclosure is selected from the compounds provided in Table A.
TABLE A
| Example | Structure |
|---|---|
| A | 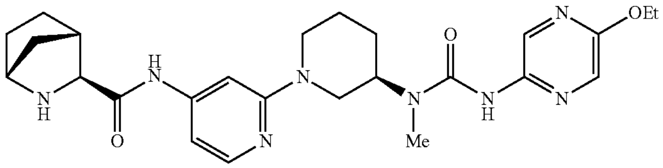 [SMILES: CCOc1cnc(NC(=O)N(C)[C@@H]2CCCN(c3cc(NC(=O)[C@H]4N[C@@H]5CC[C@H]4C5)ccn3)C2)cn1] |
| B | 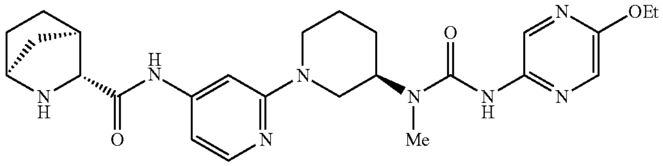 [SMILES: CCOc1cnc(NC(=O)N(C)[C@@H]2CCCN(c3cc(NC(=O)[C@@H]4N[C@H]5CC[C@@H]4C5)ccn3)C2)cn1] |
| C | 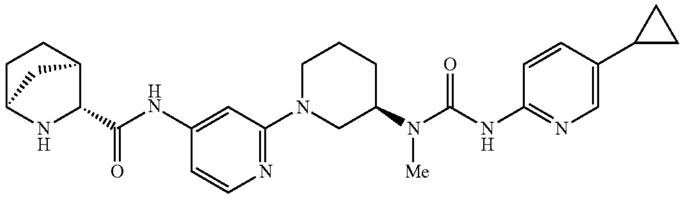 [SMILES: CN(C(=O)Nc1ccc(C2CC2)cn1)[C@@H]1CCCN(c2cc(NC(=O)[C@@H]3N[C@H]4CC[C@@H]3C4)ccn2)C1] |
| D | 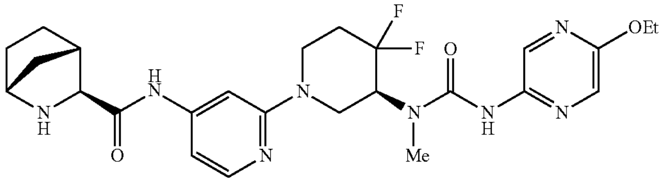 [SMILES: CCOc1cnc(NC(=O)N(C)[C@H]2CN(c3cc(NC(=O)[C@H]4N[C@@H]5CC[C@H]4C5)ccn3)CCC2(F)F)cn1] |
| E | 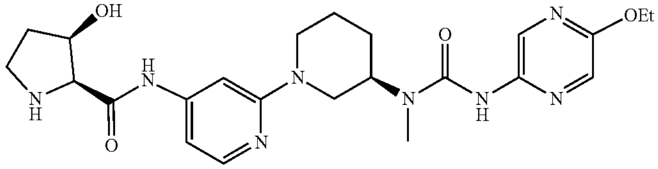 [SMILES: CCOc1cnc(NC(=O)N(C)[C@@H]2CCCN(c3cc(NC(=O)[C@H]4NCC[C@H]4O)ccn3)C2)cn1] |
| F | 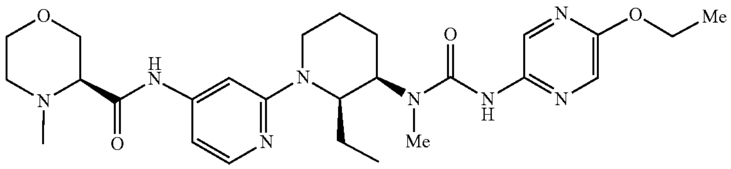 [SMILES: CCOc1cnc(NC(=O)N(C)[C@@H]2CCCN(c3cc(NC(=O)[C@@H]4COCCN4C)ccn3)[C@@H]2CC)cn1] |
| G | 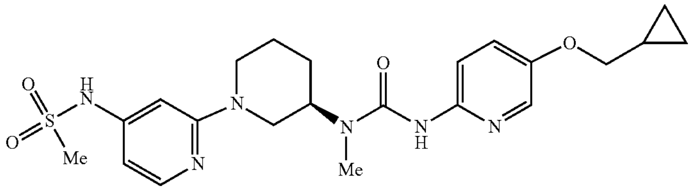 [SMILES: CN(C(=O)Nc1ccc(OCC2CC2)cn1)[C@@H]1CCCN(c2cc(NS(C)(=O)=O)ccn2)C1] |

In some embodiments, the compounds of the disclosure are selective against MRGPRX1 and/or MRGPRX4. In some embodiments, the compounds of the disclosure have at least 2000-fold or greater selectivity against MRGPRX1 and/or MRGPRX4.

Therapeutic and Prophylactic Uses

The present disclosure provides methods for using the compounds described herein in the preparation of a medicament for inhibition of MRGPRX2. As used herein, the terms "inhibit", "inhibition" and the like refer to the ability of an antagonist to decrease the function or activity of a particular target, e.g., MRGPRX2. The decrease is preferably at least a 50% and may be, for example, at least about 55%, at least about 60%, at least about 65%, at least about 70%, at least about 75%, at least about 80%, at least about 85%, at least about 90%, or at least about 95%. The present disclosure also encompasses the use of the compounds described herein in the preparation of a medicament for the treatment or prevention of diseases, disorders, and/or conditions that would benefit from inhibition of MRGPRX2. As one example, the present disclosure encompasses the use of the compounds described herein in the preparation of a medicament for the treatment of an allergic, inflammatory, neuroinflammatory, neurological, autoimmune, dermatological, respiratory, metabolic, cardiovascular or a fibrotic disease, disorder or condition. In some embodiments of the aforementioned methods, the compounds described herein are used in combination with at least one additional therapy, examples of which are set forth elsewhere herein.

As demonstrated herein, the compounds according to this disclosure potentially inhibit the G-protein coupled receptor (GPCR) MGRPX2. Mast cells are primarily found in the skin, mucosal linings of the respiratory and gastrointestinal tracts, and connective tissues surrounding blood vessels and nerves. Immunoglobin E (IgE) mediated mast cell activation occurs when IgE antibodies bind to allergens and then to receptors on mast cells causing these mast cells to release histamine and other inflammatory mediators which result in allergic reactions. In contrast non-IgE mediated mast cell activation, or IgE independent activation can be triggered by physical stimuli (like temperature changes), certain medications, or complement system components, leading to mast cell degranulation resulting in various inflammatory, allergic, and immune related conditions without the involvement of IgE antibodies. MRGPRX2 mediates IgE independent activation by numerous ligands, including certain drugs (e.g., cationic peptidergic drugs), neuropeptides, antimicrobial peptides, and basic secretagogues (small cationic molecules). Activation of MRGPRX2 on mast cells leads to degranulation and the release of pro-inflammatory mediators like histamine, cytokines, and tryptase resulting in various inflammatory, allergic, and immune related conditions. Accordingly, MRGPRX2 antagonists may decrease mast cell activation and degranulation, providing a promising therapeutic approach for mast cell-driven diseases.

Diseases, disorders, and/or conditions that would benefit from MRGPRX2 antagonists may include those in which mast cells play a contributory or vital role, or which are mediated, at least in part, by mast cell activation or mast cell degranulation. In some embodiments, the compounds described herein may include those in which mast cells play a contributory or vital role, or which are mediated, at least in part, by non-IgE mediated mast cell activation or mast cell degranulation.

Accordingly, in some embodiments, the compounds described herein are administered to a subject in need thereof in an amount effective to inhibit MRGPRX2. MRGPRX2 antagonists may be assessed using a peripheral serum sample, blood sample or a tissue sample obtained from the subject. Activity may be determined, for example, by comparison to a previous sample obtained from the subject (i.e., prior to administration of the compound described herein) or by comparison to a reference value for a control group (e.g., standard of care, a placebo, etc.).

Alternatively or in addition, in some embodiments, the compounds described herein are administered to a subject in need thereof in an amount effective to inhibit the activation of mast cells and mast cell degranulation in the subject. Mast cell activation and degranulation may be assessed using a peripheral serum sample, blood sample or a tissue sample obtained from the subject. Activity may be determined, for example, by comparison to a previous sample obtained from the subject (i.e., prior to administration of the compound) or by comparison to a reference value for a control group (e.g., standard of care, a placebo, etc.). As a specific example, mast cell activity can be assessed by measuring beta-hexosaminidase or CD107a levels in a suitable sample (e.g., a blood or serum sample) from a subject to determine mast cell burden on the subject.

Alternatively or in addition, in some embodiments, the compounds described herein are administered to a subject in need thereof in an amount effective to inhibit the activation of mast cells and mast cell degranulation in the subject, and/or to alleviate or eliminate one or more responses or reactions caused by the activation of mast cells and mast cell degranulation in the subject. In some embodiments, responses or reactions caused by the activation of mast cells and mast cell degranulation in a subject can be measured by, for example, number and/or size of wheals, and number and/or size of hives. In some embodiments, responses or reactions caused by the activation of mast cells and mast cell degranulation in a subject can be measured by, for example, Urticaria Activity Score (UAS), Urticaria Control Test (UCT), Urticaria Severity Score (USS), Cholinergic Urticaria Activity Score (CholUAS), and Angioedema Activity Score (AAS7). Other measures that can be used to determine responses or reactions caused by the activation of mast cells and mast cell degranulation in a subject include, but are not limited to, Dermatology Life Quality Index (DLQI) and Hives Severity Score (HSS). Examples of laboratory tests that can be used to determine responses or reactions caused by the activation of mast cells and mast cell degranulation in a subject include, but are not limited to, total IgE levels, biomarkers levels (e.g., C-reactive protein (CRP) level), and Basophil Histamine Release Assay (BHRA).

Alternatively or in addition, in some embodiments, the compounds described herein are administered to a subject in need thereof to treat and/prevent an allergic, inflammatory, neuroinflammatory, neurological, immune, autoimmune, dermatological, respiratory, metabolic, cardiovascular, or fibrotic disease, disorder, or condition. In some embodiments, the compounds described herein are administered in combination with one or more additional therapeutic agents, examples of which are set forth elsewhere herein.

Alternatively or in addition, in some embodiments, the compounds described herein are administered to a subject in need thereof to treat and/prevent a symptom or response associated with an allergic, inflammatory, neuroinflammatory, neurological, immune, autoimmune, dermatological, respiratory, metabolic, cardiovascular, or fibrotic disease, disorder, or condition. In some embodiments, the compounds described herein are administered in combination with one or more additional therapeutic agents, examples of which are set forth elsewhere herein.

Alternatively or in addition, in some embodiments, the compounds described herein are administered to a subject suffering from an allergic, inflammatory, neuroinflammatory, neurological, immune, autoimmune, dermatological, respiratory, metabolic, cardiovascular, or fibrotic disease, disorder, or condition in order to treat and/or prevent a response or symptom associated therewith. In some embodiments, the compounds described herein are administered in combination with one or more additional therapeutic agents, examples of which are set forth elsewhere herein.

Alternatively or in addition, in some embodiments, the compounds described herein are administered to a subject in need thereof to treat and/or prevent cancer or a cancer-related disease, disorder or condition. In some embodiments, the compounds described herein are administered to a subject in need thereof to treat cancer, optionally in combination with at least one additional therapy, examples of which are set forth elsewhere herein.

Inflammatory, Immune, and Autoimmune Indications

In one or more embodiments, the compounds described herein are useful in the treatment and/or prophylaxis of inflammatory, immune, and autoimmune-related diseases, disorders and conditions. Inflammatory, immune and autoimmune-related diseases, disorders and conditions include allergic, neuroinflammatory, neurological, dermatological, respiratory, metabolic, fibrotic, and cardiovascular diseases, disorders and conditions. A non-limiting list of inflammatory, immune, and autoimmune-related diseases, disorders and conditions which may be treated or prevented with the compounds and compositions of the present disclosure include allergies (e.g., food allergy, drug allergy, drug anaphylaxis, insect allergy, latex allergy, mold allergy, pet allergy, pollen allergy, hay-fever, ragweed allergy, allergic rhinitis, allergic conjunctivitis, eosinophilic esophagitis, and the like), arthritis (e.g., rheumatoid arthritis, inflammatory arthritis, psoriatic arthritis, osteoarthritis), asthma, chronic rhinosinusitis with nasal polyps (CRSwNP), eosinophilic asthma, multiple sclerosis, Alzheimer's disease, amyotrophic lateral sclerosis, autism, psoriasis, inflammatory bowel disease (e.g., Chrohn's disease and ulcerative colitis), irritable bowel syndrome, prurigo, lupus, Grave's disease, Hashimoto's thyroiditis, ankylosing spondylitis, Sjogren's syndrome (SjS), angioedema, anaphylaxis, bullous dermatosis, atopic dermatitis, alopecia areata, interstitial cystitis, urticaria (e.g., chronic spontaneous urticaria (CSU), acute urticaria, or physical urticaria such as popular urticaria, cold urticaria, cholinergic urticaria, solar urticaria, scleroderma, and dermatographic urticaria), mastocytosis, systemic mastocytosis, dermographism, dermatosis, dermatitis, allergic contact dermatitis, eosinophilic gastrointestinal (GI) disease, type I diabetes, type II diabetes, prurigo nodularis, rosacea, neuropathic pain, neuropathic itch, inflammatory pain, chronic itch, cough, migraine, mast cell activation syndrome, sickle cell disease, endometriosis, neurodermatitis, seborrheic dermatitis, esophageal reflux, coronary heart disease, atherosclerosis, myocardial infarction, coronary artery disease, angina, pulmonary fibrosis, pulmonary arterial hypertension, primary pulmonary hypertension, chronic obstructive pulmonary disease (COPD), acute respiratory distress syndrome, hepatic fibrosis, renal fibrosis, cardiac fibrosis, cystic fibrosis, and bronchitis.

In one or more embodiments, the compounds described herein are useful in the treatment and/or prophylaxis of asthma, chronic obstructive pulmonary disease (COPD), allergic rhinitis, eosinophilic gastrointestinal (GI) disease, inflammatory bowel disease, bullous dermatosis, alopecia areata, food allergy, psoriasis, atopic dermatitis, prurigo nudularis, chronic urticaria, or systemic mastocytosis. In one or more embodiments, the compounds described herein are useful in the treatment and/or prophylaxis of a skin disease, disorder, or condition.

In some embodiments, the inflammatory immune, or autoimmune-related disease, disorder or condition is allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis), allergic asthma, eosinophilic asthma, chronic rhinosinusitis with nasal polyps (CRSwNP), asthma, prurigo nodularis, interstitial cystitis, multiple sclerosis, inflammatory bowel disease (e.g., Chrohn's disease and ulcerative colitis), lupus, Grave's disease, Hashimoto's thyroiditis, ankylosing spondylitis, Sjdgren's syndrome (SjS), urticaria (e.g., chronic spontaneous urticaria (CSU), acute urticaria, or physical urticaria including popular urticaria, cold urticaria, cholinergic urticaria, solar urticaria, scleroderma, and dermatographic urticaria), or anaphylaxis.

In some embodiments, the compounds described herein are administered to a subject having a skin disease, disorder, or condition in an amount effective to inhibit the activation of mast cells and mast cell degranulation in the subject. In some embodiments, the inflammatory immune, or autoimmune-related disease, disorder, or condition is a skin disease, disorder, or condition. In some embodiments, the compounds described herein are administered to a subject having a skin disease, disorder, or condition in an amount effective to inhibit the activation of mast cells and mast cell degranulation in the subject. In some embodiments, the skin disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), atopic dermatitis, allergic contact dermatitis (e.g., latex allergy), dry skin, eczema, mastocytosis, systemic mastocytosis, psoriasis, angioedema, neuropathic itch, neurodermatitis, dermographism, dermatosis, dermatitis, chronic pruritus, acute pruritus, rosacea, bullous dermatosis, prurigo, or prurigo nodularis.

In some embodiments, the skin disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria). In some embodiments, the skin disease, disorder, or condition is chronic spontaneous urticaria (CSU). In some embodiments, the skin disease, disorder, or condition is atopic dermatitis. In some embodiments, the skin disease, disorder, or condition is prurigo nodularis. In some embodiments, the skin disease, disorder, or condition is mastocytosis (e.g., cutaneous mastocytosis). In some embodiments, the skin disease, disorder, or condition is psoriasis.

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), allergic asthma, eosinophilic asthma, atopic dermatitis, allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis), or mastocytosis.

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), allergic asthma, eosinophilic asthma, atopic dermatitis, or allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis).

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria), or allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis).

In some embodiments, the inflammatory immune, or autoimmune-related disease, disorder, or condition is urticaria (e.g., chronic spontaneous urticaria (CSU), acute urticaria, or physical urticaria including popular urticaria, cold urticaria, cholinergic urticaria, solar urticaria, scleroderma, and dermatographic urticaria).

In some embodiments, the inflammatory immune, or autoimmune-related disease, disorder, or condition is allergies (e.g., food allergy, drug allergy, insect allergy, latex allergy, mold allergy, pet allergy, pollen allergy, hay-fever, ragweed allergy, allergic rhinitis, allergic conjunctivitis, and eosinophilic esophagitis).

In some embodiments, the inflammatory immune, or autoimmune-related disease, disorder, or condition is a cardiovascular disease (e.g., coronary heart disease or atherosclerosis).

In some embodiments, the inflammatory immune, or autoimmune-related disease, disorder, or condition is a fibrotic disease (e.g., myocardial infarction, angina, chronic obstructive pulmonary disease (COPD), acute respiratory distress syndrome, osteoarthritis, pulmonary fibrosis, renal fibrosis, cystic fibrosis, bronchitis, or asthma).

In some embodiments, the inflammatory immune, or autoimmune-related disease, disorder or condition is arthritis, asthma, multiple sclerosis, psoriasis, inflammatory bowel disease, (e.g., Crohn's disease and ulcerative colitis), Grave's disease, Hashimoto's thyroiditis, or ankylosing spondylitis.

In one or more embodiments, the inflammatory immune, or autoimmune-related disease, disorder, or condition is an allergic, inflammatory, neuroinflammatory, neurological, immune, autoimmune, oncological, dermatological, antihistamine-refractory, respiratory, metabolic, cardiovascular, or fibrotic disease, disorder, or condition.

In one or more embodiments, the inflammatory immune, or autoimmune-related disease, disorder, or condition is antihistamine-refractory.

In one or more embodiments, the inflammatory immune, or autoimmune-related disease, disorder, or condition is anti-IgE refractory, anti-IL4R refractory, or BTK inhibitor refractory.

Oncology Indications

In one or more embodiments, the compounds described herein are useful in the treatment and/or prophylaxis of cancer (e.g., carcinomas, sarcomas, leukemias, lymphomas, myelomas, etc.). In certain embodiments, the cancer may be locally advanced and/or unresectable, metastatic, or at risk of becoming metastatic. Alternatively, or in addition, the cancer may be recurrent or no longer responding to a treatment, such as a standard of care treatment known to one of skill in the art. Exemplary types of cancer contemplated by this disclosure include melanoma, prostate cancer, pancreatic cancer, squamous cell carcinoma, Hodgkin lymphoma, leukemia (e.g., chronic myeloid leukemia, chronic eosinophilic leukemia, chronic myelomonocytic leukemia, myeloid leukemia, acute myeloid leukemia, acute megakaryoblastic leukemia, mast cell leukemia, acute lymphocytic leukemia), gastric cancer (e.g., gastrointestinal stromal cancer), small bowel cancer, salivary gland cancer, adrenocortical cancer, thyroid cancer, stomach cancer, breast cancer, endometrial cancer, renal cancer, cervical cancer, testicular cancer, esophageal cancer, lung cancer (e.g., small cell and non-small cell lung cancer), colorectal cancer, prostate cancer, liver cancer, bile duct cancer, gallbladder cancer, appendiceal cancer, ovarian cancer, urothelial cancer, neuroendocrine tumors, kidney cancer, head and neck cancer, bone cancer, brain cancer (e.g., glioblastoma, medulloblastoma), mesothelioma, and soft tissue sarcoma.

In the aforementioned embodiments, the methods of the present disclosure may be practiced in an adjuvant setting or neoadjuvant setting. The methods described herein may be indicated as a first line, second line, third line, or greater line of treatment.

Pharmaceutical Compositions

The compounds of the present disclosure may be in the form of compositions suitable for administration to a subject. In general, such compositions are pharmaceutical compositions comprising a compound according to this disclosure or a pharmaceutically acceptable salt thereof and one or more pharmaceutically acceptable excipients. In some embodiments, the pharmaceutical composition comprises a compound according to this disclosure and one or more pharmaceutically acceptable excipients. In certain embodiments, the compound may be present in an effective amount. The pharmaceutical compositions may be used in the methods of the present disclosure; thus, for example, the pharmaceutical compositions comprising a compound according to this disclosure can be administered to a subject in order to practice the therapeutic and prophylactic methods and uses described herein.

In one aspect, the compounds described herein may be administered orally. Oral administration may be via, for example, capsule or tablets. In making the pharmaceutical compositions that include the compounds of the present disclosure (e.g., a compound of Formula I or Formula II), or a pharmaceutically acceptable salt thereof, the tablet or capsule includes at least one pharmaceutically acceptable excipient. Non-limiting examples of pharmaceutically acceptable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, sterile water, syrup, and methyl cellulose. Additional pharmaceutically acceptable excipients include lubricating agents such as talc, magnesium stearate, and mineral oil; wetting agents; emulsifying and suspending agents; preserving agents such as methyl and propylhydroxy-benzoates.

In another aspect, the compounds of the present disclosure, or a pharmaceutically acceptable salt thereof, may be administered topically.

In another aspect, the compounds of the present disclosure, or a pharmaceutically acceptable salt thereof, may be administered parenterally, for example by intravenous injection. A pharmaceutical composition appropriate for parenteral administration may be formulated in solution for injection or may be reconstituted for injection in an appropriate system such as a physiological solution. Such solutions may include sterile water for injection, salts, buffers, and tonicity excipients in amounts appropriate to achieve isotonicity with the appropriate physiology.

The pharmaceutical compositions described herein may be stored in an appropriate sterile container or containers.

Administration

In general, the disclosed methods comprise administering a compound described herein, or a composition thereof, in an effective amount to a subject in need thereof. An "effective amount" with reference to a MRGPRX2 antagonist of the present disclosure means an amount of the compound that is sufficient to engage the target (e.g., by antagonizing the target) at a level that is indicative of the potency of the compound. For MRGPRX2, target engagement can be determined by one or more biochemical or cellular assays resulting in an EC50, ED50, EC90, IC50, IC90, or similar value which can be used as one assessment of the potency of the compound. Assays for determining target engagement include, but are not limited to, those described in the Examples or a CD107a LAD2 assay. Serum or buffer may be used. An alternative agonist to Substance P, for example, icatibant, may also be used. The effective amount may be administered as a single quantity or as multiple, smaller quantities (e.g., as one tablet with "x" amount, as two tablets each with "x/2" amount, etc.).

In some embodiments, the disclosed methods comprise administering a therapeutically effective amount of a compound described herein to a subject in need thereof. As used herein, the phrase "therapeutically effective amount" with reference to compound disclosed herein means a dose regimen (i.e., amount and interval) of the compound that provides the specific pharmacological effect for which the compound is administered to a subject in need of such treatment. For prophylactic use, a therapeutically effective amount may be effective to eliminate or reduce the risk, lessen the severity, or delay the onset of the disease, including biochemical, histological and/or behavioral signs or symptoms of the disease. For treatment, a therapeutically effective amount may be effective to reduce, ameliorate, or eliminate one or more signs or symptoms associated with a disease, delay disease progression, prolong survival, decrease the dose of other medication(s) required to treat the disease, or a combination thereof. With respect to cancer specifically, a therapeutically effective amount may, for example, result in the killing of cancer cells, reduce cancer cell counts, reduce tumor burden, eliminate tumors or metastasis, or reduce metastatic spread. A therapeutically effective amount may vary based on, for example, one or more of the following: the age and weight of the subject, the subject's overall health, the stage of the subject's disease, the route of administration, and prior or concomitant treatments.

Administration may comprise one or more (e.g., one, two, or three or more) dosing cycles.

In certain embodiments, the compounds contemplated by the present disclosure may be administered (e.g., orally, parenterally, etc.) at about 0.01 mg/kg to about 50 mg/kg, or about 1 mg/kg to about 25 mg/kg, of subject's body weight per day, one or more times a day, a week, or a month, to obtain the desired effect. In some embodiments, once daily or twice daily administration is contemplated. In some embodiments, a suitable weight-based dose of a compound contemplated by the present disclosure is used to determine a dose that is administered independent of a subject's body weight. In certain embodiments, the compounds of the present disclosure are administered (e.g., orally, parenterally, etc.) at fixed dosage levels of about 1 mg to about 1000 mg, particularly 1, 3, 5, 10, 15, 20, 25, 50, 75, 100, 150, 200, 250, 300, 400, 500, 600, 750, 800, 900, or 1000 mg, one or more times a day, a week, or a month, to obtain the desired effect.

Routes of Administration

In some embodiments, pharmaceutical compositions containing a compound according to this disclosure may be in a form suitable for oral administration. Oral administration may involve swallowing the formulation thereby allowing the compound to be absorbed into the bloodstream in the gastrointestinal tract.

In another embodiment, the pharmaceutical compositions containing a compound according to this disclosure may be in a form suitable for topical administration. Forms of topical administration include, but are not limited to, creams, ointments, gels, lotions, solutions, suspensions, pastes, transdermal patches, foams, powders, baths, soaks, tinctures, shake lotions, and sprays. Pharmaceutical compositions suitable for topical administration may be formulated using suitable aqueous or non-aqueous carriers.

In another embodiment, the pharmaceutical compositions containing a compound according to this disclosure may be in a form suitable for parenteral administration. Forms of parenteral administration include, but are not limited to, intravenous, intraarterial, intramuscular, intradermal, intraperitoneal, intrathecal, intracisternal, intracerebral, intracerebroventricular, intraventricular, and subcutaneous. Pharmaceutical compositions suitable for parenteral administration may be formulated using suitable aqueous or non-aqueous carriers.

Combination Therapy

The present disclosure contemplates the use of the MRGPRX2 antagonists described herein alone, or in combination with one or more additional therapeutic agents. The use of the MRGPRX2 antagonists described herein in combination with one or more additional therapies may have a synergistic therapeutic or prophylactic effect on the underlying disease, disorder, or condition. In some embodiments, the use of the MRGPRX2 antagonists described herein in combination with one or more additional therapies may have an additive therapeutic or prophylactic effect on the underlying disease, disorder, or condition. In addition or alternatively, the combination therapy may allow for a dose reduction of one or more of the therapies, thereby ameliorating, reducing or eliminating adverse effects associated with one or more of the agents.

In embodiments comprising one or more additional therapeutic agents, the MRGPRX2 antagonists described herein can be administered before, during, or after treatment with the additional therapeutic agents. In embodiments comprising one or more additional therapeutic agents, the therapeutic agents used in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy.

If the combination is formulated as separate compositions, in some embodiments, the separate compositions are provided together in a kit.

The present disclosure contemplates the use of the MRGPRX2 antagonists described herein in combination with one or more additional therapies useful in the treatment of allergic, autoimmune or immune-mediated, cardiovascular, dermatological, fibrotic, gastrointestinal, inflammatory, metabolic, neuroinflammatory, neurological, neurodegenerative, ocular, oncological, and respiratory diseases, disorders or conditions, such as those described elsewhere herein.

In some embodiments the compounds described herein in combination with one or more additional therapies are useful in the treatment of allergic, autoimmune or immune-mediated, cardiovascular, dermatological, fibrotic, gastrointestinal, inflammatory, metabolic, neuroinflammatory, neurological, neurodegenerative, ocular, oncological, and respiratory diseases, disorders or conditions. A non-limiting list of allergic, autoimmune or immune-mediated, cardiovascular, dermatological, fibrotic, gastrointestinal, inflammatory, metabolic, neuroinflammatory, neurological, neurodegenerative, ocular, and respiratory diseases, disorders or conditions include allergies (e.g., food allergy, drug allergy, drug anaphylaxis, insect allergy, latex allergy, mold allergy, pet allergy, pollen allergy, hay-fever, ragweed allergy, allergic rhinitis, allergic conjunctivitis, eosinophilic esophagitis, and the like), arthritis (e.g., rheumatoid arthritis, inflammatory arthritis, psoriatic arthritis, osteoarthritis), asthma, endometriosis, rosacea, nasal polyps, chronic rhinosinusitis with nasal polyps (CRSwNP), eosinophilic asthma, multiple sclerosis, neuropathic pain, inflammatory pain, chronic itch, cough, migraine, mast cell activation syndrome, neurodermatitis, seborrheic dermatitis, deep vein thrombosis, neuropathic itch, esophageal reflux, Alzheimer's disease, amyotrophic lateral sclerosis, sickle cell disease, autism, psoriasis, inflammatory bowel disease (e.g., Crohn's disease and ulcerative colitis), irritable bowel syndrome, prurigo, lupus, Grave's disease, Hashimoto's thyroiditis, ankylosing spondylitis, Sjogren's syndrome (SjS), angioedema, anaphylaxis, bullous dermatosis, atopic dermatitis, alopecia areata, interstitial cystitis, urticaria (e.g., chronic spontaneous urticaria (CSU), acute urticaria, or physical urticaria such as popular urticaria, cold urticaria, cholinergic urticaria, solar urticaria, scleroderma, and dermatographic urticaria), mastocytosis, systemic mastocytosis, dermographism, dermatosis, dermatitis, allergic contact dermatitis, eosinophilic gastrointestinal (GI) disease, type I diabetes, type II diabetes, prurigo nodularis, coronary heart disease, atherosclerosis, myocardial infarction, angina, coronary artery disease, pulmonary fibrosis, pulmonary arterial hypertension, primary pulmonary hypertension, chronic obstructive pulmonary disease (COPD), acute respiratory distress syndrome, hepatic fibrosis, renal fibrosis, cardiac fibrosis, cystic fibrosis, and bronchitis.

In some embodiments, one or more of the additional therapies is an additional treatment modality such as, for example, diet modification, physical therapy, skin hydration, oxygen therapy, exercise, plasmapheresis, phototherapy, use of a humidifier, surgery (e.g., coronary artery bypass graft surgery, angioplasty, stent implant, endarterectomy, and thyroidectomy), and behavioral intervention such as avoidance of external triggers (e.g., allergens) or harmful substances.

In one or more embodiments, the compounds according to the disclosure can be combined with one or more anti-inflammatory agents. A non-limiting list of anti-inflammatory agents include non-steroidal anti-inflammatory drugs (NSAIDs) (e.g., ibuprofen, aspirin, naproxen, and celecoxib, etodolac, meloxicam, nabumetone, diclofenac, diflunisal, fenoprofen, and flurbiprofen); corticosteroids (e.g., budesonide, cortisone, prednisone, prednisolone, methylprednisolone, dexamethasone, deflazacort, betamethasone, hydrocortisone, etc.); disease-modifying antirheumatic drugs (DMARDs) (e.g., methotrexate, sulfasalazine, hydroxychloroquine, and leflunomide); anti-tumor necrosis factor (anti-TNF) agents (e.g., infliximab, adalimumab, and certolizumab pegol); interferons (e.g., interferon alfa); integrin receptor antagonists (e.g., vedolizumab); mast-cell stabilizers (e.g., cromolyn sodium, nedocromil, and lodoxamide); and aminosalicylates (5-ASA) (e.g., balsalazide, mesalazine, olsalazine, and sulfasalazine).

In some embodiments, the additional therapeutic agent comprises an analgesic agent, e.g., acetaminophen, NSAIDs, cyclooxygenase-2 (COX-2) inhibitors (e.g., celecoxib), tramadol, and opiates. In one embodiment, the analgesic agent is acetaminophen.

In some embodiments, the additional therapeutic agent comprises an agent that targets one or more cytokines, such as, e.g., interleukin (IL)-1, interleukin-4, interleukin-5, interleukin-12, interleukin-13, interleukin-17, and/or interleukin-23, or a receptor thereof. In some embodiments, the agent blocks one or more pro-inflammatory cytokines (e.g., interleukin-12, interleukin-17, and/or interleukin-23) (e.g., secukinumab, ixekizumab, brodalumab, ustekinumab, guselkumab, tildrakizumab, and risankizumab). In some embodiments, the agent blocks a cytokine or cytokine receptor that regulates allergic inflammation, e.g., interleukin-4 and/or interleukin 13 (e.g., dupilumab). In some embodiments, the agent blocks a cytokine or cytokine receptor that mediates eosinophil activation, e.g., interleukin-5 (e.g., benralizumab, mepolizumab, or reslizumab).

In some embodiments, the at least one additional therapeutic agent comprises an agent that targets CD20, e.g., an anti-CD20 antibody (e.g., ocrelizumab).

In one or more embodiments, the additional therapeutic agent comprises one or more immunosuppressants. Exemplary immunosuppressants include, but are not limited to, 6-mercaptopurine, azathioprine, cyclosporine, tacrolimus, leflunomide, anti-CD20 antibodies (e.g., ocrelizumab, ofatumumab, ublituximab-xiiy, etc.), JAK-inhibitors (e.g., baricitinib, tofacitinib, upadacitinib, etc.), methotrexate, selective adhesion molecule inhibitors (e.g., natalizumab, etc.), sphingosine-1-phosphate receptor modulators, (e.g., etrasimod, fingolimod, ozanimod, ponesimod, siponimod, etc.), and targeted immunosuppressive antibodies (e.g., belimumab).

In some embodiments, the additional therapeutic agent comprises one or more agents that target mast-cell derived immunomodulators, such as, for example, histamines, and/or leukotrienes. Exemplary antihistamines include brompheniramine, cetirizine, chloropheniramine, clemastine, diphenyldramine, fexofenadine, azelastine, carbinoxamine, cyproheptadine, desloratadine, emedastine, hydroxyzine, levocabastine, levocetirizine, and loratadine. Exemplary leukotriene modifiers include montelukast, zafirlukast, and zileuton.

In one or more embodiments, the additional therapeutic agent comprises a Bruton's tyrosine kinase (BTK) inhibitor. Exemplary BTK inhibitors include ibrutinib, acalabrutinib, and zanubrutinib. Exemplary BTK inhibitors include, but are not limited to, fenebrutinib and remibrutinib. Exemplary BTK inhibitors include, but are not limited to, rilzabrutinib, catadegbrutinib, TAS-5315, HWH486, bexobrutideg, TM471-1, IMG-004, and branebrutinib.

In one or more embodiments, the additional therapeutic agent comprises an immunoglobulin E (IgE) inhibitor, e.g., an anti-IgE antibody (omalizumab or ligelizumab).

In one or more embodiments, the additional therapeutic agent comprises a complement component 5a receptor 1 (C5AR1) inhibitor, e.g., INF-904.

In some embodiments, the additional therapeutic agent comprises an anti-depressant. Exemplary anti-depressants contemplated include, but are not limited to, serotonin and norepinephrine reuptake inhibitors (SNRIs) (e.g., desvenlafaxine, duloxetine, levomilnacipran, milnacipran, and venlafaxine), selective serotonin reuptake inhibitors (SSRIs) (e.g., citalopram, escitalopram, fluoxetine, fluvoxamine, and sertraline), tricyclic antidepressants (e.g., imipramine, nortriptyline, amitriptyline, doxepin, and desipramine), and monoamine oxidase inhibitors (MAOIs) (e.g., tranylcypromine, phenelzine, and isocarboxazid).

In some embodiments, the additional therapeutic agent comprises an antipsychotic. Exemplary antipsychotics include haloperidol, loxapine, thioridazine, molindone, thiothixene, fluphenazine, mesoridazine, trifluoperazine, perphenazine, chlorpromazine, aripiprazole, clozapine, ziprasidone, risperidone, quetiapine, and olanzapine.

In some embodiments, the additional therapeutic agent comprises one or more anti-anxiety agents. Exemplary anti-anxiety agents include alprazolam, chlordiazepoxide, clonazepam, diazepam, lorazepam, and buspirone.

In some embodiments, the additional therapeutic agent comprises one or more anticonvulsants (e.g., valproic acid, phenytoin, clonazepam, and carbamazepine).

In some embodiments, the additional therapeutic agent comprises one or more respiratory agents. In some embodiments, the respiratory agent is a bronchodilator (e.g., adrenergic bronchodilator, anticholinergic bronchodilator, methylxanthines, and combinations thereof), an inhaled corticosteroid (e.g., beclomethasone, fluticasone, ciclesonide, mometasone, and budesonide), a beta adrenergic agonist (e.g., albuterol, metaproterenol, pirbuterol, terbutaline, isoetharine and levalbuterol), or leukotriene modifier (e.g., montelukast, zafirlukast, and zileuton).

In one or more embodiments, the additional therapeutic agent comprises one or more nasal decongestants. Exemplary decongestants include oxymetazoline, phenylephrine, and pseudoephedrine.

In some embodiments, the additional therapeutic agent comprises a cough suppressant. Exemplary cough suppressants include dextromethorphan, guaifenesin, and codeine.

In some embodiments, the compounds according to this disclosure are combined with a proton pump inhibitor (PPI). Exemplary PPIs include lansoprazole, omeprazole, pantoprazole, rebaprazole, and esomeprazole.

In some embodiments, the additional therapeutic agent comprises an agent that modulates cognitive function, e.g., cholinesterase inhibitors (e.g., donepezil, rivastigmine, galantamine), N-methyl-D-aspartate (NMDA) receptor antagonists (e.g., memantine), and agents targeting aggregated soluble and insoluble forms of amyloid beta (e.g., aducanumab).

In some embodiments, the additional therapeutic agent comprises an agent that targets thyroid function, such as, for example, anti-thyroid agents (e.g., radioiodine, propylthiouracil (PTU), and methimazole), or thyroid hormone replacement therapy (e.g., levothyrozine, or cytomel).

In one or more embodiments, the additional therapeutic agent comprises one or more agents useful in the treatment of diabetes, such as, e.g., insulin; synthetic glucagon; hyperglycemic agents (e.g., metformin, sulfonylureas, glinides, thiazolidinediones, dipeptidyl peptidase-4 (DPP-4) inhibitors; anti-hyperglycemic agents (e.g., sodium glucose cotransporter-2 (SGLT2) inhibitors including, e.g., canagliflozin, dapagliflozin, and empagliflozin); and GLP-1 receptor agonists (e.g., semaglutide, exenatide, dulaglutide, liraglutide, or lixisenatide).

In some embodiments, the additional therapeutic agent comprises a diuretic. Exemplary diuretics include spironolactone, bumetanide, torsemide, hydrochlorothiazide, furosemide, and metolazone, and aldosterone antagonists (e.g., spironolactone and eplerenone).

In one or more embodiments, the additional therapeutic agent comprises one or more of an antidiarrheal (e.g., eluxadoline, or alosetron), a laxative (lubiprostone, or a guanylate cyclase-C (GC-C agonist (e.g., linaclotide).

In some embodiments, the additional therapeutic agent comprises a cholinergic modulator, such as a cholinergic agonist (e.g., chantix, pilocarpine, or bethanechol), or an anticholinergic agent (e.g., atropine, belladonna alkaloids, benztropine mesylate, clidinium, cyclopentolate, darifenacin, dicylomine, fesoterodine, flavoxate, glycopyrrolate, homatropine hydrobromide, hyoscyamine, ipratropium, orphenadrine, oxybutynin, propantheline, scopolamine, methscopolamine, solifenacin, tiotropium, tolterodine, trihexphenidyl, and trospium).

In another embodiment, the additional therapeutic agent comprises an antiarrhythmic agent. Antiarrhythmic agents include calcium channel blocking agents (e.g., amlodipine, diltiazem, felodipine, isradipine, nicardipine, nifedipine, nisoldipine, and verapamil), beta-adrenergic blocking agents (i.e., beta blockers) (e.g., atenolol, bisoprolol, carvedilol, labetalol, metoprolol, propranolol, and sotalol), potassium-channel blockers (e.g., amiodarone, dronedarone, dofetilide, ibutilide, azimilide, bretylium, clofilium, nifekalant, tedisamil, and sematilide), adenosine, electrolyte supplements, atropine, and digitalis compounds.

In one or more embodiments, the additional therapeutic agent comprises a vasodilator. Exemplary vasodilators include, but are not limited to nitrates (e.g., nitroprusside, nitroglycerine, isosorbide, and amyl nitrate), hydralazine, treprostinil, minoxidil, angiotensin-converting enzyme (ACE) inhibitors (e.g., benazepril, captopril, enalapril, fosinopril, lisinopril, moexipril, perindopril, quinapril, ramipril, and trandolapril), and angiotensin receptor blockers (ARBs) (e.g., azilsartan, candesartan, eprosartan, irbesartan, losartan, olmesartan, telmisartan, and valsartan).

In some embodiments, the additional therapeutic agent comprises a cholesterol modifier. Cholesterol modifiers include statins (atorvastatin, Fluvastatin, lovastatin, pitavastatin, pravastatin, rosuvastatin, and simvastatin), cholesterol absorption inhibitors (e.g., ezetimibe), proprotein convertase subtilisin kexin 9 (PCSK9) inhibitors (e.g., alirocumab, and evolocumab), citrate lyase inhibitors (e.g., bempedoic acid, and benpedoic acid-ezetimibe), bile acid sequestrants (e.g., cholestyramine, colesevelam, and colestipol), fibrates (e.g., fenofibrate, and gemfibrozil), niacin, and omega-3 fatty acids.

In some embodiments, the additional therapeutic agent comprises a thrombolytic agent (e.g., streptokinase, alteplase, reteplase, Tenecteplase, urokinase, prourokinase, and anistreplase).

In another embodiment, the additional therapeutic agent comprises an anticoagulant. Exemplary anticoagulants include rivaroxaban, dabigatran, apixaban, eboxaban, and warfarin.

In some embodiments, the additional therapeutic agent comprises an agent useful in the treatment of fibrosis. Certain such agents include pirfenidone and nintedanib.

In another embodiment, the additional therapeutic agent comprises a targeted agent useful in the treatment of pulmonary arterial hypertension. Targeted agents useful in the treatment of pulmonary arterial hypertension include phosphodiesterase-5 (PDE5) inhibitors (e.g., sildenafil, tadalafil and vardenafil); guanylate cyclase stimulators (GCS) (e.g., adempas, riociguat, vericiguat and verquvo); endothelin receptor antagonists (e.g., bosentan, ambrisentan, and macitentan), and prostacyclin and analogues thereof.

In some embodiments, the additional therapeutic agent includes a mucolytic, e.g., guaifenesin, carbocisteine, erdosteine, mecysteine, bromhexine, hyperosmolar saline, mannitol powder, and dornase alfa.

In some embodiments, the additional therapeutic agent comprises a pancreatic enzyme, e.g., creon.

In some embodiments, the additional therapeutic agent comprises an agent that targets a mutation in the cystic fibrosis transmembrane conductance regulator (CFTR) gene. Exemplary CFTR modulators include ivacaftor, elexacaftor, lumacaftor, and tezacaftor.

In some embodiments, the additional therapeutic agent comprises an antibiotic. Exemplary antibiotics include, but are not limited to phenoxymethylpenicillin, dicloxacillin, amoxicillin, ampicillin, nafcillin, oxacillin, penicillin, cefaclor, cefazolin, cefadroxil, cephalexin, cefuroxime, cefixime, ceroxitin, ceftriaxone, doxycycline, minocycline, sarecycline, erythromycin, clarithromycin, azithromycin, fidaxomicin, roxithromycin, ciprofloxacin, ofloxacin, levofloxacin, moxifloxacin, sulfamethoxazole with trimethoprim, sulfasalazine, sulfacetamide, sulfadiazine silver, vancomycin, dalbavancin, oritavancin, and telavancin.

In some embodiments, the additional therapeutic agent comprises one or more agents selected from the groups consisting of anti-inflammatory agents, analgesic agents, agents that target one or more cytokines or cytokine receptors, immunosuppressants, agents that targets one or more mast-cell derived immunomodulators, BTK inhibitors, IgE inhibitors, anti-depressants, anti-psychotics, anti-anxiety agents, anticonvulsants, respiratory agents, nasal decongestants, cough suppressants, proton pump inhibitors (PPIs), agents that modulate cognitive function, agents that target thyroid function, agents useful in the treatment of diabetes, diuretics, antidiarrheals, laxatives, GC-C agonists, cholinergic modulators, antiarrhythmics, vasodilators, cholesterol modifiers, thrombolytic agents, anticoagulants, agents useful in the treatment of fibrosis, agents useful in the treatment of arterial hypertension, mucolytic agents, pancreatic enzymes, CFTR modulators, and/or antibiotics, HIF-2α inhibitors, and KIT inhibitors.

In some embodiments, the additional therapeutic agent comprises one or more agents selected from the group consisting of an anti-inflammatory agent, an analgesic agent, an immunosuppressant, and/or an agent that targets one or more cytokines or their receptors (e.g., IL-12, IL-17, IL-23, or their receptors).

In some embodiments, the additional therapeutic agent comprises one or more agents selected from the group consisting of a respiratory agent, an anti-inflammatory agent, an agent that targets one or more cytokines or their receptors (e.g., IL-4 and/or IL-13), a mast-cell stabilizer, and/or an agent that targets a mast-cell derived immunomodulator (e.g., leukotrienes).

In some embodiments, the additional therapeutic agent comprises one or more agents selected from the group consisting of an anti-depressant, an anti-psychotic, an anti-anxiety agent, an anticonvulsant, an agent that modulates cognitive function, an anti-CD20 antibody (e.g., ocrelizumab), an anti-inflammatory, and/or an immunosuppressant.

In some embodiments, the additional therapeutic agent comprises an anti-inflammatory and/or an immunosuppressant.

In some embodiments, the additional therapeutic agent comprises an anti-inflammatory agent, an immunosuppressant, and/or an agent that targets a mast-cell derived immunomodulator (e.g., antihistamine and/or leukotriene modulators).

In some embodiments, the additional therapeutic agent comprises an antihistamine, a BTK inhibitor, and/or an IgE inhibitor.

In some embodiments, the additional therapeutic agent comprises an antihistamine, an anti-inflammatory agent (e.g., a corticosteroid), and IgE inhibitor, and/or an immunosuppressant (e.g., cyclosporine).

In some embodiments, the additional therapeutic agent comprises an anti-inflammatory agent, an immunosuppressive agent, an agent that targets one or more cytokines or their receptors, or a combination thereof. In some embodiments, the additional therapeutic agent comprises an agent that targets the IL4 receptor (IL4R) (e.g., IL4Rα). In some embodiments, the additional therapeutic agent comprises dupilumab.

In some embodiments, the additional therapeutic agent comprises a cholesterol modifier, a diuretic, an antiarrhythmic, a vasodilator, an anti-inflammatory, an analgesic agent, or any combination thereof.

In one or more embodiments, the compounds described herein are combined with one or more additional therapeutic agents that are considered to be the standard ofcare (SOC) for one or more of the inflammatory, immune, and/or autoimmune-related indications described herein. Exemplary SOC therapies for the indications described herein are summarized in Table 3 and Table 4 below.

TABLE 3

| Disease/ Disorder/ Condition | Non-Biologics | Biologic |
|---|---|---|
| Arthritis | Acetaminophen, non-steroidal anti-inflammatory drugs (NSAIDs), corticosteroids | |
| Rheumatoid arthritis/ inflammatory arthritis | NSAIDs, corticosteroids, disease-modifying antirheumatic drugs (DMARDs) methotrexate, immunosuppressants, and JAK-inhibitors | Anti-Tumor Necrosis Factor Agents (TNFs), anti-interleukin (IL)-12, anti-IL-17, & anti-IL-23 |
| Psoriatic arthritis/ inflammatory arthritis | NSAIDs, corticosteroids, DMARDs (e.g., methotrexate), immunosuppressants, and JAK-inhibitors | Anti-TNFs, anti-IL-12, anti-IL-17, & anti-IL-23 |
| Osteoarthritis | Acetaminophen, NSAIDs, serotonin and norepinephrine reuptake inhibitors (SNRIs) | |
| Asthma | Bronchodilator, inhaled steroids, oral corticosteroids, leukotriene modifiers, cromolyn sodium | Anti-IL-4/13 (e.g., dupilumab) |
| Multiple sclerosis | Corticosteroids, immuno-modulators, and plasmapheresis | Anti-CD20 Mab (e.g., ocrelizumab) |
| Alzheimer's disease | Cholinesterase inhibitors, donepezil, memantine | Aducanumab |
| Autism | Behavioral and cognitive therapy, selective serotonin | |

TABLE 3-continued

| Disease/ Disorder/ Condition | Non-Biologics | Biologic |
|---|---|---|
| | reuptake inhibitors (SSRIs)/ antidepressants, anti-psychotics, anti-anxiety, anticonvulsants (anti-seizure) | |
| Psoriasis | Topical corticosteroids, vitamin A/D, phototherapy, DMARDs & immunosuppressants (JAK-inhibitors) | Anti-TNFs, anti-IL-12, anti-IL-17, & anti-IL-23 |
| Crohn's disease | Diet modification, corticosteroids and immunomodulators (JAK-inhibitors) | Anti-TNF (e.g.,), integrin receptor antagonists (e.g., vedolizumab), anti-IL-12 (e.g., ustekinumab), & anti-IL-23 |
| Ulcerative Colitis | Diet modification, amino salicylates (5-ASA), corticosteroids, Immunosuppressants, & JAK-inhibitors | Anti-TNF (e.g., infliximab), integrin receptor antagonists (e.g., vedolizumab), anti-IL-12 (e.g., ustekinumab), & anti-IL-23 |
| Irritable bowel syndrome | Diet modification, antidiarrheal, laxatives, selective serotonin reuptake inhibitors (SSRIs), antibiotics, linaclotide, alosetron, eluxadoline, and lubiprostone | |
| Lupus | NSAIDs, corticosteroids, and immunosuppressants | Immuno-suppressive MAb (e.g., belimumab) |
| Grave's disease | Radioiodine, beta-blockers and anti-thyroid medications, thyroidectomy | |
| Hashimoto's thyroiditis | T-4 hormone replacement (e.g., levothyroxine), T-3 hormone (e.g., Cytomel) | |
| Ankylosing spondylitis | Physical therapy, NSAIDs, corticosteroids | Anti-TNF & anti-IL-17 (e.g., secukinumab and ixekizumab) |
| Sjögren's syndrome (SjS) | hydroxychloroquine, methotrexate, cyclosporine, pilocarpine, cevimeline | |
| Angioedema | Trigger avoidance, antihistamines, oral corticosteroids, leukotriene modifiers | |
| Allergic asthma | Nasal steroids, antihistamines, inhaled steroids, anticholinergic | IgE inhibitor (e.g., anti-IgE antibody, e.g., omalizumab) |
| Eosinophilic asthma | Inhaled steroids, oral corticosteroids, and leukotriene modifiers | IgE inhibitor, anti-IL-5 (e.g., benralizumab), anti-IL-4/13 (e.g., dupilumab) |
| Anaphylaxis | Epinephrine (EpiPen) Antihistamines, cortisone, beta-agonist (e.g., albuterol) | |
| Atopic dermatitis | Topical corticosteroids, antibiotic cream, oral corticosteroids, phototherapy | Anti-IL-4/13 (e.g., dupilumab) |
| Food allergies | Diet modification/avoidance, antihistamines, corticosteroids, epinephrine (rescue) | |
| Allergic conjunctivitis | Antihistamine eye-drops, oral antihistamines, NSAIDs, corticosteroids, mast cell stabilizers (e.g., lodoxamide and nedocromil) | |
| Allergic rhinitis | Antihistamines, decongestants, corticosteroids, leukotriene modifiers, | IgE inhibitor (e.g., anti-IgE antibody, e.g., omalizumab) |

TABLE 3-continued

| Disease/ Disorder/ Condition | Non-Biologics | Biologic |
|---|---|---|
| Urticaria (e.g., chronic spontaneous urticaria (CSU) | Antihistamines, corticosteroids, cyclosporine | IgE inhibitor (e.g., anti-IgE antibody, e.g., omalizumab) |
| Acute/ physical urticaria | Avoidance, antihistamines, topical & oral corticosteroids | |
| Mastocytosis | Topical corticosteroids, anti-histamines, NSAIDs, leukotriene modifiers, mast cell stabilizers | |
| Dermo-graphism | Skin hydration, antihistamines | |
| Dermatosis/ dermatitis | Hydrocortisone, topical corticosteroids, antihistamines, immunosuppressants | |
| Allergic contact dermatitis | Allergen avoidance, hydrocortisone, topical corticosteroids, oral corticosteroids | |
| Eosinophilic GI disease | Proton pump inhibitors (PPIs), swallowed topical steroids, corticosteroids, diet-modification | |
| Eosinophilic esophagitis | Diet modification, proton pump inhibitors (PPIs), swallowed topical steroids, corticosteroids, and esophageal dilation | |
| Type I diabetes | Insulin, diet, synthetic glucagon | |
| Type II diabetes | Diet, exercise, Metformin, Sulfonylureas, Glinides, Thiazolidinediones, DPP-4 inhibitors, GLP-1 receptor agonists, SGLT2 inhibitors, insulin | |
| Prurigo nodularis | Topical corticosteroids, antihistamines, oral corticosteroids, and SSRIs | |

TABLE 4

| Disease/ Disorder/ Condition | Non-Biologics | Biologic |
|---|---|---|
| Coronary heart disease | Diet, exercise, cholesterol modifiers (e.g., statins), antiplatelets (e.g., aspirin), beta-blockers, diuretics, calcium channel blockers, nitroglycerin, angiotensin-converting enzyme inhibitors (ACEs), and angiotensin receptor blockers (ARBs), angioplasty, stent implant, and coronary artery bypass | Proprotein convertase subtilisin kexin 9 (PCSK9) inhibitors (e.g., evolocumab and alirocumab) |
| Athero-sclerosis | Diet, exercise, cholesterol modifiers (e.g., statins), antiplatelets (e.g., aspirin), beta-blockers, diuretics, calcium channel blockers, ACEs, ARBs, angioplasty, stent implant, endarterectomy, Fibrinolytic therapy, and coronary artery bypass | |
| Myocardial infarction | Oxygen, antiplatelets (e.g., aspirin), anticoagulants, nitroglycerin, thrombolytic medications, anti-arrhythmia medications, beta-blockers, calcium channel blockers, ACEs, and ARBs, | |
| Angina | Nitrates, antiplatelets (e.g., aspirin), cholesterol modifiers (e.g., statins), anticoagulants, beta-blockers, calcium channel blockers, ACEs, and ARBs | Proprotein convertase subtilisin kexin 9 (PCSK9) inhibitors (e.g., |

TABLE 4-continued

| Disease/ Disorder/ Condition | Non-Biologics | Biologic |
|---|---|---|
| | | evolocumab and alirocumab) |
| Osteoarthritis | Acetaminophen, NSAIDs, serotonin and norepinephrine reuptake inhibitors (SNRIs) | |
| Pulmonary fibrosis | Oxygen therapy, pulmonary rehabilitation, pirfenidone and nintedanib | |
| Pulmonary arterial hypertension (PAH) | Phosphodiesterase-5 inhibitor (PDE-5i), guanylate cyclase stimulator (GCS), Endothelin receptor antagonist (ERA), Prostacyclin-class therapy | |
| Primary pulmonary hypertension (PH) | Oxygen therapy, vasodilators (e.g., epoprostenol and treprostinil), guanylate cyclase (GSC) stimulators, endothelin receptor antagonists, diuretics, calcium channel blockers, and anticoagulant (e.g., warfarin) | |
| Hepatic fibrosis | Treatments focus on underline driver of fibrosis; e.g., limit alcohol consumption, modify medications causing liver damage, controlling fat/cholesterol/sugars | |
| Renal fibrosis | Focus on overall kidney function | |
| Cardiac fibrosis | ACEs, ARBs, aldosterone antagonist, (e.g., pirfenidone) | |
| Cystic fibrosis | Anti-inflammatoirecus-thinners, inhaled steroids, pancreatic enzymes, gene targeting medications (e.g., transmembrane conductance regulator (CFTR) modulators; ivacaftor, elexacaftor, lumacaftor, and tezacaftor) | |
| Bronchitis | Avoid irritants, cough suppressants, humidifier, bronchodilators (e.g., inhaled steroids) | |
| Asthma | Bronchodilator, inhaled steroids, oral corticosteroids, leukotriene modifiers, cromolyn sodium | Anti-IL-4/13 (e.g., dupilumab) |

Cancer Therapies

The present disclosure contemplates the use of the MRGPRX2 antagonists described herein in combination with one or more additional therapies useful in the treatment of cancer.

In some embodiments the compounds described herein in combination with one or more additional therapies are useful in the treatment of cancer. A non-limiting list of cancers include melanoma, prostate cancer, pancreatic cancer, squamous cell carcinoma, Hodgkin lymphoma, leukemia (e.g., chronic myeloid leukemia, chronic eosinophilic leukemia, chronic myelomonocytic leukemia, myeloid leukemia, acute myeloid leukemia, acute megakaryoblastic leukemia, mast cell leukemia, acute lymphocytic leukemia), gastric cancer (e.g., gastrointestinal stromal cancer), small bowel cancer, salivary gland cancer, adrenocortical cancer, thyroid cancer, stomach cancer, breast cancer, endometrial cancer, renal cancer, cervical cancer, testicular cancer, esophageal cancer, lung cancer (e.g., small cell and non-small cell lung cancer), colorectal cancer, prostate cancer, liver cancer, bile duct cancer, gallbladder cancer, appendiceal cancer, ovarian cancer, urothelial cancer, neuroendocrine tumors, kidney cancer, head and neck cancer, bone cancer, brain cancer (e.g., glioblastoma, medulloblastoma), prophylaxis of cancer (e.g., carcinomas, sarcomas, leukemias, lymphomas, myelomas, etc.), mesothelioma, and soft tissue sarcoma.

In some embodiments, one or more of the additional therapies is an additional treatment modality. Exemplary treatment modalities include but are not limited to surgical resection of a tumor, bone marrow transplant, radiation therapy, and photodynamic therapy.

In some embodiments, one or more of the additional therapies is a therapeutic agent. Exemplary therapeutic agents include chemotherapeutic agents, radiopharmaceuticals, hormone therapies, epigenetic modulators, ATP-adenosine axis-targeting agents (e.g., CD73 inhibitors, CD39 inhibitors, $A_{2A}R$ inhibitors, and/or $A_{2B}R$ inhibitors), signal transduction inhibitors (e.g., inhibitors of one or more of TYRO3, MERTK, EGFR, FGFR, VEGFR, HER-2, HER-3, BRAF, RET, MET, ABL, ALK, FLT-3, JAK, STAT, NF-kB), RAS signaling inhibitors (e.g., inhibitors of one or more of KRAS, HRAS, RAF, MEK, ERK, PTEN, SOS (e.g., SOSi), mTORCI, SHP2 (PTPN11), and AKT), PI3K inhibitors, arginase inhibitors, HIF inhibitors (e.g., inhibitors of HIF-2a), AXL inhibitors, PAK4 inhibitors, immunotherapeutic agents, cellular therapies, gene therapies, immune checkpoint inhibitors (e.g., inhibitors of one or more of PD-1, PD-L1, TIGIT, CTLA-4, BTLA, LAG-3, and TIM-3), and agonists of stimulatory or co-stimulatory immune checkpoints.

In some embodiments, one or more of the additional therapeutic agents is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pomalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel;

chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; proteasome inhibitors such as bortezomib, carfilzomib and ixazomib; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above. In certain embodiments, combination therapy comprises a chemotherapy regimen that includes one or more chemotherapeutic agents. In one embodiment, combination therapy comprises a chemotherapeutic regimen comprising FOLFOX (folinic acid, fluorouracil, and oxaliplatin), FOLFIRI (e.g., folinic acid, fluorouracil, and irinotecan), a taxoid (e.g., docetaxel, paclitaxel, nab-paclitaxel, etc.), and gemcitabine.

In some embodiments, one or more of the additional therapeutic agents is an immune checkpoint inhibitor. As used herein, the term "immune checkpoint inhibitor" refers to an antagonist of an inhibitory or co-inhibitory immune checkpoint. The terms "immune checkpoint inhibitor", "checkpoint inhibitor" and "CPI" may be used herein interchangeably. Immune checkpoint inhibitors may antagonize an inhibitory or co-inhibitory immune checkpoint by interfering with receptor—ligand binding and/or altering receptor signaling. Examples of immune checkpoints (ligands and receptors), some of which are selectively upregulated in various types of cancer cells, that can be antagonized include PD-1 (programmed cell death protein 1); PD-L1 (PD1 ligand); BTLA (B and T lymphocyte attenuator); CTLA-4 (cytotoxic T-lymphocyte associated antigen 4); TIM-3 (T cell immunoglobulin and mucin domain containing protein 3); LAG-3 (lymphocyte activation gene 3); TIGIT (T cell immunoreceptor with Ig and ITIM domains); CD276 (B7-H3), PD-L2, Galectin 9, CEACAM-1, CD69, Galectin-1, CD113, GPR56, VISTA, 2B4, CD48, GARP, PD1H, LAIR1, TIM-1, and TIM-4, and Killer Inhibitory Receptors, which can be divided into two classes based on their structural features: i) killer cell immunoglobulin-like receptors (KIRs), and ii) C-type lectin receptors (members of the type II transmembrane receptor family). Also contemplated are other less well-defined immune checkpoints that have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

Experimental

The following examples are put forth so as to provide those of ordinary skill in the art with a complete disclosure and description of how to make and use the present disclosure, and are not intended to limit the scope of what the inventors regard as their invention. Efforts have been made to ensure accuracy with respect to numbers used (e.g., amounts, temperature, etc.), but some experimental errors and deviations should be accounted for.

All reactions were performed using a Teflon-coated magnetic stir bar at the indicated temperature and were conducted under an inert atmosphere when stated. Purchased starting materials and reagents were generally used as received. Reactions were monitored by TLC (silica gel 60 with fluorescence F254, visualized with a short wave/long wave UV lamp) and/or LCMS (AGILENT® 1100 or 1200 series LCMS with UV detection at 254 or 280 nm using a binary solvent system [0.1% formic acid in MeCN/0.1% formic acid in $H_2O$] using one of the following columns: AGILENT® Eclipse Plus C18 [3.5 μm, 4.6 mm i.d.×100 mm], WATERS™ XSelect HSS C18 [3.5 μm, 2.1 mm i.d.×75 mm]). Flash chromatography was conducted on silica gel using an automated system (COMBIFLASH® RF+manufactured by Teledyne ISCO), with detection wavelengths of 254 and 280 nm, and optionally equipped with an evaporative light scattering detector. Reverse phase preparative HPLC was conducted on an AGILENT® 1260 or 1290 Infinity series HPLC. Samples were eluted using a binary solvent system (MeCN/$H_2O$ with an acid modifier as needed—for example 0.1% TFA or 0.1% formic acid) with gradient elution on a Gemini C18 110 A column (21.2 mm i.d. xx 250 mm) with variable wavelength detection. Final compounds obtained through preparative HPLC were concentrated through lyophilization. All assayed compounds were purified to >95% purity as determined by $^1H$ NMR or LCMS (AGILENT® 1100 or 1200 series LCMS with UV detection at 254 or 280 nm using a binary solvent system [0.1% formic acid in MeCN/0.1% formic acid in $H_2O$] using one of the following columns: AGILENT® Eclipse Plus C18 [3.5 μm, 4.6 mm i.d.×100 mm], WATERS™ XSelect HSS C18 [3.5 μm, 2.1 mm i.d.×75 mm]). $^1H$ NMR spectra were recorded on a Varian 400 MHz NMR spectrometer equipped with an Oxford AS400 magnet or a BRUKER® AVANCE NEO 400 MHz NMR. Chemical shifts (6) are reported as parts per million (ppm) relative to residual undeuterated solvent as an internal reference. The abbreviations s, br s, d, t, q, dd, dt, ddd, and m stand for singlet, broad singlet, doublet, triplet, quartet, doublet of doublets, doublet of triplets, doublet of doublet of doublets, and multiplet, respectively.

Unless indicated otherwise, temperature is in degrees Celsius (0° C.), and pressure is at or near atmospheric. Standard abbreviations are used, including the following: min=minute(s); nm=nanometers; mg=milligram; g=gram; kg=kilogram; ml or mL-milliliter; L=microliter; M=molar; mM=millimolar; mmol=millimole; N=normality; psi=pounds per square inch; calcd=calculated; equiv.=equivalents; BSA=bovine serum albumin; HEPES=4-(2-hydroxyethyl)piperazine-1-ethane-sulfonic acid; DCM=dichloromethane; THF=tetrahydrofuran; EtOAc=ethyl acetate; TFA=trifluoroacetic acid; ACN or MeCN=acetonitrile; MeOH=methanol; EtOH=ethanol; DMF=N,N-dimethylformamide; DMSO=dimethyl sulfoxide; NMP=N-methyl-2-pyrrolidone; DIPEA=N,N-diisopropylethylamine; HATU=O-(7-Azabenzotriazol-1-yl)-N,N,N',N'-tetramethyluronium hexafluorophosphate; iPrOH=isopropyl alcohol; THP=2-tetrahydropyranyl; $CDCl_3$=deuterated chloroform; MeOD=deuterated methanol; MsCl=methanesulfonyl chloride; $Et_3N$=triethylamine; $Na_2SO_4$=sodium sulfate; $NaHCO_3$=sodium bicarbonate; NaH=sodium hydride; $K_2CO_3$=potassium carbonate; KI=potassium iodide; $MgSO_4$=magnesium sulfate; $CaCl_{2\cdot 2}H_2O$=calcium dichloride dihydrate; $MgCl_{2\cdot 6}H_2O$=magnesium chloride hexahydrate; HCl=hydrochloric acid; Pd/C=palladium on carbon; DMAP=4-dimethylaminopyridine; Boc=tert-butyloxycarbonyl; Cbz=benzyloxycarbonyl; MHz=megahertz; Hz=hertz; ppm=parts per million; ESI MS=electrospray ionization mass spectrometry; LCMS=liquid chromatography-mass spectrometry; NMR=nuclear magnetic resonance; HPLC=high pressure liquid chromatography.

Example 1: (2-[(R)-3-[3-(5-ethoxy-2-pyrazinyl)-1-methylureido]-1-piperidyl]-4-pyrimidinyl (R)-1-methyl-3-piperidinecarbamate

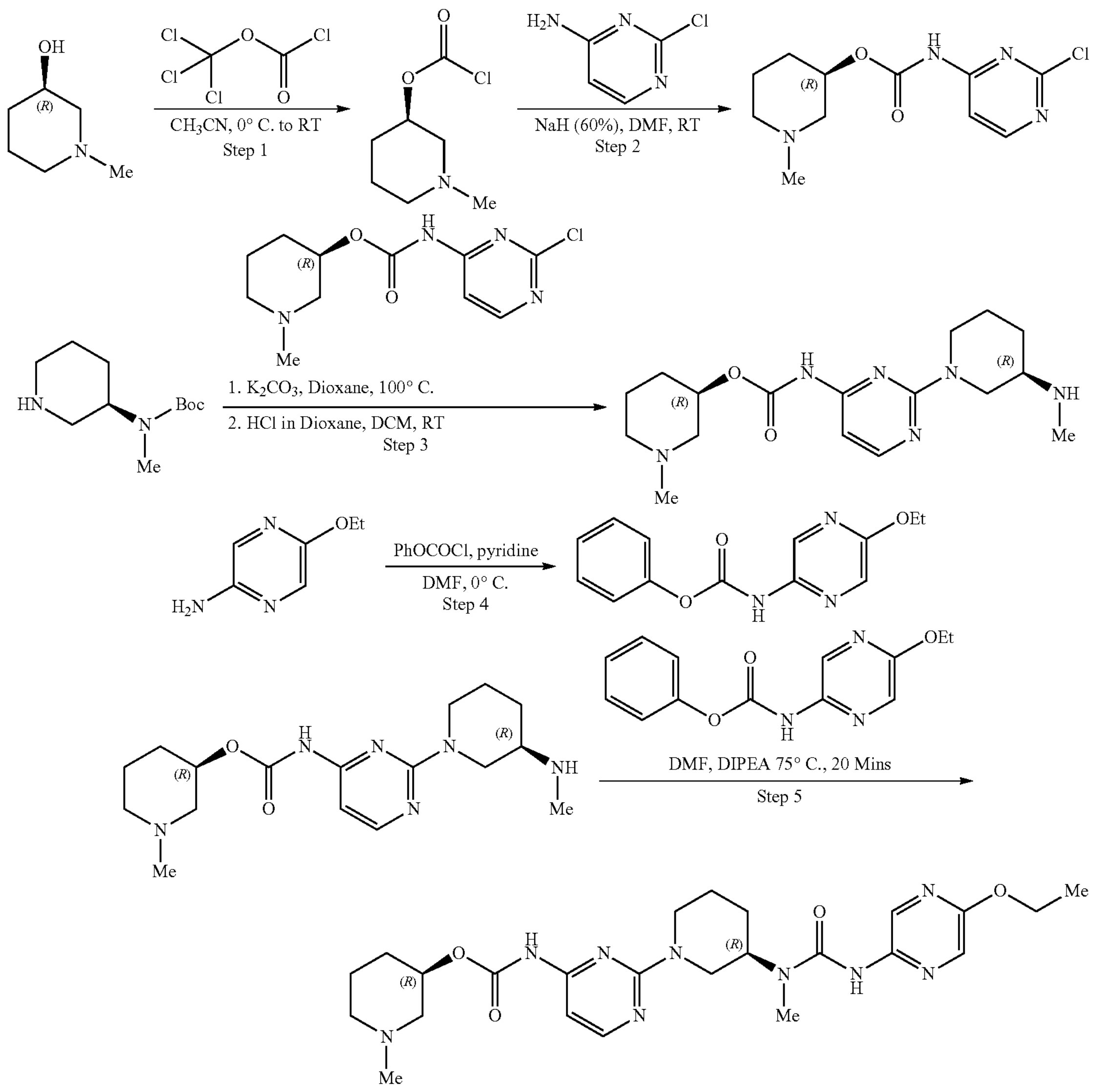

Step 1: Trichloromethyl chloroformate (893 mg, 0.54 mL, 4.51 mmol) was added dropwise to a stirred mixture of (3R)-1-methylpiperidin-3-ol (400 mg, 3.47 mmol) in acetonitrile (5 mL) in a reaction vial at 0° C. and slowly warmed to room temperature and stirred overnight (16 h). The mixture was then concentrated in vacuo to remove the volatiles to afford 1-methyl-3-piperidinyl chloroformate HCl, which was used directly in the next step without further purification.

Step 2: 1-Methyl-3-piperidinyl chloroformate HCl (129.5 mg, 1 mmol) was taken in a screw-capped reaction vial equipped with a stir bar and to this vial was added NaH [(60% dispersed in mineral oil) 80 mg, 2 mmol] followed by 2-chloro-4-amino pyrimidine (321 mg, 1.5 mmol). To this mixture, dry DMF (2 mL) was added and stirred at room temperature overnight. After confirming the completion of the reaction by LCMS, the reaction was quenched with water (5 mL) after cooling the reaction mixture to 0° C. and extracted with DCM (10 mL) thrice. The combined organic layers were again washed with water (30 mL) thrice to remove the DMF, dried over anhydrous $Na_2SO_4$, and the volatiles were evaporated under reduced pressure. The crude product was purified using flash column chromatography (using silica gel (100-200 mesh); eluted with 20% MeOH in DCM, initially grading to 30% MeOH in DCM) to afford the intermediate.

Step 3 (Part 1): The intermediate from Step 2 (73 mg, 0.27 mmol) was taken in a dry screw-capped reaction vial equipped with a stir bar and to this vial was added (R)-3-N-Boc-3-(methylamino)piperidine (58 mg, 0.27 mmol) followed by $K_2CO_3$ (112 mg, 0.81 mmol). To this mixture, dry dioxane (2 mL) was added and stirred at 100° C. overnight. After confirming the completion of the reaction, the crude reaction mixture was brought to room temperature, filtered through a small pad of CELITE® and the volatiles were removed under reduced pressure. The crude product was purified using flash column chromatography (using silica gel (100-200 mesh); eluted with 15% MeOH in DCM, initially grading to 25% MeOH in DCM) to afford the intermediate.

Step 3 (Part 2): The intermediate from Step 3 (Part 1) (103 mg, 0.23 mmol) was taken in a dry screw-capped reaction vial equipped with a stir bar and dissolved in DCM (2 mL). To this mixture, HCl in dioxane solution (4 M, 2.5 mL) was added dropwise and stirred at room temperature. Reaction progress was monitored using LCMS. After confirming the complete removal of the Boc group, volatiles were evaporated under reduced pressure to afford the intermediate as HCl salt in quantitative yield. This salt was directly used in Step 4 without further purification.

Step 4: To a stirred solution of 2-amino-5-ethoxypyrazine (25 g, 180 mmol) in 500 mL DMF was added pyridine (29 mL, 360 mmol). The mixture was cooled to 0° C. and phenyl chloroformate (29 mL, 234 mmol) was added dropwise. After complete addition, the reaction was allowed to rise to room temperature over a period of 2 h. The product was precipitated by slow addition of 500 mL of distilled water, which was separated by filtration. The filter cake was washed with 500 mL of distilled water and dried under vacuum to obtain the desired product in quantitative yield. The crude material thus obtained was taken to next step without further purification.

Step 5: The intermediate from Step 3 (Part 2) was taken in a dry screw-capped reaction vial equipped with a stir bar and to this vial was added phenyl N-(pyrazin-2-yl-5-ethoxy) carbamate (60 mg, 0.23 mmol) from Step 4 followed by dry DMF (2.5 mL). To this mixture, DIPEA (0.12 mL, 0.69 mmol) was added, and the reaction mixture was stirred at 70° C. After confirming the completion of the reaction after 30 minutes, the temperature of the reaction mixture was brought to room temperature, and the crude reaction mixture was directly purified using reversed phase preparative HPLC to afford the title compound. $^1$H NMR (400 MHz, Methanol-$d_4$) δ 8.56 (d, J=1.5 Hz, 1H), 8.23 (d, J=5.7 Hz, 1H), 7.96 (d, J=1.5 Hz, 1H), 7.18 (d, J=5.6 Hz, 1H), 5.10 (p, J=4.2 Hz, 1H), 4.73-4.56 (m, 2H), 4.34 (q, J=7.0 Hz, 2H), 4.05-3.91 (m, 1H), 3.27-3.14 (m, 1H), 3.11-2.95 (m, 6H), 2.90-2.74 (m, 5H), 2.11-1.99 (m, 1H), 1.99-1.77 (m, 7H), 1.67-1.50 (m, 1H), 1.38 (t, J=7.1 Hz, 3H). ESI MS $[M+H]^+$ for $C_{24}H_{35}N_9O_4$, calcd 514.6, found 514.2.

Example 2: (2-[(S)-3-[3-(5-ethoxy-2-pyrazinyl)-1-methylureido]-4,4-difluoro-1-piperidyl]-4-pyrimidinyl (1S,2S)-2-aminocyclopentanecarbamate)

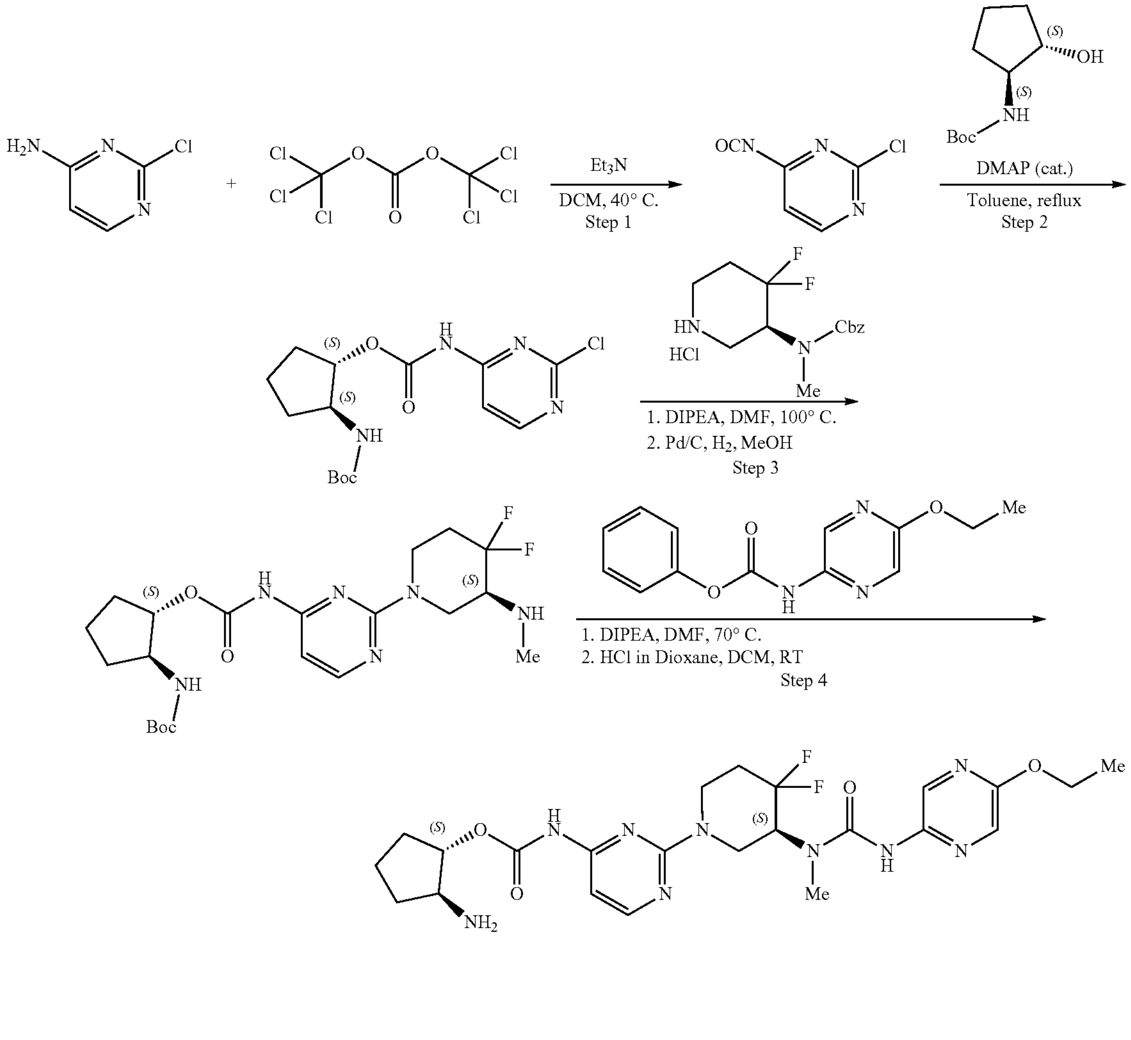

Step 1: To a solution of triphosgene (129.5 mg, 1 mmol) in dry DCM (5 mL) was added 2-chloro-4-amino pyrimidine (296.7 mg, 1 mmol) followed by $Et_3N$ (0.42 mL, 3 mmol) at 0° C. under constant stirring. The mixture was then stirred at 40° C. for 4 hours. The solvent was then removed under reduced pressure. The crude mixture was used directly in the next step without further purification.

Step 2: The crude reaction mixture from Step 1 was taken in a dry screw-capped reaction vial equipped with a stir bar. To this reaction vial was added toluene (5 mL), tert-butyl N-[(1S,2S)-2-hydroxycyclopentyl]carbamate (101 mg, 0.5 mmol) (with respect to amine starting material in Step 1) and DMAP (12 mg, 0.1 mmol) sequentially. The mixture was then heated to reflux overnight. After confirming the completion of the reaction, the temperature of the reaction mixture was brought to room temperature, and the volatiles were evaporated under reduced pressure. The crude product was purified by flash column chromatography (using silica gel (100-200 mesh); eluted with 20% MeOH in DCM, initially grading to 30% MeOH in DCM) to afford the intermediate.

Step 3 (Part 1): The intermediate from Step 2 (192 mg, 0.53 mmol) was taken in a dry screw-capped reaction vial equipped with a stir bar and to this vial was added (3S)-4,4-difluoro-3-[[(phenylmethoxy)carbonyl]aminomethyl]-1-piperidine HCl salt (173 mg, 0.53 mmol, prepared in a similar fashion to that described in Example 11, Steps 1-3) followed by dry DMF (2 mL). Then DIPEA (0.28 mL, 1.61 mmol) was added to the reaction mixture under constant stirring, and the reaction mixture was heated at 100° C. for 60 hours. After confirming the completion of reaction, the temperature of the reaction mixture was brought to room temperature and 5 mL of water was added and extracted with DCM (3×10 mL). The combined organic layers were dried over anhydrous $Na_2SO_4$ and concentrated under reduced pressure. The crude product was purified by flash column chromatography (using silica gel (100-200 mesh); eluted with 5% MeOH in DCM, initially grading to 15% MeOH in DCM) to afford the intermediate.

Step 3 (Part 2): The intermediate from Step 3 (Part 1) (212 mg, 0.37 mmol) was taken in a dry screw-capped reaction vial equipped with a stir bar and to this vial was added palladium on activated carbon, 10% Pd, (50% by weight in water) (39 mg, 1 mmol). To this mixture, MeOH (2 mL) was carefully added along the walls of the reaction vial and the screw cap was tightly closed. To this vial, a $H_2$ balloon was equipped and purged for 2 min under constant stirring and the reaction mixture was stirred under $H_2$ for 3 hours. After confirming the complete removal of the Cbz group, the reaction was stopped, and the crude reaction mixture was filtered through a small pad of CELITE® and the CELITE® pad was washed with MeOH (5 mL). The organic layer was concentrated under reduced pressure to afford the intermediate. The crude product was directly used in the next step without further purification.

Step 4 (Part 1): This transformation was performed in a similar fashion to Step 5 of the protocol for the synthesis of Example 1. After the completion of the reaction, the reaction mixture was brought to room temperature and washed with water thrice (30 mL) to remove DMF and extracted with DCM. The combined organic layers were dried over anhydrous $Na_2SO_4$ and concentrated under reduced pressure. The crude product was used directly in the next step without further purification.

Step 4 (Part 2): The crude product from Step 4 (Part 1) was then subjected to Boc removal in a similar fashion to Step 3 (Part 2) of the protocol for the synthesis of Example 1. The crude product was then purified using reversed phase preparative HPLC to afford the title compound. $^1H$ NMR (400 MHz, Methanol-$d_4$) δ 8.49 (d, J=1.4 Hz, 1H), 8.20 (d, J=5.7 Hz, 1H), 7.91 (d, J=1.4 Hz, 1H), 7.23 (d, J=5.7 Hz, 1H), 4.82-4.67 (m, 3H), 4.58 (dt, J=25.6, 12.6 Hz, 1H), 4.34 (q, J=7.0 Hz, 2H), 3.45 (dd, J=12.9, 11.4 Hz, 1H), 3.26 (td, J=7.2, 4.2 Hz, 1H), 3.15 (d, J=2.1 Hz, 4H), 2.22-1.91 (m, 5H), 1.82-1.64 (m, 3H), 1.46-1.39 (m, 1H), 1.37 (t, J=7.1 Hz, 3H). ESI MS $[M+H]^+$ for $C_{23}H_{31}F_2N_9O_4$, calcd 536.6, found 536.3.

Example 3: 2-[(R)-3-[1-methyl-3-(7-methyl-3-isoquinolyl)ureido]-1-piperidyl]-4-pyrimidinyl 1-methyl-4-piperidinecarbamate

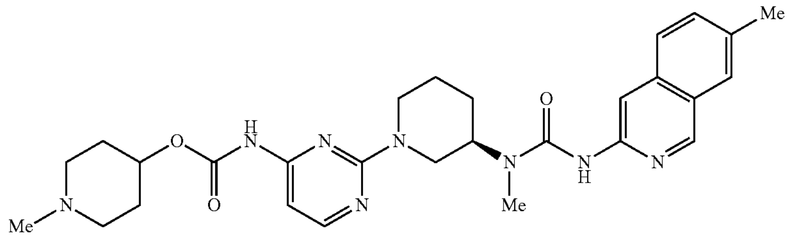 [SMILES: Cc1ccc2cc(NC(=O)N(C)[C@@H]3CCCN(c4nccc(NC(=O)OC5CCN(C)CC5)n4)C3)ncc2c1]

The title compound was synthesized in a similar fashion to Example 1 using 4-hydroxy-N-methylpiperidine in Step 1 and 7-methyl-3-isoquinolinamine in Step 4. $^1$H NMR (400 MHz, Methanol-$d_4$) δ 9.00 (s, 1H), 8.24 (d, J=5.7 Hz, 1H), 8.16 (s, 1H), 7.86-7.64 (m, 2H), 7.54 (dd, J=8.5, 1.7 Hz, 1H), 7.21 (d, J=5.7 Hz, 1H), 4.97-4.87 (m, 1H), 4.68 (t, J=14.9 Hz, 2H), 4.03 (s, 1H), 3.15-2.69 (m, 9H), 2.57 (s, 3H), 2.51 (s, 3H), 2.15-1.75 (m, 7H), 1.71-1.49 (m, 1H). ESI MS $[M+H]^+$ for $C_{28}H_{36}N_8O_3$, calcd 533.3, found 533.3.

Example 4: 2-[(R)-3-[3-(5-ethoxy-2-pyrazinyl)-1-methylureido]-1-piperidyl]-4-pyrimidinyl 2-(1-pyrazolyl)ethanecarbamate

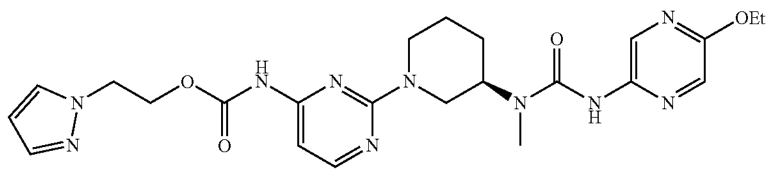 [SMILES: CCOc1cnc(NC(=O)N(C)[C@@H]2CCCN(c3nccc(NC(=O)OCCn4cccn4)n3)C2)cn1]

The title compound was synthesized in a similar fashion to Example 2 (Step 1-Step 4 Part 1, using 1H-pyrazole-1-ethanol in Step 2). $^1$H NMR (400 MHz, DMSO-$d_6$) δ 10.18 (s, 1H), 8.87 (s, 1H), 8.57 (d, J=1.5 Hz, 1H), 8.21 (d, J=5.6 Hz, 1H), 8.00 (d, J=1.4 Hz, 1H), 7.80 (d, J=2.2 Hz, 1H), 7.44 (d, J=1.9 Hz, 1H), 6.99 (d, J=5.6 Hz, 1H), 6.24 (t, J=2.1 Hz, 1H), 4.72-4.47 (m, 2H), 4.44-4.34 (m, 4H), 4.30 (q, J=7.0 Hz, 2H), 4.12-3.86 (m, 1H), 3.03-2.83 (m, 4H), 2.72 (t, J=12.3 Hz, 1H), 1.91-1.63 (m, 3H), 1.56-1.38 (m, 1H), 1.33 (t, J=7.0 Hz, 3H). ESI MS $[M+H]^+$ for $C_2H_{30}N_{10}O_4$, calcd 511.3, found 511.2.

Example 5: 2-[(R)-3-[3-(5-ethoxy-2-pyrazinyl)-1-methylureido]-1-piperidyl]-4-pyrimidinyl [(R)-1,4-dioxan-2-yl]methanecarbamate

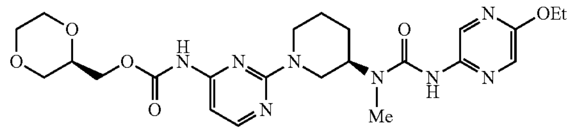 [SMILES: CCOc1cnc(NC(=O)N(C)[C@@H]2CCCN(c3nccc(NC(=O)OC[C@H]4COCCO4)n3)C2)cn1]

The title compound was synthesized in a similar fashion to Example 2 (Step 1-Step 4 Part 1, using (2S)-1,4-dioxane-2-methanol in Step 2). $^1$H NMR (400 MHz, DMSO-$d_6$) δ 10.20 (s, 1H), 8.84 (s, 1H), 8.59 (d, J=1.4 Hz, 1H), 8.23 (d, J=5.6 Hz, 1H), 8.03 (d, J=1.5 Hz, 1H), 7.02 (d, J=5.6 Hz, 1H), 4.72-4.48 (m, 2H), 4.30 (q, J=7.0 Hz, 2H), 4.15-3.91 (m, 3H), 3.79-3.70 (m, 3H), 3.68-3.53 (m, 2H), 3.46 (td, J=10.9, 2.7 Hz, 1H), 3.39-3.34 (m, 1H), 2.96 (d, J=11.8 Hz, 1H), 2.92 (s, 3H), 2.74 (t, J=12.8 Hz, 1H), 1.87-1.70 (m, 3H), 1.57-1.39 (m, 1H), 1.33 (t, J=7.0 Hz, 3H). ESI MS $[M+H]^+$ for $C_{23}H_{32}N_8O_6$, calcd 517.2, found 517.2

Example 6: 2-[(3S,4R)-3-[3-(5-ethoxy-2-pyrazinyl)-1-methylureido]-4-fluoro-1-piperidyl]-4-pyrimidinyl 1-methyl-4-piperidinecarbamate

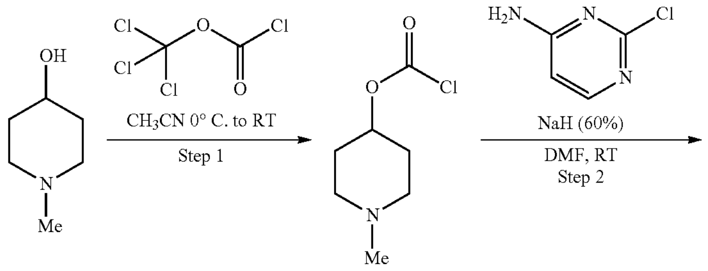

-continued

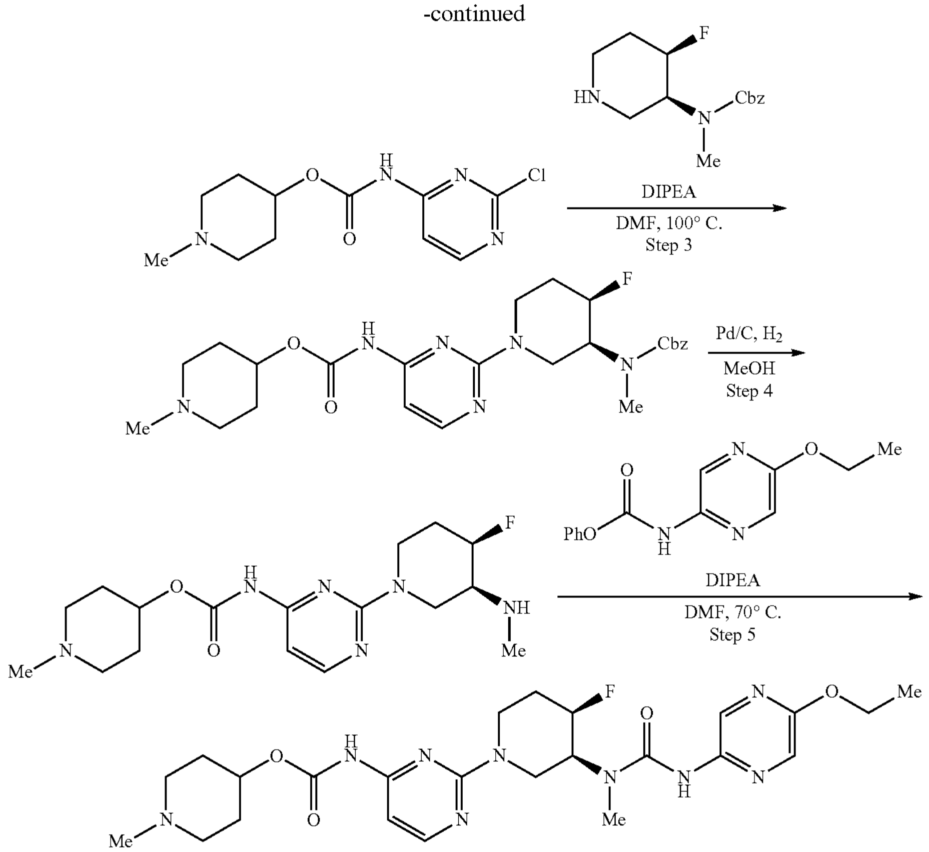

Step 1: This transformation was performed in a similar fashion to Step 1 of the protocol for the synthesis of Example 1. The product was obtained as HCl salt which was used directly in the next step without further purification.

Step 2: This transformation was performed in a similar fashion to Step 2 of the protocol for the synthesis of Example 1.

Step 3: The intermediate from Step 2 (192 mg, 0.53 mmol) was taken in a dry screw-capped reaction vial equipped with a stir bar and to this vial was added [(3S, 4R)-3-[N-(benzyloxycarbonyl)-3-methylamino]-4-fluoropiperidine (760 mg, 2.85 mmol, prepared in a similar fashion to that described in Example 11, Steps 1-3) followed by DIPEA (1.5 mL, 8.56 mmol). To this mixture, dry DMF (4 mL) was added, and the mixture was stirred at 100° C. overnight. After confirming the completion of the reaction, the crude reaction mixture was brought to room temperature. The reaction mixture was diluted with DCM and washed with water (3×20 mL). The combined organic layers were dried over anhydrous $Na_2SO_4$, and the volatiles were concentrated under reduced pressure. The crude product was purified using flash column chromatography (using silica gel (100-200 mesh); eluted with 15% MeOH in DCM, initially grading to 30% MeOH in DCM) to afford the intermediate.

Step 4: The intermediate from Step 3 (601 mg, 1.2 mmol) was taken in a dry Parr shaker vessel and to this vessel was added 10% Pd on carbon (50% by weight in water) (128 mg, 1.2 mmol). To this mixture, MeOH (8 mL) was carefully added along the walls of the reaction vessel, and the vessel was tightly closed with the rubber stopper and fixed to the Parr shaker. Then the vessel was purged with $H_2$ 3 times, and the Parr shaker was operated under $H_2$ at 30 psi pressure for 1 hour. After confirming the complete removal of the Cbz group, the reaction was stopped and the crude reaction mixture was filtered through a small pad of CELITE® and the CELITE® pad was washed with MeOH (10 mL) and the organic layer was concentrated under reduced pressure to afford the intermediate. The crude product was directly used in the next step without further purification.

Step 5: This transformation was performed in a similar fashion to Step 5 of the protocol for the synthesis of Example 1 to afford the title compound. $^1$H NMR (400 MHz, Methanol-$d_4$) δ 8.54 (d, J=1.5 Hz, 1H), 8.22 (d, J=5.7 Hz, 1H), 7.96 (d, J=1.5 Hz, 1H), 7.21 (d, J=5.7 Hz, 1H), 5.09 (d, J=51.2 Hz, 1H), 4.79 (dt, J=8.5, 4.3 Hz, 1H), 4.65 (dt, J=12.3, 5.6 Hz, 2H), 4.37 (q, J=7.1 Hz, 2H), 4.33-4.20 (m, 1H), 3.56 (t, J=12.3 Hz, 1H), 3.27-3.13 (m, 4H), 2.74 (s, 2H), 2.43-2.28 (m, 5H), 2.13-1.88 (m, 4H), 1.80 (dtd, J=12.3, 8.4, 3.4 Hz, 3H), 1.40 (t, J=7.1 Hz, 3H). ESI MS $[M+H]^+$ for $C_{24}H_{34}FN_9O_4$, calcd 532.5, found 532.3.

Example 7: 2-[(3S,4R)-3-[3-(5-ethoxy-2-pyrazinyl)-1-methylureido]-4-fluoro-1-piperidyl]-4-pyrimidinyl 4-quinuclidinecarbamate

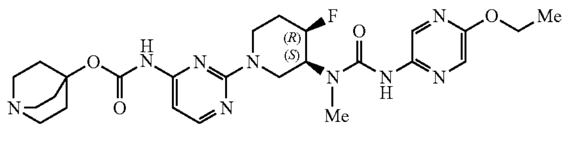

The title compound was synthesized in a similar fashion to Example 6 using 4-quinuclidinol in Step 1. $^1$H NMR (400

MHz, MeOH-$d_3$) δ 8.51 (s, 1H), 8.19 (d, J=5.7 Hz, 1H), 7.94 (s, 1H), 7.14 (d, J=5.7 Hz, 1H), 5.07 (d, J=51.3 Hz, 1H), 4.74-4.57 (m, 2H), 4.35 (q, J=7.1 Hz, 2H), 4.22 (m, 1H), 3.55 (d, J=12.3 Hz, 1H), 3.21 (d, J=8.7 Hz, 6H), 3.14 (s, 3H), 2.22 (dd, J=9.4, 6.0 Hz, 6H), 2.13-1.73 (m, 3H), 1.38 (t, J=7.1 Hz, 3H). ESI MS $[M+H]^+$ for $C_{25}H_{34}N_9FO_4$, calcd 544.3, found 544.2.

Example 8: 2-[(S)-3-[3-(5-ethoxy-2-pyrazinyl)-1-methylureido]-4,4-difluoro-1-piperidyl]-4-pyrimidinyl (1S,4S,5R)-2-ethyl-2-azabicyclo[2.2.1]heptane-5-carbamate

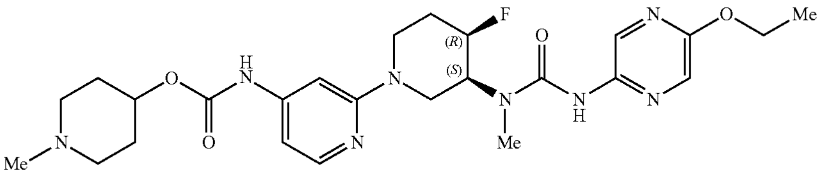

The title compound was synthesized in a similar fashion to Example 6 using 4-amino-2-chloropyridine in Step 2. $^1H$ NMR (400 MHz, $CDCl_3$) δ 8.80 (d, J=1.5 Hz, 1H), 8.37 (s, 1H), 8.20 (d, J=5.7 Hz, 1H), 7.88 (d, J=1.4 Hz, 1H), 7.20-7.06 (m, 2H), 6.53 (dd, J=5.7, 1.8 Hz, 1H), 5.22-4.88 (m, 2H), 4.36 (q, J=7.0 Hz, 2H), 4.27 (t, J=7.7 Hz, 2H), 4.01 (d, J=13.9 Hz, 1H), 3.51 (t, J=12.6 Hz, 1H), 3.36 (t, J=13.3 Hz, 1H), 3.18-2.80 (m, 6H), 2.64 (s, 3H), 2.28-2.15 (m, 2H), 2.06 (m, 4H), 1.97-1.73 (m, 1H), 1.40 (t, J=7.0 Hz, 3H). ESI MS $[M+H]^+$ for $C_{25}H_{35}N_8FO_4$, calcd 531.3, found 531.2.

Example 9: 2-[(S)-3-[3-(5-ethoxy-2-pyrazinyl)-1-methylureido]-4,4-difluoro-1-piperidyl]-4-pyrimidinyl 1-methyl-4-piperidinecarbamate

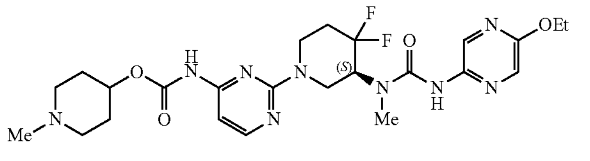

The title compound was synthesized in a similar fashion to Example 6 using [(3S)-3-[N-(benzyloxycarbonyl)-3-methylamino]-4,4-difluoropiperidine in Step 3, which was prepared in a similar fashion to that described in Example 11, Steps 1-3. $^1H$ NMR (400 MHz, MeOD) δ 8.50 (d, J=1.4 Hz, 1H), 8.20 (d, J=5.7 Hz, 1H), 7.91 (d, J=1.4 Hz, 1H), 7.22 (d, J=5.7 Hz, 1H), 4.83-4.73 (m, 3H), 4.68-4.52 (m, 1H), 4.34 (q, J=7.0 Hz, 2H), 3.45 (dd, J=13.0, 11.4 Hz, 1H), 3.21-3.08 (m, 4H), 2.74 (s, 2H), 2.46-2.33 (m, 2H), 2.32 (s, 3H), 2.23-1.90 (m, 4H), 1.79 (dtd, J=12.6, 8.4, 3.6 Hz, 2H), 1.37 (t, J=7.1 Hz, 3H). ESI MS $[M+H]^+$ for $C_{24}H_{33}F_2N_9O_4$, calcd 550.6, found 550.3.

Example 10: 2-[(3S,4R)-3-[3-(5-ethoxy-2-pyrazinyl)-1-methylureido]-4-fluoro-1-piperidyl]-4-pyrimidinyl (1R,4R,5S)-2-methyl-2-azabicyclo[2.2.1]heptane-5-carbamate

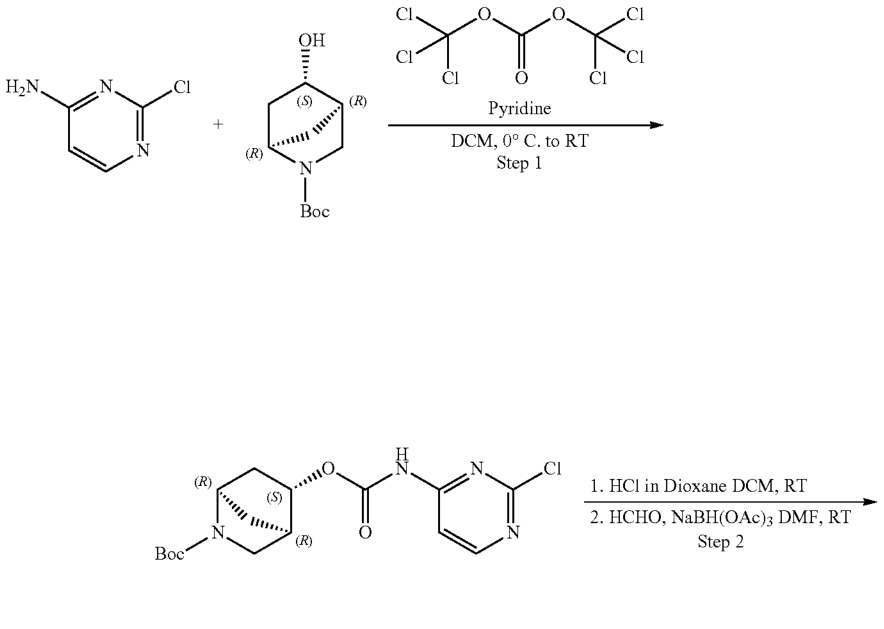

-continued

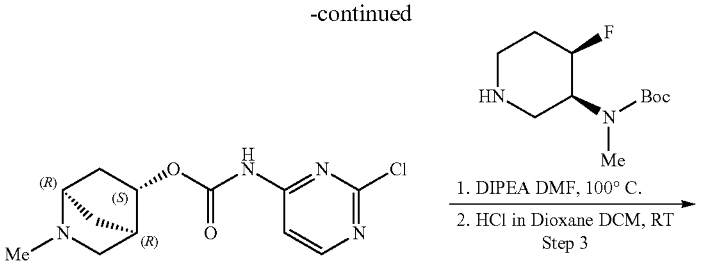

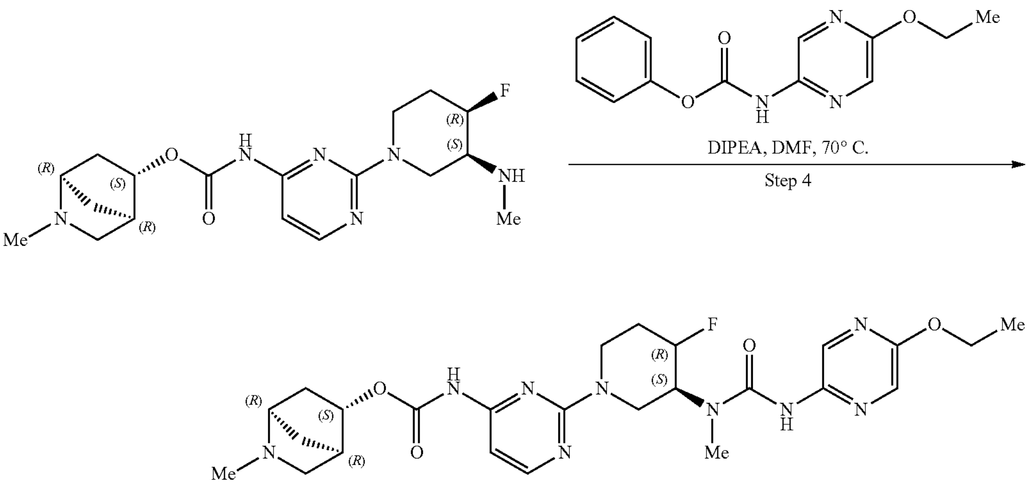

Step 1: Triphosgene (102 mg, 0.34 mmol) was taken in a dry screw-capped vial equipped with a stir bar and dissolved in dry DCM (5 mL). This mixture was cooled to 0° C. using an ice bath under constant stirring. To this reaction mixture, pyridine (0.9 mL, 11.5 mmol) was added dropwise and the reaction mixture was stirred at 0° C. for 30 min. After 30 min, 2-chloro-4-amino pyrimidine (150 mg, 1.15 mmol) dissolved in dry DCM (5 mL) was added dropwise and stirring continued at 0° C. for another hour. At this point, tert-butyl (1R,4R,5S)-5-hydroxy-2-azabicyclo[2.2.1]heptane-2-carboxylate (245 mg, 1.15 mmol) was added and the reaction mixture slowly warmed to room temperature and stirred for another 3 hours. After confirming the completion of the reaction by LCMS, volatiles were concentrated under reduced pressure. The crude product was purified using flash column chromatography (using silica gel (100-200 mesh); eluted with 15% MeOH in DCM, initially grading to 25% MeOH in DCM) to afford the intermediate.

Step 2 (Part 1): The intermediate from Step 2 (142 mg, 0.38 mmol) was taken in a dry screw-capped reaction vial equipped with a stir bar and to this vial was added dry DCM (2 mL). To this homogeneous solution in DCM, 4 M HCl in dioxane (3 mL) was added, and the reaction mixture was stirred at room temperature. After confirming the complete removal of the Boc group by LCMS, stirring was stopped, and the volatiles were concentrated under reduced pressure to obtain the crude product, which was used in the next step without further purification.

Step 2 (Part 2): The screw-capped vial containing the intermediate (103 mg, 0.38 mmol) from Step 2 (Part 1) was equipped with stir bar and to this vial was added paraformaldehyde (35 mg, 1.15 mmol) followed by dry DMF (2 mL). The reaction mixture was stirred for 5 min at room temperature. To the stirred reaction mixture was added NaBH$(OAc)_3$ (244 mg, 1.15 mmol) in one portion, and the reaction mixture was stirred at room temperature for 24 hours. After confirming completion of the reaction by LCMS, the reaction mixture was quenched with water (3 mL) and pH was adjusted to 11. Then the reaction mixture was extracted with DCM (20 mL) and the organic layer was washed with water three times to remove the DMF. The organic layer was dried over anhydrous $Na_2SO_4$, and the volatiles were concentrated under reduced pressure. The crude product was purified using flash column chromatography (using silica gel (100-200 mesh); eluted with 20% MeOH in DCM, initially grading to 30% MeOH in DCM) to afford the intermediate.

Step 3 (Part 1): This transformation was performed in a similar fashion to Step 3 of the protocol for the synthesis of Example 6.

Step 3 (Part 2): This transformation was performed in a similar fashion to Step 2 (Part 1) of the protocol described above for the synthesis of this Example.

Step 4: This transformation was performed in a similar fashion to Step 5 of the protocol for the synthesis of Example 1 to afford the title compound. $^1$H NMR (400 MHz, MeOD)$^1$H NMR (400 MHz, MeOD) δ 8.45 (s, 1H), 8.41 (d, J=1.5 Hz, 1H), 8.10 (d, J=5.7 Hz, 1H), 7.83 (d, J=1.5 Hz, 1H), 7.07 (d, J=5.7 Hz, 1H), 4.97 (d, J=51.0 Hz, 1H), 4.69 (dd, J=7.0, 2.4 Hz, 1H), 4.52 (dt, J=11.8, 5.2 Hz, 2H), 4.24 (q, J=7.0 Hz, 2H), 4.21-4.07 (m, 1H), 3.54-3.37 (m, 2H), 3.14-2.98 (m, 4H), 2.88 (dd, J=11.2, 4.3 Hz, 1H), 2.65-2.51 (m, 2H), 2.47 (s, 3H), 2.30 (dd, J=15.1, 7.0 Hz, 1H), 1.94 (ddd, J=13.5, 10.2, 6.4 Hz, 1H), 1.88-1.63 (m, 3H), 1.59 (dt, J=15.2, 3.3 Hz, 1H), 1.28 (t, J=7.1 Hz, 3H). ESI MS $[M+H]^+$ for $C_{25}H_{34}FN_9O_4$, calcd 544.3, found 544.3.

Example 11: 2-[(S)-3-[3-(5-ethoxy-2-pyrazinyl)-1-methylureido]-4,4-difluoro-1-piperidyl]-4-pyrimidinyl (1R,4R,5S)-2-methyl-2-azabicyclo[2.2.1]heptane-5-carbamate
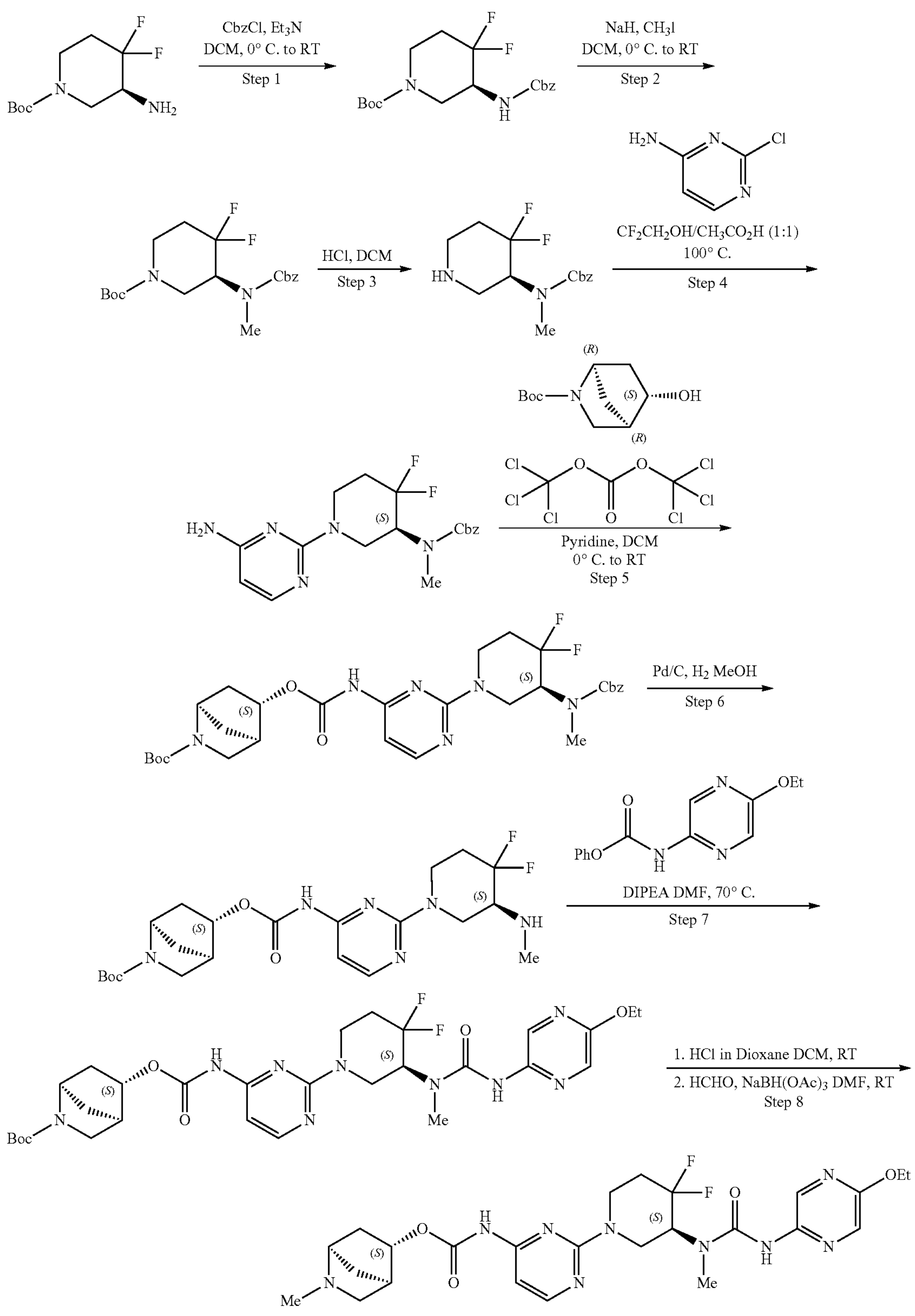

Step 1: To a stirred solution of the 1,1-dimethylethyl (3S)-3-amino-4,4-difluoro-1-piperidinecarboxylate (11.7 g, 49.6 mmol) in dichloromethane (300 mL) was added triethylamine (12.6 g, 49.6 mmol) followed by benzyl chloroformate (11 g, 65 mmol) at 0° C., and the reaction mixture was allowed to warm to room temperature and stirred for 12 h. The reaction was then diluted with water (100 mL) and extracted with dichloromethane (150 mL). The organic layer was dried over $Na_2SO_4$, concentrated under vacuum, and purified by silica gel (100-200 mesh) column chromatography (EtOAc in Hexane: 0 to 30%) to afford the desired intermediate.

Step 2: The intermediate obtained from Step 1 (16 g, 43.2 mmol) was dissolved in DMF (150 mL) at 0° C. and treated with sodium hydride, 60% dispersion in mineral oil (1.7 g, 64.8 mmol). The reaction mixture was stirred for 30 min before addition of iodomethane (12.2 g, 96.4 mmol) and then stirred at room temperature for 12 h. The reaction mixture was quenched with 30 mL of ice-cold water, and the resultant precipitate formed was collected via filtration. The residue was further purified by flash column chromatography (silica gel; gradient: 0% to 80% EtOAc in hexanes) to afford the desired compound.

Step 3: The intermediate from Step 2 (14 g, 36.4 mmol) was taken in a round bottom flask equipped with a stir bar and dissolved in DCM (75 mL). To this mixture, HCl in dioxane solution (4 M, 40 mL) was added dropwise, and the reaction mixture was stirred at room temperature. Reaction progress was monitored using LCMS. After confirming the complete removal of the Boc group, volatiles were evaporated under reduced pressure to afford the intermediate as HCl salt in quantitative yield. The salt thus obtained was dissolved in water and basified with saturated $K_2CO_3$. The resulting mixture was then extracted with dichloromethane (200 mL), dried over $Na_2SO_4$, concentrated under vacuum to afford the desired intermediate.

Step 4: The intermediate from Step 3 (16 g, 56.3 mmol) was taken in a round bottom flask equipped with a stir bar and to this flask was added 2-chloro-4-aminopyrimidine (10.9 g, 84.4 mmol). To this mixture, a 1:1 mixture of trifluoroethanol and acetic acid (100 mL) was added, and the mixture was stirred at 100° C. for 3 h. After confirming completion of the reaction, the crude reaction mixture was brought to room temperature, filtered through a small pad of CELITE® and the volatiles were removed under reduced pressure. The resulting acetic acid salt was dissolved in water and basified with saturated $K_2CO_3$. The resulting suspension was then extracted with dichloromethane (200 mL), dried over $Na_2SO_4$, concentrated under vacuum, and purified by silica gel (100-200 mesh) column chromatography (EtOAc in Hexane: 0 to 90%) to afford the desired product.

Step 5: This transformation was performed in a similar fashion to Step 1 of the protocol described for the synthesis of Example 10.

Step 6: This transformation was performed in a similar fashion to Step 4 of the protocol described for the synthesis of Example 6.

Step 7: This transformation was performed in a similar fashion to Step 5 of the protocol described for the synthesis of Example 1.

Step 8 (Part 1): This transformation was performed using the intermediate from Step 7 in a similar fashion to Step 2 (Part 1) of the protocol described for the synthesis of Example 10.

Step 8 (Part 2): Using intermediate from Step 8 (Part 1), this transformation was performed in a similar fashion to Step 2 (Part 2) of the protocol described for the synthesis of Example 10 to afford the title compound. $^1$H NMR (400 MHz, MeOD) δ 8.49 (d, J=1.4 Hz, 1H), 8.22 (d, J=5.7 Hz, 1H), 7.92 (s, 1H), 7.22 (d, J=5.7 Hz, 1H), 4.79 (q, J=5.2 Hz, 3H), 4.60 (dd, J=26.6, 10.8 Hz, 1H), 4.34 (q, J=7.1 Hz, 2H), 3.59 (s, 1H), 3.45 (t, J=12.2 Hz, 1H), 3.23-3.07 (m, 4H), 2.97 (dd, J=11.6, 4.3 Hz, 1H), 2.76-2.61 (m, 2H), 2.56 (s, 3H), 2.39 (dd, J=15.5, 6.9 Hz, 1H), 2.25-2.10 (m, 1H), 2.10-1.92 (m, 1H), 1.88 (s, 2H), 1.68 (d, J=15.0 Hz, 1H), 1.38 (t, J=7.1 Hz, 3H). ESI MS $[M+H]^+$ for $C_{25}H_{33}F_2N_9O_4$, calcd 562.6, found 562.3.

Example 12: 2-[(S)-3-[3-(5-ethoxy-2-pyrazinyl)-1-methylureido]-4,4-difluoro-1-piperidyl]-4-pyrimidinyl (1S,4S,5R)-2-methyl-2-azabicyclo[2.2.1]heptane-5-carbamate

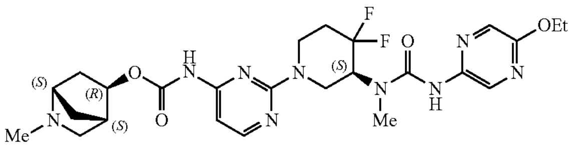

The title compound was synthesized in a similar fashion to Example 11 using tert-butyl (1S,4S,5R)-5-hydroxy-2-azabicyclo[2.2.1]heptane-2-carboxylate in Step 5. $^1$H NMR (400 MHz, Methanol-$d_4$) δ 8.51 (d, J=1.3 Hz, 1H), 8.20 (d, J=5.7 Hz, 1H), 7.91 (d, J=1.3 Hz, 1H), 7.21 (d, J=5.7 Hz, 1H), 4.84-4.75 (m, 2H), 4.69 (dd, J=7.1, 2.3 Hz, 1H), 4.66-4.54 (m, 1H), 4.34 (q, J=7.0 Hz, 2H), 3.43 (t, J=12.2 Hz, 1H), 3.31 (s, 1H), 3.25-3.21 (m, 1H), 3.14 (d, J=2.0 Hz, 4H), 2.75 (dd, J=10.5, 4.4 Hz, 1H), 2.53 (d, J=4.3 Hz, 1H), 2.34 (d, J=7.3 Hz, 1H), 2.30 (s, 3H), 2.18 (d, J=10.5 Hz, 1H), 2.12-1.86 (m, 1H), 1.70 (s, 2H), 1.50 (dt, J=14.5, 3.0 Hz, 1H), 1.37 (t, J=7.1 Hz, 3H). ESI MS for $C_{25}H_{33}F_2N_9O_4$, $[M+H]^+$calcd 562.3, found 562.3.

Example 13: 2-[(S)-3-[3-(5-ethoxy-2-pyrazinyl)-1-methylureido]-4,4-difluoro-1-piperidyl]-4-pyrimidinyl (1S,4S,5R)-2-ethyl-2-azabicyclo[2.2.1]heptane-5-carbamate

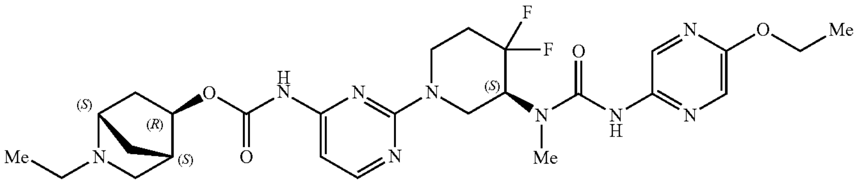

The title compound was synthesized in a similar fashion to Example 11 using tert-butyl (1S,4S,5R)-5-hydroxy-2-azabicyclo[2.2.1]heptane-2-carboxylate in Step 5 and the ethyl group was installed in a similar fashion to Step 8 Part 2 using acetaldehyde. $^1$H NMR (400 MHz, MeOH-$d_3$) δ 8.50 (d, J=1.3 Hz, 1H), 8.21 (d, J=5.7 Hz, 1H), 7.92 (d, J=1.3 Hz, 1H), 7.22 (d, J=5.7 Hz, 1H), 4.79 (m, 2H), 4.72-4.68 (m, 1H), 4.60 (dd, J=25.8, 11.2 Hz, 1H), 4.35 (q, J=7.1 Hz, 2H), 3.46 (t, J=12.2 Hz, 1H), 3.39 (d, J=2.8 Hz, 1H), 3.15 (d, J=2.0 Hz, 4H), 2.84 (dd, J=10.5, 4.5 Hz, 1H), 2.52 (dtd, J=19.2, 12.0, 6.9 Hz, 3H), 2.34 (ddd, J=14.5, 7.3, 2.1 Hz, 1H), 2.14 (d, J=10.5 Hz, 2H), 2.08-1.92 (m, 1H), 1.78-1.63 (m, 2H), 1.50 (d, J=14.5 Hz, 1H), 1.38 (t, J=7.1 Hz, 4H), 1.08 (t, J=7.2 Hz, 3H). ESI MS $[M+H]^+$ for $C_{26}H_{35}N_9FO_4$, calcd 576.2, found 576.2.

Example 14: 2-[(S)-3-[3-(5-ethoxy-2-pyrazinyl)-1-methylureido]-4,4-difluoro-1-piperidyl]-4-pyrimidinyl (3S,4R)-1-methyl-3-methyl-4-piperidinecarbamate

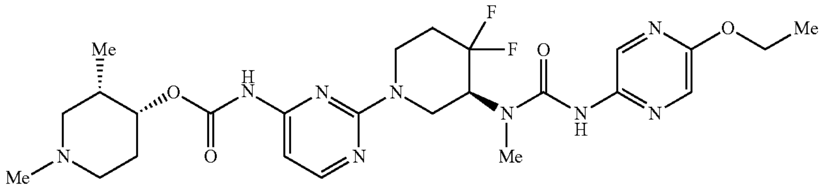 [SMILES: CCOc1cnc(NC(=O)N(C)[C@H]2CN(c3nccc(NC(=O)O[C@@H]4CCN(C)C[C@@H]4C)n3)CCC2(F)F)cn1]

The title compound was synthesized in a similar fashion to Example 11 using (3S,4R)-3-methyl-4-piperidinol in Step 5. $^1$H NMR (400 MHz, Chloroform-d) δ 8.76 (d, J=4.1 Hz, 1H), 8.19 (s, 1H), 7.81 (d, J=4.2 Hz, 1H), 7.52 (s, 1H), 7.25 (s, 1H), 4.91 (s, 1H), 4.83-4.48 (m, 4H), ), 4.30 (q, J=7.3 Hz, 2H), 3.25 (td, J=7.1, 3.9 Hz, 1H), 3.09 (s, 3H), 3.04 (d, J=13.7 Hz, 1H), 2.54 (s, 2H), 2.26 (d, J=4.9 Hz, 4H), 2.19-2.00 (m, 4H), 1.90 (s, 2H), 1.32 (d, J=7.1 Hz, 3H), 0.88 (d, J=6.4 Hz, 3H). ESI MS $[M+H]^+$ for $C_{25}H_{35}F_2N_9O_4$, calcd 564.3, found 564.3.

Example 15: 2-[(S)-3-[3-(5-ethoxy-2-pyrazinyl)-1-methylureido]-4,4-difluoro-1-piperidyl]-4-pyrimidinyl 7-methyl-7-aza-2-spiro[3.5]nonanecarbamate

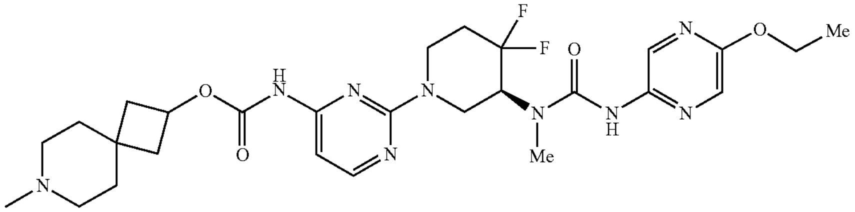 [SMILES: CCOc1cnc(NC(=O)N(C)[C@H]2CN(c3nccc(NC(=O)OC4CC5(CCN(C)CC5)C4)n3)CCC2(F)F)cn1]

The title compound was synthesized in a similar fashion to Example 11 using 7-methyl-7-azaspiro[3.5]nonan-2-ol in Step 5. $^1$H NMR (400 MHz, DMSO-$d_6$) δ 8.55 (d, J=1.4 Hz, 1H), 8.20 (d, J=5.7 Hz, 1H), 8.01 (d, J=1.4 Hz, 1H), 7.06 (d, J=5.6 Hz, 1H), 4.93 (p, J=7.1 Hz, 1H), 4.73 (s, 2H), 4.62 (dd, J=27.5, 11.4 Hz, 1H), 4.30 (q, J=7.0 Hz, 2H), 3.46-3.36 (m, 2H), 3.12-2.95 (m, 5H), 2.26 (s, 7H), 2.09 (s, 4H), 1.80-1.69 (m, 2H), 1.53 (t, J=5.5 Hz, 4H), 1.32 (t, J=7.0 Hz, 3H). ESI MS $[M+H]^+$ for $C_{27}H_{37}F_2N_9O_4$, calcd 590.3, found 590.1.

Example 16: 2-[(S)-3-[3-(5-ethoxy-2-pyrazinyl)-1-methylureido]-4,4-difluoro-1-piperidyl]-4-pyrimidinyl 1-methyl-4-methyl-4-piperidinecarbamate

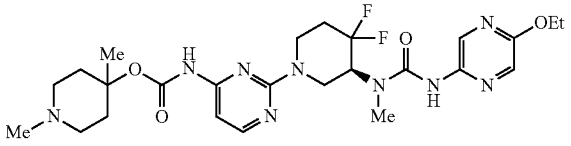 [SMILES: CCOc1cnc(NC(=O)N(C)[C@H]2CN(c3nccc(NC(=O)OC4(C)CCN(C)CC4)n3)CCC2(F)F)cn1]

The title compound was synthesized in a similar fashion to Example 11 using 1,4-dimethyl-4-piperidinol in Step 5. $^1$H NMR (400 MHz, Methanol-$d_4$) δ 8.53 (d, J=1.4 Hz, 1H), 8.22 (d, J=5.7 Hz, 1H), 7.95 (d, J=1.4 Hz, 1H), 7.24 (d, J=5.7 Hz, 1H), 4.87-4.77 (m, 3H), 4.63 (dd, J=26.3, 11.0 Hz, 1H), 4.37 (q, J=7.0 Hz, 2H), 3.49 (t, J=12.2 Hz, 1H), 3.26-3.09 (m, 4H), 2.78-2.57 (m, 2H), 2.41 (t, J=11.7 Hz, 2H), 2.38-2.26 (m, 5H), 2.27-1.94 (m, 2H), 1.74 (t, J=12.7 Hz, 2H), 1.59 (s, 3H), 1.40 (t, J=7.0 Hz, 3H). ESI MS $[M+H]^+$ for $C_{25}H_{35}F_2N_9O_4$, calcd 564.3, found 564.3.

Example 17: 2-[(S)-3-[3-(5-ethoxy-2-pyrazinyl)-1-methylureido]-4,4-difluoro-1-piperidyl]-4-pyrimidinyl 4-quinuclidinecarbamate

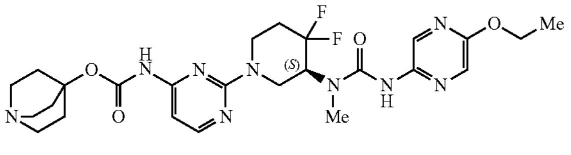

The title compound was synthesized in a similar fashion to Example 11 (Steps 1-7, using 4-quinuclidinol in Step 5). $^1$H NMR (400 MHz, MeOH-$d_3$) δ 8.50 (d, J=1.5 Hz, 1H), 8.19 (d, J=5.7 Hz, 1H), 7.92 (d, J=1.5 Hz, 1H), 7.18 (d, J=5.8 Hz, 1H), 4.79 (td, J=11.1, 6.9 Hz, 2H), 4.61 (s, 1H), 4.35 (q, J=7.0 Hz, 2H), 3.44 (t, J=12.2 Hz, 1H), 3.15 (d, J=2.1 Hz, 4H), 3.03 (dd, J=9.6, 6.0 Hz, 6H), 2.23-1.90 (m, 8H), 1.38 (t, J=7.0 Hz, 3H). ESI MS $[M+H]^+$ for $C_{25}H_{33}N_9F_2O_4$, calcd 562.3, found 562.2.

Example 18: 2-[(3S,4R)-3-[3-(5-ethoxy-2-pyrazinyl)-1-methylureido]-4-fluoro-1-piperidyl]-4-pyrimidinyl (1R,4S,6S)-2-methyl-2-azabicyclo[2.2.1]heptane-6-carbamate

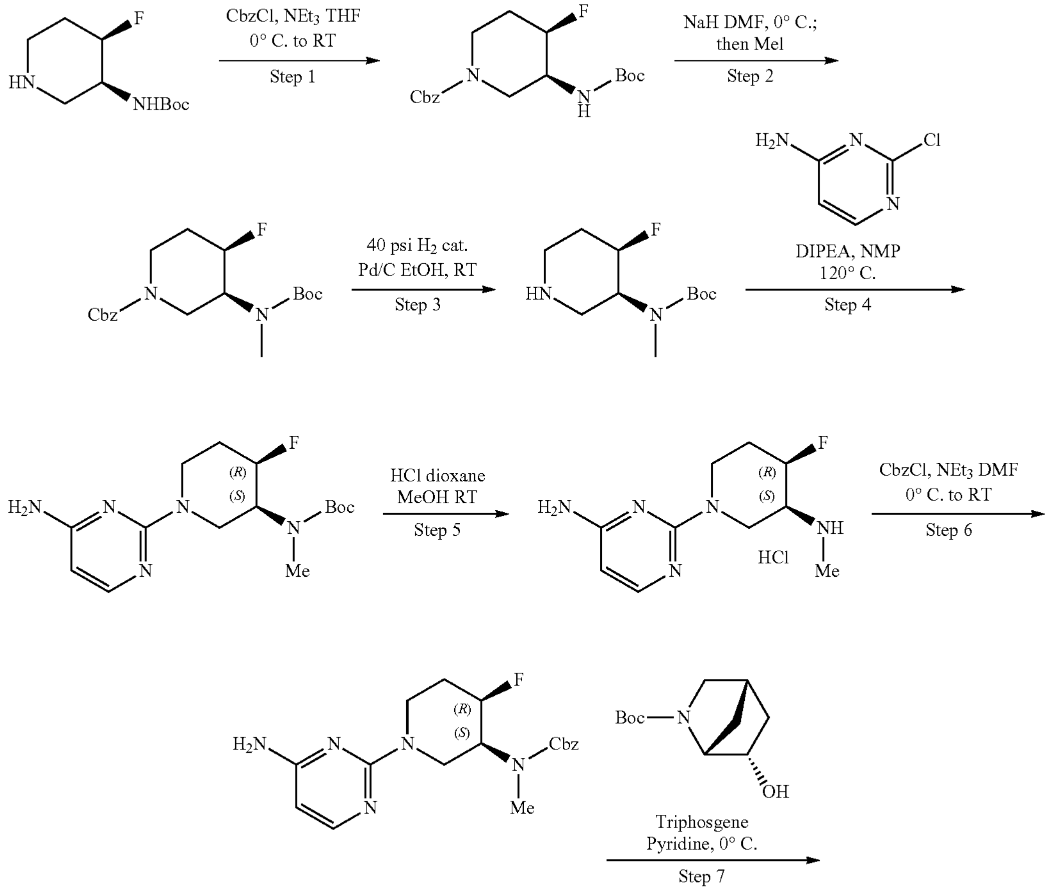

-continued

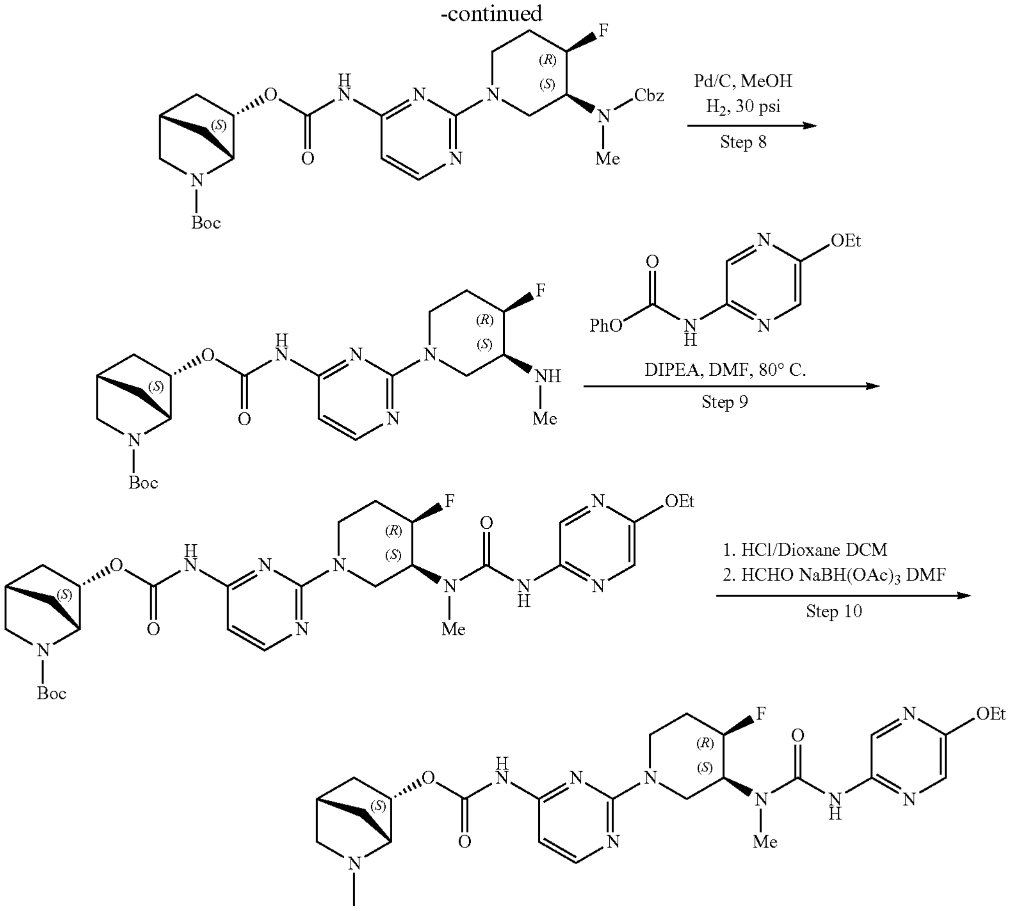

Step 1: To a solution of tert-butyl ((3S,4R)-4-fluoropiperidin-3-yl)carbamate (15 g, 68.7 mmol) in THF (170 mL, 0.4 M) was added triethylamine (11.5 mL, 82.4 mmol) prior to cooling to 0° C. At this point, benzyl chloroformate (11 mL, 75.6 mmol, 1.1 equiv.) was added dropwise and the reaction was stirred overnight at room temperature. After complete consumption of the starting materials, the reaction was concentrated to ¼ of the original volume. The concentrated mixture was then diluted with EtOAc and washed sequentially with 1 N HCl, saturated $NaHCO_3$, and saturated NaCl. The organic layer was dried over $Na_2SO_4$ and concentrated to obtain crude benzyl (3S,4R)-3-((tert-butoxycarbonyl)amino)-4-fluoropiperidine-1-carboxylate in quantitative yield that was used crude in the next step without further purification.

Step 2: The crude material from Step 1 was dissolved in DMF (270 mL, 0.25 M) and cooled to 0° C. To this solution, NaH (60% dispersion in mineral oil, 5.50 g, 137.4 mmol) was added carefully portion-wise over 10 min. The mixture was stirred at 0° C. for an hour prior to adding Mel (10 mL, 137 mmol). After 30 min, another portion of Mel (3 mL, 69 mmol) was added. The reaction was stirred overnight prior to cooling to 0° C. and quenching with $H_2O$. The crude product was diluted with EtOAc, washed five times with saturated NaCl, dried over $Na_2SO_4$, and concentrated. Crude benzyl (3S,4R)-3-((tert-butoxycarbonyl)(methyl)amino)-4-fluoropiperidine-1-carboxylate was obtained and used in the next step without further purification.

Step 3: The crude material from Step 2 was combined with Pd/C (8 g, 30% by weight) and suspended using minimal EtOH in a Parr hydrogenator. The mixture was sparged with 1 atm of $H_2$ three-times prior to shaking at 40 psi overnight. After confirming complete consumption of starting material by LCMS analysis, the mixture was filtered through a pad of CELITE®. Solvent was then removed under reduced pressure to yield crude tert-butyl ((3S,4R)-4-fluoropiperidin-3-yl)(methyl)carbamate, which was used in the next step without further purification.

Step 4: A portion of the crude material from Step 3 (9.91 g, 42.7 mmol) was combined with 4-amino-2-chloropyrimidine (5.52 g, 42.7 mmol) and dissolved in NMP (43 mL, 1 M) prior to adding N,N-diisopropylethylamine (11 mL, 64.0 mmol). The resulting mixture was heated at 120° C. overnight. After confirming complete consumption of starting material by LCMS analysis, the resulting reaction mixture was cooled to room temperature, diluted with EtOAc/$H_2O$ (1:1) and washed five-times with brine. The organic layer was dried over $Na_2SO_4$, filtered, and concentrated. The resulting crude material was purified by flash chromatography using a β-7% MeOH in DCM gradient to afford pure tert-butyl ((3S,4R)-1-(4-aminopyrimidin-2-yl)-4-fluoropiperidin-3-yl)(methyl)carbamate.

Step 5: Solid tert-butyl ((3S,4R)-1-(4-aminopyrimidin-2-yl)-4-fluoropiperidin-3-yl)(methyl)carbamate from Step 4 (7.0 g, 21.5 mmol) was suspended in 4 N HCl/dioxane (40 mL, 0.5 M), and MeOH was added to the mixture to solubilize the suspension. After stirring for 30 min at room temperature, the reaction mixture was concentrated. The resultant crude HCl salt of 2-((3S,4R)-4-fluoro-3-(methylamino)piperidin-1-yl)pyrimidin-4-amine was carried forward to the next step without further purification.

Step 6: The crude product from Step 5 was dissolved in DMF (55 mL, 0.4 M) and cooled to 0° C. prior to adding triethylamine (15 mL, 108 mmol, 5 equiv.). Benzyl chloroformate (3.7 mL, 25.9 mmol) was added dropwise and the reaction mixture was stirred until starting material was consumed according to LCMS analysis. At that point, the reaction was quenched with $H_2O$ and extracted with ethyl acetate. The organic extract was washed with saturated $NaHCO_3$ and brine sequentially, then dried over $Na_2SO_4$, filtered, and concentrated. The resulting crude solid was purified by flash chromatography using a β-7% MeOH in DCM gradient to afford the desired product.

Step 7: To a solution of triphosgene (118 mg, 0.4 mmol) in DCM (4 mL) at 0° C., pyridine (0.24 mL) was added. After stirring for 10-15 minutes, benzyl ((3S,4R)-1-(4-aminopyrimidin-2-yl)-4-fluoropiperidin-3-yl)(methyl)carbamate (359 mg, 1 mmol) from Step 6 was added to the mixture at 0° C. After 30 min, tert-butyl (1R,4S,6S)-6-hydroxy-2-azabicyclo[2.2.1]heptane-2-carboxylate (426 mg, 2.0 mmol) was added. The resulting reaction mixture was allowed to stir at room temperature overnight. The reaction was quenched by adding water (20 mL), and the aqueous layer was extracted with ethyl acetate (3×30 mL) and dried over anhydrous MgSO4 and the residue was purified by silica gel column chromatography (50 to 100% EtOAc in hexanes) to provide the desired intermediate.

Step 8: To a stirred solution of the intermediate from Step 7 (352 mg) in MeOH (15 mL), Pd/C (70 mg) was added, and the mixture was stirred at 25° C. for 30 min under a $H_2$ atmosphere (30 psi). The reaction mixture was then filtered, and the filtrate was concentrated under reduced pressure to give the desired compound, which was used in the next step without further purification.

Step 9: To a stirred solution of the crude product from Step 8 (270 mg, 0.6 mmol) and phenyl (5-ethoxypyrazin-2-yl)carbamate (155 mg, 0.6 mmol) in DMF (6 mL), DIPEA was added and the resulting reaction mixture was heated to 80° C. for 30 min. After the completion of the reaction as indicated by LCMS, water was added and the mixture extracted with EtOAc (3×20 mL). The combined organic layers were washed with brine, dried over $MgSO_4$ and filtered. EtOAc was evaporated and the crude material was purified by column chromatography (0 to 15% MeOH in DCM) to provide the desired intermediate.

Step 10 (Part 1): The intermediate from Step 9 was dissolved in DCM (5 mL). To this mixture was added 4 N HCl in dioxane (2 mL), and the resulting reaction mixture was stirred for 30 min. After completion of the reaction as indicated by LCMS, the solvent was removed under reduced pressure and the crude product was used in the next step without further purification.

Step 10 (Part 2): To a stirred solution of the crude product from Step 10 (Part 1) (154 mg, 0.3 mmol) in DMF (5 mL), HCHO (45 mg, 1.5 mmol) and $NaBH(OAc)_3$ (127 mg 0.6 mmol) was added and the resulting reaction mixture was stirred at room temperature for 24 h. After the completion of the reaction as indicated by LCMS, water was added, and the mixture was extracted with EtOAc (3×30 mL). The combined organic layers were washed with brine, dried over $MgSO_4$ and filtered. EtOAc was evaporated and the crude material was purified by reversed phase HPLC to provide the title compound. $^1H$ NMR (400 MHz, DMSO-$d_6$) δ 9.03 (s, 1H), 8.55 (d, J=1.4 Hz, 1H), 8.22 (d, J=5.7 Hz, 1H), 8.01 (d, J=1.5 Hz, 1H), 7.06 (d, J=5.6 Hz, 1H), 5.11 (s, 1H), 4.98 (s, 1H), 4.89 (d, J=3.7 Hz, 1H), 4.63-4.49 (m, 2H), 4.29 (q, J=7.0 Hz, 2H), 4.26-4.12 (m, 1H), 3.45 (t, J=12.2 Hz, 1H), 3.03 (d, J=1.6 Hz, 3H), 2.51 (s, 1H), 2.38-2.22 (m, 2H), 2.16 (s, 3H), 1.95 (q, J=15.6, 14.7 Hz, 2H), 1.84-1.61 (m, 2H), 1.50-1.39 (m, 1H), 1.32 (t, J=7.0 Hz, 3H), 0.96 (d, J=6.3 Hz, 3H). ESI MS $[M+H]^+$ for $C_{25}H_{34}FN_9O_4$, calcd 544.3, found 544.1.

Example 19: 2-[(3S,4R)-3-[3-(5-ethoxy-2-pyrazinyl)-1-methylureido]-4-fluoro-1-piperidyl]-4-pyrimidinyl (1S,4S,5R)-2-methyl-2-azabicyclo[2.2.1]heptane-5-carbamate

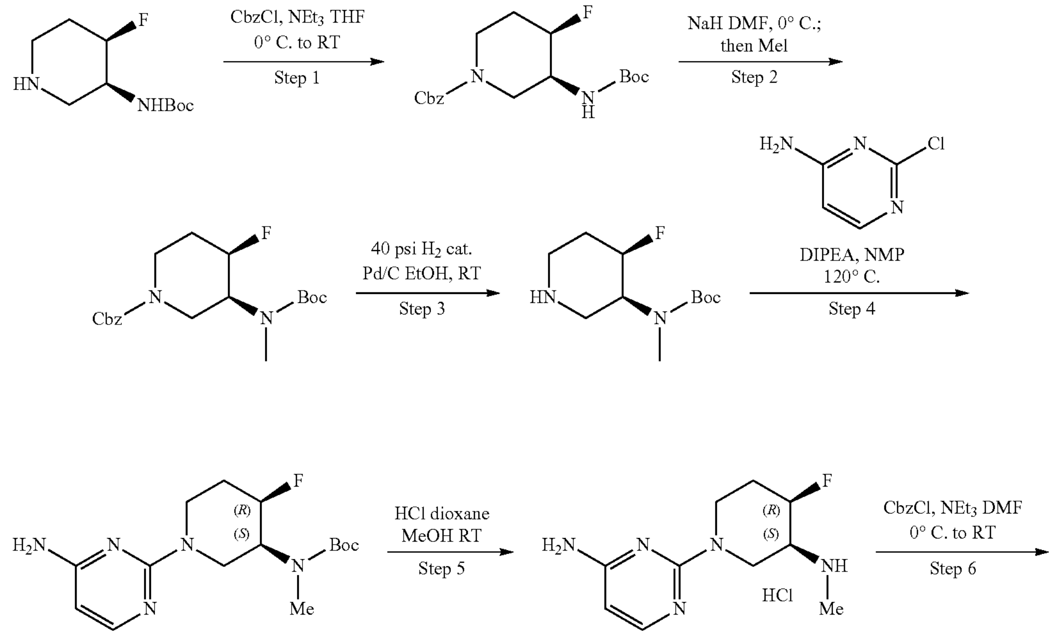

-continued

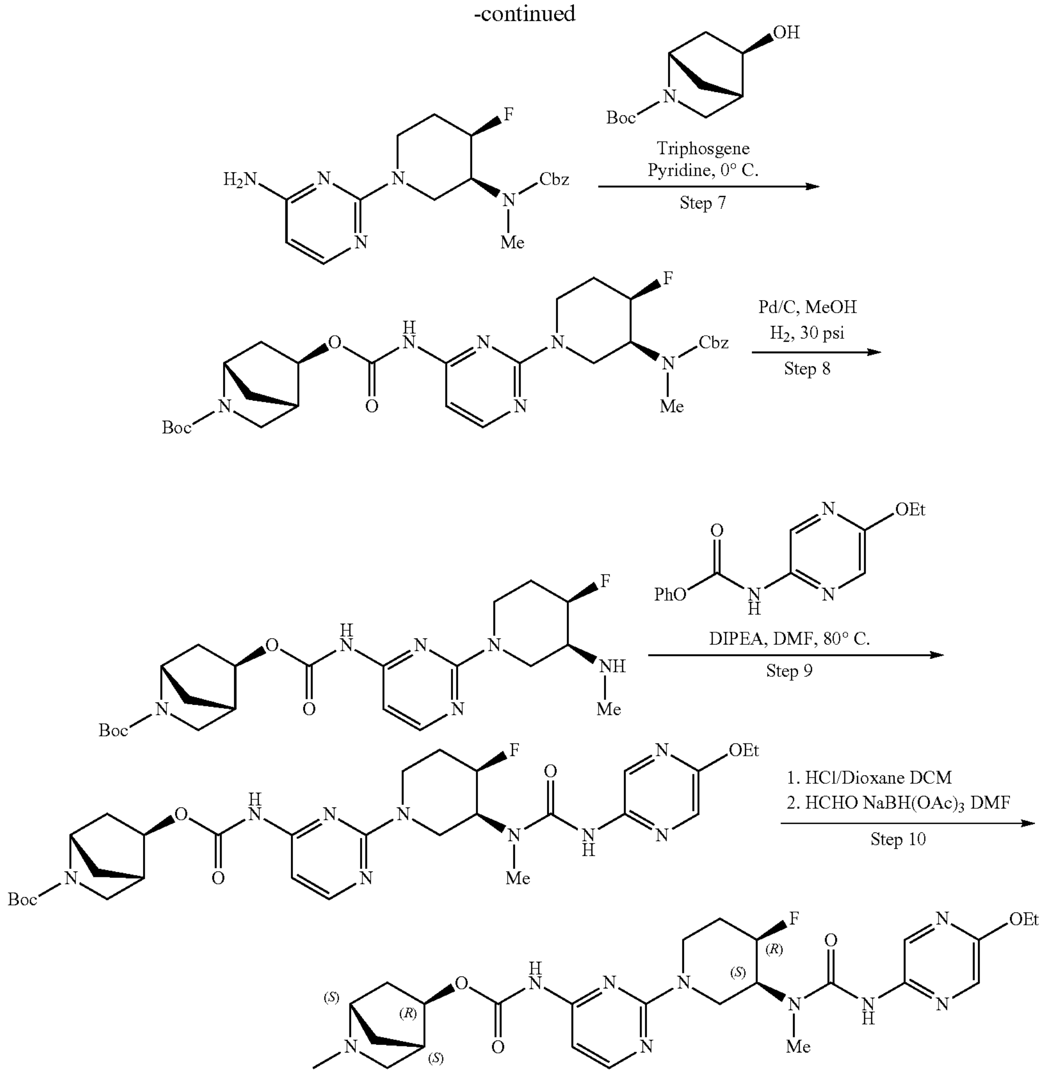

Step 1-6: Steps 1-6 were performed in a similar fashion to Example 18 (step 1-6).

Step 7: This step was performed in a similar fashion to Example 18 (step 7) using tert-butyl (1S,4S,5R)-5-hydroxy-2-azabicyclo[2.2.1]heptane-2-carboxylate instead of tert-butyl (1R,4S,6S)-6-hydroxy-2-azabicyclo[2.2.1]heptane-2-carboxylate.

Step 8-10: Steps 8-10 were performed in a similar fashion to Example 18 (step 8-10) to obtain the desired product. $^1$H NMR (400 MHz, MeOH-d$_3$) δ 8.51 (d, J=1.4 Hz, 1H), 8.20 (d, J=5.7 Hz, 1H), 7.94 (d, J=1.4 Hz, 1H), 7.18 (d, J=5.7 Hz, 1H), 5.07 (d, J=51.2 Hz, 1H), 4.80-4.68 (m, 1H), 4.66-4.56 (m, 2H), 4.35 (q, J=7.1 Hz, 2H), 4.31-4.14 (m, 1H), 3.54 (t, J=12.3 Hz, 1H), 3.27-3.18 (m, 2H), 3.14 (d, J=1.7 Hz, 3H), 2.78 (dd, J=10.6, 4.4 Hz, 1H), 2.56 (d, J=3.3 Hz, 1H), 2.33 (m, 5H), 2.23 (d, J=10.5 Hz, 1H), 2.10-1.77 (m, 3H), 1.53 (d, J=14.6 Hz, 1H), 1.38 (t, J=7.1 Hz, 3H). ESI MS [M+H]$^+$ for $C_{25}H_{34}FN_9O_4$, calcd 544.3, found 544.2.

Example 20: 2-[(3S,4R)-3-[3-(5-ethoxy-2-pyrazinyl)-1-methylureido]-4-fluoro-1-piperidyl]-4-pyrimidinyl 1-methyl-4-methyl-4-piperidinecarbamate

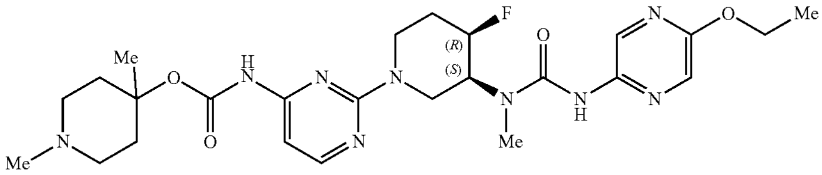

The title compound was synthesized in a similar fashion to Example 18 using 1,4-dimethyl-4-piperidinol in Step 7. $^1$H NMR (400 MHz, Methanol-$d_4$) δ 8.50 (d, J=1.5 Hz, 1H), 8.43 (s, 1H), 8.20 (d, J=5.7 Hz, 1H), 7.93 (d, J=1.4 Hz, 1H), 7.17 (d, J=5.7 Hz, 1H), 5.06 (d, J=51.1 Hz, 1H), 4.64 (td, J=12.5, 4.8 Hz, 2H), 4.42-4.18 (m, 3H), 3.55 (t, J=12.3 Hz, 1H), 3.27-3.05 (m, 8H), 2.79 (s, 3H), 2.51 (t, J=12.2 Hz, 2H), 2.05 (t, J=13.2 Hz, 1H), 1.99-1.73 (m, 3H), 1.63 (s, 3H), 1.38 (t, J=7.1 Hz, 3H). ESI MS $[M+H]^+$ for $C_{25}H_{36}FN_9O_4$, calcd 546.3, found 546.3.

Example 21: 2-[(3S,4R)-3-[3-(5-ethoxy-2-pyrazinyl)-1-methylureido]-4-fluoro-1-piperidyl]-4-pyrimidinyl (3S,4R)-1-methyl-3-methyl-4-piperidinecarbamate

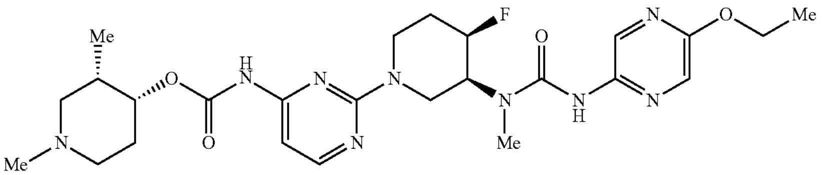 [SMILES: CCOc1cnc(NC(=O)N(C)[C@H]2CN(c3nccc(NC(=O)O[C@@H]4CCN(C)C[C@@H]4C)n3)CC[C@H]2F)cn1]

The title compound was synthesized in a similar fashion to Example 18 using (3S,4R)-3-methyl-4-piperidinol in Step 7. $^1$H NMR (400 MHz, Chloroform-d) δ 8.77 (s, 1H), 8.21 (d, J=5.5 Hz, 1H), 7.88 (s, 1H), 7.47 (s, 1H), 7.16 (d, J=5.7 Hz, 1H), 5.07 (d, J=49.9 Hz, 1H), 4.91 (s, 1H), 4.56 (ddd, J=34.0, 13.3, 4.1 Hz, 2H), 4.30 (q, J=7.1 Hz, 2H), 4.12 (d, J=33.4 Hz, 1H), 3.41 (t, J=12.4 Hz, 1H), 3.17 (t, J=7.2 Hz, 1H), 3.09 (d, J=2.5 Hz, 3H), 2.48 (s, 2H), 2.24 (s, 3H), 2.03 (m, 3H), 1.97-1.61 (m, 5H), 1.33 (t, J=7.0 Hz, 3H), 0.86 (d, J=6.4 Hz, 3H). ESI MS $[M+H]^+$ for $C_{25}H_{36}FN_9O_4$, calcd 546.3, found 546.3.

Example 22: 2-[(3S,4R)-4-fluoro-3-[1-methyl-3-(3-pyridazinyl)ureido]-1-piperidyl]-4-pyrimidinyl 1-methyl-4-piperidinecarbamate

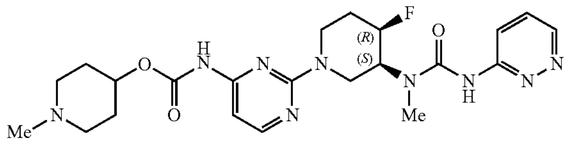

The title compound was synthesized in a similar fashion to Example 18 (Step 1-9, using (pyridazin-3-yl)carbamic acid phenyl ester in Step 9, which was prepared in a similar fashion to Example 1 Step 4). $^1$H NMR (400 MHz, Methanol-$d_4$) δ 8.82 (d, J=4.7 Hz, 1H), 8.23 (d, J=5.7 Hz, 1H), 8.17 (d, J=9.1 Hz, 1H), 7.62 (dd, J=9.1, 4.7 Hz, 1H), 7.20 (d, J=5.7 Hz, 1H), 5.24-4.97 (m, 1H), 4.65 (td, J=12.4, 4.7 Hz, 2H), 4.28 (dd, J=33.2, 11.6 Hz, 1H), 3.57 (t, J=12.2 Hz, 1H), 3.26-3.07 (m, 5H), 2.88 (s, 2H), 2.59 (s, 2H), 2.44 (s, 3H), 2.13-1.73 (m, 6H). ESI MS $[M+H]^+$ for $C_{22}H_{30}FN_9O_3$, calcd 488.3, found 488.2.

Example 23: 2-[(3S,4R)-3-[3-(5-ethoxy-2-pyrazinyl)-1-methylureido]-4-fluoro-1-piperidyl]-4-pyrimidinyl 2-(1-pyrrolidinyl)ethanecarbamate

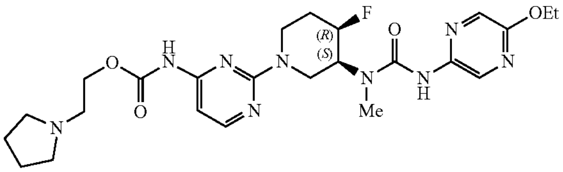

The title compound was synthesized in a similar fashion to Example 18 (Step 1-9, using 1-pyrrolidineethanol in Step 7). $^1$H NMR (400 MHz, Methanol-$d_4$) δ 8.51 (d, J=1.4 Hz, 1H), 8.20 (d, J=5.7 Hz, 1H), 7.94 (d, J=1.5 Hz, 1H), 7.20 (d, J=5.7 Hz, 1H), 5.19-4.93 (m, 1H), 4.63 (dt, J=13.2, 6.2 Hz, 2H), 4.35 (q, J=7.1 Hz, 2H), 4.30 (t, J=5.7 Hz, 2H), 4.21 (dd, J=11.8, 4.5 Hz, 1H), 3.54 (t, J=12.2 Hz, 1H), 3.20 (td, J=13.3, 2.9 Hz, 1H), 3.14 (d, J=1.8 Hz, 3H), 2.82 (t, J=5.7 Hz, 2H), 2.70-2.61 (m, 4H), 2.04 (t, J=13.1 Hz, 1H), 1.97-1.79 (m, 5H), 1.38 (t, J=7.1 Hz, 3H). ESI MS for $C_{24}H_{34}FN_9O_4$, $[M+H]^+$calcd 532.3, found 532.3.

Example 24: 2-[(S)-3-[3-(5-ethoxy-2-pyrazinyl)-1-methylureido]-4,4-difluoro-1-piperidyl]-4-pyrimidinyl (1R,4R,5S)-2-ethyl-2-azabicyclo[2.2.1]heptane-5-carbamate

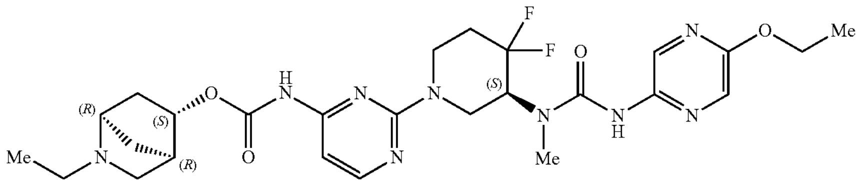

The title compound was synthesized in a similar fashion to Example 11. The ethyl group was installed in a similar fashion to Step 8 Part 2 using acetaldehyde. $^1$H NMR (400 MHz, MeOD) δ 8.51 (dd, J=3.7, 2.0 Hz, 1H), 8.19 (t, J=4.9 Hz, 1H), 7.94 (dt, J=29.9, 2.6 Hz, 1H), 7.21 (t, J=4.8 Hz, 1H), 4.82 (d, J=25.5 Hz, 2H), 4.73-4.49 (m, 2H), 4.32 (dq, J=8.0, 3.9 Hz, 2H), 3.62-3.38 (m, 1H), 3.30-2.93 (m, 4H), 2.99 (s, 1H), 2.85 (s, 1H), 2.85-2.75 (m, 1H), 2.64-2.38 (m, 3H), 2.29-1.88 (m, 3H), 1.67 (s, 2H), 1.37 (dp, J=6.6, 2.3 Hz, 4H), 1.23-0.91 (m, 3H). ESI MS $[M+H]^+$ for $C_{26}H_{35}F_2N_9O_4$, calcd 576.3, found 576.3.

Example 25: 2-[(3S,4R)-3-[3-(5-ethoxy-2-pyrazinyl)-1-methylureido]-4-fluoro-1-piperidyl]-4-pyrimidinyl (1S,4R)-4-hydroxycyclohexanecarbamate

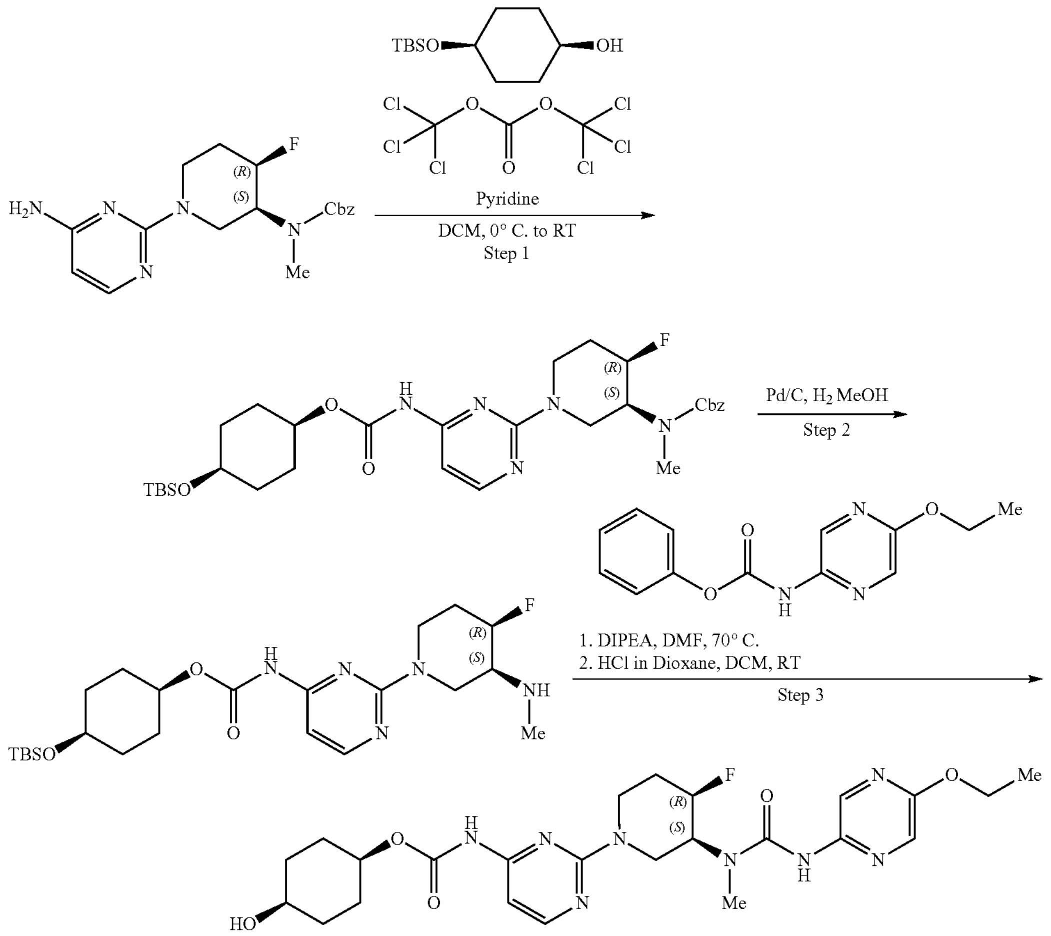

Step 1: This transformation was performed in a similar fashion to Step 1 of the protocol described for the synthesis of Example 10.

Step 2: This transformation was performed in a similar fashion to Step 4 of the protocol described for the synthesis of Example 6.

Step 3 (Part 1): This transformation was performed in a similar fashion to Step 5 of the protocol described for the synthesis of Example 1.

Step 3 (Part 2): In a dry screw-capped reaction vial equipped with a stir bar, the intermediate from Step 3 (Part 1) (39 mg, 0.06 mmol) was dissolved in DCM (1 mL) and to this homogeneous solution, HCl in dioxane (4M, 2 mL) was added. After confirming complete removal of the TBS group by LCMS, volatiles were concentrated under reduced pressure. The crude product was purified using reversed phase preparative HPLC to afford the title compound. $^1$H NMR (400 MHz, MeOD) δ 8.42 (d, J=1.5 Hz, 1H), 8.09 (d, J=5.8 Hz, 1H), 7.83 (d, J=1.5 Hz, 1H), 7.09 (d, J=5.7 Hz, 1H), 4.97 (dt, J=52.1, 2.6 Hz, 1H), 4.74-4.67 (m, 1H), 4.58-4.46 (m, 2H), 4.24 (q, J=7.1 Hz, 2H), 4.20-4.06 (m, 1H), 3.61 (q, J=5.7 Hz, 1H), 3.42 (t, J=12.3 Hz, 1H), 3.15-3.00 (m, 4H), 1.94 (td, J=12.4, 6.6 Hz, 1H), 1.88-1.76 (m, 3H), 1.76-1.65 (m, 1H), 1.60 (dd, J=8.4, 5.3 Hz, 6H), 1.28 (t, J=7.1 Hz, 3H). ESI MS $[M+H]^+$ for $C_{24}H_{33}FN_8O_5$, calcd 533.5, found 533.3.

Example 26: 2-[(3S,4R)-4-fluoro-3-[1-methyl-3-(5-methyl-1,3-thiazol-2-yl)ureido]-1-piperidyl]-4-pyridyl 1-methyl-4-piperidinecarbamate

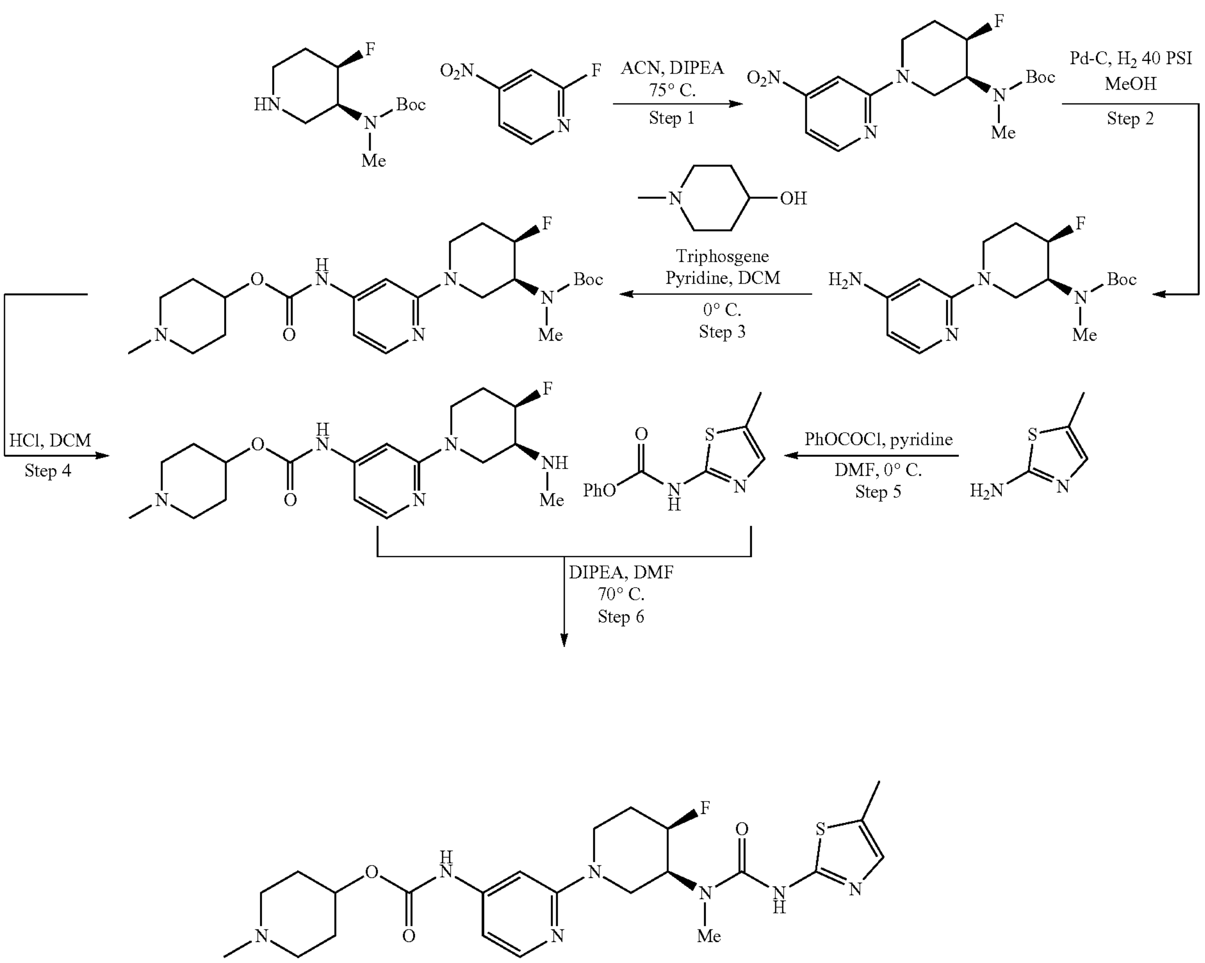

Step 1: To a mixture of tert-butyl ((3S,4R)-4-fluoropiperidin-3-yl)(methyl)carbamate (2.33 g, 10.0 mmol) and 2-fluoro-4-nitropyridine (1.42 g, 10.0 mmol) in acetonitrile (10 mL) was added DIPEA (3.9 g, 30 mmol) at 75° C. and stirred overnight (16 h). The mixture was then concentrated in vacuo and crude material purified using flash column chromatography using a β-50% Hexane/EtOAc gradient to afford the intermediate.

Step 2: In a Parr hydrogenator, to a solution of the intermediate from Step 1 (1.7 g, 4.8 mmol) in methanol (100 mL) was added Pd/C (20%). After stirring at 40 psi $H_2$ atmosphere for 2 h, the reaction mixture was filtered through CELITE®. The filtrate was concentrated under reduced pressure to obtain the desired intermediate and used in the next step without purification.

Step 3: To a solution of triphosgene (120 mg, 0.4 mmol) in DCM at 0° C., pyridine (0.55 g, 7.0 mmol) was added. After stirring for 10-15 minutes, the intermediate from Step 2 (0.31 g, 1.0 mmol) was added at the same temperature. Then 4-hydroxy-N-methylpiperidine (2.0 equivalent) was added after 30 min, and the reaction mixture was brought to room temperature. After removing the organic volatiles under reduced pressure, the crude material was purified using flash column chromatography using a β-20% MeOH in DCM gradient to afford the desired intermediate.

Step 5: This transformation was performed in a similar fashion to Step 4 of the protocol described for the synthesis of Example 1.

Step 6: The intermediate from Step 4 (85 mg, 0.23 mmol) was taken in a dry screw-capped reaction vial equipped with a stir bar, and to this vial was added the carbamate from Step 5 (60 mg, 0.23 mmol) followed by dry DMF (2.5 mL). To this mixture, DIPEA (0.12 mL, 0.69 mmol) was added, and the reaction mixture was stirred at 70° C. After confirming the completion of the reaction by LCMS, the temperature of the reaction mixture was brought to room temperature. The crude reaction mixture was directly purified using reversed phase preparative HPLC using a binary solvent system ($MeCN/H_2O$) to afford the title compound. $^1H$ NMR (400 MHz, MeOH-$d_3$) δ 8.39 (s, 1H), 8.07 (d, J=5.8 Hz, 1H), 7.08 (d, J=1.7 Hz, 1H), 6.90 (s, 1H), 6.79 (dd, J=5.8, 1.7 Hz, 1H), 5.49-4.96 (m, 2H), 4.51-4.29 (m, 1H), 4.15 (dd, J=12.8, 4.4 Hz, 1H), 4.09-3.80 (m, 1H), 3.55 (t, J=12.3 Hz, 1H), 3.28-3.19 (m, 4H), 3.12 (d, J=1.8 Hz, 3H), 2.81 (s, 3H), 2.30 (d, J=1.3 Hz, 3H), 2.16 (bs, 2H), 1.94 (m, 4H). ESI MS $[M+H]^+$ for $C_{23}H_{32}FN_7O_3S$, calcd 506.2, found 506.2.

Example 27: 2-[(S)-3-[3-(5-ethoxy-2-pyrazinyl)-1-methylureido]-4,4-difluoro-1-piperidyl]-4-pyridyl 4-quinuclidinecarbamate

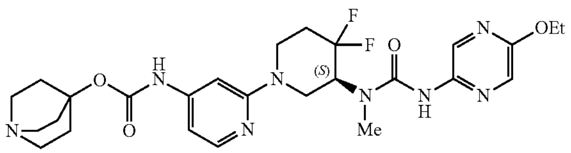

The title compound was synthesized in a similar fashion to Example 26 using 1,1-dimethylethyl N-[(3S)-4,4-difluoro-3-piperidinyl]methyl carbamate in Step 1 and 4-quinuclidinol in Step 3. $^1$H NMR (400 MHz, DMSO-$d_6$) δ 9.70 (s, 1H), 9.05 (s, 1H), 8.55 (d, J=1.4 Hz, 1H), 8.00 (d, J=1.5 Hz, 1H), 7.95 (d, J=5.6 Hz, 1H), 7.14 (dd, J=15.3, 7.4 Hz, 1H), 6.86-6.59 (m, 1H), 4.62 (d, J=23.5 Hz, 1H), 4.29 (m, 4H), 3.39 (t, J=12.2 Hz, 3H), 3.05 (s, 4H), 2.87 (dd, J=9.4, 5.9 Hz, 5H), 2.15 (s, 1H), 1.91 (t, J=7.7 Hz, 6H), 1.32 (t, J=7.0 Hz, 3H). $C_{26}H_{34}F_2N_8O_4$, calcd 561.3, found 561.1.

Example 28: 2-[(3S,4R)-3-[3-(5-ethoxy-2-pyrazinyl)-1-methylureido]-4-fluoro-1-piperidyl]-4-pyrimidinyl (1S,4S,5R)-2-ethyl-2-azabicyclo[2.2.1]heptane-5-carbamate

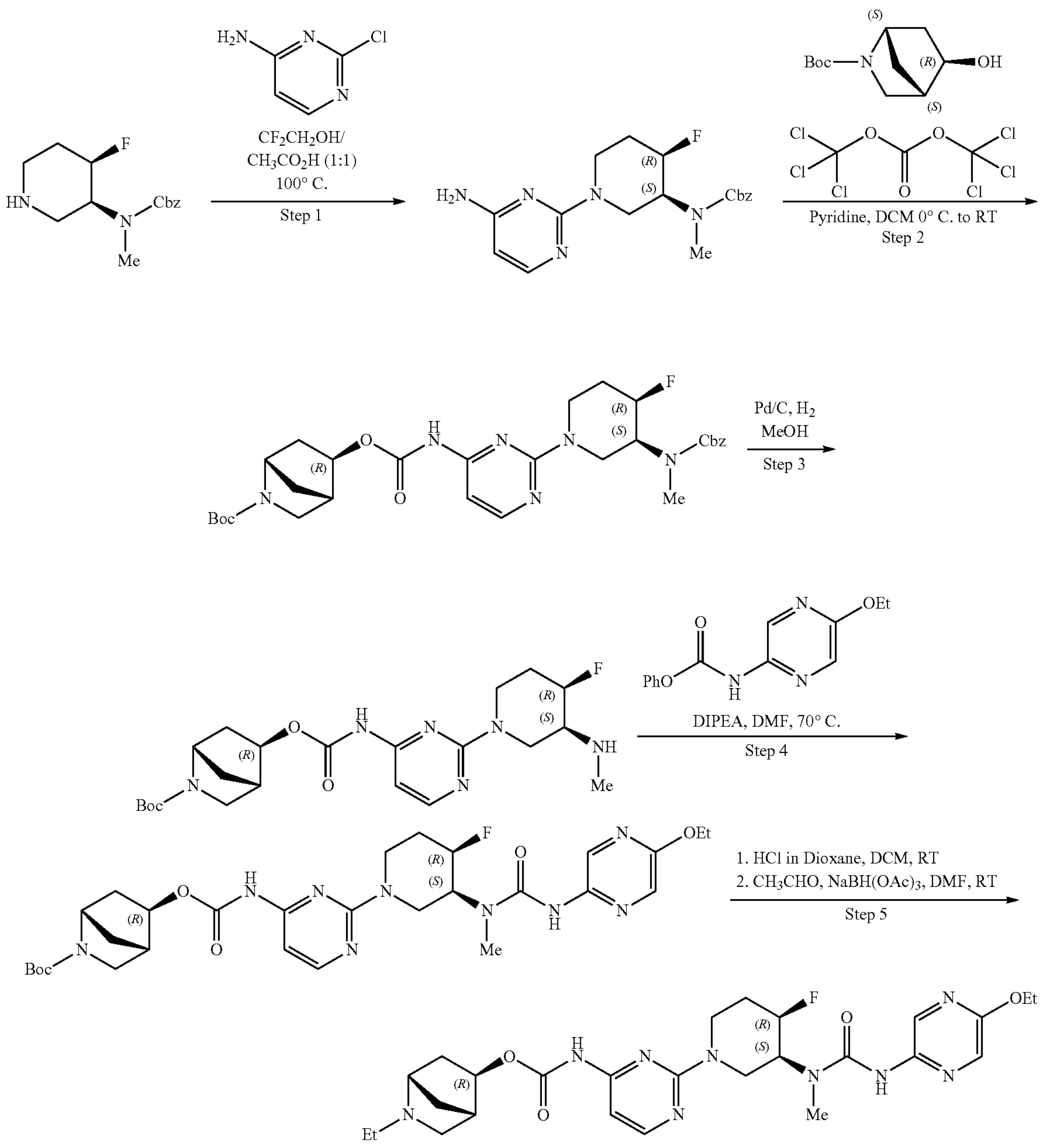

Step 1: This transformation was performed in a similar fashion to the protocol described for the synthesis of Example 11 using phenylmethyl (3S,4R)-4-fluoropiperidin-3-yl)carbamate in Step 4.

Step 2: This transformation was performed in a similar fashion to the protocol described for the synthesis of Example 11 using tert-butyl (1S,4S,5R)-5-hydroxy-2-azabicyclo[2.2.1]heptane-2-carboxylate in Step 5.

Step 3: This transformation was performed in a similar fashion to Step 6 of the protocol described for the synthesis of Example 11.

Step 4: This transformation was performed in a similar fashion to Step 7 of the protocol described for the synthesis of Example 11.

Step 5 (Part 1): This transformation was performed in a similar fashion to Step 8 part 1 of the protocol described for the synthesis of Example 11.

Step 5 (Part 2): The screw-capped vial containing the intermediate from step 5 part 1 (170 mg, 0.3 mmol) was equipped with stir bar and to this vial was added acetaldehyde (66 mg, 1.5 mmol) followed by dry DMF (2 mL). The reaction mixture was stirred for 5 min at room temperature. To the stirred reaction mixture was added $NaBH(OAc)_3$ (190 mg, 3.0 mmol) in one portion, and the reaction mixture was stirred at room temperature for 24 hours. After confirming completion of the reaction by LCMS, the reaction mixture was quenched with water (3 mL) and pH was adjusted to 11. Then the reaction mixture was extracted with DCM (20 mL) and the organic layer was washed with water three times to remove the DMF. The organic layer was dried over anhydrous $Na_2SO_4$, and the volatiles were concentrated under reduced pressure. The crude product was purified by reversed phase HPLC to provide the title compound. $^1H$ NMR (400 MHz, MeOH-$d_3$) δ 8.51 (d, J=1.4 Hz, 1H), 8.19 (d, J=5.7 Hz, 1H), 7.93 (d, J=1.4 Hz, 1H), 7.18 (d, J=5.7 Hz, 1H), 5.07 (d, J=51.2 Hz, 1H), 4.70 (d, J=7.2 Hz, 1H), 4.68-4.56 (m, 2H), 4.35 (q, J=7.0 Hz, 2H), 4.31-4.13 (m, 1H), 3.53 (t, J=12.3 Hz, 1H), 3.40 (s, 1H), 3.25-3.16 (m, 1H), 3.14 (d, J=1.8 Hz, 3H), 2.85 (dd, J=10.5, 4.4 Hz, 1H), 2.69-2.43 (m, 3H), 2.42-2.26 (m, 1H), 2.17 (d, J=10.6 Hz, 1H), 2.08-1.63 (m, 4H), 1.51 (d, J=14.6 Hz, 1H), 1.38 (t, J=7.0 Hz, 3H), 1.09 (t, J=7.2 Hz, 3H). ESI MS $[M+H]^+$ for $C_{26}H_{36}N_9FO_4$, calcd 558.3, found 558.2.

Example 29: 2-(4-methylpiperazin-1-yl)ethyl (R)-(2-(3-(3-(5-ethoxypyrazin-2-yl)-1-methylureido)piperidin-1-yl)pyrimidin-4-yl)carbamate

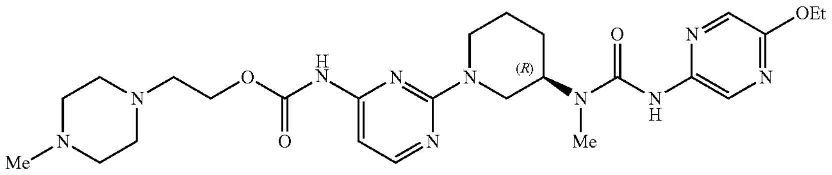

The title compound was synthesized in a similar fashion to Example 1 (Steps 1-5, using 2-(4-methylpiperazin-1-yl) ethan-1-ol in step 1). $^1$H NMR (400 MHz, MeOD) δ 8.51 (d, J=1.4 Hz, 1H), 8.14 (d, J=7.0 Hz, 1H), 7.96 (d, J=1.5 Hz, 1H), 7.54 (d, J=7.0 Hz, 1H), 4.61-4.30 (m, 6H), 4.27-4.14 (m, 1H), 3.35 (m, 4H), 3.23 (m, 1H), 3.05 (m, 6H), 2.99-2.94 (m, 4H), 2.89 (s, 3H), 2.08-1.93 (m, 3H), 1.72 (ddt, J=13.0, 8.4, 4.7 Hz, 1H), 1.39 (t, J=7.1 Hz, 3H). ESI MS for $C_{25}H_{38}N_{10}O_4$, $[M+H]^+$calcd=543.3, found=543.3.

Example 30: 2-(pyrrolidin-1-yl)ethyl (R)-(2-(3-(3-(5-ethoxypyrazin-2-yl)-1-methylureido)piperidin-1-yl)pyrimidin-4-yl)carbamate

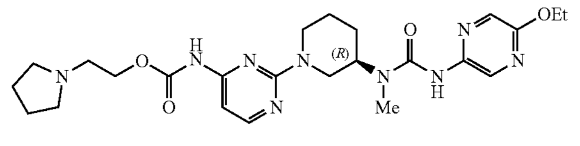

The title compound was synthesized in a similar fashion to Example 1 (Steps 1-5, using 2-(pyrrolidin-1-yl)ethan-1-ol in step 1). $^1$H NMR (400 MHz, MeOD) δ 8.51 (d, J=1.4 Hz, 1H), 8.19 (d, J=6.6 Hz, 1H), 7.94 (d, J=1.5 Hz, 1H), 7.43 (d, J=6.6 Hz, 1H), 4.58-4.50 (m, 4H), 4.35 (q, J=7.0 Hz, 2H), 4.17 (dt, J=11.1, 6.2 Hz, 1H), 3.86-3.66 (m, 2H), 3.62-3.55 (m, 2H), 3.18 (t, J=12.0 Hz, 3H), 3.04 (s, 4H), 2.29-1.85 (m, 7H), 1.70 (dd, J=16.6, 8.1 Hz, 1H), 1.38 (t, J=7.0 Hz, 3H). ESI MS for $C_{24}H_{35}N_9O_4$, $[M+H]^+$calcd=514.3, found=514.3.

Example 31: 2-morpholinoethyl (R)-(2-(3-(3-(5-ethoxypyrazin-2-yl)-1-methylureido)piperidin-1-yl) pyrimidin-4-yl)carbamate

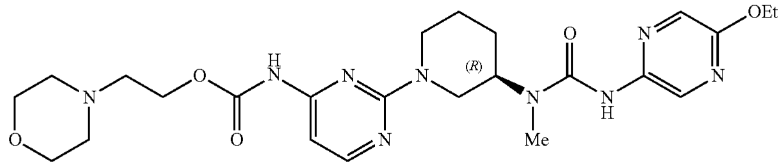

The title compound was synthesized in a similar fashion to Example 1 (Steps 1-5, using 2-morpholinoethan-1-ol in step 1). $^1$H NMR (400 MHz, MeOD) δ 8.61 (d, J=1.4 Hz, 1H), 8.22 (d, J=5.7 Hz, 1H), 8.05 (d, J=1.5 Hz, 1H), 7.22 (d, J=5.7 Hz, 1H), 4.74-4.48 (m, 2H), 4.41-4.29 (m, 4H), 3.92 (d, J=8.7 Hz, 1H), 3.72-3.60 (m, 4H), 3.02 (s, 4H), 2.88 (td, J=13.1, 2.8 Hz, 1H), 2.70 (td, J=5.3, 1.0 Hz, 2H), 2.55 (t, J=4.7 Hz, 4H), 1.99 (dq, J=9.0, 3.8 Hz, 2H), 1.87-1.79 (m, 1H), 1.61 (ddd, J=16.8, 10.3, 4.4 Hz, 1H), 1.39 (t, J=7.0 Hz, 3H). ESI MS for $C_{24}H_{35}N_9O_5$, $[M+H]^+$calcd=530.3, found=530.3.

Example 32: ((R)-4-methylmorpholin-2-yl)methyl (2-((R)-3-(3-(5-ethoxypyrazin-2-yl)-1-methylureido) piperidin-1-yl)pyrimidin-4-yl)carbamate

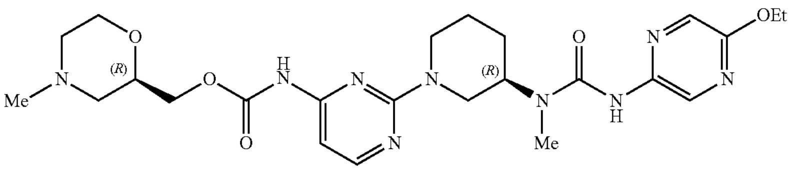

The title compound was synthesized in a similar fashion to Example 1 (Steps 1-5, using (R)-(4-methylmorpholin-2-yl)methanol in step 1). $^1$H NMR (400 MHz, MeOD) δ 8.64 (d, J=1.5 Hz, 1H), 8.22 (d, J=5.7 Hz, 1H), 8.09 (s, 1H), 7.22 (d, J=5.7 Hz, 1H), 4.73-4.64 (m, 1H), 4.59-4.52 (m, 1H), 4.36 (q, J=7.0 Hz, 2H), 4.27-4.09 (m, 2H), 3.95 (ddd, J=11.7, 3.5, 1.5 Hz, 1H), 3.82 (dddd, J=10.3, 6.2, 4.1, 2.4 Hz, 2H), 3.69 (td, J=11.7, 2.4 Hz, 1H), 3.01 (s, 4H), 2.94-2.66 (m, 3H), 2.33 (s, 3H), 2.20 (td, J=11.6, 3.4 Hz, 1H), 2.00 (t, J=11.0 Hz, 3H), 1.87-1.79 (m, 1H), 1.67-1.48 (m, 1H), 1.39 (t, J=7.1 Hz, 3H). ESI MS for $C_{24}H_{35}N_9O_5$, $[M+H]^+$ calcd=530.3, found=530.3.

Example 33: ((S)-4-methylmorpholin-2-yl)methyl (2-((R)-3-(3-(5-ethoxypyrazin-2-yl)-1-methylureido) piperidin-1-yl)pyrimidin-4-yl)carbamate

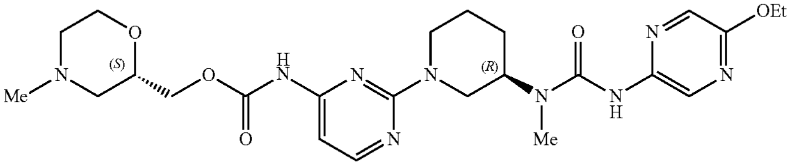

The title compound was synthesized in a similar fashion to Example 1 (Steps 1-5, using (S)-(4-methylmorpholin-2-yl)methanol in step 1). $^1$H NMR (400 MHz, MeOD) δ 8.63 (d, J=1.4 Hz, 1H), 8.22 (d, J=5.7 Hz, 1H), 8.12 (s, 1H), 7.23 (d, J=5.7 Hz, 1H), 4.69 (d, J=13.5 Hz, 1H), 4.56 (d, J=12.7 Hz, 1H), 4.41-4.30 (m, 2H), 4.20 (d, J=5.0 Hz, 2H), 3.99-3.74 (m, 3H), 3.70 (td, J=11.6, 2.4 Hz, 1H), 3.02 (s, 4H), 2.95-2.76 (m, 2H), 2.70 (dt, J=11.7, 1.9 Hz, 1H), 2.30 (s, 3H), 2.17 (td, J=11.7, 3.4 Hz, 1H), 2.05-1.92 (m, 3H), 1.83 (d, J=13.4 Hz, 1H), 1.70-1.50 (m, 1H), 1.39 (t, J=7.1 Hz, 3H). ESI MS for $C_{24}H_{35}N_9O_5$, $[M+H]^+$calcd=530.3, found=530.3.

Example 34: 2-(2-oxopyrrolidin-1-yl)ethyl (R)-(2-(3-(3-(5-ethoxypyrazin-2-yl)-1-methylureido)piperidin-1-yl)pyrimidin-4-yl)carbamate

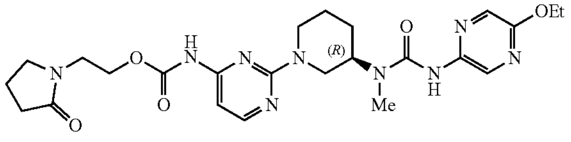

The title compound was synthesized in a similar fashion to Example 1 (Steps 1-5, using 1-(2-hydroxyethyl)pyrrolidin-2-one in step 1). $^1$H NMR (400 MHz, MeOD) δ 8.60 (d, J=1.4 Hz, 1H), 8.22 (d, J=5.8 Hz, 1H), 7.98 (d, J=1.4 Hz, 1H), 7.19 (d, J=5.7 Hz, 1H), 4.72-4.55 (m, 2H), 4.41-4.26 (m, 4H), 3.98-3.92 (m, 1H), 3.67-3.48 (m, 4H), 3.01 (s, 3H), 2.86 (td, J=13.0, 2.7 Hz, 1H), 2.42-2.28 (m, 2H), 2.10-1.90 (m, 4H), 1.87-1.79 (m, 1H), 1.61 (dtd, J=13.1, 7.7, 4.2 Hz, 1H), 1.39 (t, J=7.1 Hz, 3H), 1.11 (t, J=7.1 Hz, 1H). ESI MS for $C_{24}H_{33}N_9O_5$, $[M+H]^+$calcd=528.3, found=528.3.

Example 35: 2-(4,4-difluoropiperidin-1-yl)ethyl (R)-(2-(3-(3-(5-ethoxypyrazin-2-yl)-1-methylureido) piperidin-1-yl)pyrimidin-4-yl)carbamate

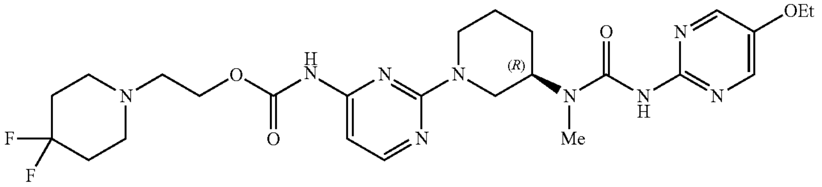

The title compound was synthesized in a similar fashion to Example 1 (Steps 1-5, using 2-(4,4-difluoropiperidin-1-yl)ethan-1-ol in step 1). $^1$H NMR (400 MHz, MeOD) δ 8.62 (d, J=1.4 Hz, 1H), 8.22 (d, J=5.7 Hz, 1H), 8.05 (d, J=1.4 Hz, 1H), 7.22 (d, J=5.7 Hz, 1H), 4.72-4.64 (m, 1H), 4.61-4.53 (m, 1H), 4.41-4.28 (m, 4H), 3.91 (d, J=9.9 Hz, 1H), 3.04-2.99 (m, 4H), 2.88 (td, J=13.1, 2.8 Hz, 1H), 2.81-2.70 (m, 2H), 2.66 (t, J=5.7 Hz, 4H), 2.05-1.90 (m, 6H), 1.83 (d, J=13.6 Hz, 1H), 1.66-1.54 (m, 1H), 1.39 (t, J=7.0 Hz, 3H). ESI MS for $C_{25}H_{35}F_2N_9O_4$, $[M+H]^+$calcd=564.3, found=564.3.

Example 36: 2-((S)-3-fluoropyrrolidin-1-yl)ethyl (2-((R)-3-(3-(5-ethoxypyrazin-2-yl)-1-methylureido) piperidin-1-yl)pyrimidin-4-yl)carbamate

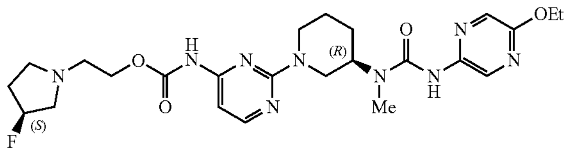

The title compound was synthesized in a similar fashion to Example 1 (Steps 1-5, using (S)-2-(3-fluoropyrrolidin-1-yl)ethan-1-ol in step 1). $^1$H NMR (400 MHz, MeOD) δ 8.54 (d, J=1.5 Hz, 1H), 7.92 (d, J=1.5 Hz, 1H), 7.74 (s, 1H), 5.79 (d, J=6.0 Hz, 1H), 4.71-4.50 (m, 3H), 4.39-4.25 (m, 4H), 4.04 (s, 1H), 3.66 (td, J=8.1, 3.3 Hz, 2H), 3.55-3.32 (m, 4H), 3.01 (s, 4H), 2.90-2.76 (m, 1H), 2.21-1.75 (m, 5H), 1.62 (dd, J=13.0, 7.2 Hz, 1H), 1.38 (t, J=7.0 Hz, 3H). ESI MS for $C_{24}H_{34}FN_9O_4$, $[M+H]^+$calcd=532.3, found=532.3

Example 37: 2-((R)-3-fluoropyrrolidin-1-yl)ethyl (2-((R)-3-(3-(5-ethoxypyrazin-2-yl)-1-methylureido) piperidin-1-yl)pyrimidin-4-yl)carbamate

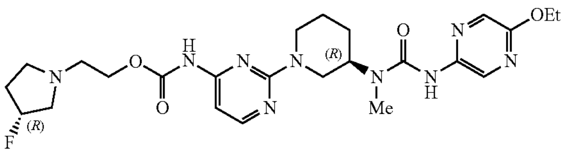

The title compound was synthesized in a similar fashion to Example 1 (Steps 1-5, using (R)-2-(3-fluoropyrrolidin-1-yl)ethan-1-ol in step 1). $^1$H NMR (400 MHz, MeOD) δ 8.54 (d, J=1.4 Hz, 1H), 7.91 (d, J=1.4 Hz, 1H), 7.75 (d, J=6.1 Hz, 1H), 5.80 (d, J=6.0 Hz, 1H), 4.72-4.53 (m, 3H), 4.39-4.28 (m, 4H), 4.03 (s, 1H), 3.71-3.62 (m, 2H), 3.56-3.37 (m, 4H), 3.01 (s, 4H), 2.81 (td, J=12.9, 2.7 Hz, 1H), 2.01-1.78 (m, 5H), 1.63 (q, J=11.4 Hz, 1H), 1.38 (t, J=7.0 Hz, 3H). ESI MS for $C_{24}H_{34}FN_9O_4$, $[M+H]^+$calcd=532.3, found=532.3.

Example 38: 2-(3-oxomorpholino)ethyl (R)-(2-(3-(3-(5-ethoxypyrazin-2-yl)-1-methylureido)piperidin-1-yl)pyrimidin-4-yl)carbamate

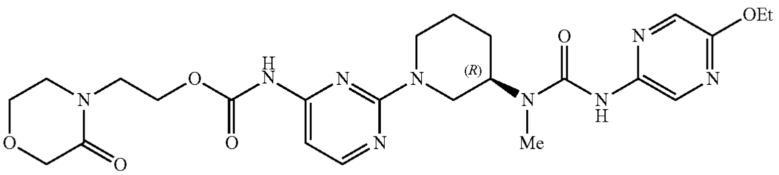

The title compound was synthesized in a similar fashion to Example 1 (Steps 1-5, using 4-(2-hydroxyethyl)morpholin-3-one in step 1). $^1$H NMR (400 MHz, MeOD) δ 8.60 (d, J=1.4 Hz, 1H), 8.22 (d, J=5.7 Hz, 1H), 7.97 (d, J=1.5 Hz, 1H), 7.20 (d, J=5.7 Hz, 1H), 4.74-4.49 (m, 2H), 4.41-4.31 (m, 4H), 4.07 (d, J=2.9 Hz, 2H), 3.98-3.91 (m, 1H), 3.86 (t, J=5.1 Hz, 2H), 3.71 (qt, J=14.5, 5.2 Hz, 2H), 3.57-3.48 (m, 2H), 3.01 (s, 4H), 2.86 (td, J=13.0, 2.7 Hz, 1H), 2.05-1.90 (m, 2H), 1.83 (dt, J=13.6, 3.0 Hz, 1H), 1.60 (tt, J=15.9, 6.2 Hz, 1H), 1.39 (t, J=7.0 Hz, 3H). ESI MS for $C_{24}H_{33}N_9O_6$, $[M+H]^+$calcd=544.3, found=544.2.

Example 39: 2-(2-oxooxazolidin-3-yl)ethyl (R)-(2-(3-(3-(5-ethoxypyrazin-2-yl)-1-methylureido)piperidin-1-yl)pyrimidin-4-yl)carbamate

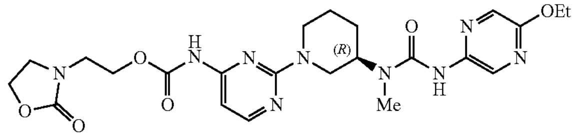

The title compound was synthesized in a similar fashion to Example 1 (Steps 1-5, using 3-(2-hydroxyethyl)oxazolidin-2-one in step 1). $^1$H NMR (400 MHz, MeOD) δ 8.59 (d, J=1.4 Hz, 1H), 8.22 (d, J=5.7 Hz, 1H), 7.98 (d, J=1.4 Hz, 1H), 7.20 (d, J=5.7 Hz, 1H), 4.72-4.56 (m, 2H), 4.41-4.26 (m, 6H), 3.95 (d, J=9.5 Hz, 1H), 3.78-3.65 (m, 2H), 3.56 (td, J=4.8, 2.1 Hz, 2H), 3.01 (s, 4H), 2.86 (td, J=13.0, 2.7 Hz, 1H), 2.05-1.90 (m, 2H), 1.88-1.79 (m, 1H), 1.66-1.55 (m, 1H), 1.39 (t, J=7.1 Hz, 3H). ESI MS for $C_{23}H_{31}N_9O_6$, $[M+H]^+$calcd=530.2, found=530.2.

Example 40: 2-((1S,4S)-2-oxa-5-azabicyclo[2.2.1]heptan-5-yl)ethyl (2-((R)-3-(3-(5-ethoxypyrazin-2-yl)-1-methylureido)piperidin-1-yl)pyrimidin-4-yl)carbamate

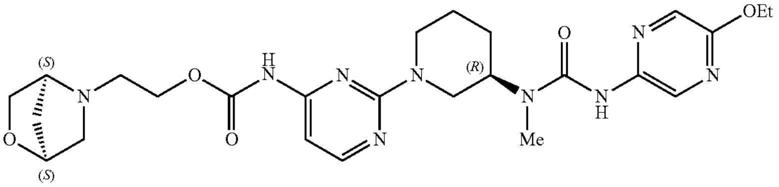

The title compound was synthesized in a similar fashion to Example 1 (Steps 1-5, using 2-((1S,4S)-2-oxa-5-azabicyclo[2.2.1]heptan-5-yl)ethan-1-ol in step 1). $^1$H NMR (400 MHz, MeOD) δ 8.61 (d, J=1.4 Hz, 1H), 8.22 (d, J=5.7 Hz, 1H), 8.04 (d, J=1.5 Hz, 1H), 7.22 (d, J=5.7 Hz, 1H), 4.72-4.63 (m, 1H), 4.59 (dd, J=13.1, 3.9 Hz, 1H), 4.41 (s, 1H), 4.36 (q, J=7.1 Hz, 2H), 4.28 (td, J=5.7, 1.1 Hz, 2H), 4.01 (dd, J=8.0, 0.9 Hz, 1H), 3.92 (d, J=9.1 Hz, 1H), 3.68-3.59 (m, 2H), 3.08-2.82 (m, 8H), 2.64 (d, J=10.4 Hz, 1H), 1.99 (dq, J=9.1, 3.9 Hz, 2H), 1.89 (dd, J=10.0, 2.2 Hz, 1H), 1.83 (dt, J=13.5, 2.8 Hz, 1H), 1.78-1.72 (m, 1H), 1.60 (tq, J=13.4, 6.5 Hz, 1H), 1.39 (t, J=7.1 Hz, 3H). ESI MS for $C_{25}H_{35}N_9O_5$, $[M+H]^+$calcd=542.3, found=542.2.

Example 41: 2-((S)-3-methylmorpholino)ethyl (2-((R)-3-(3-(5-ethoxypyrazin-2-yl)-1-methylureido)piperidin-1-yl)pyrimidin-4-yl)carbamate

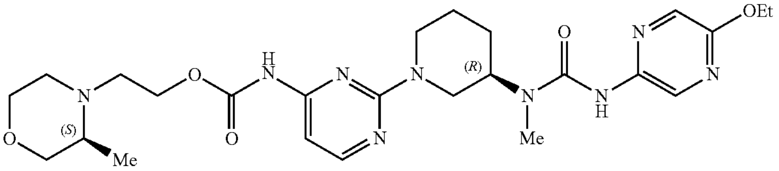

The title compound was synthesized in a similar fashion to Example 1 (Steps 1-5, using (S)-2-(3-methylmorpholino) ethan-1-ol in step 1). $^1$H NMR (400 MHz, MeOD) δ 8.61 (d, J=1.5 Hz, 1H), 8.22 (d, J=5.7 Hz, 1H), 8.03 (d, J=1.5 Hz, 1H), 7.22 (d, J=5.7 Hz, 1H), 4.72-4.63 (m, 1H), 4.59 (dd, J=12.4, 3.7 Hz, 1H), 4.41-4.22 (m, 4H), 3.92 (d, J=9.3 Hz, 1H), 3.75 (dtd, J=11.4, 3.3, 1.0 Hz, 1H), 3.68-3.56 (m, 2H), 3.21 (dd, J=11.3, 8.9 Hz, 1H), 3.14-2.97 (m, 5H), 2.93-2.82 (m, 2H), 2.61-2.39 (m, 3H), 1.98 (dt, J=9.2, 4.7 Hz, 2H), 1.87-1.79 (m, 1H), 1.70-1.50 (m, 1H), 1.39 (t, J=7.1 Hz, 3H), 1.00 (d, J=6.3 Hz, 3H). ESI MS for $C_{25}H_{37}N_9O_5$, $[M+H]^+$calcd=544.3, found=544.3.

Example 42: 2-((R)-3-methylmorpholino)ethyl (2-((R)-3-(3-(5-ethoxypyrazin-2-yl)-1-methylureido) piperidin-1-yl)pyrimidin-4-yl)carbamate

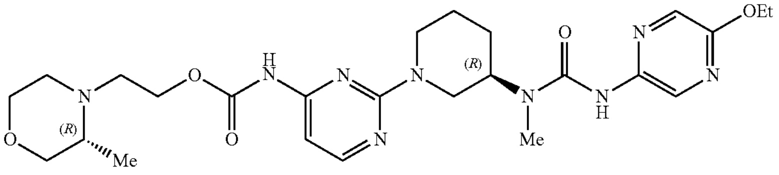

The title compound was synthesized in a similar fashion to Example 1 (Steps 1-5, using (R)-2-(3-methylmorpholino) ethan-1-ol in step 1). $^1$H NMR (400 MHz, MeOD) δ 8.61 (d, J=1.4 Hz, 1H), 8.22 (d, J=5.7 Hz, 1H), 8.04 (d, J=1.5 Hz, 1H), 7.22 (d, J=5.7 Hz, 1H), 4.72-4.64 (m, 1H), 4.59 (dd, J=13.0, 3.9 Hz, 1H), 4.41-4.22 (m, 4H), 3.92 (d, J=9.6 Hz, 1H), 3.80-3.71 (m, 1H), 3.67-3.56 (m, 2H), 3.21 (dd, J=11.3, 9.0 Hz, 1H), 3.13-2.98 (m, 5H), 2.88 (ddq, J=13.0, 6.7, 3.1 Hz, 2H), 2.61-2.39 (m, 3H), 1.99 (dq, J=9.1, 3.8 Hz, 2H), 1.87-1.79 (m, 1H), 1.61 (td, J=13.0, 6.2 Hz, 1H), 1.39 (t, J=7.0 Hz, 3H), 0.99 (d, J=6.3 Hz, 3H). ESI MS for $C_{25}H_{37}N_9O_5$, $[M+H]^+$calcd=544.3, found=544.3.

Example 43: 2-(4-fluoropiperidin-1-yl)ethyl (R)-(2-(3-(3-(5-ethoxypyrazin-2-yl)-1-methylureido)piperidin-1-yl)pyrimidin-4-yl)carbamate

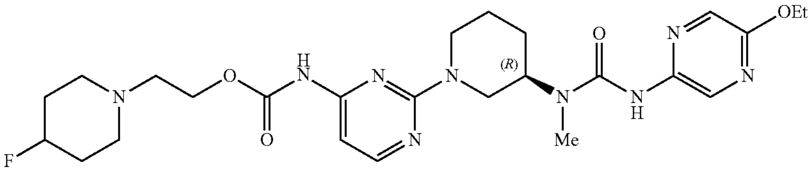

The title compound was synthesized in a similar fashion to Example 1 (Steps 1-5, using 2-(4-fluoropiperidin-1-yl) ethan-1-ol in step 1). $^1$H NMR (400 MHz, MeOD) δ 8.61 (d, J=1.5 Hz, 1H), 8.22 (d, J=5.7 Hz, 1H), 8.03 (d, J=1.4 Hz, 1H), 7.22 (d, J=5.7 Hz, 1H), 4.71-4.53 (m, 3H), 4.41-4.28 (m, 4H), 3.92 (d, J=9.4 Hz, 1H), 3.02 (s, 4H), 2.88 (td, J=12.9, 2.7 Hz, 1H), 2.77-2.64 (m, 4H), 2.51 (s, 2H), 2.04-1.74 (m, 7H), 1.68-1.51 (m, 1H), 1.39 (t, J=7.0 Hz, 3H). ESI MS for $C_{25}H_{36}FN_9O_4$, $[M+H]^+$calcd=546.3, found=546.3

Example 44: (R)-1-morpholinopropan-2-yl (2-((R)-3-(3-(5-ethoxypyrazin-2-yl)-1-methylureido)piperidin-1-yl)pyrimidin-4-yl)carbamate

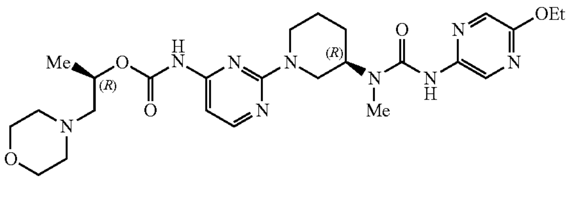

The title compound was synthesized in a similar fashion to Example 1 (Steps 1-5, using (R)-1-morpholinopropan-2-ol in step 1). $^1$H NMR (400 MHz, MeOD) δ 8.61 (d, J=1.4 Hz, 1H), 8.22 (d, J=5.7 Hz, 1H), 8.05 (d, J=1.4 Hz, 1H), 7.22 (d, J=5.7 Hz, 1H), 5.13 (dqd, J=8.4, 6.3, 4.0 Hz, 1H), 4.73-4.64 (m, 1H), 4.58 (dd, J=13.0, 4.0 Hz, 1H), 4.36 (q, J=7.1 Hz, 2H), 3.90 (d, J=9.1 Hz, 1H), 3.62 (t, J=4.7 Hz, 4H), 3.01 (s, 4H), 2.88 (td, J=13.0, 2.7 Hz, 1H), 2.67-2.51 (m, 3H), 2.47-2.37 (m, 3H), 1.99 (h, J=3.7 Hz, 2H), 1.87-1.78 (m, 1H), 1.70-1.49 (m, 1H), 1.38 (t, J=7.0 Hz, 3H), 1.30 (d, J=6.3 Hz, 3H). ESI MS for $C_{25}H_{37}N_9O_5$, $[M+H]^+$ calcd=544.3, found=544.3.

Example 45: (S)-1-morpholinopropan-2-yl (2-((R)-3-(3-(5-ethoxypyrazin-2-yl)-1-methylureido)piperidin-1-yl)pyrimidin-4-yl)carbamate

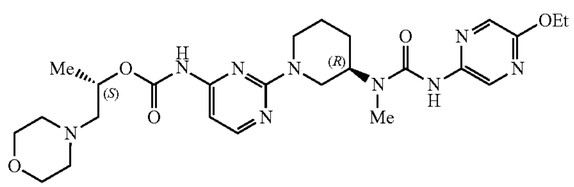

The title compound was synthesized in a similar fashion to Example 1 (Steps 1-5, using (S)-1-morpholinopropan-2-ol in step 1). $^1$H NMR (400 MHz, MeOD) δ 8.63 (d, J=1.4 Hz, 1H), 8.21 (d, J=5.7 Hz, 1H), 8.09-8.04 (m, 1H), 7.23 (d, J=5.7 Hz, 1H), 5.12 (dqd, J=8.5, 6.3, 3.9 Hz, 1H), 4.67 (dq, J=11.7, 2.4 Hz, 1H), 4.56 (dd, J=13.2, 3.9 Hz, 1H), 4.36 (q, J=7.0 Hz, 2H), 3.89 (s, 1H), 3.65 (ddd, J=5.3, 3.8, 1.1 Hz, 4H), 3.01 (s, 4H), 2.88 (td, J=13.0, 2.7 Hz, 1H), 2.69-2.54 (m, 3H), 2.46 (ddd, J=26.1, 11.5, 4.2 Hz, 3H), 1.99 (h, J=3.8 Hz, 2H), 1.82 (dt, J=13.4, 3.0 Hz, 1H), 1.64-1.52 (m, 1H), 1.38 (t, J=7.0 Hz, 3H), 1.28 (d, J=6.4 Hz, 3H). ESI MS for $C_{25}H_{37}N_9O_5$, $[M+H]^+$calcd=544.3, found=544.3.

Example 46: 2-morpholinopropyl (2-((R)-3-(3-(5-ethoxypyrazin-2-yl)-1-methylureido)piperidin-1-yl) pyrimidin-4-yl)carbamate

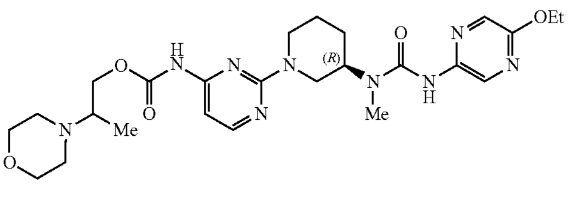

The title compound was synthesized in a similar fashion to Example 1 (Steps 1-5, using 2-morpholinopropan-1-ol in step 1). $^1$H NMR (400 MHz, MeOD) δ 8.61 (t, J=1.3 Hz, 1H), 8.22 (d, J=5.8 Hz, 1H), 8.03 (d, J=1.5 Hz, 1H), 7.22 (d, J=5.7 Hz, 1H), 4.73-4.64 (m, 1H), 4.59 (dd, J=12.7, 3.9 Hz, 1H), 4.52-4.22 (m, 3H), 4.08 (ddd, J=11.5, 5.2, 2.4 Hz, 1H), 3.93 (d, J=9.1 Hz, 1H), 3.65 (td, J=4.7, 2.1 Hz, 4H), 3.02 (s, 4H), 2.95-2.82 (m, 2H), 2.61 (tdd, J=15.8, 8.2, 4.5 Hz, 4H), 1.99 (dq, J=9.3, 3.8 Hz, 2H), 1.87-1.79 (m, 1H), 1.68-1.51 (m, 1H), 1.38 (t, J=7.0 Hz, 3H), 1.08 (dd, J=6.8, 2.3 Hz, 3H). ESI MS for $C_{25}H_{37}N_9O_5$, $[M+H]^+$calcd=544.3, found=544.3.

Example 47: (2S,4R,6R)-rel-1,2,6-trimethylpiperidin-4-yl (2-((3S,4r)-3-(3-(5-ethoxypyrazin-2-yl)-1-methylureido)-4-fluoropiperidin-1-yl)pyrimidin-4-yl)carbamate

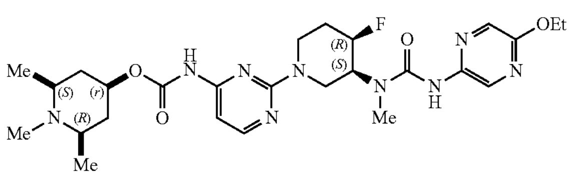

The title compound was synthesized in a similar fashion to Example 18 (Steps 1-10, using tert-butyl (2S,4R,6R)-rel-4-hydroxy-2,6-dimethylpiperidine-1-carboxylate in Step 7). $^1$H NMR (400 MHz, MeOD) δ 8.51 (d, J=1.5 Hz, 1H), 8.19 (d, J=5.7 Hz, 1H), 7.94 (d, J=1.5 Hz, 1H), 7.19 (d, J=5.7 Hz, 1H), 4.73 (td, J=11.4, 5.6 Hz, 1H), 4.66-4.55 (m, 2H), 4.35 (q, J=7.0 Hz, 2H), 4.20 (d, J=9.0 Hz, 1H), 3.54 (t, J=12.3 Hz, 1H), 3.25-3.12 (m, 5H), 2.33 (d, J=23.1 Hz, 5H), 2.04 (d, J=10.3 Hz, 3H), 1.87 (dd, J=41.3, 11.7 Hz, 1H), 1.47 (q, J=12.0 Hz, 2H), 1.38 (t, J=7.0 Hz, 3H), 1.21 (d, J=6.3 Hz, 6H). ESI MS for $C_{26}H_{38}FN_9O_4$, $[M+H]^+$calcd=560.3, found=560.3.

Example 48: (2R,6R)-rel-1,2,6-trimethylpiperidin-4-yl (2-((3S,4R)-3-(3-(5-ethoxypyrazin-2-yl)-1-methylureido)-4-fluoropiperidin-1-yl)pyrimidin-4-yl)carbamate

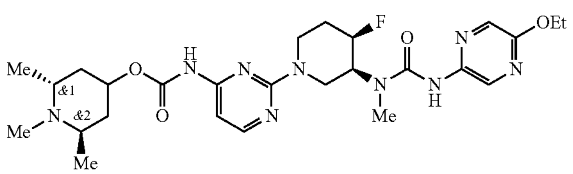

The title compound was synthesized in a similar fashion to Example 18 (Steps 1-10, using tert-butyl (2R,6R)-rel-4-hydroxy-2,6-dimethylpiperidine-1-carboxylate in Step 7). $^1$H NMR (400 MHz, MeOD) δ 8.51 (d, J=1.4 Hz, 1H), 8.20 (d, J=5.7 Hz, 1H), 7.93 (dd, J=4.3, 1.4 Hz, 1H), 7.19 (dd, J=5.7, 0.8 Hz, 1H), 5.00 (td, J=10.3, 5.1 Hz, 1H), 4.63 (d, J=12.8 Hz, 2H), 4.35 (qd, J=7.1, 2.4 Hz, 2H), 4.25 (dd, J=30.9, 10.2 Hz, 1H), 3.54 (t, J=12.3 Hz, 1H), 3.24-3.12 (m, 5H), 2.81 (s, 1H), 2.34 (s, 3H), 2.04 (t, J=13.9 Hz, 2H), 1.93 (d, J=12.7 Hz, 2H), 1.86-1.73 (m, 1H), 1.52-1.43 (m, 1H), 1.38 (t, J=7.1 Hz, 4H), 1.13 (d, J=6.7 Hz, 6H). ESI MS for $C_{26}H_{38}FN_9O_4$, $[M+H]^+$calcd=560.3, found=560.3.

Example 49: 1-methylpiperidin-4-yl (2-((3S,4R)-4-fluoro-3-(1-methyl-3-(4-methylthiazol-2-yl)ureido) piperidin-1-yl)pyrimidin-4-yl)carbamate

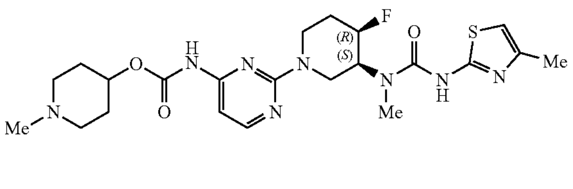

The title compound was synthesized in a similar fashion to Example 18 (Steps 1-9, using 1-methylpiperidin-4-ol in Step 7 and phenyl (4-methylthiazol-2-yl)carbamate in step 9, which was itself prepared in a similar fashion to Example 1 Step 4 with 2-amino-4-methylthiazole.). $^1$H NMR (400 MHz, MeOD) δ 8.21 (t, J=5.6 Hz, 1H), 7.27 (dd, J=6.1, 2.5 Hz, 1H), 6.38 (s, 1H), 5.05 (d, J=49.6 Hz, 2H), 4.61 (t, J=15.5 Hz, 2H), 4.43 (d, J=30.8 Hz, 1H), 3.84-3.38 (m, 3H), 3.25-3.16 (m, 3H), 3.12 (d, J=1.7 Hz, 3H), 2.89 (d, J=2.8 Hz, 3H), 2.34 (d, J=14.0 Hz, 1H), 2.22 (s, 3H), 2.18 (s, 1H), 2.07 (s, 2H), 1.99-1.76 (m, 2H). ESI MS for $C_{22}H_{31}FN_8O_3S$, $[M+H]^+$calcd=507.2, found=507.2.

Example 50: (tetrahydro-1H-pyrrolizin-7a(5H)-yl) methyl (S)-(2-(3-(3-(5-ethoxypyrazin-2-yl)-1-methylureido)-4,4-difluoropiperidin-1-yl)pyrimidin-4-yl) carbamate

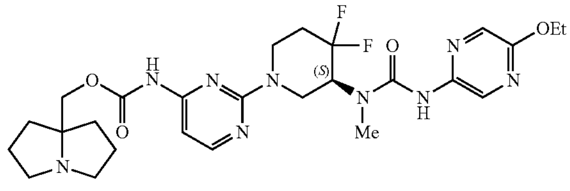

The title compound was synthesized in a similar fashion to Example 11 (Steps 1-7, using (tetrahydro-1H-pyrrolizin-7a(5H)-yl)methanol in Step 5). $^1$H NMR (400 MHz, MeOD) δ 8.49 (d, J=1.5 Hz, 1H), 8.23 (d, J=5.7 Hz, 1H), 7.92 (d, J=1.4 Hz, 1H), 7.34-7.22 (m, 1H), 4.80 (m, 2H), 4.61 (d, J=26.0 Hz, 1H), 4.35 (q, J=7.0 Hz, 2H), 4.07 (s, 2H), 3.52-3.42 (m, 1H), 3.22-3.13 (m, 7H), 2.81 (s, 2H), 2.27-1.67 (m, 10H), 1.38 (t, J=7.0 Hz, 3H). ESI MS for $C_{26}H_{36}F_2N_9O_4$, $[M+H]^+$calcd=576.3, found=576.3.

Example 51: (S)-1-(pyrrolidin-1-yl)propan-2-yl (2-((S)-3-(3-(5-ethoxypyrazin-2-yl)-1-methylureido)-4,4-difluoropiperidin-1-yl)pyrimidin-4-yl)carbamate

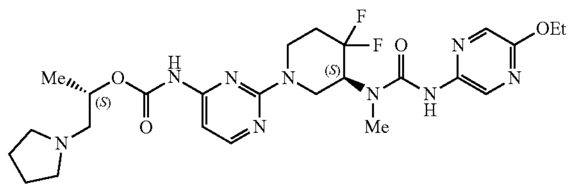

The title compound was synthesized in a similar fashion to Example 11 (Steps 1-7, using (S)-1-(pyrrolidin-1-yl) propan-2-ol in Step 5). $^1$H NMR (400 MHz, MeOD) δ 8.57-8.47 (m, 1H), 8.22 (d, J=5.7 Hz, 1H), 7.93 (d, J=1.4 Hz, 1H), 7.25 (d, J=5.8 Hz, 1H), 5.08 (td, J=7.8, 3.4 Hz, 1H), 4.80 (m, 2H), 4.60 (d, J=22.2 Hz, 1H), 4.35 (q, J=7.0 Hz, 2H), 3.52-3.41 (m, 1H), 3.16 (d, J=2.1 Hz, 4H), 2.86 (t, J=10.9 Hz, 1H), 2.69 (m, 5H), 2.42-1.89 (m, 2H), 1.83 (d, J=7.0 Hz, 4H), 1.38 (t, J=7.1 Hz, 3H), 1.29 (d, J=6.4 Hz, 3H). ESI MS for $C_{25}H_{35}F_2N_9O_4$, $[M+H]^+$calcd=564.3, found=564.3.

Example 52: 2-methyl-1-(pyrrolidin-1-yl)propan-2-yl (S)-(2-(3-(3-(5-ethoxypyrazin-2-yl)-1-methylureido)-4,4-difluoropiperidin-1-yl)pyrimidin-4-yl) carbamate

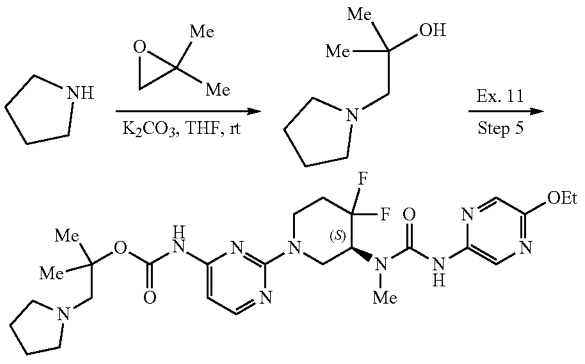

The title compound was synthesized in a similar fashion to Example 11 (Steps 1-7, using 2-methyl-1-(pyrrolidin-1-yl)propan-2-ol in Step 5). To prepare 2-methyl-1-(pyrrolidine-1-yl)propan-2-ol, dissolve and stir pyrrolidine (0.25 mL, 3 mmol) and $K_2CO_3$ (622 mg, 4.5 mmol) in THF (3 mL, 1 M) before adding isobutylene oxide (0.27 mL, 3 mmol) dropwise at room temperature. After complete consumption of starting material, the reaction was filtered through CELITE® and concentrated. Crude 2-methyl-1-(pyrrolidin-1-yl)propan-2-ol was used without further purification. $^1$H NMR (400 MHz, MeOD) δ 8.49 (d, J=1.4 Hz, 1H), 8.24 (d, J=5.8 Hz, 1H), 7.93 (d, J=1.4 Hz, 1H), 7.26 (d, J=5.8 Hz, 1H), 4.79 (d, J=11.4 Hz, 2H), 4.64 (dd, J=26.8, 11.3 Hz, 1H), 4.35 (q, J=7.0 Hz, 2H), 3.78 (d, J=14.6 Hz, 2H), 3.65 (s, 2H), 3.54-3.44 (m, 1H), 3.28-3.04 (m, 6H), 2.29-2.11 (m, 3H), 2.11-1.92 (m, 3H), 1.67 (d, J=1.9 Hz, 6H), 1.38 (t, J=7.1 Hz, 3H). ESI MS for $C_{26}H_{37}F_2N_9O_4$, $[M+H]^+$calcd=578.3, found=578.3.

Example 53: cis-3-(pyrrolidin-1-yl)cyclobutyl (2-((S)-3-(3-(5-ethoxypyrazin-2-yl)-1-methylureido)-4,4-difluoropiperidin-1-yl)pyrimidin-4-yl)carbamate

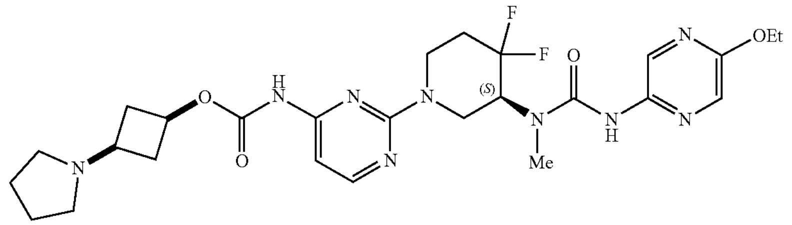

The title compound was synthesized in a similar fashion to Example 11 (Steps 1-7, using cis-3-pyrrolidinyl-cyclobutan-1-ol in Step 5). $^1$H NMR (400 MHz, MeOD) δ 8.50 (d, J=1.4 Hz, 1H), 8.21 (d, J=5.7 Hz, 1H), 7.93 (d, J=1.4 Hz, 1H), 7.21 (d, J=5.7 Hz, 1H), 4.83-4.72 (m, 3H), 4.60 (dd, J=26.7, 11.0 Hz, 1H), 4.35 (q, J=7.1 Hz, 2H), 3.51-3.41 (m, 1H), 3.16 (d, J=2.1 Hz, 4H), 2.98-2.90 (m, 1H), 2.79-2.65 (m, 6H), 2.26-1.84 (m, 8H), 1.38 (t, J=7.1 Hz, 3H). ESI MS for $C_{26}H_{35}F_2N_9O_4$, $[M+H]^+$calcd=576.3, found=576.3.

Example 54: (1-(pyrrolidin-1-yl)cyclopropyl)methyl (S)-(2-(3-(3-(5-ethoxypyrazin-2-yl)-1-methylureido)-4,4-difluoropiperidin-1-yl)pyrimidin-4-yl) carbamate

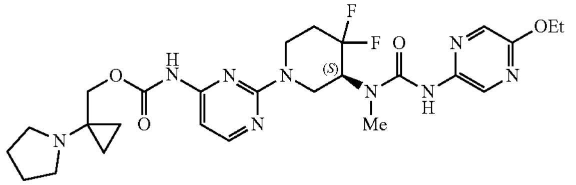

The title compound was synthesized in a similar fashion to Example 11 (Steps 1-7, using (1-(pyrrolidin-1-yl)cyclopropyl)methanol in Step 5). $^1$H NMR (400 MHz, MeOD) δ 8.49 (dd, J=4.0, 1.5 Hz, 1H), 8.24-8.11 (m, 1H), 7.91 (dd, J=15.1, 1.5 Hz, 1H), 7.24 (d, J=5.7 Hz, 1H), 4.77 (m, 1H), 4.60 (d, J=17.9 Hz, 1H), 4.40-4.25 (m, 4H), 3.52-3.41 (m, 1H), 3.20-2.99 (m, 6H), 2.87-2.76 (m, 4H), 1.74 (p, J=3.2 Hz, 4H), 1.38 (td, J=7.0, 1.3 Hz, 4H), 1.24 (dd, J=44.7, 6.7 Hz, 1H), 0.82-0.67 (m, 3H). ESI MS for $C_{26}H_{35}F_2N_9O_4$, $[M+H]^+$calcd=576.3, found=576.3.

Example 55: trans-2-(pyrrolidin-1-yl)cyclopentyl (2-((S)-3-(3-(5-ethoxypyrazin-2-yl)-1-methylureido)-4,4-difluoropiperidin-1-yl)pyrimidin-4-yl) carbamate

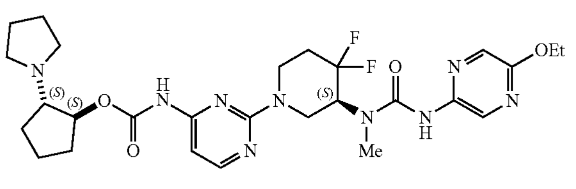

The title compound was synthesized in a similar fashion to Example 11 (Steps 1-7, using trans-2-(pyrrolidin-1-yl) cyclopentan-1-ol in Step 5). $^1$H NMR (400 MHz, MeOD) δ 8.49 (d, J=1.5 Hz, 1H), 8.22 (d, J=5.7 Hz, 1H), 7.91 (dd, J=13.5, 1.4 Hz, 1H), 7.24 (d, J=5.7 Hz, 1H), 5.31-5.07 (m, 1H), 4.80 (m, 2H), 4.60 (d, J=21.1 Hz, 1H), 4.34 (qd, J=7.1, 4.0 Hz, 2H), 3.55-3.41 (m, 1H), 3.16 (s, 4H), 3.03 (m, 2H), 2.82 (m, 4H), 2.21-1.94 (m, 4H), 1.91-1.84 (m, 3H), 1.84-1.68 (m, 3H), 1.62 (dq, J=12.8, 8.5 Hz, 1H), 1.38 (td, J=7.1, 1.5 Hz, 3H). ESI MS for $C_{27}H_{37}F_2N_9O_4$, $[M+H]^+$ calcd=590.3, found=590.3.

Example 56: (3S,4R)-4-(pyrrolidin-1-yl)tetrahydrofuran-3-yl (2-((S)-3-(3-(5-ethoxypyrazin-2-yl)-1-methylureido)-4,4-difluoropiperidin-1-yl)pyrimidin-4-yl)carbamate

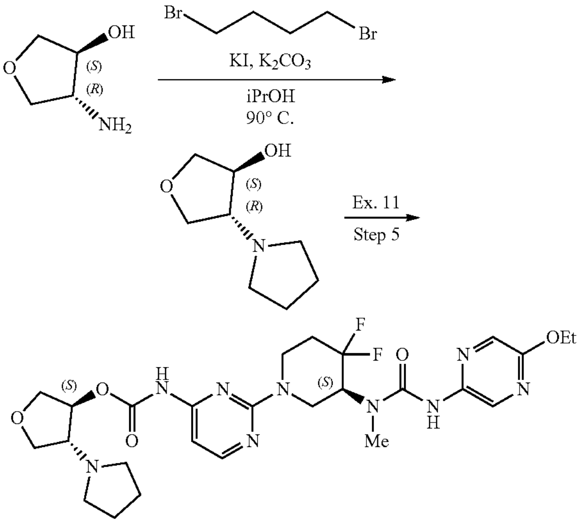

The title compound was synthesized in a similar fashion to Example 11 (Steps 1-7, using (3S,4R)-4-(pyrrolidin-1-yl) tetrahydrofuran-3-ol in Step 5). To prepare (3S,4R)-4-(pyrrolidin-1-yl)tetrahydrofuran-3-ol, (3S,4R)-4-aminotetrahydrofuran-3-ol (230 mg, 2.2 mmol), $K_2CO_3$ (800 mg, 5.8 mmol), and KI (74 mg, 0.45 mmol) were suspended in iPrOH (5.5 mL, 0.4 M) before adding 1,4-dibromobutane (0.32 mL, 2.68 mmol). The reaction was refluxed at 90° C. for 24 h. The reaction was cooled to room temperature prior to filtering through CELITE® and concentrating. Crude (3S,4R)-4-(pyrrolidin-1-yl)tetrahydrofuran-3-ol was used without further purification. $^1$H NMR (400 MHz, MeOD) δ 8.50 (d, J=1.4 Hz, 1H), 8.23 (d, J=5.7 Hz, 1H), 7.93 (d, J=1.4 Hz, 1H), 7.23 (d, J=5.7 Hz, 1H), 5.29 (dt, J=5.1, 2.4 Hz, 1H), 4.80 (m, 2H), 4.59 (dt, J=25.1, 11.8 Hz, 1H), 4.35 (q, J=7.1 Hz, 2H), 4.08 (ddd, J=16.1, 10.1, 5.8 Hz, 2H), 3.84 (dd, J=10.6, 2.4 Hz, 1H), 3.76 (dd, J=9.6, 5.4 Hz, 1H), 3.46 (t, J=12.2 Hz, 1H), 3.22-3.07 (m, 5H), 2.75 (d, J=5.8 Hz, 4H), 2.34-1.91 (m, 2H), 1.88-1.82 (m, 4H), 1.38 (t, J=7.1 Hz, 3H). ESI MS for $C_{26}H_{35}F_2N_9O_5$, $[M+H]^+$calcd=592.3, found=592.3.

Example 57: (3R,4R)-4-(pyrrolidin-1-yl)tetrahydrofuran-3-yl (2-((S)-3-(3-(5-ethoxypyrazin-2-yl)-1-methylureido)-4,4-difluoropiperidin-1-yl)pyrimidin-4-yl)carbamate

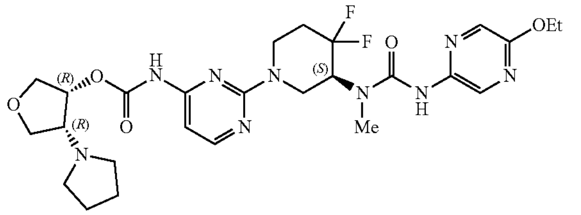

The title compound was synthesized in a similar fashion to Example 11 (Steps 1-7, using (3R,4R)-4-(pyrrolidin-1-yl)tetrahydrofuran-3-ol in Step 5). To prepare (3R,4R)-4-(pyrrolidin-1-yl)tetrahydrofuran-3-ol, (3R,4R)-4-aminotetrahydrofuran-3-ol (230 mg, 2.2 mmol), $K_2CO_3$ (800 mg, 5.8 mmol), and KI (74 mg, 0.45 mmol) were suspended in iPrOH (5.5 mL, 0.4 M) before adding 1,4-dibromobutane (0.32 mL, 2.68 mmol). The reaction was refluxed at 90° C. for 24 h. The reaction was cooled to room temperature prior to filtering through CELITE® and concentrating. Crude (3R,4R)-4-(pyrrolidin-1-yl)tetrahydrofuran-3-ol was used without further purification. $^1$H NMR (400 MHz, MeOD) δ 8.51 (d, J=1.4 Hz, 1H), 8.23 (d, J=5.7 Hz, 1H), 7.93 (d, J=1.4 Hz, 1H), 7.23 (d, J=5.7 Hz, 1H), 5.28 (t, J=4.1 Hz, 1H), 4.83-4.73 (m, 2H), 4.61 (dd, J=25.5, 11.2 Hz, 1H), 4.35 (q, J=7.0 Hz, 2H), 4.12 (dd, J=10.8, 3.6 Hz, 1H), 4.05 (t, J=7.6 Hz, 1H), 3.94 (d, J=10.9 Hz, 1H), 3.77 (dd, J=10.3, 7.7 Hz, 1H), 3.48 (dd, J=13.0, 11.4 Hz, 1H), 3.26-3.08 (m, 4H), 2.98 (ddt, J=11.1, 7.2, 4.1 Hz, 1H), 2.75-2.57 (m, 4H), 2.27-1.90 (m, 2H), 1.89-1.79 (m, 4H), 1.38 (t, J=7.1 Hz, 3H). ESI MS for $C_{26}H_{35}F_2N_9O_5$, $[M+H]^+$calcd=592.3, found=592.3.

Example 58: (3S,4S)-4-(pyrrolidin-1-yl)tetrahydrofuran-3-yl (2-((S)-3-(3-(5-ethoxypyrazin-2-yl)-1-methylureido)-4,4-difluoropiperidin-1-yl)pyrimidin-4-yl)carbamate

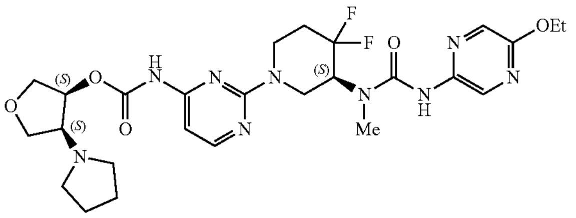

The title compound was synthesized in a similar fashion to Example 11 (Steps 1-7, using (3S,4S)-4-(pyrrolidin-1-yl) tetrahydrofuran-3-ol in Step 5). To prepare (3S,4S)-4-(pyrrolidin-1-yl)tetrahydrofuran-3-ol, (3S,4S)-4-aminotetrahydrofuran-3-ol (230 mg, 2.2 mmol), $K_2CO_3$ (800 mg, 5.8 mmol), and KI (74 mg, 0.45 mmol) were suspended in iPrOH (5.5 mL, 0.4 M) before adding 1,4-dibromobutane (0.32 mL, 2.68 mmol). The reaction was refluxed at 90° C. for 24 h. The reaction was cooled to room temperature prior to filtering through CELITE® and concentrating. Crude (3S,4S)-4-(pyrrolidin-1-yl)tetrahydrofuran-3-ol was used without further purification. $^1$H NMR (400 MHz, MeOD) δ 8.51 (d, J=1.4 Hz, 1H), 8.24 (d, J=5.7 Hz, 1H), 7.92 (d, J=1.4 Hz, 1H), 7.22 (d, J=5.6 Hz, 1H), 5.29 (t, J=4.1 Hz, 1H), 4.83-4.74 (m, 2H), 4.60 (dd, J=27.8, 10.6 Hz, 1H), 4.34 (q, J=7.1 Hz, 2H), 4.12 (dd, J=10.9, 3.6 Hz, 1H), 4.04 (t, J=7.6 Hz, 1H), 3.93 (d, J=10.9 Hz, 1H), 3.76 (dd, J=10.2, 7.8 Hz, 1H), 3.48 (t, J=12.2 Hz, 1H), 3.24-3.13 (m, 4H), 3.00 (s, 1H), 2.66 (d, J=23.2 Hz, 4H), 2.28-1.91 (m, 2H), 1.84-1.76 (m, 4H), 1.38 (t, J=7.0 Hz, 3H). ESI MS for $C_{26}H_{35}F_2N_9O_5$, $[M+H]^+$calcd=592.3, found=592.3.

Example 59: 1-methylpiperidin-4-yl (S)-(2-(4,4-difluoro-3-(1-methyl-3-phenylureido)piperidin-1-yl) pyrimidin-4-yl)carbamate

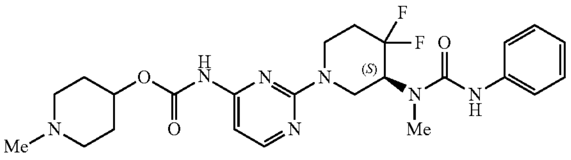

The title compound was synthesized in a similar fashion to Example 11 (Steps 1-7, using 1-methylpiperidin-4-ol in Step 5 and phenyl phenylcarbamate in step 7, which was itself prepared in a similar fashion to Example 1 Step 4 with aniline). $^1$H NMR (400 MHz, MeOD) δ 8.25-8.17 (m, 1H), 7.37 (t, J=5.5 Hz, 2H), 7.25 (dd, J=16.4, 5.4 Hz, 3H), 7.05 (p, J=5.8 Hz, 1H), 6.78 (d, J=12.2 Hz, 1H), 4.79 (d, J=15.3 Hz, 2H), 4.70-4.55 (m, 1H), 3.50-3.39 (m, 1H), 3.22-3.11 (m, 4H), 2.95 (m, 2H), 2.70 (m, 2H), 2.51 (s, 3H), 2.16 (s, 1H), 1.96 (m, 5H). ESI MS for $C_{24}H_{31}F_2N_7O_3$, $[M+H]^+$ calcd=504.3, found=504.3.

Example 60: 2-[(R)-3-[3-(5-ethoxy-2-pyrazinyl)-1-methylureido]-1-piperidyl]-4-pyrimidinyl [(S)-5-oxo-2-pyrrolidinyl]methanecarbamate

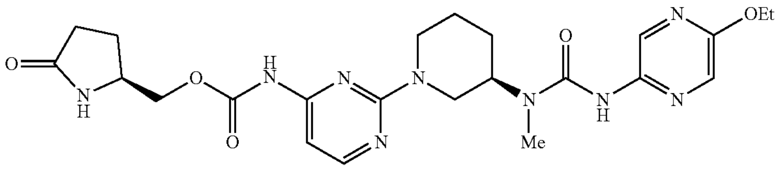 [SMILES: CCOc1cnc(NC(=O)N(C)[C@@H]2CCCN(c3nccc(NC(=O)OC[C@@H]4CCC(=O)N4)n3)C2)cn1]

The title compound was synthesized in a similar fashion to Example 2 (Step 1-4 (Part 1)) using (5S)-5-(hydroxymethyl)-2-pyrrolidinone in Step 2 and phenylmethyl N-methyl-N-(3R)-3-piperidinylcarbamate in step 3 (part1). $^{1}$H NMR (400 MHz, $CDCl_3$) δ 9.97 (bs, 1H), 8.95 (d, J=1.4 Hz, 1H), 8.30 (d, J=5.6 Hz, 1H), 8.07 (s, 1H), 7.99 (d, J=0.9 Hz, 1H), 7.28 (d, J=5.4 Hz, 1H), 5.74 (s, 1H), 4.80 (d, J=13.6 Hz, 1H), 4.49 (d, J=13.4 Hz, 1H), 4.46-4.33 (m, 3H), 4.13 (dd, J=11.3, 6.8 Hz, 1H), 4.00 (d, J=7.0 Hz, 1H), 3.64 (s, 1H), 3.04 (s, 3H), 3.00-2.83 (m, 2H), 2.41-2.24 (m, 3H), 2.24-2.09 (m, 1H), 2.05-1.91 (m, 1H), 1.91-1.79 (m, 2H), 1.62 (d, J=12.9 Hz, 1H), 1.41 (t, J=7.0 Hz, 3H). ESI MS $[M+H]^+$ for $C_{23}H_{31}N_{905}$, calcd 514.2, found 513.7

Example 61: 2-[(R)-3-[3-(5-ethoxy-2-pyrazinyl)-1-methylureido]-1-piperidyl]-4-pyrimidinyl [(S)-1-methyl-5-oxo-2-pyrrolidinyl]methanecarbamate

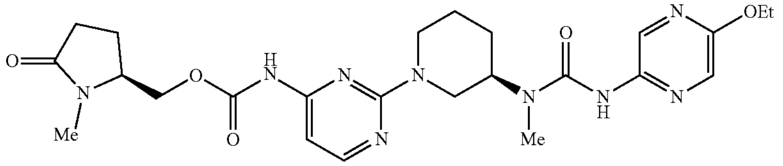 [SMILES: CCOc1cnc(NC(=O)N(C)[C@@H]2CCCN(c3nccc(NC(=O)OC[C@@H]4CCC(=O)N4C)n3)C2)cn1]

The title compound was synthesized in a similar fashion to Example 2 (Step 1-Step 4 Part 1, using (5S)-5-(hydroxymethyl)-1-methyl-2-pyrrolidinone in Step 2 and phenylmethyl N-methyl-N-(3R)-3-piperidinylcarbamate in step 3 (part1). $^{1}$H NMR (400 MHz, DMSO-$d_6$) δ 10.25 (s, 1H), 8.89 (s, 1H), 8.57 (d, J=1.5 Hz, 1H), 8.22 (d, J=5.6 Hz, 1H), 8.01 (d, J=1.4 Hz, 1H), 7.03 (d, J=5.6 Hz, 1H), 4.60 (dd, J=27.5, 12.3 Hz, 2H), 4.37 (dd, J=11.7, 3.2 Hz, 1H), 4.30 (q, J=7.0 Hz, 2H), 4.11-3.98 (m, 2H), 3.75 (dq, J=7.5, 3.8 Hz, 1H), 3.00-2.89 (m, 4H), 2.79-2.68 (m, 4H), 2.47-2.42 (m, 1H), 2.18-2.02 (m, 2H), 1.86-1.71 (m, 4H), 1.59-1.41 (m, 1H), 1.32 (t, J=7.0 Hz, 3H). ESI MS $[M+H]^+$ for $C_{24}H_{33}N_9O_5$, calcd 528.3, found 528.2

Example 62: 2-[(R)-3-[3-(5-ethoxy-2-pyrazinyl)-1-methylureido]-1-piperidyl]-4-pyrimidinyl [(S)-1,4-dioxan-2-yl]methanecarbamate

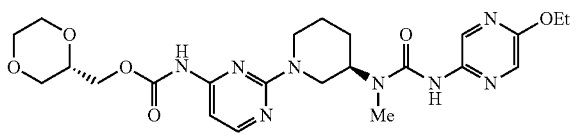 [SMILES: CCOc1cnc(NC(=O)N(C)[C@@H]2CCCN(c3nccc(NC(=O)OC[C@@H]4COCCO4)n3)C2)cn1]

The title compound was synthesized in a similar fashion to Example 2 (Step 1-4 (Part 1) using (2R)-1,4-dioxane-2-methanol in Step 2 and phenylmethyl N-methyl-N-(3R)-3-piperidinylcarbamate in step 3 (part1). $^{1}$H NMR (400 MHz, DMSO-$d_6$) δ 10.20 (s, 1H), 8.83 (s, 1H), 8.59 (d, J=1.5 Hz, 1H), 8.23 (d, J=5.6 Hz, 1H), 8.03 (d, J=1.5 Hz, 1H), 7.02 (d, J=5.6 Hz, 1H), 4.58 (dd, J=36.2, 13.0 Hz, 2H), 4.30 (q, J=7.0 Hz, 2H), 4.11-4.05 (m, 2H), 4.05-3.95 (m, 1H), 3.81-3.70 (m, 3H), 3.68-3.54 (m, 2H), 3.46 (td, J=10.7, 2.7 Hz, 1H), 3.39-3.33 (m, 1H), 2.97 (d, J=11.9 Hz, 1H), 2.92 (s, 3H), 2.74 (t, J=12.7 Hz, 1H), 1.93-1.67 (m, 3H), 1.60-1.39 (m, 1H), 1.33 (t, J=7.0 Hz, 3H). ESI MS $[M+H]^+$ for $C_{23}H_{32}N_8O_6$, calcd 517.2, found 517.2

Example 63: 2-[(R)-3-[3-(5-ethoxy-2-pyrazinyl)-1-methylureido]-1-piperidyl]-4-pyrimidinyl [(S)-1-methyl-2-pyrrolidinyl]methanecarbamate

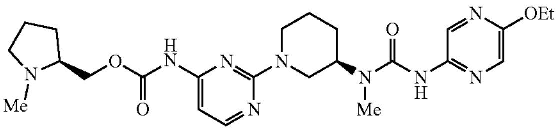 [SMILES: CCOc1cnc(NC(=O)N(C)[C@@H]2CCCN(c3nccc(NC(=O)OC[C@@H]4CCCN4C)n3)C2)cn1]

The title compound was synthesized in a similar fashion to Example 2 (Step 1-4 (Part 1)) using (2S)-1-methyl-2-pyrrolidinemethanol in Step 2 and phenylmethyl N-methyl-N-(3R)-3-piperidinylcarbamate in step 3 (part1). $^{1}$H NMR (400 MHz, DMSO-$d_6$) δ 10.14 (s, 1H), 8.85 (s, 1H), 8.58 (d, J=1.5 Hz, 1H), 8.22 (d, J=5.6 Hz, 1H), 8.02 (d, J=1.5 Hz, 1H), 7.04 (d, J=5.6 Hz, 1H), 4.59 (dd, J=32.5, 13.3 Hz, 2H), 4.30 (q, J=7.0 Hz, 2H), 4.16-3.91 (m, 3H), 3.00-2.89 (m, 5H), 2.73 (t, J=12.6 Hz, 1H), 2.45-2.26 (m, 4H), 2.23-2.06 (m, 1H), 1.95-1.73 (m, 4H), 1.71-1.43 (m, 4H), 1.33 (t, J=7.0 Hz, 3H). ESI MS $[M+H]^+$ for $C_{24}H_{35}N_9O_4$, calcd 514.3, found 514.3

Example 64: 2-[(R)-3-[3-(5-ethoxy-2-pyrazinyl)-1-methylureido]-1-piperidyl]-4-pyrimidinyl [(R)-1-methyl-2-pyrrolidinyl]methanecarbamate

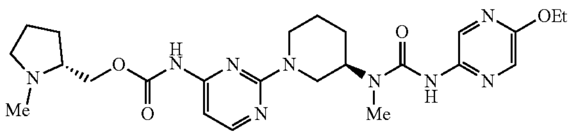 [SMILES: CCOc1cnc(NC(=O)N(C)[C@@H]2CCCN(c3nccc(NC(=O)OC[C@H]4CCCN4C)n3)C2)cn1]

The title compound was synthesized in a similar fashion to Example 2 Step 1-4 (Part 1) using (2R)-1-methyl-2- pyrrolidinemethanol in Step 2 and phenylmethyl N-methyl-N-(3R)-3-piperidinylcarbamate in step 3 (part1). $^1$H NMR (400 MHz, DMSO-$d_6$) δ 10.12 (s, 1H), 8.84 (s, 1H), 8.58 (d, J=1.4 Hz, 1H), 8.22 (d, J=5.6 Hz, 1H), 8.03 (d, J=1.5 Hz, 1H), 7.04 (d, J=5.6 Hz, 1H), 4.59 (dd, J=34.5, 12.3 Hz, 2H), 4.30 (q, J=7.0 Hz, 2H), 4.07-3.92 (m, 3H), 2.99-2.88 (m, 5H), 2.73 (t, J=12.7 Hz, 1H), 2.41 (dq, J=11.1, 5.6 Hz, 1H), 2.31 (s, 3H), 2.15 (q, J=8.7 Hz, 1H), 1.92-1.71 (m, 4H), 1.67-1.42 (m, 4H), 1.33 (t, J=7.0 Hz, 3H). ESI MS $[M+H]^+$ for $C_{24}H_{35}N_9O_4$, calcd 514.3, found 514.3

Example 65: 2-[(3S,4R)-3-[3-(5-ethoxy-2-pyrazinyl)-1-methylureido]-4-fluoro-1-piperidyl]-4-pyrimidinyl (1-methyl-4-piperidyl)methanecarbamate

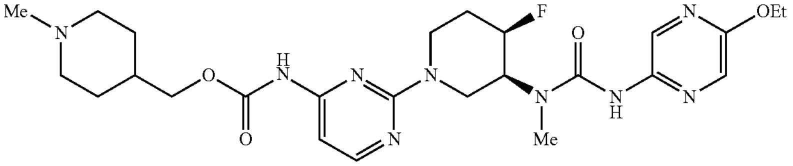 [SMILES: CCOc1cnc(NC(=O)N(C)[C@H]2CN(c3nccc(NC(=O)OCC4CCN(C)CC4)n3)CC[C@H]2F)cn1]

The title compound was synthesized in a similar fashion to Example 18 (Step 1-9) using 1-methyl-4-piperidinemethanol in Step 7. $^1$H NMR (400 MHz, Methanol-$d_4$) δ 8.41 (s, 1H), 8.11 (d, J=5.7 Hz, 1H), 7.84 (s, 1H), 7.10 (d, J=5.7 Hz, 1H), 4.97 (d, J=51.2 Hz, 1H), 4.54 (dt, J=14.5, 7.0 Hz, 2H), 4.25 (q, J=7.1 Hz, 2H), 4.21-4.09 (m, 1H), 3.97 (d, J=5.7 Hz, 2H), 3.45 (t, J=12.3 Hz, 1H), 3.14-3.01 (m, 6H), 2.54-2.36 (m, 5H), 1.95 (t, J=13.1 Hz, 1H), 1.88-1.59 (m, 4H), 1.38 (q, J=13.1 Hz, 2H), 1.29 (t, J=7.0 Hz, 3H). ESI MS $[M+H]^+$ for $C_{25}H_{36}FN_9O_4$, calcd 546.3, found 546.3

Example 66: 2-[(3S,4R)-3-[3-(1,3-benzoxazol-2-yl)-1-methylureido]-4-fluoro-1-piperidyl]-4-pyrimidinyl 1-methyl-4-piperidinecarbamate

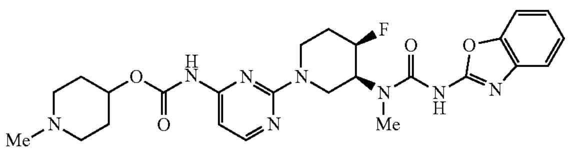 [SMILES: CN1CCC(OC(=O)Nc2ccnc(N3CC[C@@H](F)[C@@H](N(C)C(=O)Nc4nc5ccccc5o4)C3)n2)CC1]

The title compound was synthesized in a similar fashion to Example 6, using phenyl N-2-benzoxazolylcarbamate in Step 5 (which was prepared in a similar fashion to Example 1 Step 4, using 2-benzoxazolamine). $^1$H NMR (400 MHz, Methanol-$d_4$) δ 8.26-8.11 (m, 1H), 7.46-7.31 (m, 2H), 7.31-7.14 (m, 3H), 5.08 (d, J=51.3 Hz, 1H), 4.85-4.74 (m, 1H), 4.74-4.38 (m, 3H), 3.54 (t, J=12.3 Hz, 1H), 3.26-3.05 (m, 4H), 2.90-2.64 (m, 2H), 2.48-2.23 (m, 5H), 2.12-1.88 (m, 4H), 1.86-1.70 (m, 2H). ESI MS $[M+H]^+$ for $C_{25}H_{31}FN_8O_4$, calcd 527.2, found 527.2

Example 67: 2-[(3S,4R)-3-[3-(1H-1,3-benzimidazol-2-yl)-1-methylureido]-4-fluoro-1-piperidyl]-4-pyrimidinyl 1-methyl-4-piperidinecarbamate

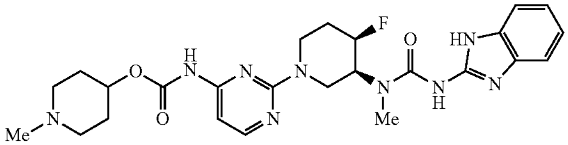 [SMILES: CN1CCC(OC(=O)Nc2ccnc(N3CC[C@@H](F)[C@@H](N(C)C(=O)Nc4nc5ccccc5[nH]4)C3)n2)CC1]

The title compound was synthesized in a similar fashion to Example 6 using phenyl 2-[(tert-butoxycarbonyl)amino]-1H-benzimidazole-1-carboxylate in Step 5 (which was prepared in a similar fashion to Example 1, Step 4 using 1,1-dimethylethyl 2-amino-1H-benzimidazole-1-carboxylate). $^1$H NMR (400 MHz, Methanol-$d_4$) δ 8.23-8.13 (m, 1H), 7.37-7.24 (m, 2H), 7.24-7.16 (m, 1H), 7.17-7.06 (m, 2H), 5.10 (d, J=51.4 Hz, 1H), 4.81-4.74 (m, 1H), 4.73-4.47 (m, 3H), 3.69-3.41 (m, 1H), 3.26-3.08 (m, 4H), 2.83-2.57 (m, 2H), 2.42-2.23 (m, 5H), 2.14-1.84 (m, 4H), 1.84-1.70 (m, 2H). ESI MS $[M+H]^+$ for $C_{25}H_{32}FN_9O_3$, calcd 526.3, found 526.3

Example 68: 2-[(S)-4,4-difluoro-3-[1-methyl-3-(1-thia-3,4-diaza-2-indenyl)ureido]-1-piperidyl]-4-pyrimidinyl 1-methyl-4-piperidinecarbamate

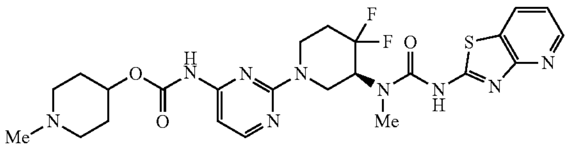 [SMILES: CN1CCC(OC(=O)Nc2ccnc(N3CCC(F)(F)[C@@H](N(C)C(=O)Nc4nc5ncccc5s4)C3)n2)CC1]

The title compound was synthesized in a similar fashion to Example 11 (step 1-7) using N-methyl 4-hydroxy piperidine in step 1 and phenyl N-(thiazolo[4,5-b]pyridin-2-yl) carbamate in Step 7 (which was prepared in a similar fashion to Example 1, Step 4 using thiazolo[4,5-b]pyridin-2-amine). $^1$H NMR (400 MHz, Methanol-$d_4$) δ 8.36-8.19 (m, 1H), 8.19-8.10 (m, 1H), 8.10-7.93 (m, 1H), 7.18-7.12 (m, 1H), 7.12-7.00 (m, 1H), 4.75-4.60 (m, 4H), 3.38 (t, J=11.3 Hz, 1H), 3.17-2.95 (m, 4H), 2.72-2.43 (m, 2H), 2.33-2.20 (m, 2H), 2.17 (s, 3H), 2.14-1.76 (m, 5H), 1.76-1.55 (m, 2H). ESI MS [M+H]$^+$ for $C_{24}H_{29}F_2N_9O_3S$, calcd 562.2, found 562.2

Example 69: 2-[(S)-3-[3-(5-ethoxy-2-pyrazinyl)-1-methylureido]-4,4-difluoro-1-piperidyl]-4-pyrimidinyl 4-methyl-4-piperidinecarbamate

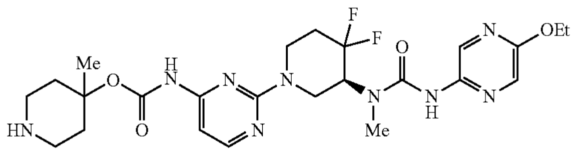 [SMILES: CCOc1cnc(NC(=O)N(C)[C@H]2CN(c3nccc(NC(=O)OC4(C)CCNCC4)n3)CCC2(F)F)cn1]

The title compound was synthesized in a similar fashion to Example 11 Step 1-8 (Part 1) using 1,1-dimethylethyl 4-hydroxy-4-methyl-1-piperidinecarboxylate in Step 5. $^1$H NMR (400 MHz, Methanol-$d_4$) δ 8.50 (s, 1H), 8.27-8.10 (m, 1H), 7.92 (s, 1H), 7.28-7.12 (m, 1H), 4.82-4.76 (m, 2H), 4.72-4.48 (m, 1H), 4.42-4.24 (m, 2H), 3.46 (t, J=12.0 Hz, 1H), 3.19-3.08 (m, 4H), 2.93-2.72 (m, 4H), 2.34-2.10 (m, 3H), 2.12-1.89 (m, 1H), 1.62 (t, J=10.0 Hz, 2H), 1.56 (s, 3H), 1.43-1.33 (m, 3H). ESI MS [M+H]$^+$ for $C_{24}H_{33}F_2N_9O_4$, calcd 550.3, found 550.3

Example 70: 2-[(S)-3-[3-(5-ethoxy-2-pyrazinyl)-1-methylureido]-4,4-difluoro-1-piperidyl]-4-pyrimidinyl 1-ethyl-4-methyl-4-piperidinecarbamate

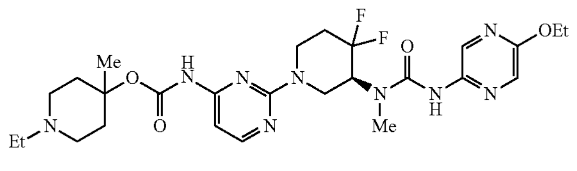 [SMILES: CCOc1cnc(NC(=O)N(C)[C@H]2CN(c3nccc(NC(=O)OC4(C)CCN(CC)CC4)n3)CCC2(F)F)cn1]

The title compound was synthesized in a similar fashion to Example 11 using 1,1-dimethylethyl 4-hydroxy-4-methyl-1-piperidinecarboxylate in Step 5. The ethyl group was installed in a similar fashion to Step 8, Part 2 using acetaldehyde. $^1$H NMR (400 MHz, Methanol-$d_4$) δ 8.50 (s, 1H), 8.23-8.16 (m, 1H), 7.92 (s, 1H), 7.24-7.16 (m, 1H), 4.83-4.74 (m, 2H), 4.73-4.47 (m, 1H), 4.47-4.18 (m, 2H), 3.46 (t, J=12.2 Hz, 1H), 3.22-3.10 (m, 4H), 2.76-2.65 (m, 2H), 2.50-2.42 (m, 2H), 2.41-2.22 (m, 4H), 2.22-1.92 (m, 2H), 1.80-1.65 (m, 2H), 1.56 (s, 3H), 1.45-1.32 (m, 3H), 1.15-1.05 (m, 3H). ESI MS [M+H]$^+$ for $C_{26}H_{37}F_2N_9O_4$, calcd 578.3, found 578.3

Example 71: 2-[(3S,4R)-3-[3-(5-ethoxy-2-pyrazinyl)-1-methylureido]-4-fluoro-1-piperidyl]-4-pyrimidinyl 4-methyl-4-piperidinecarbamate

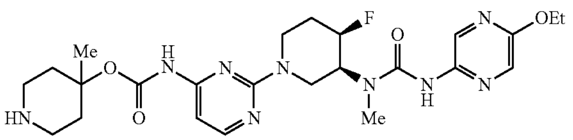 [SMILES: CCOc1cnc(NC(=O)N(C)[C@H]2CN(c3nccc(NC(=O)OC4(C)CCNCC4)n3)CC[C@H]2F)cn1]

The title compound was synthesized in a similar fashion to Example 18 (Step 1-10 (Part 1)) using 1,1-dimethylethyl 4-hydroxy-4-methyl-1-piperidinecarboxylate in Step 7. $^1$H NMR (400 MHz, Methanol-$d_4$) δ 8.51 (d, J=1.4 Hz, 1H), 8.18 (d, J=5.7 Hz, 1H), 7.93 (d, J=1.5 Hz, 1H), 7.17 (d, J=5.7 Hz, 1H), 5.07 (d, J=51.2 Hz, 1H), 4.63 (td, J=12.1, 4.7 Hz, 2H), 4.35 (q, J=7.0 Hz, 2H), 4.30-4.15 (m, 1H), 3.54 (t, J=12.2 Hz, 1H), 3.19 (td, J=13.2, 2.8 Hz, 1H), 3.14 (d, J=1.7 Hz, 3H), 2.92-2.75 (m, 4H), 2.22 (d, J=13.9 Hz, 2H), 2.10-1.98 (m, 1H), 1.87 (dtd, J=43.9, 13.6, 5.0 Hz, 1H), 1.62 (ddd, J=14.7, 10.6, 4.6 Hz, 2H), 1.56 (s, 3H), 1.38 (t, J=7.0 Hz, 3H). ESI MS [M+H]$^+$ for $C_{24}H_{34}FN_9O_4$, calcd 532.3, found 532.3

Example 72: 2-[(S)-3-[3-(5-ethoxy-2-pyrazinyl)-1-methylureido]-4,4-difluoro-1-piperidyl]-4-pyrimidinyl 1-methyl-4-(trifluoromethyl)-4-piperidinecarbamate

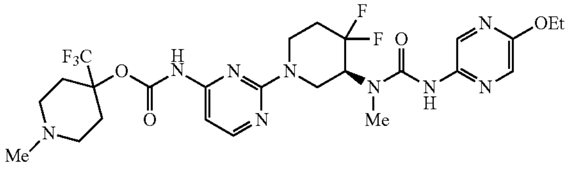 [SMILES: CCOc1cnc(NC(=O)N(C)[C@H]2CN(c3nccc(NC(=O)OC4(C(F)(F)F)CCN(C)CC4)n3)CCC2(F)F)cn1]

The title compound was synthesized in a similar fashion to Example 11 using 1,1-dimethylethyl 4-hydroxy-4-(trifluoromethyl)-1-piperidinecarboxylate in Step 5. $^1$H NMR (400 MHz, Methanol-$d_4$) δ 8.50 (d, J=1.4 Hz, 1H), 8.24 (d, J=5.7 Hz, 1H), 7.92 (d, J=1.4 Hz, 1H), 7.19 (d, J=5.7 Hz, 1H), 4.84-4.76 (m, 2H), 4.76-4.51 (m, 1H), 4.35 (q, J=7.0 Hz, 2H), 3.55-3.37 (m, 1H), 3.20-3.11 (m, 4H), 2.85 (d, J=12.1 Hz, 2H), 2.70-2.52 (m, 2H), 2.30 (s, 3H), 2.24 (dt, J=12.0, 2.3 Hz, 2H), 2.21-2.11 (m, 1H), 2.12-1.97 (m, 1H), 1.92 (td, J=13.4, 4.3 Hz, 2H), 1.38 (t, J=7.0 Hz, 3H). ESI MS [M+H]$^+$ for $C_{25}H_{32}F_5N_9O_4$, calcd 618.2, found 618.3

Example 73: 2-[(S)-3-[3-(5-ethoxy-2-pyrazinyl)-1-methylureido]-4,4-difluoro-1-piperidyl]-4-pyrimidinyl 4-(methoxymethyl)-1-methyl-4-piperidinecarbamate

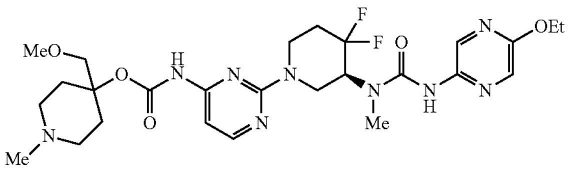 [SMILES: CCOc1cnc(NC(=O)N(C)[C@H]2CN(c3nccc(NC(=O)OC4(COC)CCN(C)CC4)n3)CCC2(F)F)cn1]

The title compound was synthesized in a similar fashion to Example 11 using 1,1-dimethylethyl 4-hydroxy-4-(methoxymethyl)-1-piperidinecarboxylate in Step 5. $^1H$ NMR (400 MHz, Methanol-$d_4$) δ 8.50 (d, J=1.4 Hz, 1H), 8.20 (d, J=5.7 Hz, 1H), 7.93 (d, J=1.4 Hz, 1H), 7.20 (d, J=5.7 Hz, 1H), 4.84-4.76 (m, 2H), 4.61 (dd, J=26.4, 10.9 Hz, 1H), 4.35 (q, J=7.0 Hz, 2H), 3.76 (s, 2H), 3.53-3.42 (m, 1H), 3.35 (s, 3H), 3.22-3.11 (m, 4H), 2.77-2.64 (m, 2H), 2.38 (t, J=12.2 Hz, 2H), 2.35-2.26 (m, 5H), 2.23-2.10 (m, 1H), 2.11-1.90 (m, 1H), 1.83-1.68 (m, 2H), 1.38 (t, J=7.1 Hz, 3H). ESI MS $[M+H]^+$ for $C_{26}H_{37}F_2N_9O_4$, calcd 594.3, found 594.3

Example 74: 2-[(S)-3-[3-(5-ethoxy-2-pyrazinyl)-1-methylureido]-4,4-difluoro-1-piperidyl]-4-pyrimidinyl [(S)-2-methyl-2-pyrrolidinyl]methanecarbamate

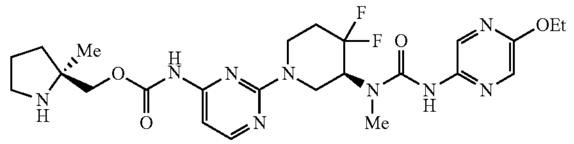 [SMILES: CCOc1cnc(NC(=O)N(C)[C@H]2CN(c3nccc(NC(=O)OC[C@]4(C)CCCN4)n3)CCC2(F)F)cn1]

The title compound was synthesized in a similar fashion to Example 11 (Step 1-Step 8 Part 1) using 1,1-dimethylethyl (2S)-2-(hydroxymethyl)-2-methyl-1-pyrrolidinecarboxylate in Step 5. $^1H$ NMR (400 MHz, Methanol-$d_4$) δ 8.50 (d, J=1.4 Hz, 1H), 8.22 (d, J=5.7 Hz, 1H), 7.92 (d, J=1.4 Hz, 1H), 7.25 (d, J=5.7 Hz, 1H), 4.83-4.76 (m, 2H), 4.61 (dd, J=26.2, 11.3 Hz, 1H), 4.34 (q, J=7.0 Hz, 2H), 4.04 (d, J=10.8 Hz, 1H), 4.00 (d, J=10.9 Hz, 1H), 3.47 (t, J=12.2 Hz, 1H), 3.25-3.09 (m, 4H), 2.95 (qt, J=10.9, 6.8 Hz, 2H), 2.24-2.11 (m, 1H), 2.11-1.92 (m, 1H), 1.92-1.80 (m, 2H), 1.80-1.68 (m, 1H), 1.57 (ddd, J=12.6, 8.1, 6.5 Hz, 1H), 1.38 (t, J=7.1 Hz, 3H), 1.20 (s, 3H). ESI MS $[M+H]^+$ for $C_{24}H_{33}F_2N_9O_4$, calcd 550.3, found 550.3

Example 75: 2-[(S)-3-[3-(5-ethoxy-2-pyrazinyl)-1-methylureido]-4,4-difluoro-1-piperidyl]-4-pyrimidinyl [(R)-1-methyl-2-methyl-2-pyrrolidinyl]methanecarbamate

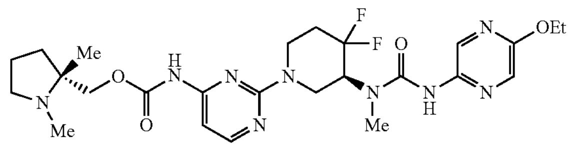 [SMILES: CCOc1cnc(NC(=O)N(C)[C@H]2CN(c3nccc(NC(=O)OC[C@@]4(C)CCCN4C)n3)CCC2(F)F)cn1]

The title compound was synthesized in a similar fashion to Example 11 using 1,1-dimethylethyl (2R)-2-(hydroxymethyl)-2-methyl-1-pyrrolidinecarboxylate in Step 5. $^1H$ NMR (400 MHz, Methanol-$d_4$) δ 8.49 (d, J=1.4 Hz, 1H), 8.22 (d, J=5.7 Hz, 1H), 7.92 (d, J=1.4 Hz, 1H), 7.25 (d, J=5.7 Hz, 1H), 4.83-4.76 (m, 2H), 4.61 (dd, J=25.7, 11.1 Hz, 1H), 4.35 (q, J=7.0 Hz, 2H), 4.09 (d, J=11.1 Hz, 1H), 4.06 (d, J=11.1 Hz, 1H), 3.47 (t, J=12.2 Hz, 1H), 3.22-3.07 (m, 4H), 2.97-2.87 (m, 1H), 2.71 (q, J=8.0 Hz, 1H), 2.35 (s, 3H), 2.23-2.11 (m, 1H), 2.11-1.97 (m, 1H), 1.95-1.88 (m, 1H), 1.86-1.73 (m, 2H), 1.73-1.58 (m, 1H), 1.38 (t, J=7.0 Hz, 3H), 1.08 (s, 3H). ESI MS $[M+H]^+$ for $C_{25}H_{35}F_2N_9O_4$, calcd 564.3, found 564.3

Example 76: 2-[(S)-3-[3-(5-ethoxy-2-pyrazinyl)-1-methylureido]-4,4-difluoro-1-piperidyl]-4-pyrimidinyl 4-(trifluoromethyl)-4-piperidinecarbamate

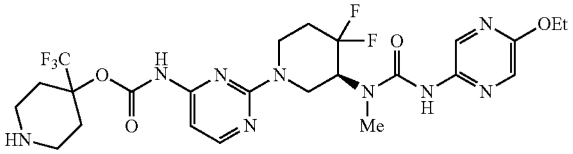 [SMILES: CCOc1cnc(NC(=O)N(C)[C@H]2CN(c3nccc(NC(=O)OC4(C(F)(F)F)CCNCC4)n3)CCC2(F)F)cn1]

The title compound was synthesized in a similar fashion to Example 11 (Step 1-Step 8 Part 1) using 1,1-dimethylethyl 4-hydroxy-4-(trifluoromethyl)-1-piperidinecarboxylate in Step 5.

$^1H$ NMR (400 MHz, Methanol-$d_4$) δ 8.50 (d, J=1.4 Hz, 1H), 8.24 (d, J=5.7 Hz, 1H), 7.92 (d, J=1.4 Hz, 1H), 7.19 (d, J=5.7 Hz, 1H), 4.84-4.77 (m, 2H), 4.62 (dd, J=25.4, 11.3 Hz, 1H), 4.35 (q, J=7.1 Hz, 2H), 3.47 (t, J=12.2 Hz, 1H), 3.22-3.11 (m, 4H), 3.01 (d, J=13.3 Hz, 2H), 2.83 (t, J=12.6 Hz, 2H), 2.64-2.45 (m, 2H), 2.25-2.11 (m, 1H), 2.13-1.91 (m, 1H), 1.81 (td, J=13.2, 4.5 Hz, 2H), 1.38 (t, J=7.1 Hz, 3H). ESI MS $[M+H]^+$ for $C_{24}H_{30}F_5N_9O_4$, calcd 604.2, found 604.2

Example 77: 2-[(S)-3-[3-(5-ethoxy-2-pyrazinyl)-1-methylureido]-4,4-difluoro-1-piperidyl]-4-pyrimidinyl 4-(methoxymethyl)-4-piperidinecarbamate

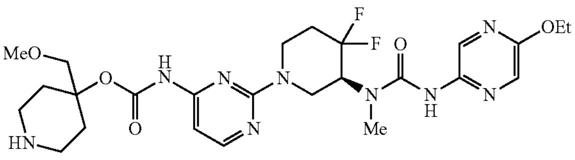 [SMILES: CCOc1cnc(NC(=O)N(C)[C@H]2CN(c3nccc(NC(=O)OC4(COC)CCNCC4)n3)CCC2(F)F)cn1]

The title compound was synthesized in a similar fashion to Example 11 (Step 1-Step 8 Part 1) using 1,1-dimethylethyl 4-hydroxy-4-(methoxymethyl)-1-piperidinecarboxylate in Step 5.

$^1H$ NMR (400 MHz, Methanol-$d_4$) δ 8.50 (d, J=1.4 Hz, 1H), 8.20 (d, J=5.7 Hz, 1H), 7.93 (d, J=1.4 Hz, 1H), 7.21 (d, J=5.7 Hz, 1H), 4.83-4.75 (m, 2H), 4.60 (dd, J=26.0, 11.2 Hz, 1H), 4.35 (q, J=7.1 Hz, 2H), 3.76 (s, 2H), 3.46 (t, J=12.2 Hz, 1H), 3.35 (s, 3H), 3.21-3.12 (m, 4H), 2.93-2.82 (m, 4H), 2.25 (d, J=14.5 Hz, 2H), 2.19-2.11 (m, 1H), 2.11-1.90 (m, 1H), 1.78-1.54 (m, 2H), 1.38 (t, J=7.1 Hz, 3H). ESI MS $[M+H]^+$ for $C_{25}H_{35}F_2N_9O_5$, calcd 580.3, found 580.3

Example 78: 2-[(3S,4S)-3-[3-(5-ethoxy-2-pyrazinyl)-1-methylureido]-4-fluoro-1-piperidyl]-4-pyrimidinyl 4-quinuclidinecarbamate

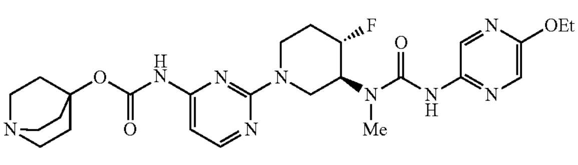 [SMILES: CCOc1cnc(NC(=O)N(C)[C@H]2CN(c3nccc(NC(=O)OC45CCN(CC4)CC5)n3)CC[C@@H]2F)cn1]

The title compound was synthesized in a similar fashion to Example 18 (Step 1-Step 9) using 1,1-dimethylethyl N-[(3S,4S)-4-fluoro-3-piperidinyl]carbamate in Step 1 and 4-quinuclidinol in Step 7. $^1$H NMR (400 MHz, Methanol-$d_4$) δ 8.56 (d, J=1.4 Hz, 1H), 8.21 (d, J=5.8 Hz, 1H), 7.97 (d, J=1.4 Hz, 1H), 7.18 (d, J=5.7 Hz, 1H), 5.04 (dtd, J=50.8, 10.3, 5.2 Hz, 1H), 4.76 (d, J=13.8 Hz, 1H), 4.70-4.59 (m, 1H), 4.36 (q, J=7.1 Hz, 2H), 4.13-3.94 (m, 1H), 3.10 (s, 3H), 3.08-3.01 (m, 7H), 2.97 (t, J=13.1 Hz, 1H), 2.32-2.18 (m, 1H), 2.18-2.00 (m, 6H), 1.78-1.56 (m, 1H), 1.38 (t, J=7.0 Hz, 3H). ESI MS $[M+H]^+$ for $C_{25}H_{34}FN_9O_4$, calcd 544.3, found 544.3

Example 79: 2-[(3S,4R)-3-[3-(5-ethoxy-2-pyrazinyl)-1-methylureido]-4-fluoro-1-piperidyl]-4-pyrimidinyl 1-ethyl-4-piperidinecarbamate

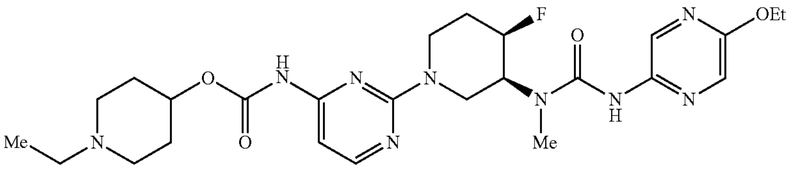 [SMILES: CCOc1cnc(NC(=O)N(C)[C@H]2CN(c3nccc(NC(=O)OC4CCN(CC)CC4)n3)CC[C@H]2F)cn1]

The title compound was synthesized in a similar fashion to Example 6 using 4-hydroxy-N-ethylpiperidine in Step 1. $^1$H NMR (400 MHz, DMSO-$d_6$) δ 10.13 (s, 1H), 9.03 (s, 1H), 8.55 (d, J=1.5 Hz, 1H), 8.23 (d, J=5.6 Hz, 1H), 8.01 (d, J=1.4 Hz, 1H), 7.05 (d, J=5.6 Hz, 1H), 5.04 (d, J=51.3 Hz, 1H), 4.66 (dt, J=8.4, 4.3 Hz, 1H), 4.64-4.51 (m, 2H), 4.29 (q, J=7.1 Hz, 2H), 4.27-4.08 (m, 1H), 3.45 (t, J=12.2 Hz, 1H), 3.03 (m, 4H), 2.66 (d, J=9.3 Hz, 2H), 2.32 (q, J=7.1 Hz, 2H), 2.17 (t, J=10.0 Hz, 2H), 1.86 (td, J=34.2, 9.5 Hz, 4H), 1.59 (ddt, J=13.3, 8.8, 4.3 Hz, 2H), 1.32 (t, J=7.0 Hz, 3H), 0.98 (t, J=7.1 Hz, 3H). ESI MS $[M+H]^+$ for $C_{25}H_{36}N_9FO_4$, calcd 546.3, found 546.2.

Example 80: 2-[(3S,4R)-3-[3-(5-ethoxy-2-pyrazinyl)-1-methylureido]-4-fluoro-1-piperidyl]-4-pyrimidinyl 1-cyclopropyl-4-piperidinecarbamate

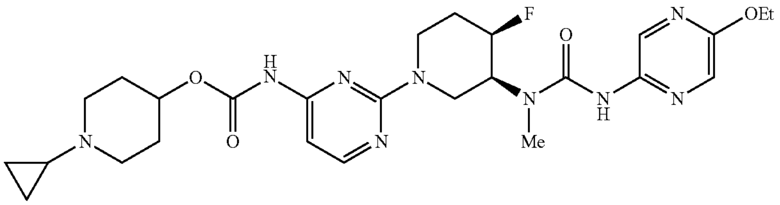 [SMILES: CCOc1cnc(NC(=O)N(C)[C@H]2CN(c3nccc(NC(=O)OC4CCN(C5CC5)CC4)n3)CC[C@H]2F)cn1]

The title compound was synthesized in a similar fashion to Example 6 using 4-hydroxy-N-cyclopropylpiperidine in Step 1. $^1$H NMR (400 MHz, DMSO-$d_6$) δ 10.13 (s, 1H), 9.03 (s, 1H), 8.55 (d, J=1.5 Hz, 1H), 8.23 (d, J=5.6 Hz, 1H), 8.01 (d, J=1.5 Hz, 1H), 7.05 (d, J=5.6 Hz, 1H), 5.04 (d, J=51.3 Hz, 1H), 4.67 (dd, J=8.3, 4.2 Hz, 1H), 4.58 (dd, J=12.4, 5.6 Hz, 2H), 4.29 (q, J=7.0 Hz, 2H), 4.27-4.09 (m, 1H), 3.45 (t, J=12.2 Hz, 1H), 3.32 (s, 1H), 3.15-2.98 (m, 4H), 2.85-2.71 (m, 2H), 2.40 (t, J=9.3 Hz, 2H), 2.14-1.73 (m, 4H), 1.57 (ddt, J=21.4, 8.2, 3.6 Hz, 2H), 1.32 (t, J=7.0 Hz, 3H), 0.40 (dd, J=6.4, 2.3 Hz, 2H), 0.28 (dd, J=3.6, 2.3 Hz, 2H).

ESI MS $[M+H]^+$ for $C_{26}H_{37}N_9FO_4$, calcd 558.3, found 558.2.

Example 81: 2-[(3S,4R)-3-[3-(5-ethoxy-2-pyrazinyl)-1-methylureido]-4-fluoro-1-piperidyl]-4-pyrimidinyl 1-(2,2-difluoroethyl)-4-piperidinecarbamate

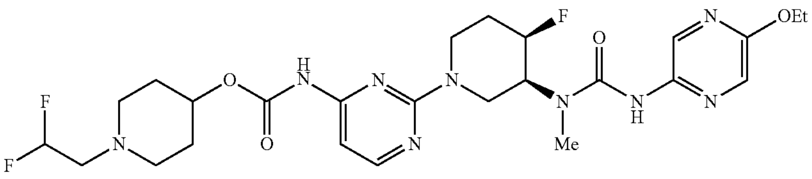 [SMILES: CCOc1cnc(NC(=O)N(C)[C@H]2CN(c3nccc(NC(=O)OC4CCN(CC(F)F)CC4)n3)CC[C@H]2F)cn1]

The title compound was synthesized in a similar fashion to Example 6 using 1-(2,2-difluoroethyl)piperidin-4-ol in Step 1. $^1$H NMR (400 MHz, DMSO-$d_6$) δ 10.14 (s, 1H), 9.02 (s, 1H), 8.55 (d, J=1.5 Hz, 1H), 8.23 (d, J=5.6 Hz, 1H), 8.01 (d, J=1.5 Hz, 1H), 7.05 (d, J=5.6 Hz, 1H), 6.11 (tt, J=55.8, 4.3 Hz, 1H), 5.04 (d, J=51.4 Hz, 1H), 4.85-4.63 (m, 1H), 4.64-4.49 (m, 2H), 3.45 (t, J=12.2 Hz, 1H), 3.03 (d, J=1.6 Hz, 4H), 2.72 (td, J=15.8, 4.5 Hz, 4H), 2.42 (t, J=9.5 Hz, 2H), 2.08-1.71 (m, 4H), 1.75-1.51 (m, 2H), 1.32 (t, J=7.0 Hz, 3H). ESI MS $[M+H]^+$ for $C_{25}H_{34}N_9F_{304}$, calcd 582.3, found 582.2.

Example 82: 2-[(3S,4R)-3-[3-(5-ethoxy-2-pyrazinyl)-1-methylureido]-4-fluoro-1-piperidyl]-4-pyrimidinyl 1-phenyl-4-piperidinecarbamate

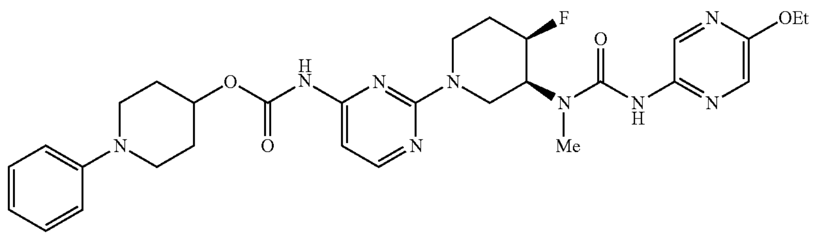 [SMILES: CCOc1cnc(NC(=O)N(C)[C@H]2CN(c3nccc(NC(=O)OC4CCN(c5ccccc5)CC4)n3)CC[C@H]2F)cn1]

The title compound was synthesized in a similar fashion to Example 6 using 1-Phenylpiperidin-4-ol in Step 1. $^1$H NMR (400 MHz, DMSO-d$_6$) δ 10.17 (s, 1H), 9.02 (s, 1H), 8.54 (d, J=1.5 Hz, 1H), 8.24 (d, J=5.6 Hz, 1H), 8.01 (d, J=1.4 Hz, 1H), 7.20 (dd, J=8.7, 7.2 Hz, 2H), 7.07 (d, J=5.6 Hz, 1H), 7.02-6.91 (m, 2H), 6.83-6.69 (m, 1H), 5.04 (d, J=51.4 Hz, 1H), 4.86 (dd, J=7.9, 4.0 Hz, 1H), 4.68-4.52 (m, 2H), 4.29 (q, J=7.0 Hz, 2H), 4.28-4.06 (m, 1H), 3.46 (d, J 12.0 Hz, 3H), 3.19-2.98 (m, 6H), 1.95 (d, J=10.4 Hz, 3H), 1.70 (dq, J=8.5, 4.3 Hz, 2H), 1.32 (t, J=7.0 Hz, 3H). ESI MS [M+H]$^+$ for $C_{29}H_{36}N_9FO_4$, calcd 594.3, found 594.2.

Example 83: 2-[(3S,4R)-3-[3-(5-ethoxy-2-pyrazinyl)-1-methylureido]-4-fluoro-1-piperidyl]-4-pyrimidinyl 1-(2-methoxyethyl)-4-piperidinecarbamate

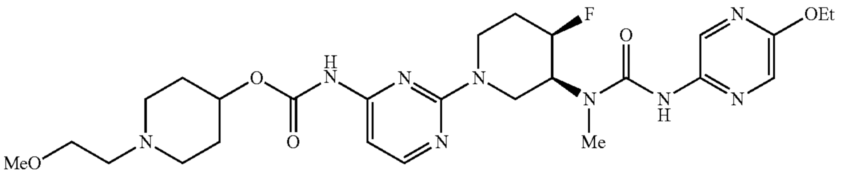 [SMILES: CCOc1cnc(NC(=O)N(C)[C@H]2CN(c3nccc(NC(=O)OC4CCN(CCOC)CC4)n3)CC[C@H]2F)cn1]

The title compound was synthesized in a similar fashion to Example 6 using 1-(2-methoxyethyl)piperidin-4-ol in Step 1. $^1$H NMR (400 MHz, DMSO-d$_6$) δ 10.13 (s, 1H), 9.02 (s, 1H), 8.55 (d, J=1.5 Hz, 1H), 8.23 (d, J=5.6 Hz, 1H), 8.01 (d, J=1.5 Hz, 1H), 7.05 (d, J=5.6 Hz, 1H), 5.04 (d, J=51.3 Hz, 1H), 4.66 (dt, J=8.3, 4.2 Hz, 1H), 4.65-4.47 (m, 2H), 4.29 (q, J=7.0 Hz, 3H), 4.27-4.08 (m, 1H), 3.65-3.38 (m, 3H), 3.22 (s, 3H), 3.03 (d, J=1.6 Hz, 3H), 2.78-2.63 (m, 2H), 2.46 (t, J=5.9 Hz, 2H), 2.24 (t, J=10.3 Hz, 2H), 2.04-1.69 (m, 4H), 1.59 (dd, J=11.0, 7.0 Hz, 2H), 1.32 (t, J=7.0 Hz, 3H). ESI MS [M+H]$^+$ for $C_{26}H_{38}N_9FO_5$, calcd 576.3, found 576.2.

Example 84: 2-[(3S,4R)-3-[3-(5-ethoxy-2-pyrazinyl)-1-methylureido]-4-fluoro-1-piperidyl]-4-pyrimidinyl 1-isopropyl-4-piperidinecarbamate

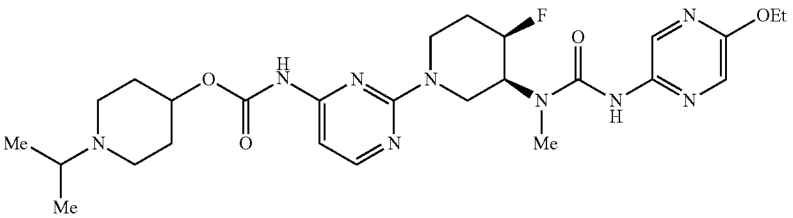 [SMILES: CCOc1cnc(NC(=O)N(C)[C@H]2CN(c3nccc(NC(=O)OC4CCN(C(C)C)CC4)n3)CC[C@H]2F)cn1]

The title compound was synthesized in a similar fashion to Example 6 using 1-Isopropylpiperidin-4-ol in Step 1. $^1$H NMR (400 MHz, DMSO-d$_6$) δ 10.12 (s, 1H), 9.02 (s, 1H), 8.55 (d, J=1.5 Hz, 1H), 8.23 (d, J=5.6 Hz, 1H), 8.01 (d, J=1.4 Hz, 1H), 7.05 (d, J=5.6 Hz, 1H), 5.04 (d, J=51.3 Hz, 1H), 4.64 (s, 1H), 4.64-4.51 (m, 1H), 4.29 (q, J=7.1 Hz, 2H), 4.27-4.11 (m, OH), 3.45 (t, J=12.2 Hz, 1H), 3.03 (d, J=1.6 Hz, 4H), 2.68 (s, 3H), 2.28 (s, 2H), 1.92 (d, J=55.5 Hz, 4H), 1.57 (s, 2H), 1.32 (t, J=7.0 Hz, 3H), 0.96 (d, J=6.5 Hz, 6H). ESI MS [M+H]$^+$ for $C_{26}H_{38}N_9FO_4$, calcd 560.3, found 560.2.

Example 85: 2-[(R)-3-[3-(5-ethoxy-2-pyrazinyl)-1-methylureido]-1-piperidyl]-4-pyrimidinyl (1R,3R)-3-hydroxycyclobutanecarbamate

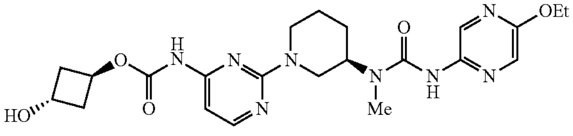 [SMILES: CCOc1cnc(NC(=O)N(C)[C@@H]2CCCN(c3nccc(NC(=O)O[C@H]4C[C@H](O)C4)n3)C2)cn1]

The title compound was synthesized in a similar fashion to Example 1 using trans-3-(Phenylmethoxy)cyclobutanol in Step 1. The Benzyl group was removed by hydrogenation similar to step 3 (part 3) in Example 2. $^{1}H$ NMR (400 MHz, DMSO-$d_6$) δ 10.12 (s, 1H), 8.85 (s, 1H), 8.59 (d, J=1.4 Hz, 1H), 8.21 (d, J=5.6 Hz, 1H), 8.02 (d, J=1.4 Hz, 1H), 7.00 (d, J=5.6 Hz, 1H), 5.06 (ddd, J=7.1, 4.5, 2.6 Hz, 1H), 4.62 (d, J=13.0 Hz, 1H), 4.54 (dd, J=12.7, 4.2 Hz, 1H), 4.30 (q, J=7.0 Hz, 2H), 4.23 (ddd, J=6.9, 4.6, 2.2 Hz, 1H), 4.01 (d, J=7.1 Hz, 1H), 3.08-2.88 (m, 4H), 2.73 (t, J=12.6 Hz, 1H), 2.38 (ddd, J=13.7, 7.2, 4.6 Hz, 2H), 2.34-2.23 (m, 2H), 1.89-1.65 (m, 3H), 1.56-1.39 (m, 1H), 1.32 (t, J=7.0 Hz, 3H). ESI MS $[M+H]^+$ for $C_{22}H_{30}N_8O_5$, calcd 487.3, found 487.2.

Example 86: 2-[(3S,4R)-3-[3-(5-ethoxy-2-pyrazinyl)-1-methylureido]-4-fluoro-1-piperidyl]-4-pyrimidinyl (1S,4R,6S)-2-methyl-2-azabicyclo[2.2.1]heptane-6-carbamate

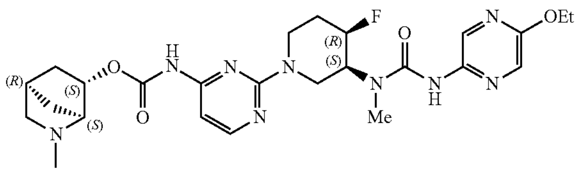

The title compound was synthesized in a similar fashion to Example 18 using tert-butyl (1S,4R,6S)-6-hydroxy-2-azabicyclo[2.2.1]heptane-2-carboxylate in Step 7. $^{1}H$ NMR (400 MHz, DMSO-$d_6$) δ 10.10 (s, 1H), 9.05 (s, 1H), 8.57 (d, J=1.4 Hz, 1H), 8.24 (d, J=5.7 Hz, 1H), 8.03 (d, J=1.5 Hz, 1H), 7.08 (d, J=5.6 Hz, 1H), 5.09 (s, 1H), 4.98 (s, 1H), 4.89 (d, J=3.7 Hz, 1H), 4.63-4.49 (m, 2H), 4.29 (q, J=7.0 Hz, 2H), 4.26-4.10 (m, 1H), 3.42 (t, J=12.2 Hz, 1H), 3.03 (d, J=1.6 Hz, 3H), 2.50 (s, 1H), 2.37-2.22 (m, 2H), 2.16 (s, 3H), 1.95 (q, J=15.6, 14.7 Hz, 2H), 1.82-1.61 (m, 2H), 1.51-1.39 (m, 1H), 1.32 (t, J=7.0 Hz, 3H), 0.95 (d, J=6.3 Hz, 3H). ESI MS $[M+H]^+$ for $C_{22}H_{34}FN_9O_4$, calcd 544.3, found 544.1.

Example 87: 2-[(3S,4R)-3-[3-(5-ethoxy-2-pyrazinyl)-1-methylureido]-4-fluoro-1-piperidyl]-4-pyridyl 1-methyl-4-piperidinecarbamate

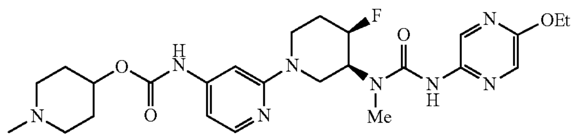 [SMILES: CCOc1cnc(NC(=O)N(C)[C@H]2CN(c3cc(NC(=O)OC4CCN(C)CC4)ccn3)CC[C@H]2F)cn1]

The title compound was synthesized in a similar fashion to Example 26 using 5-Ethoxy-2-pyrazinamine in Step 5. $^{1}H$ NMR (400 MHz, $CDCl_3$) δ 8.80 (d, J=1.5 Hz, 1H), 8.37 (s, 2H), 8.20 (d, J=5.6 Hz, 1H), 7.88 (d, J=1.4 Hz, 1H), 7.15 (s, 1H), 7.14-7.08 (m, 1H), 6.53 (dd, J=5.7, 1.8 Hz, 1H), 5.11 (d, J=51.3 Hz, 1H), 4.97 (s, 1H), 4.36 (q, J=7.0 Hz, 2H), 4.27 (t, J=7.1 Hz, 2H), 4.01 (d, J=13.9 Hz, 1H), 3.51 (t, J=12.6 Hz, 1H), 3.36 (t, J=13.3 Hz, 1H), 3.14 (bs, 4H), 2.97 (bs, 3H), 2.38-2.16 (m, 3H), 2.06 (t, J=12.8 Hz, 3H), 2.00-1.66 (m, 1H), 1.40 (t, J=7.0 Hz, 3H). ESI MS $[M+H]^+$ for $C_{25}H_{35}N_8FO_4$, calcd 531.3, found 531.2.

Example 88: 2-[(3S,4R)-3-[3-(5-ethoxy-2-pyrazinyl)-1-methylureido]-4-fluoro-1-piperidyl]-4-pyrimidinyl (2S,4S)-1-ethyl-2-methyl-4-piperidinecarbamate

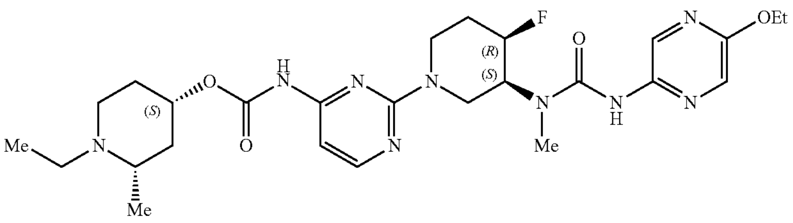

The title compound was synthesized in a similar fashion to Example 18 using tert-butyl (2S,4S)-4-hydroxy-2-methyl-1-piperidinecarboxylate in Step 7 and acetaldehyde instead of formaldehyde in step 10, part 2. $^1$H NMR (400 MHz, $CDCl_3$) δ 8.82 (d, J=1.4 Hz, 1H), 8.27 (d, J=5.6 Hz, 1H), 7.96 (s, 1H), 7.24 (d, J=5.7 Hz, 1H), 5.16 (d, J=50.6 Hz, 1H), 4.84-4.58 (m, 2H), 4.51 (d, J=13.0 Hz, 1H), 4.45-4.28 (m, 2H), 3.51 (t, J=12.5 Hz, 1H), 3.26 (t, J=13.1 Hz, 1H), 3.16 (d, J=3.0 Hz, 3H), 3.10 (s, 1H), 2.93 (s, 1H), 2.66-2.44 (m, 2H), 2.35 (s, 1H), 2.06 (bs, 2H), 2.00-1.68 (m, 2H), 1.71-1.49 (m, 1H), 1.39 (t, J=7.0 Hz, 3H), 1.20 (d, J=6.2 Hz, 3H), 1.06 (t, J=7.1 Hz, 3H). ESI MS $[M+H]^+$ for $C_{26}H_{38}N_9FO_4$, calcd 560.3, found 560.2.

Example 89: 2-[(3S,4R)-3-[3-(5-ethoxy-2-pyrazinyl)-1-methylureido]-4-fluoro-1-piperidyl]-4-pyrimidinyl 1-(cyclopropylmethyl)-4-piperidinecarbamate

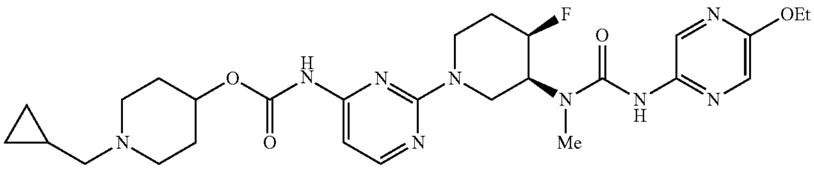 [SMILES: CCOc1cnc(NC(=O)N(C)[C@H]2CN(c3nccc(NC(=O)OC4CCN(CC5CC5)CC4)n3)CC[C@H]2F)cn1]

The title compound was synthesized in a similar fashion to Example 6 using 1-(Cyclopropylmethyl)-4-piperidinol in Step 1. $^1$H NMR (400 MHz, $CDCl_3$) δ 8.82 (d, J=1.4 Hz, 1H), 8.27 (d, J=5.6 Hz, 1H), 7.98 (s, 1H), 7.66 (s, 1H), 5.16 (d, J=50.6 Hz, 1H), 4.81 (dt, J=9.0, 4.6 Hz, 1H), 4.68 (d, J=13.6 Hz, 1H), 4.52 (d, J=13.1 Hz, 1H), 4.50-4.30 (m, 2H), 3.51 (t, J=12.5 Hz, 1H), 3.26 (t, J=13.2 Hz, 1H), 3.16 (d, J=3.0 Hz, 3H), 2.87 (s, 2H), 2.42-2.23 (m, 4H), 2.17-1.96 (m, 3H), 1.90-1.73 (m, 3H), 1.40 (t, J=7.0 Hz, 3H), 0.86 (ddd, J=8.9, 6.6, 2.5 Hz, 2H), 0.61-0.46 (m, 2H), 0.11 (d, J=5.0 Hz, 2H). ESI MS $[M+H]^+$ for $C_{27}H_{38}N_9FO_4$, calcd 572.3, found 572.2.

Example 90: 2-[(3S,4R)-3-[3-(5-ethoxy-2-pyrazinyl)-1-methylureido]-4-fluoro-1-piperidyl]-4-pyrimidinyl 1-azabicyclo[2.2.1]heptane-4-carbamate

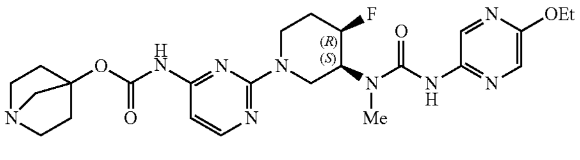

The title compound was synthesized in a similar fashion to Example 6 using 1-Azabicyclo[2.2.1]heptan-4-ol in Step 1. $^1$H NMR (400 MHz, DMSO-d6) δ 10.24 (s, 1H), 9.02 (s, 1H), 8.55 (d, J=1.5 Hz, 1H), 8.23 (d, J=5.8 Hz, 1H), 8.01 (d, J=1.4 Hz, 1H), 7.03 (d, J=5.6 Hz, 1H), 5.04 (d, J=51.3 Hz, 1H), 4.67-4.51 (m, 2H), 4.29 (q, J=7.0 Hz, 2H), 3.45 (t, J=12.2 Hz, 1H), 3.14-2.88 (m, 5H), 2.69 (q, J=6.1 Hz, 2H), 2.60 (s, 2H), 2.10-1.70 (m, 7H), 1.32 (t, J=7.0 Hz, 3H). ESI MS $[M+H]^+$ for $C_{24}H_{32}N_9FO_4$, calcd 530.3, found 530.2.

Example 91: 2-[(3S,4R)-3-[3-(5-ethoxy-2-pyrazinyl)-1-methylureido]-4-fluoro-1-piperidyl]-4-pyrimidinyl (4-fluoro-1-methyl-4-piperidyl)methanecarbamate

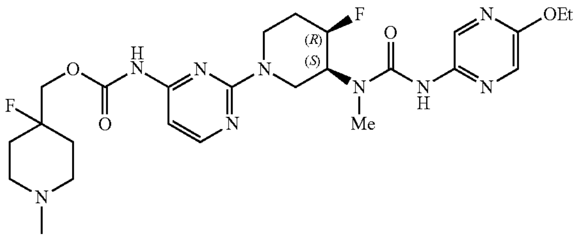

The title compound was synthesized in a similar fashion to Example 6 using 4-Fluoro-1-methyl-4-piperidinemethanol in Step 1. $^1$H NMR (400 MHz, DMSO-d6) δ 10.34 (s, 1H), 9.03 (s, 1H), 8.55 (d, J=1.5 Hz, 1H), 8.25 (d, J=5.6 Hz, 1H), 8.01 (d, J=1.4 Hz, 1H), 7.05 (d, J=5.6 Hz, 1H), 5.04 (d, J=51.3 Hz, 1H), 4.72-4.46 (m, 2H), 4.46-4.23 (m, 2H), 4.18 (d, J=21.5 Hz, 2H), 3.46 (t, J=12.2 Hz, 1H), 3.17-2.96 (m, 4H), 2.56 (dd, J=9.5, 5.9 Hz, 2H), 2.17 (s, 3H), 2.11 (t, J=11.4 Hz, 2H), 2.05-1.57 (m, 6H), 1.32 (t, J=7.0 Hz, 3H). ESI MS $[M+H]^+$ for $C_{25}H_{35}N_9F_2O_4$, calcd 564.3, found 564.2.

Example 92: 2-[(3S,4R)-3-[3-(5-ethoxy-2-pyrazinyl)-1-methylureido]-4-fluoro-1-piperidyl]-4-pyrimidinyl (1S,4R,6R)-2-ethyl-2-azabicyclo[2.2.1]heptane-6-carbamate

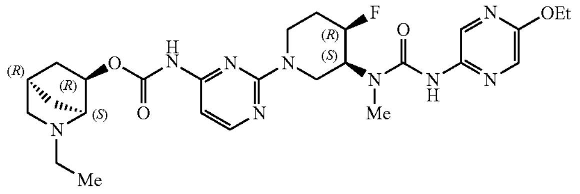

The title compound was synthesized in a similar fashion to Example 18 using tert-butyl (1S,4R,6R)-6-hydroxy-2-azabicyclo[2.2.1]heptane-2-carboxylate in Step 7 and acetaldehyde instead of formaldehyde in step 10, part 2. $^1$H NMR (400 MHz, DMSO-d6) δ 8.83 (d, J=1.4 Hz, 1H), 8.28 (d, J=5.6 Hz, 1H), 7.75 (s, 1H), 7.33 (d, J=5.3 Hz, 1H), 5.18 (d, J=50.4 Hz, 1H), 5.03-4.89 (m, 1H), 4.71 (d, J=13.9 Hz, 1H), 4.51 (d, J=13.0 Hz, 1H), 4.38 (qd, J=7.0, 1.1 Hz, 2H), 3.54 (dd, J=23.7, 11.2 Hz, 2H), 3.30 (t, J=13.0 Hz, 1H), 3.18 (d, J=3.2 Hz, 3H), 3.01 (s, 1H), 2.68 (dd, J=12.0, 6.9 Hz, 1H), 2.48 (m, 2H), 2.11 (dd, J=14.1, 10.3 Hz, 2H), 1.94-1.76 (m, 1H), 1.68 (d, J=25.2 Hz, 6H), 1.41 (t, J=7.0 Hz, 3H), 1.09-0.77 (m, 3H). ESI MS [M+H]$^+$for $C_{26}H_{36}N_9FO_4$, calcd 558.3, found 558.2.

Example 93: 2-[(S)-3-[3-(5-ethoxy-2-pyrazinyl)-1-methylureido]-4,4-difluoro-1-piperidyl]-4-pyrimidinyl (R)-3-quinuclidinecarbamate

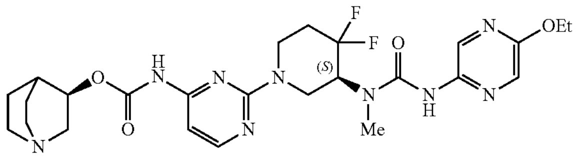

The title compound was synthesized in a similar fashion to Example 6 using (+)-Quinuclidin-3-ol in Step 1 and [(3S)-3-[N-(benzyloxycarbonyl)-3-methylamino]-4,4-difluoropiperidine in Step 3, which was prepared in a similar fashion to that described in Example 11, Steps 1-3.. $^1$H NMR (400 MHz, MeOH-$d_3$) δ 8.50 (d, J=1.4 Hz, 1H), 8.22 (d, J=5.7 Hz, 1H), 7.92 (d, J=1.4 Hz, 1H), 7.23 (d, J=5.7 Hz, 1H), 4.82 (m, 4H), 4.61 (dd, J=26.0, 11.4 Hz, 1H), 4.35 (q, J=7.0 Hz, 2H), 3.46 (t, J=12.2 Hz, 1H), 3.23-3.09 (m, 4H), 3.00-2.75 (m, 5H), 2.28-2.05 (m, 2H), 2.04-1.91 (m, 2H), 1.80 (tt, J=9.5, 4.6 Hz, 1H), 1.68 (ddt, J=10.4, 7.1, 3.5 Hz, 1H), 1.53 (q, J=10.3 Hz, 1H), 1.38 (t, J=7.1 Hz, 3H). ESI MS [M+H]$^+$for $C_{25}H_{34}N_9FO_4$, calcd 544.3, found 544.2.

Example 94: 2-[(S)-4,4-difluoro-3-[1-methyl-3-(1,3-thiazol-2-yl)ureido]-1-piperidyl]-4-pyrimidinyl (1S,4S,5R)-2-methyl-2-azabicyclo[2.2.1]heptane-5-carbamate

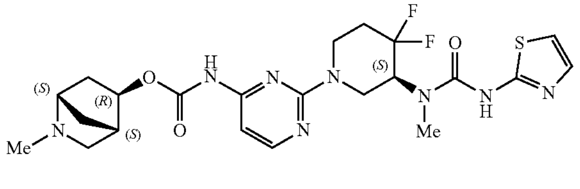

The title compound was synthesized in a similar fashion to Example 11 using tert-butyl (1S,4R,6R)-6-hydroxy-2-azabicyclo[2.2.1]heptane-2-carboxylate in Step 5 and using (N-2-thiazolyl)carbamic acid phenyl ester in Step 9, which was prepared in a similar fashion to Example 1 Step 4. $^1$H NMR (400 MHz, MeOH-$d_3$) δ 8.21 (d, J=5.7 Hz, 1H), 7.24 (dd, J=10.9, 4.8 Hz, 2H), 6.88 (d, J=4.1 Hz, 1H), 4.82-4.47 (m, 3H), 3.45 (t, J=11.9 Hz, 1H), 3.23 (d, J=3.1 Hz, 1H), 3.14 (s, 4H), 2.92 (d, J=52.8 Hz, 1H), 2.75 (dd, J=10.5, 4.4 Hz, 1H), 2.54 (d, J=4.3 Hz, 1H), 2.31 (s, 4H), 2.22-2.11 (m, 2H), 1.99 (d, J=33.4 Hz, 1H), 1.71 (s, 2H), 1.51 (d, J=14.1 Hz, 1H). ESI MS [M+H]$^+$ for $C_{22}H_{28}N_8F_2O_3S$, calcd 523.2, found 523.2.

Example 95: 2-[(3S,4R)-4-fluoro-3-[3-(5-fluoro-1,3-thiazol-2-yl)-1-methylureido]-1-piperidyl]-4-pyrimidinyl (1S,4S,5R)-2-methyl-2-azabicyclo[2.2.1]heptane-5-carbamate

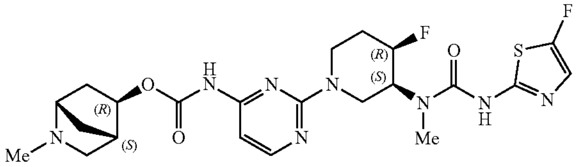

The title compound was synthesized in a similar fashion to Example 18 using tert-butyl (1S,4R,6R)-6-hydroxy-2-azabicyclo[2.2.1]heptane-2-carboxylate in Step 7 and N-(5-fluoro-2-thiazolyl)carbamic acid phenyl ester in Step 9, which was prepared in a similar fashion to Example 1 Step 4. $^1$H NMR (400 MHz, DMSO-$d_6$) δ 10.13 (s, 1H), 8.24 (d, J=5.7 Hz, 2H), 7.38 (s, 1H), 7.04 (d, J=5.6 Hz, 1H), 5.02 (d, J=51.3 Hz, 1H), 4.64 (d, J=7.2 Hz, 1H), 4.60-4.52 (m, 2H), 4.33-4.05 (m, 1H), 3.46 (t, J=12.1 Hz, 1H), 3.26 (s, 1H), 3.18-2.92 (m, 4H), 2.75 (dd, J=10.1, 4.4 Hz, 1H), 2.45 (d, J=4.3 Hz, 1H), 2.27 (s, 4H), 2.17 (d, J=10.1 Hz, 1H), 2.06-1.72 (m, 2H), 1.65 (d, J=10.1 Hz, 1H), 1.57 (d, J=9.9 Hz, 1H), 1.37 (d, J=14.1 Hz, 1H). ESI MS [M+H]$^+$for $C_{22}H_{28}N_8F_2O_3S$, calcd 523.2, found 523.2.

Example 96: 2-[(3S,4R)-3-[3-(5-chloro-1,3-thiazol-2-yl)-1-methylureido]-4-fluoro-1-piperidyl]-4-pyrimidinyl (1S,4S,5R)-2-methyl-2-azabicyclo[2.2.1]heptane-5-carbamate

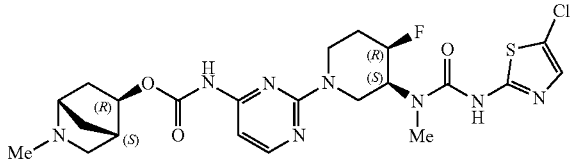

The title compound was synthesized in a similar fashion to Example 18 using tert-butyl (1S,4R,6R)-6-hydroxy-2-azabicyclo[2.2.1]heptane-2-carboxylate in Step 7 and N-(5-chloro-2-thiazolyl)carbamic acid phenyl ester in Step 9, which was prepared in a similar fashion to Example 1, Step 4. $^1$H NMR (400 MHz, DMSO-$d_6$) δ 10.13 (s, 1H), 8.24 (d, J=5.7 Hz, 2H), 7.38 (s, 1H), 7.04 (d, J=5.6 Hz, 1H), 5.02 (d, J=51.3 Hz, 1H), 4.64 (d, J=7.2 Hz, 1H), 4.60-4.52 (m, 2H), 4.33-4.05 (m, 1H), 3.46 (t, J=12.1 Hz, 1H), 3.26 (s, 1H), 3.18-2.92 (m, 4H), 2.75 (dd, J=10.1, 4.4 Hz, 1H), 2.45 (d, J=4.3 Hz, 1H), 2.27 (s, 4H), 2.17 (d, J=10.1 Hz, 1H), 2.06-1.72 (m, 2H), 1.65 (d, J=10.1 Hz, 1H), 1.57 (d, J=9.9 Hz, 1H), 1.37 (d, J=14.1 Hz, 1H). ESI MS [M+H]$^+$for $C_{22}H_{28}N_8FClO_3S$, calcd 539.2, found 539.2.

Example 97: 2-[(3S,4R)-3-[3-(5-chloro-1,3-thiazol-2-yl)-1-methylureido]-4-fluoro-1-piperidyl]-4-pyrimidinyl 4-quinuclidinecarbamate

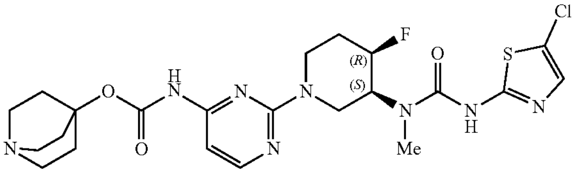

The title compound was synthesized in a similar fashion to Example 18 (step 1-9) using Quinuclidin-4-ol in Step 7 and N-(5-chloro-2-thiazolyl)carbamic acid phenyl ester in Step 9, which was prepared in a similar fashion to Example 1, Step 4. $^1$H NMR (400 MHz, MeOH-d$_3$) δ 10.01 (s, 1H), 8.22 (d, J=5.6 Hz, 1H), 7.40 (s, 1H), 7.15 (dd, J=8.6, 7.2 Hz, 1H), 7.00 (d, J=5.6 Hz, 1H), 6.86-6.67 (m, 1H), 5.02 (d, J=51.3 Hz, 1H), 4.72-4.47 (m, 2H), 4.35-4.01 (m, 1H), 3.45 (t, J=12.1 Hz, 1H), 3.16-2.82 (m, 10H), 1.98 (t, J=7.7 Hz, 6H). ESI MS [M+H]$^+$ for $C_{22}H_{28}N_8FO_3SCl$, calcd 539.2, found 539.1.

Example 98: 2-[(3S,4R)-3-[3-(5-ethoxy-2-pyrazinyl)-1-methylureido]-4-fluoro-1-piperidyl]-4-pyrimidinyl (1S,4S,5R)-2-azabicyclo[2.2.1]heptane-5-carbamate

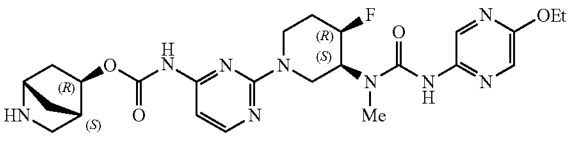

The title compound was synthesized in a similar fashion to Example 18 (steps 1-10, part 1) using tert-butyl (1S,4S,5R)-5-hydroxy-2-azabicyclo[2.2.1]heptane-2-carboxylate in Step 7. $^1$H NMR (400 MHz, MeOD) δ 8.50 (d, J=1.5 Hz, 1H), 8.19 (d, J=5.8 Hz, 1H), 7.93 (d, J=1.5 Hz, 1H), 7.18 (d, J=5.8 Hz, 1H), 5.06 (d, J=50.8 Hz, 1H), 4.78 (d, J=5.8 Hz, 1H), 4.67-4.57 (m, 2H), 4.39-4.17 (m, 3H), 3.61 (s, 1H), 3.53 (t, J=12.4 Hz, 1H), 3.25-3.10 (m, 4H), 2.90 (dd, J=10.8, 4.3 Hz, 1H), 2.68-2.58 (m, 2H), 2.14-1.97 (m, 2H), 1.97-1.74 (m, 2H), 1.69 (d, J=14.3 Hz, 1H), 1.54 (d, J=10.1 Hz, 1H), 1.37 (t, J=7.1 Hz, 3H).ESI MS [M+H]$^+$ for $C_{24}H_{32}N_9FO_4$, calcd 530.3, found 530.2.

Example 99: 2-[(3S,4R)-4-fluoro-3-[3-(5-fluoro-1,3-thiazol-2-yl)-1-methylureido]-1-piperidyl]-4-pyrimidinyl (1S,4S,5R)-2-ethyl-2-azabicyclo[2.2.1]heptane-5-carbamate

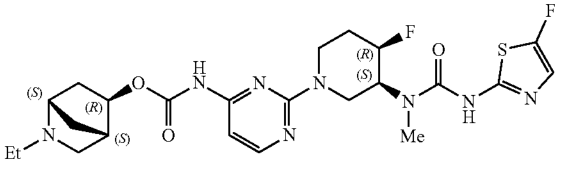

The title compound was synthesized in a similar fashion to Example 28 using N-(5-fluoro-2-thiazolyl)carbamic acid phenyl ester in Step 4, which was prepared in a similar fashion to Example 1, Step 4). $^1$H NMR (400 MHz, MeOD) δ 8.23 (d, J=5.7 Hz, 1H), 7.20 (d, J=5.7 Hz, 1H), 6.97 (d, J=2.0 Hz, 1H), 5.06 (d, J=51.1 Hz, 1H), 4.70 (dd, J=7.2, 2.5 Hz, 1H), 4.60 (td, J=14.8, 4.7 Hz, 2H), 4.23 (dd, J=33.2, 11.7 Hz, 1H), 3.52 (t, J=12.3 Hz, 1H), 3.39 (d, J=2.9 Hz, 1H), 3.21 (dd, J=13.2, 2.8 Hz, 1H), 3.10 (d, J=1.9 Hz, 3H), 2.84 (dd, J=10.5, 4.5 Hz, 1H), 2.67-2.41 (m, 3H), 2.35 (ddd, J=14.4, 7.4, 2.2 Hz, 1H), 2.16 (d, J=10.5 Hz, 1H), 2.03 (t, J=13.1 Hz, 1H), 1.94-1.61 (m, 3H), 1.51 (d, J=14.4 Hz, 1H), 1.08 (t, J=7.2 Hz, 3H).ESI MS [M+H]$^+$ for $C_{23}H_{30}N_8F_2O_3S$, calcd 537.3, found 537.2.

Example 100: 2-[(3S,4R)-4-fluoro-3-[3-(5-fluoro-1,3-thiazol-2-yl)-1-methylureido]-1-piperidyl]-4-pyrimidinyl (1S,4S,5R)-2-azabicyclo[2.2.1]heptane-5-carbamate

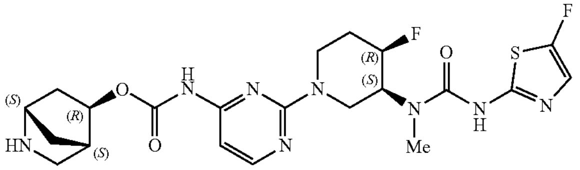

The title compound was synthesized in a similar fashion to Example 28 (steps 1-5 part 1) using N-(5-fluoro-2-thiazolyl)carbamic acid phenyl ester in Step 5, which was prepared in a similar fashion to Example 1, Step 4). $^1$H NMR (400 MHz, MeOD) δ 8 8.54 (s, 1H), 8.25 (d, J=5.7 Hz, 1H), 7.20 (d, J=5.7 Hz, 1H), 6.98 (d, J=2.1 Hz, 1H), 5.06 (d, J=51.1 Hz, 1H), 4.90 (m, 2H), 4.61 (td, J=12.8, 4.7 Hz, 2H), 4.22 (dd, J=32.7, 11.6 Hz, 1H), 4.11 (t, J=2.5 Hz, 1H), 3.55 (d, J=12.3 Hz, 1H), 3.21 (dd, J=11.8, 4.1 Hz, 2H), 3.11 (d, J=1.9 Hz, 3H), 2.98 (dd, J=11.6, 1.6 Hz, 1H), 2.89-2.84 (m, 2H), 2.30 (ddd, J=15.4, 7.0, 2.8 Hz, 1H), 2.06 (d, J=12.0 Hz, 2H), 1.96-1.81 (m, 1H), 1.76 (d, J=12.1 Hz, 1H). ESI MS [M+H]$^+$ for $C_{21}H_{26}N_8F_2O_3S$, calcd 509.2, found 509.2.

Example 101: 2-[(3S,4R)-3-[3-(5-ethoxy-2-pyrazinyl)-1-methylureido]-4-fluoro-1-piperidyl]-4-pyrimidinyl (1S,4S,5S)-2-azabicyclo[2.2.2]octane-5-carbamate

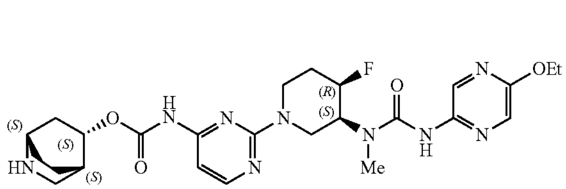

The title compound was synthesized in a similar fashion to Example 18 (Step 1-10 part 1) using tert-butyl (1S,4S,5S)-5-hydroxy-2-azabicyclo[2.2.2]octane-2-carboxylate in Step 7. $^1$H NMR (400 MHz, MeOD) δ 8.55 (s, 1H), 8.50 (d, J=1.4 Hz, 1H), 8.22 (d, J=5.7 Hz, 1H), 7.93 (d, J=1.4 Hz, 1H), 7.20 (d, J=5.7 Hz, 1H), 5.18-4.96 (m, 2H), 4.64 (td, J=12.1, 4.7 Hz, 2H), 4.22 (dd, J=32.7, 11.6 Hz, 1H), 4.34 (q, J=7.1 Hz, 2H), 3.55 (t, J=12.2 Hz, 1H), 3.49-3.41 (m, 2H), 3.25-3.09 (m, 5H), 2.39 (ddd, J=15.6, 9.9, 2.4 Hz, 1H), 2.17

(d, J=3.0 Hz, 1H), 2.12-1.68 (m, 7H), 1.38 (t, J=7.0 Hz, 3H).ESI MS $[M+H]^+$ for $C_{25}H_{34}N_9FO_4$, calcd 544.3, found 544.2.

Example 102: 2-[(3S,4R)-4-fluoro-3-[3-(5-fluoro-1,3-thiazol-2-yl)-1-methylureido]-1-piperidyl]-4-pyrimidinyl (1S,4S,5S)-2-ethyl-2-azabicyclo[2.2.2]octane-5-carbamate

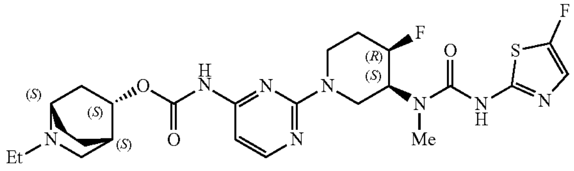

The title compound was synthesized in a similar fashion to Example 28 using tert-butyl (1S,4S,5S)-5-hydroxy-2-azabicyclo[2.2.2]octane-2-carboxylate in Step 2 and N-(5-fluoro-2-thiazolyl)carbamic acid phenyl ester in Step 4, which was prepared in a similar fashion to Example 1, Step 4). $^1H$ NMR (400 MHz, MeOD) δ 8.55 (s, 1H), 8.24 (d, J=5.7 Hz, 1H), 7.22 (d, J=5.7 Hz, 2H), 7.01 (d, J=2.0 Hz, 2H), 5.33-4.98 (m, 1H), 4.98-4.92 (m, 1H), 4.62 (dt, J=12.8, 6.4 Hz, 2H), 4.24 (dd, J=32.8, 11.8 Hz, 1H), 3.54 (t, J=12.3 Hz, 1H), 3.20 (td, J=13.2, 2.8 Hz, 2H), 3.11 (d, J=1.9 Hz, 3H), 2.97-2.82 (m, 2H), 2.37-2.16 (m, 1H), 2.03 (ddd, J=12.9, 6.5, 3.5 Hz, 4H), 1.96-1.52 (m, 4H), 1.20 (t, J=7.2 Hz, 3H). ESI MS $[M+H]^+$ for $C_{23}H_{32}N_8F_2SO_3$, calcd 551.2, found 551.2.

Example 103: 2-[(S)-4,4-difluoro-3-[3-(5-fluoro-4-methyl-1,3-thiazol-2-yl)-1-methylureido]-1-piperidyl]-4-pyrimidinyl 4-quinuclidinecarbamate

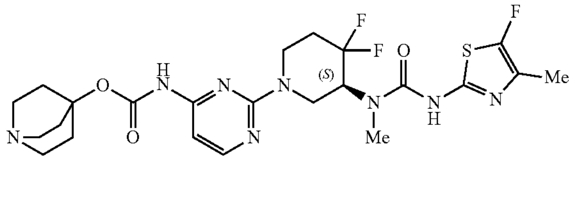

The title compound was synthesized in a similar fashion to Example 6, Quinuclidin-4-ol in Step 1 and using (N-(5-chloro-2-thiazolyl)carbamic acid phenyl ester in Step 5, which was prepared in a similar fashion to Example 1, Step 4). $^1H$ NMR (400 MHz, DMSO) δ 10.01 (s, 1H), 8.24 (s, 1H), 8.21 (s, 1H), 7.04 (d, J=5.7 Hz, 1H), 4.63 (d, J=68.5 Hz, 1H), 3.42 (t, J=12.0 Hz, 1H), 3.14-2.98 (m, 4H), 2.90 (t, J=7.7 Hz, 6H), 2.29-2.01 (m, 4H), 1.91 (t, J=7.7 Hz, 6H). ESI MS $[M+H]^+$ for $C_{23}H_{29}N_8F_3O_3S$, calcd 555.2, found 555.1.

Example 104: 2-[(3S,4R)-4-fluoro-3-[3-(5-fluoro-1,3-thiazol-2-yl)-1-methylureido]-1-piperidyl]-4-pyridyl 1-methyl-4-piperidinecarbamate

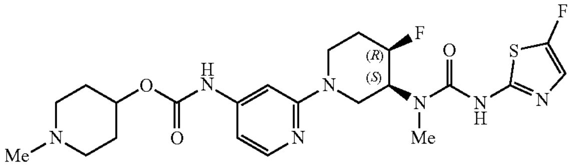

The title compound was synthesized in a similar fashion to Example 26 using 4-fluoro-2-aminothiozle in step 5. $^1H$ NMR (400 MHz, MeOD) δ 7.96 (d, J=5.7 Hz, 1H), 7.25 (bs, 1H), 6.73 (bs, 1H), 5.16 (d, J=51.3 Hz, 1H), 4.64 (dt, J=9.6, 5.0 Hz, 1H), 4.51 (s, 1H), 4.24 (dd, J=37.6, 11.3 Hz, 1H), 3.74 (d, J=13.3 Hz, 1H), 3.36 (d, J=13.1 Hz, 1H), 3.07 (t, J=13.0 Hz, 1H), 2.94 (d, J=4.0 Hz, 3H), 2.68 (d, J=10.3 Hz, 2H), 2.17 (s, 3H), 2.09 (t, J=11.2 Hz, 3H), 1.88 (d, J=34.2 Hz, 4H), 1.77-1.47 (m, 2H). ESI MS $[M+H]^+$ for $C_{22}H_{29}N_7F_2SO_3$, calcd 510.2, found 510.2.

Example 105: 2-[(3S,4R)-3-[3-(5-chloro-1,3-thiazol-2-yl)-1-methylureido]-4-fluoro-1-piperidyl]-4-pyridyl 1-methyl-4-piperidinecarbamate

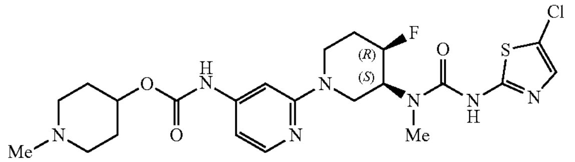

The title compound was synthesized in a similar fashion to Example 26 using 4-Chloro-2-aminothiozle in step 5. $^1H$ NMR (400 MHz, MeOD) δ 8.01 (d, J=5.7 Hz, 1H), 7.26 (bs, 1H), 6.95 (bs, 1H), 5.08 (d, J=51.5 Hz, 1H), 4.63 (dt, J=9.3, 4.9 Hz, 1H), 4.21 (dd, J=36.2, 11.2 Hz, 2H), 3.99 (bs, 1H), 3.42 (t, J=12.3 Hz, 1H), 3.12 (d, J=13.3 Hz, 1H), 2.99 (d, J=2.6 Hz, 3H), 2.63 (s, 2H), 2.17 (s, 3H), 2.13 (d, J=10.5 Hz, 2H), 1.89 (d, J=12.6 Hz, 3H), 1.67-1.54 (m, 4H). ESI MS $[M+H]^+$ for $C_{22}H_{29}N_7FClSO_3$, calcd 526.2, found 526.2.

Example 106: 2-[(3S,4R)-4-fluoro-3-[3-(5-fluoro-1,3-thiazol-2-yl)-1-methylureido]-1-piperidyl]-4-pyrimidinyl (R)-3-quinuclidinecarbamate

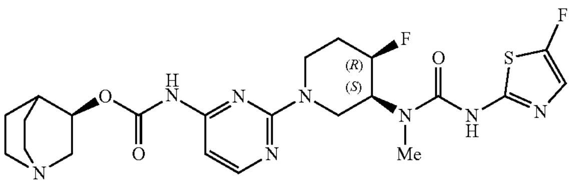

The title compound was synthesized in a similar fashion to Example 6 using (+)-Quinuclidin-3-ol in Step 1 and using (N-(5-fluoro-2-thiazolyl)carbamic acid phenyl ester in Step 5, which was prepared in a similar fashion to Example 1, Step 4). $^1H$ NMR (400 MHz, MeOD) δ 8.24 (d, J=5.7 Hz, 1H), 7.21 (d, J=5.7 Hz, 1H), 6.97 (d, J=2.0 Hz, 1H), 5.06 (d, J=51.0 Hz, 1H), 4.63 (m, 2H), 4.24 (dd, J=33.8, 11.1 Hz, 1H), 3.54 (t, J=12.3 Hz, 1H), 3.28-3.15 (m, 2H), 3.11 (d, J=1.9 Hz, 3H), 2.97-2.70 (m, 4H), 2.22-2.07 (m, 1H), 2.02 (d, J=12.7 Hz, 1H), 1.93 (m, 2H), 1.78 (m, 2H), 1.67 (m, 1H), 1.59-1.44 (m, 1H). ESI MS $[M+H]^+$ for $C_{22}H_{28}N_8F_2SO_3$, calcd 523.2, found 523.2.

Example 107: 2-[(3S,4R)-3-[3-(5-ethoxy-2-pyrazinyl)-1-methylureido]-4-fluoro-1-piperidyl]-4-pyrimidinyl_(1R,4R,5S)-2-azabicyclo[2.2.2]octane-5-carbamate

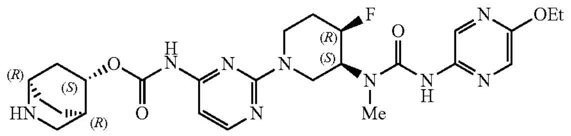

The title compound was synthesized in a similar fashion to Example 18 (Step 1-10 part1) using tert-butyl (1R,4R,5S)-5-hydroxy-2-azabicyclo[2.2.2]octane-2-carboxylate in Step 7. $^1$H NMR (400 MHz, MeOD) δ 8.51 (d, J=1.6 Hz, 1H), 8.19 (d, J=5.7 Hz, 1H), 7.94 (t, J=1.3 Hz, 1H), 7.48-7.14 (m, 1H), 4.14 (m, 1H), 5.07 (m, 2H), 4.63 (dt, J=12.2, 5.5 Hz, 2H), 4.34 (q, J=7.1 Hz, 2H), 4.32-4.12 (m, 1H), 4.05 (m, 1H), 3.54 (t, J=12.3 Hz, 1H), 3.48-3.35 (m, 1H), 3.26-3.15 (m, 1H), 3.14 (d, J=1.7 Hz, 3H), 3.01-2.77 (m, 2H), 2.34 (td, J=10.2, 5.0 Hz, 1H), 2.19-1.54 (m, 6H), 1.38 (t, J=7.0 Hz, 3H). ESI MS $[M+H]^+$ for $C_{25}H_{34}N_9FO_4$, calcd 544.3, found 544.2.

Example 108: 2-[(3S,4R)-4-fluoro-3-[1-methyl-3-(2-pyridyl)ureido]-1-piperidyl]-4-pyrimidinyl 1-methyl-4-piperidinecarbamate

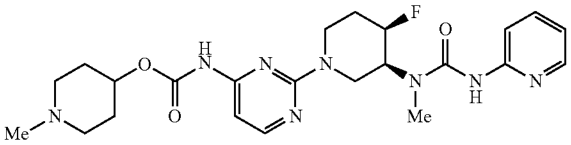 [SMILES: CN1CCC(OC(=O)Nc2ccnc(N3CC[C@@H](F)[C@@H](N(C)C(=O)Nc4ccccn4)C3)n2)CC1]

The title compound was synthesized in a similar fashion to Example 18 (Step 1-9) using 4-hydroxy-N-methylpiperidine in Step 7 and (pyridin-2-yl)carbamic acid phenyl ester in Step 9, which was prepared in a similar fashion to Example 1 Step 4. $^1$H NMR (400 MHz, Methanol-$d_4$) δ 8.26 (ddd, J=5.0, 1.9, 0.9 Hz, 1H), 8.20 (d, J=5.7 Hz, 1H), 7.83 (dt, J=8.5, 1.1 Hz, 1H), 7.78-7.69 (m, 1H), 7.20 (d, J=5.7 Hz, 1H), 7.05 (ddd, J=7.3, 5.0, 1.1 Hz, 1H), 5.21-4.96 (m, 1H), 4.83-4.72 (m, 1H), 4.68-4.58 (m, 2H), 4.26 (ddd, J=32.7, 11.6, 4.4 Hz, 1H), 3.54 (t, J=12.2 Hz, 1H), 3.26-3.08 (m, 4H), 2.76 (s, 2H), 2.53-2.25 (m, 5H), 2.11-1.70 (m, 6H). ESI MS $[M+H]^+$ for $C_{23}H_{32}FN_8O_3$, calcd 487.3, found 487.2.

Example 109: 2-[(3S,4R)-4-fluoro-3-[1-methyl-3-(5-phenyl-2-pyridyl)ureido]-1-piperidyl]-4-pyrimidinyl 1-methyl-4-piperidinecarbamate

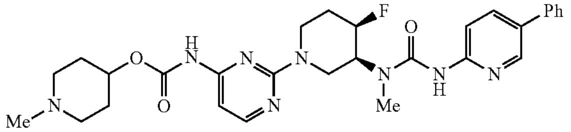 [SMILES: CN1CCC(OC(=O)Nc2ccnc(N3CC[C@@H](F)[C@@H](N(C)C(=O)Nc4ccc(-c5ccccc5)cn4)C3)n2)CC1]

The title compound was synthesized in a similar fashion to Example 18 (Step 1-9) using 4-hydroxy-N-methylpiperidine in Step 7 and (3-phenyl-pyridin-5-yl)carbamic acid phenyl ester in Step 9, which was prepared in a similar fashion to Example 1 Step 4. $^1$H NMR (400 MHz, Methanol-$d_4$) δ 8.56-8.50 (m, 1H), 8.22 (d, J=5.7 Hz, 1H), 8.00 (dd, J=8.7, 2.5 Hz, 1H), 7.93 (dd, J=8.7, 0.8 Hz, 1H), 7.65-7.58 (m, 2H), 7.51-7.41 (m, 2H), 7.41-7.32 (m, 1H), 7.20 (d, J=5.7 Hz, 1H), 5.21-5.10 (m, 1H), 4.72-4.58 (m, 2H), 4.29 (ddd, J=32.9, 11.7, 4.5 Hz, 1H), 3.57 (t, J=12.3 Hz, 1H), 3.27-3.15 (m, 4H), 2.88 (s, 2H), 2.61 (s, 2H), 2.45 (s, 3H), 2.14-1.76 (m, 6H). ESI MS $[M+H]^+$ for $C_{29}H_{36}FN_8O_3$, calcd 563.3, found 563.3.

Example 110: 2-[(3S,4R)-3-(3-{5-[(3,5-difluorophenyl)methyl]-1,3,4-thiadiazol-2-yl}-1-methylureido)-4-fluoro-1-piperidyl]-4-pyrimidinyl 1-methyl-4-piperidinecarbamate

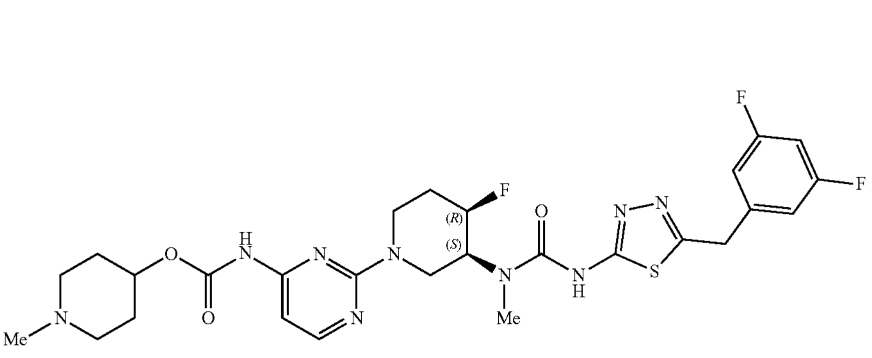

The title compound was synthesized in a similar fashion to Example 18 (Step 1-9) using 4-hydroxy-N-methylpiperidine in Step 7 and (5-[(3,5-difluorophenyl)methyl]-1,3,4-thiadiazol-2-yl)carbamic acid phenyl ester in Step 9, which was prepared in a similar fashion to Example 1 Step 4. $^1$H NMR (400 MHz, Methanol-$d_4$) δ 8.49 (s, 1H), 8.23 (d, J=5.8 Hz, 1H), 7.20 (d, J=5.7 Hz, 1H), 7.00-6.82 (m, 2H), 5.04 (d, J=51.3 Hz, 1H), 4.66-4.51 (m, 3H), 4.42-4.17 (m, 3H), 3.54 (t, J=12.2 Hz, 1H), 3.24-2.99 (m, 6H), 2.88 (s, 2H), 2.62 (s, 3H), 2.15-1.71 (m, 6H). ESI MS $[M+H]^+$ for $C_{27}H_{33}F_3N_9O_3S$, calcd 620.2, found 620.2.

Example 111: 2-[(3S,4R)-4-fluoro-3-[1-methyl-3-(2-pyridyl)ureido]-1-piperidyl]-4-pyridyl (S)-1-methyl-3-piperidinecarbamate

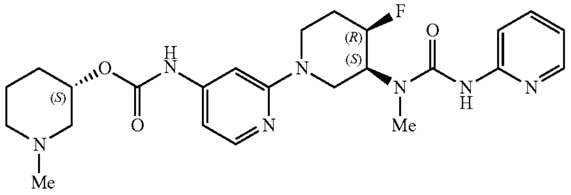

The title compound was synthesized in a similar fashion to Example 18 (Step 1-9) using (3S)-1-methyl-3-piperidinol in Step 7 and (pyridin-2-yl)carbamic acid phenyl ester in Step 9, which was prepared in a similar fashion to Example 1 Step 4. $^1$H NMR (400 MHz, Methanol-$d_4$) δ 8.25 (ddd, J=5.0, 1.9, 0.9 Hz, 1H), 8.01 (d, J=5.7 Hz, 1H), 7.81 (dt, J=8.5, 1.0 Hz, 1H), 7.72 (ddd, J=8.5, 7.2, 1.9 Hz, 1H), 7.09 (d, J=1.8 Hz, 1H), 7.04 (ddd, J=7.2, 5.0, 1.1 Hz, 1H), 6.77 (dd, J=5.8, 1.7 Hz, 1H), 5.08 (d, J=51.4 Hz, 1H), 4.92-4.79 (m, 1H), 4.44-4.27 (m, 1H), 4.20 (dd, J=12.8, 4.4 Hz, 1H), 4.10-4.00 (m, 1H), 3.57 (t, J=12.2 Hz, 1H), 3.30-3.20 (m, 1H), 3.16 (d, J=1.8 Hz, 3H), 2.83 (d, J=11.7 Hz, 1H), 2.64-2.40 (m, 3H), 2.37 (s, 3H), 2.11-1.82 (m, 4H), 1.73-1.48 (m, 2H). ESI MS $[M+H]^+$ for $C_{24}H_{33}FN_7O_3$, calcd 486.3, found 486.2.

Example 112: 2-[(S)-3-[3-(5-ethoxy-2-pyrazinyl)-1-methylureido]-4,4-difluoro-1-piperidyl]-4-pyrimidinyl [(R)-1-methyl-3-piperidyl]methanecarbamate

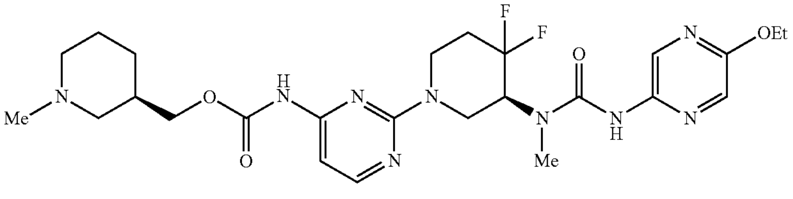 [SMILES: CCOc1cnc(NC(=O)N(C)[C@H]2CN(c3nccc(NC(=O)OC[C@@H]4CCCN(C)C4)n3)CCC2(F)F)cn1]

The title compound was synthesized in a similar fashion to Example 11 using 1,1-dimethylethyl (3R)-3-(hydroxymethyl)-1-piperidinecarboxylate in Step 5. $^1$H NMR (400 MHz, Methanol-$d_4$) δ 8.50 (d, J=1.4 Hz, 1H), 8.21 (d, J=5.7 Hz, 1H), 7.92 (d, J=1.4 Hz, 1H), 7.23 (d, J=5.7 Hz, 1H), 4.88-4.74 (m, 2H), 4.60 (dd, J=26.3, 11.0 Hz, 1H), 4.35 (q, J=7.0 Hz, 2H), 4.10 (dd, J=10.9, 5.4 Hz, 1H), 3.98 (dd, J=10.9, 7.3 Hz, 1H), 3.45 (d, J=12.2 Hz, 1H), 3.21-3.08 (m, 4H), 3.05-2.77 (m, 2H), 2.33 (s, 3H), 2.24-1.49 (m, 8H), 1.38 (t, J=7.0 Hz, 3H), 1.16-0.96 (m, 1H). ESI MS $[M+H]^+$ for $C_{25}H_{36}F_2N_9O_4$, calcd 564.3, found 564.3.

Example 113: 2-[(S)-3-[3-(5-ethoxy-2-pyrazinyl)-1-methylureido]-4,4-difluoro-1-piperidyl]-4-pyrimidinyl (1S,4R,6S)-2-azabicyclo[2.2.1]heptane-6-carbamate

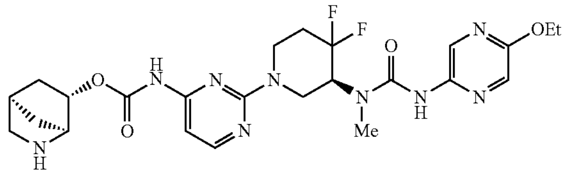 [SMILES: CCOc1cnc(NC(=O)N(C)[C@H]2CN(c3nccc(NC(=O)O[C@H]4C[C@@H]5CN[C@H]4C5)n3)CCC2(F)F)cn1]

The title compound was synthesized in a similar fashion to Example 11 (step 1-8 (part 1)) using 1,1-dimethylethyl (1S,4R,6S)-6-hydroxy-2-azabicyclo[2.2.1]heptane-2-carboxylate in Step 5. $^1$H NMR (400 MHz, Methanol-$d_4$) δ 8.50 (d, J=1.4 Hz, 1H), 8.21 (d, J=5.7 Hz, 1H), 7.92 (d, J=1.4 Hz, 1H), 7.22 (d, J=5.7 Hz, 1H), 4.84-4.69 (m, 2H), 4.60 (dd, J=26.0, 11.3 Hz, 1H), 4.35 (q, J=7.1 Hz, 2H), 3.51-3.40 (m, 2H), 3.23-3.06 (m, 4H), 2.73 (dt, J=9.5, 2.9 Hz, 1H), 2.52-2.45 (m, 2H), 2.22-1.84 (m, 4H), 1.70 (d, J=10.3 Hz, 1H), 1.65-1.56 (m, 1H), 1.53-1.44 (m, 1H), 1.38 (t, J=7.1 Hz, 3H). ESI MS $[M+H]^+$ for $C_{24}H_{32}F_2N_9O_4$, calcd 446.3, found 446.3.

Example 114: 2-[(S)-3-[3-(5-ethoxy-2-pyrazinyl)-1-methylureido]-4,4-difluoro-1-piperidyl]-4-pyrimidinyl [(S)-1-methyl-3-piperidyl]methanecarbamate

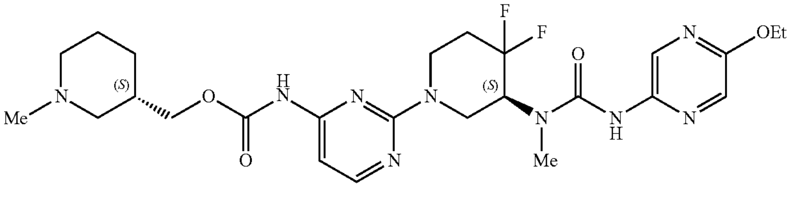

The title compound was synthesized in a similar fashion to Example 11 using 1,1-dimethylethyl (3S)-3-(hydroxymethyl)-1-piperidinecarboxylate in Step 5. $^1$H NMR (400 MHz, Methanol-$d_4$) δ 8.50 (d, J=1.4 Hz, 1H), 8.21 (d, J=5.7 Hz, 1H), 7.92 (d, J=1.5 Hz, 1H), 7.23 (d, J=5.7 Hz, 1H), 4.84-4.76 (m, 2H), 4.60 (d, J=21.0 Hz, 1H), 4.35 (q, J=7.0 Hz, 2H), 4.08 (dd, J=10.9, 5.6 Hz, 1H), 3.98 (dd, J=10.9, 7.4 Hz, 1H), 3.51-3.41 (m, 1H), 3.16 (d, J=2.0 Hz, 4H), 2.95 (d, J=11.0 Hz, 1H), 2.83 (d, J=11.6 Hz, 1H), 2.29 (s, 3H), 2.22-1.51 (m, 8H), 1.38 (t, J=7.0 Hz, 3H), 1.06 (tt, J=12.3, 6.2 Hz, 1H). ESI MS $[M+H]^+$ for $C_{25}H_{36}F_2N_9O_4$, calcd 564.3, found 564.3.

Example 115: 2-[(R)-3-[3-(1,3-benzothiazol-2-yl)-1-methylureido]-1-piperidyl]-4-pyrimidinyl 1-methyl-4-piperidinecarbamate

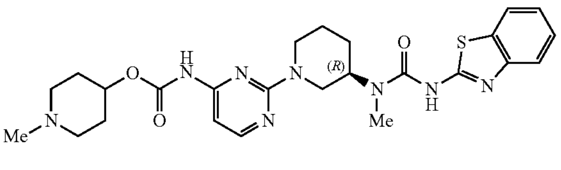

The title compound was synthesized in a similar fashion to Example 1 using 4-hydroxy-N-methylpiperidine in Step 1 and 2-aminobenzothiazole in Step 4. $^1$H NMR (400 MHz, Methanol-$d_4$) δ 8.25 (d, J=5.0 Hz, 1H), 7.70 (d, J=7.9 Hz, 1H), 7.49 (s, 1H), 7.35 (t, J=7.7 Hz, 1H), 7.25-7.15 (m, 2H), 4.84-4.74 (m, 1H), 4.67 (dd, J=14.8, 11.2 Hz, 2H), 4.24 (s, 1H), 3.16-2.92 (m, 4H), 2.88-2.63 (m, 3H), 2.55-2.22 (m, 5H), 1.99-1.54 (m, 8H). ESI MS [M+H]$^+$ for $C_{25}H_{33}N_8O_3S$, calcd 525.2, found 525.2.

Example 116: 2-[(R)-3-[1-methyl-3-(3-pyridazinyl)ureido]-1-piperidyl]-4-pyrimidinyl 1-methyl-4-piperidinecarbamate

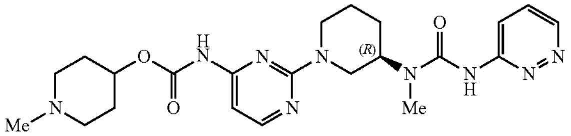

The title compound was synthesized in a similar fashion to Example 1 using 4-hydroxy-N-methylpiperidine in Step 1 and 3-aminopyridazine in Step 4. $^1$H NMR (400 MHz, Methanol-$d_4$) δ 8.83 (d, J=4.7 Hz, 1H), 8.28 (d, J=5.7 Hz, 1H), 8.20 (d, J=9.1 Hz, 1H), 7.62 (dd, J=9.1, 4.7 Hz, 1H), 7.19 (d, J=5.7 Hz, 1H), 4.98-4.82 (m, 1H), 4.66 (t, J=15.7 Hz, 2H), 4.03 (s, 1H), 3.17-2.99 (m, 7H), 2.95-2.76 (m, 3H), 2.61 (s, 3H), 2.18-1.72 (m, 7H), 1.68-1.50 (m, 1H). ESI MS [M+H]$^+$ for $C_{22}H_{32}N_9O_3$, calcd 470.3, found 470.2.

Example 117: 2-[(3S,4R)-3-[3-(1,3-benzothiazol-2-yl)-1-methylureido]-4-fluoro-1-piperidyl]-4-pyrimidinyl 1-methyl-4-piperidinecarbamate

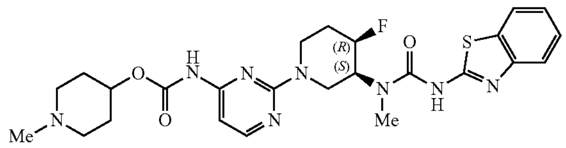

The title compound was synthesized in a similar fashion to Example 18 (Step 1-9, using 4-hydroxy-N-methylpiperidine in Step 7 and (benzothiazol-2-yl)carbamic acid phenyl ester in Step 9, which was prepared in a similar fashion to Example 1 Step 4). $^1$H NMR (400 MHz, Methanol-$d_4$) δ 8.22 (t, J=6.0 Hz, 1H), 7.66 (d, J=7.8 Hz, 1H), 7.48-7.28 (m, 3H), 7.21 (t, J=7.6 Hz, 1H), 5.28-4.90 (m, 2H), 4.72-4.41 (m, 3H), 3.72-3.52 (m, 2H), 3.46-3.23 (m, 2H), 3.23-3.07 (m, 5H), 2.87 (m, 3H), 2.45-1.76 (m, 6H). ESI MS [M+H]$^+$ for $C_{25}H_{32}FN_8O_3S$, calcd 543.2, found 543.2.

Example 118: 2-[(S)-3-[3-(1,3-benzothiazol-2-yl)-1-methylureido]-4,4-difluoro-1-piperidyl]-4-pyrimidinyl 1-methyl-4-piperidinecarbamate

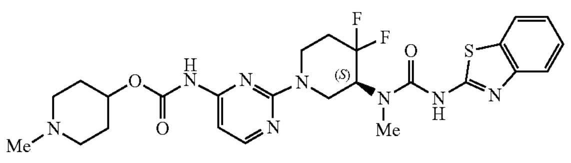

The title compound was synthesized in a similar fashion to Example 11 (Step 1-7, using 4-hydroxy-N-methylpiperidine in Step 5 and (benzothiazol-2-yl)carbamic acid phenyl ester in Step 7, which was prepared in a similar fashion to Example 1 Step 4). $^1$H NMR (400 MHz, Methanol-$d_4$) δ 8.32-8.13 (m, 1H), 7.65 (s, 1H), 7.54-7.03 (m, 4H), 5.15-4.15 (br m, 3H), 3.59-3.39 (m, 1H), 3.17 (br s, 5H), 2.98-2.29 (m, 7H), 2.23-1.67 (m, 6H). ESI MS [M+H]$^+$ for $C_{25}H_{31}F_2N_8O_3S$, calcd 561.2, found 561.2.

Example 119: 2-[(S)-3-[3-(6-ethoxy-3-pyridazinyl)-1-methylureido]-4,4-difluoro-1-piperidyl]-4-pyrimidinyl 1-methyl-4-piperidinecarbamate

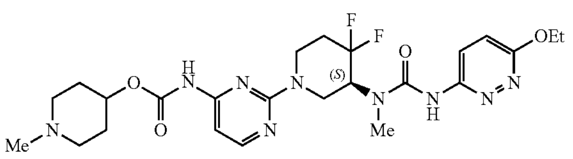

The title compound was synthesized in a similar fashion to Example 11 (Step 1-7, using 4-hydroxy-N-methylpiperidine in Step 5 and (6-ethoxy-pyridazin-2-yl)carbamic acid phenyl ester in Step 7, which was prepared in a similar fashion to Example 1 Step 4). $^1$H NMR (400 MHz, Methanol-$d_4$) δ 8.22 (t, J=5.3 Hz, 1H), 7.96 (d, J=9.9 Hz, 1H), 7.27-7.19 (m, 1H), 7.17-7.07 (m, 1H), 4.97-4.75 (m, 3H), 4.72-4.51 (m, 1H), 4.48-4.37 (m, 2H), 3.48 (t, J=12.3 Hz, 1H), 3.22-3.10 (m, 4H), 3.00 (br s, 2H), 2.78 (br s, 2H), 2.56 (s, 3H), 2.26-1.78 (m, 6H), 1.46-1.36 (m, 3H). ESI MS [M+H]$^+$ for $C_{24}H_{34}F_2N_9O_4$, calcd 550.3, found 550.3.

Example 120: 2-[(S)-3-[3-(6-cyclopropyl-3-pyridazinyl)-1-methylureido]-4,4-difluoro-1-piperidyl]-4-pyrimidinyl 1-methyl-4-piperidinecarbamate

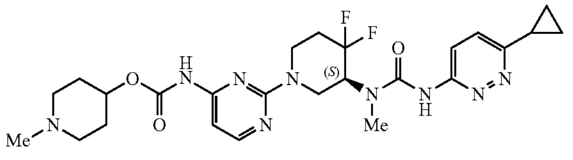

The title compound was synthesized in a similar fashion to Example 11 (Step 1-7, using 4-hydroxy-N-methylpiperidine in Step 5 and (6-cyclopropyl-pyridazin-2-yl)carbamic acid phenyl ester in Step 7, which was prepared in a similar fashion to Example 1 Step 4). $^1$H NMR (400 MHz, Methanol-$d_4$) δ 8.30-8.16 (m, 1H), 8.07-7.93 (m, 1H), 7.38 (d, J=9.5 Hz, 1H), 7.28-7.15 (m, 1H), 4.96-4.76 (m, 3H), 4.70-4.51 (m, 1H), 3.58-3.40 (m, 1H), 3.24-3.09 (m, 4H), 2.98 (br s, 2H), 2.75 (br s, 2H), 2.54 (s, 3H), 2.29-1.78 (m, 7H), 1.17-0.94 (m, 4H). ESI MS [M+H]$^+$for $C_{25}H_{34}F_2N_9O_3$, calcd 546.3, found 546.3.

Example 121A: 2-[(S)-3-[3-(5-ethoxy-2-pyrazinyl)-1-methylureido]-4,4-difluoro-1-piperidyl]-4-pyrimidinyl (R)-1-(1-methyl-4-piperidyl)-1-ethanecarbamate

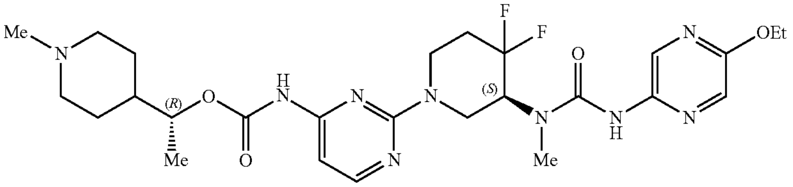

The title compound was synthesized in a similar fashion to Example 11 using 1,1-dimethylethyl 4-[(1R)-1-hydroxyethyl]-1-piperidinecarboxylate in Step 5. $^1H$ NMR (400 MHz, Methanol-$d_4$) δ 8.50 (s, 1H), 8.28-8.15 (m, 1H), 7.93 (s, 1H), 7.26-7.19 (m, 1H), 4.94-4.70 (m, 3H), 4.67-4.53 (m, 1H), 4.42-4.27 (m, 2H), 3.46 (t, J=11.6 Hz, 1H), 3.21-3.02 (m, 6H), 2.45 (s, 3H), 2.38-1.33 (m, 12H), 1.31-1.24 (d, J=5.9 Hz, 3H). ESI MS $[M+H]^+$ for $C_{26}H_{38}F_2N_9O_4$, calcd 578.3, found 578.3.

Example 121B: 2-[(S)-3-[3-(5-ethoxy-2-pyrazinyl)-1-methylureido]-4,4-difluoro-1-piperidyl]-4-pyrimidinyl 1-acetyl-4-piperidinecarbamate

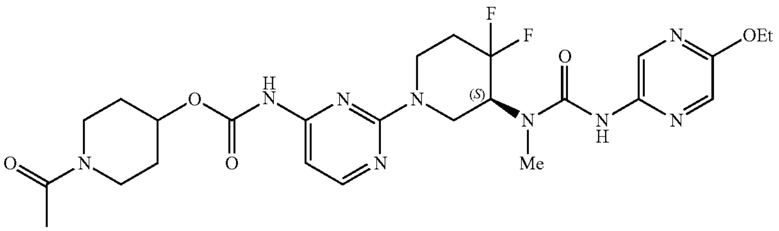

The title compound was synthesized in a similar fashion to Example 11 (Step 1-7) using 1-acetylpiperidin-4-ol in Step 5. $^1$H NMR (400 MHz, Methanol-$d_4$) δ 8.50 (s, 1H), 8.26-8.16 (m, 1H), 7.92 (s, 1H), 7.28-7.20 (m, 1H), 4.99 (br s, 1H), 4.91-4.73 (m, 2H), 4.70-4.47 (m, 1H), 4.40-4.29 (m, 2H), 3.77 (br d, J=40.1 Hz, 2H), 3.56-3.39 (m, 3H), 3.23-3.09 (m, 4H), 2.29-1.83 (m, 7H), 1.81-1.56 (m, 2H), 1.43-1.31 (m, 3H). ESI MS $[M+H]^+$ for $C_{25}H_{34}F_2N_9O_5$, calcd 578.3, found 578.1.

Example 122: 2-[(S)-3-[3-(5-ethoxy-2-pyrazinyl)-1-methylureido]-4,4-difluoro-1-piperidyl]-4-pyrimidinyl (S)-1-(4-piperidyl)-1-ethanecarbamate

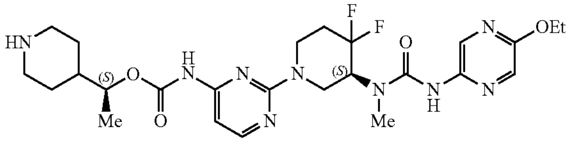

The title compound was synthesized in a similar fashion to Example 11 (steps 1-8 (part 1)) using 1,1-dimethylethyl 4-[(1S)-1-hydroxyethyl]-1-piperidinecarboxylate in Step 5. $^1$H NMR (400 MHz, Methanol-$d_4$) δ 8.49 (t, J=3.6 Hz, 1H), 8.26-8.18 (m, 1H), 7.93 (t, J=3.6 Hz, 1H), 7.30-7.12 (m, 3H), 4.93-4.72 (m, 3H), 4.71-4.50 (m, 1H), 4.39-4.27 (m, 2H), 3.56-3.28 (m, 3H), 3.22-3.08 (m, 4H), 3.02-2.83 (m, 2H), 2.31-1.77 (m, 5H), 1.57-1.21 (m, 8H). ESI MS $[M+H]^+$ for $C_{25}H_{36}F_2N_9O_4$, calcd 564.3, found 564.3.

Example 123: 2-[(S)-3-[3-(5-ethoxy-2-pyrazinyl)-1-methylureido]-4,4-difluoro-1-piperidyl]-4-pyrimidinyl (S)-1-(1-methyl-4-piperidyl)-1-ethanecarbamate

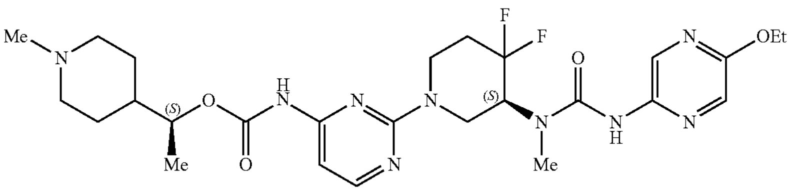

The title compound was synthesized in a similar fashion to Example 11 using 1,1-dimethylethyl 4-[(1S)-1-hydroxyethyl]-1-piperidinecarboxylate in Step 5. $^1$H NMR (400 MHz, Methanol-$d_4$) δ 8.50 (s, 1H), 8.24-8.16 (m, 1H), 7.92 (s, 1H), 7.28-7.19 (m, 1H), 4.89-4.68 (m, 3H), 4.67-4.49 (m, 1H), 4.39-4.28 (m, 2H), 3.46 (t, J=12.3 Hz, 1H), 3.24-2.98 (m, 6H), 2.39 (s, 3H), 2.30-1.31 (m, 12H), 1.32-1.21 (m, 3H). ESI MS $[M+H]^+$ for $C_{26}H_{38}F_2N_9O_4$, calcd 578.3, found 578.3.

Example 124: 2-[(S)-3-[3-(5-ethoxy-2-pyrazinyl)-1-methylureido]-4,4-difluoro-1-piperidyl]-4-pyrimidinyl 2-(4-piperidyl)-2-propanecarbamate

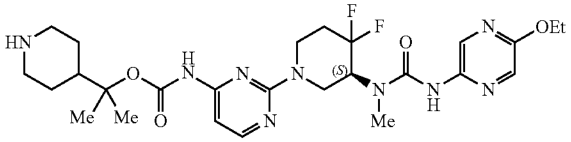

The title compound was synthesized in a similar fashion to Example 11 (steps 1-8 (part 1)) using 1,1-dimethylethyl 4-(1-hydroxy-1-methylethyl)-1-piperidinecarboxylate in Step 5. $^1$H NMR (400 MHz, Methanol-$d_4$) δ 8.49 (d, J=1.4 Hz, 1H), 8.20 (d, J=5.7 Hz, 1H), 7.93 (d, J=1.4 Hz, 1H), 7.21 (d, J=5.7 Hz, 1H), 4.83-4.70 (m, 3H), 4.65-4.54 (m, 1H), 4.35 (q, J=7.0 Hz, 2H), 3.48-3.40 (m, 1H), 3.39-3.32 (m, 1H), 3.20-3.09 (m, 4H), 2.87 (t, J=12.7 Hz, 2H), 2.33-1.85 (m, 5H), 1.62-1.44 (m, 8H), 1.38 (t, J=7.1 Hz, 3H). ESI MS $[M+H]^+$ for $C_{26}H_{38}F_2N_9O_4$, calcd 578.3, found 578.3.

Example 125: 2-[(S)-3-[3-(5-ethoxy-2-pyrazinyl)-1-methylureido]-4,4-difluoro-1-piperidyl]-4-pyrimidinyl 1-glycoloyl-4-piperidinecarbamate

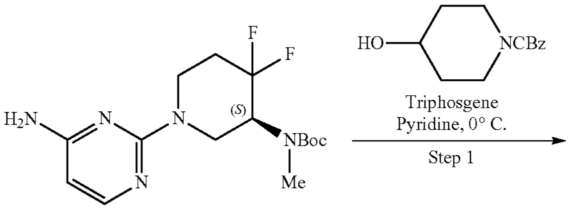

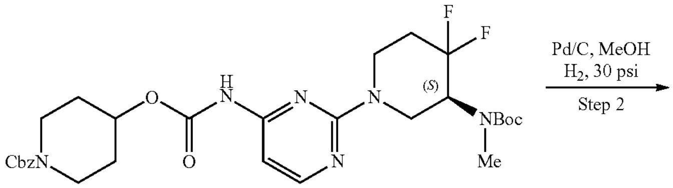

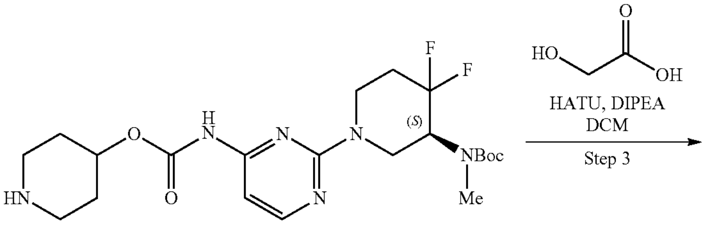

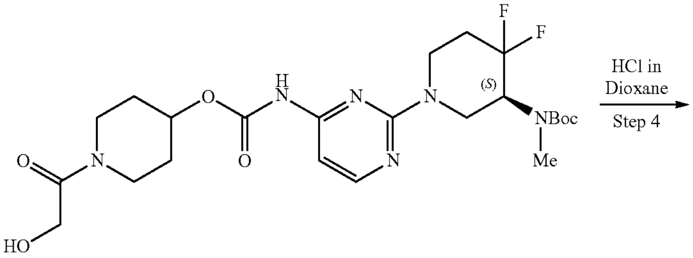

-continued

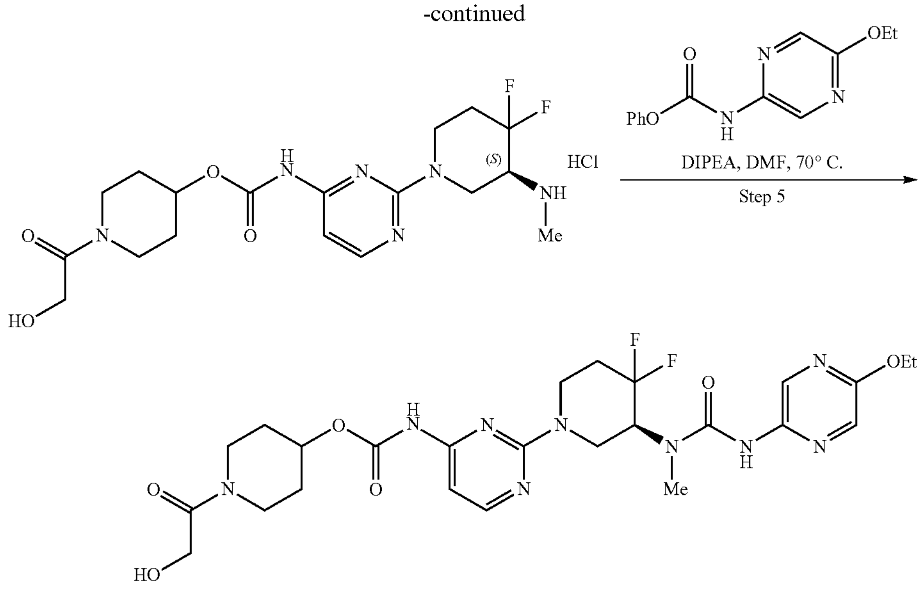

Step 1: This transformation was performed in a similar fashion to Step 5 of the protocol described for the synthesis of Example 11 using benzyl 4-hydroxypiperidine-1-carboxylate and tert-butyl (S)-(1-(4-aminopyrimidin-2-yl)-4,4-difluoropiperidin-3-yl)(methyl)carbamate (synthesized in a similar fashion to example 18, Step 1-4 using tert-butyl (S)-(4,4-difluoropiperidin-3-yl)carbamate in Step 1).

Step 2: A heterogenous mixture of carbamate intermediate from Step 1 (2.5 g, 4.0 mmol), methanol (40 mL), and Pd/C (1.5 g, 50% by weight in $H_2O$) was subjected to a parr shaker under $H_2$ (30 psi) environment for 1 h. Then the reaction mixture was filtered through a pad of CELITE®, and the filtrate was concentrated to obtain desired product, which was forwarded to the next step without further purification.

Step 3: To a combined mixture of amine intermediate from Step 2 (282 mg, 0.60 mmol), HATU (250 mg, 0.66 mmol), in dichloromethane (3 mL) were added glycolic acid (60 mg, 0.80 mmol) and DIPEA (0.27 mL, 1.2 mmol) one after the other. The reaction was stirred for 16 h at room temperature and then quenched with sat. $NaHCO_3$. The resultant mixture was extracted with dichloromethane, dried over anhydrous $Na_2SO_4$, concentrated, and purified using flash column chromatography (20-100% EtOAc/Hexane) to afford desired product.

Step 4: To a solution of intermediate from Step 3 (302 mg, 0.57 mmol) in dioxane (2 mL) was added HCl in dioxane (3 mL, 4M in dioxane) at room temperature. The resultant mixture was stirred for 1 h, diluted with EtOAc (5 mL), and filtered to obtain a hydrochloride salt of the desired product.

Step 5: This transformation was performed in a similar fashion to Step 5 of the protocol described for the synthesis of Example 1. $^1$H NMR (400 MHz, Methanol-$d_4$) δ 8.56-8.46 (m, 1H), 8.22 (d, J=5.7 Hz, 1H), 7.92 (d, J=1.4 Hz, 1H), 7.24 (d, J=5.7 Hz, 1H), 5.00 (tt, J=7.4, 3.6 Hz, 1H), 4.88-4.73 (m, 2H), 4.71-4.52 (m, 1H), 4.35 (q, J=7.0 Hz, 2H), 4.23 (s, 2H), 3.91-3.78 (m, 1H), 3.67-3.40 (m, 3H), 3.41-3.32 (m, 1H), 3.22-3.05 (m, 4H), 2.26-1.85 (m, 4H), 1.81-1.64 (m, 2H), 1.38 (t, J=7.0 Hz, 3H). ESI MS $[M+H]^+$ for $C_{25}H_{34}F_2N_9O_6$, calcd 594.3, found 594.3.

Example 126: 2-[(S)-3-[3-(5-ethoxy-2-pyrazinyl)-1-methylureido]-4,4-difluoro-1-piperidyl]-4-pyrimidinyl (S)-3,3-dimethyl-4-piperidinecarbamate

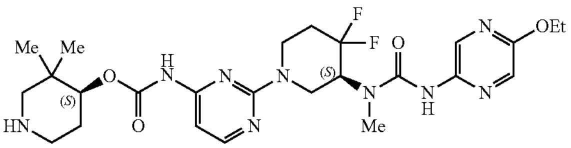

The title compound was synthesized in a similar fashion to Example 11 (steps 1-8 (part 1)) using 1,1-dimethylethyl (4S)-4-hydroxy-3,3-dimethyl-1-piperidinecarboxylate in Step 5. $^1$H NMR (400 MHz, Methanol-$d_4$) δ 8.49 (d, J=1.4 Hz, 1H), 8.23 (d, J=5.7 Hz, 1H), 7.92 (d, J=1.4 Hz, 1H), 7.24 (d, J=5.7 Hz, 1H), 4.85-4.77 (m, 2H), 4.73 (dd, J=7.9, 3.6 Hz, 1H), 4.61 (dd, J=26.0, 10.9 Hz, 1H), 4.35 (q, J=7.0 Hz, 2H), 3.52-3.42 (m, 1H), 3.22-3.10 (m, 5H), 3.01-2.91 (m, 2H), 2.77 (d, J=13.1 Hz, 1H), 2.26-1.76 (m, 4H), 1.38 (t, J=7.0 Hz, 3H), 1.09-1.03 (m, 6H). ESI MS $[M+H]^+$ for $C_{25}H_{36}F_2N_9O_4$, calcd 564.3, found 564.3.

Example 127: 2-[(S)-3-[3-(5-ethoxy-2-pyrazinyl)-1-methylureido]-4,4-difluoro-1-piperidyl]-4-pyrimidinyl (S)-1-methyl-3,3-dimethyl-4-piperidinecarbamate

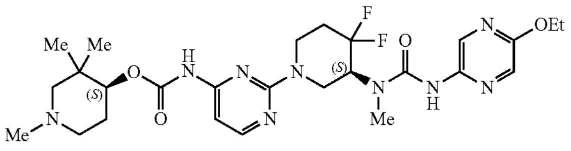

The title compound was synthesized in a similar fashion to Example 11 using 1,1-dimethylethyl (4S)-4-hydroxy-3,3-dimethyl-1-piperidinecarboxylate in Step 5. $^1$H NMR (400 MHz, Methanol-$d_4$) δ 8.50 (d, J=1.4 Hz, 1H), 8.22 (d, J=5.7

Hz, 1H), 7.92 (d, J=1.5 Hz, 1H), 7.23 (d, J=5.7 Hz, 1H), 4.89-4.74 (m, 2H), 4.69-4.48 (m, 2H), 4.35 (q, J=7.0 Hz, 2H), 3.47 (t, J=12.1 Hz, 1H), 3.22-3.09 (m, 4H), 2.74 (br s, 1H), 2.59-1.77 (m, 10H), 1.38 (t, J=7.1 Hz, 3H), 1.06 (s, 3H), 1.00 (s, 3H). ESI MS $[M+H]^+$ for $C_{26}H_{38}F_2N_9O_4$, calcd 578.3, found 578.3.

Example 128: 2-[(S)-4,4-difluoro-3-[1-methyl-3-(3-pyridazinyl)ureido]-1-piperidyl]-4-pyrimidinyl (3S,4R)-3-methyl-4-piperidinecarbamate

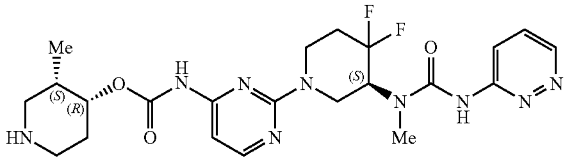

The title compound was synthesized in a similar fashion to Example 11 (steps 1-8 (part 1)) using 1,1-dimethylethyl (3S,4R)-4-hydroxy-3-methyl-1-piperidinecarboxylate in Step 5 and (pyridazin-2-yl)carbamic acid phenyl ester in Step 7, which was prepared in a similar fashion to Example 1 Step 4. $^1H$ NMR (400 MHz, Methanol-$d_4$) δ 8.83 (d, J=4.7 Hz, 1H), 8.25 (d, J=5.7 Hz, 1H), 8.16 (d, J=9.1 Hz, 1H), 7.62 (dd, J=9.1, 4.7 Hz, 1H), 7.25 (d, J=5.7 Hz, 1H), 5.04 (s, 1H), 4.90-4.78 (m, 2H), 4.63 (dd, J=25.6, 11.2 Hz, 1H), 3.52 (t, J=12.1 Hz, 1H), 3.25-2.98 (m, 7H), 2.89 (t, J=12.1 Hz, 1H), 2.26-1.82 (m, 5H), 0.97 (d, J=6.8 Hz, 3H). ESI MS $[M+H]^+$ for $C_{22}H_{30}F_2N_9O_3$, calcd 506.2, found 506.2.

Example 129: 2-[(S)-4,4-difluoro-3-[1-methyl-3-(3-pyridazinyl)ureido]-1-piperidyl]-4-pyrimidinyl (3S,4R)-1-methyl-3-methyl-4-piperidinecarbamate

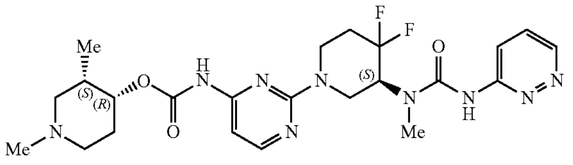

The title compound was synthesized in a similar fashion to Example 11 using 1,1-dimethylethyl (3S,4R)-4-hydroxy-3-methyl-1-piperidinecarboxylate in Step 5 and (pyridazin-2-yl)carbamic acid phenyl ester in Step 7, which was prepared in a similar fashion to Example 1 Step 4. $^1H$ NMR (400 MHz, Methanol-$d_4$) δ 8.83 (d, J=4.6 Hz, 1H), 8.25 (d, J=5.7 Hz, 1H), 8.16 (d, J=9.1 Hz, 1H), 7.62 (dd, J=9.1, 4.7 Hz, 1H), 7.25 (d, J=5.7 Hz, 1H), 4.99 (s, 1H), 4.91-4.74 (m, 2H), 4.63 (dd, J=23.4, 11.5 Hz, 1H), 3.51 (t, J=12.1 Hz, 1H), 3.26-2.98 (m, 6H), 2.86 (t, J=12.6, 1H), 2.75-2.63 (m, 4H), 2.22-1.92 (m, 5H), 0.98 (d, J=6.9 Hz, 3H). ESI MS $[M+H]^+$ for $C_{23}H_{32}F_2N_9O_3$, calcd 520.3, found 520.2.

Example 130: 2-[(3S,4R)-4-fluoro-3-[1-methyl-3-(7-methyl-3-isoquinolyl)ureido]-1-piperidyl]-4-pyrimidinyl (1S,4S,5R)-2-azabicyclo[2.2.1]heptane-5-carbamate

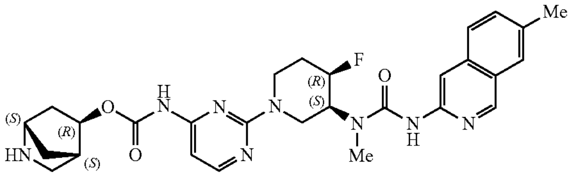

The title compound was synthesized in a similar fashion to Example 18 (steps 1-10 (part 1)) using 1,1-dimethylethyl (1S,4S,5R)-5-hydroxy-2-azabicyclo[2.2.1]heptane-2-carboxylate in Step 7 and (7-methyl-isoquinolinamine-3-yl) carbamic acid phenyl ester in Step 9, which was prepared in a similar fashion to Example 1 Step 4). $^1H$ NMR (400 MHz, Methanol-$d_4$) δ 8.94 (s, 1H), 8.22 (d, J=5.7 Hz, 1H), 8.09 (s, 1H), 7.75 (s, 1H), 7.71 (d, J=8.5 Hz, 1H), 7.54 (dd, J=8.5, 1.7 Hz, 1H), 7.18 (d, J=5.7 Hz, 1H), 5.10 (d, J=51.1 Hz, 1H), 4.89-4.79 (m, 1H), 4.65 (td, J=13.4, 4.8 Hz, 2H), 4.44-4.24 (m, 1H), 3.95 (s, 1H), 3.57 (t, J=12.2 Hz, 1H), 3.26-3.17 (m, 4H), 3.13-3.06 (m, 1H), 2.86 (d, J=11.4 Hz, 1H), 2.79 (s, 1H), 2.51 (s, 3H), 2.27-2.17 (m, 1H), 2.12-1.76 (m, 4H), 1.66 (d, J=11.3 Hz, 1H). ESI MS $[M+H]^+$ for $C_{28}H_{34}FN_8O_3$, calcd 549.3, found 549.3.

Example 131: 2-[(3S,4R)-4-fluoro-3-[1-methyl-3-(7-methyl-3-isoquinolyl)ureido]-1-piperidyl]-4-pyrimidinyl (1S,4S,5R)-2-methyl-2-azabicyclo[2.2.1]heptane-5-carbamate

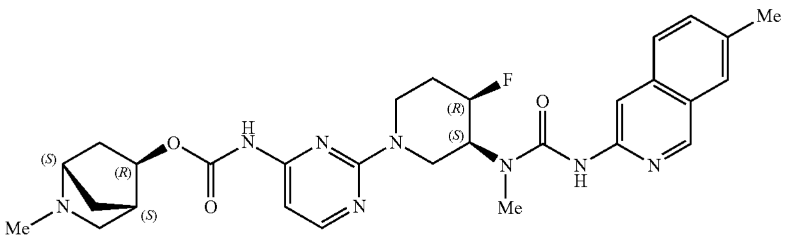

The title compound was synthesized in a similar fashion to Example 18 using 1,1-dimethylethyl (1S,4S,5R)-5-hydroxy-2-azabicyclo[2.2.1]heptane-2-carboxylate in Step 7 and (7-methyl-isoquinolinamine-3-yl)carbamic acid phenyl ester in Step 9, which was prepared in a similar fashion to Example 1 Step 4). $^{1}H$ NMR (400 MHz, Methanol-$d_4$) δ 8.94 (s, 1H), 8.22 (d, J=5.7 Hz, 1H), 8.09 (s, 1H), 7.75 (s, 1H), 7.71 (d, J=8.5 Hz, 1H), 7.54 (dd, J=8.5, 1.7 Hz, 1H), 7.18 (d, J=5.7 Hz, 1H), 5.10 (d, J=51.1 Hz, 1H), 4.79 (dd, J=7.1, 2.3 Hz, 1H), 4.65 (td, J=13.3, 4.8 Hz, 2H), 4.33 (ddd, J=33.4, 11.9, 4.6 Hz, 1H), 3.64 (d, J=3.0 Hz, 1H), 3.56 (t, J=12.2 Hz, 1H), 3.27-3.15 (m, 4H), 3.00 (dd, J=11.4, 4.4 Hz, 1H), 2.77-2.67 (m, 2H), 2.61 (s, 3H), 2.51 (s, 3H), 2.38 (dd, J=15.3, 7.2 Hz, 1H), 2.18-2.00 (m, 1H), 2.00-1.78 (m, 3H), 1.72 (d, J=15.3 Hz, 1H). ESI MS $[M+H]^+$ for $C_{29}H_{36}FN_8O_3$, calcd 563.3, found 563.3.

Example 132: 2-[(3S,4R)-3-[3-(5-ethoxy-2-pyrazinyl)-1-methylureido]-4-fluoro-1-piperidyl]-4-pyridyl (1R,4R,5S)-2-methyl-2-azabicyclo[2.2.1]heptane-5-carbamate

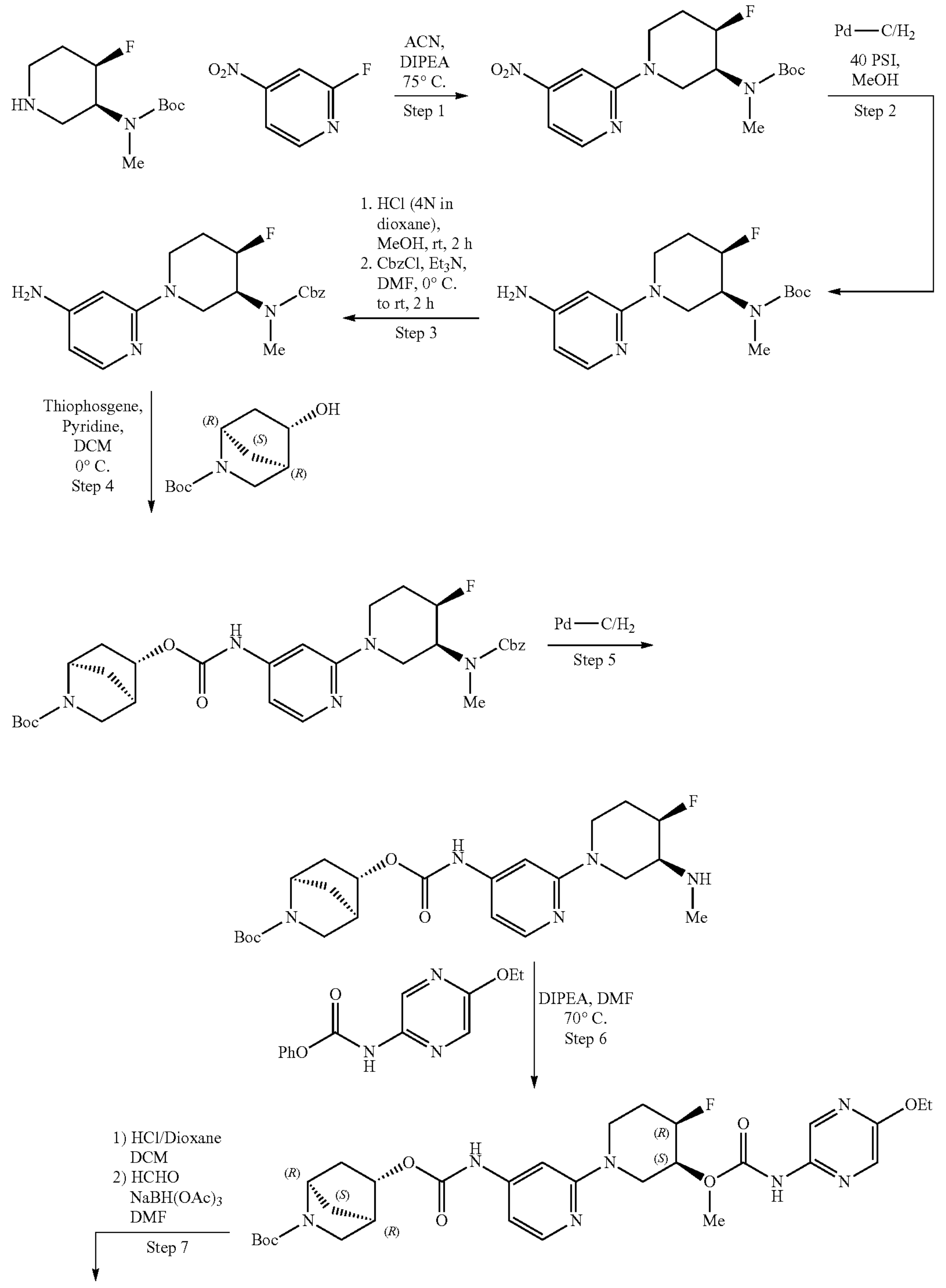

-continued

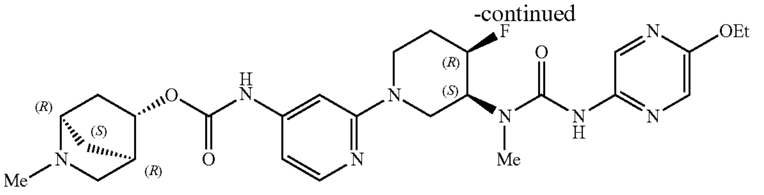

Step 1: This transformation was performed in a similar fashion to Step 1 of the protocol described for the synthesis of Example 26 using phenylmethyl (3S,4R)-4-fluoropiperidin-3-yl)(methyl)carbamate Step 2: This transformation was performed in a similar fashion to Step 2 of the protocol described for the synthesis of Example 26.

Step 3: This transformation was performed in a similar fashion to Step 5 and Step 6 of the protocol described for the synthesis of Example 18.

Step 4: This transformation was performed in a similar fashion to Step 7 of the protocol described for the synthesis of Example 18 using tert-butyl (1R,4R,6S)-6-hydroxy-2-azabicyclo[2.2.1]heptane-2-carboxylat.

Step 5: This transformation was performed in a similar fashion to Step 8 of the protocol described for the synthesis of Example 18.

Step 6: This transformation was performed in a similar fashion to Step 9 of the protocol described for the synthesis of Example 18.

Step 7: This transformation was performed in a similar fashion to Step 10 of the protocol described for the synthesis of Example 18. $^1$H NMR (400 MHz, MeOD) δ 8.51 (d, J=1.4 Hz, 1H), 8.00 (d, J=5.8 Hz, 1H), 7.93 (d, J=1.4 Hz, 1H), 7.09 (d, J=1.8 Hz, 1H), 6.75 (dd, J=5.8, 1.8 Hz, 1H), 5.18-4.94 (m, 1H), 4.69 (dd, J=7.1, 2.5 Hz, 1H), 4.35 (q, J=7.0 Hz, 2H), 4.28 (dd, J=12.1, 4.2 Hz, 1H), 4.17 (dd, J=12.7, 4.2 Hz, 1H), 4.11-3.96 (m, 1H), 3.56 (t, J=12.3 Hz, 1H), 3.29-3.22 (m, 2H), 3.14 (d, J=1.9 Hz, 3H), 2.76 (dd, J=10.5, 4.5 Hz, 1H), 2.59-2.50 (m, 1H), 2.31 (s, 4H), 2.19 (d, J=10.4 Hz, 1H), 2.09-1.79 (m, 2H), 1.72 (s, 2H), 1.57-1.45 (m, 1H), 1.38 (t, J=7.0 Hz, 3H). ESI MS $[M+H]^+$ for $C_{26}H_{35}N_8FO_4$, calcd 543.3, found 543.3.

Example 133: 2-[(3S,4R)-3-[3-(5-ethoxy-2-pyrazinyl)-1-methylureido]-4-fluoro-1-piperidyl]-4-pyridyl (3S,4R)-3-methyl-4-piperidinecarbamate

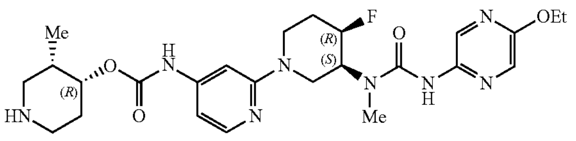

The title compound was synthesized in a similar fashion to Example 132 (steps 1-7 (part1)) using tert-butyl (3R,4S)-4-hydroxy-3-methyl-piperidine-1-carboxylate in Step 4. $^1$H NMR (400 MHz, MeOD) δ 8.65-8.46 (m, 1H), 8.03 (d, J=5.8 Hz, OH), 7.93 (d, J=1.4 Hz, 1H), 7.13 (d, J=1.8 Hz, 1H), 6.78 (dd, J=5.8, 1.7 Hz, 1H), 5.18-5.01 (m, 2H), 4.34 (q, J=7.0 Hz, 1H), 4.29 (dd, J=12.8, 3.6 Hz, 1H), 4.19 (dd, J=12.9, 4.4 Hz, 1H), 4.05 (dd, J=14.1, 4.7 Hz, 1H), 3.57 (t, J=12.3 Hz, 1H), 3.29-3.20 (m, 2H), 3.20-3.06 (m, 5H), 2.96 (t, J=12.4 Hz, 1H), 2.18 (dt, J=12.0, 3.4 Hz, 1H), 2.10-1.93 (m, 3H), 1.88 (m, 3H), 1.38 (t, J=7.1 Hz, 3H), 1.03 (d, J=6.9 Hz, 3H). ESI MS $[M+H]^+$ for $C_{25}H_{35}N_8FO_4$, calcd 531.3, found 531.3.

Example 134: 2-[(3S,4R)-3-[3-(5-ethoxy-2-pyrazinyl)-1-methylureido]-4-fluoro-1-piperidyl]-4-pyridyl (1S,4S,5R)-2-azabicyclo[2.2.1]heptane-5-carbamate

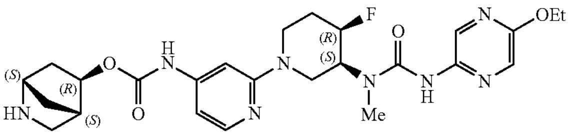

The title compound was synthesized in a similar fashion to Example 132 (steps 1-7 (part1)) using tert-butyl (1S,4S,6R)-6-hydroxy-2-azabicyclo[2.2.1]heptane-2-carboxylate in Step 4. $^1$H NMR (400 MHz, MeOD) δ 8.50 (d, J=1.4 Hz, 1H), 8.43 (s, 2H), 8.01 (d, J=5.8 Hz, 1H), 7.95-7.89 (m, 1H), 7.07 (d, J=1.8 Hz, 1H), 6.78 (dd, J=5.8, 1.7 Hz, 1H), 5.08 (d, J=51.4 Hz, 1H), 4.34 (q, J=7.1 Hz, 3H), 4.28 (dd, J=12.3, 4.0 Hz, 1H), 4.22-4.10 (m, 2H), 4.04 (dd, J=13.7, 4.7 Hz, 1H), 3.56 (t, J=12.3 Hz, 1H), 3.28-3.20 (m, 2H), 3.14 (d, J=1.9 Hz, 3H), 3.00 (dd, J=11.6, 1.7 Hz, 1H), 2.88 (d, J=4.2 Hz, 1H), 2.32 (ddd, J=15.5, 6.9, 2.7 Hz, 1H), 2.17-1.94 (m, 3H), 1.94-1.66 (m, 3H), 1.38 (t, J=7.1 Hz, 3H). ESI MS $[M+H]^+$ for $C_{25}H_{33}N_8FO_4$, calcd 529.3, found 529.3.

Example 135: 2-[(3S,4R)-3-[3-(5-ethoxy-2-pyrazinyl)-1-methylureido]-4-fluoro-1-piperidyl]-4-pyridyl (3S,4R)-1-methyl-3-methyl-4-piperidinecarbamate

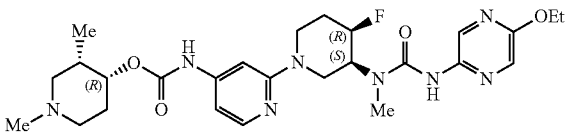

The title compound was synthesized in a similar fashion to Example 132 using tert-butyl (3R,4S)-4-hydroxy-3-methyl-piperidine-1-carboxylate in Step 4. $^1$H NMR (400 MHz, MeOD) δ 8.51 (d, J=1.4 Hz, 1H), 8.49 (s, 1H), 8.03 (d, J=5.8 Hz, 1H), 7.93 (d, J=1.5 Hz, 1H), 7.14 (d, J=1.8 Hz, 1H), 6.78 (dd, J=5.8, 1.7 Hz, 1H), 5.24-5.02 (m, 1H), 4.99 (d, J=3.1 Hz, 1H), 4.34 (q, J=7.1 Hz, 2H), 4.36-4.22 (m, 1H), 4.19 (dd, J=12.8, 4.4 Hz, 1H), 4.05 (dd, J=13.0, 4.5 Hz, 1H), 3.57 (t, J=12.3 Hz, 1H), 3.27-3.16 (m, 3H), 3.15 (d, J=1.9 Hz, 3H), 3.08-2.90 (m, 1H), 2.78 (s, 4H), 2.20 (ddt, J=18.3, 11.9, 3.4 Hz, 2H), 2.10-1.94 (m, 2H), 1.92-1.81 (m, 1H), 1.38 (t, J=7.1 Hz, 3H), 1.02 (d, J=6.9 Hz, 3H). ESI MS $[M+H]^+$ for $C_{26}H_{37}N_8FO_4$, calcd 545.3, found 545.3.

Example 136: 2-[(R)-3-[3-(5-ethoxy-2-pyrazinyl)-1-methylureido]-1-piperidyl]-4-pyrimidinyl 3,3-difluorocyclobutanecarbamate

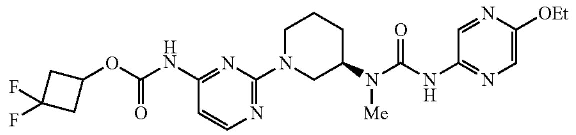 [SMILES: CCOc1cnc(NC(=O)N(C)[C@@H]2CCCN(c3nccc(NC(=O)OC4CC(F)(F)C4)n3)C2)cn1]

The title compound was synthesized in a similar fashion to Example 1 using 3,3-difluorocyclobutan-1-ol in step 1. $^1$H NMR (400 MHz, DMSO) δ 10.47 (s, 1H), 8.88 (s, 1H), 8.58 (d, J=1.4 Hz, 1H), 8.23 (d, J=5.8 Hz, 1H), 8.01 (d, J=1.5 Hz, 1H), 7.03 (d, J=5.8 Hz, 1H), 4.93 (t, J=6.3 Hz, 1H), 4.55 (dd, J=25.7, 12.5 Hz, 1H), 4.30 (d, J=7.1 Hz, 3H), 4.04 (t, J=10.8 Hz, 2H), 3.21-2.96 (m, 3H), 2.93 (s, 3H), 2.82-2.64 (m, 2H), 1.92-1.72 (m, 3H), 1.50 (d, J=13.6 Hz, 1H), 1.32 (t, J=7.0 Hz, 3H). ESI MS $[M+H]^+$ for $C_{22}H_{28}F_2N_8O_4$, calcd 535.3, found 535.1. ESI MS $[M+H]^+$ for $C_{22}H_{28}F_2N_8O_4$, calcd 507.3, found 507.3.

Example 137: 2-[(R)-3-[3-(5-ethoxy-2-pyrazinyl)-1-methylureido]-1-piperidyl]-4-pyrimidinyl (1sS,4S)-4-hydroxy-4-methylcyclohexanecarbamate

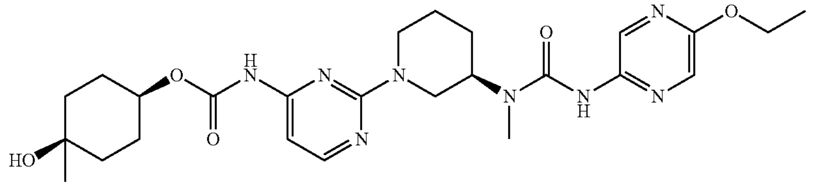 [SMILES: CCOc1cnc(NC(=O)N(C)[C@@H]2CCCN(c3nccc(NC(=O)O[C@H]4CC[C@@](C)(O)CC4)n3)C2)cn1]

The title compound was synthesized in a similar fashion to Example 1 using (1S,4S)-1-methylcyclohexane-1,4-diol in step 1. $^1$H NMR (400 MHz, MeOD) δ 8.40 (d, J=5.0 Hz, 2H), 7.96 (d, J=2.9 Hz, 1H), 7.78 (dd, J=9.3, 2.9 Hz, 1H), 7.69 (d, J=9.3 Hz, 1H), 6.71 (t, J=5.0 Hz, 1H), 4.99 (dt, J=12.0, 4.4 Hz, 1H), 4.89 (s, 7H), 4.57-4.45 (m, 1H), 3.93 (d, J=7.0 Hz, 2H), 3.14-3.00 (m, 1H), 2.54 (dd, J=14.8, 6.5 Hz, 1H), 2.44 (dd, J=14.8, 8.2 Hz, 1H), 2.34 (qd, J=7.2, 3.4 Hz, 1H), 1.96 (ddd, J=14.2, 12.0, 7.2 Hz, 1H), 1.87-1.49 (m, 7H), 1.34-1.20 (m, 1H), 0.82 (t, J=7.3 Hz, 3H), 0.72-0.58 (m, 2H), 0.45-0.31 (m, 2H). ESI MS $[M+H]^+$ for $C_{25}H_{36}N_8O_5$, calcd 529.3, found 529.1.

Example 138: 2-[(R)-3-[3-(5-ethoxy-2-pyrazinyl)-1-methylureido]-1-piperidyl]-4-pyrimidinyl 4,4-difluorocyclohexanecarbamate

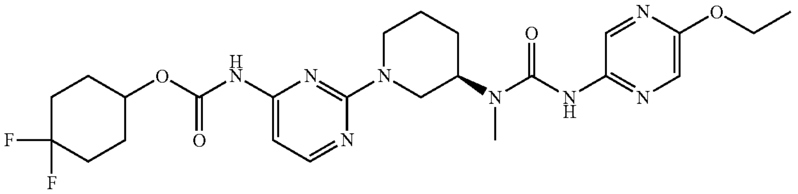 [SMILES: CCOc1cnc(NC(=O)N(C)[C@@H]2CCCN(c3nccc(NC(=O)OC4CCC(F)(F)CC4)n3)C2)cn1]

The title compound was synthesized in a similar fashion to Example 1 using 4,4-difluorocyclohexan-1-ol in step 1. $^1$H NMR (400 MHz, DMSO) δ 10.24 (s, 1H), 8.89 (s, 1H), 8.57 (d, J=1.5 Hz, 1H), 8.23 (d, J=5.8 Hz, 1H), 8.01 (d, J=1.5 Hz, 1H), 7.06 (d, J=5.8 Hz, 1H), 4.89 (q, J=4.6 Hz, 1H), 4.67-4.49 (m, 2H), 4.29 (q, J=6.9 Hz, 2H), 4.05 (t, J=10.2 Hz, 1H), 2.99 (t, J=11.8 Hz, 2H), 2.93 (s, 3H), 2.77 (t, J=12.6 Hz, 2H), 2.01 (ddt, J=29.1, 21.6, 6.4 Hz, 4H), 1.82 (dtq, J=14.9, 9.8, 4.5 Hz, 5H), 1.50 (dd, J=12.9, 4.7 Hz, 1H), 1.32 (t, J=7.0 Hz, 3H). ESI MS $[M+H]^+$ for $C_{24}H_{32}F_2N_8O_4$, calcd 535.3, found 535.1.

Example 139: 2-[(R)-3-[1-methyl-3-(1,3,4-thiadiazol-2-yl)ureido]-1-piperidyl]-4-pyrimidinyl 1-methyl-4-piperidinecarbamate

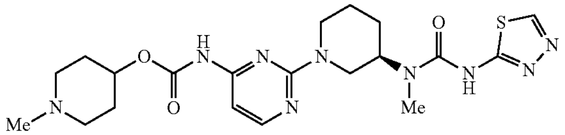 [SMILES: CN1CCC(OC(=O)Nc2ccnc(N3CCC[C@@H](N(C)C(=O)Nc4nncs4)C3)n2)CC1]

The title compound was synthesized in a similar fashion to Example 1 using 1-methylpiperidin-4-ol in step 1 and 2-amino-1,3,4-thiadiazole in step 4. $^1$H NMR (400 MHz, DMSO) δ 11.54 (s, 1H), 10.08 (s, 1H), 8.94 (s, 1H), 8.22 (d, J=5.6 Hz, 1H), 7.01 (d, J=5.6 Hz, 1H), 4.81-4.39 (m, 3H), 4.11 (s, 1H), 2.95 (m, 3H), 2.81-2.65 (m, 1H), 2.58 (brs, 2H), 2.17 (m, 6H), 1.92-1.69 (m, 4H), 1.61 (qd, J=8.6, 4.2 Hz, 2H), 1.49 (d, J=13.2 Hz, 1H), 1.24 (s, 1H). ESI MS $[M+H]^+$ for $C_{20}H_{29}N_9O_3S$, calcd 476.3, found 476.1.

Example 140: 2-[(R)-3-[1-methyl-3-(5-methyl-1,3,4-thiadiazol-2-yl)ureido]-1-piperidyl]-4-pyrimidinyl 1-methyl-4-piperidinecarbamate

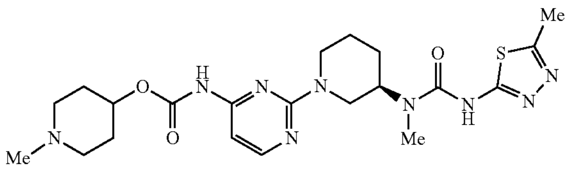 [SMILES: Cc1nnc(NC(=O)N(C)[C@@H]2CCCN(c3nccc(NC(=O)OC4CCN(C)CC4)n3)C2)s1]

The title compound was synthesized in a similar fashion to Example 1 using 1-methylpiperidin-4-ol in step 1 and 2-amino-5-methyl1,3,4-thiadiazole in step 4. $^1$H NMR (400 MHz, DMSO) δ 10.07 (s, 1H), 8.21 (d, J=5.6 Hz, 1H), 7.01 (d, J=5.6 Hz, 1H), 4.77-4.51 (m, 3H), 4.12 (s, 1H), 3.01-2.85 (m, 4H), 2.71 (t, J=13.0 Hz, 1H), 2.58 (s, 2H), 2.17 (s, 6H), 1.94-1.67 (m, 6H), 1.61 (dtd, J=12.2, 8.4, 3.5 Hz, 3H), 1.56-1.38 (m, 1H). ESI MS $[M+H]^+$ for $C_{21}H_{31}N_9O_3S$, calcd 490.3, found 490.1.

Example 141: 2-[(R)-3-{3-[5-(p-fluorophenoxy)-1,3,4-thiadiazol-2-yl]-1-methylureido}-1-piperidyl]-4-pyrimidinyl 1-methyl-4-piperidinecarbamate

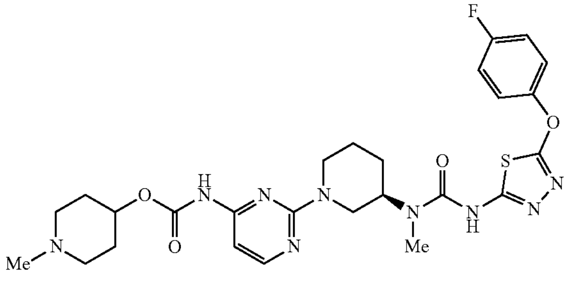 [SMILES: CN1CCC(OC(=O)Nc2ccnc(N3CCC[C@@H](N(C)C(=O)Nc4nnc(Oc5ccc(F)cc5)s4)C3)n2)CC1]

The title compound was synthesized in a similar fashion to Example 1 using 1-methylpiperidin-4-ol in step 1 and 2-amino-(5-(4-fluorophenoxy)-1,3,4-thiadiazole in step 4. $^1$H NMR (400 MHz, DMSO) δ 10.08 (s, 1H), 8.15 (d, J=5.6 Hz, 1H), 7.27-7.07 (m, 4H), 6.98 (d, J=5.6 Hz, 1H), 4.75-4.60 (m, 2H), 4.55 (d, J=11.1 Hz, 2H), 4.34 (s, 1H), 2.79 (d, J=9.9 Hz, 4H), 2.69-2.53 (m, 3H), 2.15 (s, 3H), 1.91-1.72 (m, 3H), 1.65 (dq, J=22.1, 10.5 Hz, 3H), 1.45 (s, 1H).ESI MS $[M+H]^+$ for $C_{26}H_{32}FN_9O_4S$, calcd 586.3, found 586.1.

Example 142: 2-[(R)-3-[3-(5-ethoxy-2-pyrazinyl)-1-methylureido]-1-piperidyl]-4-pyridyl (3-pyridyl) methanecarbamate

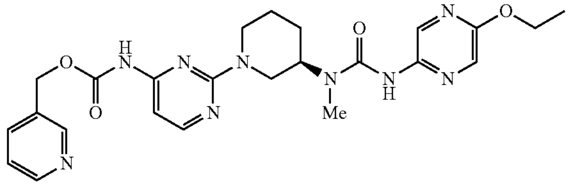 [SMILES: CCOc1cnc(NC(=O)N(C)[C@@H]2CCCN(c3nccc(NC(=O)OCc4cccnc4)n3)C2)cn1]

The title compound was synthesized in a similar fashion to Example 1 using pyridin-3-ylmethanol in step 1. $^1$H NMR (400 MHz, DMSO) δ 9.99 (s, 1H), 9.07 (s, 1H), 8.65 (d, J=2.3 Hz, 1H), 8.62-8.48 (m, 2H), 8.09-7.96 (m, 2H), 7.85 (dt, J=7.8, 2.0 Hz, 1H), 7.43 (ddd, J=7.9, 4.8, 0.9 Hz, 1H), 6.98 (d, J=1.8 Hz, 1H), 6.74 (dd, J=5.7, 1.7 Hz, 1H), 5.19 (s, 2H), 4.29 (q, J=7.0 Hz, 2H), 4.13 (d, J=12.0 Hz, 1H), 4.09-3.92 (m, 2H), 2.92 (s, 3H), 2.80 (t, J=12.7 Hz, 1H), 1.79 (q, J=13.0 Hz, 3H), 1.60-1.46 (m, 1H), 1.32 (t, J=7.0 Hz, 3H). ESI MS $[M+H]^+$ for $C_{24}H_{29}N_8O_4$, calcd 508.3, found 508.1.

Example 143: 2-[(R)-3-[3-(5-cyclopropyl-1,3,4-thiadiazol-2-yl)-1-methylureido]-1-piperidyl]-4-pyrimidinyl 1-methyl-4-piperidinecarbamate

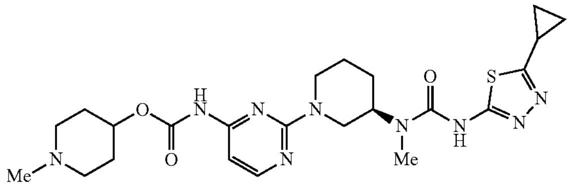 [SMILES: CN1CCC(OC(=O)Nc2ccnc(N3CCC[C@@H](N(C)C(=O)Nc4nnc(C5CC5)s4)C3)n2)CC1]

The title compound was synthesized in a similar fashion to Example 1 using 1-methylpiperidin-4-ol in step 1 and 2-amino-5-cyclopropyl-1,3,4-thiadiazol in Step 4. 2: $^1$H NMR (400 MHz, DMSO) δ 10.07 (s, 1H), 8.20 (d, J=5.6 Hz, 1H), 7.01 (d, J=5.6 Hz, 1H), 4.71-4.59 (m, 2H), 4.55 (dd, J=12.1, 4.2 Hz, 1H), 4.07 (d, J=26.7 Hz, 1H), 2.93 (d, J=4.7 Hz, 4H), 2.71 (t, J=12.6 Hz, 1H), 2.58 (s, 2H), 2.26 (ddd, J=8.4, 6.7, 4.2 Hz, 1H), 2.16 (s, 5H), 1.91-1.80 (m, 2H), 1.80-1.68 (m, 3H), 1.66-1.38 (m, 3H), 1.27-1.22 (m, 1H), 1.14-1.04 (m, 2H), 0.98-0.78 (m, 2H). ESI MS [M+H]$^+$ for $C_{23}H_{33}N_9O_3S$, calcd 516.3, found 516.1.

Example 144: 2-[(R)-3-[1-methyl-3-(1,3-thiazol-2-yl)ureido]-1-piperidyl]-4-pyrimidinyl 1-methyl-4-piperidinecarbamate

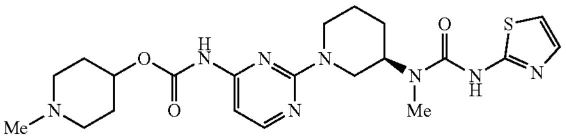 [SMILES: CN1CCC(OC(=O)Nc2ccnc(N3CCC[C@@H](N(C)C(=O)Nc4nccs4)C3)n2)CC1]

The title compound was synthesized in a similar fashion to Example 1 using 1-methylpiperidin-4-ol in step 1 and 2-amino thiazol in Step 4. $^1$H NMR (400 MHz, DMSO) δ 10.50 (d, J=119.7 Hz, 2H), 8.24 (d, J=5.6 Hz, 1H), 7.36 (d, J=3.7 Hz, 1H), 7.15-6.97 (m, 2H), 4.66 (qd, J=10.2, 3.1 Hz, 2H), 4.50 (d, J=12.5 Hz, 1H), 4.01 (s, 1H), 2.97 (d, J=11.9 Hz, 1H), 2.93 (s, 3H), 2.75 (t, J=12.7 Hz, 1H), 2.61 (s, 2H), 2.17 (s, 4H), 1.94-1.71 (m, 4H), 1.63 (ddt, J=16.4, 11.3, 5.3 Hz, 2H), 1.48 (d, J=12.5 Hz, 1H), 0.93-0.81 (m, 1H). ESI MS [M+H]$^+$ for $C_{21}H_{30}N_8O_3S$, calcd 475.3, found 475.1.

Example 145: 2-[(R)-3-[3-(5-ethyl-1,3,4-thiadiazol-2-yl)-1-methylureido]-1-piperidyl]-4-pyrimidinyl 1-methyl-4-piperidinecarbamate

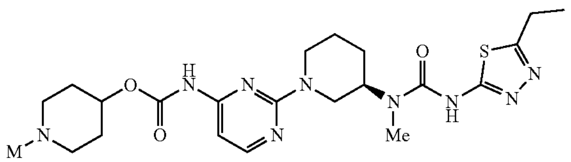 [SMILES: CCc1nnc(NC(=O)N(C)[C@@H]2CCCN(c3nccc(NC(=O)OC4CCN(C)CC4)n3)C2)s1]

The title compound was synthesized in a similar fashion to Example 1 using 1-methylpiperidin-4-ol in step 1 and 2-amino-5-ethyl-1,3,4-thiadiazol in Step 4. $^1$H NMR (400 MHz, DMSO) δ 11.66 (s, 1H), 10.08 (s, 1H), 8.21 (d, J=5.6 Hz, 1H), 7.01 (d, J=5.6 Hz, 1H), 4.65 (td, J=10.0, 6.0 Hz, 2H), 4.61-4.35 (m, 1H), 4.12 (s, 1H), 3.01-2.90 (m, 4H), 2.86 (t, J=7.6 Hz, 2H), 2.71 (t, J=12.9 Hz, 1H), 2.57 (s, 2H), 2.16 (s, 4H), 1.91-1.70 (m, 4H), 1.61 (dt, J=12.5, 4.2 Hz, 2H), 1.47 (d, J=12.3 Hz, 1H), 1.25 (t, J=7.5 Hz, 4H), 0.85 (dt, J=10.8, 6.5 Hz, 1H). ESI MS [M+H]$^+$ for $C_{22}H_{33}N_9O_3S$, calcd 504.3, found 504.1.

Example 146: 2-[(S)-4,4-difluoro-3-[1-methyl-3-(5-methyl-1,3-thiazol-2-yl)ureido]-1-piperidyl]-4-pyrimidinyl 7-aza-2-spiro[3.5]nonanecarbamate

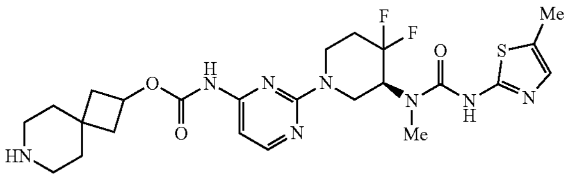 [SMILES: Cc1cnc(NC(=O)N(C)[C@H]2CN(c3nccc(NC(=O)OC4CC5(CCNCC5)C4)n3)CCC2(F)F)s1]

The title compound was synthesized in a similar fashion to Example 11 (Step 1-8 (part-1)) using tert-butyl 2-hydroxy-7-azaspiro[3.5]nonane-7-carboxylate in Step 5 and phenyl (5-methylthiazol-2-yl)carbamate in step 7, which was synthesized in a similar fashion to Example 1 Step 4 using 2-amino-5-methylthiazol. $^1$H NMR (400 MHz, $CDCl_3$) δ 8.47 (s, 1H), 8.21 (s, 1H), 7.36 (s, 1H), 7.02 (s, 1H), 5.03 (d, J=8.5 Hz, 1H), 4.85 (d, J=14.0 Hz, 1H), 3.80 (s, 3H), 3.18 (d, J=24.4 Hz, 6H), 2.96-2.80 (m, 5H), 2.40 (s, 2H), 2.35-2.23 (m, 3H), 2.14 (s, 2H), 1.91 (d, J=11.1 Hz, 2H), 1.74 (s, 3H). ESI MS [M+H]$^+$ for $C_{24}H_{32}F_2N_8O_3S$, calcd 551.3, found 551.1.

Example 147: 2-[(S)-4,4-difluoro-3-[1-methyl-3-(5-methyl-1,3-thiazol-2-yl)ureido]-1-piperidyl]-4-pyrimidinyl 7-methyl-7-aza-2-spiro[3.5]nonanecarbamate

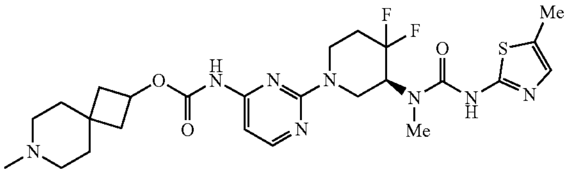 [SMILES: Cc1cnc(NC(=O)N(C)[C@H]2CN(c3nccc(NC(=O)OC4CC5(CCN(C)CC5)C4)n3)CCC2(F)F)s1]

The title compound was synthesized in a similar fashion to Example 11 using tert-butyl 2-hydroxy-7-azaspiro[3.5]nonane-7-carboxylate in Step 5 and phenyl (5-methylthiazol-2-yl)carbamate in step 7, which was synthesized in a similar fashion to Example 1 Step 4 using 2-amino-5-methylthiazol. $^1$H NMR (400 MHz, $CDCl_3$) δ 9.41 (s, 1H), 8.28 (s, 1H), 7.47 (s, 1H), 7.16 (s, 1H), 5.10 (t, J=8.1 Hz, 1H), 4.93 (d, J=13.9 Hz, 1H), 4.51 (s, 1H), 3.87 (s, 1H), 3.44-3.12 (m, 4H), 2.32 (dd, J=56.1, 3.2 Hz, 10H), 2.05-1.21 (m, 12H). ESI MS [M+H]$^+$ for $C_{25}H_{34}F_2N_8O_3S$, calcd 565.3, found 565.1.

Example 148: 2-[(S)-3-[3-(5-cyclopropyl-1,3-thiazol-2-yl)-1-methylureido]-4,4-difluoro-1-piperidyl]-4-pyrimidinyl 1-methyl-4-piperidinecarbamate

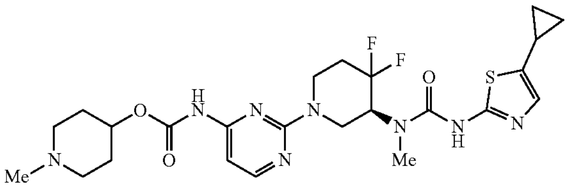 [SMILES: CN1CCC(OC(=O)Nc2ccnc(N3CCC(F)(F)[C@@H](N(C)C(=O)Nc4ncc(C5CC5)s4)C3)n2)CC1]

The title compound was synthesized in a similar fashion to Example 11 (step 1-7) using 1-methylpiperidin-4-ol in Step 5 and phenyl (5-cyclopropylthiazol-2-yl)carbamate in step 7, which was synthesized in a similar fashion to Example 1 Step 4 using 2-amino 5-cyclopropylthiazol: $^1$H NMR (400 MHz, DMSO) δ 10.32 (s, 1H), 8.23 (t, J=5.3 Hz, 1H), 7.08 (d, J=5.3 Hz, 1H), 6.74 (s, 1H), 5.04-4.47 (m, 3H), 3.03 (t, J=13.3 Hz, 1H), 2.94 (s, 2H), 2.56 (s, 5H), 2.15 (d, J=3.9 Hz, 6H), 1.97 (d, J=14.7 Hz, 1H), 1.85 (d, J=14.0 Hz, 4H), 1.62 (t, J=10.5 Hz, 2H), 0.78 (t, J=5.8 Hz, 2H), 0.50 (s, 2H).ESI MS $[M+H]^+$ for $C_{24}H_{32}F_2N_8O_3S$, calcd 551.3, found 551.1

Example 149: 2-[(S)-3-[3-(5-ethoxy-2-pyrazinyl)-1-methylureido]-4,4-difluoro-1-piperidyl]-4-pyrimidinyl (2S,4R)-2-methyl-4-piperidinecarbamate

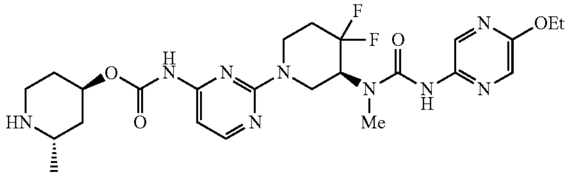 [SMILES: CCOc1cnc(NC(=O)N(C)[C@H]2CN(c3nccc(NC(=O)O[C@@H]4CCN[C@@H](C)C4)n3)CCC2(F)F)cn1]

The title compound was synthesized in a similar fashion to Example 11 (Step 1-8 (part-1)) using tert-butyl 2-hydroxy-7-azaspiro[3.5]nonane-7-carboxylate in Step 5. $^1$H NMR (400 MHz, DMSO) δ 9.03 (s, 1H), 8.54 (s, 1H), 8.21 (s, 1H), 8.00 (s, 1H), 7.09 (dd, J=13.6, 5.7 Hz, 1H), 4.96 (s, 1H), 4.66 (d, J=59.7 Hz, 3H), 4.29 (q, J=7.0 Hz, 2H), 3.43 (d, J=12.1 Hz, 1H), 3.05 (s, 3H), 2.94-2.60 (m, 4H), 2.16 (s, 2H), 1.65 (dt, J=36.5, 22.5 Hz, 3H), 1.45-1.10 (m, 6H), 0.95 (dd, J=21.0, 6.7 Hz, 3H). ESI MS $[M+H]^+$ for $C_{24}H_{33}F_2N_9O_4$, calcd 550.3, found 550.1

Example 150: 2-[(S)-3-[3-(5-ethoxy-2-pyrazinyl)-1-methylureido]-4,4-difluoro-1-piperidyl]-4-pyrimidinyl (2S,4R)-1-methyl-2-methyl-4-piperidinecarbamate

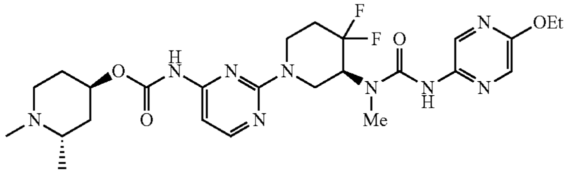 [SMILES: CCOc1cnc(NC(=O)N(C)[C@H]2CN(c3nccc(NC(=O)O[C@@H]4CCN(C)[C@@H](C)C4)n3)CCC2(F)F)cn1]

The title compound was synthesized in a similar fashion to Example 11 using tert-butyl 2-hydroxy-7-azaspiro[3.5] nonane-7-carboxylate in Step 5. H NMR (400 MHz, DMSO) δ 9.03 (s, 1H), 8.55 (s, 1H), 8.22 (d, J=5.7 Hz, 1H), 8.01 (s, 1H), 4.89 (t, J=3.4 Hz, 1H), 4.74 (s, 2H), 4.71-4.54 (m, 1H), 4.30 (q, J=7.0 Hz, 2H), 3.49-3.37 (m, 2H), 3.05 (s, 6H), 2.40-2.21 (m, 2H), 2.16 (s, 3H), 1.83-1.58 (m, 5H), 1.46 (d, J=12.6 Hz, 1H), 1.32 (t, J=7.0 Hz, 3H), 0.96 (d, J=6.2 Hz, 3H). ESI MS $[M+H]^+$ for $C_{25}H_{35}F_2N_9O_4$, calcd 564.3, found 564.1.

Example 151: 2-[(S)-3-[3-(5-ethoxy-2-pyrazinyl)-1-methylureido]-4,4-difluoro-1-piperidyl]-4-pyrimidinyl 7-ethyl-7-aza-2-spiro[3.5]nonanecarbamate

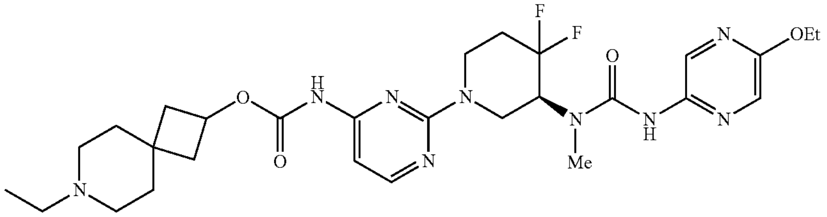 [SMILES: CCOc1cnc(NC(=O)N(C)[C@H]2CN(c3nccc(NC(=O)OC4CC5(CCN(CC)CC5)C4)n3)CCC2(F)F)cn1]

The title compound was synthesized in a similar fashion to Example 11 using tert-butyl 2-hydroxy-7-azaspiro[3.5] nonane-7-carboxylate in Step 5.and the ethyl group was installed in a similar fashion to Step 8 Part 2 using acetaldehyde. $^1$H NMR (400 MHz, MeOD) δ 8.58-8.43 (m, 1H), 8.20 (dt, J=4.8, 2.2 Hz, 1H), 7.97-7.89 (m, 1H), 7.21 (dt, J=5.0, 2.3 Hz, 1H), 5.04 (s, 1H), 4.84-4.69 (m, 2H), 4.71-4.45 (m, 1H), 4.39-4.26 (m, 2H), 3.46 (t, J=11.8 Hz, 1H), 3.15 (s, 4H), 2.53-2.27 (m, 9H), 2.06 (d, J=79.5 Hz, 3H), 1.89 (t, J=9.1 Hz, 2H), 1.68 (d, J=6.2 Hz, 4H), 1.38 (td, J=6.6, 3.5 Hz, 3H), 1.09 (td, J=8.1, 2.5 Hz, 3H).ESI MS $[M+H]^+$ for $C_{28}H_{39}F_2N_9O_4$, calcd 604.3, found 604.1

Example 152: 2-[(S)-3-[3-(5-ethoxy-2-pyrazinyl)-1-methylureido]-4,4-difluoro-1-piperidyl]-4-pyrimidinyl 2-methyl-2-aza-6-spiro[3.3]heptanecarbamate

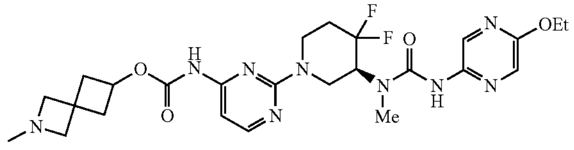 [SMILES: CCOc1cnc(NC(=O)N(C)[C@H]2CN(c3nccc(NC(=O)OC4CC5(C4)CN(C)C5)n3)CCC2(F)F)cn1]

The title compound was synthesized in a similar fashion to Example 11 (step 1-7) using 2-methyl-2-azaspiro[3.3] heptan-6-ol in Step 5. $^1$H NMR (400 MHz, DMSO) δ 8.54 (d, J=1.5 Hz, 1H), 8.19 (d, J=5.7 Hz, 1H), 8.01 (d, J=1.5 Hz, 1H), 7.05 (d, J=5.7 Hz, 1H), 4.87-4.66 (m, 3H), 4.66-4.47 (m, 1H), 4.30 (q, J=7.0 Hz, 3H), 3.47-3.21 (m, 5H), 3.21-2.94 (m, 8H), 2.48-2.42 (m, 3H), 2.12-1.99 (m, 3H), 1.32 (t, J=7.0 Hz, 3H). ESI MS $[M+H]^+$ for $C_{25}H_{33}F_2N_9O_4$, calcd 562.3, found 562.3.

Example 153: 2-[(S)-3-[3-(5-ethoxy-2-pyrazinyl)-1-methylureido]-4,4-difluoro-1-piperidyl]-4-pyrimidinyl 3-methyl-3-aza-9-spiro[5.5]undecanecarbamate

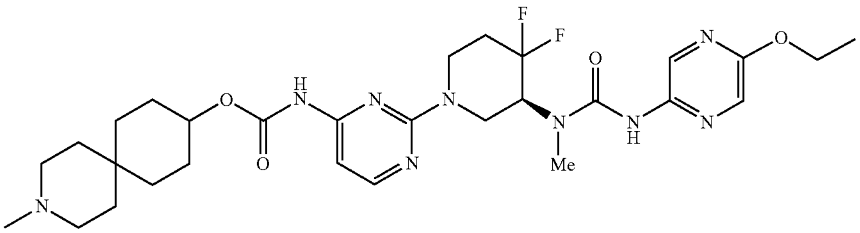 [SMILES: CCOc1cnc(NC(=O)N(C)[C@H]2CN(c3nccc(NC(=O)OC4CCC5(CC4)CCN(C)CC5)n3)CCC2(F)F)cn1]

The title compound was synthesized in a similar fashion to Example 11 (Steps 1-7), using 3-methyl-3-azaspiro[5.5]undecan-9-ol in Step 5. $^1$H NMR (400 MHz, DMSO) δ 8.54 (d, J=1.5 Hz, 1H), 8.20 (d, J=5.6 Hz, 1H), 8.00 (d, J=1.5 Hz, 1H), 7.08 (d, J=5.7 Hz, 1H), 4.69 (d, J=33.8 Hz, 4H), 4.29 (q, J=7.0 Hz, 2H), 3.40 (t, J=11.9 Hz, 5H), 3.05 (s, 5H), 2.18 (d, J=41.5 Hz, 8H), 1.87-1.62 (m, 2H), 1.63-1.44 (m, 3H), 1.44-1.34 (m, 4H), 1.32 (t, J=7.0 Hz, 2H), 1.22 (t, J=11.4 Hz, 2H). ESI MS $[M+H]^+$ for $C_{29}H_{41}F_2N_9O_4$, calcd 618.3, found 618.3.

Example 154: 2-[(S)-4,4-difluoro-3-[3-(5-fluoro-2-pyridyl)-1-methylureido]-1-piperidyl]-4-pyrimidinyl 4-quinuclidinecarbamate

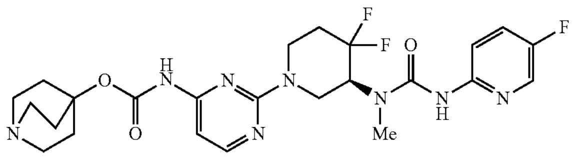 [SMILES: CN(C(=O)Nc1ccc(F)cn1)[C@H]1CN(c2nccc(NC(=O)OC34CCN(CC3)CC4)n2)CCC1(F)F]

The title compound was synthesized in a similar fashion to Example 11 (Steps 1-7), using 4-quinuclidinol in Step 5, and phenyl (5-fluoropyridin-2-yl)carbamate in step 7, which was synthesized in a similar fashion to Example 1 Step 4 using 2-amino-5-fluoropyridin. $^1$H NMR (400 MHz, MeOD) δ 8.25-8.05 (m, 2H), 7.84 (dd, J=9.2, 4.1 Hz, 1H), 7.54 (ddd, J=9.2, 8.0, 3.1 Hz, 1H), 7.14 (d, J=5.7 Hz, 1H), 5.13 (d, J=3.6 Hz, 1H), 4.61 (dd, J=12.9, 4.6 Hz, 2H), 4.24 (ddt, J=33.2, 12.0, 2.7 Hz, 1H), 3.52 (t, J=12.3 Hz, 1H), 3.20 (dd, J=13.3, 2.8 Hz, 1H), 3.13 (d, J=1.9 Hz, 3H), 3.11-2.96 (m, 5H), 2.21-2.07 (m, 5H), 2.07-1.97 (m, 1H), 1.97-1.73 (m, 1H), 1.37-1.22 (m, 2H), 0.96-0.78 (m, 1H). ESI MS $[M+H]^+$ for $C_{24}H_{29}F_3N_8O_3$, calcd 535.3, found 535.1.

Example 155: 2-[(R)-3-[3-(5-ethoxy-2-pyrazinyl)-1-methylureido]-1-piperidyl]-4-pyridyl [(S)-3-morpholinyl]methanecarbamate

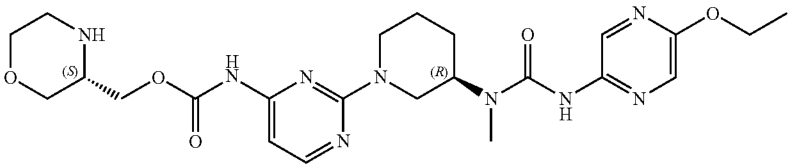

The title compound was synthesized in a similar fashion to Example 11 (step 1-8 (part1)) using benzyl (R)-methyl (piperidin-3-yl)carbamate in step 4 and tert-butyl (R)-3-(hydroxymethyl)morpholine-4-carboxylate in step 5.: $^1$H NMR (400 MHz, DMSO) δ 10.13 (s, 1H), 9.07 (s, 1H), 8.59 (d, J=1.5 Hz, 1H), 8.10-8.00 (m, 2H), 7.14 (d, J=1.7 Hz, 1H), 6.80 (dd, J=5.6, 1.6 Hz, 1H), 4.30 (q, J=7.0 Hz, 2H), 4.17-3.93 (m, 3H), 3.74-3.58 (m, 2H), 3.40-3.34 (m, 1H), 3.07 (d, J=6.7 Hz, 2H), 2.92 (s, 4H), 2.85-2.70 (m, 2H), 2.34-2.26 (m, 2H), 1.89-1.71 (m, 3H), 1.53 (d, J=11.6 Hz, 1H), 1.33 (t, J=7.0 Hz, 3H). ESI MS $[M+H]^+$ for $C_{24}H_{33}F_2N_8O_4$, calcd 535.3, found 535.1. ESI MS $[M+H]^+$ for $C_{23}H_{33}N_9O_5$, calcd 515.3, found 515.3.

Example 156: 2-[(R)-3-[3-(5-ethoxy-2-pyrazinyl)-1-methylureido]-1-piperidyl]-4-pyridyl [(R)-3-morpholinyl]methanecarbamate

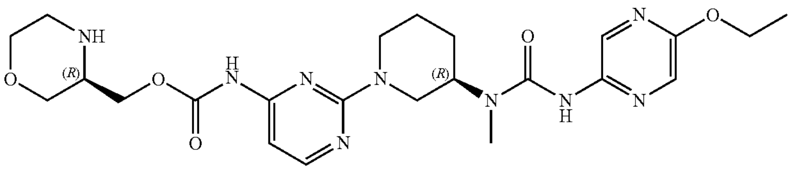

The title compound was synthesized in a similar fashion to Example 11 (step 1-8 (part1)) using benzyl (R)-methyl (piperidin-3-yl)carbamate in step 4 and tert-butyl (R)-3-(hydroxymethyl)morpholine-4-carboxylate in step 5. $^1$H NMR (400 MHz, DMSO) δ 10.13 (s, 1H), 9.07 (s, 1H), 8.59 (d, J=1.5 Hz, 1H), 8.10-8.00 (m, 2H), 7.14 (d, J=1.7 Hz, 1H), 6.80 (dd, J=5.6, 1.6 Hz, 1H), 4.30 (q, J=7.0 Hz, 2H), 4.17-3.93 (m, 3H), 3.74-3.58 (m, 2H), 3.40-3.34 (m, 1H), 3.07 (d, J=6.7 Hz, 2H), 2.92 (s, 4H), 2.85-2.70 (m, 2H), 2.34-2.26 (m, 2H), 1.89-1.71 (m, 3H), 1.53 (d, J=11.6 Hz, 1H), 1.33 (t, J=7.0 Hz, 3H). ESI MS $[M+H]^+$ for $C_{24}H_{33}F_2N_8O_4$, calcd 535.3, found 535.1. ESI MS $[M+H]^+$ for $C_{23}H_{33}N_9O_5$, calcd 515.3, found 515.3.

Example 157: 2-[(3S,4R)-3-[3-(5-ethoxy-2-pyrazinyl)-1-methylureido]-4-fluoro-1-piperidyl]-4-pyrimidinyl 4-ethyl-4-piperidinecarbamate

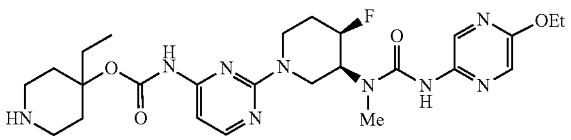 [SMILES: CCOc1cnc(NC(=O)N(C)[C@H]2CN(c3nccc(NC(=O)OC4(CC)CCNCC4)n3)CC[C@H]2F)cn1]

The title compound was synthesized in a similar fashion to Example 18 (step 1-10 (part1)) using tert-butyl 4-ethyl-4-hydroxypiperidine-1-carboxylate in Step 7. $^1$H NMR (400 MHz, DMSO) δ 9.94 (d, J=13.8 Hz, 1H), 9.03 (s, 1H), 8.55 (d, J=1.5 Hz, 1H), 8.20 (d, J=5.6 Hz, 1H), 8.01 (d, J=1.5 Hz, 1H), 7.05 (d, J=5.6 Hz, 1H), 5.04 (d, J=51.4 Hz, 1H), 4.64-4.52 (m, 2H), 4.29 (q, J=7.0 Hz, 2H), 4.27-4.09 (m, 1H), 3.64 (d, J=12.9 Hz, 1H), 3.45 (t, J=12.1 Hz, 1H), 3.04 (d, J=3.7 Hz, 2H), 3.03 (s, 3H), 2.86 (s, 1H), 2.81-2.61 (m, 3H), 2.11-1.69 (m, 6H), 1.50-1.37 (m, 2H), 1.32 (t, J=7.0 Hz, 2H), 0.81 (t, J=7.4 Hz, 3H). ESI MS $[M+H]^+$ for $C_{25}H_{36}FN_9O_4$, calcd 546.3, found 546.1

Example 158: 2-[(3S,4R)-3-[3-(5-ethoxy-2-pyrazinyl)-1-methylureido]-4-fluoro-1-piperidyl]-4-pyrimidinyl 4-ethyl-1-methyl-4-piperidinecarbamate

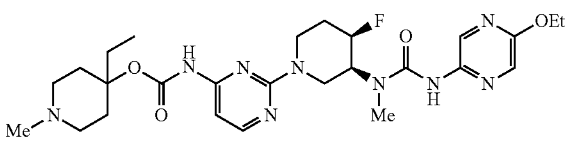 [SMILES: CCOc1cnc(NC(=O)N(C)[C@H]2CN(c3nccc(NC(=O)OC4(CC)CCN(C)CC4)n3)CC[C@H]2F)cn1]

The title compound was synthesized in a similar fashion to Example 18 using tert-butyl 4-ethyl-4-hydroxypiperidine-1-carboxylate in Step 7. $^1$H NMR (400 MHz, DMSO) δ 9.94 (s, 1H), 9.04 (s, 1H), 8.55 (d, J=1.4 Hz, 1H), 8.19 (d, J=5.6 Hz, 1H), 8.00 (d, J=1.4 Hz, 1H), 7.04 (d, J=5.6 Hz, 2H), 5.04 (d, J=51.4 Hz, 1H), 4.65-4.54 (m, 2H), 4.29 (q, J=7.0 Hz, 2H), 4.24-4.12 (m, 1H), 3.46 (d, J=12.2 Hz, 1H), 3.03 (d, J=1.6 Hz, 3H), 2.47 (s, 1H), 2.25-2.07 (m, 7H), 2.07-1.86 (m, 4H), 1.80 (d, J=12.9 Hz, 1H), 1.56 (d, J=12.7 Hz, 2H), 1.32 (t, J=7.0 Hz, 3H), 0.81 (t, J=7.5 Hz, 3H). ESI MS $[M+H]^+$ for $C_{26}H_{38}FN_9O_4$, calcd 560.3, found 560.1.

Example 159: 2-[(3S,4R)-3-[3-(5-ethoxy-2-pyrazinyl)-1-methylureido]-4-fluoro-1-piperidyl]-4-pyrimidinyl (1R,4S,6R)-2-methyl-2-azabicyclo[2.2.1]heptane-6-carbamate

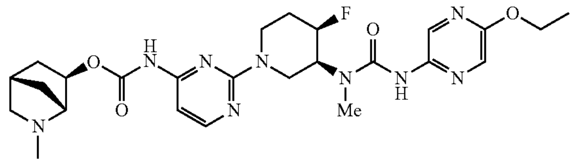 [SMILES: CCOc1cnc(NC(=O)N(C)[C@H]2CN(c3nccc(NC(=O)O[C@@H]4C[C@@H]5C[C@H]4N(C)C5)n3)CC[C@H]2F)cn1]

The title compound was synthesized in a similar fashion to Example 18 using tert-butyl (1R,4S,6R)-6-hydroxy-2-azabicyclo[2.2.1]heptane-2-carboxylate in Step 7. $^1$H NMR (400 MHz, DMSO) δ 9.04 (s, 1H), 8.55 (d, J=1.5 Hz, 1H), 8.20 (d, J=5.6 Hz, 1H), 8.01 (d, J=1.5 Hz, 1H), 5.04 (d, J=51.7 Hz, 1H), 4.73 (d, J=7.0 Hz, 1H), 4.62-4.41 (m, 2H), 4.29 (q, J=7.1 Hz, 2H), 4.19 (d, J=35.1 Hz, 1H), 3.44 (t, J=12.2 Hz, 2H), 3.03 (d, J=1.6 Hz, 6H), 2.47-2.35 (m, 2H), 2.29 (s, 2H), 2.17 (d, J=8.5 Hz, 1H), 2.05-1.84 (m, 2H), 1.84-1.71 (m, 2H), 1.49 (d, J=9.8 Hz, 1H), 1.39 (d, J=10.4 Hz, 2H), 1.32 (t, J=7.0 Hz, 3H). ESI MS $[M+H]^+$ for $C_{25}H_{34}FN_9O_4$, calcd 544.3, found 544.1.

Example 160: 2-[(3S,4R)-3-[3-(5-cyclopropoxy-2-pyrazinyl)-1-methylureido]-4-fluoro-1-piperidyl]-4-pyrimidinyl (S)-1-methyl-3-piperidinecarbamate

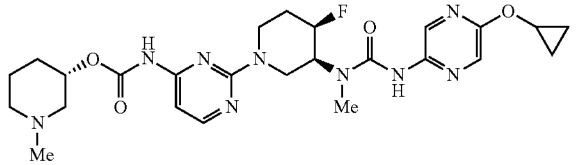 [SMILES: CN1CCC[C@H](OC(=O)Nc2ccnc(N3CC[C@@H](F)[C@@H](N(C)C(=O)Nc4cnc(OC5CC5)cn4)C3)n2)C1]

The title compound was synthesized in a similar fashion to Example 18 (Step 1-9, using (S)-1-methylpiperidin-3-ol in Step 7 and phenyl (5-cyclopropoxypyrazin-2-yl)carbamate in Step 9, which was prepared in a similar fashion to Example 1 Step 4 using 2-amino-5-cyclopropoxypyrazin. $^1$H NMR (400 MHz, DMSO) δ 10.15 (s, 1H), 9.09 (s, 1H), 8.60 (d, J=1.5 Hz, 1H), 8.23 (d, J=5.6 Hz, 1H), 8.06 (d, J=1.4 Hz, 1H), 7.04 (d, J=5.6 Hz, 1H), 5.05 (d, J=51.5 Hz, 1H), 4.69 (tt, J=8.0, 3.9 Hz, 1H), 4.64-4.50 (m, 2H), 4.32-4.09 (m, 2H), 3.45 (t, J=12.2 Hz, 1H), 3.03 (d, J=1.6 Hz, 4H), 2.70 (d, J=11.7 Hz, 1H), 2.45-2.38 (m, 1H), 2.16 (s, 3H), 2.07 (dt, J=18.3, 9.7 Hz, 2H), 1.95 (d, J=14.3 Hz, 2H), 1.86-1.64 (m, 2H), 1.56-1.31 (m, 2H), 0.82-0.74 (m, 2H), 0.74-0.65 (m, 2H). ESI MS $[M+H]^+$ for $C_{25}H_{34}FN_9O_4$, calcd 544.3, found 544.1.

Example 161: 2-[(3S,4R)-3-[3-(5-cyclopropyl-2-pyrazinyl)-1-methylureido]-4-fluoro-1-piperidyl]-4-pyrimidinyl (S)-1-methyl-3-piperidinecarbamate

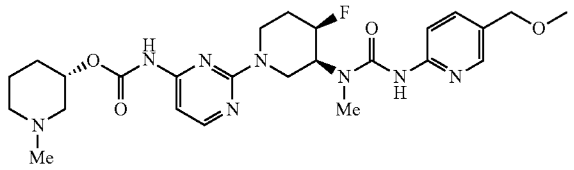 [SMILES: COCc1ccc(NC(=O)N(C)[C@H]2CN(c3nccc(NC(=O)O[C@H]4CCCN(C)C4)n3)CC[C@H]2F)nc1]

The title compound was synthesized in a similar fashion to Example 18 (Step 1-9) using (S)-1-methylpiperidin-3-ol in Step 7 and phenyl phenyl (5-(methoxymethyl)pyridin-2-yl)carbamate in Step 9, which was prepared in a similar fashion to Example 1 Step 4 using 2-amino-5-(methoxymethyl)pyridin. $^1$H NMR (400 MHz, DMSO) δ 10.19 (s, 1H), 9.00 (s, 1H), 8.35-8.17 (m, 2H), 7.82 (d, J=8.6 Hz, 1H), 7.65 (dd, J=8.6, 2.4 Hz, 1H), 7.05 (d, J=5.6 Hz, 1H), 5.05 (d, J=51.4 Hz, 1H), 4.70 (s, 1H), 4.63-4.52 (m, 2H), 4.36 (s, 2H), 4.28-4.11 (m, 1H), 3.46 (q, J=13.3 Hz, 3H), 3.27 (s, 2H), 3.07 (d, J=14.6 Hz, 1H), 3.03 (d, J=1.7 Hz, 3H), 2.13 (d, J=37.0 Hz, 4H), 1.95 (d, J=13.8 Hz, 3H), 1.76 (d, J=43.6 Hz, 3H), 1.43 (d, J=49.0 Hz, 2H). ESI MS [M+H]$^+$ for $C_{25}H_{35}FN_8O_4$, calcd 531.3, found 531.1.

Example 162: 2-[(3S,4R)-4-fluoro-3-[1-methyl-3-(5-phenyl-1,3-thiazol-2-yl)ureido]-1-piperidyl]-4-pyrimidinyl (1S,4S,5R)-2-methyl-2-azabicyclo[2.2.1]heptane-5-carbamate

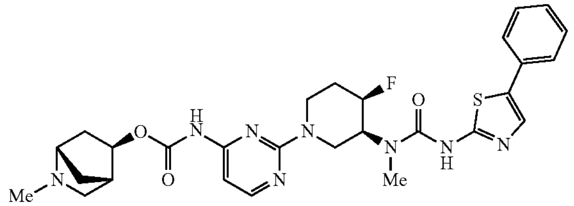 [SMILES: CN1C[C@@H]2C[C@H]1C[C@H]2OC(=O)Nc1ccnc(N2CC[C@@H](F)[C@@H](N(C)C(=O)Nc3ncc(-c4ccccc4)s3)C2)n1]

The title compound was synthesized in a similar fashion to Example 18 using tert-butyl (1S,4S,5R)-6-hydroxy-2-azabicyclo[2.2.1]heptane-2-carboxylate in Step 7 and (phenyl (5-phenylthiazol-2-yl)carbamate in Step 9, which was prepared in a similar fashion to Example 1 Step 4 using 20amino-5-phenylthiazol. $^1$H NMR (400 MHz, DMSO) δ 10.25 (s, 1H), 8.21 (d, J=5.6 Hz, 1H), 7.51 (s, 1H), 7.41 (d, J=7.7 Hz, 2H), 7.28 (t, J=7.6 Hz, 2H), 7.06 (dd, J=22.6, 6.5 Hz, 2H), 5.02 (d, J=51.3 Hz, 1H), 4.59 (d, J=7.9 Hz, 3H), 4.45 (d, J=34.2 Hz, 1H), 3.36 (d, J=13.6 Hz, 2H), 3.12-2.92 (m, 5H), 2.64 (dd, J=9.7, 4.4 Hz, 1H), 2.41-2.35 (m, 1H), 2.26-2.16 (m, 1H), 2.14 (s, 3H), 1.94 (dd, J=18.2, 10.8 Hz, 2H), 1.89-1.63 (m, 1H), 1.60-1.45 (m, 2H), 1.30 (d, J=13.8 Hz, 1H). ESI MS [M+H]$^+$ for $C_{28}H_{33}FN_8O_3S$, calcd 581.3, found 581.1.

Example 163: 2-[(3S,4R)-4-fluoro-3-{1-methyl-3-[5-(2-pyridyl)-1,3-thiazol-2-yl]ureido}-1-piperidyl]-4-pyrimidinyl 1-methyl-4-piperidinecarbamate

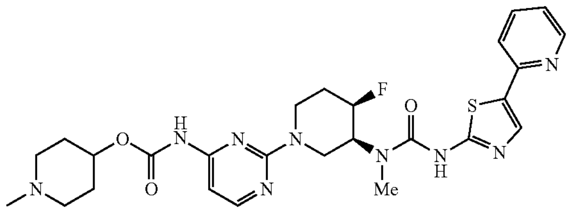 [SMILES: CN1CCC(OC(=O)Nc2ccnc(N3CC[C@@H](F)[C@@H](N(C)C(=O)Nc4ncc(-c5ccccn5)s4)C3)n2)CC1]

The title compound was synthesized in a similar fashion to Example 18 (Step 1-9) N-methyl-4-hydroxypiperidine in step 7 and phenyl (5-(pyridin-2-yl)thiazol-2-yl)carbamate in Step 9, which was prepared in a similar fashion to Example 1 Step 4 using 2-amino-5-(pyridin-2-yl)thiazol. $^1$H NMR (400 MHz, DMSO) δ 10.24 (s, 1H), 8.37 (s, 1H), 8.21 (s, 1H), 7.81 (s, 1H), 7.56 (d, J=40.0 Hz, 2H), 7.01 (d, J=22.8 Hz, 2H), 5.02 (d, J=51.3 Hz, 2H), 4.61 (s, 4H), 3.01 (d, J=23.2 Hz, 5H), 2.54 (s, 3H), 2.20-2.03 (m, 4H), 1.98 (s, 2H), 1.83 (s, 2H), 1.72 (s, 1H), 1.60 (s, 1H). ESI MS [M+H]$^+$ for $C_{26}H_{32}FN_9O_3S$, calcd 570.3, found 570.1.

Example 164: 2-[(3S,4R)-4-fluoro-3-[1-methyl-3-(2-pyridyl)ureido]-1-piperidyl]-4-pyrimidinyl 4-quinuclidinecarbamate

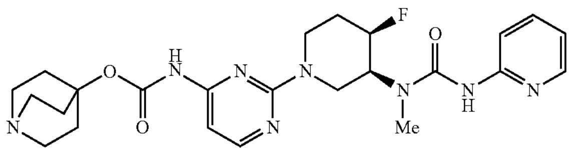 [SMILES: CN(C(=O)Nc1ccccn1)[C@H]1CN(c2nccc(NC(=O)OC34CCN(CC3)CC4)n2)CC[C@H]1F]

The title compound was synthesized in a similar fashion to Example 18 (step 1-9) using quinuclidin-4-ol in Step 7 and phenyl pyridin-2-ylcarbamate in Step 9, which was prepared in a similar fashion to Example 1 Step 4 using 2-amino pyridine. $^1$H NMR (400 MHz, $CDCl_3$) δ 8.37 (d, J=5.0 Hz, 1H), 8.34-8.17 (m, 1H), 8.12-7.99 (m, 1H), 7.99 (s, 1H), 7.75-7.60 (m, 1H), 7.21 (d, J=5.6 Hz, 1H), 7.02-6.94 (m, 1H), 5.13 (dd, J=50.8, 24.0 Hz, 2H), 4.70-4.62 (m, 1H), 4.51 (d, J=12.8 Hz, 2H), 4.16-3.80 (m, 2H), 3.48 (dt, J=17.1, 12.4 Hz, 1H), 3.40-3.21 (m, 1H), 3.16 (d, J=3.1 Hz, 1H), 3.12 (d, J=1.5 Hz, 1H), 3.09-2.95 (m, 4H), 2.10 (d, J=12.0 Hz, 1H), 2.03 (t, J=7.8 Hz, 4H), 1.91-1.74 (m, 1H), 1.35-1.12 (m, 3H). ESI MS [M+H]$^+$ for $C_{24}H_{31}FN_8O_3$, calcd 499.3, found 499.1.

Example 165: 2-[(3S,4R)-4-fluoro-3-{3-[5-(m-fluorophenyl)-1,3-thiazol-2-yl]-1-methylureido}-1-piperidyl]-4-pyrimidinyl 1-methyl-4-piperidinecarbamate

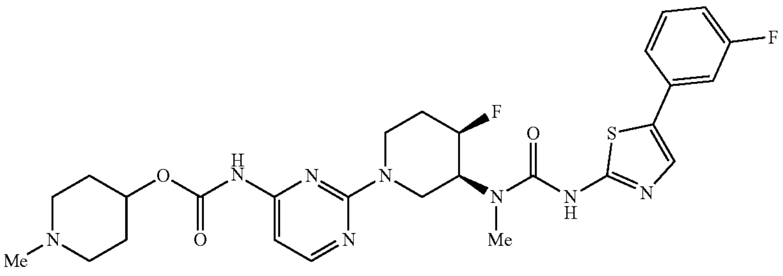 [SMILES: CN1CCC(OC(=O)Nc2ccnc(N3CC[C@@H](F)[C@@H](N(C)C(=O)Nc4ncc(-c5cccc(F)c5)s4)C3)n2)CC1]

The title compound was synthesized in a similar fashion to Example 18 (step 1-9) using 1-methylpiperidin-4-ol in Step 7 and phenyl (5-(3-fluorophenyl)thiazol-2-yl)carbamate in Step 9, which was prepared in a similar fashion to Example 1 Step 4 using 2-amino (5-(3-fluorophenyl)thiazol. $^1$H NMR (400 MHz, DMSO) δ 10.22 (s, 1H), 8.22 (d, J=5.6 Hz, 1H), 7.64 (s, 1H), 7.32 (q, J=7.6 Hz, 1H), 7.24 (t, J=8.1 Hz, 2H), 7.04 (d, J=5.6 Hz, 1H), 6.90 (t, J=8.6 Hz, 1H), 5.08 (s, 1H), 4.77-4.58 (m, 2H), 4.48 (d, J=70.5 Hz, 2H), 3.39 (d, J=12.3 Hz, 2H), 3.06 (dd, J=13.2, 2.8 Hz, 1H), 2.99 (s, 3H), 2.55 (s, 2H), 2.14 (s, 5H), 1.98 (t, J=13.0 Hz, 1H), 1.91-1.79 (m, 2H), 1.80-1.67 (m, 1H), 1.60 (dtd, J=12.4, 8.6, 3.7 Hz, 2H). ESI MS $[M+H]^+$for $C_{27}H_{32}F_2N_8O_3S$, calcd 587.3, found 587.3.

Example 166: 2-[(3S,4R)-4-fluoro-3-{1-methyl-3-[5-(o-tolyl)-1,3-thiazol-2-yl]ureido}-1-piperidyl]-4-pyrimidinyl 1-methyl-4-piperidinecarbamate

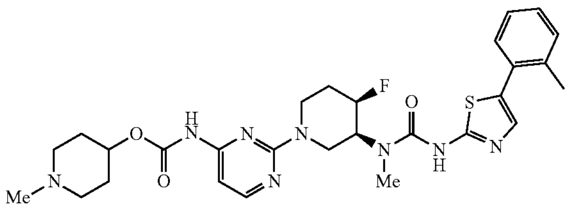 [SMILES: Cc1ccccc1-c1cnc(NC(=O)N(C)[C@H]2CN(c3nccc(NC(=O)OC4CCN(C)CC4)n3)CC[C@H]2F)s1]

The title compound was synthesized in a similar fashion to Example 18 (step 1-9) using 1-methylpiperidin-4-ol in Step 7 and phenyl (5-(o-tolyl)thiazol-2-yl)carbamate in Step 9, which was prepared in a similar fashion to Example 1 Step 4 using 2-amino-5-(o-tolyl)thiazol. 1H NMR (400 MHz, DMSO) δ 10.26 (s, 1H), 8.22 (d, J=5.6 Hz, 1H), 7.29 (dd, J=7.6, 1.6 Hz, 1H), 7.20 (td, J=7.8, 4.0 Hz, 2H), 7.12 (dtd, J=14.6, 7.4, 1.6 Hz, 2H), 7.05 (d, J=5.6 Hz, 1H), 5.19-4.92 (m, 1H), 4.62 (ddd, J=19.3, 10.5, 5.0 Hz, 3H), 4.43 (d, J=36.1 Hz, 1H), 3.39 (d, J=12.2 Hz, 2H), 3.10-3.01 (m, 1H), 2.99 (s, 3H), 2.56 (s, 2H), 2.37 (s, 3H), 2.14 (s, 5H), 1.98 (t, J=13.2 Hz, 1H), 1.85 (d, J=13.0 Hz, 2H), 1.72 (d, J=5.1 Hz, 1H), 1.60 (dtd, J=12.4, 8.6, 3.6 Hz, 2H). ESI MS $[M+H]^+$ for $C_{28}H_{35}FN_8O_3S$, calcd 583.3, found 583.3.

Example 167: 2-[(3S,4R)-4-fluoro-3-[1-methyl-3-(5-phenyl-1,3-thiazol-2-yl)ureido]-1-piperidyl]-4-pyrimidinyl 1-methyl-4-piperidinecarbamate

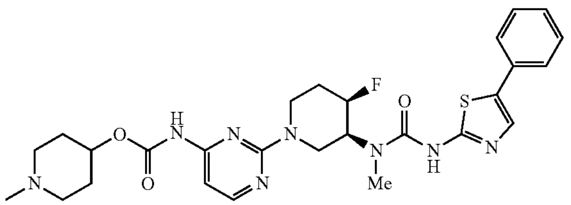 [SMILES: CN1CCC(OC(=O)Nc2ccnc(N3CC[C@@H](F)[C@@H](N(C)C(=O)Nc4ncc(-c5ccccc5)s4)C3)n2)CC1]

The title compound was synthesized in a similar fashion to Example 18 (Step 1-9) using 1-methylpiperidin-4-ol in Step 7 and phenyl (5-phenylthiazol-2-yl)carbamate in Step 9, which was prepared in a similar fashion to Example 1 Step 4 using 2-amino-5-phenylthiazol. $^1$H NMR (400 MHz, $CDCl_3$) δ 12.16 (s, 1H), 9.87 (s, 1H), 8.30 (s, 1H), 7.70 (s, 1H), 7.53 (d, J=7.2 Hz, 1H), 7.47 (s, 1H), 7.39 (t, J=7.3 Hz, 1H), 7.26 (s, 5H), 5.27 (d, J=49.8 Hz, 1H), 4.86-4.66 (m, 2H), 4.38 (d, J=12.6 Hz, 1H), 3.56 (t, J=12.4 Hz, 2H), 3.37 (t, J=13.4 Hz, 1H), 3.23 (d, J=3.5 Hz, 3H), 2.80 (s, 1H), 2.28 (t, J=2.2 Hz, 2H), 2.13 (t, J=29.3 Hz, 5H), 1.86 (t, J=11.2 Hz, 2H), 1.73 (d, J=13.9 Hz, 1H). ESI MS $[M+H]^+$ for $C_{27}H_{33}FN_8O_3S$, calcd 569.3, found 569.1.

Example 168: 2-[(3S,4R)-3-[3-(5-chloro-1,3-thiazol-2-yl)-1-methylureido]-4-fluoro-1-piperidyl]-4-pyrimidinyl 1-methyl-4-piperidinecarbamate

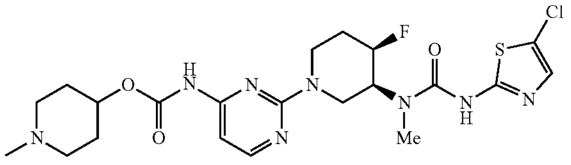 [SMILES: CN1CCC(OC(=O)Nc2ccnc(N3CC[C@@H](F)[C@@H](N(C)C(=O)Nc4ncc(Cl)s4)C3)n2)CC1]

The title compound was synthesized in a similar fashion to Example 18 (step 1-9) using 1-methylpiperidin-4-ol in Step 7 and phenyl (5-chlorothiazol-2-yl)carbamate in Step 9, which was prepared in a similar fashion to Example 1 Step 4 using 2-amino-5-chlorothiazol. $^1$H NMR (400 MHz, $CDCl_3$) δ 11.76 (s, 1H), 9.87 (s, 1H), 8.29 (s, 1H), 7.46 (s, 1H), 7.32 (s, 1H), 5.25 (d, J=49.9 Hz, 1H), 4.79 (s, 2H), 4.32 (d, J=11.7 Hz, 1H), 3.55 (t, J=12.3 Hz, 2H), 3.36 (t, J=13.2 Hz, 1H), 3.20 (d, J=3.6 Hz, 2H), 2.82 (s, 1H), 2.31 (t, J=2.2 Hz, 2H), 2.09 (dd, J=39.0, 23.7 Hz, 4H), 1.77 (dt, J=41.0, 12.6 Hz, 3H), 1.57 (s, 4H). ESI MS $[M+H]^+$ for $C_{21}H_{28}C_1FN_8O_3S$, calcd 527.3, found 527.1.

Example 169: 2-[(3S,4R)-4-fluoro-3-[3-(5-fluoro-1,3-thiazol-2-yl)-1-methylureido]-1-piperidyl]-4-pyrimidinyl 1-methyl-4-piperidinecarbamate

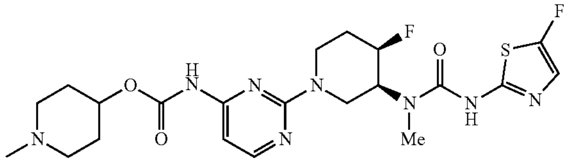 [SMILES: CN1CCC(OC(=O)Nc2ccnc(N3CC[C@@H](F)[C@@H](N(C)C(=O)Nc4ncc(F)s4)C3)n2)CC1]

The title compound was synthesized in a similar fashion to Example 18 (step 1-9) using 1-methylpiperidin-4-ol in Step 7 and phenyl (5-fluorothiazol-2-yl)carbamate in Step 9, which was prepared in a similar fashion to Example 1 Step 4 using 2-amino-5-fluorothiazol. $^1H$ NMR (400 MHz, DMSO) δ 10.24 (s, 1H), 8.19 (t, J=4.3 Hz, 1H), 7.03 (dt, J=4.6, 2.3 Hz, 1H), 6.53 (s, 1H), 4.96 (d, J=51.4 Hz, 1H), 4.74-4.30 (m, 4H), 3.28 (d, J=12.0 Hz, 2H), 3.01 (t, J=13.1 Hz, 1H), 2.90 (s, 3H), 2.56 (s, 2H), 2.15 (d, J=2.9 Hz, 5H), 1.96 (t, J=12.9 Hz, 1H), 1.84 (d, J=13.6 Hz, 2H), 1.61 (t, J=10.2 Hz, 3H). ESI MS $[M+H]^+$ for $C_{21}H_{28}F_2N_8O_3S$, calcd 511.3, found 511.1.

Example 170: 2-[(3S,4R)-3-[3-(5-ethyl-1,3-thiazol-2-yl)-1-methylureido]-4-fluoro-1-piperidyl]-4-pyrimidinyl 1-methyl-4-piperidinecarbamate

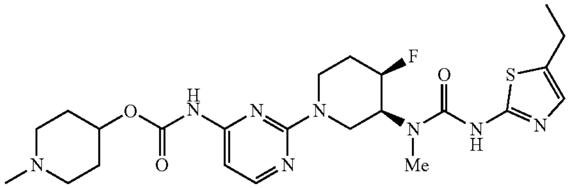 [SMILES: CCc1cnc(NC(=O)N(C)[C@H]2CN(c3nccc(NC(=O)OC4CCN(C)CC4)n3)CC[C@H]2F)s1]

The title compound was synthesized in a similar fashion to Example 18 (step 1-9) using 1-methylpiperidin-4-ol in Step 7 and phenyl (5-ethylthiazol-2-yl)carbamate in Step 9, which was prepared in a similar fashion to Example 1 Step 4 using 2-amino-5-ethylthiazol. $^1H$ NMR (400 MHz, DMSO) δ 10.36 (s, 1H), 8.29-8.09 (m, 1H), 7.02 (d, J=2.9 Hz, 1H), 6.63 (s, 1H), 4.98 (d, J=51.4 Hz, 1H), 4.60 (t, J=15.8 Hz, 4H), 3.01 (t, J=13.1 Hz, 1H), 2.91 (s, 3H), 2.55 (d, J=7.6 Hz, 2H), 2.15 (d, J=2.7 Hz, 6H), 1.95 (t, J=12.6 Hz, 1H), 1.83 (s, 2H), 1.60 (d, J=10.2 Hz, 6H), 1.12 (td, J=7.9, 2.3 Hz, 3H). ESI MS $[M+H]^+$ for $C_{23}H_{33}FN_8O_3S$, calcd 521.3, found 521.1.

Example 171: 2-[(3S,4R)-3-[3-(5-cyclopropyl-1,3-thiazol-2-yl)-1-methylureido]-4-fluoro-1-piperidyl]-4-pyrimidinyl 1-methyl-4-piperidinecarbamate

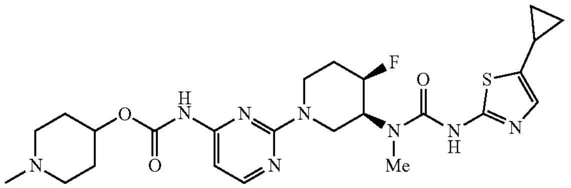 [SMILES: CN1CCC(OC(=O)Nc2ccnc(N3CC[C@@H](F)[C@@H](N(C)C(=O)Nc4ncc(C5CC5)s4)C3)n2)CC1]

The title compound was synthesized in a similar fashion to Example 18 (step 1-9) using 1-methylpiperidin-4-ol in Step 7 and phenyl (5-cyclopropylthiazol-2-yl)carbamate in Step 9, which was prepared in a similar fashion to Example 1 Step 4 using 2-amino-5-cyclopropylthiazol.

$^1H$ NMR (400 MHz, DMSO) δ 10.30 (s, 1H), 8.21 (t, J=4.4 Hz, 1H), 7.04 (t, J=4.4 Hz, 1H), 6.78 (s, 1H), 4.99 (d, J=51.3 Hz, 1H), 4.66 (dt, J=8.6, 4.3 Hz, 1H), 4.58 (d, J=12.9 Hz, 2H), 4.36 (dd, J=36.4, 11.2 Hz, 1H), 3.37 (s, 2H), 3.03 (t, J=13.2 Hz, 1H), 2.94 (s, 3H), 2.58 (d, J=9.1 Hz, 2H), 2.24-2.04 (m, 4H), 1.96 (t, J=13.0 Hz, 1H), 1.91-1.78 (m, 5H), 1.77-1.45 (m, 2H), 0.80 (q, J=3.5 Hz, 2H), 0.51 (dd, J=5.3, 2.9 Hz, 2H). ESI MS $[M+H]^+$ for $C_{24}H_{33}FN_8O_3S$, calcd 533.3, found 533.1

Example 172: 2-[(3S,4R)-3-[3-(5-ethoxy-2-pyrazinyl)-1-methylureido]-4-fluoro-1-piperidyl]-4-pyrimidinyl 7-methyl-7-aza-2-spiro[3.5]nonanecarbamate

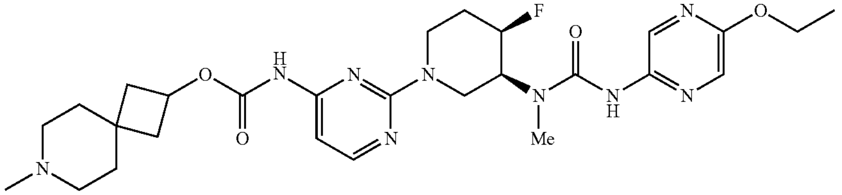 [SMILES: CCOc1cnc(NC(=O)N(C)[C@H]2CN(c3nccc(NC(=O)OC4CC5(CCN(C)CC5)C4)n3)CC[C@H]2F)cn1]

The title compound was synthesized in a similar fashion to Example 18 (step 1-9) using 7-methyl-7-azaspiro[3.5]nonan-2-ol in Step 7. $^1$H NMR (400 MHz, DMSO) δ 9.05 (s, 1H), 8.55 (d, J=1.5 Hz, 1H), 8.20 (d, J=5.7 Hz, 1H), 8.01 (d, J=1.5 Hz, 1H), 7.02 (d, J=5.6 Hz, 1H), 5.10 (s, 1H), 4.93 (dt, J=14.1, 7.8 Hz, 2H), 4.64-4.45 (m, 2H), 4.29 (q, J=7.0 Hz, 2H), 4.27-4.07 (m, 1H), 3.44 (t, J=12.1 Hz, 1H), 3.03 (d, J=1.6 Hz, 4H), 2.29-2.11 (m, 4H), 2.09 (s, 3H), 1.94 (q, J=16.2 Hz, 2H), 1.74 (dd, J=12.4, 6.6 Hz, 2H), 1.53 (t, J=5.4 Hz, 4H), 1.32 (t, J=7.0 Hz, 3H). ESI MS $[M+H]^+$ for $C_{27}H_{38}FN_9O_4$, calcd 572.3, found 572.1.

Example 173: 2-[(3S,4R)-3-[3-(5-ethoxy-2-pyrazinyl)-1-methylureido]-4-fluoro-1-piperidyl]-4-pyrimidinyl (4-hydroxy-1-methyl-4-piperidyl)methanecarbamate

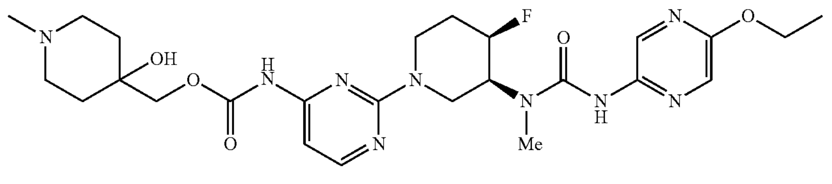 [SMILES: CCOc1cnc(NC(=O)N(C)[C@H]2CN(c3nccc(NC(=O)OCC4(O)CCN(C)CC4)n3)CC[C@H]2F)cn1]

The title compound was synthesized in a similar fashion to Example 18 using tert-butyl 4-hydroxy-4-(hydroxymethyl)piperidine-1-carboxylate in Step 7. $^1$H NMR (400 MHz, DMSO) δ 10.13 (s, 1H), 9.02 (s, 1H), 8.55 (d, J=1.5 Hz, 1H), 8.24 (d, J=5.6 Hz, 1H), 8.01 (d, J=1.5 Hz, 1H), 7.06 (d, J=5.6 Hz, 1H), 5.04 (d, J=51.5 Hz, 1H), 4.68-4.48 (m, 2H), 4.39 (s, 1H), 4.29 (q, J=7.1 Hz, 2H), 4.24 (d, J=4.7 Hz, 1H), 4.17 (dd, J=12.0, 4.7 Hz, 1H), 3.91 (s, 2H), 3.46 (t, J=12.1 Hz, 1H), 3.13-3.03 (m, 2H), 3.03 (s, 2H), 2.45 (s, 1H), 2.33 (s, 2H), 2.17 (s, 2H), 2.04-1.70 (m, 2H), 1.68-1.53 (m, 2H), 1.47 (s, 2H), 1.32 (t, J=7.0 Hz, 2H), 1.25 (d, J=3.2 Hz, 1H), 0.85 (dt, J=10.7, 6.6 Hz, 1H). ESI MS $[M+H]^+$ for $C_{25}H_{36}FN_9O_5$, calcd 562.3, found 562.1.

Example 174: 2-[(R)-3-[3-(5-ethoxy-2-pyrazinyl)-1-methylureido]-1-piperidyl]-4-pyridyl [(2S,4S)-4-fluoro-2-pyrrolidinyl]methanecarbamate

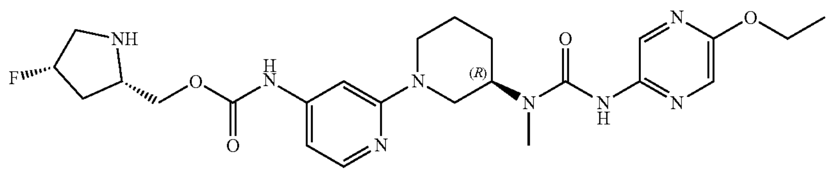

The title compound was synthesized in a similar fashion to Example 132 (step 1-7 (part1)) using (R)-3-N-Boc-3-(methylamino)piperidine in Step 1 and tert-butyl (2S,4S)-4-fluoro-2-(hydroxymethyl)pyrrolidine-1-carboxylate in Step 4: $^{1}$H NMR (400 MHz, DMSO) δ 9.87 (s, 1H), 9.08 (s, 1H), 8.59 (d, J=1.5 Hz, 1H), 8.09-7.85 (m, 2H), 6.99 (s, 1H), 6.75 (dd, J=5.6, 1.7 Hz, 1H), 5.23 (d, J=55.4 Hz, 1H), 4.30 (q, J=7.0 Hz, 2H), 4.20-3.88 (m, 5H), 3.38 (s, 1H), 3.22-3.01 (m, 2H), 2.92 (s, 4H), 2.80 (t, J=12.7 Hz, 1H), 2.17 (ddt, J=33.1, 14.7, 8.0 Hz, 2H), 1.87-1.62 (m, 3H), 1.53 (s, 2H), 1.33 (t, J=7.0 Hz, 3H). ESI MS $[M+H]^+$ for $C_{24}H_{33}FN_8O_4$, calcd 517.3, found 517.3.

Example 175: 2-[(S)-3-[3-(5-ethoxy-2-pyrazinyl)-1-methylureido]-1-piperidyl]-4-pyridyl [(2S,4R)-4-fluoro-2-pyrrolidinyl]methanecarbamate

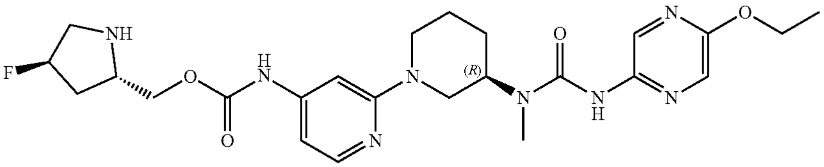

The title compound was synthesized in a similar fashion to Example 132 (step 1-7 (part1)) using (R)-3-N-Boc-3-(methylamino)piperidine in Step 1 and tert-butyl (2S,4R)-4-fluoro-2-(hydroxymethyl)pyrrolidine-1-carboxylate in Step 4. $^{1}$H NMR (400 MHz, DMSO) δ 9.84 (s, 1H), 9.08 (s, 1H), 8.59 (d, J=1.4 Hz, 1H), 8.09-7.96 (m, 2H), 7.04-6.91 (m, 1H), 6.75 (dd, J=5.6, 1.7 Hz, 1H), 5.33-5.12 (m, 1H), 4.30 (q, J=7.0 Hz, 2H), 4.13 (d, J=10.9 Hz, 1H), 4.08-3.92 (m, 4H), 3.52 (p, J=6.6 Hz, 1H), 3.02 (d, J=2.7 Hz, 1H), 2.92 (s, 4H), 2.80 (t, J=12.7 Hz, 2H), 2.05 (ddd, J=22.9, 14.4, 6.9 Hz, 1H), 1.79 (d, J=8.8 Hz, 3H), 1.62 (dddd, J=38.8, 14.0, 8.4, 4.6 Hz, 3H), 1.33 (t, J=7.0 Hz, 3H). ESI MS $[M+H]^+$ for $C_{24}H_{33}FN_8O_4$, calcd 517.3, found 517.3.

Example 176: 2-[(S)-3-[3-(5-ethoxy-2-pyrazinyl)-1-methylureido]-4,4-difluoro-1-piperidyl]-4-pyrimidinyl (2R,4R)-1-methyl-2-methyl-4-piperidinecarbamate

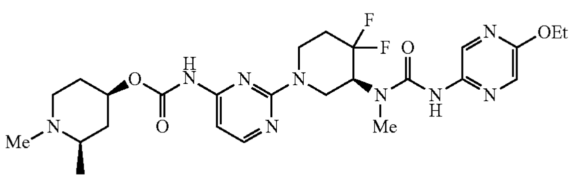 [SMILES: CCOc1cnc(NC(=O)N(C)[C@H]2CN(c3nccc(NC(=O)O[C@@H]4CCN(C)[C@H](C)C4)n3)CCC2(F)F)cn1]

The title compound was synthesized in a similar fashion to Example 11 using (2R,4R)-4-hydroxy-2-methylpiperidine-1-carboxylic acid tert-butyl ester in Step 5. $^{1}$H NMR (400 MHz, $CDCl_3$) δ 8.82 (s, 1H), 8.26 (d, J=5.6 Hz, 1H), 7.93 (s, 1H), 7.40 (s, 1H), 7.29 (s, 1H), 4.86 (d, J=13.8 Hz, 1H), 4.73 (tt, J=11.4, 4.5 Hz, 2H), 4.36 (q, J=7.1 Hz, 2H), 3.33 (d, J=12.4 Hz, 1H), 3.17 (d, J=2.8 Hz, 3H), 3.13 (d, J=12.8 Hz, 1H), 2.92 (dt, J=12.3, 3.7 Hz, 1H), 2.28 (s, 3H), 2.25-2.13 (m, 2H), 2.12-1.93 (m, 3H), 1.78-1.67 (m, 1H), 1.66 (s, 3H), 1.50-1.33 (m, 3H), 1.14 (d, J=6.0 Hz, 3H). ESI MS $[M+H]^+$ for $C_{25}H_{35}F_2N_9O_4$, calcd 564.3, found 564.2.

Example 177: 2-[(S)-3-[3-(5-ethoxy-2-pyrazinyl)-1-methylureido]-4,4-difluoro-1-piperidyl]-4-pyrimidinyl (2R,4R)-2-methyl-4-piperidinecarbamate

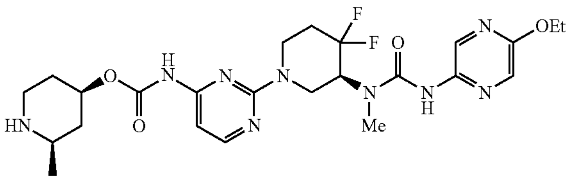 [SMILES: CCOc1cnc(NC(=O)N(C)[C@H]2CN(c3nccc(NC(=O)O[C@@H]4CCN[C@H](C)C4)n3)CCC2(F)F)cn1]

The title compound was synthesized in a similar fashion to Example 11 (step 1-8, part 1) using (2R,4R)-4-hydroxy-2-methylpiperidine-1-carboxylic acid tert-butyl ester in Step 5. $^{1}$H NMR (400 MHz, DMSO) δ 10.20 (s, 1H), 9.01 (s, 1H), 8.55 (d, J=1.5 Hz, 1H), 8.25 (d, J=5.6 Hz, 1H), 8.02 (t, J=1.2 Hz, 1H), 7.09 (d, J=5.6 Hz, 1H), 4.80-4.49 (m, 4H), 4.34-4.19 (m, 2H), 3.04 (d, J=14.4 Hz, 5H), 2.76-2.54 (m, 2H), 2.24-1.87 (m, 5H), 1.46-1.34 (m, 1H), 1.34-1.27 (m, 3H), 1.13 (d, J=11.9 Hz, 1H), 1.09-0.99 (m, 3H). ESI MS $[M+H]^+$ for $C_{24}H_{33}F_2N_9O_4$, calcd 550.3, found 550.2.

Example 178: 2-[(S)-3-[3-(5-ethoxy-2-pyrazinyl)-1-methylureido]-4,4-difluoro-1-piperidyl]-4-pyrimidinyl (3S,4R)-3-methyl-4-piperidinecarbamate

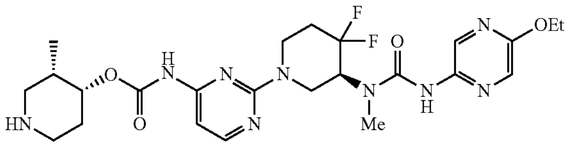 [SMILES: CCOc1cnc(NC(=O)N(C)[C@H]2CN(c3nccc(NC(=O)O[C@@H]4CCNC[C@@H]4C)n3)CCC2(F)F)cn1]

The title compound was synthesized in a similar fashion to Example 11 (step 1-8, part 1) using tert-butyl (3S,4R)-4- hydroxy-3-methyl-piperidine-1-carboxylate in Step 5. $^1$H NMR (400 MHz, DMSO) δ 10.22 (s, 1H), 8.54 (d, J=1.4 Hz, 1H), 8.39 (s, 1H), 8.02 (d, J=1.4 Hz, 1H), 7.12 (d, J=5.7 Hz, 1H), 4.91-4.84 (m, 1H), 4.75 (s, 2H), 4.63 (dd, J=27.1, 11.2 Hz, 1H), 4.30 (q, J=7.0 Hz, 2H), 3.07-3.02 (m, 2H), 3.00-2.88 (m, 4H), 2.77 (d, J=16.5 Hz, 2H), 2.75-2.58 (m, 2H), 2.26-1.61 (m, 4H), 1.32 (t, J=7.0 Hz, 3H), 0.84 (d, J=6.9 Hz, 3H). ESI MS $[M+H]^+$ for $C_{24}H_{33}F_2N_9O_4$, calcd 550.3, found 550.2.

Example 179: 2-[(S)-4,4-difluoro-3-[1-methyl-3-(5-methyl-1,3-thiazol-2-yl)ureido]-1-piperidyl]-4-pyrimidinyl (3R,4S)-1-methyl-3-methyl-4-piperidinecarbamate

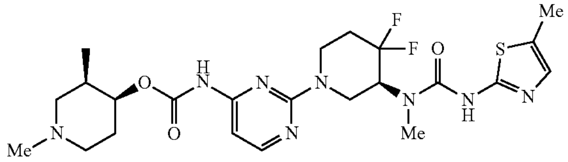 [SMILES: Cc1cnc(NC(=O)N(C)[C@H]2CN(c3nccc(NC(=O)O[C@H]4CCN(C)C[C@H]4C)n3)CCC2(F)F)s1]

The title compound was synthesized in a similar fashion to Example 11 using tert-butyl (3R,4S)-4-hydroxy-3-methyl-piperidine-1-carboxylate in Step 5 and phenyl N-(5-methyl-1,3-thiazol-2-yl)carbamate in step 7, which was prepared in a similar fashion to Example 1 Step 4. $^1$H NMR (400 MHz, $CDCl_3$) δ 8.33 (s, 1H), 8.31 (d, J=5.9 Hz, 1H), 7.31-7.26 (m, 1H), 7.06 (s, 1H), 5.03 (s, 1H), 4.89 (d, J=13.9 Hz, 1H), 4.69-4.64 (m, 1H), 4.29 (s, 1H), 3.30 (t, J=12.3 Hz, 1H), 2.23-3.14 (m, 4H), 2.91-2.86 (m, 3H), 2.47-2.45 (m, 1H), 2.43 (s, 3H), 2.37 (t, J=2.8 Hz, 3H), 2.25 (d, J=41.5 Hz, 2H), 2.00 (d, J=47.5 Hz, 3H), 1.01 (d, J=5.6 Hz, 3H). ESI MS $[M+H]^+$ for $C_{23}H_{32}F_2N_8O_3S$, calcd 539.2, found 539.1.

Example 180: 2-[(S)-4,4-difluoro-3-[1-methyl-3-(5-methyl-1,3-thiazol-2-yl)ureido]-1-piperidyl]-4-pyrimidinyl (3S,4R)-1-methyl-3-methyl-4-piperidinecarbamate

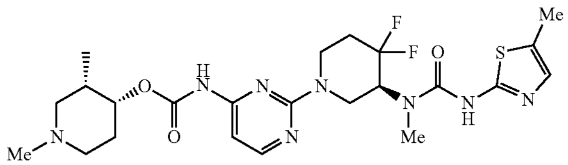 [SMILES: Cc1cnc(NC(=O)N(C)[C@H]2CN(c3nccc(NC(=O)O[C@@H]4CCN(C)C[C@@H]4C)n3)CCC2(F)F)s1]

The title compound was synthesized in a similar fashion to Example 11 using tert-butyl (3S,4R)-4-hydroxy-3-methyl-piperidine-1-carboxylate in Step 5 and phenyl N-(5-methyl-1,3-thiazol-2-yl)carbamate in step 7, which was prepared in a similar fashion to Example 1 Step 4. $^1$H NMR (400 MHz, $CDCl_3$) δ 8.33 (s, 1H), 8.31 (d, J=6.8 Hz, 1H), 7.28-7.26 (m, 1H), 7.07 (s, 1H), 5.03 (s, 1H), 4.89 (d, J=13.9 Hz, 1H), 4.70-4.63 (m, 1H), 4.30 (s, 1H), 3.30 (t, J=12.3 Hz, 1H), 2.23-3.16 (m, 4H), 2.90-2.86 (m, 3H), 2.47-2.45 (m, 1H), 2.44 (s, 3H), 2.37 (t, J=2.8 Hz, 3H), 2.26 (d, J=41.5 Hz, 2H), 2.01 (d, J=47.5 Hz, 3H), 1.01 (d, J=5.6 Hz, 3H). ESI MS $[M+H]^+$for $C_{23}H_{32}F_2N_8O_3S$, calcd 539.2, found 539.1.

Example 181: 2-[(S)-4,4-difluoro-3-[1-methyl-3-(5-methyl-1,3-thiazol-2-yl)ureido]-1-piperidyl]-4-pyrimidinyl (3R,4R)-3-methyl-4-piperidinecarbamate

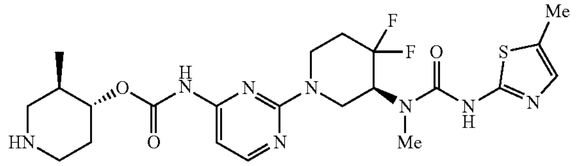 [SMILES: Cc1cnc(NC(=O)N(C)[C@H]2CN(c3nccc(NC(=O)O[C@@H]4CCNC[C@H]4C)n3)CCC2(F)F)s1]

The title compound was synthesized in a similar fashion to Example 11 (step 1-8, part 1) using tert-butyl (3R,4R)-4-hydroxy-3-methyl-piperidine-1-carboxylate in Step 5 and phenyl N-(5-methyl-1,3-thiazol-2-yl)carbamate in step 7, which was prepared in a similar fashion to Example 1 Step 4. $^1$H NMR (400 MHz, DMSO) δ 10.52 (s, 1H), 9.18 (d, J=10.7 Hz, 1H), 9.02 (s, 1H), 8.28 (d, J=5.9 Hz, 1H), 7.14 (d, J=5.8 Hz, 1H), 7.00 (s, 1H), 4.72 (t, J=14.1 Hz, 3H), 4.61 (td, J=10.0, 4.2 Hz, 1H), 3.26 (t, J=15.1 Hz, 3H), 3.11-2.95 (m, 6H), 2.88-2.55 (m, 2H), 2.25 (s, 3H), 2.17-1.85 (m, 2H), 1.76 (d, J=12.5 Hz, 1H), 0.94 (d, J=6.6 Hz, 3H). ESI MS $[M+H]^+$ for $C_{22}H_{30}F_2N_8O_3S$, calcd 525.2, found 525.1.

Example 182: 2-[(S)-4,4-difluoro-3-[1-methyl-3-(5-methyl-1,3-thiazol-2-yl)ureido]-1-piperidyl]-4-pyrimidinyl (3R,4R)-1-methyl-3-methyl-4-piperidinecarbamate

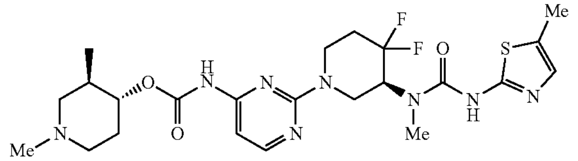 [SMILES: Cc1cnc(NC(=O)N(C)[C@H]2CN(c3nccc(NC(=O)O[C@@H]4CCN(C)C[C@H]4C)n3)CCC2(F)F)s1]

The title compound was synthesized in a similar fashion to Example 11 using tert-butyl (3R,4R)-4-hydroxy-3-methyl-piperidine-1-carboxylate in Step 5 and phenyl N-(5-methyl-1,3-thiazol-2-yl)carbamate in step 7, which was prepared in a similar fashion to Example 1 Step 4. $^1$H NMR (400 MHz, $CDCl_3$) δ 12.08 (s, 1H), 9.46 (s, 1H), 8.30 (d, J=5.4 Hz, 1H), 7.51 (s, 1H), 7.11 (s, 1H), 4.93 (d, J=13.7 Hz, 1H), 4.47 (q, J=13.7 Hz, 2H), 3.87 (s, 1H), 3.27-23.23 (m, 4H), 2.88 (t, J=13.9 Hz, 1H), 2.36 (s, 3H), 2.30 (s, 3H), 2.21 (d, J=10.1 Hz, 1H), 2.17-2.01 (m, 1H), 1.97 (dt, J=21.8, 9.9 Hz, 1H), 1.78 (ddq, J=19.4, 12.8, 6.1 Hz, 2H), 1.58 (s, 2H), 1.38-1.16 (m, 2H), 0.94 (d, J=6.6 Hz, 3H). ESI MS $[M+H]^+$ for $C_{23}H_{32}F_2N_8O_3S$, calcd 539.2, found 539.1.

Example 183: 2-[(S)-4,4-difluoro-3-[1-methyl-3-(1-methyl-1H-1,2,3-triazol-4-yl)ureido]-1-piperidyl]-4-pyrimidinyl 1-methyl-4-piperidinecarbamate

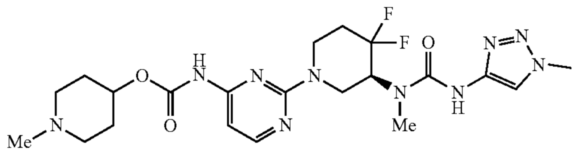 [SMILES: CN1CCC(OC(=O)Nc2ccnc(N3CCC(F)(F)[C@@H](N(C)C(=O)Nc4cn(C)nn4)C3)n2)CC1]

The title compound was synthesized in a similar fashion to Example 11 (step 1-7) using N-methyl-4-hydroxypiperidine in Step 5 and phenyl N-(1-methyl-1H-1,2,3-triazol-4-yl)carbamate in step 7, which was prepared in a similar fashion to Example 1 Step 4. $^1H$ NMR (400 MHz, $CDCl_3$) δ 8.22 (d, J=5.9 Hz, 1H), 8.05 (s, 1H), 7.76 (t, J=3.0 Hz, 1H), 7.24 (s, 1H), 7.19 (d, J=3.2 Hz, 1H), 4.79 (d, J=17.5 Hz, 2H), 4.63 (d, J=13.0 Hz, 1H), 4.27 (s, 1H), 3.97 (t, J=3.0 Hz, 3H), 3.29-3.18 (m, 1H), 3.10 (d, J=3.6 Hz, 3H), 3.05 (d, J=12.5 Hz, 1H), 2.65 (s, 2H), 2.24 (d, J=3.8 Hz, 3H), 2.17 (d, J=35.9 Hz, 3H), 1.94-1.90 (m, 2H), 1.77-1.72 (m, 3H). ESI MS $[M+H]^+$ for $C_{21}H_{30}F_2N_{10}O_3$, calcd 509.2, found 509.1.

Example 184: 2-[(S)-3-[3-(5-ethoxy-2-pyrazinyl)-1-methylureido]-4,4-difluoro-1-piperidyl]-4-pyrimidinyl (3S,4R)-1-ethyl-3-methyl-4-piperidinecarbamate The title compound was synthesized in a similar fashion to Example 11 using tert-butyl (3S,4R)-4-hydroxy-3-methyl-piperidine-i-carboxylate in Step 5 and acetaldehyde instead of paraformaldehyde in step 8, part 2. $^1H$ NMR (400 MHz, $CDCl_3$) δ 8.84-8.68 (m, 1H), 8.26-8.06 (m, 1H), 7.82 (d, J=3.9 Hz, 1H), 7.50 (s, 1H), 7.19 (s, 1H), 4.92 (s, 1H), 4.85-4.70 (m, 2H), 4.49 (s, 1H), 4.29 (q, J=6.8, 2H), 3.24 (td, J=12.6, 3.8 Hz, 1H), 3.09 (d, J=3.9 Hz, 3H), 3.04 (d, J=13.3 Hz, 1H), 2.65-2.47 (m, 2H), 2.35 (t, J=6.1 Hz, 2H), 2.15 (d, J=14.0 Hz, 2H), 2.03-1.75 (m, 6H), 1.32 (dd, J=7.8, 4.6 Hz, 3H), 1.02 (dt, J=9.2, 5.5 Hz, 2H), 0.87 (d, J=6.1 Hz, 3H).). ESI MS $[M+H]^+$ for $C_{26}H_{37}F_2N_9O_4$, calcd 578.3, found 578.1.

Example 185 and Example 186: 2-[(S)-3-[3-(5-ethoxy-2-pyrazinyl)-1-methylureido]-4,4-difluoro-1-piperidyl]-4-pyrimidinyl (1R,5S,6S)-3-methyl-3-azabicyclo[3.1.0]hexane-6-carbamate and 2-[(S)-3-[3-(5-ethoxy-2-pyrazinyl)-1-methylureido]-4,4-difluoro-1-piperidyl]-4-pyrimidinyl (1R,5S,6R)-3-methyl-3-azabicyclo[3.1.0]hexane-6-carbamate

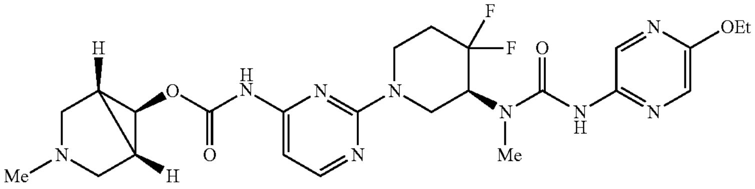

and

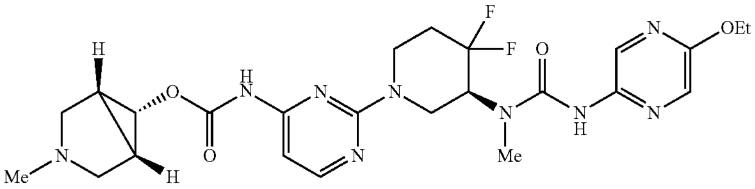

The title compound was synthesized in a similar fashion to Example 11 using 3-azabicyclo[3.1.0]hexane-3-carboxylic acid, 6-hydroxy-, 1,1-dimethylethyl ester in Step 5. The diastereomers were separated via column chromatography after step 8.

Less polar diastereomer: $^1$H NMR (400 MHz, CDCl3) δ 8.74 (d, J=3.8 Hz, 1H), 8.19 (d, J=5.2 Hz, 1H), 7.81 (d, J=3.7 Hz, 1H), 7.23 (d, J=4.7 Hz, 1H), 7.19 (d, J=3.6 Hz, 1H), 4.79 (d, J=13.8 Hz, 1H), 4.61 (d, J=13.1 Hz, 1H), 4.30-4.25 (m, 3H), 3.24 (t, J=12.2 Hz, 1H), 3.09-3.07 (m, 5H), 2.42 (d, J=32.0 Hz, 2H), 2.24 (s, 2H), 2.10 (d, J=15.7 Hz, 2H), 1.87 (dt, J=31.0, 14.1 Hz, 2H), 1.67-1.64 (m, 2H), 1.33 (dt, J=8.8, 5.5 Hz, 2H), 1.20-1.14 (m, 2H). ESI MS [M+H]$^+$ for $C_{24}H_{31}F_2N_9O_4$, calcd 548.2, found 548.1.

More polar diastereomer: $^1$H NMR (400 MHz, $CDCl_3$) δ 8.76 (s, 1H), 8.19 (d, J=5.1 Hz, 1H), 7.87 (s, 1H), 7.27 (s, 1H), 7.20 (d, J=3.6 Hz, 1H), 4.81 (d, J=13.9 Hz, 1H), 4.75-4.58 (m, 1H), 4.60-4.38 (m, 1H), 4.28 (p, J=6.5 Hz, 2H), 3.25 (t, J=12.5 Hz, 2H), 3.10-3.04 (m, 5H), 2.42 (d, J=39.7 Hz, 2H), 2.16 (d, J=31.5 Hz, 2H), 1.87-1.80 (m, 4H), 1.32 (q, J=6.2 Hz, 3H), 1.20-1.17 (m, 2H). ESI MS [M+H]$^+$ for $C_{24}H_{31}F_2N_9O_4$, calcd 548.2, found 548.1.

Example 187: 2-[(S)-3-[3-(5-ethoxy-2-pyrazinyl)-1-methylureido]-4,4-difluoro-1-piperidyl]-4-pyrimidinyl (1R,5S)-3-azabicyclo[3.1.0]hexane-6-carbamate

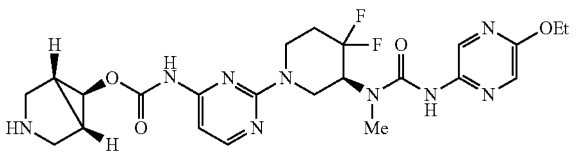 [SMILES: CCOc1cnc(NC(=O)N(C)[C@H]2CN(c3nccc(NC(=O)O[C@H]4[C@@H]5CNC[C@@H]54)n3)CCC2(F)F)cn1]

The title compound was synthesized in a similar fashion to Example 11 (step 1-8, part 1) using 3-azabicyclo[3.1.0]

hexane-3-carboxylic acid, 6-hydroxy-, 1,1-dimethylethyl ester in Step 5. $^1$H NMR (400 MHz, $CD_3OD$_SPE) δ 8.52 (s, 1H), 8.48 (t, J=3.4 Hz, 1H), 8.28 (d, J=7.1 Hz, 1H), 7.91 (t, J=3.3 Hz, 1H), 7.21 (d, J=5.8 Hz, 1H), 4.81 (d, J=15.2 Hz, 2H), 4.69-4.49 (m, 1H), 4.33 (t, J=6.6 Hz, 2H), 3.95 (d, J=4.3 Hz, 1H), 3.43 (ddd, J=18.0, 8.1, 3.6 Hz, 3H), 3.34 (d, J=11.6 Hz, 1H), 3.30 (s, 2H), 3.23-3.04 (m, 3H), 2.26-1.83 (m, 4H), 1.37 (dq, J=9.1, 4.1 Hz, 3H). ESI MS [M+H]$^+$ for $C_{23}H_{29}F_2N_9O_4$ calcd 534.2, found 534.2.1

Example 188: 2-[(S)-3-[3-(5-ethoxy-2-pyrazinyl)-1-methylureido]-4,4-difluoro-1-piperidyl]-4-pyrimidinyl (2S,4S)-6-aza-2-spiro[3.5]nonanecarbamate

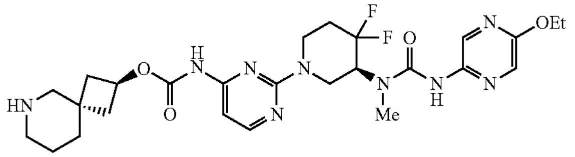 [SMILES: CCOc1cnc(NC(=O)N(C)[C@H]2CN(c3nccc(NC(=O)O[C@H]4C[C@@]5(CCCNC5)C4)n3)CCC2(F)F)cn1]

The title compound was synthesized in a similar fashion to Example 11 (step 1-8, part 1) using tert-butyl (2S,4R)-2-hydroxy-6-azaspiro[3.5]nonane-6-carboxylate in Step 5. $^1$H NMR (400 MHz, $CD_3OD$_SPE) δ 8.54 (s, 1H), 8.49 (s, 1H), 8.20 (d, J=6.4 Hz, 1H), 7.91 (s, 1H), 7.19 (s, 1H), 5.03 (q, J=6.5 Hz, 1H), 4.86 (d, J=3.4 Hz, 2H), 4.60 (dd, J=26.0, 10.8 Hz, 1H), 4.33 (dq, J=9.0, 4.5 Hz, 2H), 3.56-3.36 (m, 1H), 3.20-3.14 (m, 2H), 3.14 (s, 3H), 3.08 (s, 2H), 2.99 (s, 2H), 2.48 (qd, J=7.9, 4.8 Hz, 2H), 2.15 (s, 1H), 1.98 (qd, J=12.3, 8.3 Hz, 3H), 1.79-1.64 (m, 3H), 1.36 (q, J=7.0, 3H). ESI MS [M+H]$^+$ for $C_{26}H_{35}F_2N_9O_4$ calcd 576.3, found 576.1.

Example 189: 2-[(S)-3-[3-(5-ethoxy-2-pyrazinyl)-1-methylureido]-4,4-difluoro-1-piperidyl]-4-pyrimidinyl (2S,4S)-6-methyl-6-aza-2-spiro[3.5]nonanecarbamate

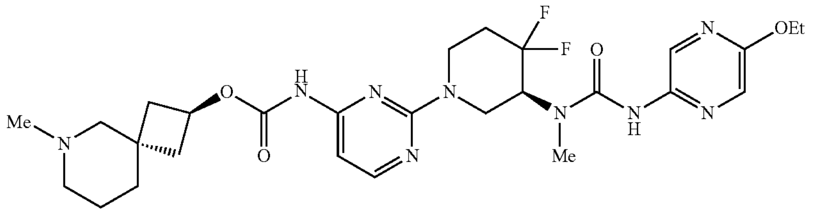 [SMILES: CCOc1cnc(NC(=O)N(C)[C@H]2CN(c3nccc(NC(=O)O[C@H]4C[C@@]5(CCCN(C)C5)C4)n3)CCC2(F)F)cn1]

The title compound was synthesized in a similar fashion to Example 11 using tert-butyl (2S,4R)-2-hydroxy-6-azaspiro[3.5]nonane-6-carboxylate in Step 5. $^1$H NMR (400 MHz, $CDCl_3$) δ 8.76 (s, 1H), 8.19 (d, J=5.4 Hz, 1H), 7.92 (s, 1H), 7.38 (s, 1H), 7.23 (s, 1H), 5.10-4.98 (m, 1H), 4.81 (d, J=13.9 Hz, 1H), 4.63 (d, J=13.1 Hz, 1H), 4.30 (t, J=6.5 Hz, 3H), 3.26 (t, J=12.8 Hz, 1H), 3.12-3.08 (m, 4H), 2.48-2.23 (m, 6H), 2.05 (d, J=71.1 Hz, 1H), 1.89-1.84 (m, 4H), 1.55-1.46 (m, 5H), 1.33 (q, J=6.4 Hz, 4H). ESI MS $[M+H]^+$ for $C_{27}H_{37}F_2N_{904}$ calcd 590.3, found 590.3.

Example 190: 2-[(S)-4,4-difluoro-3-[1-methyl-3-(3-pyrazolyl)ureido]-1-piperidyl]-4-pyrimidinyl 1-methyl-4-piperidinecarbamate

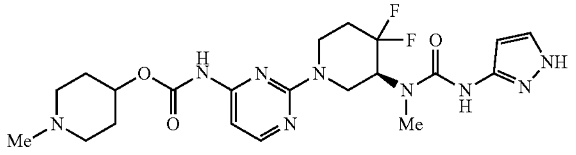 [SMILES: CN1CCC(OC(=O)Nc2ccnc(N3CCC(F)(F)[C@@H](N(C)C(=O)Nc4cc[nH]n4)C3)n2)CC1]

The title compound was synthesized in a similar fashion to Example 11 (step 1-7) using N-methyl-4-hydroxypiperidine in Step 5 and Phenyl N-1H-pyrazol-3-ylcarbamate in step 7, which was prepared in a similar fashion to Example 1 Step 4. $^1$H NMR (400 MHz, $CDCl_3$) δ 8.35 (d, J=4.1 Hz, 1H), 8.27-8.16 (m, 1H), 8.08 (s, 1H), 7.46 (d, J=4.0 Hz, 1H), 7.19 (d, J=6.1 Hz, 1H), 6.59 (d, J=4.3 Hz, 1H), 4.96 (dt, J=10.5, 5.1 Hz, 1H), 4.85 (d, J=14.2 Hz, 1H), 4.59-4.40 (m, 2H), 3.29-3.15 (m, 3H), 3.11 (s, 3H), 2.98-2.79 (m, 1H), 2.70 (d, J=12.2 Hz, 2H), 2.59 (s, 3H), 2.44-2.40 (m, 2H), 2.13-2.11 (m, 3H), 1.84 (td, J=34.6, 19.9 Hz, 1H). ESI MS $[M+H]^+$for $C_{21}H_{29}F_2N_9O_3$ calcd 494.2, found 494.1.

Example 191: 2-[(S)-4,4-difluoro-3-{3-[5-(methoxymethyl)-1,3-thiazol-2-yl]-1-methylureido}-1-piperidyl]-4-pyrimidinyl 1-methyl-4-piperidinecarbamate

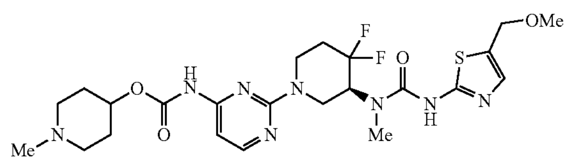 [SMILES: COCc1cnc(NC(=O)N(C)[C@H]2CN(c3nccc(NC(=O)OC4CCN(C)CC4)n3)CCC2(F)F)s1]

The title compound was synthesized in a similar fashion to Example 11 (step 1-7) using N-methyl-4-hydroxypiperidine in Step 5 and phenyl 5-(methoxymethyl)-1,3-thiazol-2-amin) carbamate in step 7, which was prepared in a similar fashion to Example 1 Step 4. $^1$H NMR (400 MHz, $CDCl_3$) δ 9.40 (s, 1H), 8.24 (s, 1H), 7.41 (s, 1H), 7.30 (s, 1H), 4.86 (d, J=13.8 Hz, 1H), 4.74 (s, 1H), 4.50 (d, J=3.4 Hz, 3H), 3.83 (s, 1H), 3.29 (d, J=3.5 Hz, 3H), 3.19 (s, 3H), 3.11 (d, J=12.9 Hz, 1H), 2.75-2.71 (m, 2H), 2.24 (t, J=3.4 Hz, 3H), 2.15 (d, J=11.7 Hz, 2H), 1.97 (d, J=13.2 Hz, 2H), 1.77 (d, J=13.9 Hz, 2H), 1.58-1.52 (m, 3H). ESI MS $[M+H]^+$ for $C_{23}H_{32}F_2N_8O_4S$ calcd 555.2, found 555.3.

Example 192: 2-[(S)-3-[3-(5-ethoxy-2-pyrazinyl)-1-methylureido]-4,4-difluoro-1-piperidyl]-4-pyridyl (3S,4R)-1-methyl-3-methyl-4-piperidinecarbamate

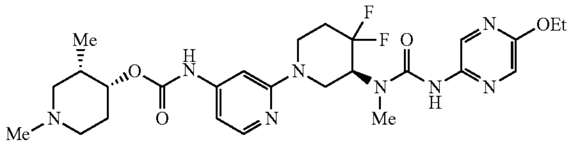 [SMILES: CCOc1cnc(NC(=O)N(C)[C@H]2CN(c3cc(NC(=O)O[C@@H]4CCN(C)C[C@@H]4C)ccn3)CCC2(F)F)cn1]

The title compound was synthesized in a similar fashion to Example 132 using 1,1-dimethylethyl N-[(3S)-4,4-difluoro-3-piperidinyl]methyl carbamate in step 1 and 1,1-dimethylethyl (3S,4R)-4-hydroxy-3-methyl-1-piperidinecarboxylate in Step 5. $^1$H NMR (400 MHz, $CDCl_3$) δ 8.80-8.65 (m, 1H), 8.08 (d, J=5.5 Hz, 1H), 7.79 (t, J=3.3 Hz, 1H), 7.62 (s, 1H), 7.11 (s, 1H), 6.77 (d, J=4.4 Hz, 1H), 6.47 (d, J=5.4 Hz, 1H), 4.85 (s, 1H), 4.55 (d, J=22.6 Hz, 1H), 4.41-4.33 (m, 1H), 4.25 (dt, J=29.3, 10.0 Hz, 3H), 3.26 (t, J=12.0 Hz, 1H), 3.16 (t, J=13.8 Hz, 1H), 3.08 (d, J=4.3 Hz, 3H), 2.46 (s, 2H), 2.20 (d, J=4.4 Hz, 3H), 2.15-2.12 (d, J=19.9 Hz, 1H), 2.05-1.83 (m, 4H), 1.77 (t, J=12.7 Hz, 1H), 1.68-1.64 (m, 1H), 1.32 (q, J=6.2 Hz, 3H), 0.89 (t, J=5.8 Hz, 3H). ESI MS $[M+H]^+$ for $C_{26}H_{36}F_2N_8O_4$ calcd 563.3, found 563.1.

Example 193: 2-[(S)-3-[3-(5-ethoxy-2-pyrazinyl)-1-methylureido]-4,4-difluoro-1-piperidyl]-4-pyridyl (3S,4R)-3-methyl-4-piperidinecarbamate

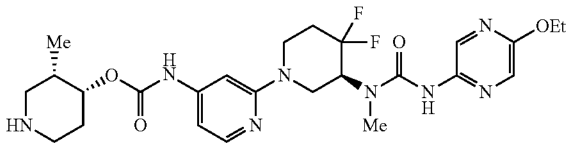 [SMILES: CCOc1cnc(NC(=O)N(C)[C@H]2CN(c3cc(NC(=O)O[C@@H]4CCNC[C@@H]4C)ccn3)CCC2(F)F)cn1]

The title compound was synthesized in a similar fashion to Example 132 (step 1-7, part 1) using 1,1-dimethylethyl N-[(3S)-4,4-difluoro-3-piperidinyl]methyl carbamate in step 1 and 1,1-dimethylethyl (3S,4R)-4-hydroxy-3-methyl-1-piperidinecarboxylate in Step 4. $^1$H NMR (400 MHz, $CD_3OD$_SPE) δ 8.57-8.42 (m, 2H), 8.04-7.95 (m, 1H), 7.91 (t, J=3.3 Hz, 1H), 7.20-6.98 (m, 1H), 6.82 (d, J=5.7 Hz, 1H), 5.03 (s, 1H), 4.78-4.53 (m, 1H), 4.33 (td, J=8.1, 4.6 Hz, 4H), 3.48 (ddd, J=17.9, 9.6, 3.4 Hz, 1H), 3.23 (d, J=16.2 Hz, 2H), 3.16 (s, 3H), 3.14-3.11 (m, 2H), 2.95 (td, J=13.5, 3.7 Hz, 1H), 2.25-1.87 (m, 5H), 1.37 (dt, J=9.1, 5.8 Hz, 3H), 1.02 (t, J=5.8 Hz, 3H). ESI MS $[M+H]^+$ for $C_{25}H_{34}F_2N_8O_4$ calcd 549.3, found 549.2.

Example 194: 2-[(S)-3-[3-(5-ethoxy-2-pyrazinyl)-1-methylureido]-4,4-difluoro-1-piperidyl]-4-pyrimidinyl 3-oxa-9-azabicyclo[3.3.1]nonane-7-carbamate

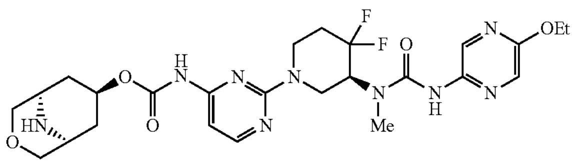 [SMILES: CCOc1cnc(NC(=O)N(C)[C@H]2CN(c3nccc(NC(=O)O[C@H]4C[C@H]5COC[C@@H](C4)N5)n3)CCC2(F)F)cn1]

The title compound was synthesized in a similar fashion to Example 11 (step 1-8, part 1) using tert-butyl endo-7-hydroxy-3-oxa-9-azabicyclo[3.3.1]nonane-9-carboxylat in Step 5. $^1$H NMR (400 MHz, $CDCl_3$) δ 8.74 (d, J=1.5 Hz, 1H), 8.17 (d, J=5.6 Hz, 1H), 7.93 (s, 1H), 7.82 (d, J=1.5 Hz, 1H), 7.20 (d, J=5.7 Hz, 1H), 5.10 (dt, J=6.1, 2.6 Hz, 1H), 4.73 (dd, J=30.6, 13.2 Hz, 2H), 4.47 (s, 1H), 4.28 (q, J=7.0 Hz, 2H), 3.80 (d, J=11.4 Hz, 2H), 3.71 (dd, J=11.4, 7.7 Hz, 2H), 3.24 (d, J=12.3 Hz, 1H), 3.13-2.98 (m, 5H), 2.44-2.06 (m, 5H), 2.00-1.75 (m, 2H), 1.31 (t, J=7.0 Hz, 3H). ESI MS $[M+H]^+$ for $C_{25}H_{33}F_2N_9O_5$ calcd 578.3, found 578.1.

Example 195: 2-[(S)-3-[3-(5-ethoxy-2-pyrazinyl)-1-methylureido]-4,4-difluoro-1-piperidyl]-4-pyrimidinyl 9-methyl-3-oxa-9-azabicyclo[3.3.1]nonane-7-carbamate

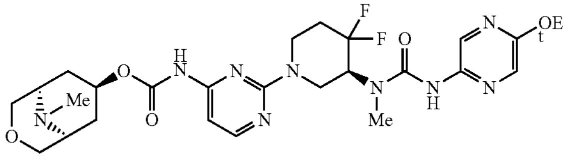 [SMILES: CCOc1cnc(NC(=O)N(C)[C@H]2CN(c3nccc(NC(=O)O[C@H]4C[C@H]5COC[C@@H](C4)N5C)n3)CCC2(F)F)cn1]

The title compound was synthesized in a similar fashion to Example 11 using tert-butyl endo-7-hydroxy-3-oxa-9-azabicyclo[3.3.1]nonane-9-carboxylat in Step 5. $^1$H NMR (400 MHz, $CDCl_3$) δ 8.76 (t, J=3.4 Hz, 1H), 8.18 (d, J=5.9 Hz, 1H), 7.83 (s, 1H), 7.60 (s, 1H), 7.22 (t, J=6.5 Hz, 1H), 5.17-5.06 (m, 1H), 4.83-4.64 (m, 2H), 4.60-4.39 (m, 1H), 4.28 (p, J=6.6 Hz, 2H), 3.91-3.79 (m, 2H), 3.57 (q, J=7.3 Hz, 2H), 3.32-3.18 (m, 1H), 3.14-2.97 (m, 4H), 2.59 (s, 2H), 2.44 (t, J=3.3 Hz, 3H), 2.36 (dd, J=15.1, 6.7 Hz, 2H), 2.10 (d, J=14.1 Hz, 1H), 2.03-1.74 (m, 2H), 1.63 (d, J=15.5 Hz, 2H), 1.32 (q, J=6.3 Hz, 3H). ESI MS $[M+H]^+$ for $C_{26}H_{35}F_2N_9O_{5\ z}$ calcd 592.3, found 592.1.

Example 196: 2-[(S)-3-[3-(5-ethoxy-2-pyrazinyl)-1-methylureido]-4,4-difluoro-1-piperidyl]-4-pyrimidinyl (1R,5S,7S)-3-azabicyclo[3.3.0]octane-7-carbamate

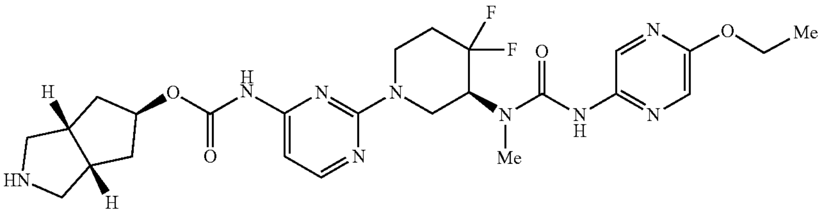 [SMILES: CCOc1cnc(NC(=O)N(C)[C@H]2CN(c3nccc(NC(=O)O[C@@H]4C[C@H]5CNC[C@H]5C4)n3)CCC2(F)F)cn1]

The title compound was synthesized in a similar fashion to Example 11 (step 1-8, part 1) using tert-butyl rel-(3aS,5S,6aR)-5-hydroxy-3,3a,4,5,6,6a-hexahydro-1H-cyclopenta[c]pyrrole-2-carboxylate in Step 5. $^1$H NMR (400 MHz, $CDCl_3$) δ 8.84 (d, J=1.4 Hz, 1H), 8.44 (s, 1H), 8.26 (d, J=5.7 Hz, 1H), 7.90 (d, J=1.4 Hz, 1H), 7.39 (s, 1H), 5.38 (s, 1H), 4.87 (d, J=14.0 Hz, 1H), 4.72 (d, J=13.1 Hz, 1H), 4.36 (q, J=7.1 Hz, 3H), 3.36-3.21 (m, 3H), 3.17 (s, 3H), 3.15-2.97 (m, 5H), 2.23-2.19 (m, 3H), 2.10-1.81 (m, 3H), (t, J=7.0 Hz, 3H). ESI MS $[M+H]^+$ for $C_{25}H_{33}F_2N_9O_4$ calcd 562.3, found 562.2.

Example 197: 2-[(S)-3-[3-(5-ethoxy-2-pyrazinyl)-1-methylureido]-4,4-difluoro-1-piperidyl]-4-pyrimidinyl (1R,5S,7S)-3-methyl-3-azabicyclo[3.3.0]octane-7-carbamate

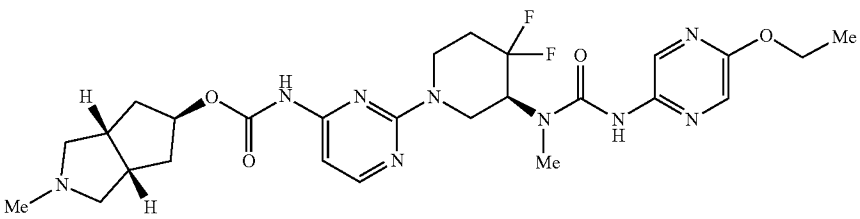 [SMILES: CCOc1cnc(NC(=O)N(C)[C@H]2CN(c3nccc(NC(=O)O[C@H]4C[C@@H]5CN(C)C[C@@H]5C4)n3)CCC2(F)F)cn1]

The title compound was synthesized in a similar fashion to Example 11 using tert-butyl rel-(3aS,5S,6aR)-5-hydroxy-3,3a,4,5,6,6a-hexahydro-1H-cyclopenta[c]pyrrole-2-carboxylate in Step 5. $^1$H NMR (400 MHz, $CDCl_3$) δ 8.77 (d, J=1.5 Hz, 1H), 8.19 (d, J=5.6 Hz, 1H), 7.86 (d, J=1.5 Hz, 1H), 7.35 (s, 1H), 7.22 (d, J=5.6 Hz, 1H), 5.28 (td, J=4.5, 2.3 Hz, 1H), 4.80 (d, J=13.7 Hz, 1H), 4.65 (d, J=13.2 Hz, 1H), 4.29 (q, J=7.1 Hz, 2H), 3.31-3.21 (m, 1H), 3.10 (d, J=2.9 Hz, 3H), 3.06 (dd, J=13.4, 2.8 Hz, 1H), 2.74 (s, 2H), 2.52 (d, J=9.4 Hz, 2H), 2.37 (s, 2H), 2.30 (s, 3H), 2.16-2.13 (q, J=6.9 Hz, 2H), 2.08-1.99 (m, 2H), 1.74 (d, J=13.5 Hz, 2H), 1.32 (t, J=7.1 Hz, 3H). ESI MS $[M+H]^+$ for $C_{26}H_{35}F_2N_9O_4$ calcd 576.3, found 576.1.

Example 198: 2-[(S)-3-[3-(5-ethoxy-2-pyrazinyl)-1-methylureido]-4,4-difluoro-1-piperidyl]-4-pyrimidinyl (1R,5S,7r)-3-azabicyclo[3.3.0]octane-7-carbamate

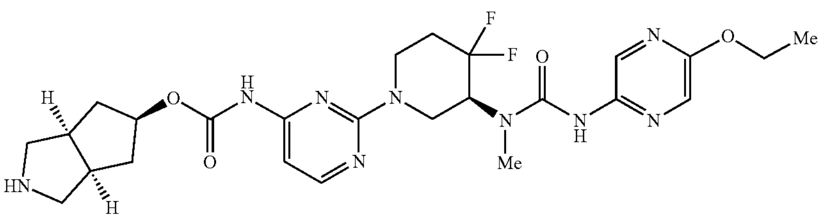 [SMILES: CCOc1cnc(NC(=O)N(C)[C@H]2CN(c3nccc(NC(=O)O[C@H]4C[C@H]5CNC[C@H]5C4)n3)CCC2(F)F)cn1]

The title compound was synthesized in a similar fashion to Example 11 (step 1-8, part 1) using tert-butyl rel-(3aS,5R,6aR)-5-hydroxy-3,3a,4,5,6,6a-hexahydro-1H-cyclopenta[c]pyrrole-2-carboxylate in Step 5. $^1$H NMR (400 MHz, MeOD) δ 8.49 (d, J=1.6 Hz, 1H), 8.28-8.12 (m, 1H), 7.92 (d, J=1.5 Hz, 1H), 7.22 (dd, J=5.6, 2.7 Hz, 1H), 5.05 (p, J=5.6 Hz, 1H), 4.86-4.77 (m, 2H), 4.72-4.50 (m, 1H), 4.34 (q, J=7.1 Hz, 2H), 3.46 (dd, J=14.0, 10.6 Hz, 1H), 3.15 (s, 3H), 3.14-3.12 (m, 1H), 2.89 (dd, J=11.9, 6.5 Hz, 2H), 2.74 (dt, J=11.6, 2.8 Hz, 1H), 2.65 (dt, J=8.1, 4.0 Hz, 2H), 2.20 (ddd, J=20.4, 10.3, 6.2 Hz, 3H), 2.03 (dd, J=32.7, 14.0 Hz, 1H), 1.69 (dt, J=14.2, 5.0 Hz, 1H), 1.59 (dt, J=13.9, 4.7 Hz, 2H), 1.38 (t, J=7.0 Hz, 3H). ESI MS $[M+H]^+$ for $C_{25}H_{33}F_2N_9O_4$ calcd 562.3, found 562.2.

Example 199: 2-[(S)-3-[3-(5-ethoxy-2-pyrazinyl)-1-methylureido]-4,4-difluoro-1-piperidyl]-4-pyrimidinyl (1R,5S,8r)-3-azabicyclo[3.2.1]octane-8-carbamate

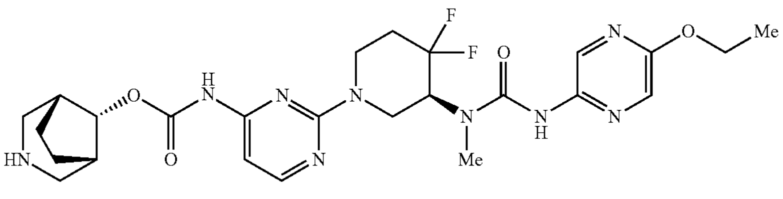 [SMILES: CCOc1cnc(NC(=O)N(C)[C@H]2CN(c3nccc(NC(=O)O[C@H]4[C@@H]5CC[C@H]4CNC5)n3)CCC2(F)F)cn1]

The title compound was synthesized in a similar fashion to Example 11 (step 1-8, part 1) using endo-tert-butyl 8-hydroxy-3-azabicyclo[3.2.1]octane-3-carboxylatein Step 5. $^1$H NMR (400 MHz, MeOD) δ 8.50 (d, J=1.4 Hz, 1H), 8.25-8.19 (m, 1H), 7.92 (d, J=1.4 Hz, 1H), 7.26 (dd, J=5.8, 1.3 Hz, 1H), 4.85-4.77 (m, 2H), 4.62 (dd, J=26.0, 10.7 Hz, 1H), 4.34 (q, J=7.0 Hz, 2H), 3.47 (t, J=12.2 Hz, 1H), 3.25-3.06 (m, 6H), 2.45 (dd, J=13.1, 2.9 Hz, 2H), 2.25-1.94 (m, 5H), 1.92-1.80 (m, 2H), 1.79-1.64 (m, 2H), 1.38 (t, J=7.1 Hz, 3H). ESI MS $[M+H]^+$for $C_{25}H_{33}F_2N_9O_4$ calcd 562.3, found 562.1.

Example 200: 2-[(S)-3-[3-(5-ethoxy-2-pyrazinyl)-1-methylureido]-4,4-difluoro-1-piperidyl]-4-pyrimidinyl (1R,3s,5S)-8-azabicyclo[3.2.1]octane-3-carbamate

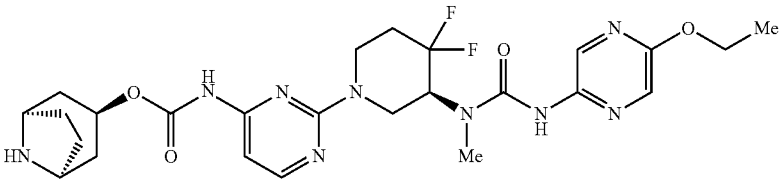 [SMILES: CCOc1cnc(NC(=O)N(C)[C@H]2CN(c3nccc(NC(=O)O[C@@H]4C[C@H]5CC[C@@H](C4)N5)n3)CCC2(F)F)cn1]

The title compound was synthesized in a similar fashion to Example 11 (step 1-8, part 1) using tert-butyl (1R,3S,5S)-3-hydroxy-8-azabicyclo[3.2.1]octane-8-carboxylate Step 5. $^1$H NMR (400 MHz, MeOD) δ 8.50 (d, J=1.4 Hz, 1H), 8.20 (d, J=5.7 Hz, 1H), 7.92 (d, J=1.5 Hz, 1H), 7.21 (d, J=5.7 Hz, 1H), 5.02 (tt, J=11.2, 6.0 Hz, 1H), 4.84-4.70 (m, 2H), 4.68-4.48 (m, 1H), 4.35 (q, J=7.0 Hz, 2H), 3.61-3.52 (m, 2H), 3.45 (t, J=12.2 Hz, 1H), 3.15 (d, J=2.0 Hz, 4H), 2.22-2.10 (m, 1H), 2.10-1.93 (m, 3H), 1.84 (h, J=4.6 Hz, 2H), 1.76 (q, J=6.6 Hz, 2H), 1.70-1.57 (m, 2H), 1.38 (t, J=7.0 Hz, 3H). ESI MS $[M+H]^+$ for $C_{25}H_{33}F_2N_9O_4$ calcd 562.3, found 562.1.

Example 201: 2-[(S)-3-[3-(5-ethoxy-2-pyrazinyl)-1-methylureido]-4,4-difluoro-1-piperidyl]-4-pyrimidinyl (1R,3S,5S)-8-methyl-8-azabicyclo[3.2.1]octane-3-carbamate

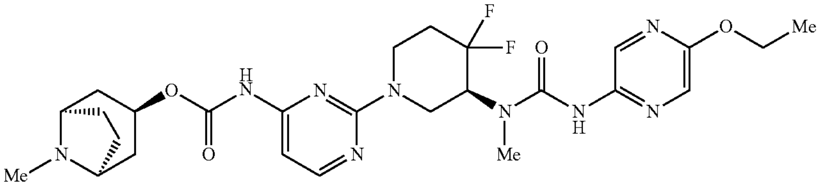 [SMILES: CCOc1cnc(NC(=O)N(C)[C@H]2CN(c3nccc(NC(=O)O[C@@H]4C[C@H]5CC[C@@H](C4)N5C)n3)CCC2(F)F)cn1]

The title compound was synthesized in a similar fashion to Example 11 using tert-butyl (1R,3S,5S)-3-hydroxy-8-azabicyclo[3.2.1]octane-8-carboxylate Step 5. $^1$H NMR (400 MHz, CDCl3) δ 8.75 (d, J=1.4 Hz, 1H), 8.18 (d, J=5.6 Hz, 1H), 7.85 (d, J=1.4 Hz, 1H), 7.32 (s, 1H), 7.19 (d, J=6.7 Hz, 1H), 4.96 (tt, J=10.8, 6.3 Hz, 1H), 4.85-4.73 (m, 1H), 4.65 (d, J=13.3 Hz, 1H), 4.29 (q, J=7.0 Hz, 2H), 3.24 (t, J=12.4 Hz, 1H), 3.17 (p, J=3.1 Hz, 2H), 3.09 (d, J=2.8 Hz, 3H), 3.05 (dd, J=13.5, 2.8 Hz, 1H), 2.28 (s, 3H), 2.18-2.06 (m, 1H), 2.01-1.91 (m, 2H), 1.90-1.77 (m, 3H), 1.74 (ddd, J=13.1, 11.1, 2.8 Hz, 2H), 1.62 (d, J=12.6 Hz, 3H), 1.32 (t, J=7.1 Hz, 3H). ESI MS $[M+H]^+$ for $C_{26}H_{35}F_2N_9O_4$ calcd 576.3, found 576.3.

Example 202: 2-[(S)-3-[3-(5-ethoxy-2-pyrazinyl)-1-methylureido]-4,4-difluoro-1-piperidyl]-4-pyrimidinyl (1R,4S)-4-(1-azetidinyl)cyclohexanecarbamate

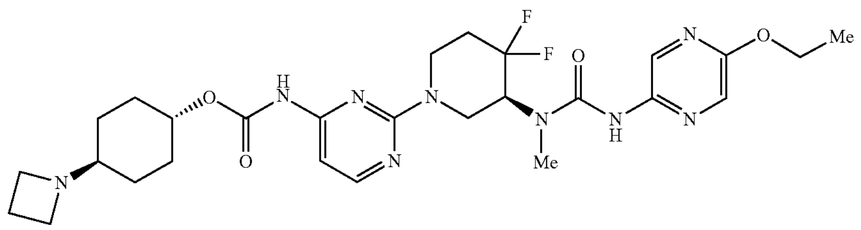 [SMILES: CCOc1cnc(NC(=O)N(C)[C@H]2CN(c3nccc(NC(=O)O[C@H]4CC[C@H](N5CCC5)CC4)n3)CCC2(F)F)cn1]

The title compound was synthesized in a similar fashion to Example 11 using trans-4-(azetidin-1-yl)cyclohexanol in Step 5. $^1$H NMR (400 MHz, $CDCl_3$) δ 8.75 (d, J=1.4 Hz, 1H), 8.19 (d, J=5.7 Hz, 1H), 7.80 (s, 1H), 7.33 (s, 1H), 7.21 (d, J=5.6 Hz, 1H), 4.86-4.75 (m, 1H), 4.65 (tt, J=10.5, 4.4 Hz, 2H), 4.30 (q, J=7.0 Hz, 3H), 3.25 (t, J=12.5 Hz, 1H), 3.17-3.00 (m, 7H), 2.22-2.09 (m, 1H), 1.96 (qt, J=14.0, 6.8 Hz, 6H), 1.80-1.67 (m, 2H), 1.33 (t, J=7.0 Hz, 5H), 1.12-0.97 (m, 3H). ESI MS $[M+H]^+$ for $C_{27}H_{37}F_2N_9O_4$ calcd 590.3, found 590.1.

Example 203: 2-[(S)-3-[3-(5-ethoxy-2-pyrazinyl)-1-methylureido]-4,4-difluoro-1-piperidyl]-4-pyrimidinyl (1R,5S,8s)-3-methyl-3-azabicyclo[3.2.1]octane-8-carbamate

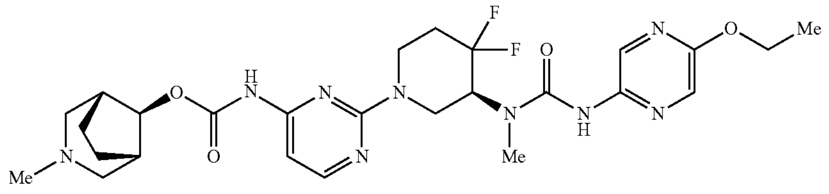 [SMILES: CCOc1cnc(NC(=O)N(C)[C@H]2CN(c3nccc(NC(=O)O[C@@H]4[C@@H]5CC[C@H]4CN(C)C5)n3)CCC2(F)F)cn1]

The title compound was synthesized in a similar fashion to Example 11 using exo-tert-butyl-8-hydroxy-3-azabicyclo [3.2.1]octane-3-carboxylate Step 5. $^1H$ NMR (400 MHz, $CDCl_3$) δ 8.76 (d, J=1.4 Hz, 1H), 8.19 (d, J=5.6 Hz, 1H), 7.83 (d, J=1.5 Hz, 1H), 7.27 (s, 1H), 7.18 (s, 1H), 4.79 (dd, J=12.4, 4.3 Hz, 1H), 4.75-4.58 (m, 2H), 4.42 (d, J=32.0 Hz, 1H), 4.29 (q, J=7.0 Hz, 2H), 3.24 (t, J=12.4 Hz, 1H), 3.09 (d, J=2.6 Hz, 3H), 3.05 (dd, J=13.4, 2.9 Hz, 1H), 2.66 (dd, J=11.3, 4.0 Hz, 2H), 2.24 (d, J=4.4 Hz, 2H), 2.18 (s, 3H), 2.13 (d, J=11.0 Hz, 3H), 2.01-1.79 (m, 1H), 1.70 (d, J=3.3 Hz, 4H), 1.32 (t, J=7.0 Hz, 3H). ESI MS $[M+H]^+$ for $C_{26}H_{35}F_2N_9O_4$ calcd 576.3, found 576.1.

Example 204: 2-[(S)-3-[3-(5-ethoxy-2-pyrazinyl)-1-methylureido]-4,4-difluoro-1-piperidyl]-4-pyrimidinyl (2R,7aS)-3a,6-diazaperhydro-2-indenecarbamate

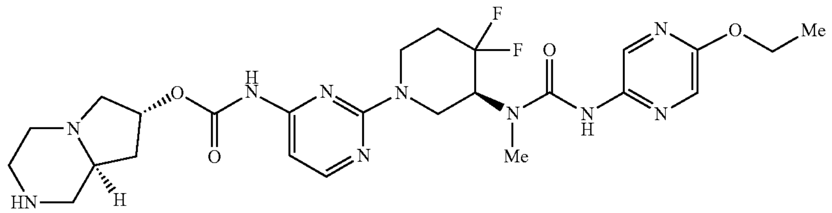 [SMILES: CCOc1cnc(NC(=O)N(C)[C@H]2CN(c3nccc(NC(=O)O[C@@H]4C[C@H]5CNCCN5C4)n3)CCC2(F)F)cn1]

The title compound was synthesized in a similar fashion to Example 11 (step 1-8, part 1) using tert-butyl (7R,8aS)-7-hydroxyoctahydropyrrolo[1,2-a]piperazine-2-carboxylate Step 5.

$^1H$ NMR (400 MHz, $CDCl_3$) δ 8.76 (d, J=1.5 Hz, 1H), 8.20 (d, J=5.6 Hz, 1H), 7.87 (s, 1H), 7.33 (s, 1H), 7.19 (s, 1H), 5.23-5.05 (m, 1H), 4.80 (d, J=13.9 Hz, 1H), 4.67 (dd, J=15.0, 10.3 Hz, 1H), 4.30 (q, J=7.0 Hz, 3H), 3.57 (dd, J=10.2, 6.9 Hz, 1H), 3.25 (t, J=12.4 Hz, 1H), 3.10 (d, J=2.9 Hz, 3H), 3.06 (d, J=12.1 Hz, 1H), 2.92 (ddd, J=14.5, 9.1, 3.3 Hz, 2H), 2.81-2.70 (m, 1H), 2.42 (dd, J=11.8, 10.0 Hz, 1H), 2.23 (tt, J=10.2, 4.3 Hz, 2H), 2.12 (dd, J=13.2, 6.6 Hz, 1H), 2.01-1.68 (m, 5H), 1.33 (t, J=7.0 Hz, 3H). ESI MS $[M+H]^+$ for $C_{25}H_{34}F_2N_{10}O_4$ calcd 577.3, found 577.2

Example 205: 2-[(S)-3-[3-(5-ethoxy-2-pyrazinyl)-1-methylureido]-4,4-difluoro-1-piperidyl]-4-pyrimidinyl (2R,7aS)-6-methyl-3a,6-diazaoctahydro-2-indenecarbamate

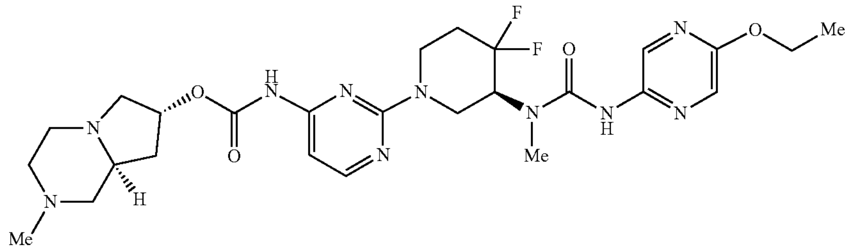 [SMILES: CCOc1cnc(NC(=O)N(C)[C@H]2CN(c3nccc(NC(=O)O[C@@H]4C[C@H]5CN(C)CCN5C4)n3)CCC2(F)F)cn1]

The title compound was synthesized in a similar fashion to Example 11 using tert-butyl (7R,8aS)-7-hydroxyoctahydropyrrolo[1,2-a]piperazine-2-carboxylate Step 5. $^1H$ NMR (400 MHz, CDCl3) δ 8.76 (d, J=1.4 Hz, 1H), 8.19 (d, J=5.6 Hz, 1H), 7.86 (d, J=1.5 Hz, 1H), 7.31 (s, 1H), 7.19 (s, 1H), 5.19 (tdd, J=7.0, 5.0, 2.0 Hz, 1H), 4.86-4.71 (m, 1H), 4.65 (d, J=13.2 Hz, 1H), 4.30 (q, J=7.0 Hz, 3H), 3.56 (dd, J=10.1, 6.9 Hz, 1H), 3.25 (t, J=12.4 Hz, 1H), 3.10 (d, J=2.8 Hz, 3H), 3.06 (dd, J=13.5, 2.8 Hz, 1H), 2.93-2.82 (m, 2H), 2.72 (dq, J=11.1, 2.5 Hz, 1H), 2.37 (dtd, J=18.7, 10.6, 2.8 Hz, 2H), 2.26 (s, 3H), 2.23-2.18 (m, 1H), 2.09 (td, J=11.3, 3.1 Hz, 2H), 1.87-1.68 (m, 3H), 1.61-1.57 (m, 1H), 1.33 (t, J=7.1 Hz, 3H). ESI MS $[M+H]^+$ for $C_{26}H_{36}F_2N_{10}O_4$ calcd 591.3, found 591.1.

Example 206: 2-[(S)-3-[3-(5-ethoxy-2-pyrazinyl)-1-methylureido]-4,4-difluoro-1-piperidyl]-4-pyrimidinyl (R)-1,3a-diaza-4,5,6,7-tetrahydro-6-indenecarbamate

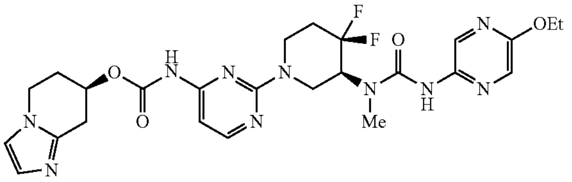

The title compound was synthesized in a similar fashion to Example 11 (step 1-7) using 5H,6H, 7H,8H-imidazo[1,2-a]pyridin-7-ol hydrobromide in Step 5. $^1$H NMR (400 MHz, $CDCl_3$) δ 8.73 (dd, J=3.6, 1.3 Hz, 1H), 8.19 (d, J=5.6 Hz, 1H), 7.78 (d, J=1.4 Hz, 1H), 7.68 (s, 1H), 7.23 (s, 1H), 7.14 (dd, J=5.7, 1.8 Hz, 1H), 6.98 (s, 1H), 6.80 (s, 1H), 5.34 (s, 1H), 4.88-4.64 (m, 2H), 4.45 (d, J=23.6 Hz, 1H), 4.28 (q, J=7.0 Hz, 2H), 4.10-3.88 (m, 2H), 3.23 (td, J=12.3, 3.8 Hz, 1H), 3.15 (s, 1H), 3.07 (d, J=2.3 Hz, 3H), 3.03 (dd, J=13.3, 2.9 Hz, 1H), 2.33-2.05 (m, 2H), 1.98 (s, 3H), 1.32 (t, J=7.1 Hz, 3H). ESI MS $[M+H]^+$ for $C_{25}H_{30}F_2N_{10}O_4$ calcd 573.2, found 573.2.

Example 207: 2-[(S)-4,4-difluoro-3-[3-(2-imidazolyl)-1-methylureido]-1-piperidyl]-4-pyrimidinyl 1-methyl-4-piperidinecarbamate

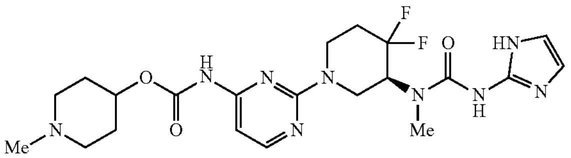 [SMILES: CN1CCC(OC(=O)Nc2ccnc(N3CCC(F)(F)[C@@H](N(C)C(=O)Nc4ncc[nH]4)C3)n2)CC1]

The title compound was synthesized in a similar fashion to Example 11 (step 1-7) using N-methyl-4-hydroxypiperidine in Step 5 and phenyl-1-(tetrahydro-2H-pyran-2-yl)-1H-imidazol-2-amine carbamate in step 7, which was prepared in a similar fashion to Example 1, Step 4. The THP group on the product after Step 7 was deprotected using HCl in methanol solution (2M, 3 mL), similar to as described in Example 11, Step 8-Par A. $^1$H NMR (400 MHz, $CDCl_3$) δ 11.82 (s, 1H), 9.83 (s, 1H), 8.28 (s, 1H), 8.17 (d, J=5.6 Hz, 1H), 7.36 (d, J=2.5 Hz, 1H), 7.22 (s, 1H), 6.62 (s, 1H), 5.29-4.99 (m, 1H), 4.78 (tt, J=9.4, 4.5 Hz, 1H), 4.65 (dd, J=13.7, 4.8 Hz, 1H), 4.40-4.21 (m, 1H), 3.61 (d, J=30.9 Hz, 1H), 3.43 (t, J=12.7 Hz, 1H), 3.24 (td, J=13.4, 2.6 Hz, 1H), 3.08 (d, J=3.7 Hz, 3H), 3.05 (d, J=2.5 Hz, 1H), 2.75 (s, 2H), 2.25 (s, 3H), 2.20-2.10 (m, 2H), 2.08-1.96 (m, 2H), 1.83-1.66 (m, 2H). ESI MS $[M+H]^+$ for $C_{21}H_{29}F_2N_9O_3$ calcd 494.2, found 494.1.

Example 208: 2-[(S)-3-[3-(5-ethoxy-2-pyrazinyl)-1-methylureido]-4,4-difluoro-1-piperidyl]-4-pyrimidinyl (2S,7aR)-3a,6-diazaperhydro-2-indenecarbamate

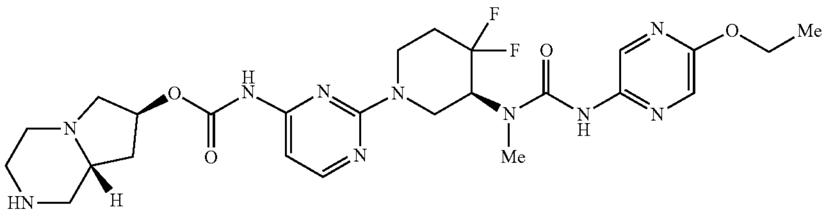 [SMILES: CCOc1cnc(NC(=O)N(C)[C@H]2CN(c3nccc(NC(=O)O[C@H]4C[C@@H]5CNCCN5C4)n3)CCC2(F)F)cn1]

The title compound was synthesized in a similar fashion to Example 11 (step 1-8, part 1) using tert-butyl (7S,8aR)-7-hydroxy-octahydropyrrolo[1,2-a]piperazine-2-carboxylate in Step 5. $^1$H NMR (400 MHz, $CDCl_3$) δ 8.76 (d, J=1.4 Hz, 1H), 8.20 (d, J=5.6 Hz, 1H), 7.93-7.76 (m, 1H), 7.33 (s, 1H), 7.19 (s, 1H), 5.16 (td, J=7.0, 4.9 Hz, 1H), 4.80 (d, J=13.9 Hz, 1H), 4.65 (d, J 12.6 Hz, 1H), 4.30 (q, J=7.0 Hz, 3H), 3.59 (dd, J=10.2, 6.9 Hz, 1H), 3.25 (t, J=12.4 Hz, 1H), 3.15 (d, J=11.9 Hz, 1H), 3.10 (d, J=2.8 Hz, 3H), 3.03 (d, J=9.8 Hz, 1H), 2.93 (d, J=11.3 Hz, 1H), 2.79 (td, J=11.9, 3.2 Hz, 1H), 2.51-2.41 (m, 1H), 2.37-2.07 (m, 6H), 1.89-1.71 (m, 2H), 1.33 (t, J=7.0 Hz, 3H). ESI MS $[M+H]^+$ for $C_{25}H_{34}F_2N_{10}O_4$ calcd 577.3, found 577.3.

Example 209: 2-[(S)-3-[3-(5-ethoxy-2-pyrazinyl)-1-methylureido]-4,4-difluoro-1-piperidyl]-4-pyrimidinyl (2S,7aR)-6-methyl-3a,6-diazaoctahydro-2-indenecarbamate

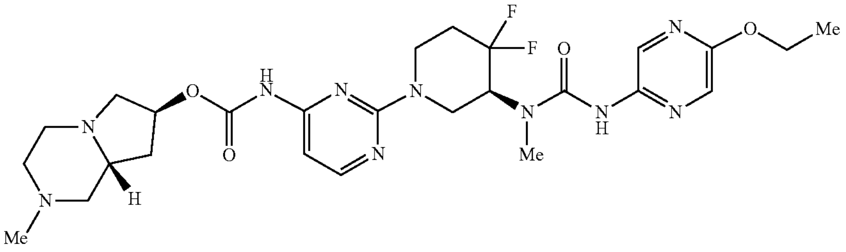 [SMILES: CCOc1cnc(NC(=O)N(C)[C@H]2CN(c3nccc(NC(=O)O[C@H]4C[C@@H]5CN(C)CCN5C4)n3)CCC2(F)F)cn1]

The title compound was synthesized in a similar fashion to Example 11 using tert-butyl (7S,8aR)-7-hydroxy-octahydropyrrolo[1,2-a]piperazine-2-carboxylate in Step 5. $^1$H NMR (400 MHz, $CDCl_3$) δ 8.75 (d, J=1.4 Hz, 1H), 8.18 (d, J=5.6 Hz, 1H), 7.85 (s, 1H), 7.31 (s, 1H), 7.19 (s, 1H), 5.17 (tdd, J=7.1, 5.0, 2.0 Hz, 1H), 4.78 (d, J=13.9 Hz, 1H), 4.64 (d, J=13.0 Hz, 1H), 4.29 (q, J=7.0 Hz, 2H), 3.57 (dd, J=10.2, 6.9 Hz, 1H), 3.23 (t, J=12.4 Hz, 1H), 3.09 (d, J=2.8 Hz, 3H), 3.05 (dd, J=13.3, 2.8 Hz, 1H), 2.87 (ddt, J=10.1, 7.4, 2.6 Hz, 2H), 2.71 (d, J=11.2 Hz, 1H), 2.42-2.30 (m, 2H), 2.25 (s, 3H), 2.21 (dd, J=10.1, 5.0 Hz, 1H), 2.15-2.05 (m, 2H), 1.79 (dddd, J=20.5, 14.8, 8.1, 4.2 Hz, 3H), 1.64 (s, 2H), 1.32 (t, J=7.0 Hz, 3H). ESI MS $[M+H]^+$for $C_{26}H_{36}F_2N_{10}O_4$ calcd 591.3, found 591.1.

Example 210: 2-[(S)-3-[3-(5-ethoxy-2-pyrazinyl)-1-methylureido]-4,4-difluoro-1-piperidyl]-4-pyrimidinyl (4aS,8aS)-perhydro-4a-isoquinolinecarbamate

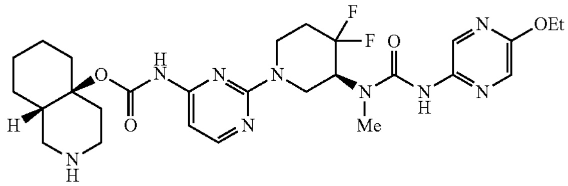 [SMILES: CCOc1cnc(NC(=O)N(C)[C@H]2CN(c3nccc(NC(=O)O[C@]45CCCC[C@H]4CNCC5)n3)CCC2(F)F)cn1]

The title compound was synthesized in a similar fashion to Example 11 (step 1-8, part 1) using tert-butyl (4aR,8aR)-4a-hydroxy-decahydroisoquinoline-2-carboxylate in Step 5. $^1$H NMR (400 MHz, $CDCl_3$) δ 8.75 (d, J=1.5 Hz, 1H), 8.16 (d, J=5.7 Hz, 1H), 7.80 (d, J=1.5 Hz, 1H), 7.44 (s, 1H), 7.22 (s, 1H), 7.13 (d, J=5.6 Hz, 1H), 4.74 (dd, J=25.4, 13.3 Hz, 2H), 4.47 (s, 1H), 4.27 (q, J=7.1 Hz, 2H), 3.23 (t, J=12.3 Hz, 1H), 3.08 (d, J=2.3 Hz, 3H), 3.06-2.94 (m, 2H), 2.83 (d, J=22.6 Hz, 2H), 2.68 (s, 1H), 2.21-2.07 (m, 3H), 1.95 (s, 5H), 1.57 (d, J=17.4 Hz, 5H), 1.31 (t, J=7.0 Hz, 3H). ESI MS $[M+H]^+$ for $C_{27}H_{37}F_2N_9O_4$ calcd 590.3, found 590.1.

Example 211: 2-[(S)-3-[3-(5-ethoxy-2-pyrazinyl)-1-methylureido]-4,4-difluoro-1-piperidyl]-4-pyrimidinyl (4aS,8aS)-2-methyldecahydro-4a-isoquinolinecarbamate

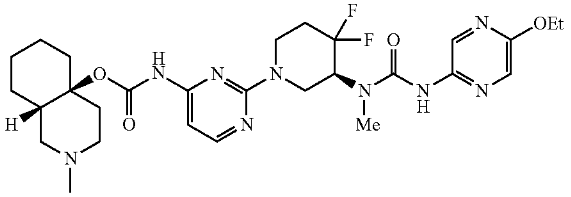 [SMILES: CCOc1cnc(NC(=O)N(C)[C@H]2CN(c3nccc(NC(=O)O[C@]45CCCC[C@H]4CN(C)CC5)n3)CCC2(F)F)cn1]

The title compound was synthesized in a similar fashion to Example 11 using tert-butyl (4aR,8aR)-4a-hydroxy-decahydroisoquinoline-2-carboxylate in Step 5. $^1$H NMR (400 MHz, $CDCl_3$) δ 8.83 (d, J=1.4 Hz, 1H), 8.24 (d, J=5.6 Hz, 1H), 7.88 (s, 1H), 7.48 (s, 1H), 7.29 (s, 1H), 7.23 (d, J=5.6 Hz, 1H), 4.93-4.72 (m, 2H), 4.71-4.47 (m, 1H), 4.36 (q, J=7.0 Hz, 2H), 3.31 (t, J=12.3 Hz, 1H), 3.16 (d, J=2.3 Hz, 3H), 3.11 (dd, J=13.3, 2.9 Hz, 1H), 2.60-2.29 (m, 6H), 2.23 (s, 3H), 2.19-1.91 (m, 5H), 1.72 (s, 3H), 1.64-1.62 (m, 2H), 1.39 (t, J=7.1 Hz, 3H). ESI MS $[M+H]^+$ for $C_{28}H_{39}F_2N_9O_4$ calcd 604.3, found 604.2.

Example 212: 2-[(S)-3-[3-(5-ethoxy-2-pyrazinyl)-1-methylureido]-4,4-difluoro-1-piperidyl]-4-pyrimidinyl (1R,6S)-2-azabicyclo[4.2.0]octane-5-carbamate

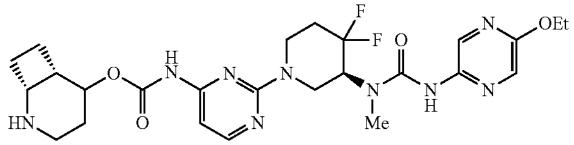 [SMILES: CCOc1cnc(NC(=O)N(C)[C@H]2CN(c3nccc(NC(=O)OC4CCN[C@@H]5CC[C@H]45)n3)CCC2(F)F)cn1]

The title compound was synthesized in a similar fashion to Example 11 (step 1-8, part 1) using tert-butyl (1R,6S)-5-hydroxy-2-azabicyclo[4.2.0]octane-2-carboxylate in Step 5. $^1$H NMR (400 MHz, $CDCl_3$) δ 8.74 (d, J=1.5 Hz, 1H), 8.18 (dd, J=5.7, 2.6 Hz, 1H), 7.83 (s, 1H), 7.29 (s, 1H), 7.18 (s, 1H), 4.88-4.72 (m, 1H), 4.66 (d, J=13.2 Hz, 1H), 4.31 (s, 1H), 4.28 (t, J=7.1 Hz, 2H), 3.51 (s, 1H), 3.23 (t, J=12.4 Hz, 1H), 3.08 (d, J=2.8 Hz, 3H), 3.07-2.99 (m, 1H), 2.90 (d, J=6.2 Hz, 1H), 2.70 (t, J=7.7 Hz, 1H), 2.54-2.38 (m, 1H), 2.35-2.23 (m, 1H), 2.19-2.00 (m, 3H), 2.00-1.69 (m, 4H), 1.55 (t, J=10.2 Hz, 1H), 1.31 (t, J=7.0 Hz, 3H). ESI MS $[M+H]^+$ for $C_{25}H_{33}F_2N_9O_4$ calcd 562.3, found 562.2.

Example 213: 2-[(S)-3-[3-(5-ethoxy-2-pyrazinyl)-1-methylureido]-4,4-difluoro-1-piperidyl]-4-pyrimidinyl (1R,6S)-2-methyl-2-azabicyclo[4.2.0]octane-5-carbamate

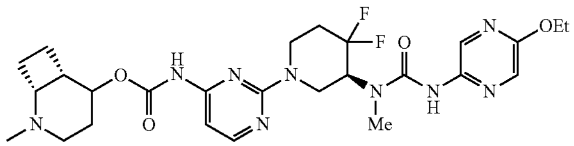 [SMILES: CCOc1cnc(NC(=O)N(C)[C@H]2CN(c3nccc(NC(=O)OC4CCN(C)[C@@H]5CC[C@H]45)n3)CCC2(F)F)cn1]

The title compound was synthesized in a similar fashion to Example 11 using tert-butyl (1R,6S)-5-hydroxy-2-azabicyclo[4.2.0]octane-2-carboxylate in Step 5. $^1$H NMR (400 MHz, $CDCl_3$) δ 8.82 (q, J=1.7 Hz, 1H), 8.26 (dd, J=5.7, 2.8 Hz, 1H), 7.94-7.89 (m, 1H), 7.36 (s, 1H), 7.26 (s, 1H), 4.88 (t, J=11.2 Hz, 1H), 4.80-4.71 (m, 2H), 4.47 (s, 1H), 4.36 (q, J=7.1 Hz, 2H), 3.33 (d, J=12.3 Hz, 1H), 3.16 (d, J=2.6 Hz, 3H), 3.12 (d, J=13.2 Hz, 1H), 2.84 (dq, J=11.2, 5.9 Hz, 1H), 2.74 (dt, J=9.9, 4.5 Hz, 2H), 2.59-2.44 (m, 1H), 2.35 (p, J=9.8 Hz, 1H), 2.26-2.21 (m, 2H), 2.22-2.06 (m, 1H), 2.04-1.86 (m, 3H), 1.80 (t, J=8.2 Hz, 1H), 1.70-1.55 (m, 3H), 1.39 (t, J=7.0 Hz, 3H). ESI MS $[M+H]^+$ for $C_{26}H_{35}F_2N_9O_4$ calcd 576.3, found 576.3.

Example 214: 2-[(3S,4R)-3-[3-(5-ethoxy-2-pyrazinyl)-1-methylureido]-4-fluoro-1-piperidyl]-4-pyrimidinyl (3R,4R)-1-methyl-3-methyl-4-piperidinecarbamate

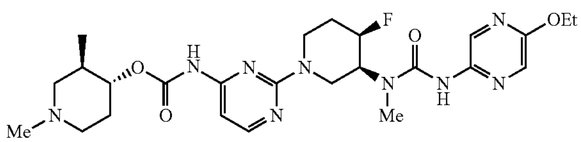 [SMILES: CCOc1cnc(NC(=O)N(C)[C@H]2CN(c3nccc(NC(=O)O[C@@H]4CCN(C)C[C@H]4C)n3)CC[C@H]2F)cn1]

The title compound was synthesized in a similar fashion to Example 18 using 1,1-dimethylethyl (3R,4R)-4-hydroxy-3-methyl-1-piperidinecarboxylate in Step 7. $^1$H NMR (400 MHz, $CDCl_3$) δ 8.75 (d, J=1.5 Hz, 1H), 8.20 (d, J=5.6 Hz, 1H), 7.88 (s, 1H), 7.56 (s, 1H), 7.17 (d, J=5.6 Hz, 1H), 5.20-4.90 (m, 1H), 4.60 (d, J=12.8 Hz, 1H), 4.4 (m, J=12.4 Hz, 1H), 4.30z (q, J=7.0 Hz, 2H), 3.99 (d, J=32.1 Hz, 1H), 3.44 (t, J=12.5 Hz, 1H), 3.19 (td, J=13.6, 2.7 Hz, 1H), 2.95 (m, 4H), 2.81 (dt, J=11.9, 6.5 Hz, 2H), 2.24 (s, 3H), 2.05 (m, 4H), 1.88-1.62 (m, 3H), 1.32 (t, J=7.0 Hz, 3H), 0.90 (dd, J=6.5, 2.3 Hz, 3H). ESI MS $[M+H]^+$ for $C_{25}H_{36}FN_9O_4$, calcd 546.3, found 546.1.

Example 215: 2-[(3S,4R)-3-[3-(5-ethoxy-2-pyrazinyl)-1-methylureido]-4-fluoro-1-piperidyl]-4-pyrimidinyl (3S,4S)-1-methyl-3-methyl-4-piperidinecarbamate

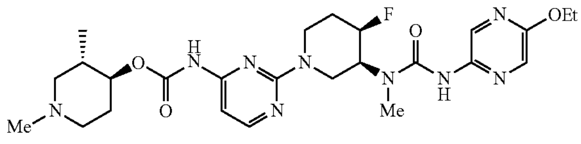 [SMILES: CCOc1cnc(NC(=O)N(C)[C@H]2CN(c3nccc(NC(=O)O[C@H]4CCN(C)C[C@@H]4C)n3)CC[C@H]2F)cn1]

The title compound was synthesized in a similar fashion to Example 18 using 1,1-dimethylethyl (3S,4S)-4-hydroxy-3-methyl-1-piperidinecarboxylate in Step 7. $^1$H NMR (400 MHz, $CDCl_3$) δ 8.75 (d, J=1.5 Hz, 1H), 8.20 (d, J=5.6 Hz, 1H), 7.88 (s, 1H), 7.56 (s, 1H), 7.17 (d, J=5.6 Hz, 1H), 5.20-4.90 (m, 1H), 4.60 (d, J=12.8 Hz, 1H), 4.46 (d, J=12.4 Hz, 1H), 4.30 (q, J=7.0 Hz, 2H), 3.99 (d, J=32.1 Hz, 1H), 3.44 (t, J=12.5 Hz, 1H), 3.19 (td, J=13.6, 2.7 Hz, 1H), 3.09 (d, J=2.9 Hz, 4H), 2.81 (dt, J=11.9, 6.5 Hz, 2H), 2.24 (s, 3H), 2.05 (m, 4H), 1.88-1.62 (m, 3H), 1.32 (t, J=7.0 Hz, 3H), 0.90 (dd, J=6.5, 2.3 Hz, 3H). ESI MS $[M+H]^+$ for $C_{25}H_{36}FN_9O_4$, calcd 546.3, found 546.1.

Example 216: 2-[(3S,4R)-4-fluoro-3-[3-(5-fluoro-2-pyridyl)-1-methylureido]-1-piperidyl]-4-pyrimidinyl 1-methyl-4-piperidinecarbamate

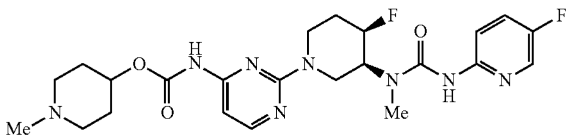 [SMILES: CN1CCC(OC(=O)Nc2ccnc(N3CC[C@@H](F)[C@@H](N(C)C(=O)Nc4ccc(F)cn4)C3)n2)CC1]

The title compound was synthesized in a similar fashion to Example 6, using phenyl N-(5-fluoro-2-pyridinyl)carbamate in Step 5, which was prepared in a similar fashion to Example 1 Step 4. $^1$H NMR (400 MHz, $CDCl_3$) δ 8.28-8.25 (m, 2H), 8.05 (dd, J=9.2, 4.2 Hz, 1H), 7.94 (s, 1H), 7.42 (ddd, J=9.7, 7.6, 3.0 Hz, 1H), 7.28 (s, 1H), 5.16 (d, J=50.5 Hz, 1H), 4.81 (tt, J=9.1, 4.2 Hz, 1H), 4.69 (dd, J=14.4, 4.7 Hz, 1H), 4.56-4.44 (m, 1H), 3.99 (d, J=31.1 Hz, 1H), 3.52 (t, J=12.5 Hz, 1H), 3.28 (t, J=13.1 Hz, 1H), 3.16 (d, J=3.2 Hz, 3H), 2.70 (s, 2H), 2.29 (s, 3H), 2.27-2.18 (m, 2H), 2.13-1.94 (m, 3H), 1.92-1.70 (m, 3H). ESI MS $[M+H]^+$ for $C_{23}H_{30}F_2N_8O_3$, calcd 505.2, found 505.2.

Example 217: 2-[(3S,4R)-3-[3-(5-ethoxy-2-pyrazinyl)-1-methylureido]-4-fluoro-1-piperidyl]-4-pyrimidinyl (7R,8aR)-perhydro-7-indolizinecarbamate

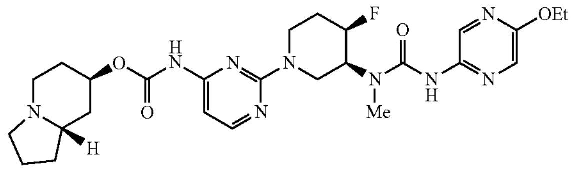 [SMILES: CCOc1cnc(NC(=O)N(C)[C@H]2CN(c3nccc(NC(=O)O[C@@H]4CCN5CCC[C@H]5C4)n3)CC[C@H]2F)cn1]

The title compound was synthesized in a similar fashion to Example 18 (step 1-9) using (7R,8aR)-octahydro-7-indolizinolin in Step 7. $^1$H NMR (400 MHz, $CDCl_3$) δ 8.82 (d, J=1.4 Hz, 1H), 8.27 (d, J=5.6 Hz, 1H), 7.98 (s, 1H), 7.69 (s, 1H), 7.26 (s, 1H), 5.16 (d, J=50.6 Hz, 1H), 4.78 (td, J=11.1, 5.6 Hz, 1H), 4.68 (d, J=12.8 Hz, 1H), 4.50 (d, J=13.1 Hz, 1H), 4.41-4.28 (m, 2H), 3.96 (s, 1H), 3.51 (t, J=12.5 Hz, 1H), 3.27 (t, J=13.1 Hz, 1H), 3.16 (d, J=3.1 Hz, 4H), 3.06 (t, J=8.5 Hz, 1H), 2.28 (d, J=11.5 Hz, 1H), 2.13 (dd, J=21.8, 11.4 Hz, 4H), 1.97 (s, 1H), 1.92-1.80 (m, 3H), 1.81-1.65 (m, 3H), 1.47 (dd, J=20.2, 9.8 Hz, 1H), 1.39 (t, J=7.0 Hz, 3H). ESI MS $[M+H]^+$ for $C_{26}H_{36}FN_9O_4$, calcd 558.3, found 558.2

Example 218: 2-[(3S,4R)-3-[3-(5-ethoxy-2-pyrazinyl)-1-methylureido]-4-fluoro-1-piperidyl]-4-pyrimidinyl (7S,8aS)-perhydro-7-indolizinecarbamate

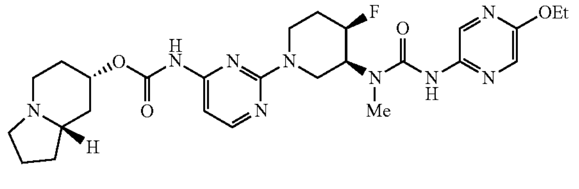 [SMILES: CCOc1cnc(NC(=O)N(C)[C@H]2CN(c3nccc(NC(=O)O[C@H]4CCN5CCC[C@H]5C4)n3)CC[C@H]2F)cn1]

The title compound was synthesized in a similar fashion to Example 18 (step 1-9) using (7S,8aS)-octahydro-7-indolizinol in Step 7. $^1$H NMR (400 MHz, $CDCl_3$) δ 8.82 (d, J=1.4 Hz, 1H), 8.27 (d, J=5.6 Hz, 1H), 7.98 (s, 1H), 7.69 (s, 1H), 7.26 (s, 1H), 5.16 (d, J=50.6 Hz, 1H), 4.78 (td, J=11.1, 5.6 Hz, 1H), 4.68 (d, J=12.8 Hz, 1H), 4.50 (d, J=13.1 Hz, 1H), 4.41-4.28 (m, 2H), 3.96 (s, 1H), 3.51 (t, J=12.5 Hz, 1H), 3.27 (t, J=13.1 Hz, 1H), 3.16 (d, J=3.1 Hz, 4H), 3.06 (t, J=8.5 Hz, 1H), 2.28 (d, J=11.5 Hz, 1H), 2.13 (dd, J=21.8, 11.4 Hz, 4H), 1.97 (s, 1H), 1.92-1.80 (m, 3H), 1.81-1.65 (m, 3H), 1.47 (dd, J=20.2, 9.8 Hz, 1H), 1.39 (t, J=7.0 Hz, 3H). ESI MS $[M+H]^+$ for $C_{26}H_{36}FN_9O_4$, calcd 558.3, found 558.1.

Example 219: 2-[(3S,4R)-4-fluoro-3-{3-[5-(methoxymethyl)-2-pyridyl]-1-methylureido}-1-piperidyl]-4-pyrimidinyl 1-methyl-4-piperidinecarbamate

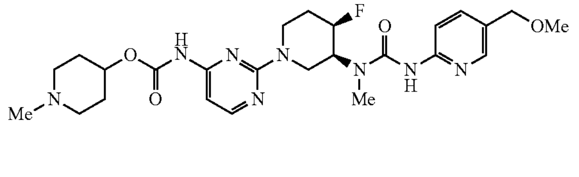 [SMILES: COCc1ccc(NC(=O)N(C)[C@H]2CN(c3nccc(NC(=O)OC4CCN(C)CC4)n3)CC[C@H]2F)nc1]

The title compound was synthesized in a similar fashion to Example 6, using phenyl 5-(methoxymethyl)-2-pyridinamine carbamate in Step 5, which was prepared in a similar fashion to Example 1 Step 4. $^1$H NMR (400 MHz, $CDCl_3$) δ 8.36 (s, 1H), 8.27 (d, J=5.6 Hz, 1H), 8.04 (d, J=8.6 Hz, 1H), 7.95 (s, 1H), 7.66 (dd, J=8.6, 2.4 Hz, 1H), 7.28 (s, 1H), 5.26-5.06 (m, 1H), 4.81 (tt, J=9.0, 4.2 Hz, 1H), 4.69 (dd, J=14.5, 4.8 Hz, 1H), 4.51 (d, J=12.9 Hz, 1H), 4.41 (s, 2H), 4.02 (d, J=31.5 Hz, 1H), 3.51 (t, J=12.5 Hz, 1H), 3.38 (s, 3H), 3.34-3.22 (m, 1H), 3.16 (d, J=3.1 Hz, 3H), 2.70 (d, J=11.5 Hz, 2H), 2.28 (s, 3H), 2.22 (t, J=10.3 Hz, 2H), 2.13-1.98 (m, 3H), 1.80 (s, 3H). ESI MS $[M+H]^+$ for $C_{25}H_{35}FN_8O_4$, calcd 531.3, found 531.1.

Example 220: 2-[(3S,4R)-4-fluoro-3-[1-methyl-3-(5-methyl-2-pyrazinyl)ureido]-1-piperidyl]-4-pyrimidinyl 1-methyl-4-piperidinecarbamate

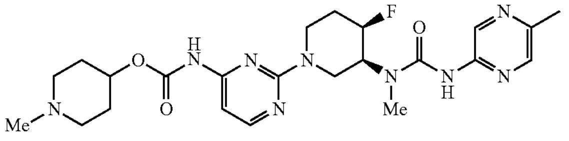 [SMILES: Cc1cnc(NC(=O)N(C)[C@H]2CN(c3nccc(NC(=O)OC4CCN(C)CC4)n3)CC[C@H]2F)cn1]

The title compound was synthesized in a similar fashion to Example 6, using phenyl N-(5-methyl-2-pyrazinyl)carbamate in Step 5, which was prepared in a similar fashion to Example 1 Step 4. $^1$H NMR (400 MHz, $CDCl_3$) δ 9.27 (d, J=1.5 Hz, 1H), 8.28 (d, J=5.6 Hz, 1H), 8.20 (s, 1H), 7.87 (s, 1H), 7.28 (s, 1H), 5.17 (d, J=50.5 Hz, 1H), 4.81 (tt, J=9.0, 4.2 Hz, 1H), 4.76-4.65 (m, 1H), 4.50 (d, J=13.1 Hz, 1H), 3.99 (s, 1H), 3.53 (t, J=12.5 Hz, 1H), 3.28 (t, J=13.2 Hz, 1H), 3.18 (d, J=3.0 Hz, 3H), 2.72 (d, J=11.5 Hz, 2H), 2.52 (s, 3H), 2.29 (s, 3H), 2.23 (t, J=10.4 Hz, 2H), 2.07 (dd, J=35.0, 9.8 Hz, 3H), 1.82 (dddt, J=23.3, 13.7, 10.5, 4.7 Hz, 3H). ESI MS $[M+H]^+$ for $C_{23}H_{32}FN_9O_3$, calcd 502.3, found 502.3.

Example 221: 2-[(3S,4R)-4-fluoro-3-[1-methyl-3-(1,3-thiazol-2-yl)ureido]-1-piperidyl]-4-pyrimidinyl (3S,4S)-3-methyl-4-piperidinecarbamate

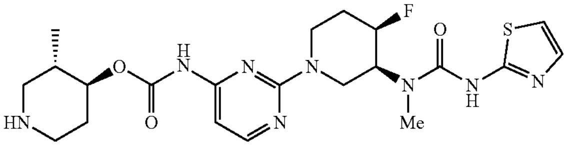 [SMILES: C[C@H]1CNCC[C@@H]1OC(=O)Nc1ccnc(N2CC[C@@H](F)[C@@H](N(C)C(=O)Nc3nccs3)C2)n1]

The title compound was synthesized in a similar fashion to Example 18 (step 1-10, part 1) using (3S,4S)-1-boc-4-hydroxy-3-methylpiperidine in in Step 7 and phenyl N-(1,3-thiazol-2-yl)carbamate in step 9, which was prepared in a similar fashion to Example 1 Step 4. $^1$H NMR (400 MHz, DMSO) δ 10.25 (s, 1H), 8.25 (d, J=5.6 Hz, 1H), 7.33 (d, J=3.8 Hz, 1H), 7.06 (d, J=5.6 Hz, 1H), 7.00 (d, J=3.8 Hz, 1H), 5.04 (d, J=51.3 Hz, 1H), 4.57 (dd, J=12.8, 4.6 Hz, 2H), 4.43 (td, J=10.2, 4.3 Hz, 1H), 4.36-4.17 (m, 1H), 3.69-3.37 (m, 3H), 3.11-3.05 (m, 1H), 3.03 (s, 3H), 3.00 (s, 1H), 2.65 (dd, J=13.3, 10.6 Hz, 1H), 2.38 (t, J=11.8 Hz, 1H), 1.98 (t, J=13.1 Hz, 1H), 1.86-1.60 (m, 2H), 1.46 (qd, J=11.9, 4.2 Hz, 1H), 0.87 (d, J=6.6 Hz, 3H). ESI MS $[M+H]^+$ for $C_{21}H_{29}FN_8O_3S$, calcd 493.2, found 493.2.

Example 222: 2-[(3S,4R)-4-fluoro-3-[1-methyl-3-(1,3-thiazol-2-yl)ureido]-1-piperidyl]-4-pyrimidinyl (3R,4R)-1-methyl-3-methyl-4-piperidinecarbamate

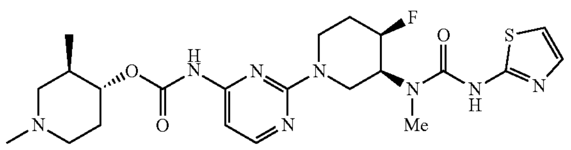 [SMILES: C[C@@H]1CN(C)CC[C@H]1OC(=O)Nc1ccnc(N2CC[C@@H](F)[C@@H](N(C)C(=O)Nc3nccs3)C2)n1]

The title compound was synthesized in a similar fashion to Example 18 using tert-butyl (3R,4R)-4-hydroxy-3-methyl-piperidine-1-carboxylate in in Step 7 and phenyl N-(1,3-thiazol-2-yl)carbamate in step 9, which was prepared in a similar fashion to Example 1 Step 4. $^1$H NMR (400 MHz, DMSO) δ 10.89 (s, 1H), 10.25 (s, 1H), 8.24 (d, J=5.6 Hz, 1H), 7.33 (d, J=3.9 Hz, 1H), 7.06 (d, J=5.6 Hz, 1H), 6.99 (d, J=3.8 Hz, 1H), 5.04 (d, J=51.2 Hz, 1H), 4.64-4.48 (m, 2H), 4.38-4.10 (m, 2H), 3.45 (t, J=12.1 Hz, 1H), 3.12-3.05 (m, 2H), 3.02 (s, 3H), 2.72 (d, J=8.7 Hz, 2H), 2.14 (s, 3H), 2.06-1.83 (m, 3H), 1.73 (q, J=12.0 Hz, 2H), 1.63-1.42 (m, 1H), 0.85 (d, J=5.8 Hz, 3H). ESI MS $[M+H]^+$ for $C_{22}H_{31}FN_8O_3S$, calcd 507.2, found 507.3.

Example 223: 2-[(3S,4R)-3-[3-(5-ethoxy-2-pyrazinyl)-1-methylureido]-4-fluoro-1-piperidyl]-4-pyrimidinyl (3S,4R)-3-methyl-4-piperidinecarbamate

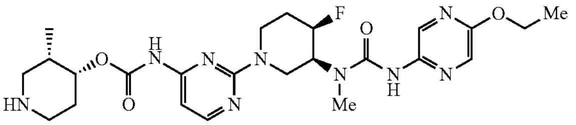 [SMILES: CCOc1cnc(NC(=O)N(C)[C@H]2CN(c3nccc(NC(=O)O[C@@H]4CCNC[C@@H]4C)n3)CC[C@H]2F)cn1]

The title compound was synthesized in a similar fashion to Example 18 (step 1-10, part 1) using 1,1-dimethylethyl (3S,4R)-4-hydroxy-3-methyl-1-piperidinecarboxylate in Step 7. $^1$H NMR (400 MHz, MeOD) δ 8.49 (d, J=4.0 Hz, 1H), 8.19 (d, J=6.1 Hz, 1H), 7.93 (d, J=3.9 Hz, 1H), 7.20 (d, J=6.3 Hz, 1H), 5.13 (s, 1H), 4.99 (s, 1H), 4.73-4.56 (m, 2H), 4.33 (q, J=7.1 Hz, 2H), 4.23 (d, J=11.4 Hz, 1H), 3.54 (t, J=12.0 Hz, 1H), 3.21 (d, J=13.5 Hz, 1H), 3.14 (d, J=3.7 Hz, 3H), 2.85 (d, J=11.8 Hz, 1H), 2.81-2.64 (m, 3H), 2.03 (d, J=12.6 Hz, 1H), 1.87 (d, J=14.1 Hz, 3H), 1.73 (s, 1H), 1.38 (q, J=6.6 Hz, 3H), 0.91 (d, J=6.5 Hz, 3H). ESI MS $[M+H]^+$ for $C_{24}H_{34}FN_9O_4$, calcd 532.3, found 532.2.

Example 224: 2-[(3S,4R)-4-fluoro-3-[3-(5-fluoro-1,3-thiazol-2-yl)-1-methylureido]-1-piperidyl]-4-pyrimidinyl (3S,4R)-3-methyl-4-piperidinecarbamate

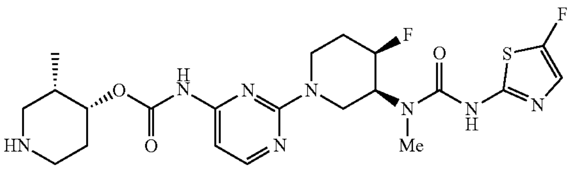 [SMILES: C[C@H]1CNCC[C@H]1OC(=O)Nc1ccnc(N2CC[C@@H](F)[C@@H](N(C)C(=O)Nc3ncc(F)s3)C2)n1]

The title compound was synthesized in a similar fashion to Example 18 (step 1-10, part 1) using 1,1-dimethylethyl (3S,4R)-4-hydroxy-3-methyl-1-piperidinecarboxylate in in Step 7 and phenyl N-(5-fluoro-2-thiazolyl)carbamate in step 9, which was prepared in a similar fashion to Example 1 Step 4. $^1$H NMR (400 MHz, MeOD) δ 8.23 (d, J=5.7 Hz, 1H), 7.21 (d, J=5.7 Hz, 1H), 6.95 (d, J=2.0 Hz, 1H), 5.11 (s, 1H), 5.00 (dd, J=5.3, 2.8 Hz, 2H), 4.69-4.53 (m, 2H), 4.28 (ddd, J=32.2, 11.9, 4.1 Hz, 1H), 3.53 (t, J=12.2 Hz, 1H), 3.19 (td, J=13.2, 2.9 Hz, 1H), 3.10 (d, J=1.8 Hz, 3H), 2.89 (td, J=12.2, 3.2 Hz, 1H), 2.84-2.64 (m, 3H), 2.03 (t, J=12.7 Hz, 1H), 1.98-1.84 (m, 2H), 1.76 (tdd, J=13.9, 10.8, 5.1 Hz, 1H), 0.91 (d, J=6.9 Hz, 3H). ESI MS $[M+H]^+$ for $C_{21}H_{28}F_2N_8O_3S$ calcd 511.2, found 511.1.

Example 225: 2-[(3S,4R)-4-fluoro-3-[3-(5-fluoro-1,3-thiazol-2-yl)-1-methylureido]-1-piperidyl]-4-pyrimidinyl (3S,4R)-1-methyl-3-methyl-4-piperidinecarbamate

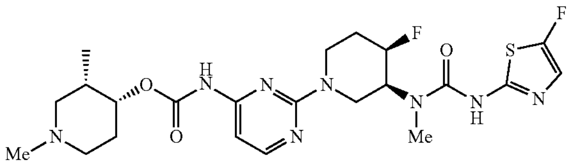 [SMILES: C[C@H]1CN(C)CC[C@H]1OC(=O)Nc1ccnc(N2CC[C@@H](F)[C@@H](N(C)C(=O)Nc3ncc(F)s3)C2)n1]

The title compound was synthesized in a similar fashion to Example 18 using 1,1-dimethylethyl (3S,4R)-4-hydroxy-3-methyl-1-piperidinecarboxylate in in Step 7 phenyl N-(5-fluoro-2-thiazolyl)carbamate in step 9, which was prepared in a similar fashion to Example 1 Step 4. $^1$H NMR (400 MHz, $CDCl_3$) δ 8.28 (s, 1H), 7.31 (d, J=5.7 Hz, 1H), 7.04 (s, 1H), 5.15 (d, J=50.1 Hz, 1H), 4.96 (d, J=5.0 Hz, 1H), 4.64 (d, J=13.7 Hz, 1H), 4.30 (d, J=13.0 Hz, 1H), 3.65 (s, 1H), 3.47 (t, J=12.6 Hz, 1H), 3.27 (t, J=13.0 Hz, 1H), 3.11 (d, J=3.4 Hz, 3H), 2.45 (s, 3H), 2.27 (s, 3H), 2.05-2.0' (m, 1H), 1.99-1.81 (m, 2H), 1.76-1.71 (m, 2H), 0.87 (d, J=6.9 Hz, 3H). ESI MS $[M+H]^+$ for $C_{22}H_{30}F_2N_8O_3S$ calcd 525.2, found 525.1.

Example 226: 2-[(3S,4R)-4-fluoro-3-{3-[5-(methoxymethyl)-1,3-thiazol-2-yl]-1-methylureido}-1-piperidyl]-4-pyrimidinyl (3S,4R)-1-methyl-3-methyl-4-piperidinecarbamate

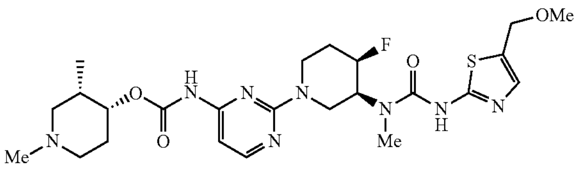 [SMILES: COCc1cnc(NC(=O)N(C)[C@H]2CN(c3nccc(NC(=O)O[C@@H]4CCN(C)C[C@@H]4C)n3)CC[C@H]2F)s1]

The title compound was synthesized in a similar fashion to Example 18 using 1,1-dimethylethyl (3S,4R)-4-hydroxy-3-methyl-1-piperidinecarboxylate in in Step 7 and phenyl 5-(methoxymethyl)-1,3-thiazol-2-amin) carbamate in step 9, which was prepared in a similar fashion to Example 1 Step 4. $^1$H NMR (400 MHz, $CDCl_3$) δ 12.00 (s, 1H), 9.74 (s, 1H), 8.26 (s, 1H), 7.38 (s, 1H), 7.33 (d, J=5.4 Hz, 1H), 5.17 (d, J=50.1 Hz, 1H), 4.67 (d, J=10.2 Hz, 1H), 4.50 (s, 2H), 4.33 (d, J=13.2 Hz, 1H), 3.67 (s, 1H), 3.46 (t, J=12.6 Hz, 1H), 3.28 (s, 3H), 3.27-3.24 (m, 1H), 3.13 (d, J=3.5 Hz, 3H), 2.57-2.31 (m, 2H), 2.22 (s, 3H), 2.21-2.05 (m, 1H), 2.03 (d, J=10.9 Hz, 2H), 1.99-1.61 (m, 4H), 1.18 (s, 1H), 0.86 (d, J=6.8 Hz, 3H). ESI MS $[M+H]^+$ for $C_{24}H_{35}FN_8O_4S$ calcd 551.2, found 551.3.

Example 227: 2-[(3S,4R)-3-[3-(5-ethoxy-2-pyrazinyl)-1-methylureido]-4-fluoro-1-piperidyl]-4-pyrimidinyl (3S,4R)-3-methyl-1-(tetrahydro-4H-pyran-4-yl)-4-piperidinecarbamate

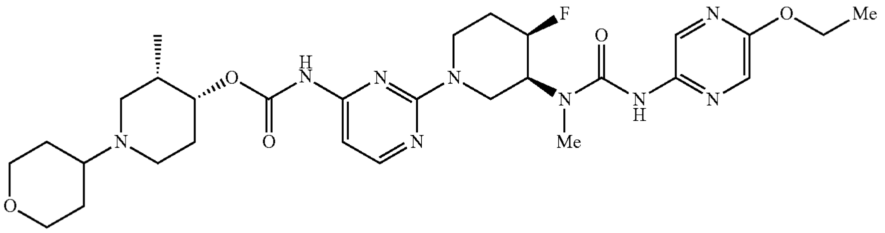 [SMILES: CCOc1cnc(NC(=O)N(C)[C@H]2CN(c3nccc(NC(=O)O[C@@H]4CCN(C5CCOCC5)C[C@@H]4C)n3)CC[C@H]2F)cn1]

The title compound was synthesized in a similar fashion to Example 18 using 1,1-dimethylethyl (3S,4R)-4-hydroxy-3-methyl-1-piperidinecarboxylate in Step 7 and tetrahydro-4H-pyran-4-one instead of paraformaldehyde in step 10, part 2. $^1H$ NMR (400 MHz, $CDCl_3$) δ 8.76 (d, J=1.5 Hz, 1H), 8.20 (d, J=5.6 Hz, 1H), 7.88 (s, 1H), 7.44 (d, J=46.8 Hz, 1H), 7.16 (d, J=5.6 Hz, 1H), 5.07 (d, J=50.7 Hz, 1H), 4.91 (q, J=3.6 Hz, 1H), 4.56 (ddd, J=33.9, 13.4, 4.7 Hz, 2H), 4.29 (q, J=7.0 Hz, 2H), 4.12 (d, J=32.4 Hz, 1H), 4.03-3.86 (m, 2H), 3.41 (t, J=12.3 Hz, 1H), 3.31 (tt, J=11.8, 1.9 Hz, 2H), 3.17 (td, J=13.3, 2.7 Hz, 1H), 3.09 (d, J=2.5 Hz, 3H), 2.57 (s, 2H), 2.41 (s, 2H), 2.23 (s, 1H), 2.08-1.88 (m, 2H), 1.88-1.73 (m, 1H), 1.68 (d, J=14.3 Hz, 2H), 1.54 (s, 4H), 1.33 (t, J=7.1 Hz, 3H), 0.86 (d, J=6.9 Hz, 3H). ESI MS $[M+H]^+$ for $C_{29}H_{42}FN_9O_5$ calcd 616.3, found 616.2.

Example 228: 2-[(R)-3-[3-(5-ethoxy-2-pyridyl)-1-methylureido]-1-piperidyl]-4-pyridyl methanecarbamate

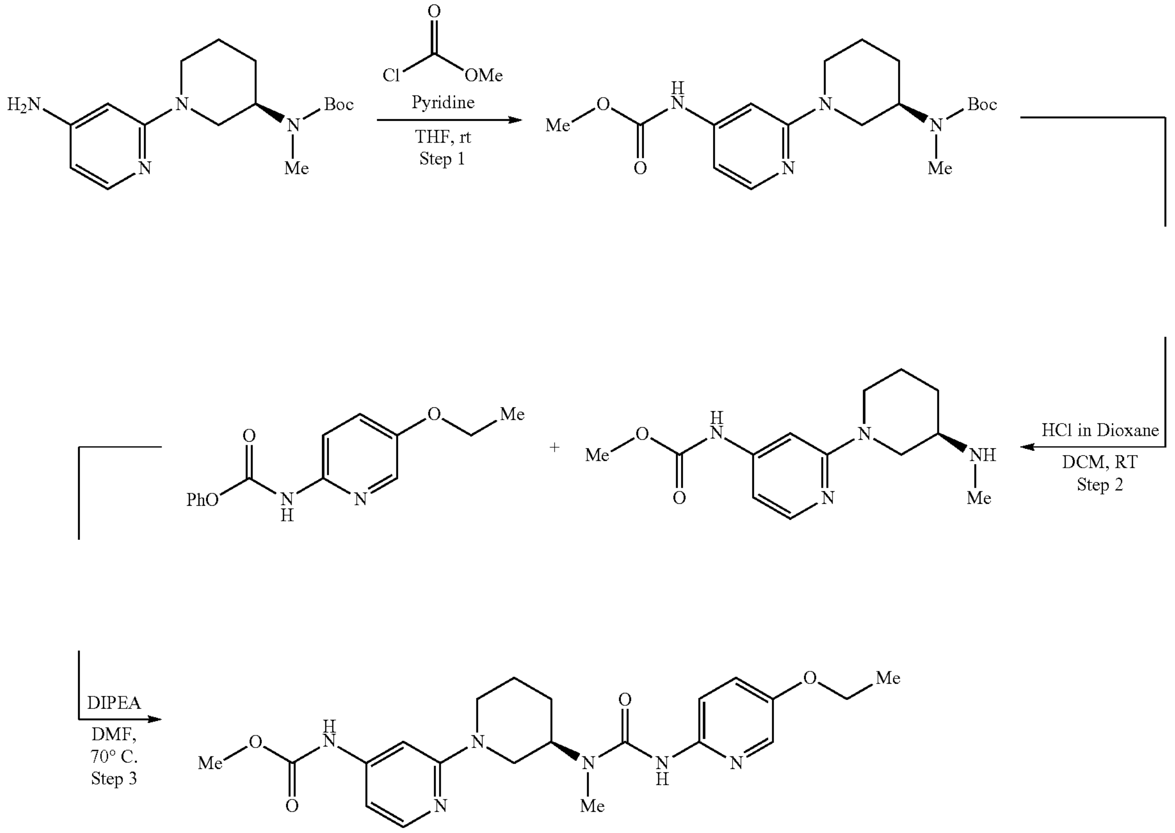

Step 1: 4-amino pyridine substituted tert-butyl N-methyl-N-[(3R)-piperidin-3-yl]carbamate intermediate (100 mg, 0.32 mmol) was taken in a dry reaction vial equipped with a screw cap and stir bar and to this dry THF (1 mL) was added. This reaction mixture was cooled to 0° C. under constant stirring followed by the addition of pyridine (53 μL, 0.65 mmol). After stirring for half an hour at this temperature, methyl chloroformate (38 μL, 0.49 mmol) was added dropwise and slowly brought the reaction temperature to room temperature and stirred overnight. After confirming the completion of the reaction by LCMS, reaction was stopped and diluted the reaction mixture with DCM. The organic layer was washed with 0.5 N HCl followed by a saturated aqueous solution of $NaHCO_3$. The combined organic layers were dried over anhydrous sodium sulfate and concentrated. Crude product was purified by column chromatography to afford the intermediate.

Step 2: The intermediate from Step 1 was then subjected to Boc removal in a similar fashion to Step 3 (Part 2) of the protocol for the synthesis of Example 1. The HCl salt obtained in this step was directly used in the next step.

Step 3: This transformation was performed in a similar fashion to Step 5 of the protocol for the synthesis of Example 1 using 2-amino-5-ethoxy-pyridine phenyl carbamate. The crude product was then purified using reversed phase preparative HPLC to afford the title compound. $^1$H NMR (400 MHz, $CDCl_3$) δ 8.33 (d, J=5.8 Hz, 1H), 7.98 (d, J=3.0 Hz, 1H), 7.92 (d, J=9.1 Hz, 1H), 7.38 (s, 1H), 7.20 (dd, J=9.1, 3.0 Hz, 1H), 7.01 (s, 1H), 6.59 (dd, J=5.8, 2.0 Hz, 1H), 4.35 (d, J=12.8 Hz, 1H), 4.03 (q, J=7.0 Hz, 4H), 3.74 (s, 3H), 3.01-2.83 (m, 5H), 1.98 (d, J=12.4 Hz, 1H), 1.91-1.69 (m, 2H), 1.58 (dtd, J=16.7, 12.7, 3.9 Hz, 1H), 1.39 (t, J=7.0 Hz, 3H). ESI MS $[M+H]^+$ for $C_{21}H_{28}N_6O_4$, calcd 429.2, found 429.2.

Example 229: 2-[(R)-3-[3-(5-ethoxy-2-pyridyl)-1-methylureido]-1-piperidyl]-4-pyrimidinyl 2-propanecarbamate

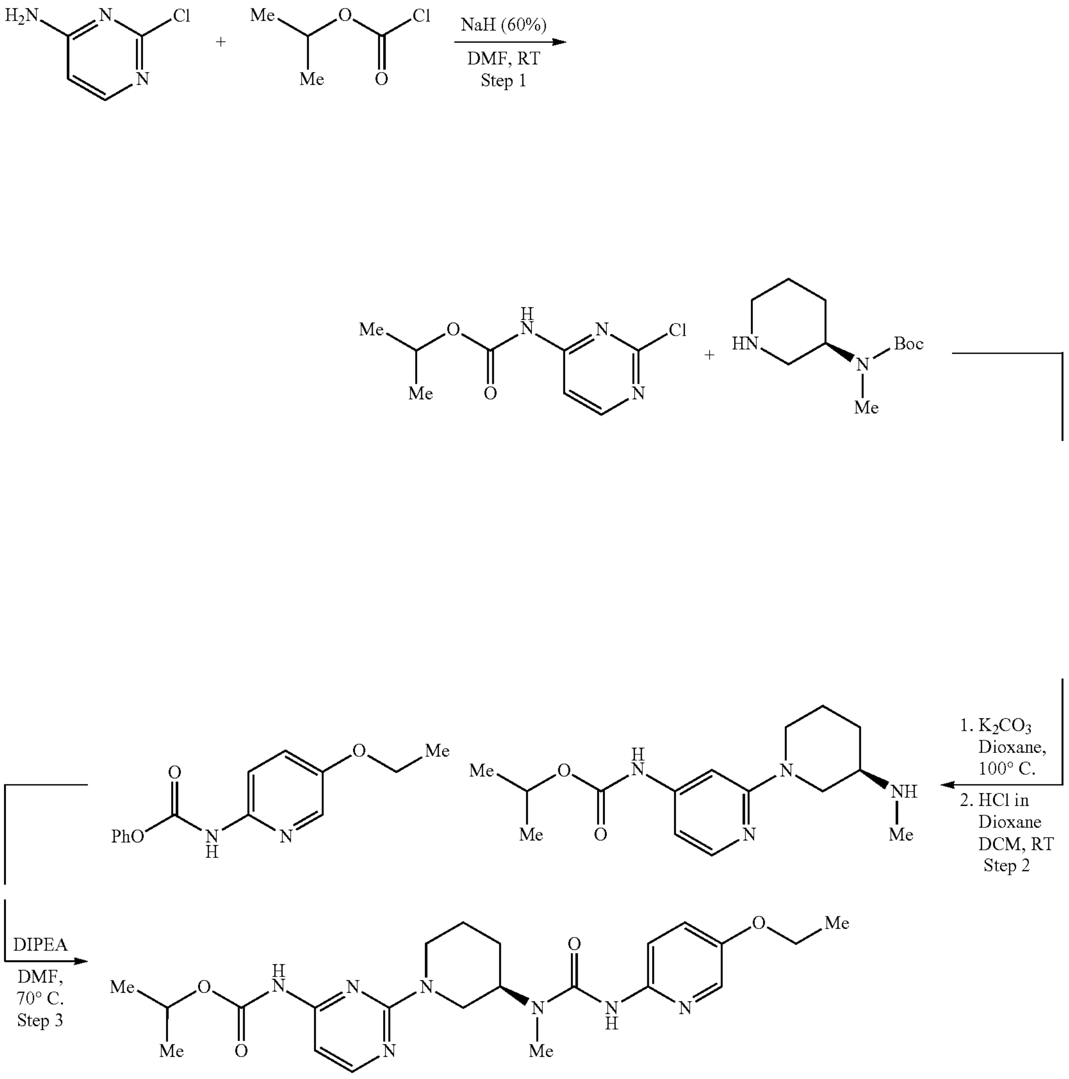

Step 1: This step was performed in a similar fashion to Step 2 of the protocol for the synthesis of Example 1.

Step 2: This step was performed in a similar fashion to Step 3 of the protocol for the synthesis of Example 1.

Step 3: This transformation was performed in a similar fashion to Step 5 of the protocol for the synthesis of Example 1 using 2-amino-5-ethoxy-pyridine in Step 4. The crude product was then purified using reversed phase preparative HPLC to afford the title compound. $^1$H NMR (400 MHz, $CDCl_3$) δ 10.28 (s, 1H), 8.28-8.21 (m, 2H), 8.15 (s, 1H), 7.99 (d, J=9.1 Hz, 1H), 7.33 (d, J=5.6 Hz, 1H), 7.25 (dd, J=9.1, 3.1 Hz, 1H), 5.08 (hept, J=6.3 Hz, 1H), 4.76 (d, J=13.3 Hz, 1H), 4.48 (d, J=13.6 Hz, 1H), 4.03 (qd, J=7.0, 2.7 Hz, 2H), 3.61 (dt, J=7.6, 3.7 Hz, 1H), 3.00 (s, 3H), 2.96-2.82 (m, 2H), 2.10 (d, J=12.1 Hz, 1H), 1.95 (qd, J=12.4, 4.1 Hz, 1H), 1.84-1.75 (m, 1H), 1.62-1.47 (m, 1H), 1.42-1.35 (m, 6H), 1.33 (d, J=6.4 Hz, 3H). ESI MS $[M+H]^+$ for $C_{22}H_{31}N_7O_4$, calcd 458.2, found 458.3.

Example 230: 2-[(R)-3-[3-(5-ethoxy-2-pyridyl)-1-methylureido]-1-piperidyl]-4-pyrimidinyl cyclopropanecarbamate

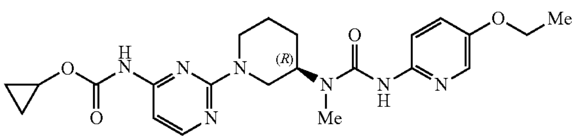

The title compound was synthesized in a similar fashion to the synthesis of Example 229 using cyclopropyl chloroformate in Step 1 to afford the title compound. $^1$H NMR (400 MHz, cdcl$_3$) δ 10.41 (s, 1H), 8.24 (d, J=5.6 Hz, 1H), 8.12 (s, 1H), 8.07 (d, J=3.1 Hz, 1H), 7.98 (d, J=9.2 Hz, 1H), 7.33 (d, J=5.6 Hz, 1H), 7.27-7.21 (m, 1H), 4.75 (dd, J=15.5, 4.0 Hz, 1H), 4.49-4.37 (m, 1H), 4.21-4.12 (m, 1H), 4.04 (qd, J=7.0, 1.8 Hz, 2H), 3.59 (tt, J=11.4, 3.7 Hz, 1H), 2.99 (s, 3H), 2.95-2.80 (m, 2H), 2.08 (d, J=11.9 Hz, 1H), 2.01-1.87 (m, 1H), 1.78 (dt, J=13.5, 3.3 Hz, 1H), 1.53 (qt, J=12.6, 3.9 Hz, 1H), 1.40 (t, J=7.0 Hz, 3H), 0.87-0.71 (m, 4H). ESI MS $[M+H]^+$ for $C_{22}H_{29}N_7O_4$, calcd 456.2, found 456.2.

Example 231: 2-[(R)-3-[3-(5-ethoxy-2-pyrazinyl)-1-methylureido]-1-piperidyl]-4-pyrimidinyl cyclopropanecarbamate

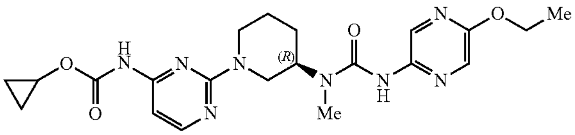

The title compound was synthesized in a similar fashion to the synthesis of Example 229 using cyclopropyl chloroformate in Step 1. Step 3 was performed in a similar fashion to Step 5 of Example 1 using 2-amino-5-ethoxy-pyrazine in Step 4 of Example 1 to afford the title compound.

$^1$H NMR (400 MHz, MeOD)$^1$H NMR (400 MHz, MeOD) δ 8.51 (d, J=1.5 Hz, 1H), 8.13 (d, J=6.9 Hz, 1H), 7.92 (d, J=1.4 Hz, 1H), 7.50 (d, J=7.0 Hz, 1H), 4.45 (s, 2H), 4.34 (q, J=7.0 Hz, 2H), 4.24-4.09 (m, 2H), 3.27-3.05 (m, 2H), 3.03 (s, 3H), 2.05-1.89 (m, 3H), 1.69 (tdt, J=13.4, 9.3, 5.1 Hz, 1H), 1.38 (t, J=7.1 Hz, 3H), 0.76 (d, J=4.8 Hz, 4H). ESI MS $[M+H]^+$ for $C_{21}H_{28}N_8O_4$, calcd 457.2, found 457.2.

Example 232: 2-[(R)-3-[3-(5-ethoxy-2-pyrazinyl)-1-methylureido]-1-piperidyl]-4-pyrimidinyl tetrahydro-4H-pyran-4-carbamate

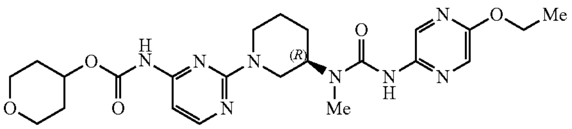

The title compound was synthesized in a similar fashion to Example 1 using tetrahydro-4-pyranol in Step 1. $^1$H NMR (400 MHz, MeOD) δ 8.61 (s, 1H), 8.20 (d, J=5.8 Hz, 1H), 7.99 (s, 1H), 7.19 (d, J=5.8 Hz, 1H), 4.93 (dp, J=8.8, 4.3 Hz, 1H), 4.66 (d, J=13.4 Hz, 1H), 4.56 (d, J=13.8 Hz, 1H), 4.35 (q, J=7.1 Hz, 2H), 3.93 (dt, J=11.9, 4.3 Hz, 3H), 3.61-3.50 (m, 2H), 3.00 (s, 4H), 2.85 (td, J=13.0, 2.8 Hz, 1H), 2.06-1.87 (m, 4H), 1.81 (dt, J=13.4, 2.9 Hz, 1H), 1.71 (ddp, J=13.1, 9.1, 4.6 Hz, 2H), 1.65-1.49 (m, 1H), 1.38 (t, J=7.1 Hz, 3H). ESI MS $[M+H]^+$ for $C_{23}H_{33}N_8O_5$, calcd 501.2, found 501.2.

Example 233: 2-[(R)-3-[3-(5-ethoxy-2-pyrazinyl)-1-methylureido]-1-piperidyl]-4-pyrimidinyl 1-methyl-4-piperidinecarbamate

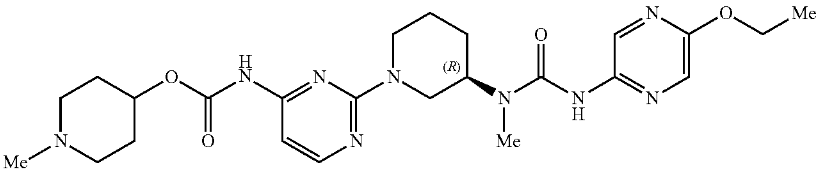

The title compound was synthesized in a similar fashion to Example 1 using 4-hydroxy-1-methyl piperidine in Step 1. $^1$H NMR (400 MHz, MeOD) δ 8.59 (d, J=1.5 Hz, 1H), 8.21 (d, J=5.8 Hz, 1H), 7.97 (d, J=1.5 Hz, 1H), 7.18 (d, J=5.6 Hz, 1H), 4.89 (dt, J=7.5, 3.9 Hz, 1H), 4.67 (dt, J=13.5, 2.3 Hz, 1H), 4.60 (dd, J=12.4, 4.2 Hz, 1H), 4.35 (q, J=7.1 Hz, 2H), 3.95 (d, J=3.9 Hz, 1H), 3.01 (s, 6H), 2.90-2.70 (m, 3H), 2.55 (s, 3H), 2.08 (ddt, J=11.8, 8.0, 3.9 Hz, 2H), 2.01-1.86 (m, 4H), 1.86-1.77 (m, 1H), 1.68-1.50 (m, 1H), 1.38 (t, J=7.1 Hz, 3H). ESI MS $[M+H]^+$ for $C_{24}H_{36}N_9O_4$, calcd 514.3, found 514.4.
Example 234: 2-[(R)-3-[3-(5-ethoxy-2-pyrazinyl)-1-methylureido]-1-piperidyl]-4-pyrimidinyl (S)-3-piperidinecarbamate
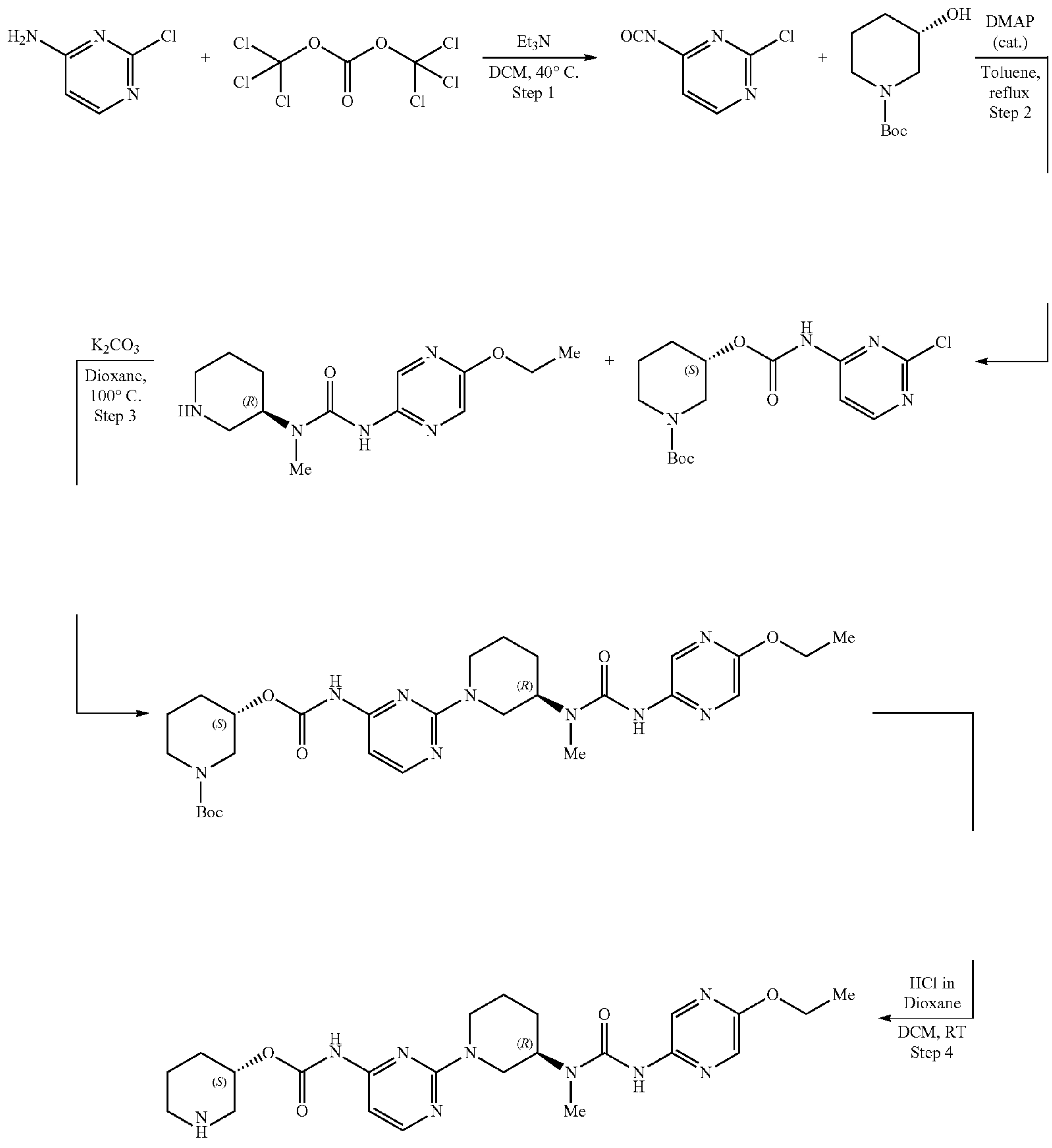

Step 1: This step was performed in a similar fashion to Step 1 of the protocol for the synthesis of Example 2.

Step 2: This step was performed in a similar fashion to Step 2 of the protocol for the synthesis of Example 2.

Step 3: This step was performed in a similar fashion to Step 3 (Part 1) of the protocol for the synthesis of Example 2 using 2-[(R)-3-[3-(5-ethoxy-2-pyrazinyl)-1-methylureido]-1-piperidine.

Step 4: This transformation was performed in a similar fashion to Step 4 (Part 2) of the protocol for the synthesis of Example 2 to afford the title compound. $^1$H NMR (400 MHz, MeOD) δ 8.60 (d, J=1.5 Hz, 1H), 8.21 (d, J=5.8 Hz, 1H), 7.99 (d, J=1.5 Hz, 1H), 7.19 (d, J=5.6 Hz, 1H), 4.77 (dp, J=7.4, 3.7 Hz, 1H), 4.72-4.63 (m, 1H), 4.58 (dd, J=12.9, 4.5 Hz, 1H), 4.35 (q, J=7.0 Hz, 2H), 3.91 (s, 1H), 3.10 (dd, J=12.8, 3.9 Hz, 1H), 3.00 (s, 4H), 2.91-2.66 (m, 4H), 1.98 (qd, J=9.4, 4.0 Hz, 3H), 1.80 (tq, J=10.1, 3.5 Hz, 2H), 1.71 (dtd, J=12.4, 8.2, 4.2 Hz, 1H), 1.57 (tdq, J=12.0, 7.6, 4.2 Hz, 2H), 1.38 (t, J=7.0 Hz, 3H), 1.28 (s, 1H). ESI MS $[M+H]^+$ for $C_{23}H_{33}N_9O_4$, calcd 500.3, found 500.3.

Example 235: 2-[(R)-3-[3-(5-cyclopropyl-2-pyridyl)-1-methylureido]-1-piperidyl]-4-pyrimidinyl 1-methyl-4-piperidinecarbamate

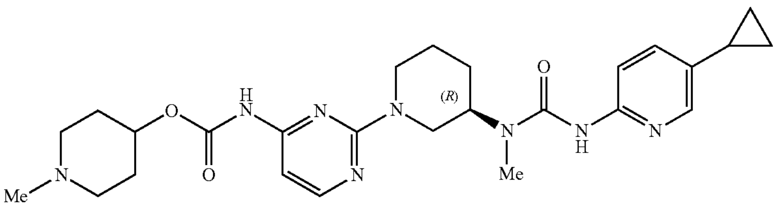

The title compound was synthesized in a similar fashion to Example 1 using N-methyl 4-hydroxy piperidine in step 1 and 2-amino-5-cyclopropyl pyridine in Step 4. $^1$H NMR (400 MHz, MeOD) δ 8.19-8.02 (m, 3H), 7.69 (d, J=9.0 Hz, 1H), 7.55 (dd, J=7.1, 4.2 Hz, 1H), 5.16 (s, 1H), 5.08-4.94 (m, 1H), 4.56 (s, 2H), 4.31 (d, J=16.1 Hz, 1H), 3.60 (d, J=12.6 Hz, 1H), 3.45 (d, J=12.8 Hz, 2H), 3.13 (s, 5H), 2.90 (d, J=10.0 Hz, 3H), 2.40-2.28 (m, 1H), 2.18 (d, J=12.3 Hz, 2H), 2.12-1.92 (m, 5H), 1.77 (d, J=13.1 Hz, 1H), 1.13 (q, J=6.6 Hz, 2H), 0.90-0.79 (m, 2H). ESI MS $[M+H]^+$ for $C_{26}H_{36}N_8O_3$, calcd 509.3, found 509.2.

Example 236: 2-[(R)-3-[3-(5-ethoxy-2-pyrazinyl)-1-methylureido]-1-piperidyl]-4-pyrimidinyl (3R,4R)-3-fluoro-1-methyl-4-piperidinecarbamate

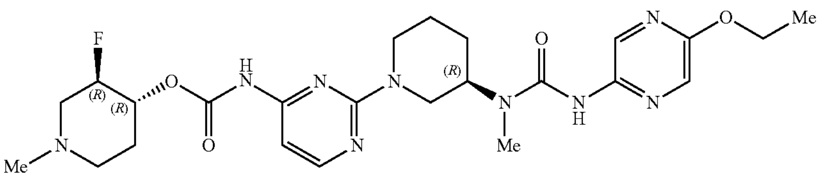

The title compound was synthesized in a similar fashion to Example 10 using (3R,4R)-1-Boc-3-fluoro-4-hydroxypiperidine in Step 1 and tert-butyl N-methyl-N-[(3R)-piperidin-3-yl]carbamate in Step 3 (Part 1). $^1$H NMR (400 MHz, MeOD) δ 8.58 (s, 1H), 8.22 (d, J=5.6 Hz, 1H), 7.98 (s, 1H), 7.19 (d, J=5.6 Hz, 1H), 4.87-4.81 (m, 1H), 4.75-4.52 (m, 3H), 4.35 (q, J=7.1 Hz, 2H), 3.95 (s, 1H), 3.01 (s, 5H), 2.92-2.71 (m, 2H), 2.50 (s, 1H), 2.39 (s, 4H), 2.24-2.09 (m, 1H), 1.97 (q, J=5.8 Hz, 2H), 1.89-1.70 (m, 2H), 1.61 (d, J=8.0 Hz, 1H), 1.38 (t, J=7.1 Hz, 3H). ESI MS [M+H]$^+$ for $C_{24}H_{34}FN_9O_4$, calcd 532.3, found 532.1.

Example 237: 2-[(R)-3-[3-(5-ethoxy-2-pyrazinyl)-1-methylureido]-1-piperidyl]-4-pyrimidinyl (3R,4S)-3-fluoro-1-methyl-4-piperidinecarbamate

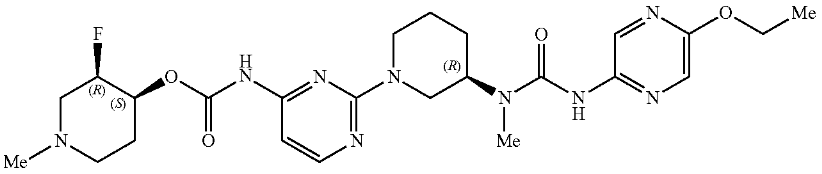

The title compound was synthesized in a similar fashion to Example 10 using (3R,4S)-1-Boc-3-fluoro-4-hydroxypiperidine in Step 1 and tert-butyl N-methyl-N-[(3R)-piperidin-3-yl]carbamate in Step 3 (Part 1). $^1$H NMR (400 MHz, MeOD) δ 8.50 (d, J=1.4 Hz, 1H), 8.16 (d, J=7.0 Hz, 1H), 7.95 (d, J=1.4 Hz, 1H), 7.51 (d, J=7.0 Hz, 1H), 5.37-5.03 (m, 2H), 4.35 (q, J=7.0 Hz, 4H), 4.16 (d, J=4.3 Hz, 1H), 3.91 (s, 1H), 3.54 (d, J=40.0 Hz, 2H), 3.30-3.08 (m, 3H), 3.05 (s, 3H), 2.94 (s, 3H), 2.41-2.18 (m, 2H), 2.08-1.91 (m, 3H), 1.79-1.62 (m, 1H), 1.38 (t, J=7.1 Hz, 3H). ESI MS [M+H]$^+$ for $C_{24}H_{34}FN_9O_4$, calcd 532.3, found 532.3.

Example 238: 2-[(R)-3-[3-(5-ethoxy-2-pyrazinyl)-1-methylureido]-1-piperidyl]-4-pyrimidinyl (3S,4R)-3-fluoro-1-methyl-4-piperidinecarbamate

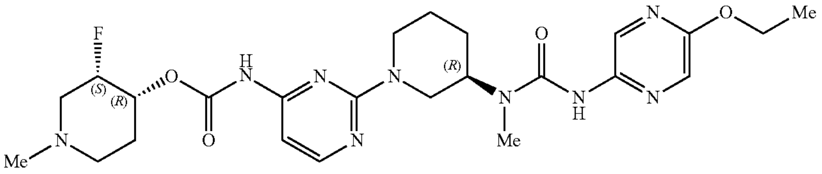

The title compound was synthesized in a similar fashion to Example 10 using (3S,4R)-1-Boc-3-fluoro-4-hydroxypiperidine in Step 1 and tert-butyl N-methyl-N-[(3R)-piperidin-3-yl]carbamate in Step 3 (Part 1). $^1$H NMR (400 MHz, MeOD) δ 8.61 (s, 1H), 8.21 (d, J=5.6 Hz, 1H), 8.02 (s, 1H), 7.19 (d, J=5.8 Hz, 1H), 4.93 (s, 1H), 4.81 (s, 1H), 4.67 (d, J=13.4 Hz, 1H), 4.55 (d, J=10.6 Hz, 1H), 4.34 (q, J=7.0 Hz, 2H), 3.88 (s, 1H), 3.07 (s, 1H), 3.00 (d, J=3.3 Hz, 4H), 2.86 (td, J=13.1, 2.8 Hz, 2H), 2.50 (dd, J=30.1, 12.4 Hz, 1H), 2.33 (s, 4H), 2.12 (q, J=11.0 Hz, 1H), 2.03-1.87 (m, 3H), 1.81 (d, J=13.4 Hz, 1H), 1.69-1.49 (m, 1H), 1.38 (t, J=7.0 Hz, 3H). ESI MS [M+H]$^+$ for $C_{24}H_{34}FN_9O_4$, calcd 532.3, found 532.3.

Example 239: 2-[(R)-3-[3-(5-ethoxy-2-pyrazinyl)-1-methylureido]-1-piperidyl]-4-pyrimidinyl (3S,4S)-3-fluoro-1-methyl-4-piperidinecarbamate

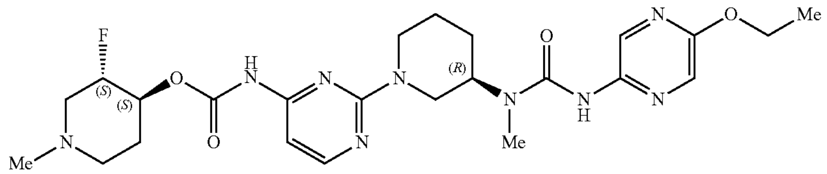

The title compound was synthesized in a similar fashion to Example 10 using (3S,4S)-1-Boc-3-fluoro-4-hydroxypiperidine in Step 1 and tert-butyl N-methyl-N-[(3R)-piperidin-3-yl]carbamate in Step 3 (Part 1). $^1$H NMR (400 MHz, MeOD) δ 8.58 (d, J=1.5 Hz, 1H), 8.22 (d, J=5.8 Hz, 1H), 7.97 (d, J=1.5 Hz, 1H), 7.18 (d, J=5.8 Hz, 1H), 4.84-4.78 (m, 1H), 4.72-4.50 (m, 3H), 4.35 (q, J=7.1 Hz, 2H), 4.01-3.87 (m, 1H), 3.01 (s, 5H), 2.85 (td, J=12.9, 2.8 Hz, 1H), 2.76-2.66 (m, 1H), 2.38 (dd, J=12.2, 7.4 Hz, 1H), 2.32 (s, 3H), 2.31-2.22 (m, 1H), 2.13 (ddd, J=13.4, 7.6, 2.6 Hz, 1H), 2.01-1.91 (m, 2H), 1.82 (dt, J=13.5, 2.8 Hz, 1H), 1.77-1.50 (m, 2H), 1.38 (t, J=7.1 Hz, 3H). ESI MS [M+H]$^+$ for $C_{24}H_{34}FN_9O_4$, calcd 532.3, found 532.3.

Example 240: 2-[(S)-3-[3-(5-ethoxy-2-pyrazinyl)-1-methylureido]-4,4-difluoro-1-piperidyl]-4-pyrimidinyl (1R,2R)-2-aminocyclopentanecarbamate

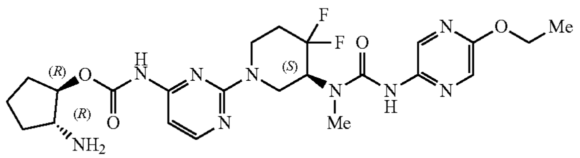

The title compound was prepared in a similar fashion to Example 2 using tert-butyl N-[(1R,2R)-2-hydroxycyclopentyl]carbamate in Step 2. $^1$H NMR (400 MHz, MeOD) δ 8.49 (d, J=1.5 Hz, 1H), 8.21 (d, J=5.8 Hz, 1H), 7.92 (d, J=1.5 Hz, 1H), 7.23 (d, J=5.6 Hz, 1H), 4.81-4.75 (m, 1H), 4.75-4.70 (m, 1H), 4.60 (dd, J=26.5, 10.6 Hz, 1H), 4.34 (q, J=7.0 Hz, 2H), 3.50-3.40 (m, 1H), 3.26 (td, J=7.1, 4.3 Hz, 1H), 3.15 (d, J=2.1 Hz, 4H), 2.22-2.10 (m, 2H), 2.10-1.90 (m, 2H), 1.74 (tdd, J=9.6, 7.7, 4.8 Hz, 3H), 1.47-1.39 (m, 1H), 1.37 (t, J=7.1 Hz, 3H), 1.32-1.25 (m, 1H). ESI MS [M+H]$^+$ for $C_{23}H_{31}F_2N_9O_4$, calcd 536.2, found 536.3.

Example 241: 2-[(S)-3-[3-(5-ethoxy-2-pyrazinyl)-1-methylureido]-4,4-difluoro-1-piperidyl]-4-pyrimidinyl 4-piperidinecarbamate

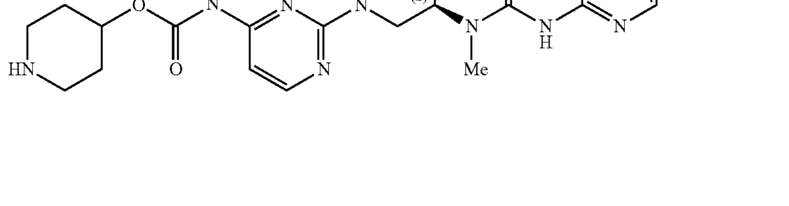

The title compound was prepared in a similar fashion to Example 2 using 1-Boc-4-piperidinol in Step 2. $^1$H NMR (400 MHz, MeOD) δ 8.49 (d, J=1.5 Hz, 1H), 8.22 (d, J=5.6 Hz, 1H), 7.92 (d, J=1.5 Hz, 1H), 7.23 (d, J=5.8 Hz, 1H), 4.99 (hept, J=3.5 Hz, 1H), 4.83-4.74 (m, 2H), 4.61 (dd, J=25.6, 9.8 Hz, 1H), 4.34 (q, J=7.0 Hz, 2H), 3.46 (t, J=12.3 Hz, 1H), 3.26 (dt, J=8.4, 4.1 Hz, 2H), 3.21-3.04 (m, 6H), 2.24-1.84 (m, 6H), 1.37 (t, J=7.1 Hz, 3H). ESI MS $[M+H]^+$ for $C_{23}H_{31}F_2N_9O_4$, calcd 536.2, found 536.3.

Example 242: 2-[(S)-3-[3-(5-ethoxy-2-pyrazinyl)-1-methylureido]-4,4-difluoro-1-piperidyl]-4-pyrimidinyl (R)-3-piperidinecarbamate

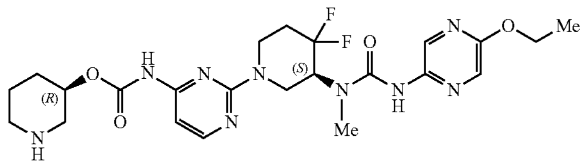

The title compound was prepared in a similar fashion to Example 2 using (R)-1-Boc-3-hydroxypiperidine in Step 2. $^1$H NMR (400 MHz, MeOD) δ 8.50 (d, J=1.5 Hz, 1H), 8.20 (d, J=5.8 Hz, 1H), 7.90 (d, J=1.5 Hz, 1H), 7.22 (d, J=5.6 Hz, 1H), 4.79 (dd, J=11.4, 3.1 Hz, 2H), 4.74 (dq, J=7.0, 3.6 Hz, 1H), 4.60 (dd, J=25.1, 10.6 Hz, 1H), 4.33 (q, J=7.1 Hz, 2H), 3.50-3.38 (m, 1H), 3.14 (d, J=2.3 Hz, 4H), 3.03 (dd, J=12.7, 3.4 Hz, 1H), 2.83-2.62 (m, 3H), 2.23-1.88 (m, 3H), 1.74 (dddd, J=31.4, 16.6, 7.5, 3.8 Hz, 2H), 1.53 (ddd, J=16.9, 7.8, 3.8 Hz, 1H), 1.37 (t, J=7.1 Hz, 3H), 1.27 (s, 1H). ESI MS $[M+H]^+$ for $C_{23}H_{31}F_2N_9O_4$, calcd 536.2, found 536.2.

Example 243: 2-[(S)-3-[3-(5-ethoxy-2-pyrazinyl)-1-methylureido]-4,4-difluoro-1-piperidyl]-4-pyrimidinyl (S)-1-methyl-3-pyrrolidinecarbamate

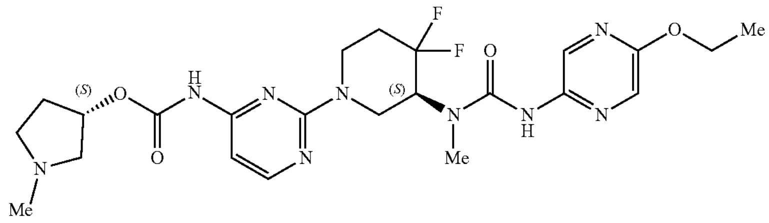

The title compound was prepared in a similar fashion to Example 6 using (R)-3-hydroxy-1-methyl pyrrolidine in Step 1 and (3S)-4,4-difluoro-3-[[(phenylmethoxy)carbonyl] aminomethyl]-1-piperidine HCl salt in Step 3. $^1$H NMR (400 MHz, MeOD) δ 8.51 (d, J=1.5 Hz, 1H), 7.91 (d, J=1.5 Hz, 1H), 7.71 (d, J=6.1 Hz, 1H), 5.89 (d, J=6.1 Hz, 1H), 4.77-4.52 (m, 4H), 4.33 (q, J=7.1 Hz, 2H), 3.67-3.50 (m, 2H), 3.50-3.37 (m, 2H), 3.23-3.07 (m, 5H), 2.76 (s, 3H), 2.22-1.84 (m, 4H), 1.37 (t, J=7.1 Hz, 3H). ESI MS $[M+H]^+$ for $C_{23}H_{31}F_2N_9O_4$, calcd 536.2, found 536.3.

Example 244: 2-[(3S,4R)-3-[3-(5-ethoxy-2-pyrazinyl)-1-methylureido]-4-fluoro-1-piperidyl]-4-pyrimidinyl (S)-1-methyl-3-piperidinecarbamate

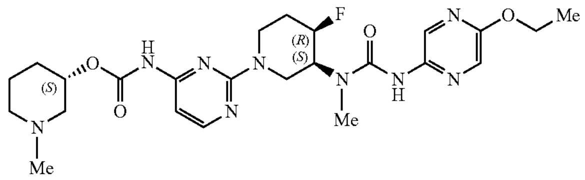

The title compound was prepared in a similar fashion to Example 6 using (S)-3-hydroxy-1-methyl piperidine in Step 1. $^1$H NMR (400 MHz, MeOD) δ 8.51 (d, J=2.1 Hz, 1H), 8.19 (d, J=5.8 Hz, 1H), 7.93 (s, 1H), 7.19 (d, J=5.8 Hz, 1H), 5.07 (d, J=49.9 Hz, 1H), 4.86 (q, J=3.6 Hz, 1H), 4.62 (dt, J=11.8, 5.3 Hz, 2H), 4.33 (q, J=6.9 Hz, 2H), 4.30-4.16 (m, 1H), 3.52 (t, J=12.3 Hz, 1H), 3.24-3.08 (m, 4H), 2.71 (d, J=9.8 Hz, 1H), 2.54-2.32 (m, 3H), 2.29 (s, 3H), 2.09-1.97 (m, 1H), 1.96-1.73 (m, 3H), 1.67-1.50 (m, 2H), 1.37 (t, J=7.1 Hz, 3H). ESI MS $[M+H]^+$for $C_{24}H_{34}FN_9O_4$, calcd 532.3, found 532.3.

Example 245: 2-[(R)-3-[3-(5-ethoxy-2-pyrazinyl)-1-methylureido]-1-piperidyl]-4-pyrimidinyl (S)-1-methyl-3-pyrrolidinecarbamate

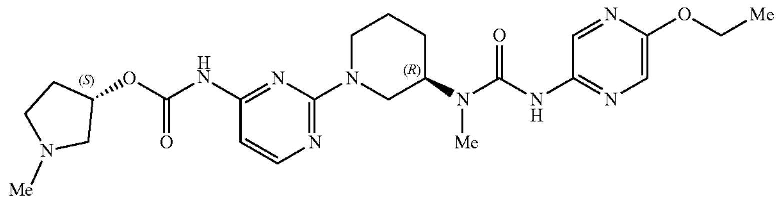

The title compound was prepared in a similar fashion to Example 1 using (S)-3-hydroxy-1-methyl pyrrolidine in Step 1. $^1$H NMR (400 MHz, MeOD) δ 8.54 (s, 1H), 7.91 (s, 1H), 7.75 (d, J=6.1 Hz, 1H), 5.78 (d, J=6.0 Hz, 1H), 4.64-4.53 (m, 3H), 4.33 (q, J=7.1 Hz, 2H), 4.03 (d, J=4.4 Hz, 1H), 3.63 (t, J=8.6 Hz, 1H), 3.56-3.35 (m, 2H), 3.25-3.16 (m, 1H), 2.99 (s, 4H), 2.84-2.73 (m, 4H), 2.04-1.84 (m, 4H), 1.79 (dt, J=13.4, 3.1 Hz, 1H), 1.68-1.52 (m, 1H), 1.37 (t, J=7.1 Hz, 3H). ESI MS $[M+H]^+$ for $C_{23}H_{33}N_9O_4$, calcd 500.3, found 500.2.

Example 246: 2-[(3S,4R)-3-[3-(5-ethoxy-2-pyrazinyl)-1-methylureido]-4-fluoro-1-piperidyl]-4-pyrimidinyl 4-piperidinecarbamate

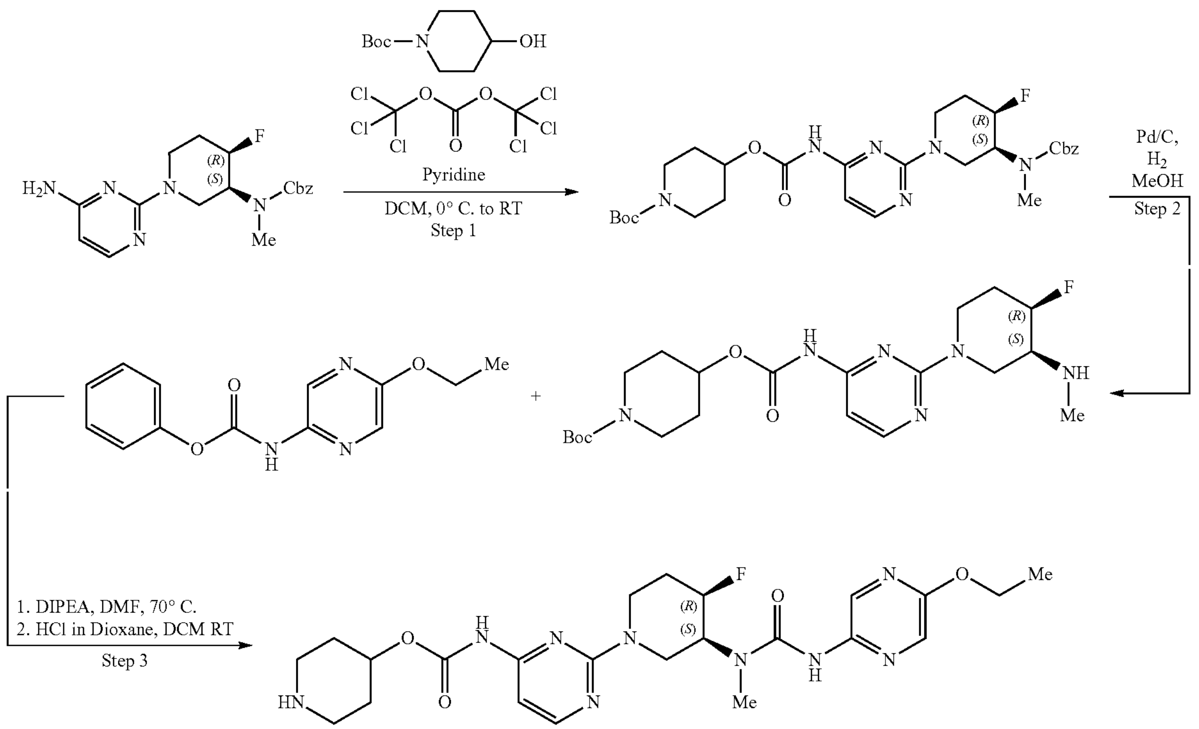

Step 1: This transformation was performed in a similar fashion to Step 1 of the protocol described for the synthesis of Example 10.

Step 2: This transformation was performed in a similar fashion to Step 4 of the protocol described for the synthesis of Example 6.

Step 3: This transformation was performed in a similar fashion to Step 4 of the protocol described for the synthesis of Example 2 to afford the title compound. $^1$H NMR (400 MHz, MeOD) δ 8.50 (d, J=1.5 Hz, 1H), 8.20 (d, J=5.6 Hz, 1H), 7.92 (d, J=1.4 Hz, 1H), 7.18 (d, J=5.6 Hz, 1H), 5.15-4.94 (m, 2H), 4.68-4.57 (m, 2H), 4.39-4.17 (m, 3H), 3.53 (t, J=12.3 Hz, 1H), 3.29-3.03 (m, 8H), 2.16-1.96 (m, 3H), 1.96-1.73 (m, 3H), 1.37 (t, J=7.1 Hz, 3H). ESI MS $[M+H]^+$ for $C_{23}H_{32}FN_9O_4$, calcd 518.3, found 518.2.

Example 247: 2-[(3S,4R)-3-[3-(5-ethoxy-2-pyrazinyl)-1-methylureido]-4-fluoro-1-piperidyl]-4-pyrimidinyl 1-mesyl-4-piperidinecarbamate

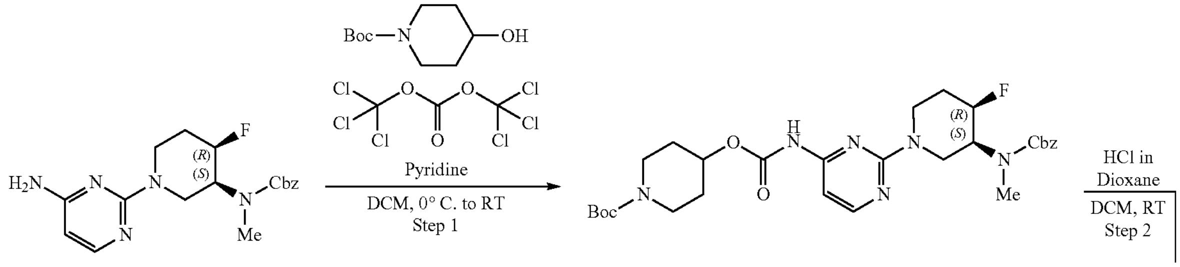

-continued

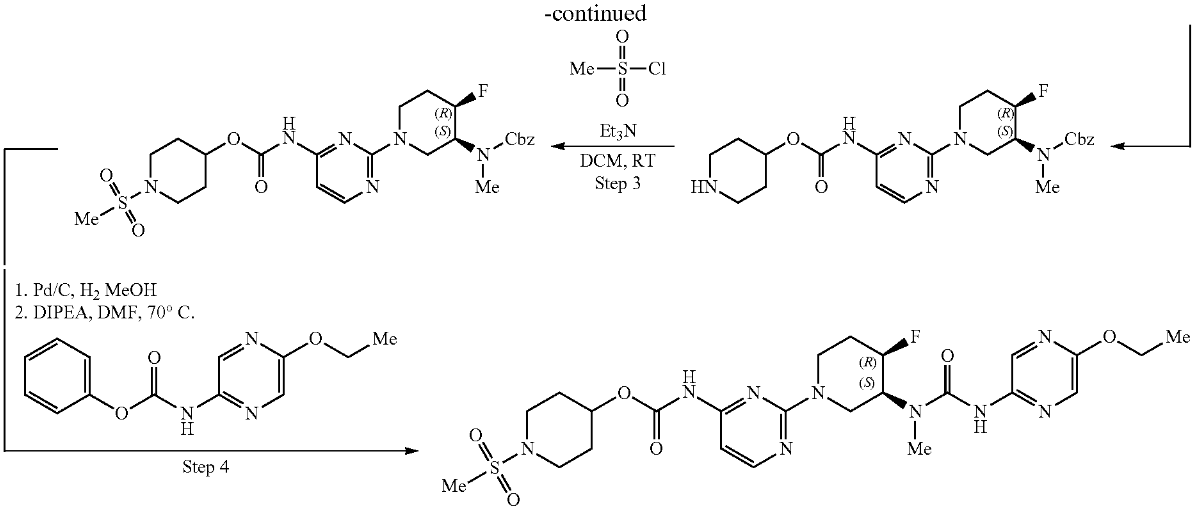

Step 1: This transformation was performed in a similar fashion to Step 1 of the protocol described for the synthesis of Example 10.

Step 2: This transformation was performed in a similar fashion to Step 4 (Part 2) of the protocol described for the synthesis of Example 2. The HCl salt thus obtained was neutralized using Aq. $K_2CO_3$ solution and extracted with DCM. The organic layer was then dried over anhydrous $Na_2SO_4$ and concentrated to afford the intermediate which is used in the next step.

Step 3: The intermediate from Step 2 (72 mg, 0.14 mmol) was taken in a screw capped reaction vial equipped with a stir bar and to this dry DCM (3 mL) was added. This reaction mixture was cooled to 0° C. and under constant stirring, $Et_3N$ (62.3 μL, 0.44 mmol) was added. After stirring for 5 minutes at this temperature, MsCl (11.45 μL, 0.14 mmol) was added and warmed the reaction mixture to room temperature. Progress of the reaction was monitered by LCMS. After confirming the complete consumption of the starting material, solid $K_2CO_3$ (61.3 mg, 0.44 mmol) was added to the reaction mixture and stirred for 30 min. The reaction mixture was then filtered through a small pad of CELITE® and concentrated. The crude product was purified by flash column chromatography to afford the intermediate.

Step 4 (Part 1): This transformation was performed in a similar fashion to Step 4 of the protocol described for the synthesis of Example 6.

Step 4 (Part 2): This transformation was performed in a similar fashion to Step 5 of the protocol described for the synthesis of Example 6 to afford the title compound. $^1H$ NMR (400 MHz, MeOD) δ 8.50 (d, J=1.5 Hz, 1H), 8.20 (d, J=5.6 Hz, 1H), 7.92 (d, J=1.5 Hz, 1H), 7.19 (d, J=5.6 Hz, 1H), 5.06 (d, J=51.2 Hz, 1H), 4.91 (tt, J=7.4, 3.6 Hz, 1H), 4.68-4.57 (m, 2H), 4.34 (q, J=7.0 Hz, 2H), 4.31-4.17 (m, 1H), 3.53 (t, J=12.3 Hz, 1H), 3.46-3.36 (m, 2H), 3.26-3.16 (m, 3H), 3.13 (d, J=1.8 Hz, 3H), 2.84 (s, 3H), 2.09-1.96 (m, 3H), 1.96-1.75 (m, 3H), 1.37 (t, J=7.1 Hz, 3H). ESI MS $[M+H]^+$ for $C_{24}H_{36}FN_9O_6S$, calcd 596.2, found 596.2.

Example 248: 2-[(3S,4R)-3-[3-(5-ethoxy-2-pyrazinyl)-1-methylureido]-4-fluoro-1-piperidyl]-4-pyrimidinyl (S)-1-mesyl-3-piperidinecarbamate

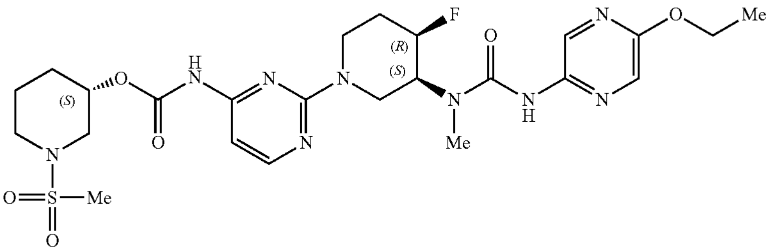

The title compound was prepared in a similar fashion to the protocol for the synthesis of Example 247 using (S)-1-Boc-3-hydroxypiperidine in Step 1. $^1$H NMR (400 MHz, MeOD) δ 8.51 (d, J=1.4 Hz, 1H), 8.19 (d, J=5.8 Hz, 1H), 7.93 (d, J=1.4 Hz, 1H), 7.19 (d, J=5.8 Hz, 1H), 5.06 (d, J=50.9 Hz, 1H), 4.87 (h, J=3.2 Hz, 1H), 4.66-4.55 (m, 2H), 4.33 (q, J=7.0 Hz, 2H), 4.30-4.16 (m, 1H), 3.52 (t, J=12.3 Hz, 1H), 3.47-3.30 (m, 3H), 3.29-3.08 (m, 5H), 2.85 (s, 3H), 2.09-1.97 (m, 1H), 1.96-1.72 (m, 4H), 1.65 (dtd, J=13.9, 6.9, 3.5 Hz, 1H), 1.37 (t, J=7.0 Hz, 3H). ESI MS $[M+H]^+$ for $C_{24}H_{35}FN_9O_6S$, calcd 596.3, found 596.1.

Example 249: 2-[(3S,4R)-3-{3-[5-(2,4-difluorophenoxy)-2-pyrazinyl]-1-methylureido}-4-fluoro-1-piperidyl]-4-pyrimidinyl 1-methyl-4-piperidinecarbamate

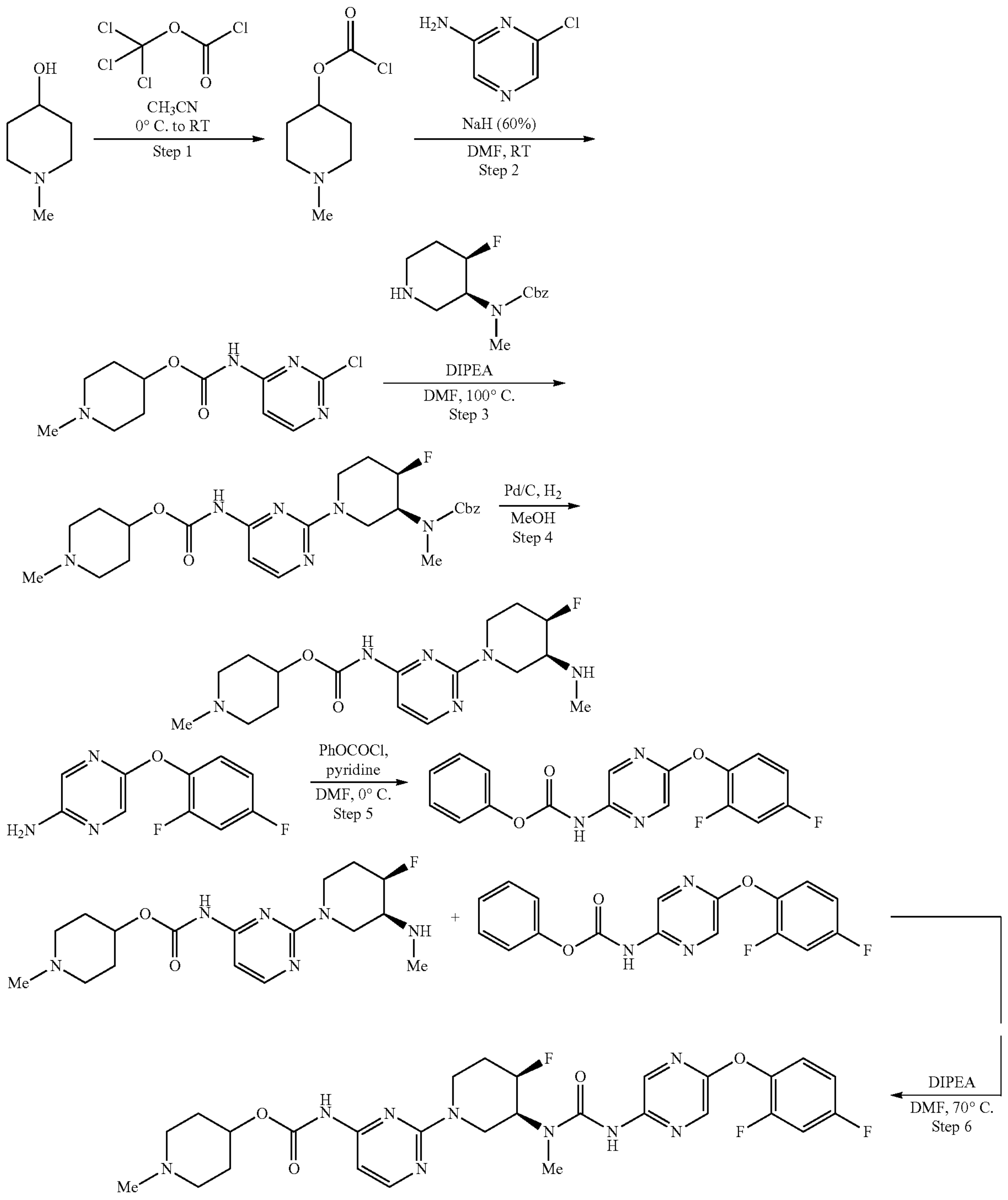

Step 1: This transformation was performed in a similar fashion to Step 1 of the protocol for the synthesis of Example 6.

Step 2: This transformation was performed in a similar fashion to Step 2 of the protocol for the synthesis of Example 6.

Step 3: This transformation was performed in a similar fashion to Step 3 of the protocol for the synthesis of Example 6.

Step 4: This transformation was performed in a similar fashion to Step 4 of the protocol for the synthesis of Example 6.

Step 5: This transformation was performed in a similar fashion to Step 4 of the protocol for the synthesis of Example 1 using 2-Amino-5-difluorophenoxy pyrazine.

Step 6: This transformation was performed in a similar fashion to Step 5 of the protocol for the synthesis of Example 1 to afford the title compound. $^1$H NMR (400 MHz, MeOD) δ 8.52 (d, J=1.5 Hz, 1H), 8.22-8.17 (m, 2H), 7.29 (td, J=9.0, 5.6 Hz, 1H), 7.18 (d, J=5.6 Hz, 1H), 7.15-7.07 (m, 1H), 7.03-6.95 (m, 1H), 5.06 (d, J=51.2 Hz, 1H), 4.82 (d, J=3.5 Hz, 1H), 4.68-4.56 (m, 2H), 4.24 (ddd, J=33.1, 11.6, 3.7 Hz, 1H), 3.53 (t, J=12.3 Hz, 1H), 3.24-3.10 (m, 4H), 2.86 (d, J=7.5 Hz, 2H), 2.56 (s, 2H), 2.43 (s, 3H), 2.09-1.96 (m, 3H), 1.96-1.72 (m, 3H). ESI MS $[M+H]^+$ for $C_{28}H_{32}F_3N_9O_4$, calcd 616.2, found 616.6.

Example 250: 2-[(3S,4R)-3-{3-[5-(2,4-difluorophenoxy)-2-pyrazinyl]-1-methylureido}-4-fluoro-1-piperidyl]-4-pyrimidinyl (S)-1-methyl-3-piperidinecarbamate

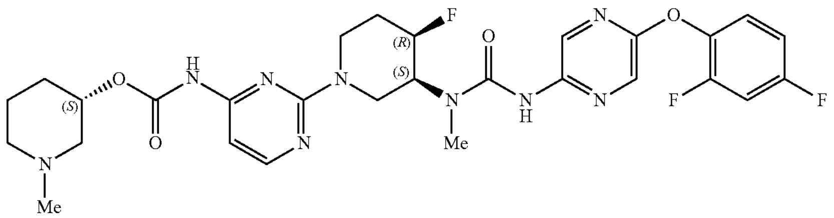

The title compound was prepared in a similar fashion to the protocol for the synthesis of Example 249 using (S)-3-hydroxy-1-methyl piperidine in Step 1. $^1$H NMR (400 MHz, MeOD) δ 8.52 (d, J=1.5 Hz, 1H), 8.24-8.17 (m, 2H), 7.29 (td, J=8.9, 5.5 Hz, 1H), 7.19 (d, J=5.6 Hz, 1H), 7.11 (ddd, J=11.6, 8.6, 3.0 Hz, 1H), 6.99 (dddd, J=9.3, 8.0, 3.1, 1.7 Hz, 1H), 5.06 (d, J=51.0 Hz, 1H), 4.88 (s, 1H), 4.62 (dt, J=11.6, 5.6 Hz, 2H), 4.24 (ddd, J=33.0, 11.7, 3.9 Hz, 1H), 3.54 (t, J=12.3 Hz, 1H), 3.25-3.09 (m, 4H), 2.75 (d, J=10.9 Hz, 1H), 2.49 (s, 3H), 2.33 (s, 3H), 2.03 (t, J=13.8 Hz, 1H), 1.96-1.73 (m, 3H), 1.61 (s, 2H). ESI MS $[M+H]^+$ for $C_{28}H_{32}F_3N_9O_4$, calcd 616.2, found 616.3.

Example 251: 2-[(3S,4R)-3-[3-(5-ethoxy-2-pyrazinyl)-1-methylureido]-4-fluoro-1-piperidyl]-4-pyrimidinyl (S)-tetrahydro-2H-pyran-3-carbamate

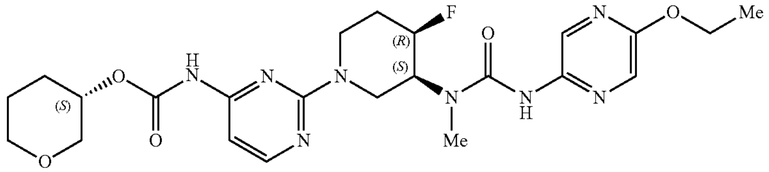

The title compound was prepared in a similar fashion to the protocol for the synthesis of Example 6 using (S)-Tetrahydro-2H-pyran-2-ol in Step 1. $^1H$ NMR (400 MHz, DMSO) δ 10.22 (s, 1H), 9.02 (s, 1H), 8.55 (t, J=1.6 Hz, 1H), 8.23 (d, J=5.6 Hz, 1H), 8.01 (d, J=1.5 Hz, 1H), 7.04 (d, J=5.5 Hz, 1H), 5.04 (d, J=51.4 Hz, 1H), 4.65 (hept, J=3.4 Hz, 1H), 4.57 (dt, J=11.9, 6.0 Hz, 2H), 4.29 (q, J=7.1 Hz, 2H), 4.25-4.12 (m, 1H), 3.72 (dd, J=10.8, 3.1 Hz, 1H), 3.55 (t, J=5.3 Hz, 2H), 3.52-3.39 (m, 2H), 3.11-2.98 (m, 4H), 2.03-1.87 (m, 2H), 1.85-1.62 (m, 3H), 1.55-1.42 (m, 1H), 1.32 (t, J=7.0 Hz, 3H). ESI MS $[M+H]^+$ for $C_{23}H_{31}FN_8O_5$, calcd 519.2, found 519.2.

Example 252: 2-[(3S,4R)-3-[3-(5-ethoxy-2-pyrazinyl)-1-methylureido]-4-fluoro-1-piperidyl]-4-pyrimidinyl (3R,4S)-3-fluoro-1-methyl-4-piperidinecarbamate

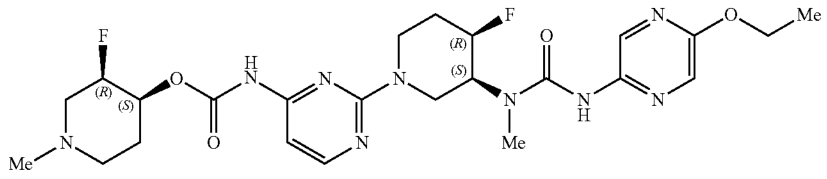

The title compound was synthesized in a similar fashion to Example 10 using (3R,4S)-1-Boc-3-fluoro-4-hydroxypiperidine in Step 1. $^1H$ NMR (400 MHz, MeOD) δ 8.51 (d, J=1.5 Hz, 1H), 8.20 (d, J=5.6 Hz, 1H), 7.93 (d, J=1.4 Hz, 1H), 7.18 (d, J=5.6 Hz, 1H), 5.07 (d, J=51.0 Hz, 1H), 4.93 (d, J=5.1 Hz, 1H), 4.82 (s, 1H), 4.62 (dd, J=12.0, 3.9 Hz, 2H), 4.34 (q, J=7.1 Hz, 2H), 4.30-4.16 (m, 1H), 3.52 (t, J=12.3 Hz, 1H), 3.24-3.04 (m, 5H), 2.84 (d, J=6.1 Hz, 1H), 2.68-2.50 (m, 1H), 2.37 (s, 4H), 2.18-1.96 (m, 2H), 1.96-1.73 (m, 2H), 1.37 (t, J=7.1 Hz, 3H). ESI MS $[M+H]^+$ for $C_{24}H_{33}F_2N_9O_4$, calcd 550.2, found 550.2.

Example 253: 2-[(3S,4R)-3-[3-(5-ethoxy-2-pyrazinyl)-1-methylureido]-4-fluoro-1-piperidyl]-4-pyrimidinyl (3S,4S)-3-fluoro-1-methyl-4-piperidinecarbamate

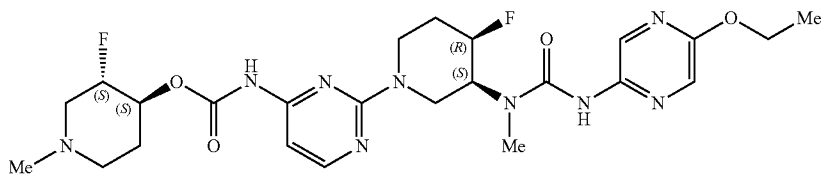

The title compound was synthesized in a similar fashion to Example 10 using (3S,4S)-1-Boc-3-fluoro-4-hydroxypiperidine in Step 1. $^1$H NMR (400 MHz, MeOD) δ 8.51 (d, J=1.5 Hz, 1H), 8.20 (d, J=5.8 Hz, 1H), 7.92 (s, 1H), 7.18 (d, J=5.6 Hz, 1H), 5.06 (d, J=51.0 Hz, 1H), 4.91-4.85 (m, 1H), 4.73-4.51 (m, 3H), 4.34 (q, J=7.1 Hz, 2H), 4.30-4.16 (m, 1H), 3.53 (t, J=12.3 Hz, 1H), 3.24-3.10 (m, 4H), 3.10-2.96 (m, 1H), 2.81-2.69 (m, 1H), 2.57-2.43 (m, 1H), 2.37 (s, 4H), 2.20-2.08 (m, 1H), 2.09-1.97 (m, 1H), 1.97-1.68 (m, 2H), 1.37 (t, J=7.1 Hz, 3H). $C_{24}H_{33}F_2N_9O_4$, calcd 550.2, found 550.2.

Example 254: 2-[(3S,4R)-3-[3-(5-ethoxy-2-pyrazinyl)-1-methylureido]-4-fluoro-1-piperidyl]-4-pyrimidinyl (1r,4S)-4-hydroxycyclohexanecarbamate

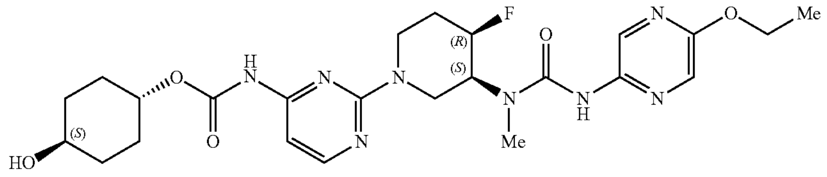

The title compound was synthesized in a similar fashion to Example 25 using trans-4-[tert-butyl(dimethyl)silyl]oxycyclohexanol in Step 1. $^1$H NMR (400 MHz, MeOD) δ 8.51 (d, J=1.5 Hz, 1H), 8.18 (d, J=5.8 Hz, 1H), 7.92 (d, J=1.5 Hz, 1H), 7.17 (d, J=5.8 Hz, 1H), 5.06 (d, J=51.0 Hz, 1H), 4.68 (tt, J=9.8, 4.0 Hz, 1H), 4.60 (dd, J=12.9, 4.3 Hz, 2H), 4.33 (q, J=7.1 Hz, 2H), 4.30-4.14 (m, 1H), 3.67-3.58 (m, 1H), 3.51 (t, J 12.3 Hz, 1H), 3.22-3.09 (m, 4H), 2.11-1.72 (m, 6H), 1.57-1.40 (m, 3H), 1.37 (t, J=7.1 Hz, 4H). ESI MS $[M+H]^+$ for $C_{24}H_{33}FN_8O_5$, calcd 533.2, found 533.2.

Example 255: 2-[(3S,4R)-3-[3-(5-ethoxy-2-pyrazinyl)-1-methylureido]-4-fluoro-1-piperidyl]-4-pyrimidinyl (1S,4S,5S)-2-methyl-2-azabicyclo[2.2.1]heptane-5-carbamate

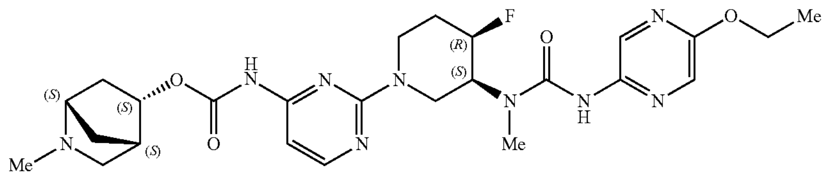

The title compound was synthesized in a similar fashion to Example 10 using tert-butyl (1S,4S,5S)-5-hydroxy-2-azabicyclo[2.2.1]heptane-2-carboxylate in Step 1. $^1$H NMR (400 MHz, MeOD) δ 8.50 (d, J=1.5 Hz, 1H), 8.20 (d, J=5.8 Hz, 1H), 7.92 (d, J=1.5 Hz, 1H), 7.17 (d, J=5.6 Hz, 1H), 5.18-4.95 (m, 2H), 4.63 (td, J=12.6, 5.1 Hz, 2H), 4.39-4.17 (m, 3H), 3.72 (s, 1H), 3.55 (q, J=11.9 Hz, 2H), 3.24-3.08 (m, 4H), 2.91 (d, J=7.1 Hz, 2H), 2.74 (s, 3H), 2.27 (ddd, J=13.9, 10.3, 3.5 Hz, 1H), 2.12-1.97 (m, 2H), 1.97-1.67 (m, 3H), 1.37 (t, J=7.1 Hz, 4H). ESI MS $[M+H]^+$ for $C_{25}H_{34}FN_9O_4$, calcd 544.2, found 544.3.

Example 256: 2-[(3S,4R)-3-[3-(5-ethoxy-2-pyrazinyl)-1-methylureido]-4-fluoro-1-piperidyl]-4-pyrimidinyl (3S,4R)-4-fluoro-1-methyl-3-piperidinecarbamate

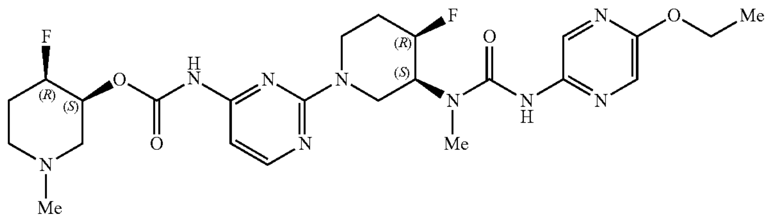

The title compound was synthesized in a similar fashion to Example 10 using tert-Butyl (3S,4R)-4-fluoro-3-hydroxypiperidine-1-carboxylate in Step 1. $^1$H NMR (400 MHz, MeOD) δ 8.51 (d, J=1.5 Hz, 1H), 8.20 (d, J=5.8 Hz, 1H), 7.95 (d, J=1.5 Hz, 1H), 7.19 (d, J=5.8 Hz, 1H), 5.18-4.87 (m, 3H), 4.64 (d, J=4.9 Hz, 2H), 4.34 (q, J=7.0 Hz, 2H), 4.29 (d, J=3.6 Hz, 1H), 3.53 (t, J=12.3 Hz, 1H), 3.25-3.08 (m, 4H), 2.66 (d, J=29.9 Hz, 2H), 2.55-2.39 (m, 2H), 2.32 (s, 3H), 2.18-1.98 (m, 2H), 1.97-1.69 (m, 2H), 1.37 (t, J=7.0 Hz, 3H). ESI MS $[M+H]^+$for $C_{24}H_{33}F_2N_9O_4$, calcd 550.2, found 550.3.

Example 257: 2-[(S)-3-[3-(5-ethoxy-2-pyrazinyl)-1-methylureido]-4,4-difluoro-1-piperidyl]-4-pyrimidinyl (2R,4S)-2-methyl-4-piperidinecarbamate

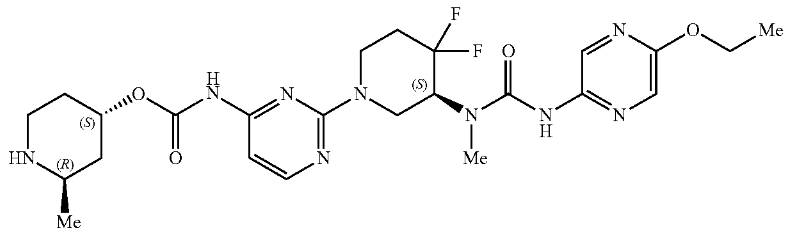

The title compound was synthesized in a similar fashion to Example 11 1,1-Dimethylethyl (2R,4S)-4-hydroxy-2-methyl-1-piperidinecarboxylate in Step 1. In this there is no need of doing Step 8 (Part 2). After the boc deprotection, volatiles were evaporated and the HCl salt thus obtained was purified by reversed phase preparative HPLC. $^1$H NMR (400 MHz, MeOD) δ 8.49 (s, 1H), 8.26-8.17 (m, 1H), 7.91 (s, 1H), 7.27-7.19 (m, 1H), 5.13 (s, 1H), 4.80 (d, J=12.5 Hz, 1H), 4.61 (dd, J=25.5, 12.4 Hz, 1H), 4.33 (q, J=7.8 Hz, 2H), 3.44 (dd, J=29.4, 16.6 Hz, 2H), 3.17 (d, J=15.0 Hz, 6H), 2.91 (d, J=52.8 Hz, 1H), 2.26-1.81 (m, 5H), 1.68 (t, J=13.7 Hz, 1H), 1.43-1.19 (m, 6H). ESI MS $[M+H]^+$ for $C_{24}H_{33}F_2N_9O_4$, calcd 550.2, found 550.2.

Example 258: 2-[(S)-3-[3-(5-ethoxy-2-pyrazinyl)-1-methylureido]-4,4-difluoro-1-piperidyl]-4-pyrimidinyl (2R,4S)-1-methyl-2-methyl-4-piperidinecarbamate

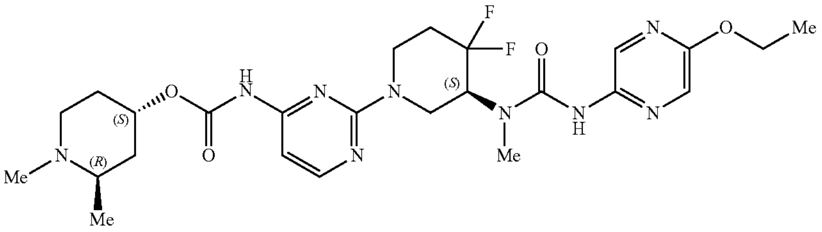

The title compound was synthesized in a similar fashion to Example 11 using 1,1-Dimethylethyl (2R,4S)-4-hydroxy-2-methyl-1-piperidinecarboxylate in Step 1. $^1$H NMR (400 MHz, MeOD) δ 8.50 (d, J=3.3 Hz, 1H), 8.26-8.16 (m, 1H), 7.92 (d, J=2.9 Hz, 1H), 7.27-7.19 (m, 1H), 5.03 (d, J=3.3 Hz, 1H), 4.83-4.74 (m, 2H), 4.60 (dd, J=26.5, 10.6 Hz, 1H), 4.33 (tq, J=6.9, 3.3 Hz, 2H), 3.46 (t, J=12.1 Hz, 1H), 3.15 (s, 4H), 2.87 (d, J=13.9 Hz, 1H), 2.79-2.62 (m, 2H), 2.45 (s, 3H), 2.24-2.10 (m, 1H), 1.96 (d, J=14.5 Hz, 4H), 1.65 (t, J=13.1 Hz, 1H), 1.38 (d, J=5.1 Hz, 3H), 1.16 (d, J=5.0 Hz, 3H). ESI MS $[M+H]^+$ for $C_{25}H_{35}F_2N_9O_4$, calcd 564.2, found 564.2.

Example 259: 2-[(3S,4R)-3-[3-(5-chloro-1,3-thiazol-2-yl)-1-methylureido]-4-fluoro-1-piperidyl]-4-pyrimidinyl (1R,4R,5S)-2-methyl-2-azabicyclo[2.2.1]heptane-5-carbamate

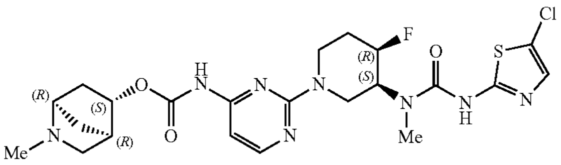

The title compound was synthesized in a similar fashion to Example 10 using phenyl carbamate of 5-chloro-1,3-thiazol-2-amine in Step 4, which was prepared in a similar fashion to Example 1 Step 4 using 2-amino-5-chloro-1,3-thiazol. $^1$H NMR (400 MHz, MeOD). $^1$H NMR (400 MHz, MeOD) δ 8.24 (d, J=5.8 Hz, 1H), 7.20 (d, J=6.3 Hz, 2H), 5.07 (d, J=51.0 Hz, 1H), 4.77 (dd, J=7.1, 2.6 Hz, 1H), 4.66-4.52 (m, 2H), 4.19 (dd, J=32.8, 8.3 Hz, 1H), 3.58-3.47 (m, 2H), 3.19 (td, J=13.4, 3.1 Hz, 1H), 3.11 (d, J=2.0 Hz, 3H), 2.93 (dd, J=11.0, 4.4 Hz, 1H), 2.67 (d, J=3.8 Hz, 1H), 2.57 (d, J=11.0 Hz, 1H), 2.52 (s, 3H), 2.38 (dd, J=15.0, 7.0 Hz, 1H), 2.10-1.97 (m, 1H), 1.96-1.73 (m, 3H), 1.65 (dd, J=15.0, 3.6 Hz, 1H). ESI MS $[M+H]^+$ for $C_{22}H_{28}ClFN_8O_3S$, calcd 539.2, found 539.2.

Example 260: 2-[(3S,4R)-4-fluoro-3-[3-(5-fluoro-1,3-thiazol-2-yl)-1-methylureido]-1-piperidyl]-4-pyrimidinyl (1R,4R,5S)-2-azabicyclo[2.2.1]heptane-5-carbamate

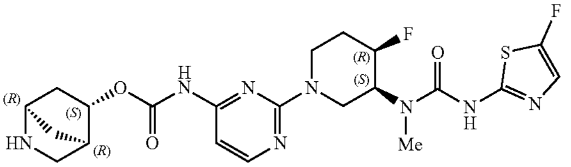

The title compound was synthesized in a similar fashion to Example 246 using tert-butyl (1R,4R,5S)-5-hydroxy-2-azabicyclo[2.2.1]heptane-2-carboxylate in Step 1 and phenyl carbamate of 5-fluoro-1,3-thiazol-2-amine in Step 3, which was prepared in a similar fashion to Example 1 Step 4 using 2-amino-5-fluoro-1,3-thiazol. $^1$H NMR (400 MHz, MeOD) δ 8.54 (s, 1H), 8.24 (d, J=5.8 Hz, 1H), 7.20 (d, J=5.8 Hz, 1H), 6.98 (d, J=2.0 Hz, 1H), 5.06 (d, J=50.9 Hz, 1H), 4.60 (td, J=13.5, 5.1 Hz, 2H), 4.30-4.12 (m, 1H), 4.10-4.03 (m, 1H), 3.53 (t, J=12.3 Hz, 1H), 3.25-3.14 (m, 2H), 3.10 (d, J=1.9 Hz, 3H), 2.95 (d, J=11.6 Hz, 1H), 2.86 (d, J=4.8 Hz, 1H), 2.29 (ddd, J=15.4, 7.0, 2.9 Hz, 1H), 2.04 (d, J=5.5 Hz, 2H), 1.96-1.69 (m, 3H). ESI MS $[M+H]^+$for $C_{21}H_{267}F_2N_8O_3S$, calcd 509.2, found 509.2.

Example 261: 2-[(3S,4R)-4-fluoro-3-[3-(5-fluoro-1,3-thiazol-2-yl)-1-methylureido]-1-piperidyl]-4-pyrimidinyl (1R,4R,5S)-2-methyl-2-azabicyclo[2.2.1]heptane-5-carbamate

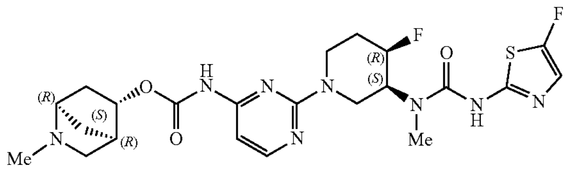

The title compound was synthesized in a similar fashion to Example 10 using phenyl carbamate of 5-fluoro-1,3-thiazol-2-amine in Step 4 using 2-amino-5-fluoro-1,3-thiazol. $^1$H NMR (400 MHz, MeOD) δ 8.22 (d, J=5.8 Hz, 1H), 7.20 (d, J=5.8 Hz, 1H), 6.97 (d, J=2.1 Hz, 1H), 5.06 (d, J=50.8 Hz, 1H), 4.70 (dd, J=7.1, 2.6 Hz, 1H), 4.59 (ddd, J=17.0, 13.0, 4.9 Hz, 2H), 4.20 (ddd, J=32.8, 11.4, 3.3 Hz, 1H), 3.51 (t, J=12.3 Hz, 1H), 3.26 (d, J=1.6 Hz, 1H), 3.18 (td, J=13.3, 2.9 Hz, 1H), 3.10 (d, J=2.0 Hz, 3H), 2.77 (dd, J=10.6, 4.4 Hz, 1H), 2.56 (d, J=4.5 Hz, 1H), 2.33 (s, 4H), 2.23 (d, J=10.5 Hz, 1H), 2.03 (t, J=12.1 Hz, 1H), 1.96-1.74 (m, 1H), 1.72 (s, 2H), 1.52 (dt, J=14.5, 3.6 Hz, 1H). ESI MS $[M+H]^+$ for $C_{22}H_{28}F_2N_8O_3S$, calcd 523.2, found 523.2.

Example 262: 2-[(3S,4R)-3-[3-(5-ethoxy-2-pyrazinyl)-1-methylureido]-4-fluoro-1-piperidyl]-4-pyrimidinyl (1R,4R,5S)-2-ethyl-2-azabicyclo[2.2.1]heptane-5-carbamate

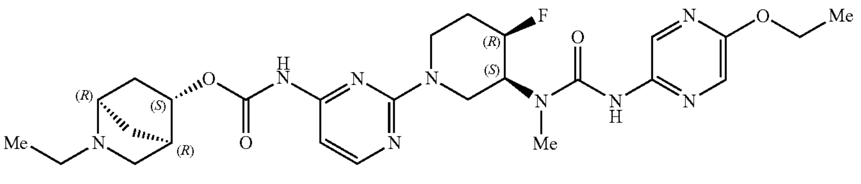

The title compound was synthesized in a similar fashion to Example 10 using acetaldehyde in Step 2 (Part 2) instead of formaldehyde. $^1$H NMR (400 MHz, MeOD) δ 8.51 (s, 1H), 8.18 (d, J=5.6 Hz, 1H), 7.92 (s, 1H), 7.17 (d, J=5.8 Hz, 1H), 5.06 (d, J=52.0 Hz, 1H), 4.73-4.54 (m, 3H), 4.38-4.14 (m, 3H), 3.51 (t, J=12.3 Hz, 1H), 3.42 (s, 1H), 3.24-3.07 (m, 4H), 2.89-2.82 (m, 2H), 2.67-2.44 (m, 3H), 2.34 (dd, J=13.3, 6.0 Hz, 1H), 2.20 (d, J=10.6 Hz, 1H), 2.10-1.96 (m, 1H), 1.86 (ddd, J=44.0, 13.2, 5.3 Hz, 1H), 1.71 (d, J=5.1 Hz, 2H), 1.51 (dt, J=14.5, 3.3 Hz, 1H), 1.37 (t, J=7.0 Hz, 3H), 1.09 (t, J=7.2 Hz, 3H). ESI MS $[M+H]^+$ for $C_{26}H_{36}FN_9O_4$, calcd 558.2, found 558.3.

Example 263: 2-[(S)-4,4-difluoro-3-[3-(5-fluoro-1,3-thiazol-2-yl)-1-methylureido]-1-piperidyl]-4-pyrimidinyl (1R,4R,5S)-2-methyl-2-azabicyclo[2.2.1]heptane-5-carbamate

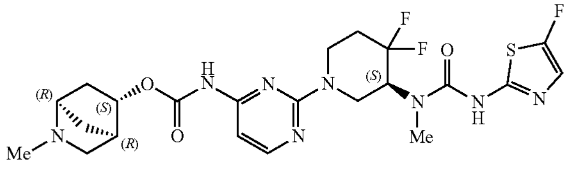

The title compound was synthesized in a similar fashion to Example 11 using phenyl carbamate of 5-fluoro-1,3-thiazol-2-amine in Step 7, which was prepared in a similar fashion to Example 1 Step 4 using 2-amino-5-fluoro-1,3-thiazole. $^1$H NMR (400 MHz, MeOD) δ 8.22 (d, J=5.6 Hz, 1H), 7.22 (d, J=5.8 Hz, 1H), 6.96 (d, J=2.1 Hz, 1H), 4.83-4.72 (m, 3H), 4.60 (dd, J=25.9, 11.3 Hz, 1H), 3.69 (d, J=2.6 Hz, 1H), 3.44 (t, J=12.1 Hz, 1H), 3.20-3.07 (m, 4H), 3.03 (dd, J=11.4, 4.4 Hz, 1H), 2.82-2.71 (m, 2H), 2.63 (s, 3H), 2.40 (dd, J=15.2, 7.6 Hz, 1H), 2.23-2.09 (m, 1H), 1.92 (s, 3H), 1.78-1.68 (m, 1H). ESI MS $[M+H]^+$ for $C_{22}H_{27}F_3N_8O_3S$, calcd 541.2, found 541.2.

Example 264: 2-[(S)-3-[3-(5-ethoxy-2-pyrazinyl)-1-methylureido]-4,4-difluoro-1-piperidyl]-4-pyridyl (1S,4S,5R)-2-methyl-2-azabicyclo[2.2.1]heptane-5-carbamate

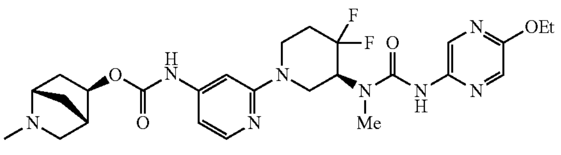 [SMILES: CCOc1cnc(NC(=O)N(C)[C@H]2CN(c3cc(NC(=O)O[C@@H]4C[C@@H]5C[C@H]4CN5C)ccn3)CCC2(F)F)cn1]

The title compound was synthesized in a similar fashion to Example 132 using 1,1-dimethylethyl N-[(3S)-4,4-difluoro-3-piperidinyl]methyl carbamate in Step 1. $^1$H NMR (400 MHz, DMSO) δ 9.83 (s, 1H), 9.04 (s, 1H), 8.54 (d, J=1.5 Hz, 1H), 8.02 (d, J=1.4 Hz, 1H), 7.97 (d, J=5.6 Hz, 1H), 7.09 (d, J=1.7 Hz, 1H), 6.77 (dd, J=5.6, 1.6 Hz, 1H), 4.67-4.54 (m, 2H), 4.35-4.19 (m, 4H), 3.41 (t, J=12.2 Hz, 1H), 3.13-3.03 (m, 5H), 2.66 (dd, J=9.8, 4.4 Hz, 1H), 2.43-2.39 (m, 1H), 2.26-2.10 (m, 5H), 1.98 (d, J=9.8 Hz, 2H), 1.59 (d, J=9.8 Hz, 1H), 1.51 (d, J=9.6 Hz, 1H), 1.38-1.27 (m, 4H). ESI MS $[M+H]^+$ for $C_{26}H_{34}F_2N_8O_4$, calcd 561.3, found 561.3.

Example 265: 2-[(R)-3-[3-(5-ethoxy-2-pyrazinyl)-1-methylureido]-1-piperidyl]-4-pyrimidinyl (1R,4R,5S)-2-methyl-2-azabicyclo[2.2.1]heptane-5-carbamate

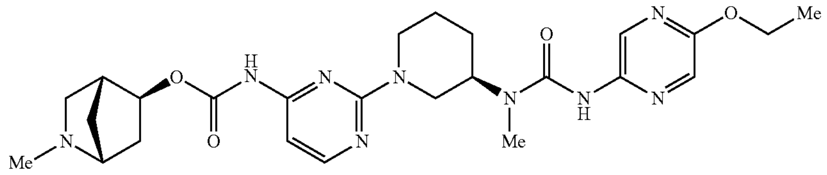 [SMILES: CCOc1cnc(NC(=O)N(C)[C@@H]2CCCN(c3nccc(NC(=O)O[C@H]4C[C@H]5C[C@@H]4CN5C)n3)C2)cn1]

The title compound was synthesized in a similar fashion to Example 18 using 1,1-Dimethylethyl N-methyl-N-(3R)-3-piperidinylcarbamate in step 1 and tert-butyl (1R,4R,5S)-6-hydroxy-2-azabicyclo[2.2.1]heptane-2-carboxylate in Step 7. $^1H$ NMR (400 MHz, DMSO) δ 10.03 (d, J=2.0 Hz, 1H), 8.86 (s, 1H), 8.58 (d, J=1.5 Hz, 1H), 8.22 (d, J=5.6 Hz, 1H), 8.01 (d, J=1.7 Hz, 1H), 7.00 (d, J=5.6 Hz, 1H), 4.68-4.58 (m, 2H), 4.58-4.51 (m, 1H), 4.30 (q, J=7.0 Hz, 2H), 4.00 (s, 1H), 3.26 (s, 1H), 2.96-2.87 (m, 4H), 2.80-2.71 (m, 2H), 2.46 (s,, 1H), 2.27 (s, 4H), 2.18 (d, J=10.1 Hz, 1H), 1.85-1.70 (m, 3H), 1.65 (d, J=10.0 Hz, 1H), 1.57 (d, J=10.0 Hz, 1H), 1.48 (d, J=12.4 Hz, 1H), 1.38 (d, J=13.9 Hz, 1H), 1.32 (t, J=7.0 Hz, 3H). ESI MS $[M+H]^+$ for $C_{25}H_{35}N_9O_4$, calcd 526.3, found 526.3.

Example 266: 2-[(R)-3-[3-(5-ethoxy-2-pyrazinyl)-1-methylureido]-1-piperidyl]-4-pyrimidinyl (1r,3R)-3-(methylamino)cyclobutanecarbamate

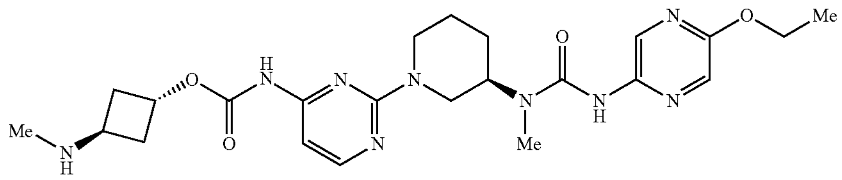 [SMILES: CCOc1cnc(NC(=O)N(C)[C@@H]2CCCN(c3nccc(NC(=O)O[C@H]4C[C@H](NC)C4)n3)C2)cn1]

The title compound was synthesized in a similar fashion to Example 18 (step 1-9) using tert-butyl-(R)-methyl(piperidin-3-yl)carbamate in step 1 and 1,1-Dimethylethyl N-(trans-3-hydroxycyclobutyl)-N-methylcarbamate in step 7. $^1$H NMR (400 MHz, DMSO) δ 9.94 (s, 1H), 8.93 (d, J=1.4 Hz, 1H), 8.26 (d, J=5.6 Hz, 1H), 8.17 (s, 1H), 8.09 (s, 1H), 7.32 (d, J=5.6 Hz, 1H), 7.27 (s, 1H), 5.29-5.20 (m, 1H), 4.80 (d, J=13.5 Hz, 1H), 4.49 (d, J=13.4 Hz, 1H), 4.43-4.34 (m, 2H), 3.67-3.56 (m, 1H), 3.49 (s, 1H), 3.04 (s, 3H), 3.00-2.85 (m, 2H), 2.50-2.27 (m, 5H), 2.14 (d, J=12.4 Hz, 1H), 2.08-1.90 (m, 3H), 1.88-1.78 (m, 1H), 1.58 (ddt, J=13.0, 8.0, 3.9 Hz, 1H), 1.39 (t, J=7.0 Hz, 3H). ESI MS $[M+H]^+$ for $C_{23}H_{33}N_9O_4$, calcd 500.3, found 500.3.

Examples 267-351

Additional compounds were prepared in an analogous manner as in Procedures described above for the synthesis of Examples 1-266 from the appropriate starting materials and are shown in Table 5.

TABLE 5

| Ex. No. | Chemical Structure | [M + H] Calcd. | [M + H] Found | Procedure Example |
|---|---|---|---|---|
| 267 | 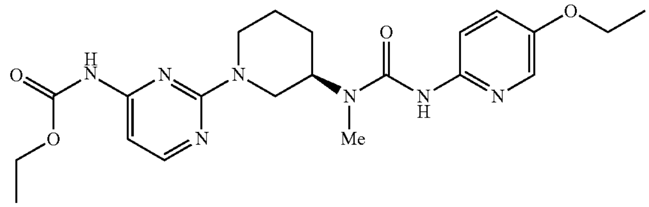 [SMILES: CCOC(=O)Nc1ccnc(N2CCC[C@@H](N(C)C(=O)Nc3ccc(OCC)cn3)C2)n1] | 444.3 | 554.3 | 11 |
| 268 | 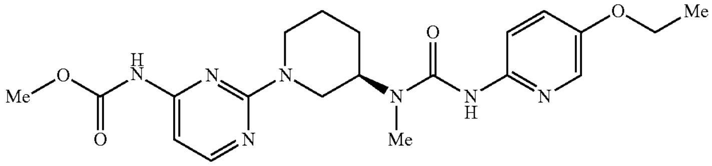 [SMILES: CCOc1ccc(NC(=O)N(C)[C@@H]2CCCN(c3nccc(NC(=O)OC)n3)C2)nc1] | 430.5 | 430.3 | 228 |
| 269 | 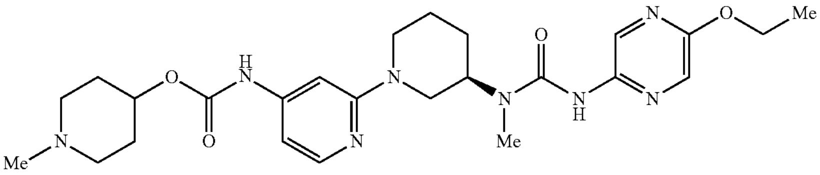 [SMILES: CCOc1cnc(NC(=O)N(C)[C@@H]2CCCN(c3cc(NC(=O)OC4CCN(C)CC4)ccn3)C2)cn1] | 513.3 | 513.3 | 26 |
| 270 | 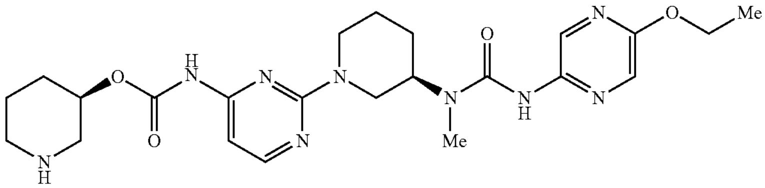 [SMILES: CCOc1cnc(NC(=O)N(C)[C@@H]2CCCN(c3nccc(NC(=O)O[C@@H]4CCCNC4)n3)C2)cn1] | 5003 | 500.3 | 2 |
| 271 | 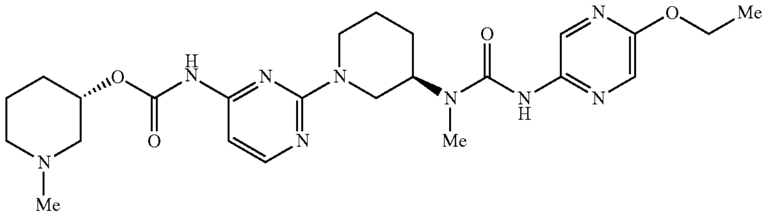 [SMILES: CCOc1cnc(NC(=O)N(C)[C@@H]2CCCN(c3nccc(NC(=O)O[C@H]4CCCN(C)C4)n3)C2)cn1] | 514.3 | 514.3 | 1 |
| 272 | 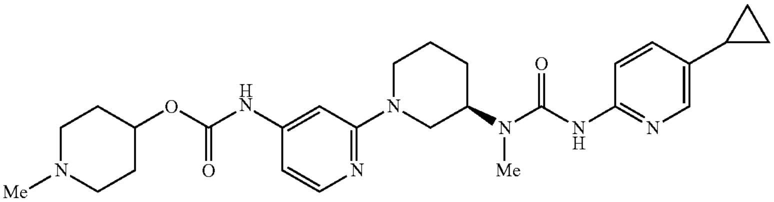 [SMILES: CN1CCC(OC(=O)Nc2ccnc(N3CCC[C@@H](N(C)C(=O)Nc4ccc(C5CC5)cn4)C3)c2)CC1] | 508.3 | 508.2 | 26 |

TABLE 5-continued
| Ex. No. | Chemical Structure | [M + H] Calcd. | [M + H] Found | Procedure Example |
|---|---|---|---|---|
| 273 | 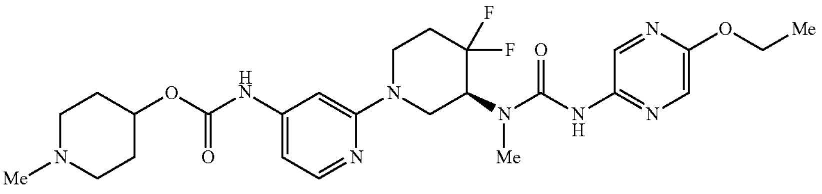 [SMILES: CCOc1cnc(NC(=O)N(C)[C@H]2CN(c3cc(NC(=O)OC4CCN(C)CC4)ccn3)CCC2(F)F)cn1] | 549.3 | 549.2 | 26 |
| 274 | 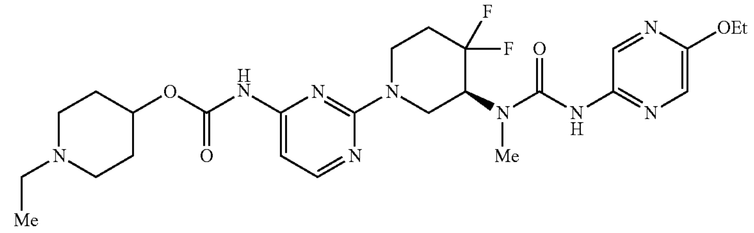 [SMILES: CCOc1cnc(NC(=O)N(C)[C@H]2CN(c3nccc(NC(=O)OC4CCN(CC)CC4)n3)CCC2(F)F)cn1] | 564.3 | 564.3 | 2 |
| 275 | 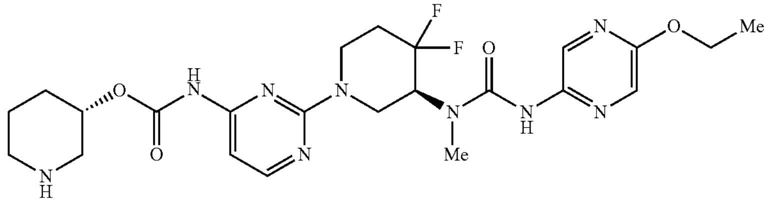 [SMILES: CCOc1cnc(NC(=O)N(C)[C@H]2CN(c3nccc(NC(=O)O[C@H]4CCCNC4)n3)CCC2(F)F)cn1] | 536.2 | 536.1 | 2 |
| 276 | 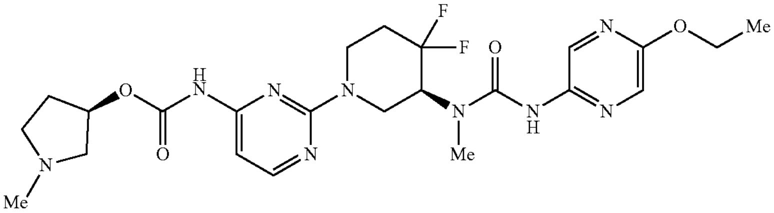 [SMILES: CCOc1cnc(NC(=O)N(C)[C@H]2CN(c3nccc(NC(=O)O[C@@H]4CCN(C)C4)n3)CCC2(F)F)cn1] | 536.2 | 536.2 | 2 |
| 277 | 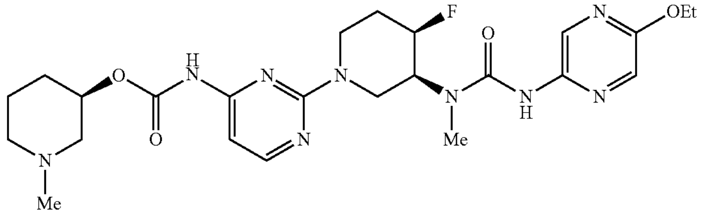 [SMILES: CCOc1cnc(NC(=O)N(C)[C@H]2CN(c3nccc(NC(=O)O[C@@H]4CCCN(C)C4)n3)CC[C@H]2F)cn1] | 532.3 | 532.2 | 1 |
| 278 | 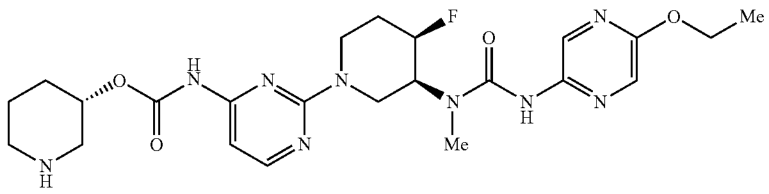 [SMILES: CCOc1cnc(NC(=O)N(C)[C@H]2CN(c3nccc(NC(=O)O[C@H]4CCCNC4)n3)CC[C@H]2F)cn1] | 518.3 | 518.1 | 10 |
| 279 | 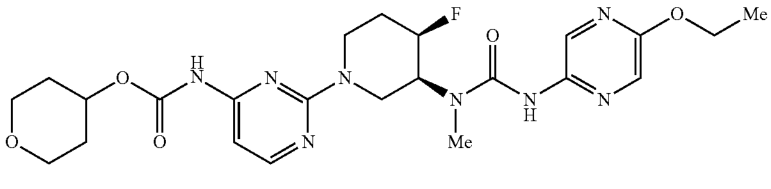 [SMILES: CCOc1cnc(NC(=O)N(C)[C@H]2CN(c3nccc(NC(=O)OC4CCOCC4)n3)CC[C@H]2F)cn1] | 519.3 | 519.3 | 1 |

TABLE 5-continued
| Ex. No. | Chemical Structure | [M + H] Calcd. | [M + H] Found | Procedure Example |
|---|---|---|---|---|
| 280 | 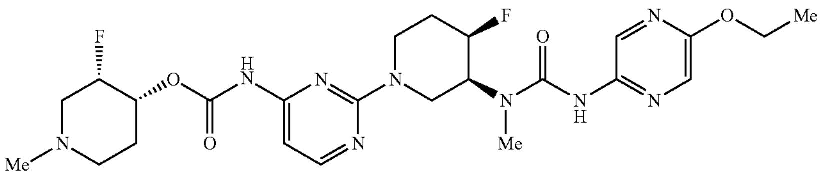 [SMILES: CCOc1cnc(NC(=O)N(C)[C@H]2CN(c3nccc(NC(=O)O[C@@H]4CCN(C)C[C@@H]4F)n3)CC[C@H]2F)cn1] | 550.2 | 550.2 | 10 |
| 281 | 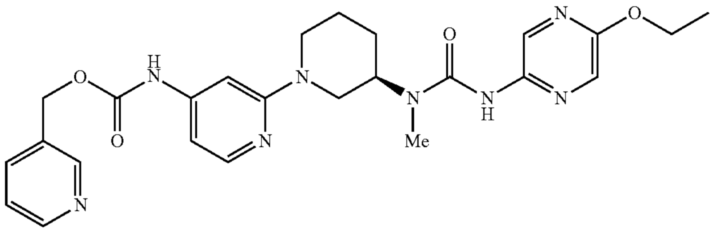 [SMILES: CCOc1cnc(NC(=O)N(C)[C@@H]2CCCN(c3cc(NC(=O)OCc4cccnc4)ccn3)C2)cn1] | 507.3 | 507.1 | 132 |
| 282 | 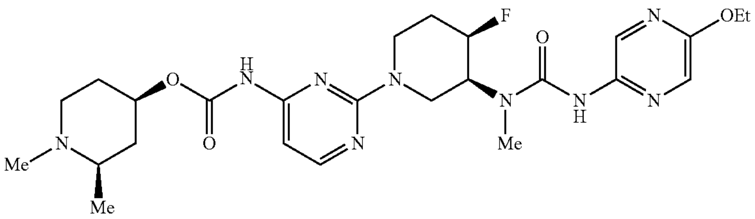 [SMILES: CCOc1cnc(NC(=O)N(C)[C@H]2CN(c3nccc(NC(=O)O[C@@H]4CCN(C)[C@H](C)C4)n3)CC[C@H]2F)cn1] | 546.3 | 546.3 | 10 |
| 283 | 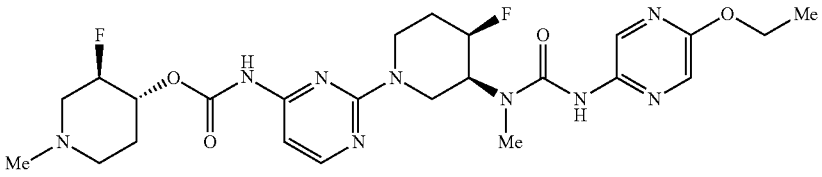 [SMILES: CCOc1cnc(NC(=O)N(C)[C@H]2CN(c3nccc(NC(=O)O[C@@H]4CCN(C)C[C@H]4F)n3)CC[C@H]2F)cn1] | 550.2 | 550.3 | 18 |
| 284 | 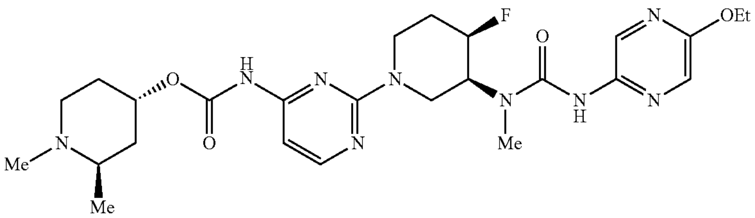 [SMILES: CCOc1cnc(NC(=O)N(C)[C@H]2CN(c3nccc(NC(=O)O[C@H]4CCN(C)[C@H](C)C4)n3)CC[C@H]2F)cn1] | 546.2 | 546.2 | 18 |
| 285 | 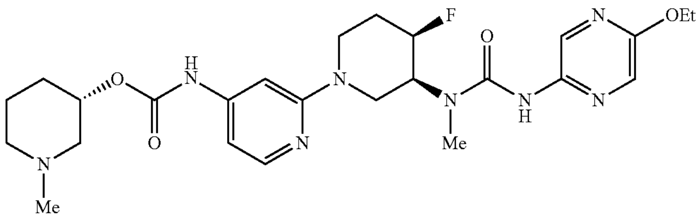 [SMILES: CCOc1cnc(NC(=O)N(C)[C@H]2CN(c3cc(NC(=O)O[C@H]4CCCN(C)C4)ccn3)CC[C@H]2F)cn1] | 532.3 | 532.2 | 26 |
| 286 | 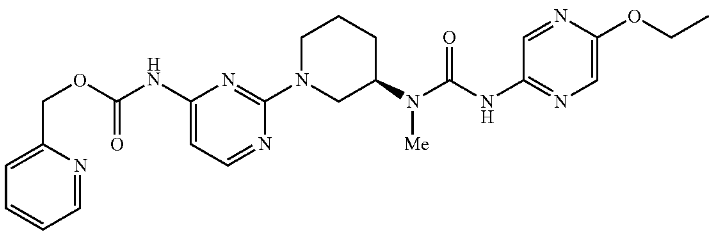 [SMILES: CCOc1cnc(NC(=O)N(C)[C@@H]2CCCN(c3nccc(NC(=O)OCc4ccccn4)n3)C2)cn1] | 508.3 | 508.1 | 1 |

TABLE 5-continued
| Ex. No. | Chemical Structure | [M + H] Calcd. | [M + H] Found | Procedure Example |
|---|---|---|---|---|
| 287 | 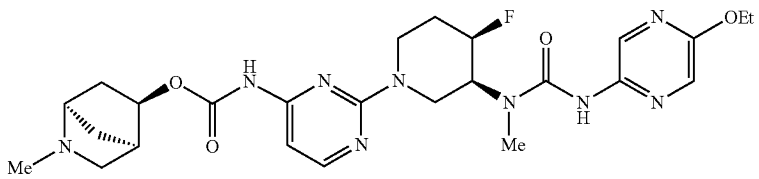 [SMILES: CCOc1cnc(NC(=O)N(C)[C@H]2CN(c3nccc(NC(=O)O[C@@H]4C[C@H]5C[C@@H]4CN5C)n3)CC[C@H]2F)cn1] | 544.3 | 544.1 | 10 |
| 288 | 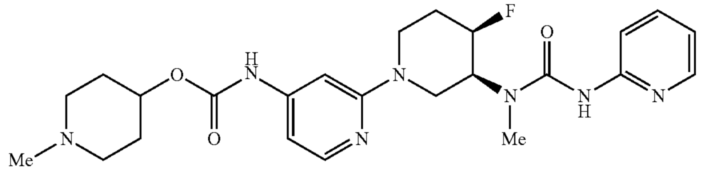 [SMILES: CN1CCC(OC(=O)Nc2ccnc(N3CC[C@@H](F)[C@@H](N(C)C(=O)Nc4ccccn4)C3)c2)CC1] | 486.3 | 486.2 | 26 |
| 289 | 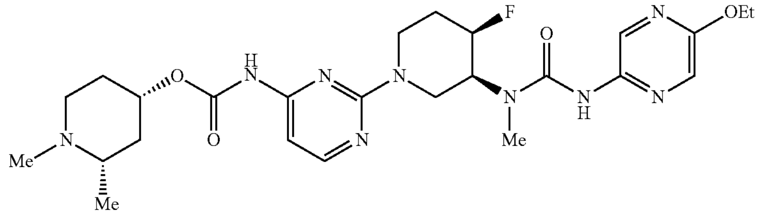 [SMILES: CCOc1cnc(NC(=O)N(C)[C@H]2CN(c3nccc(NC(=O)O[C@H]4CCN(C)[C@@H](C)C4)n3)CC[C@H]2F)cn1] | 546.3 | 546.3 | 10 |
| 290 | 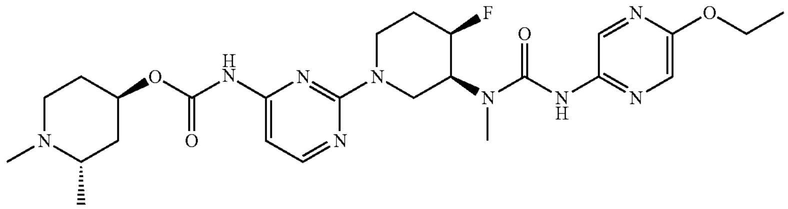 [SMILES: CCOc1cnc(NC(=O)N(C)[C@H]2CN(c3nccc(NC(=O)O[C@@H]4CCN(C)[C@@H](C)C4)n3)CC[C@H]2F)cn1] | 546.3 | 546.1 | 18 |
| 291 | 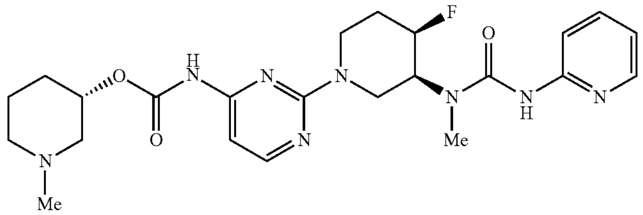 [SMILES: CN1CCC[C@H](OC(=O)Nc2ccnc(N3CC[C@@H](F)[C@@H](N(C)C(=O)Nc4ccccn4)C3)n2)C1] | 487.3 | 487.2 | 1 |
| 292 | 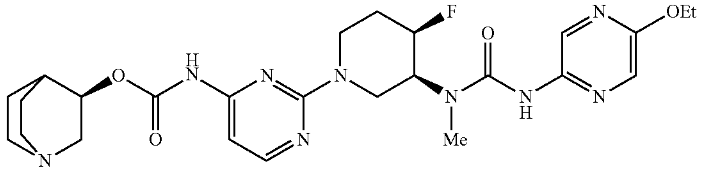 [SMILES: CCOc1cnc(NC(=O)N(C)[C@H]2CN(c3nccc(NC(=O)O[C@H]4CN5CCC4CC5)n3)CC[C@H]2F)cn1] | 544.3 | 544.2 | 1 |
| 293 | 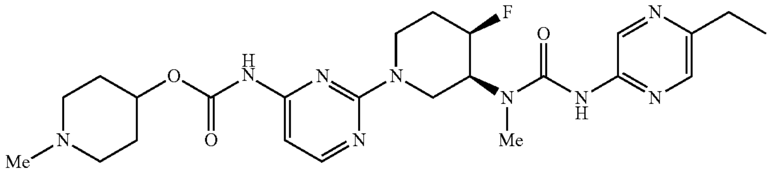 [SMILES: CCc1cnc(NC(=O)N(C)[C@H]2CN(c3nccc(NC(=O)OC4CCN(C)CC4)n3)CC[C@H]2F)cn1] | 516.3 | 516.1 | 6 |
| 294 | 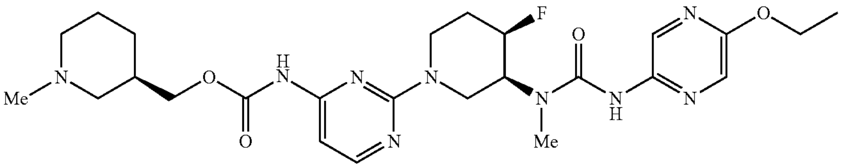 [SMILES: CCOc1cnc(NC(=O)N(C)[C@H]2CN(c3nccc(NC(=O)OC[C@@H]4CCCN(C)C4)n3)CC[C@H]2F)cn1] | 546.3 | 546.3 | 1 |

TABLE 5-continued
| Ex. No. | Chemical Structure | [M + H] Calcd. | [M + H] Found | Procedure Example |
|---|---|---|---|---|
| 295 | 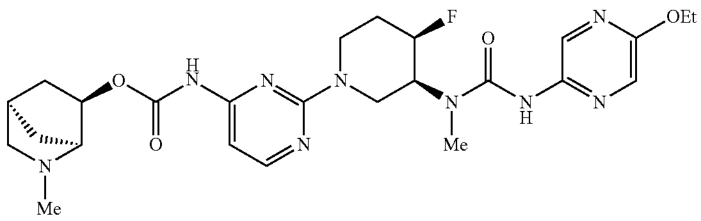 [SMILES: CCOc1cnc(NC(=O)N(C)[C@H]2CN(c3nccc(NC(=O)O[C@@H]4C[C@H]5C[C@@H]4N(C)C5)n3)CC[C@H]2F)cn1] | 544.3 | 544.2 | 18 |
| 296 | 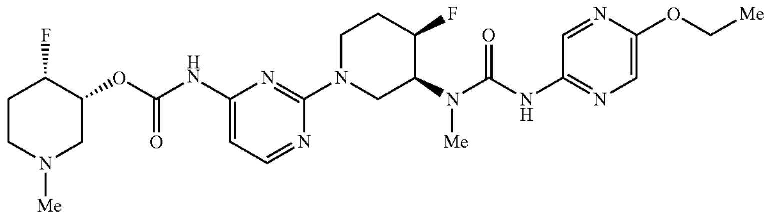 [SMILES: CCOc1cnc(NC(=O)N(C)[C@H]2CN(c3nccc(NC(=O)O[C@@H]4CN(C)CC[C@@H]4F)n3)CC[C@H]2F)cn1] | 550.2 | 550.2 | 18 |
| 297 | 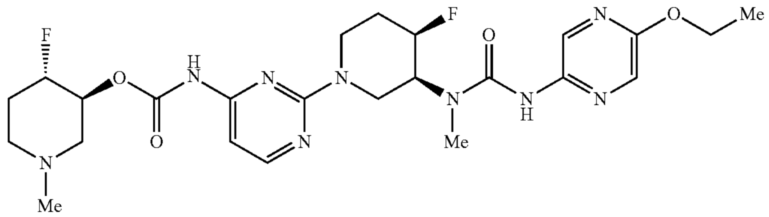 [SMILES: CCOc1cnc(NC(=O)N(C)[C@H]2CN(c3nccc(NC(=O)O[C@H]4CN(C)CC[C@@H]4F)n3)CC[C@H]2F)cn1] | 550.3 | 550.3 | 18 |
| 298 | 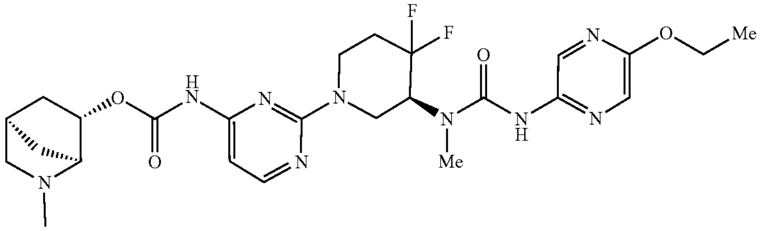 [SMILES: CCOc1cnc(NC(=O)N(C)[C@H]2CN(c3nccc(NC(=O)O[C@H]4C[C@H]5C[C@@H]4N(C)C5)n3)CCC2(F)F)cn1] | 562.3 | 562.3 | 10 |
| 299 | 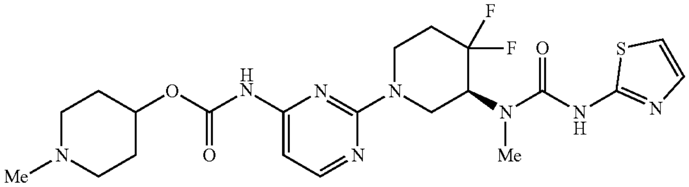 [SMILES: CN1CCC(OC(=O)Nc2ccnc(N3CCC(F)(F)[C@@H](N(C)C(=O)Nc4nccs4)C3)n2)CC1] | 511.2 | 511.2 | 6 |
| 300 | 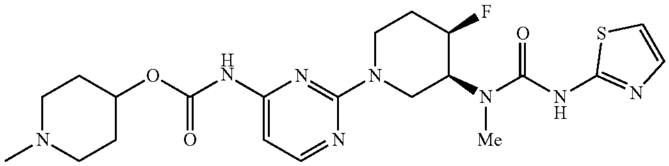 [SMILES: CN1CCC(OC(=O)Nc2ccnc(N3CC[C@@H](F)[C@@H](N(C)C(=O)Nc4nccs4)C3)n2)CC1] | 493.2 | 493.1 | 6 |
| 301 | 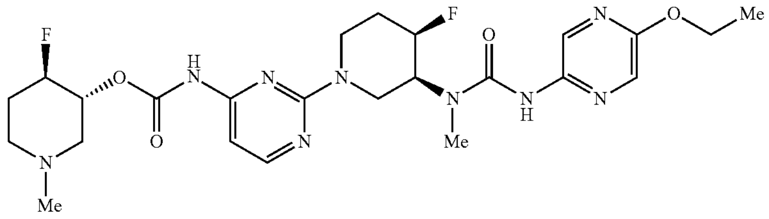 [SMILES: CCOc1cnc(NC(=O)N(C)[C@H]2CN(c3nccc(NC(=O)O[C@@H]4CN(C)CC[C@H]4F)n3)CC[C@H]2F)cn1] | 550.2 | 550.2 | 18 |

TABLE 5-continued
| Ex. No. | Chemical Structure | [M + H] Calcd. | [M + H] Found | Procedure Example |
|---|---|---|---|---|
| 302 | 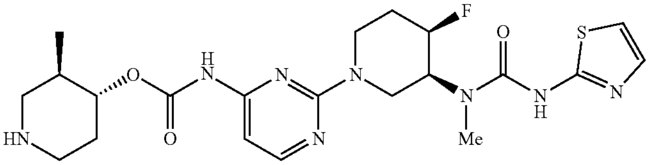 [SMILES: C[C@@H]1CNCC[C@H]1OC(=O)Nc1ccnc(N2CC[C@@H](F)[C@@H](N(C)C(=O)Nc3nccs3)C2)n1] | 493.2 | 493.1 | 10 |
| 303 | 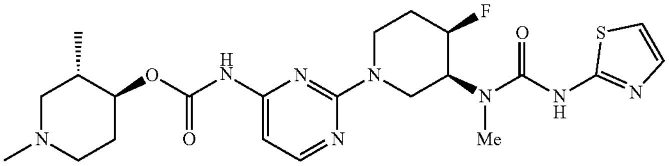 [SMILES: C[C@H]1CN(C)CC[C@@H]1OC(=O)Nc1ccnc(N2CC[C@@H](F)[C@@H](N(C)C(=O)Nc3nccs3)C2)n1] | 507.2 | 507.2 | 6 |
| 304 | 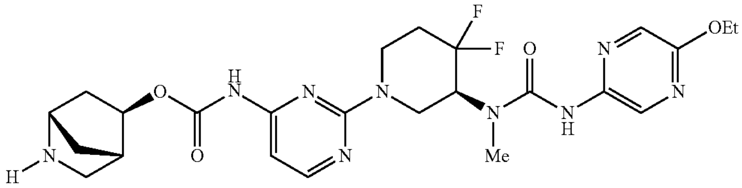 [SMILES: CCOc1cnc(NC(=O)N(C)[C@H]2CN(c3nccc(NC(=O)O[C@@H]4C[C@@H]5C[C@H]4CN5)n3)CCC2(F)F)cn1] | 548.2 | 548.2 | 10 |
| 305 | 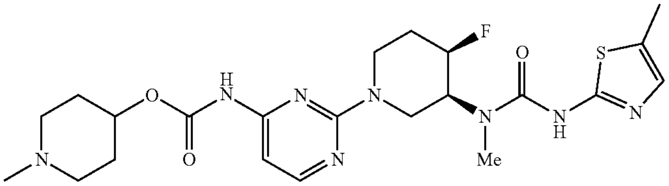 [SMILES: Cc1cnc(NC(=O)N(C)[C@H]2CN(c3nccc(NC(=O)OC4CCN(C)CC4)n3)CC[C@H]2F)s1] | 507.2 | 507.2 | 1 |
| 306 | 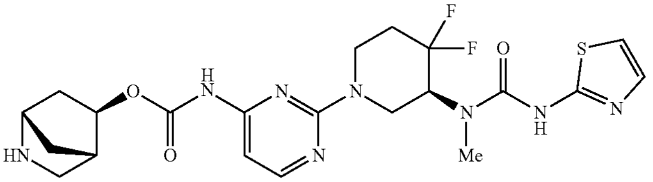 [SMILES: CN(C(=O)Nc1nccs1)[C@H]1CN(c2nccc(NC(=O)O[C@@H]3C[C@@H]4C[C@H]3CN4)n2)CCC1(F)F] | 509.2 | 509.2 | 10 |
| 307 | 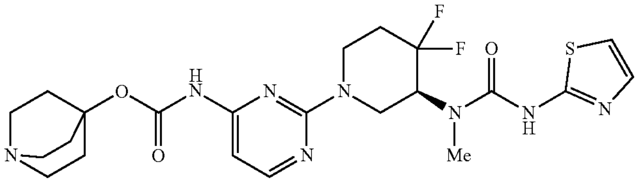 [SMILES: CN(C(=O)Nc1nccs1)[C@H]1CN(c2nccc(NC(=O)OC34CCN(CC3)CC4)n2)CCC1(F)F] | 523.2 | 523.2 | 1 |
| 308 | 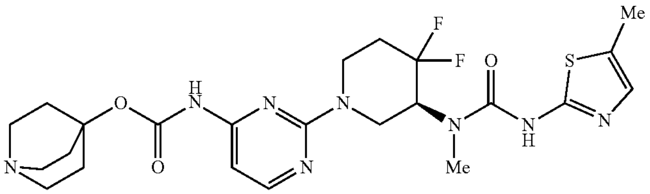 [SMILES: Cc1cnc(NC(=O)N(C)[C@H]2CN(c3nccc(NC(=O)OC45CCN(CC4)CC5)n3)CCC2(F)F)s1] | 537.2 | 537.2 | 1 |
| 309 | 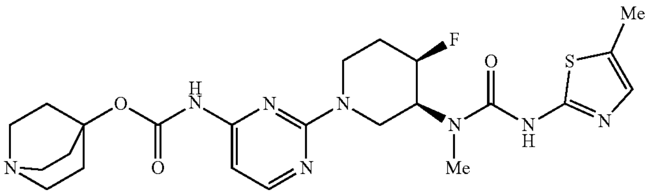 [SMILES: Cc1cnc(NC(=O)N(C)[C@H]2CN(c3nccc(NC(=O)OC45CCN(CC4)CC5)n3)CC[C@H]2F)s1] | 519.2 | 519.2 | 1 |

TABLE 5-continued
| Ex. No. | Chemical Structure | [M + H] Calcd. | [M + H] Found | Procedure Example |
|---|---|---|---|---|
| 310 | 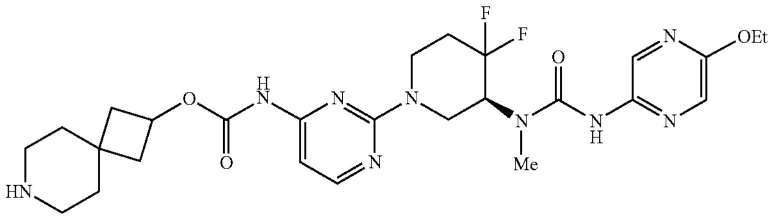 [SMILES: CCOc1cnc(NC(=O)N(C)[C@H]2CN(c3nccc(NC(=O)OC4CC5(CCNCC5)C4)n3)CCC2(F)F)cn1] | 576.3 | 576.1 | 2 |
| 311 | 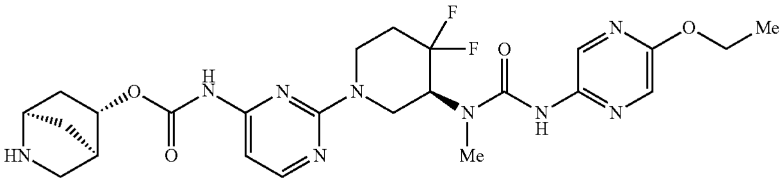 [SMILES: CCOc1cnc(NC(=O)N(C)[C@H]2CN(c3nccc(NC(=O)O[C@H]4C[C@H]5C[C@@H]4CN5)n3)CCC2(F)F)cn1] | 548.2 | 548.3 | 2 |
| 312 | 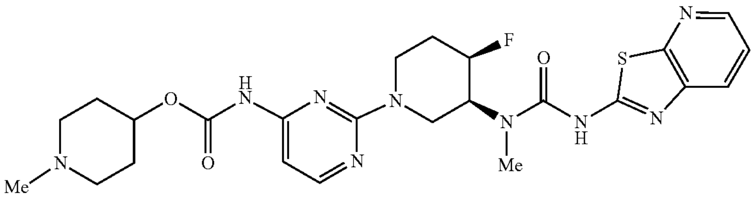 [SMILES: CN1CCC(OC(=O)Nc2ccnc(N3CC[C@@H](F)[C@@H](N(C)C(=O)Nc4nc5cccnc5s4)C3)n2)CC1] | 544.2 | 544.2 | 1 |
| 313 | 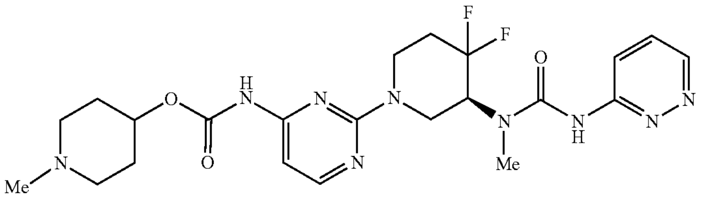 [SMILES: CN1CCC(OC(=O)Nc2ccnc(N3CCC(F)(F)[C@@H](N(C)C(=O)Nc4cccnn4)C3)n2)CC1] | 506.2 | 506.2 | 1 |
| 314 | 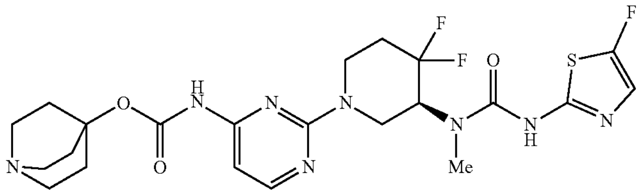 [SMILES: CN(C(=O)Nc1ncc(F)s1)[C@H]1CN(c2nccc(NC(=O)OC34CCN(CC3)CC4)n2)CCC1(F)F] | 541.2 | 541.2 | 1 |
| 315 | 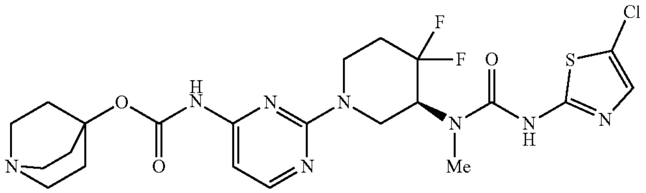 [SMILES: CN(C(=O)Nc1ncc(Cl)s1)[C@H]1CN(c2nccc(NC(=O)OC34CCN(CC3)CC4)n2)CCC1(F)F] | 557.2. | 557.2. | 1 |
| 316 | 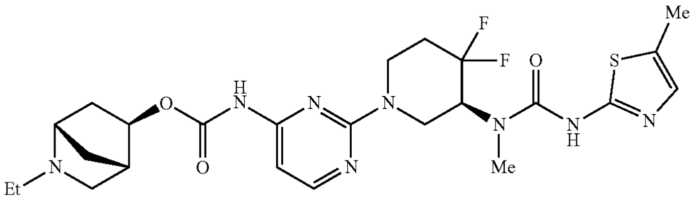 [SMILES: CCN1C[C@@H]2C[C@H]1C[C@H]2OC(=O)Nc1ccnc(N2CCC(F)(F)[C@@H](N(C)C(=O)Nc3ncc(C)s3)C2)n1] | 551.2 | 551.2 | 10 |

TABLE 5-continued
| Ex. No. | Chemical Structure | [M + H] Calcd. | [M + H] Found | Procedure Example |
|---|---|---|---|---|
| 317 | 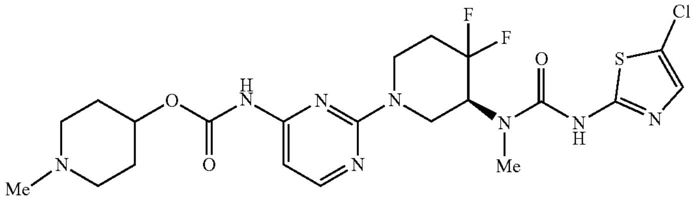 [SMILES: CN1CCC(OC(=O)Nc2ccnc(N3CCC(F)(F)[C@@H](N(C)C(=O)Nc4ncc(Cl)s4)C3)n2)CC1] | 545.3 | 545.1 | 11 |
| 318 | 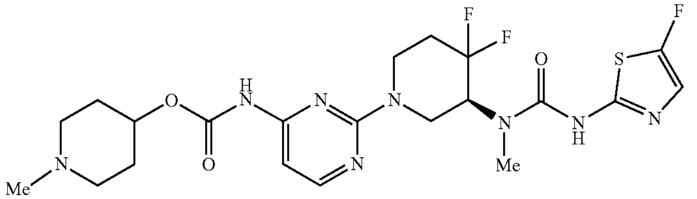 [SMILES: CN1CCC(OC(=O)Nc2ccnc(N3CCC(F)(F)[C@@H](N(C)C(=O)Nc4ncc(F)s4)C3)n2)CC1] | 529.3 | 529.1 | 11 |
| 319 | 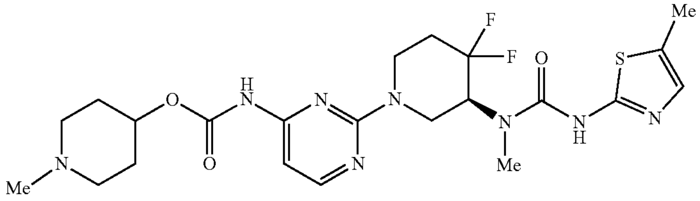 [SMILES: Cc1cnc(NC(=O)N(C)[C@H]2CN(c3nccc(NC(=O)OC4CCN(C)CC4)n3)CCC2(F)F)s1] | 525.2 | 525.2 | 1 |
| 320 | 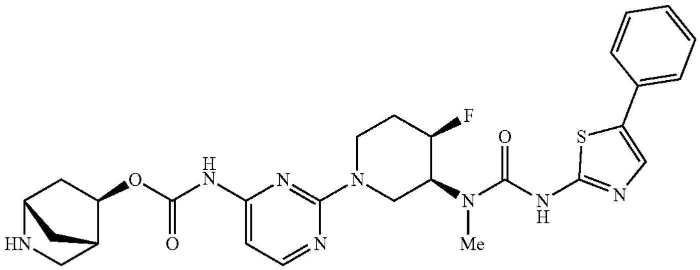 [SMILES: CN(C(=O)Nc1ncc(-c2ccccc2)s1)[C@H]1CN(c2nccc(NC(=O)O[C@@H]3C[C@@H]4C[C@H]3CN4)n2)CC[C@H]1F] | 568.3 | 568.1 | 2 |
| 321 | 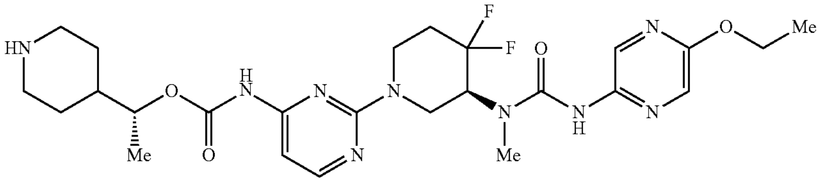 [SMILES: CCOc1cnc(NC(=O)N(C)[C@H]2CN(c3nccc(NC(=O)O[C@H](C)C4CCNCC4)n3)CCC2(F)F)cn1] | 564.3 | 564.3 | 2 |
| 322 | 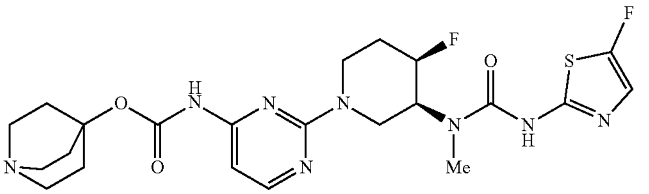 [SMILES: CN(C(=O)Nc1ncc(F)s1)[C@H]1CN(c2nccc(NC(=O)OC34CCN(CC3)CC4)n2)CC[C@H]1F] | 523.2 | 523.2 | 1 |
| 323 | 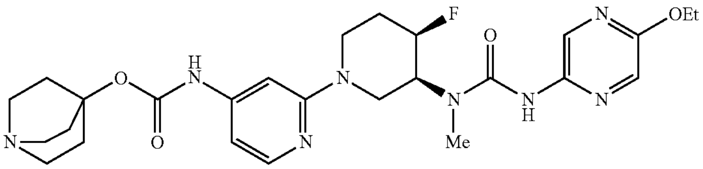 [SMILES: CCOc1cnc(NC(=O)N(C)[C@H]2CN(c3cc(NC(=O)OC45CCN(CC4)CC5)ccn3)CC[C@H]2F)cn1] | 543.3 | 543.3 | 26 |

TABLE 5-continued
| Ex. No. | Chemical Structure | [M + H] Calcd. | [M + H] Found | Procedure Example |
|---|---|---|---|---|
| 324 | 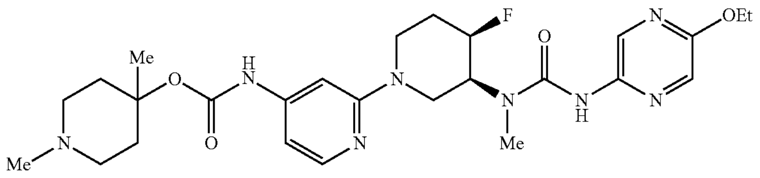 [SMILES: CCOc1cnc(NC(=O)N(C)[C@H]2CN(c3cc(NC(=O)OC4(C)CCN(C)CC4)ccn3)CC[C@H]2F)cn1] | 545.3 | 545.3 | 26 |
| 325 | 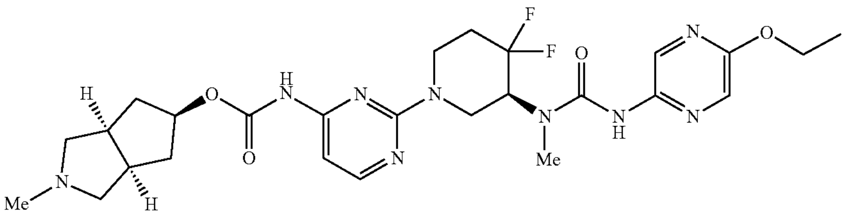 [SMILES: CCOc1cnc(NC(=O)N(C)[C@H]2CN(c3nccc(NC(=O)O[C@@H]4C[C@@H]5CN(C)C[C@@H]5C4)n3)CCC2(F)F)cn1] | 576.3 | 576.3 | 1 |
| 326 | 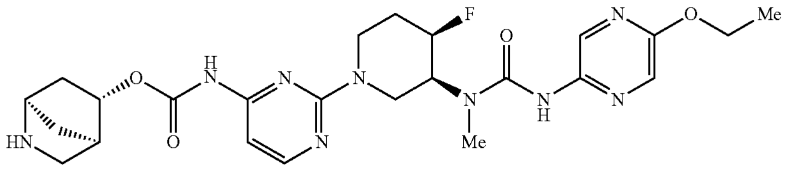 [SMILES: CCOc1cnc(NC(=O)N(C)[C@H]2CN(c3nccc(NC(=O)O[C@H]4C[C@H]5C[C@@H]4CN5)n3)CC[C@H]2F)cn1] | 530.2 | 530.2 | 2 |
| 327 | 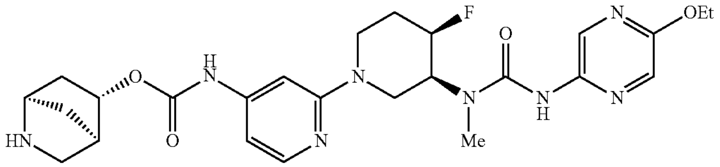 [SMILES: CCOc1cnc(NC(=O)N(C)[C@H]2CN(c3cc(NC(=O)O[C@H]4C[C@H]5C[C@@H]4CN5)ccn3)CC[C@H]2F)cn1] | 529.3 | 529.3 | 132 |
| 328 | 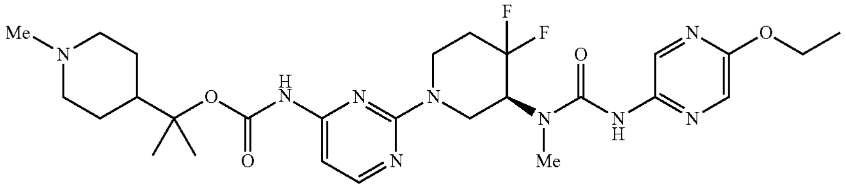 [SMILES: CCOc1cnc(NC(=O)N(C)[C@H]2CN(c3nccc(NC(=O)OC(C)(C)C4CCN(C)CC4)n3)CCC2(F)F)cn1] | 592.3 | 592.3 | 11 |
| 329 | 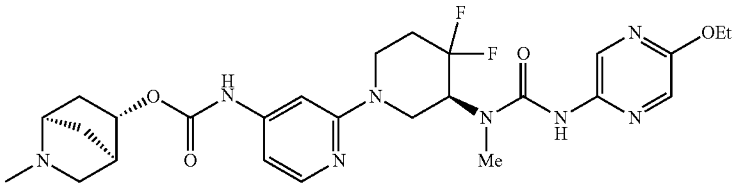 [SMILES: CCOc1cnc(NC(=O)N(C)[C@H]2CN(c3cc(NC(=O)O[C@H]4C[C@H]5C[C@@H]4CN5C)ccn3)CCC2(F)F)cn1] | 561.3 | 561.3 | 26 |
| 330 | 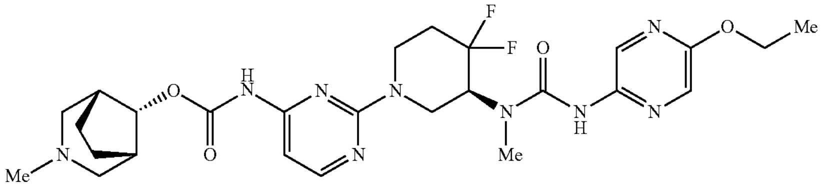 [SMILES: CCOc1cnc(NC(=O)N(C)[C@H]2CN(c3nccc(NC(=O)O[C@H]4[C@@H]5CC[C@H]4CN(C)C5)n3)CCC2(F)F)cn1] | 576.3 | 576.1 | 11 |
| 331 | 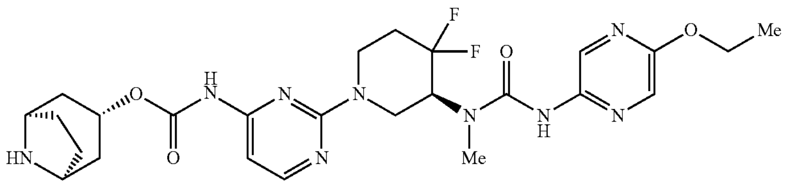 [SMILES: CCOc1cnc(NC(=O)N(C)[C@H]2CN(c3nccc(NC(=O)O[C@H]4C[C@H]5CC[C@@H](C4)N5)n3)CCC2(F)F)cn1] | 562.3 | 562.5 | 11 |

TABLE 5-continued
| Ex. No. | Chemical Structure | [M + H] Calcd. | [M + H] Found | Procedure Example |
|---|---|---|---|---|
| 332 | 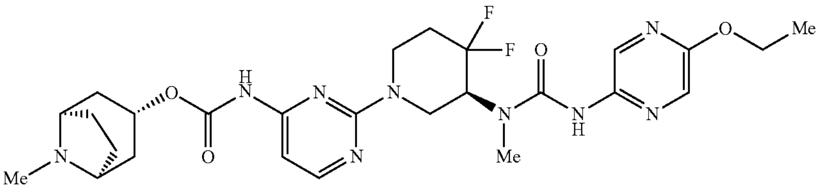 [SMILES: CCOc1cnc(NC(=O)N(C)[C@H]2CN(c3nccc(NC(=O)O[C@H]4C[C@H]5CC[C@@H](C4)N5C)n3)CCC2(F)F)cn1] | 576.3 | 576.1 | 11 |
| 333 | 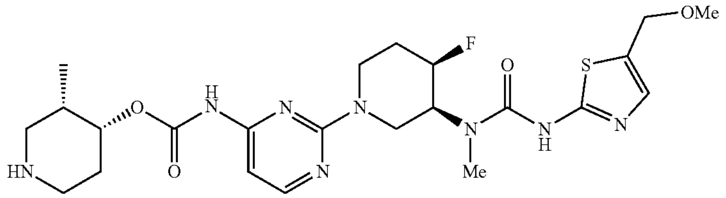 [SMILES: COCc1cnc(NC(=O)N(C)[C@H]2CN(c3nccc(NC(=O)O[C@@H]4CCNC[C@@H]4C)n3)CC[C@H]2F)s1] | 537.2 | 537.1 | 10 |
| 334 | 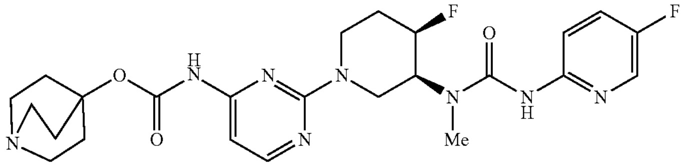 [SMILES: CN(C(=O)Nc1ccc(F)cn1)[C@H]1CN(c2nccc(NC(=O)OC34CCN(CC3)CC4)n2)CC[C@H]1F] | 517.2 | 517.1 | 18 |
| 335 | 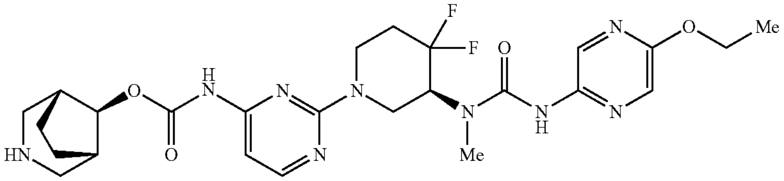 [SMILES: CCOc1cnc(NC(=O)N(C)[C@H]2CN(c3nccc(NC(=O)O[C@@H]4[C@@H]5CC[C@H]4CNC5)n3)CCC2(F)F)cn1] | 562.3 | 562.5 | 11 |
| 336 | 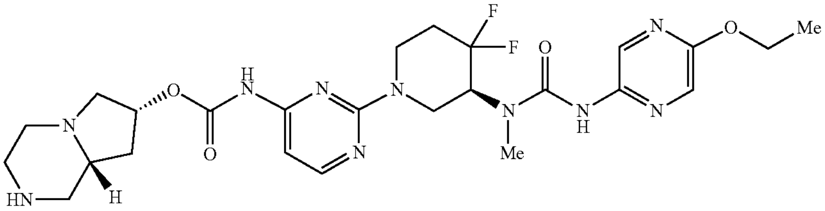 [SMILES: CCOc1cnc(NC(=O)N(C)[C@H]2CN(c3nccc(NC(=O)O[C@@H]4C[C@@H]5CNCCN5C4)n3)CCC2(F)F)cn1] | 577.3 | 577.3 | 11 |
| 337 | 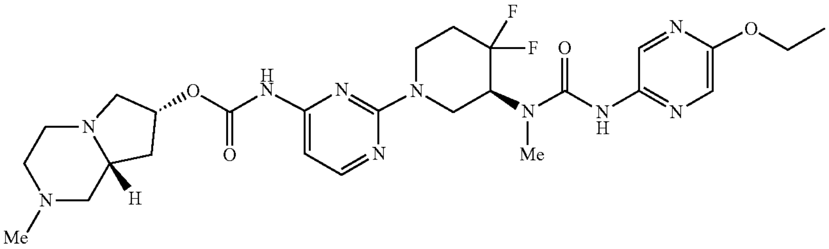 [SMILES: CCOc1cnc(NC(=O)N(C)[C@H]2CN(c3nccc(NC(=O)O[C@@H]4C[C@@H]5CN(C)CCN5C4)n3)CCC2(F)F)cn1] | 591.3 | 591.1 | 11 |
| 338 | 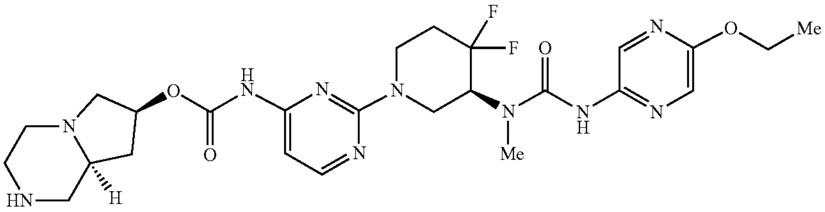 [SMILES: CCOc1cnc(NC(=O)N(C)[C@H]2CN(c3nccc(NC(=O)O[C@H]4C[C@H]5CNCCN5C4)n3)CCC2(F)F)cn1] | 577.3 | 577.3 | 11 |

TABLE 5-continued
| Ex. No. | Chemical Structure | [M + H] Calcd. | [M + H] Found | Procedure Example |
|---|---|---|---|---|
| 339 | 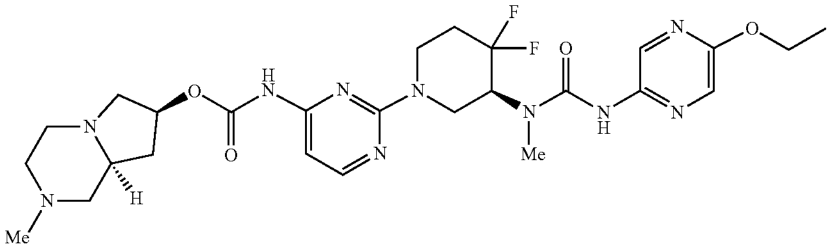 [SMILES: CCOc1cnc(NC(=O)N(C)[C@H]2CN(c3nccc(NC(=O)O[C@H]4C[C@H]5CN(C)CCN5C4)n3)CCC2(F)F)cn1] | 591.3 | 591.1 | 11 |
| 340 | 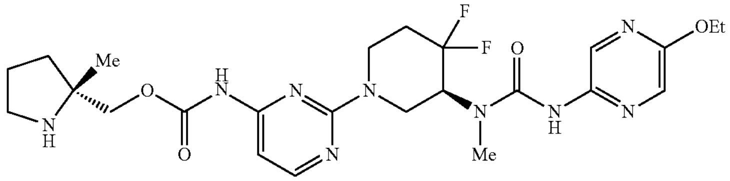 [SMILES: CCOc1cnc(NC(=O)N(C)[C@H]2CN(c3nccc(NC(=O)OC[C@@]4(C)CCCN4)n3)CCC2(F)F)cn1] | 550.3 | 550.3 | 11 |
| 341 | 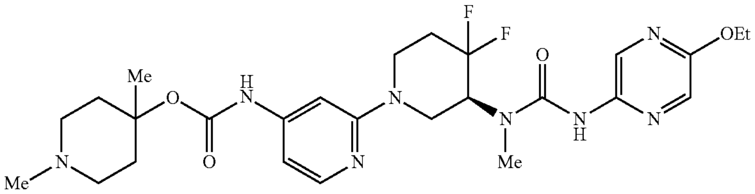 [SMILES: CCOc1cnc(NC(=O)N(C)[C@H]2CN(c3cc(NC(=O)OC4(C)CCN(C)CC4)ccn3)CCC2(F)F)cn1] | 563.3 | 563.3 | 26 |
| 342 | 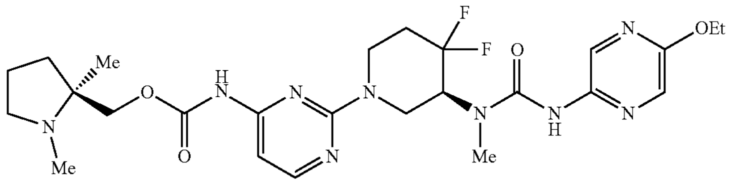 [SMILES: CCOc1cnc(NC(=O)N(C)[C@H]2CN(c3nccc(NC(=O)OC[C@]4(C)CCCN4C)n3)CCC2(F)F)cn1] | 564.3 | 564.3 | 18 |
| 343 | 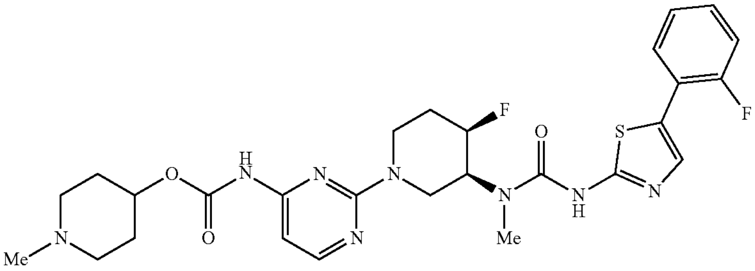 [SMILES: CN1CCC(OC(=O)Nc2ccnc(N3CC[C@@H](F)[C@@H](N(C)C(=O)Nc4ncc(-c5ccccc5F)s4)C3)n2)CC1] | 587.3 | 587.3 | 18 |
| 344 | 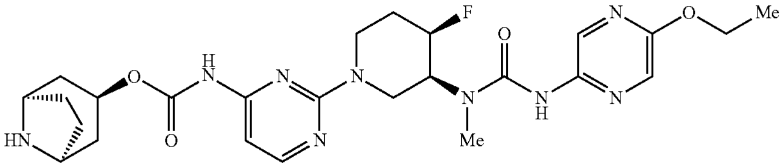 [SMILES: CCOc1cnc(NC(=O)N(C)[C@H]2CN(c3nccc(NC(=O)O[C@@H]4C[C@H]5CC[C@@H](C4)N5)n3)CC[C@H]2F)cn1] | 544.3 | 544.3 | 18 |
| 345 | 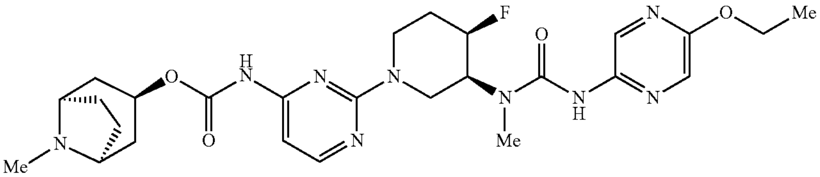 [SMILES: CCOc1cnc(NC(=O)N(C)[C@H]2CN(c3nccc(NC(=O)O[C@@H]4C[C@H]5CC[C@@H](C4)N5C)n3)CC[C@H]2F)cn1] | 558.3 | 558.3 | 18 |

TABLE 5-continued
| Ex. No. | Chemical Structure | [M + H] Calcd. | [M + H] Found | Procedure Example |
|---|---|---|---|---|
| 346 | 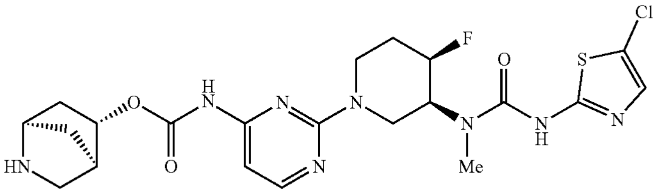 [SMILES: CN(C(=O)Nc1ncc(Cl)s1)[C@H]1CN(c2nccc(NC(=O)O[C@H]3C[C@H]4C[C@@H]3CN4)n2)CC[C@H]1F] | 525.2 | 525.2 | 10 |
| 347 | 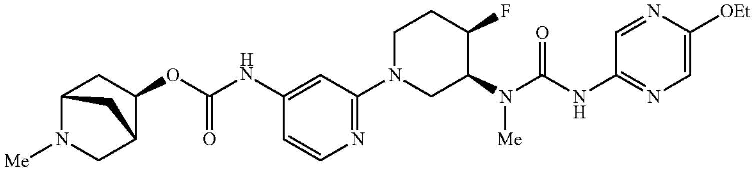 [SMILES: CCOc1cnc(NC(=O)N(C)[C@H]2CN(c3cc(NC(=O)O[C@@H]4C[C@@H]5C[C@H]4CN5C)ccn3)CC[C@H]2F)cn1] | 543.3 | 543.3 | 132 |
| 348 | 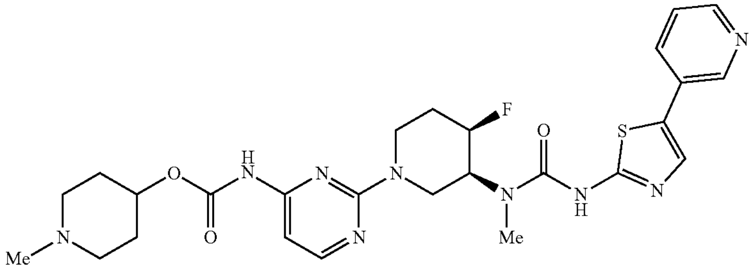 | 570.3 | 570.3 | 18 |
| 349 | 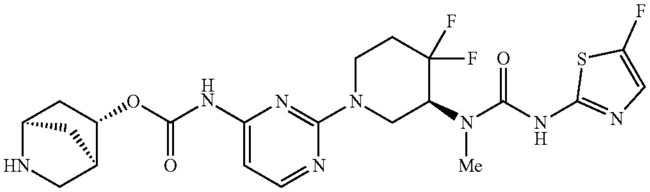 [SMILES: CN(C(=O)Nc1ncc(F)s1)[C@H]1CN(c2nccc(NC(=O)O[C@H]3C[C@H]4C[C@@H]3CN4)n2)CCC1(F)F] | 527.2 | 527.2 | 28 |
| 350 | 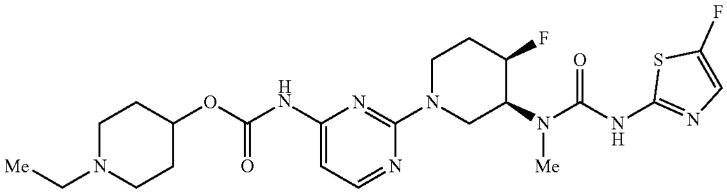 [SMILES: CCN1CCC(OC(=O)Nc2ccnc(N3CC[C@@H](F)[C@@H](N(C)C(=O)Nc4ncc(F)s4)C3)n2)CC1] | 525.3 | 525.3 | 18 |
| 351 | 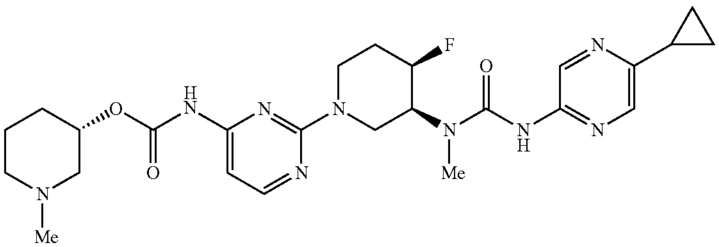 [SMILES: CN1CCC[C@H](OC(=O)Nc2ccnc(N3CC[C@@H](F)[C@@H](N(C)C(=O)Nc4cnc(C5CC5)cn4)C3)n2)C1] | 528.3 | 528.1 | 18 |

Example 352: 2-[(S)-4,4-difluoro-3-[1-methyl-3-(1,3-thiazol-2-yl)ureido]-1-piperidyl]-4-pyrimidinyl (1S,4S,5R)-2-methyl-2-azabicyclo[2.2.1]heptane-5-carbamate

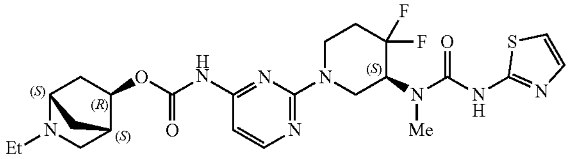

The title compound was synthesized in a similar fashion to Example 11 using tert-butyl (1S,4R,6R)-6-hydroxy-2-azabicyclo[12.2.1]heptane-2-carboxylate in Step 5 and using (N-2-thiazolyl)carbamic acid phenyl ester in Step 9, which was prepared in a similar fashion to Example 1 Step 4). The N-ethyl group was installed in step 8, part 2 by using acetaldehyde instead of paraformnaldehyde. $^1$H NMR (400 MHz, MeOH-$d_3$) δ 8.23 (d, J=5.7 Hz, 1H), 7.25 (bs, 1H), 7.22 (d, J=5.7 Hz, 1H), 6.89 (bs, 1H), 4.84-4.64 (m, 3H), 3.98 (s, 1H), 3.46 (t, J=12.1 Hz, 1H), 3.23 (m, 1H), 3.24-3.05 (m, 6H), 3.02-2.89 (m, 2H), 2.82 (t, J=3.0 Hz, 1H), 2.54-2.36 (m, 1H), 2.17 (d, J=6.2 Hz, 1H), 2.11-1.89 (m, 3H), 1.82 (d, J=15.5 Hz, 1H), 1.26 (t, J=7.2 Hz, 3H). ESI MS $[M+H]^+$ for $C_{23}H_{30}N_8F_2O_3S$, calcd 537.2, found 537.2.

Example A: N-{2-[(R)-3-[3-(5-ethoxy-2-pyrazinyl)-1-methylureido]-1-piperidyl]-4-pyridyl}-(1R,3S,4S)-2-azabicyclo[2.2.1]heptane-3-carboxamide

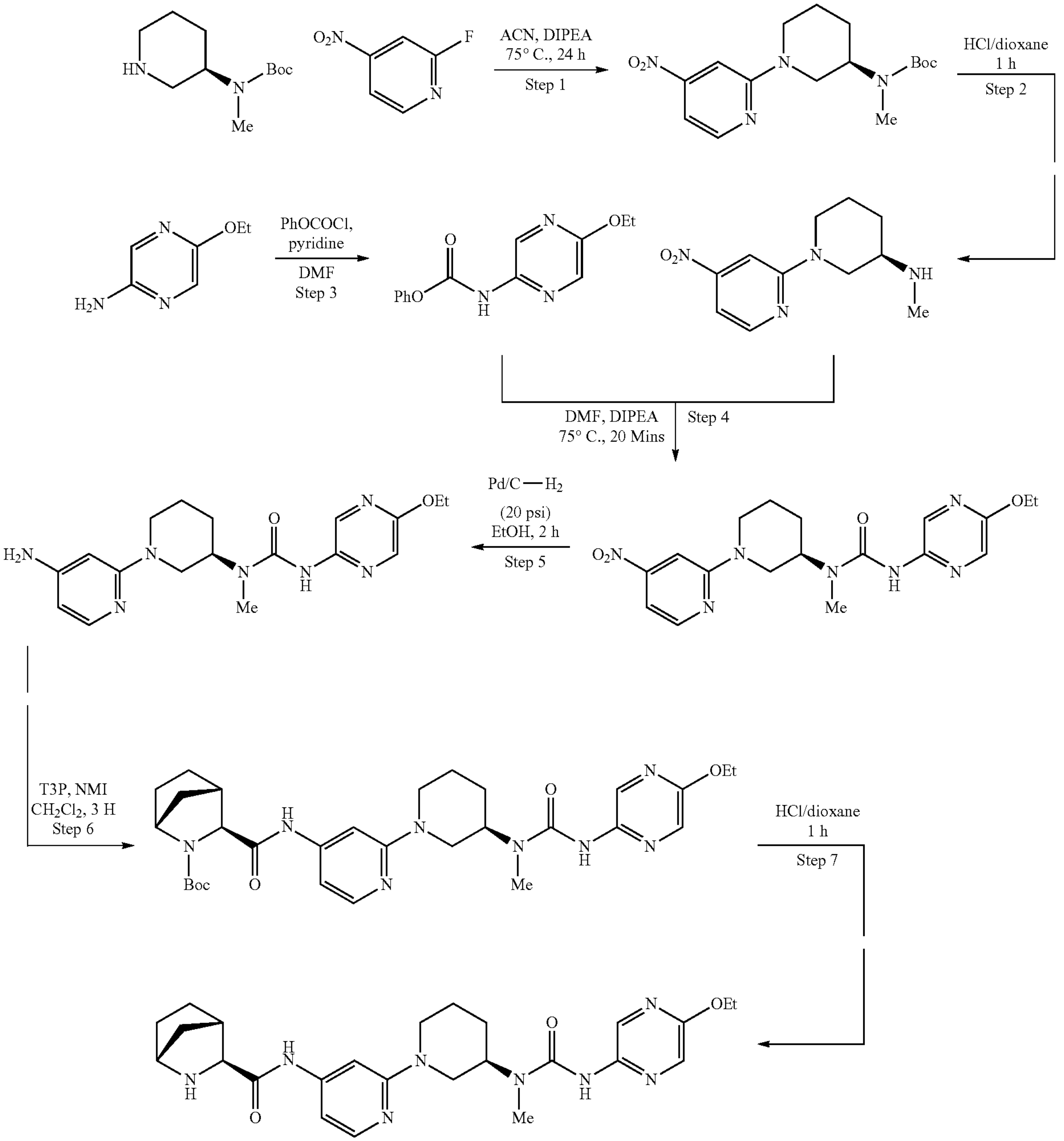

Step 1: To a stirred solution of 2-fluoro-4-nitropyridine (1.2 g, 8.4 mmol) in $CH_3CN$ (6 ml) were added 1,1-dimethylethyl N-methyl-N-(3R)-3-piperidinylcarbamate (1.45 g, 6.8 mmol) and diisopropylethylamine (3.2 g, 24.8 mmol) and heated at 75° C. for 24 h under $N_2$. After cooling to room temperature, 20 mL EtOAc was added. The organic mixture was washed with water (3×20 mL), dried over $Na_2SO_4$ and concentrated. The resulting residue a was purified by flash column chromatography (silica gel; gradient: 0% to 50% EtOAc in hexanes) to get desired compound.

Step 2: To the intermediate obtained from step 1 (1.65 g, 5.0 mmol) was dissolved in $CH_2Cl_2$ (5 mL) and was added 6 mL of HCl/dioxane (4 M) dropwise at room temperature. The reaction was stirred for 2 h and then concentrated under reduced pressure. This material was used in the next step without further purification.

Step 3: To a stirred solution of 2-amino-5-ethoxypyrazine (25 g, 180 mmol) in 500 mL DMF was added pyridine (29 mL, 360 mmol). The mixture was cooled to ° C. and phenyl chloroformate (29 mL, 234 mmol) was added dropwise. After complete addition, the reaction was allowed to raise to room temperature over a period of 2 h. Product was precipitated by slow addition of 500 mL of distilled water, which was separated by filtration. The filter cake was washed with 500 mL of distilled water and dried under vacuum to obtain the desired product in quantitative yield. The crude material thus obtained was taken to next step without further purification.

Step 4: To a stirred solution of product obtained from Step 2 (1 g, 3.7 mmol) in DMF (5 mL) were added product obtained from Step 3 (950 mg, 2.7 mmol) and diisopropylethylamine (710 mg, 5.4 mmol) and heated at 75° C. for 20 minutes. After cooling to room temperature, 20 mL EtOAc was added. The organic mixture was washed with water (3×20 mL), dried over $Na_2SO_4$ and concentrated. The resulting residue a was purified by flash column chromatography (silica gel; gradient: 0% to 80% EtOAc in hexanes) to afford the desired compound.

Step 5: In Parr hydrogenator, a solution of compound obtained from step 4 (1.3 g, 3.2 mmol) in ethanol (10 mL) was added Pd/C (130 mg, 10%). After stirring at 20 psi $H_2$ atmosphere for 2 h, the reaction mixture was filtered through CELITE®. The filtrate was concentrated under reduced pressure to obtain the desired product. This material was used in the next step without further purification.

Step 6: To a stirred solution of amine intermediate from step 5 (150 mg, 0.4 mmol) (1R,3S,4S)-2-azabicyclo[2.2.1]heptane-3-carboxylic acid (68 mg, 0.48 mmol in DCM (5 mL) were added T3P (382 mg, 0.6 mmol (50% solution in Ethyl Acetate)) and 1-methylimidazole (99 mg, 1.2 mmol). The reaction mixture was stirred at RT for 3 h. The resulting solution was directly loaded on to the column and purified by flash column chromatography (silica gel; gradient: 70% to 100% Hexane in EtOAc) to afford the desired compound.

Step 7: To the Boc-protected intermediate obtained from step 6 (100 mg, 1.6 mmol) was dissolved in $CH_2Cl_2$ (1 mL) and was added 2 mL of HCl/dioxane (4 M) dropwise at room temperature. The reaction was stirred for 2 h and then concentrated under reduced pressure. The crude material was purified by reverse phase preparative HPLC to afford the desired compound.

$^1H$ NMR (400 MHz, DMSO-$d_6$) δ 10.02 (s, 1H), 9.05 (s, 1H), 8.59 (d, J=1.5 Hz, 1H), 8.06 (d, J=5.6 Hz, 1H), 8.02 (d, J=1.5 Hz, 1H), 7.15 (d, J=1.7 Hz, 1H), 7.05 (dd, J=5.6, 1.6 Hz, 1H), 4.30 (q, J=7.0 Hz, 2H), 4.16 (d, J=7.6 Hz, 2H), 4.02 (s, 1H), 3.49 (s, 1H), 3.29 (s, 1H), 3.20 (s, 1H), 2.92 (s, 4H), 2.78 (t, J=12.7 Hz, 1H), 2.58 (s, 1H), 1.89-1.69 (m, 3H), 1.58 (dt, J=21.7, 7.0 Hz, 5H), 1.33 (t, J=7.1 Hz, 4H), 1.13 (d, J=9.7 Hz, 1H). ESI MS $[M+H]^+$ for $C_{25}H_{34}N_8O_3$, calcd 495.3, found 495.1.

Example B: N-{2-[(R)-3-[3-(5-ethoxy-2-pyrazinyl)-1-methylureido]-1-piperidyl]-4-pyridyl}-(1S,3R,4R)-2-azabicyclo[2.2.1]heptane-3-carboxamide

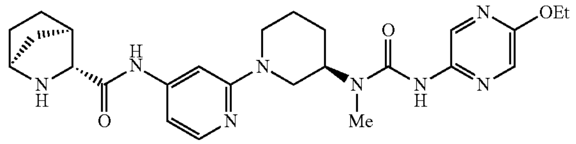 [SMILES: CCOc1cnc(NC(=O)N(C)[C@@H]2CCCN(c3cc(NC(=O)[C@@H]4N[C@H]5CC[C@@H]4C5)ccn3)C2)cn1]

The title compound was synthesized in a similar fashion to Example 1. $^1H$ NMR (400 MHz, DMSO-$d_6$) δ 9.99 (s, 1H), 9.05 (s, 1H), 8.59 (d, J=1.5 Hz, 1H), 8.06 (d, J=5.6 Hz, 1H), 8.02 (d, J=1.5 Hz, 1H), 7.16 (d, J=1.6 Hz, 1H), 7.04 (dd, J=5.6, 1.6 Hz, 1H), 4.30 (q, J=7.0 Hz, 2H), 4.15 (t, J=9.9 Hz, 2H), 4.02 (s, 1H), 3.46 (s, 1H), 3.17 (s, 1H), 2.92 (m, 4H), 2.78 (t, J=12.7 Hz, 1H), 2.58 (d, J=3.6 Hz, 1H), 1.90-1.68 (m, 3H), 1.67-1.36 (m, 3H), 1.33 (m, 5H), 1.12 (m, 2H). ESI MS $[M+H]^+$ for $C_{25}H_{34}N_8O_3$, calcd 495.3, found 495.2.

Example C: N-{2-[(R)-3-[3-(5-cyclopropyl-2-pyridyl)-1-methylureido]-1-piperidyl]-4-pyridyl}-(1S,3R,4R)-2-azabicyclo[2.2.1]heptane-3-carboxamide

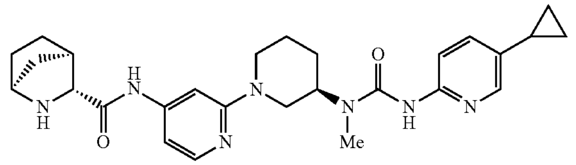 [SMILES: CN(C(=O)Nc1ccc(C2CC2)cn1)[C@@H]1CCCN(c2cc(NC(=O)[C@@H]3N[C@H]4CC[C@@H]3C4)ccn2)C1]

The title compound was synthesized in a similar fashion to Example 1 using 2-amino-5-cyclopropyl pyridine as a starting material in step 3. $^1H$ NMR (400 MHz, DMSO-$d_6$) δ 10.01 (s, 1H), 8.90 (s, 1H), 8.15-8.02 (m, 2H), 7.73 (d, J=8.7 Hz, 1H), 7.33 (dd, J=8.7, 2.5 Hz, 1H), 7.16 (d, J=1.6 Hz, 1H), 7.04 (dd, J=5.7, 1.5 Hz, 1H), 4.14 (t, J=15.4 Hz, 2H), 4.00 (s, 1H), 3.46 (s, 1H), 3.19 (s, 1H), 2.91 (m, 4H), 2.79 (t, J=12.8 Hz, 1H), 2.59 (d, J=3.6 Hz, 1H), 1.89 (ddd, J=13.5, 8.7, 5.1 Hz, 1H), 1.77 (t, J=12.0 Hz, 2H), 1.64-1.40 (m, 5H), 1.29 (d, J=9.9 Hz, 1H), 1.12 (d, J=9.7 Hz, 1H), 0.97-0.88 (m, 2H), 0.75-0.59 (m, 2H). ESI MS $[M+H]^+$ for $C_{27}H_{37}N_7O_2$, calcd 491.1, found 491.2.

Example D: N-{2-[(S)-3-[3-(5-ethoxy-2-pyrazinyl)-1-methylureido]-4,4-difluoro-1-piperidyl]-4-pyridyl}-(1R,3S,4S)-2-azabicyclo[2.2.1]heptane-3-carboxamide

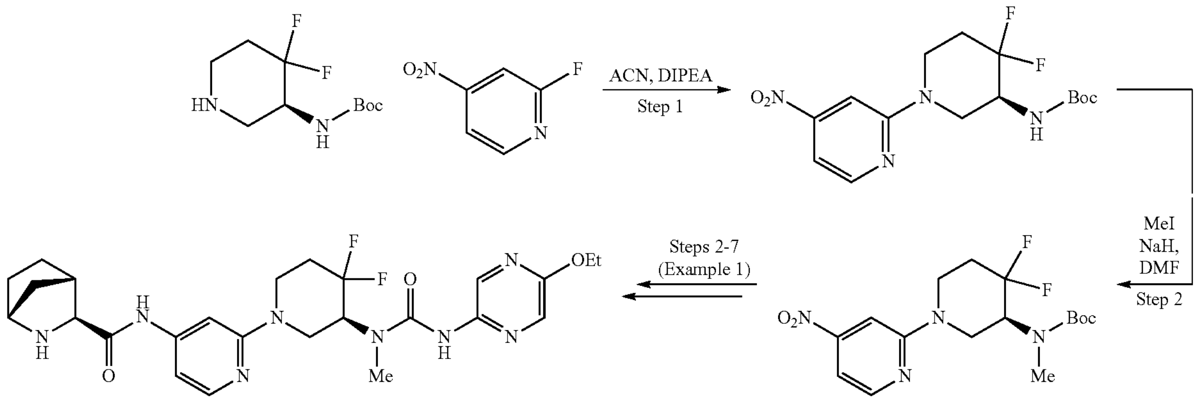 [SMILES: CC(C)(C)OC(=O)N[C@H]1CNCCC1(F)F ; O=[N+]([O-])c1ccnc(F)c1 ; "ACN, DIPEA" ; CC(C)(C)OC(=O)N[C@H]1CN(c2cc([N+](=O)[O-])ccn2)CCC1(F)F ; CCOc1cnc(NC(=O)N(C)[C@H]2CN(c3cc(NC(=O)[C@H]4N[C@@H]5CC[C@H]4C5)ccn3)CCC2(F)F)cn1 ; CN(C(=O)OC(C)(C)C)[C@H]1CN(c2cc([N+](=O)[O-])ccn2)CCC1(F)F]

Step 1: The $S_NAr$ reaction was performed following protocol for the synthesis of Example 1 (Step 1)

Step 2: To the intermediate obtained from step 1 (1.8 g, 5.0 mmol) was dissolved in DMF (12 mL) at β-5° C. and treated with a 60% suspension of sodium hydride (320 mg, 8.0 mmol). The reaction mixture was allowed to warm to room temperature for 10 min then re-cooled and iodomethane (1.42 g, 10.0 mmol) added and was stirred at RT for 12 h. The reaction mixture was quenched with 30 mL of ice-cold water and the resultant precipitate formed in the reaction mixture was collected via filtration. The residue was further purified by flash column chromatography (silica gel; gradient: 0% to 80% EtOAc in hexanes) to afford the desired compound.

The title compound was synthesized similar to Example 1 (Step 2-7). $^1H$ NMR (400 MHz, Chloroform-d) δ 9.85 (s, 1H), 8.82 (d, J=1.5 Hz, 1H), 8.20 (d, J=5.5 Hz, 1H), 7.87 (d, J=1.6 Hz, 1H), 7.72 (s, 1H), 7.45 (s, 1H), 6.68 (dd, J=5.6, 1.8 Hz, 1H), 4.63-4,57 (m, 1H), 4.49-4.45 (m, 1H), 4.36 (q, J=7.0 Hz, 2H), 4.32-4.23 (m, 1H), 3.61 (s, 1H), 3.38-3.29 (m, 2H), 3.29-3.20 (m, 1H), 3.16 (s, 3H), 2.84 (s, 1H), 2.26-2.14 (m, 1H), 2.07-1.95 (m, 1H), 1.78-1.71 (m, 1H), 1.64 (s, 2H), 1.57-1.52 (m, 1H), 1.45-1.41 (m, 1H), 1.39 (t, J=7.1 Hz, 3H), 1.33-1.16 (m, 2H). ESI MS $[M+H]^+$ for $C_{25}H_{32}F_2N_8O_3$, calcd 530.58, found 531.2.

Example E: N-(2-{(R)-3-[3-(5-ethoxy-2-pyrazinyl)-1-methylureido]-1-piperidyl}-4-pyridyl)-(2S,3R)-3-hydroxy-2-pyrrolidinecarboxamide

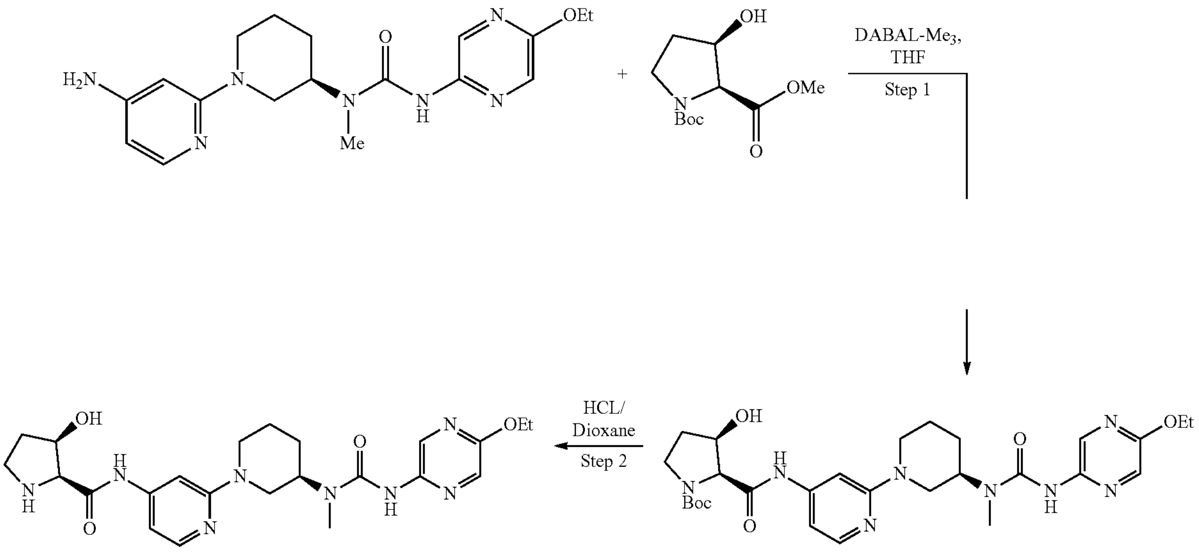

Step 1: A mixture of amine intermediate (111 mg, 0.3 mmol) from step 5, Example 1 (2S,3R)-1-tert-Butyl 2-methyl 3-hydroxypyrrolidine-1,2-dicarboxylate (147 mg, 0.6 mmol), and DABAL-Me3 (154 mg, 0.6 mmol) was refluxed in THF (3 mL) for 12 h. The mixture was cooled, filtered through CELITE®, and concentrated. The residue was purified by flash column chromatography (silica gel; gradient: 0% to 30% MeOH in DCM) to afford the intermediate product.

Step 2: To a stirred solution of amide intermediate (100 mg, 0.17 mmol) from step 1 was dissolved in dioxane (1 mL). A 4 M solution of HCl in dioxane (2 mL) was added dropwise at room temperature. The reaction was allowed to stir for 1 h, and the resultant precipitate formed in the reaction mixture was collected via filtration. The crude precipitate was then subjected to reverse phase HPLC for purification, which afforded the desired product. $^1$H NMR (400 MHz, Methanol-$d_4$) δ 8.56 (d, J=1.5 Hz, 1H), 8.14 (d, J=5.7 Hz, 1H), 7.95 (d, J=1.5 Hz, 1H), 7.30 (d, J=1.7 Hz, 1H), 6.88 (dd, J=5.7, 1.7 Hz, 1H), 4.61 (td, J=4.7, 1.9 Hz, 1H), 4.35 (q, J=7.0 Hz, 2H), 4.27 (d, J=12.7 Hz, 1H), 4.17-4.01 (m, 2H), 3.81 (d, J=4.7 Hz, 1H), 3.34-3.20 (m, 2H), 3.10-2.87 (m, 6H), 2.13-1.53 (m, 6H), 1.39 (t, J=7.0 Hz, 3H). ESI MS $[M+H]^+$ for $C_{23}H_{32}N_8O_4$, calcd 485.3, found 485.2.

Example F: N-{2-[(2R,3R)-3-[3-(5-ethoxy-2-pyrazinyl)-1-methylureido]-2-ethyl-1-piperidyl]-4-pyridyl}-(S)-4-methyl-3-morpholinecarboxamide

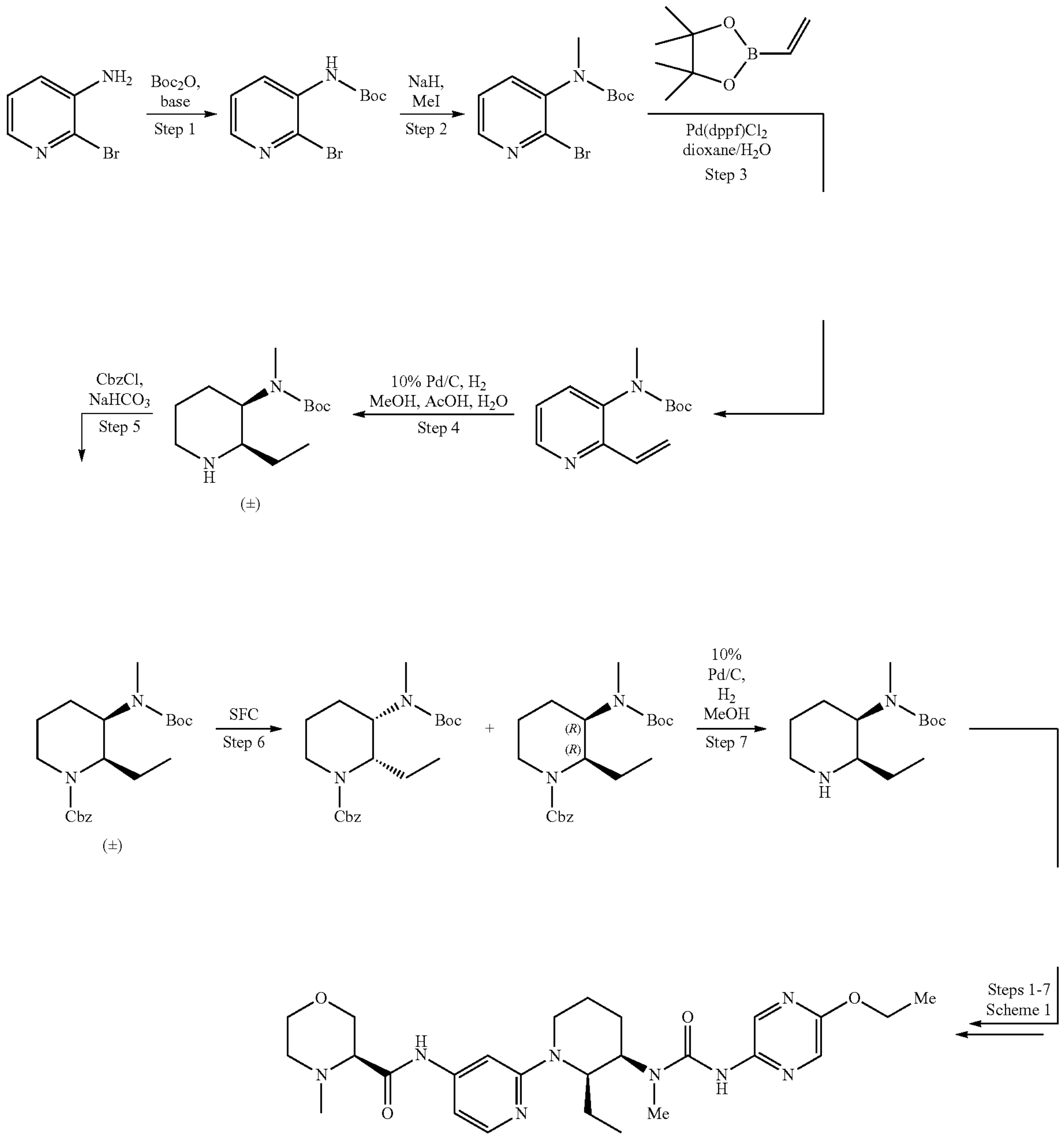

Step 1: To a stirred solution of 2-bromopyridin-3-amine (100 g, 1 equiv.) in dry THF (1 L, 10 V) at 0 to −20° C. was added slowly a 2 M solution of sodium bis(trimethylsilyl) amide in THF (578 mL, 2 equiv.) and stirred for 30 min at the same temperature. A solution of $Boc_2O$(141 g, 1.12 equiv.) in dry THF 140 mL (1 V) was added to the reaction mass at the same temperature and stirred for 1-2 h. After completion of the reaction (check the TLC) pour the reaction mass into the saturated $NH_4Cl$ solution (Reverse quenching), and extract with EtOAc (2×500 mL). The organic layers were combined, dried over $Na_2SO_4$, concentrated under vacuum, and purified by silica gel (100-200 mesh) column chromatography (EtOAc in Hexane: 0 to 30%) to afford the desired product.

Step 2: To a stirred solution of the product from step 1 (90 g, 1 equiv.) in dry THF (1080 mL, 12 V) was added 60% NaH (19.8 g, 1.5 equiv.) at 0° C. and stirred for 30 min. Then, iodomethane (70 g, 1.5 equiv.) was added at 0° C. and stirred at room temperature for another 48 h. The reaction mixture was poured into the aqueous ammonium chloride solution (Reverse quenching) at 0° C. and extracted with EtOAc (2×500 mL). The combined organic layer was dried over $Na_2SO_4$, concentrated under vacuum, and purified by silica gel (100-200 mesh) column chromatography (EtOAc in Hexane: 0 to 25%) to afford the desired product.

Step 3: To a stirred solution of the product from step 2 (83 g, 1 equiv.) and vinylboronic acid pinacol ester (58 g, 1.3 equiv.) in Dioxane (299 mL, 3.6 V)/$H_2O$ (83 mL, 1 V) was added $PdCl_2$(dppf) (10.6 g, 0.05 equiv.) and $K_2CO_3$ (80 g, 2 equiv.). After degassing for 25 min with $N_2$, the reaction mixture was heated to 100° C. and stirred for 5 h. The reaction mixture was cooled down to RT, evaporated the solvent under reduced pressure, diluted with water (166 mL, 2 V), and extracted with EtOAc (2×250 mL). The combined organic layer was dried over $Na_2SO_4$, concentrated under vacuum, and purified by silica gel (100-200 mesh) column chromatography (EtOAc in Hexane: 0 to 15%) to afford the desired product.

Step 4: In Parr hydrogenator, a solution of the product from step 3 (15 g, 1 equiv.) in ethanol (75 mL, 5 V), AcOH (7.5 mL, 0.5V), and water (7.5 mL, 0.5 V) was added 10% Pd/C (3 g, 20% wt/wt) at room temperature. After stirring the reaction mass under $H_2$ pressure (5-7 Kg) for 2 days, the reaction mixture was filtered through CELITE®. The filtrate was concentrated under vacuum, and purified by neutral aluminium oxide column chromatography (MeOH in DCM: 0 to 50%) to afford the desired racemic product.

Step 5: To a stirred solution of the racemic product from step 4 (12 g, 1 equiv.) in dichloromethane (120 mL, 10 V) was added triethyl amine (12.6 g, 2.5 equiv.) followed by Benzyl chloroformate at ° C. and stirred the reaction mass for 12 h. Diluted the reaction mass with water (100 mL) and extracted with dichloromethane (100 mL). The organic layer was dried over $Na_2SO_4$, concentrated under vacuum, and purified by silica gel (100-200 mesh) column chromatography (EtOAc in Hexane: 0 to 30%) to afford the desired product.

Step 6: The racemic compound from step 5 was used for the chiral separation using the following conditions.

Chiral HPLC Conditions:

Column: I-Amylose-3

MOBILE PHASE-A: Hexane:IPA=90:10

Flow: 1.0 mL/min

UV: 215 nm

Step 6: In Parr hydrogenator, a solution of the R, R isomer (15 g, 1 equiv.) in methanol (150 mL, 10 V) was added 5% Pd/C (1.5 g, 10% wt/wt) at room temperature. After stirring the reaction mass under $H_2$ pressure (5 Kg) for 12 hours, the reaction mixture was filtered through CELITE®. The filtrate was concentrated under vacuum and purified by neutral aluminium oxide column chromatography (MeOH in DCM: 0 to 50%) to afford the desired product.

The title compound was synthesized in a similar fashion to Example 1 (Step 1-7). $^1H$ NMR (400 MHz, Methanol-$d_4$) δ 8.64 (d, J=1.5 Hz, 1H), 8.28 (d, J=5.9 Hz, 1H), 7.99 (d, J=1.5 Hz, 1H), 7.35 (d, J=1.8 Hz, 1H), 6.91 (dd, J=5.9, 1.7 Hz, 1H), 4.63 (d, J=11.3 Hz, 1H), 4.36 (q, J=7.0 Hz, 2H), 4.09 (dd, J=12.3, 4.4 Hz, 1H), 3.94 (dd, J=11.3, 3.6 Hz, 1H), 3.91-3.80 (m, 2H), 3.68 (td, J=11.4, 2.4 Hz, 1H), 3.59-3.48 (m, 1H), 3.20 (t, J=13.8 Hz, 1H), 3.06 (s, 1H), 2.99 (s, 3H), 2.97-2.83 (m, 2H), 2.38 (td, J=11.5, 3.4 Hz, 1H), 2.08 (ddd, J=13.9, 11.8, 7.0 Hz, 1H), 1.79 (d, J=13.0 Hz, 2H), 1.57 (tdd, J=14.1, 8.0, 4.1 Hz, 3H), 1.39 (t, J=7.0 Hz, 4H), 0.95-0.85 (m, 6H). ESI MS $[M+H]^+$ for $C_{26}H_{39}N_8O_4$, calcd 527.3, found 527.1.

Example G: (2-[(R)-3-{3-[5-(cyclopropylmethoxy)-2-pyridyl]-1-methylureido}-1-piperidyl]-4-(mesylamino)pyridine)

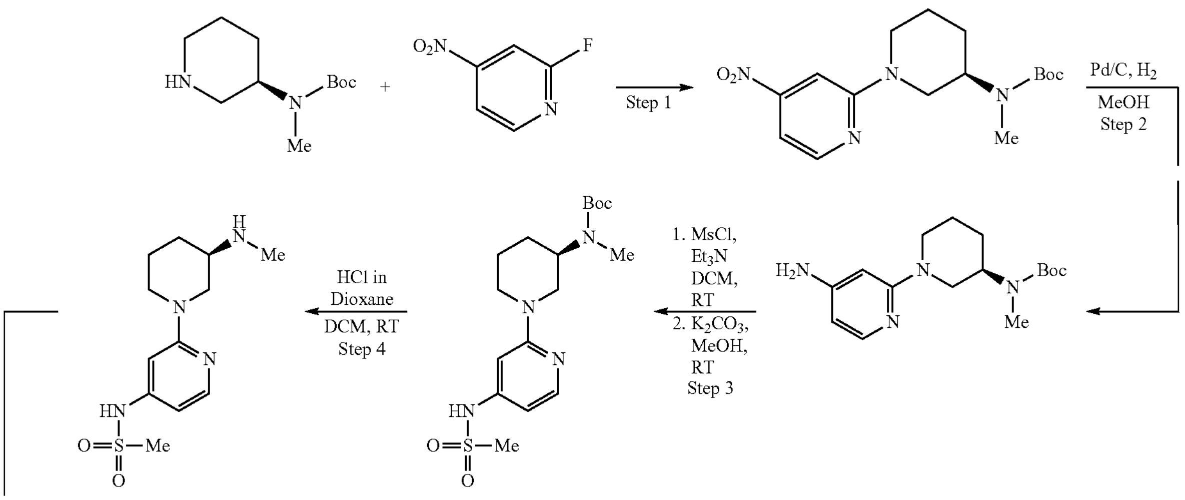

-continued

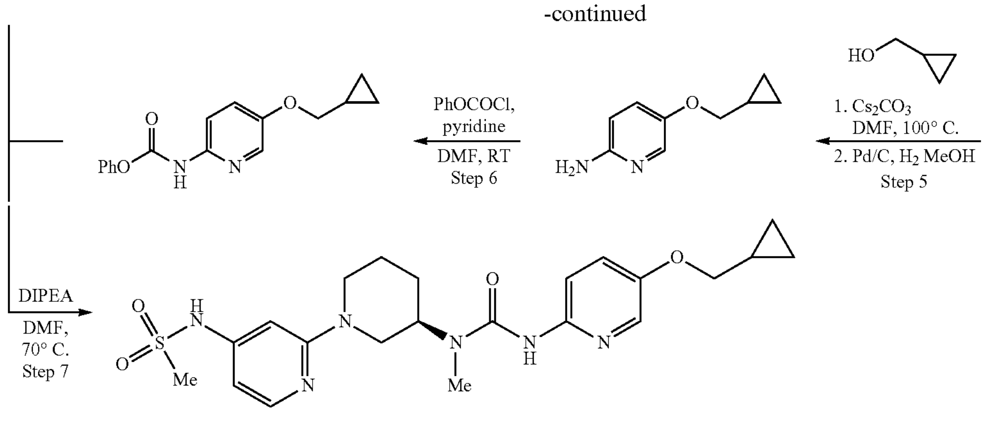

Step-1: This transformation was performed in a similar fashion to step 1 for the synthesis of Example 1.

Step-2: The intermediate from step 1 (20 g, 59.45 mmol) was dissolved in MeOH (20 mL) and taken in a parr shaker vessel under $N_2$ atmosphere. To this mixture palladium on activated carbon, 10% Pd, (50% wet with water) (1.3 g, 5.94 mmol) was carefully added. This vessel was connected to parr shaker hydrogenation apparatus and agitated for 1 hour. After confirming the completion of the reaction, the crude reaction mixture was filtered on a CELITE® pad and the CELITE® pad was washed with MeOH (20 mL) thrice and the organic layer was evaporated under reduced pressure to afford the intermediate. The crude product was directly used in the next step without further purification.

Step-3 (Part 1): The intermediate from step-2 (60 mg, 0.19 mmol) was taken in a dry screw capped reaction vial equipped with a stir bar and dissolved in dry DCM (3 mL). This reaction mixture was cooled to 0° C. and MsCl (14.4 µL, 0.18 mmol) was added dropwise followed by $Et_3N$ (41.2 µL, 0.29 mmol) under constant stirring. Then the reaction mixture was brought to room temperature and stirred for 2 hours. After the complete consumption of the starting material, the reaction was stopped, and the volatiles were evaporated under reduced pressure to afford the intermediate as bis mesylated product.

Step-3 (Part 2): The crude intermediate from step-3 (part 1) was then taken in a screw capped reaction vial with stir bar and dissolved in MeOH (3 mL). To this mixture $K_2CO_3$ (27 mg, 0.19 mmol) was added and stirred at room temperature for 1 hour. After confirming the completion of the reaction, the reaction was stopped, and the reaction mixture was filtered through a small pad of CELITE®. The CELITE® pad was washed with MeOH (5 mL) thrice and the organic layer was evaporated under reduced pressure to afford the mono mesylated intermediate. This crude product was directly used in the next step without further purification.

Step-4: This transformation was performed in a similar fashion to step-3 (part 2) protocol for the synthesis of Example 7. The crude HCl salt was directly used in the next step (step 7) without further purification.

Step-5 (Part 1): In a dry screw capped reaction vial equipped with a stir bar, 5-chloro-2-nitropyridine (1 g, 6.27 mmol) was taken and cyclopropylmethanol (452 mg, 6.27 mmol) followed by $Cs_2CO_3$ (6.12 g, 18.80 mmol) were added. This mixture was then dissolved in dry DMF (3 mL) and heated at 100° C. under constant stirring overnight. After confirming the completion of the reaction, the reaction mixture was brought to room temperature and 10 mL of water was added and extracted with DCM. The combined organic layers were washed with water (20 mL) thrice to remove the DMF and the combined organic layers were dried over anhydrous $Na_2SO_4$ and concentrated under reduced pressure. The crude product was directly used in the next step without further purification.

Step-5 (Part 2): This transformation was performed in a similar fashion to step 2 in the synthesis of Example 9 which was described above.

Step-6: This transformation was performed in a similar fashion to step-3 protocol for the synthesis of Example 1.

Step-7: This transformation was performed in a similar fashion to step 4 protocol for the synthesis of Example 7 to afford the desired final product. $^1H$ NMR (400 MHz, Chloroform-d) δ 8.54 (s, 1H), 8.27 (d, J=5.3 Hz, 1H), 7.97 (d, J=3.0 Hz, 1H), 7.86 (d, J=9.1 Hz, 1H), 7.21 (dd, J=9.1, 3.0 Hz, 1H), 6.54 (dd, J=5.7, 1.8 Hz, 1H), 6.42 (s, 1H), 4.21 (d, J=13.3 Hz, 2H), 4.07-3.93 (m, 1H), 3.78 (d, J=7.0 Hz, 2H), 3.06 (s, 3H), 2.98 (s, 3H), 2.89 (dt, J=14.2, 11.5 Hz, 2H), 2.01 (d, J=12.0 Hz, 1H), 1.93-1.77 (m, 2H), 1.69-1.53 (m, 2H), 1.34-1.20 (m, 2H), 0.69-0.59 (m, 2H), 0.34 (dt, J=5.9, 4.6 Hz, 2H). ESI MS $[M+H]^+$ for $C_{22}H_{31}N_6O_4S$, calcd 474.6, found 475.2.

Biological Assay Examples

Beta-Hexosaminidase Assay in LAD2 Mast Cells

Degranulation response in LAD2 mast cells (National Institutes of Health) was assessed by measuring the β-hexosaminidase levels released into the culture supernatant. Briefly, LAD2 cells (unmodified) were washed twice and resuspended in Tyrode's Solution, pH 7.4 (140 mM NaCl, 5 mM KCl, 2 mM $CaCl_2$.$_2H_2O$, $_2$ mM $MgCl_{26}H_2O$, 25 mM HEPES, and 10 mM D-glucose). Subsequently, 10,000 cells were seeded per well in 384-well plates. The cells were incubated with test compounds (starting at 10 µM) diluted in DMSO for 1 hour at 37° C. Following this preincubation, the cells were stimulated with 5.8 µM Substance P for 30 minutes at 37° C. to induce degranulation. The plates were centrifuged at 400×g for 5 min, after which 10 µL aliquots of the supernatants were collected and incubated with 10 µL of 4-methylumbelliferyl N-acetyl-p-D-glucosaminide (Sigma, cat #M-2133) in citrate-sodium phosphate buffer (pH 5.5) in black microtiter plates for 3 hours at 37° C. To terminate the reaction, 400 mM glycine (pH 10.7) was added to each well. Fluorescence intensity was measured using an excitation wavelength of 355 nm and emission wavelength of 460 nm. $IC_{50}$ values were determined by fitting the data to a standard 4-parameter logistic equation.

TABLE 6

| Potency of select compounds | |
|---|---|
| Example No. | Beta-Hexosaminidase assay in LAD2 mast cells ($IC_{50}$) |
| 1 | ++++ |
| 2 | +++ |
| 3 | ++++ |
| 4 | +++ |
| 5 | +++ |
| 6 | +++ |
| 7 | +++ |
| 8 | ++ |
| 9 | +++ |
| 10 | +++ |
| 11 | +++ |
| 12 | ++++ |
| 13 | +++ |
| 14 | ++++ |
| 15 | +++ |
| 16 | ++++ |
| 17 | +++ |
| 18 | +++ |
| 19 | +++ |
| 20 | +++ |
| 21 | +++ |
| 22 | ++ |
| 23 | +++ |
| 24 | +++ |
| 25 | +++ |
| 26 | +++ |
| 27 | ++ |
| 28 | +++ |
| 29 | +++ |
| 30 | +++ |
| 31 | +++ |
| 32 | +++ |
| 33 | +++ |
| 34 | +++ |
| 35 | +++ |
| 36 | ++ |
| 37 | ++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | + |
| 50 | +++ |
| 51 | +++ |
| 52 | +++ |
| 53 | +++ |
| 54 | +++ |
| 55 | +++ |
| 56 | +++ |
| 57 | ++++ |
| 58 | +++ |
| 59 | + |
| 60 | +++ |
| 61 | +++ |
| 62 | +++ |
| 63 | +++ |
| 64 | +++ |
| 65 | +++ |
| 66 | + |
| 67 | ++ |
| 68 | +++ |
| 69 | ++++ |
| 70 | ++++ |
| 71 | +++ |
| 72 | ++++ |

TABLE 6-continued

| Potency of select compounds | |
|---|---|
| Example No. | Beta-Hexosaminidase assay in LAD2 mast cells ($IC_{50}$) |
| 73 | ++++ |
| 74 | +++ |
| 75 | +++ |
| 76 | ++++ |
| 77 | +++ |
| 78 | ++++ |
| 79 | +++ |
| 80 | +++ |
| 81 | +++ |
| 82 | ++ |
| 83 | +++ |
| 84 | +++ |
| 85 | ++ |
| 86 | +++ |
| 87 | +++ |
| 88 | +++ |
| 89 | +++ |
| 90 | +++ |
| 91 | +++ |
| 92 | +++ |
| 93 | +++ |
| 94 | ++++ |
| 95 | +++ |
| 96 | ++++ |
| 97 | ++++ |
| 98 | +++ |
| 99 | ++++ |
| 100 | ++++ |
| 101 | ++++ |
| 102 | ++++ |
| 103 | + |
| 104 | ++++ |
| 105 | +++ |
| 106 | +++ |
| 107 | +++ |
| 108 | ++ |
| 109 | +++ |
| 110 | ++++ |
| 111 | +++ |
| 112 | ++++ |
| 113 | +++ |
| 114 | +++ |
| 115 | +++ |
| 116 | ++ |
| 117 | +++ |
| 118 | +++ |
| 119 | ++ |
| 120 | ++ |
| 121A | +++ |
| 121B | +++ |
| 122 | ++++ |
| 123 | ++++ |
| 124 | +++ |
| 125 | +++ |
| 126 | +++ |
| 127 | +++ |
| 128 | +++ |
| 129 | +++ |
| 130 | ++++ |
| 131 | ++++ |
| 132 | ++ |
| 133 | +++ |
| 134 | ++ |
| 135 | +++ |
| 136 | +++ |
| 137 | +++ |
| 138 | +++ |
| 139 | ++ |
| 140 | ++ |
| 141 | +++ |
| 142 | +++ |
| 143 | ++ |

TABLE 6-continued

| Potency of select compounds | |
|---|---|
| Example No. | Beta-Hexosaminidase assay in LAD2 mast cells ($IC_{50}$) |
| 144 | ++++ |
| 145 | ++ |
| 146 | +++ |
| 147 | ++++ |
| 148 | ++++ |
| 149 | +++ |
| 150 | +++ |
| 151 | +++ |
| 152 | +++ |
| 153 | +++ |
| 154 | ++ |
| 155 | +++ |
| 156 | +++ |
| 157 | ++++ |
| 158 | ++++ |
| 159 | +++ |
| 160 | +++ |
| 161 | +++ |
| 162 | ++++ |
| 163 | +++ |
| 164 | ++ |
| 165 | ++++ |
| 166 | +++ |
| 167 | +++ |
| 168 | ++++ |
| 169 | ++++ |
| 170 | +++ |
| 171 | ++++ |
| 172 | +++ |
| 173 | +++ |
| 174 | +++ |
| 175 | +++ |
| 176 | ++++ |
| 177 | +++ |
| 178 | ++++ |
| 179 | +++ |
| 180 | ++++ |
| 181 | ++++ |
| 182 | ++++ |
| 183 | + |
| 184 | ++++ |
| 185/186 less polar | +++ |
| 185/186 more polar | ++ |
| 187 | +++ |
| 188 | +++ |
| 189 | +++ |
| 190 | ++ |
| 191 | ++ |
| 192 | ++++ |
| 193 | ++++ |
| 194 | +++ |
| 195 | +++ |
| 196 | +++ |
| 197 | +++ |
| 198 | +++ |
| 199 | +++ |
| 200 | +++ |
| 201 | +++ |
| 202 | +++ |
| 203 | +++ |
| 204 | +++ |
| 205 | +++ |
| 206 | ++++ |
| 207 | ++ |
| 208 | +++ |
| 209 | +++ |
| 210 | +++ |
| 211 | ++++ |
| 212 | +++ |
| 213 | +++ |

TABLE 6-continued

| Potency of select compounds | |
|---|---|
| Example No. | Beta-Hexosaminidase assay in LAD2 mast cells ($IC_{50}$) |
| 214 | +++ |
| 215 | +++ |
| 216 | ++ |
| 217 | +++ |
| 218 | +++ |
| 219 | +++ |
| 220 | ++ |
| 221 | ++++ |
| 222 | ++++ |
| 223 | ++++ |
| 224 | ++++ |
| 225 | ++++ |
| 226 | +++ |
| 227 | +++ |
| 228 | ++ |
| 229 | +++ |
| 230 | +++ |
| 231 | +++ |
| 232 | +++ |
| 233 | ++++ |
| 234 | ++++ |
| 235 | ++++ |
| 236 | ++++ |
| 237 | ++++ |
| 238 | ++++ |
| 239 | ++++ |
| 240 | +++ |
| 241 | ++++ |
| 242 | +++ |
| 243 | ++ |
| 244 | ++++ |
| 245 | ++ |
| 246 | +++ |
| 247 | +++ |
| 248 | ++ |
| 249 | +++ |
| 250 | ++++ |
| 251 | +++ |
| 252 | +++ |
| 253 | +++ |
| 254 | ++ |
| 255 | ++++ |
| 256 | +++ |
| 257 | ++++ |
| 258 | ++++ |
| 259 | ++++ |
| 260 | ++++ |
| 261 | ++++ |
| 262 | +++ |
| 263 | ++++ |
| 264 | +++ |
| 265 | ++++ |
| 266 | ++++ |
| 267 | +++ |
| 268 | +++ |
| 269 | +++ |
| 270 | +++ |
| 271 | ++++ |
| 272 | ++++ |
| 273 | +++ |
| 274 | +++ |
| 275 | +++ |
| 276 | ++ |
| 277 | +++ |
| 278 | +++ |
| 279 | +++ |
| 280 | +++ |
| 281 | +++ |
| 282 | +++ |
| 283 | +++ |
| 284 | +++ |
| 285 | +++ |

TABLE 6-continued

Potency of select compounds

| Example No. | Beta-Hexosaminidase assay in LAD2 mast cells ($IC_{50}$) |
|---|---|
| 286 | +++ |
| 287 | +++ |
| 288 | ++ |
| 289 | +++ |
| 290 | +++ |
| 291 | +++ |
| 292 | +++ |
| 293 | + |
| 294 | +++ |
| 295 | +++ |
| 296 | +++ |
| 297 | +++ |
| 298 | +++ |
| 299 | ++++ |
| 300 | ++++ |
| 301 | +++ |
| 302 | ++++ |
| 303 | +++ |
| 304 | +++ |
| 305 | ++++ |
| 306 | ++++ |
| 307 | +++ |
| 308 | ++++ |
| 309 | ++++ |
| 310 | +++ |
| 311 | +++ |
| 312 | ++ |
| 313 | ++ |
| 314 | ++++ |
| 315 | ++++ |
| 316 | +++ |
| 317 | ++++ |
| 318 | ++++ |
| 319 | ++++ |
| 320 | +++ |
| 321 | +++ |
| 322 | +++ |
| 323 | ++ |
| 324 | +++ |
| 325 | +++ |
| 326 | +++ |
| 327 | ++ |
| 328 | +++ |
| 329 | +++ |
| 330 | +++ |
| 331 | +++ |
| 332 | +++ |
| 333 | +++ |
| 334 | ++ |
| 335 | +++ |
| 336 | ++ |
| 337 | ++ |
| 338 | +++ |
| 339 | +++ |
| 340 | +++ |
| 341 | +++ |
| 342 | +++ |
| 343 | +++ |
| 344 | +++ |
| 345 | +++ |
| 346 | ++++ |
| 347 | ++ |
| 348 | + |
| 349 | ++++ |
| 350 | ++++ |
| 351 | +++ |
| 352 | +++ |
| A | +++ |
| B | ++++ |
| C | ++++ |
| D | +++ |
| E | +++ |
| F | ++++ |
| G | +++ |

$IC_{50}$ values:
Less than 10 nM (++++),
10 nM to less than 100 nM (+++),
100 nM to 1 μM (++),
greater than 1 μM (+) (e.g., greater than 1 μM to less than 5 μM),
n.d. = not determined.

Certain Embodiments

Embodiment 1. A compound having a structure of Formula I:

(Formula I)

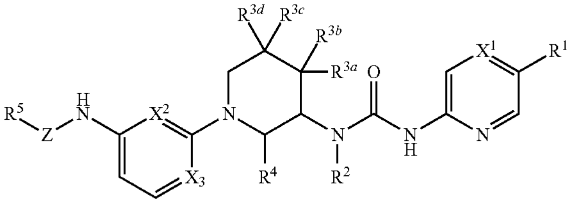

or a pharmaceutically acceptable salt thereof, wherein:

$X^1$ is $CX^{1a}$ or N; wherein:

$X^{1a}$ is H, halo, $C_1$-$C_6$ alkyl, $C_1$-$C_6$ haloalkyl, $C_1$-$C_6$ alkoxy, or $C_3$-$C_8$ cycloalkyl;

$X^2$ is CH or N;

$X^3$ is CH or N;

Z is —C(O)—, —OC(O)—, or —$S(O)_2$—;

$R^1$ is H, halo, $C_1$-$C_6$ alkyl, $C_1$-$C_6$ haloalkyl, $C_3$-$C_6$ cycloalkyl, —O—$R^{1a}$, or -Q-$R^{1b}$; wherein:

Q is $C_1$-$C_6$ alkylene, $C_1$-$C_6$ haloalkylene, or $C_3$-$C_6$ cycloalkylene;

$R^{5a}$ is $C_1$-$C_6$ alkyl, $C_3$-$C_6$ cycloalkyl, —($C_1$-$C_6$ alkylene)-($C_3$-$C_6$ cycloalkyl), or —($C_1$-$C_6$ alkylene)-(4- to 9-membered heterocycloalkyl), wherein the 4- to 9-membered heterocycloalkyl has 1-2 ring heteroatoms or heteroatom groups independently selected from N, O, S, and $S(O)_2$; and wherein $R^{1a}$ is unsubstituted or substituted with 1-3 halo; and $R^{1b}$ is $C_1$-$C_6$ alkoxy, or $C_3$-$C_6$ cycloalkyl; wherein $R^{1b}$ is unsubstituted or substituted with 1-3 halo;

$R^2$ is H or $C_1$-$C_3$ alkyl;

$R^{3a}$, $R^{3b}$, $R^{3c}$, $R^{3d}$ are each independently H, halo, or $C_1$-$C_6$ alkyl;

$R^4$ is H, $C_1$-$C_6$ alkyl, $C_1$-$C_6$ haloalkyl, $C_1$-$C_6$ alkoxy, or $C_1$-$C_6$ hydroxyalkyl;

$R^5$ is —Y—$R^{5a}$; wherein:

Y is absent or $C_1$-$C_6$ alkylene;

$R^{5a}$ is $C_1$-$C_6$ alkyl, $C_1$-$C_6$ alkoxy, $C_3$-$C_8$ cycloalkyl, phenyl, 5- to 10-membered heteroaryl, or 4- to 10-membered heterocycloalkyl; and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl; wherein the 5- to 10-membered heteroaryl has 1-4 ring heteroatoms independently selected from N, O, and S; and the 4- to 10-membered heterocycloalkyl has 1-3 ring heteroatoms or ring heteroatom groups independently selected from N, O, S, and $S(O)_2$; and $R^{5b}$ and $R^{5c}$ are independently selected from H and $C_1$-$C_3$ alkyl.

Embodiment 2. The compound of Embodiment 1, or a pharmaceutically acceptable salt thereof, wherein $X^1$ is N.

Embodiment 3. The compound of Embodiments 1 or 2, or a pharmaceutically acceptable salt thereof, wherein $X^2$ is CH.

Embodiment 4. The compound of any one of Embodiments 1-3, or a pharmaceutically acceptable salt thereof, wherein $X^3$ is N.

Embodiment 5. The compound of any one of Embodiments 1-4, or a pharmaceutically acceptable salt thereof, wherein Z is —C(O)—.

Embodiment 6. The compound of any one of Embodiments 1-5, or a pharmaceutically acceptable salt thereof, wherein:

$R^1$ is H, halo, $C_1$-$C_6$ alkyl, $C_1$-$C_6$ haloalkyl, $C_3$-$C_6$ cycloalkyl, —O—$R^{1a}$, or Q-$R^{1b}$; wherein Q is $C_1$-$C_6$ alkylene, $C_1$-$C_6$ haloalkylene, or $C_3$-$C_6$ cycloalkylene;

$R^{1a}$ is $C_1$-$C_6$ alkyl, $C_3$-$C_6$ cycloalkyl, —($C_1$-$C_6$ alkylene)-($C_3$-$C_6$ cycloalkyl), or —($C_1$-$C_6$ alkylene)-(4- to 9-membered heterocycloalkyl), wherein the 4- to 9-membered heterocycloalkyl has 1-2 ring heteroatoms independently selected from N and O; and wherein $R^{1a}$ is unsubstituted or substituted with 1-3 halo; and $R^{1b}$ is $C_1$-$C_6$ alkoxy; wherein $R^{1b}$ is unsubstituted or substituted with 1-3 halo.

Embodiment 7. The compound of any one of Embodiments 1-6, or a pharmaceutically acceptable salt thereof, wherein:

$R^1$ is $C_3$-$C_6$ cycloalkyl, —O—$R^{1a}$, or Q-$R^{1b}$;

Q is $C_1$-$C_6$ alkylene;

$R^{1a}$ is $C_1$-$C_6$ alkyl, $C_3$-$C_6$ cycloalkyl, or —($C_1$-$C_6$ alkylene)-($C_3$-$C_6$ cycloalkyl), wherein $R^{1a}$ is unsubstituted or substituted with 1-3 halo; and $R^{1b}$ is $C_1$-$C_6$ alkoxy; wherein $R^{1b}$ is unsubstituted or substituted with 1-3 halo.

Embodiment 8. The compound any one of Embodiments 1-7, or a pharmaceutically acceptable salt thereof, wherein $R^1$ is $C_3$-$C_6$ cycloalkyl or —O—$R^{1a}$; and $R^{1a}$ is $C_1$-$C_6$ alkyl or —($C_1$-$C_6$ alkylene)-($C_3$-$C_6$ cycloalkyl).

Embodiment 9. The compound of any one of Embodiments 1-8, or a pharmaceutically acceptable salt thereof, wherein $R^1$ is —O—$C_1$-$C_6$ alkyl.

Embodiment 10. The compound of any one of Embodiments 1-9, or a pharmaceutically acceptable salt thereof, wherein $R^2$ is $C_1$-$C_3$ alkyl.

Embodiment 11. The compound of any one of Embodiments 1-10, or a pharmaceutically acceptable salt thereof, wherein $R^{3a}$ and $R^{3b}$ are each independently H or halo; and $R^{3c}$ and $R^{3d}$ are H.

Embodiment 12. The compound of any one of Embodiments 1-11, or a pharmaceutically acceptable salt thereof, wherein $R^4$ is H or $C_1$-$C_6$ alkyl.

Embodiment 13. The compound of any one of Embodiments 1-12, or a pharmaceutically acceptable salt thereof, wherein $R^5$ is Y—$R^{5a}$; Y is absent or $C_1$-$C_6$ alkylene; $R^{5a}$ is a 4- to 10-membered heterocycloalkyl having 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl.

Embodiment 14. The compound of any one of Embodiments 1-13, or a pharmaceutically acceptable salt thereof, wherein $R^5$ is Y—$R^{5a}$, and Y is absent.

Embodiment 15. The compound of any one of Embodiments 1-12, or a pharmaceutically acceptable salt thereof, wherein $R^5$ is Y—$R^{5a}$; Y is absent; and $R^{5a}$ is $C_1$-$C_6$ alkyl, $C_3$-$C_8$ cycloalkyl, phenyl, 5- to 10-membered heteroaryl, or 4- to 10-membered heterocycloalkyl, wherein the 5- to 10-membered heteroaryl has 1-4 ring heteroatoms independently selected from N, O, and S; the 4- to 10-membered heterocycloalkyl has 1-3 ring heteroatoms or ring heteroatom groups independently selected from N, O, S, and $S(O)_2$, and $R^{5a}$ is unsubstituted or substituted with 1-4 substituents independently selected from oxo, halo, OH, $NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), —C(O)OH, —$C(O)NH_2$, and phenyl.

Embodiment 16. The compound of Embodiment 15, or a pharmaceutically acceptable salt thereof, wherein $R^{5a}$ is —$C_1$-$C_3$-alkyl, phenyl, pyridinyl, oxazolyl, imidazolyl, pyrazolyl, 1,2,4-triazolyl, cyclopropyl, cyclobutyl, cyclopentyl, cyclohexyl, bicyclo[1.1.1]pentyl, bicyclo[2.2.1]heptyl, azetidinyl, pyrrolidinyl, azabicyclo[2.1.1]hexyl, tetrahydrofuranyl, tetrahydropyranyl, 7-oxabicyclo[2.2.1]heptyl, 1,4-diazabicyclo[2.2.2]octyl, piperazinyl, piperidinyl, 1-azabicyclo[2.2.1]heptyl, 2-azabicyclo[2.2.1]heptyl, 6-azaspiro[2.5]octyl, 2-azabicyclo[3.1.1]heptyl, 1,3-oxazinanyl, morpholinyl, 2-oxa-5-azabicyclo[2.2.1]heptyl, 1-azabicyclo[2.2.2]octyl, 1,4-dioxanyl, 3-azabicyclo[3.1.0]hexyl, 2-azabicyclo[3.1.0]hexyl, 4-azaspiro[2.4]heptyl, 5-azaspiro[2.4]heptyl, 3-oxabicyclo[3.1.0]hexyl, octahydrocyclopenta[c]pyrrolyl, oxazolidinyl, or thiomorpholinyl dioxide; and $R^{5a}$ is unsubstituted or substituted with 1-4 substituents independently selected from oxo, halo, OH, $C_1$-$C_6$ alkyl, $C_1$-$C_6$ alkoxy, $NR^{5b}R^{5c}$, —($C_1$-$C_5$ alkylene)-($C_3$-$C_8$ cycloalkyl), —$S(O)_2$—($C_1$-$C_3$ alkyl), $C_1$-$C_3$ haloalkoxy, $C_1$-$C_6$ haloalkyl, phenyl, —($C_1$-$C_4$ alkylene)-($C_1$-$C_3$ alkoxy), —C(O)—($C_1$-$C_4$ alkyl), —C(O)O—($C_1$-$C_4$ alkyl), $C_3$-$C_8$ cycloalkyl, $C_1$-$C_4$ hydroxyalkyl, and —$C(O)NH_2$; and $R^{5b}$ and $R^{5c}$ are independently selected from H and $C_1$-$C_3$ alkyl.

Embodiment 17. The compound of Embodiment 16, or a pharmaceutically acceptable salt thereof, wherein $R^{5a}$ is methyl, ethyl, n-propyl, isopropyl, phenyl,

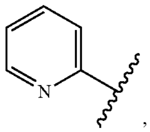, 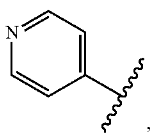, 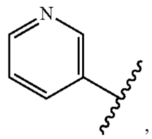,

-continued

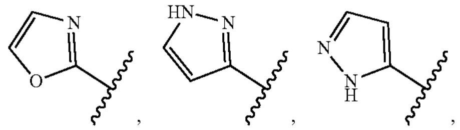,

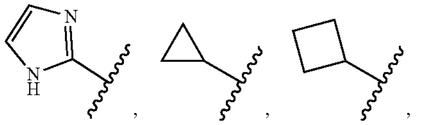,

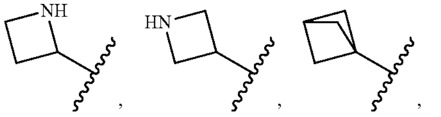,

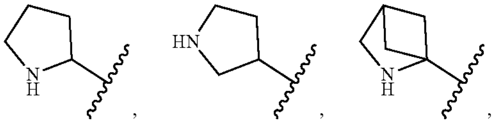,

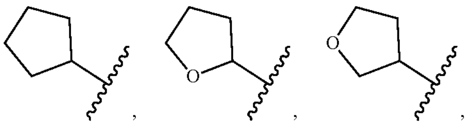,

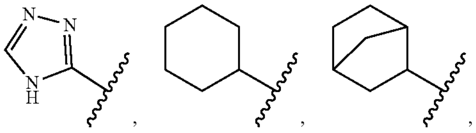,

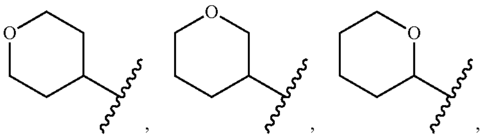,

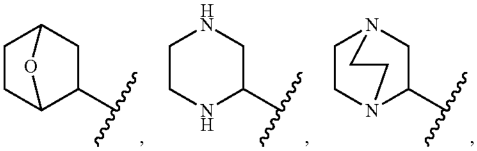,

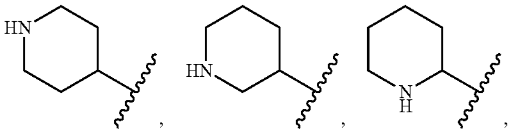,

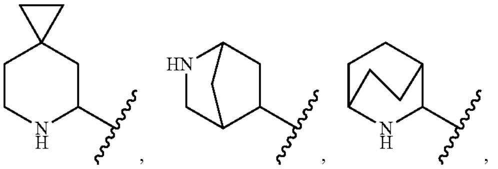,

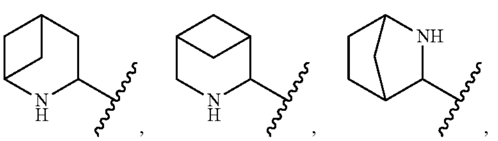,

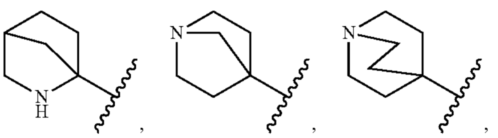,

-continued

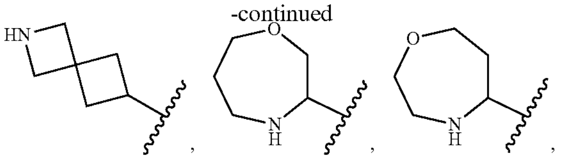,

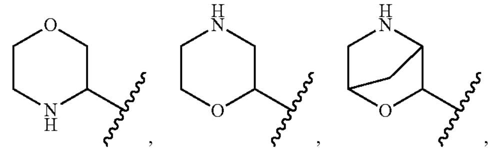,

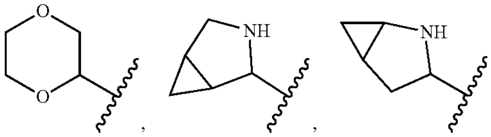,

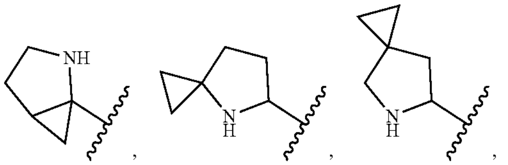,

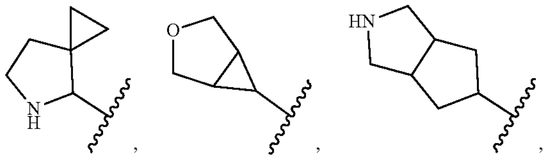,

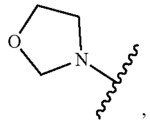, or 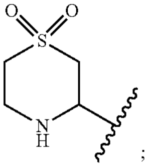;

and $R^{5a}$ is unsubstituted or substituted with 1-4 substituents independently selected from oxo, halo, OH, $C_1$-$C_6$ alkyl, $C_1$-$C_6$ alkoxy, $NR^{5b}R^{5c}$, —($C_1$-$C_5$ alkylene)-($C_3$-$C_8$ cycloalkyl), —$S(O)_2$—($C_1$-$C_3$ alkyl), $C_1$-$C_3$ haloalkoxy, $C_1$-$C_6$ haloalkyl, phenyl, —($C_1$-$C_4$ alkylene)-($C_1$-$C_3$ alkoxy), —C(O)—($C_1$-$C_4$ alkyl), —C(O)O—($C_1$-$C_4$ alkyl), $C_3$-$C_8$ cycloalkyl, $C_1$-$C_4$ hydroxyalkyl, and —C(O)$NH_2$; and $R^{5b}$ and $R^{5c}$ are independently selected from H and $C_1$-$C_3$ alkyl.

Embodiment 18. The compound of any one of Embodiments 1-12, or a pharmaceutically acceptable salt thereof, wherein $R^5$ is Y—$R^{5a}$; Y is absent; and $R^{5a}$ is $C_1$-$C_6$ alkyl or 4- to 10-membered heterocycloalkyl; and $R^{5a}$ is unsubstituted or substituted with 1-2 substituents independently selected from OH, $NR^{5b}R^{5c}$, or $C_1$-$C_6$ alkyl; wherein the 4- to 10-membered heterocycloalkyl has 1-3 ring heteroatoms or ring heteroatom groups independently selected from N and O; and $R^{5b}$ and $R^{5c}$ are independently selected from H and $C_1$-$C_3$ alkyl.

Embodiment 19. The compound of any one of Embodiments 1-12, or a pharmaceutically acceptable salt thereof, wherein $R^5$ is Y—$R^{5a}$, wherein Y is $C_1$-$C_6$ alkylene; and $R^{5a}$ is phenyl or 4- to 6 membered heterocycloalkyl having 1-2 ring heteroatoms independently selected from N and O; wherein $R^{5a}$ is unsubstituted or substituted with 1-4 substituents independently selected from oxo, halo, OH, $NR^{5b}R^{5c}$, $C_1$-$C_6$ alkoxy, and $C_1$-$C_6$ alkyl; and $R^{5b}$ and $R^{5c}$ are independently selected from H and $C_1$-$C_3$ alkyl.

Embodiment 20. The compound of Embodiment 19, wherein $R^{5a}$ is phenyl, piperidinyl, pyrrolidinyl, oxazolidinyl, tetrahydrofuranyl, tetrahydropyranyl, or morpholinyl, wherein $R^{5a}$ is unsubstituted or substituted with 1-4 substituents independently selected from oxo, halo, OH, $NR^{5b}R^{5c}$, $C_1$-$C_6$ alkoxy, and $C_1$-$C_6$ alkyl; and $R^{5b}$ and $R^{5c}$ are independently selected from H and $C_1$-$C_3$ alkyl.

Embodiment 21. The compound of Embodiment 20, or a pharmaceutically acceptable salt thereof, wherein $R^{5a}$ is phenyl,

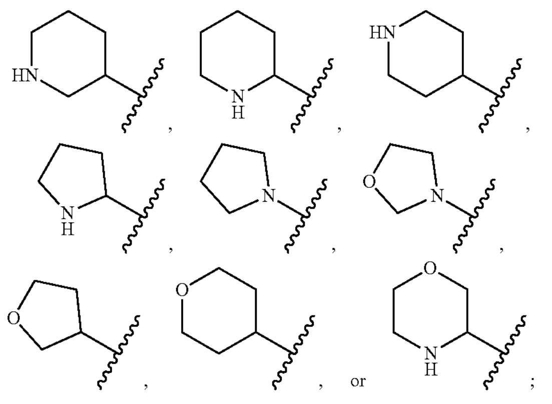

and $R^{5a}$ is unsubstituted or substituted with 1-4 substituents independently selected from oxo, halo, OH, $NR^{5b}R^{5c}$, $C_1$-$C_6$ alkoxy, and $C_1$-$C_6$ alkyl; and wherein $R^{5b}$ and $R^{5c}$ are independently selected from H and $C_1$-$C_3$ alkyl.

Embodiment 22. A compound selected from the group consisting of

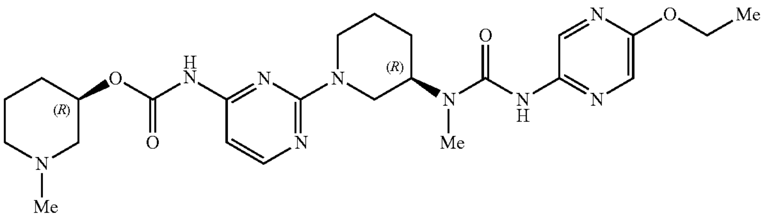

and

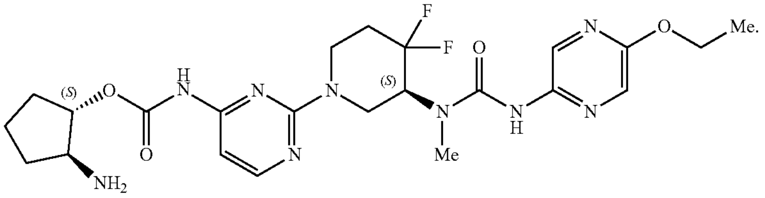

Embodiment 23. A pharmaceutical composition comprising a compound of any one of Embodiments 1-22, or a pharmaceutically acceptable salt of a compound of any one of Embodiments 1-22, and one or more pharmaceutically acceptable excipients.

Embodiment 24. A method of treating a disease, disorder, or condition, mediated at least in part by mast cell activation, said method comprising administering a compound of any one of Embodiments 1-22, or a pharmaceutically acceptable salt thereof, or the pharmaceutical composition according to Embodiment 23, to a subject in need thereof.

Embodiment 25. The method according to Embodiment 24, wherein the compound or pharmaceutical composition is administered in an effective amount to inhibit MRGPRX2.

Embodiment 26. The method according to any one of Embodiments 24 or 25, wherein the disease, disorder, or condition is an allergic, inflammatory, neuroinflammatory, neurological, immune, autoimmune, oncological, dermatological, antihistamine-refractory, respiratory, metabolic, cardiovascular, or fibrotic disease, disorder, or condition.

Embodiment 27. The method according to Embodiment 26, wherein the disease, disorder, or condition is arthritis, rheumatoid arthritis, inflammatory arthritis, osteoarthritis, asthma, multiple sclerosis, Alzheimer's disease, autism, psoriasis, Crohn's disease, inflammatory bowel disease, ulcerative colitis, irritable bowel syndrome, lupus, Grave's disease, Hashimoto's thyroiditis, ankylosing spondylitis, Sjögren's syndrome (SjS), angioedema, allergic asthma, eosinophilic asthma, anaphylaxis, drug anaphylaxis, atopic dermatitis, food allergies, allergic conjunctivitis, allergic rhinitis, urticaria (e.g., chronic spontaneous urticaria (CSU), acute urticaria, or physical urticaria including popular urticaria, cold urticaria, cholinergic urticaria, solar urticaria, scleroderma, and dermatographic urticaria), mastocytosis, systemic mastocytosis, mast cell activation syndrome, neuropathic itch, neurodermatitis, dermographism, dermatosis, dermatitis, allergic contact dermatitis, dry skin, eczema, chronic pruritus, acute pruritus, rosacea, bullous dermatosis, alopecia areata, chronic rhinosinusitis with nasal polyps (CRSwNP), interstitial cystitis, eosinophilic gastrointestinal disease, eosinophilic esophagitis, type I diabetes, type II diabetes, prurigo, prurigo nodularis, coronary heart disease, atherosclerosis, myocardial infarction, angina, pulmonary fibrosis, chronic obstructive pulmonary disease (COPD), pulmonary arterial hypertension, primary pulmonary hypertension, hepatic fibrosis, renal fibrosis, cardiac fibrosis, cystic fibrosis, or bronchitis.

Particular embodiments of this disclosure are described herein, including the best mode known to the inventors for carrying out the disclosure. Upon reading the foregoing, description, variations of the disclosed embodiments may become apparent to individuals working in the art, and it is expected that those skilled artisans may employ such variations as appropriate. Accordingly, it is intended that the disclosure be practiced otherwise than as specifically described herein, and that the disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A compound having a structure of Formula II:

(Formula II)

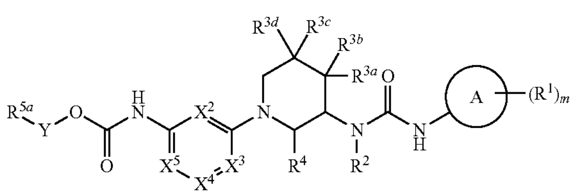

or a pharmaceutically acceptable salt thereof, wherein:

A is phenyl or 5- to 10-membered heteroaryl having 1-4 ring heteroatoms independently selected from N, O, and S;

$X^2$ is $CR^7$ or N; wherein $R^7$, if present, is H, halogen, $C_1$-$C_3$ alkyl, or —$NH_2$;

$X^3$ is $CR^8$ or N; wherein $R^8$, if present, is H, halogen, $C_1$-$C_3$ alkyl, or —$NH_2$;

$X^4$ is $CR^9$; and $X^5$ is $CR^{10}$; wherein $R^9$ and $R^{10}$ are independently H, halogen, $C_1$-$C_3$ alkyl, or —$NH_2$;

m is 0, 1, 2, or 3;

$R^1$ is halogen, $C_1$-$C_6$ alkyl, $C_1$-$C_6$ haloalkyl, $C_3$-$C_6$ cycloalkyl, phenyl, 4- to 9-membered heterocycloalkyl, 5- to 10-membered heteroaryl, —O—$R^{1a}$, or -Q-$R^{1b}$; wherein the 4- to 9-membered heterocycloalkyl has 1-2 ring heteroatoms or heteroatom groups independently selected from N, O, S, and $S(O)_2$; and the 5- to 10-membered heteroaryl has 1-4 ring heteroatoms independently selected from N, O, and S; the phenyl is unsubstituted or substituted with 1 or 2 substituents independently selected from halogen, —CN, $C_1$-$C_3$ alkyl, and $C_1$-$C_3$ haloalkyl; and the 5- to 10-membered heteroaryl is unsubstituted or substituted with $C_1$-$C_6$ alkyl;

Q is $C_1$-$C_6$ alkylene, $C_1$-$C_6$ haloalkylene, or $C_3$-$C_6$ cycloalkylene;

$R^{1a}$ is $C_1$-$C_6$ alkyl, $C_3$-$C_6$ cycloalkyl, —($C_1$-$C_6$ alkylene)-($C_3$-$C_6$ cycloalkyl), —($C_1$-$C_6$ alkylene)-(4 to 9-membered heterocycloalkyl), or phenyl; wherein the 4- to 9-membered heterocycloalkyl has 1-2 ring heteroatoms or heteroatom groups independently selected from N, O, S, and $S(O)_2$; and wherein $R^{1a}$ is unsubstituted or substituted with 1-3 halogens; and $R^{1b}$ is $C_1$-$C_6$ alkoxy, $C_3$-$C_6$ cycloalkyl, or phenyl; wherein $R^{1b}$ is unsubstituted or substituted with 1-3 halogens;

$R^2$ is H or $C_1$-$C_3$ alkyl;

$R^{3a}$, $R^{3b}$, $R^{3c}$, $R^{3d}$ are each independently H, halogen, or $C_1$-$C_6$ alkyl; and $R^4$ is H, $C_1$-$C_6$ alkyl, $C_1$-$C_6$ haloalkyl, $C_1$-$C_6$ alkoxy, —($C_1$-$C_4$ alkylene)-($C_1$-$C_3$ alkoxy), or $C_1$-$C_6$ hydroxyalkyl; or $R^{3c}$ and $R^4$ together form a $C_1$-$C_2$ alkylene group;

Y is absent or $C_1$-$C_6$ alkylene;

$R^{5a}$ is $C_1$-$C_6$ alkyl, $C_3$-$C_8$ cycloalkyl, phenyl, 5- to 10-membered heteroaryl, or 4- to 10-membered heterocycloalkyl; wherein the 5- to 10-membered heteroaryl has 1-4 ring heteroatoms independently selected from N, O, and S; the 4- to 10-membered heterocycloalkyl has 1-3 ring heteroatoms or ring heteroatom groups independently selected from N, O, S, and $S(O)_2$; and $R^{5a}$ is unsubstituted or substituted with 1-4 $R^{5d}$;

each $R^{5d}$ when present is independently selected from oxo, halogen, —OH, —$NR^{5b}R^{5c}$, $C_1$-$C_6$ alkyl, $C_1$-$C_6$ haloalkyl, $C_1$-$C_3$ haloalkoxy, $C_1$-$C_6$ alkoxy, $C_3$-$C_8$ cycloalkyl, $C_1$-$C_4$ hydroxyalkyl, —($C_1$-$C_4$ alkylene)-($C_1$-$C_3$ alkoxy), —($C_1$-$C_5$ alkylene)-($C_3$-$C_8$ cycloalkyl), —($C_1$-$C_6$ alkylene)-(4- to 10-membered heterocycloalkyl), —($C_1$-$C_4$ alkylene)-C(O)N$(CH_3)_2$, —$S(O)_2$ —($C_1$-$C_3$ alkyl), —C(O)—($C_1$-$C_4$ alkyl), —C(O)—($C_1$-$C_4$ hydroxyalkyl), —C(O)O—($C_1$-$C_4$ alkyl), —C(O)OH, —C(O)$NH_2$, 4- to 10-membered heterocycloalkyl, and phenyl; and each of the 4- to 10-membered heterocycloalkyl independently has 1-3 ring heteroatoms or ring heteroatom groups independently selected from N, O, S, and $S(O)_2$ and is independently unsubstituted or substituted with 1 or 2 substituents independently selected from OH, halo, and $C_1$-$C_6$ alkyl; and the $C_3$-$C_8$ cycloalkyl is unsubstituted or substituted with OH; or two $R^{5d}$ are taken together with the atoms to which they are attached to form phenyl, 5- or 6-membered heteroaryl, or 4- to 6-membered heterocycloalkyl; wherein the 5- or 6-membered heteroaryl has 1-2 ring heteroatoms independently selected from N, O, and S; the 4- to 6-membered heterocycloalkyl has 1-3 ring heteroatoms or ring heteroatom groups independently selected from N, O, S, and $S(O)_2$; and the 4- to 6-membered heterocycloalkyl is unsubstituted or substituted with $C_1$-$C_6$ alkyl; and $R^{5b}$ and $R^{5c}$ are independently selected from H, $C_1$-$C_3$ alkyl, —C(O)—($C_1$-$C_4$ alkyl), 4- to 9-membered heterocycloalkyl; wherein the 4- to 9-membered heterocycloalkyl has 1-3 ring heteroatoms or ring heteroatom groups independently selected from N, O, S, and $S(O)_2$.

2. The compound of claim 1 having a structure of Formula II-1:

(Formula II-1)

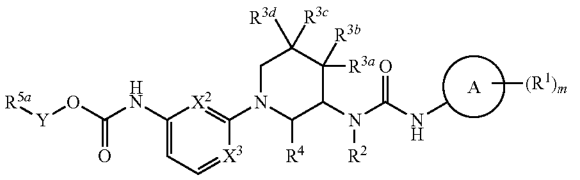

wherein:

A is 5- to 10-membered heteroaryl having 1-4 ring heteroatoms independently selected from N, O, and S;

$X^2$ is CH or N;

$X^3$ is CH or N;

m is 0 or 1;

$R^1$ is halogen, $C_1$-$C_6$ alkyl, $C_3$-$C_6$ cycloalkyl, phenyl, —($C_1$-$C_6$ alkylene)-$C_1$-$C_6$ alkoxy, —O—$R^{1a}$, or -Q-$R^{1b}$; wherein:

$R^{1a}$ is $C_1$-$C_6$ alkyl, $C_3$-$C_6$ cycloalkyl, or phenyl; and $R^{1a}$ is unsubstituted or substituted with 1-3 halogens;

Q is $C_1$-$C_6$ alkylene; and $R^{1b}$ is phenyl; wherein $R^{1b}$ is unsubstituted or substituted with 1-3 halogens;

$R^2$ is H or $C_1$-$C_3$ alkyl;

$R^{3a}$, $R^{3b}$, $R^{3c}$, $R^{3d}$ are each independently H, halogen, or $C_1$-$C_6$ alkyl;

$R^4$ is H, $C_1$-$C_6$ alkyl, $C_1$-$C_6$ haloalkyl, $C_1$-$C_6$ alkoxy, or $C_1$-$C_6$ hydroxyalkyl;

Y is absent or $C_1$-$C_6$ alkylene;

$R^{5a}$ is $C_1$-$C_6$ alkyl, $C_3$-$C_8$ cycloalkyl, phenyl, 5- to 10-membered heteroaryl, or 4- to 10-membered heterocycloalkyl; wherein the 5- to 10-membered heteroaryl has 1-4 ring heteroatoms independently selected from N, O, and S; the 4- to 10-membered heterocycloalkyl has 1-3 ring heteroatoms or ring heteroatom groups independently selected from N, O, S, and $S(O)_2$; and $R^{5a}$ is unsubstituted or substituted with 1-4 $R^{5d}$;

each $R^{5d}$ when present is independently selected from oxo, halo, —OH, —$NR^{5b}R^{5c}$, $C_1$-$C_6$ alkyl, $C_1$-$C_6$ haloalkyl, $C_1$-$C_6$ alkoxy, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), —C(O)—($C_1$-$C_4$ alkyl), —C(O)O—($C_1$-$C_4$ alkyl), and phenyl; and $R^{5b}$ and $R^{5c}$ are independently selected from H and $C_1$-$C_3$ alkyl.

3. The compound of claim 1, wherein $X^2$ is N or CH and/or $X^3$ is N.

4. The compound of claim 1, wherein (a) $R^2$ is $C_1$-$C_3$ alkyl;

(b) $R^{3c}$ and $R^{3d}$ are H;

(c) $R^{3a}$ and $R^{3b}$ are independently H or F; and/or (d) $R^4$ is H.

5. The compound of claim 1, wherein A is pyrazinyl, pyridinyl, pyridazinyl, isoquinolinyl, 1,3,4-thiadiazolyl, or thiazolyl.

6. The compound of claim 1, wherein A is

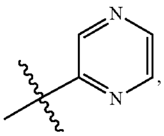,
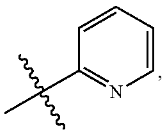,
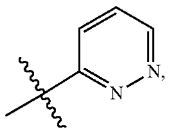

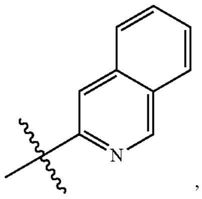,
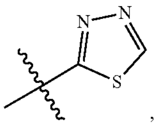, or

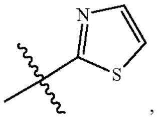, each of which is unsubstituted or substituted with 1 $R^1$.

7. The compound of claim 1, wherein m is 1.

8. The compound of claim 1, wherein $R^1$ is halogen, $C_1$-$C_6$ alkyl, $C_3$-$C_6$ cycloalkyl, phenyl, —($C_1$-$C_6$ alkylene)-$C_1$-$C_6$ alkoxy, or —O—$R^{1a}$.

9. The compound of claim 1, wherein $R^1$ is —O—$R^{1a}$.

10. The compound of claim 1, wherein Y is absent.

11. The compound of claim 1, having a structure of Formula IIj or Formula IIj-1:

(Formula IIj)

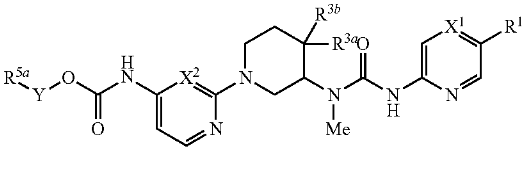

or

-continued (Formula IIj-1)

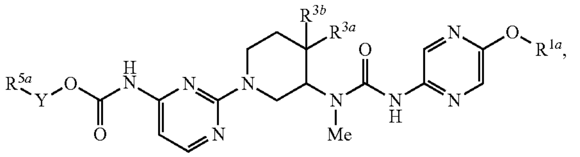

wherein for Formula IIj, $X^1$ is CH or N.

12. The compound of claim 11, wherein for Formula IIj, $X^1$ is N and $X^2$ is N.

13. The compound of claim 11, wherein $R^{3a}$ is H and $R^{3b}$ is F.

14. The compound of claim 11, having a structure of Formula IIj-2, Formula IIj-3a, or Formula IIj-3b:

(Formula IIj-2)

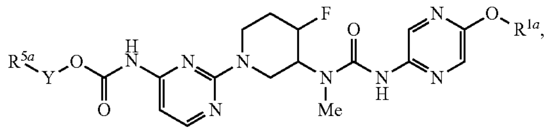

(Formula IIj-3a)

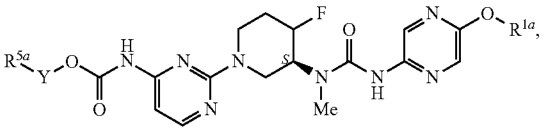

or (Formula IIj-3b)

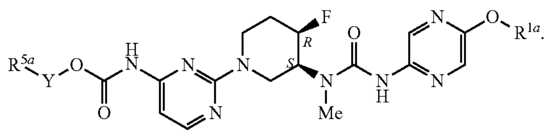

15. The compound of claim 11, wherein $R^{1a}$ is ethyl.

16. The compound of claim 1, having a structure of Formula IIo or Formula IIo-1:

(Formula IIo)

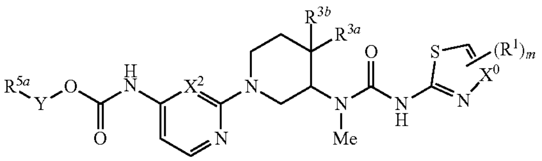

or (Formula IIo-1)

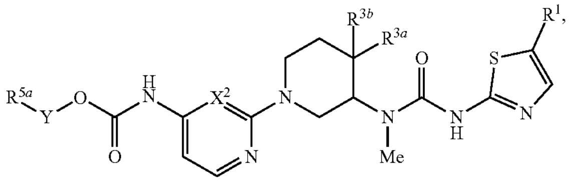

wherein for Formula IIo, $X^0$ is CH or N and m is 0 or 1.

17. The compound of claim 16, wherein for Formula IIo, $X^0$ is N and $X^2$ is N.

18. The compound of claim 16, wherein $R^{3a}$ is H and $R^{3b}$ is F and/or $R^1$ is halogen or $C_1$-$C_6$ alkyl.

19. The compound of claim 1, having a structure of Formula IIp:

(Formula IIp)

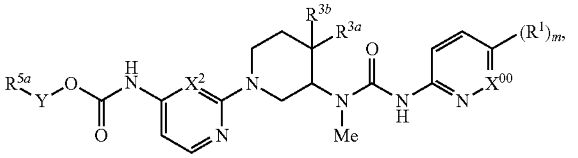

wherein $X^{00}$ is CH or N and m is 0 or 1.

20. The compound of claim 19, wherein $X^{00}$ is N and $X^2$ is and/or $R^{3a}$ and $R^{3b}$ are each independently H or F.

21. The compound of claim 1, wherein $R^{5a}$ is $C_1$-$C_6$ alkyl, $C_3$-$C_8$ cycloalkyl, 5- to 6-membered heteroaryl, or 5- to 9-membered heterocycloalkyl; wherein the 5- to 6-membered heteroaryl has 1 or 2 nitrogen ring heteroatoms; the 5- to 9-membered heterocycloalkyl has 1 or 2 ring heteroatoms independently selected from N and O; and $R^{5a}$ is unsubstituted or substituted with 1-3 $R^{5d}$;

each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl.

22. The compound of claim 1, wherein $R^{5a}$ is 5- to 9-membered heterocycloalkyl; wherein the 5- to 9-membered heterocycloalkyl has 1 or 2 ring heteroatoms independently selected from N and O; and $R^{5a}$ is unsubstituted or substituted with 1-3 $R^{5d}$;

each $R^{5d}$ when present is independently selected from oxo, halogen, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl.

23. The compound of claim 1, wherein $R^{5a}$ is methyl, ethyl, isopropyl,

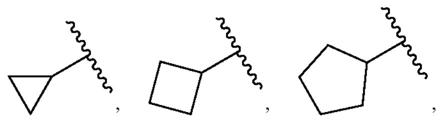

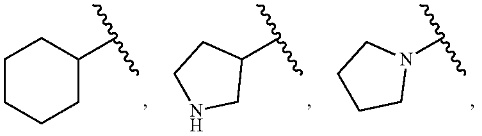

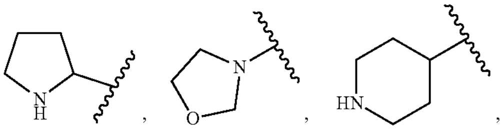

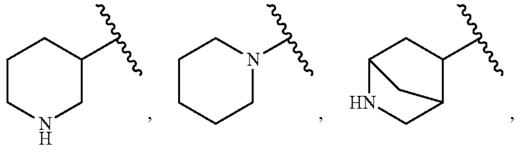

-continued

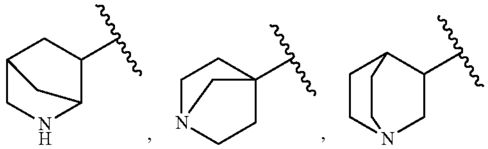

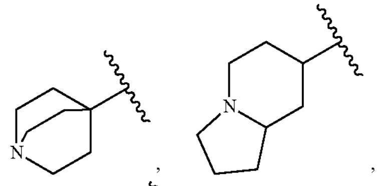

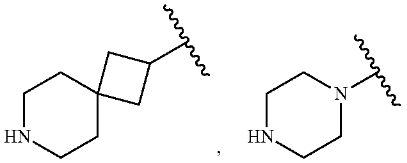

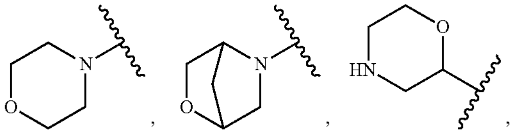

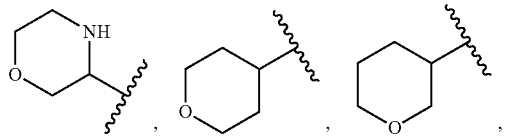

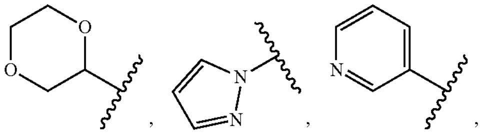

or

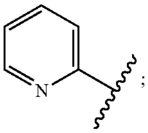

;

and $R^{5a}$ is unsubstituted or substituted with 1-3 $R^{5d}$;

each $R^{5d}$ when present is independently selected from oxo, halo, —OH, —$NR^{5b}R^{5c}$, $C_1$-$C_6$ alkyl, $C_1$-$C_6$ haloalkyl, $C_3$-$C_8$ cycloalkyl, —($C_1$-$C_4$ alkylene)-($C_1$-$C_3$ alkoxy), —($C_1$-$C_5$ alkylene)-($C_3$-$C_8$ cycloalkyl), —$S(O)_2$—($C_1$-$C_3$ alkyl), and phenyl; and $R^{5b}$ and $R^{5c}$ are independently selected from H and $C_1$-$C_3$ alkyl.

24. The compound of claim 1, wherein —Y—$R^{5a}$ is methyl, ethyl, isopropyl,

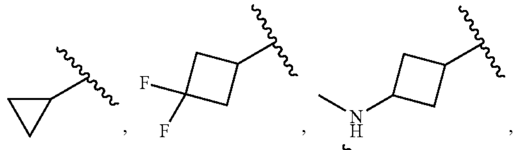

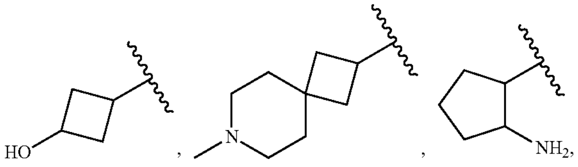

-continued
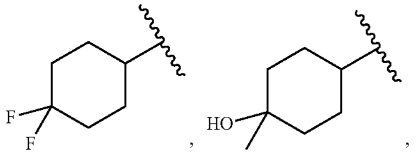
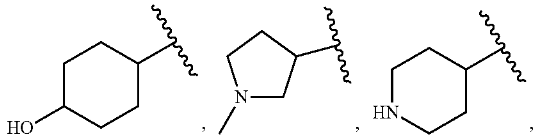
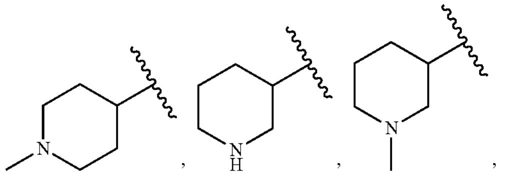
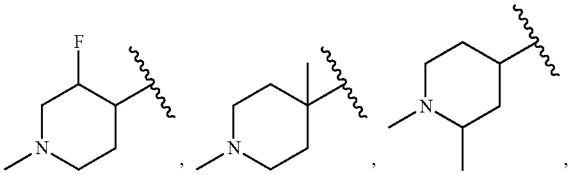
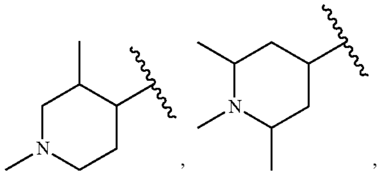
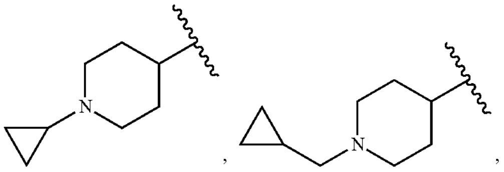
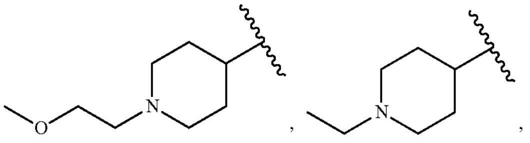
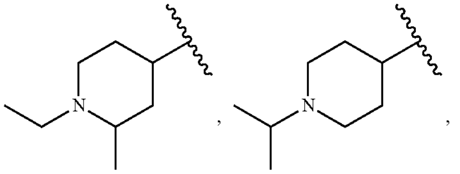
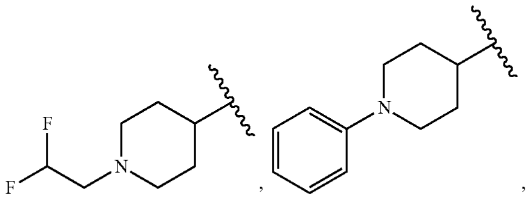
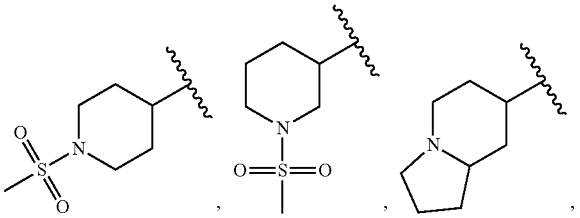
-continued
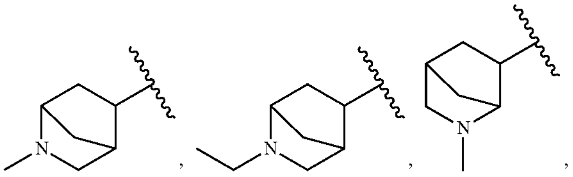
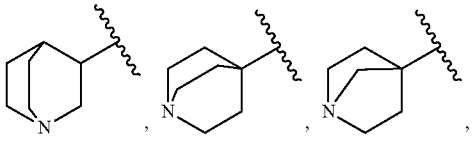
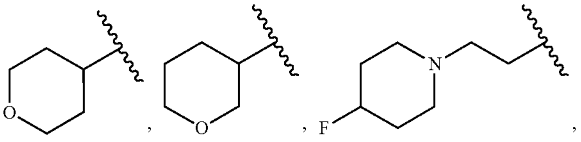
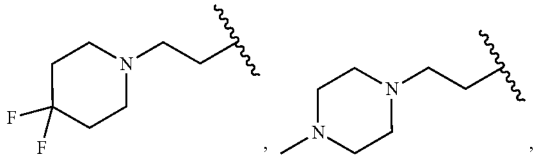
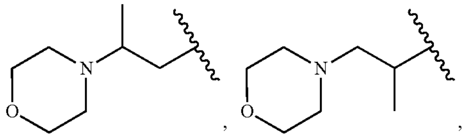
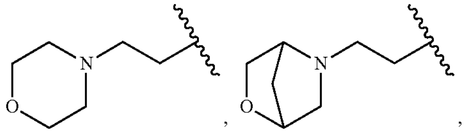
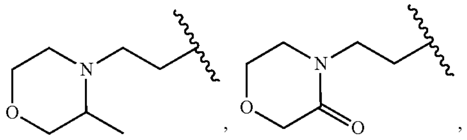
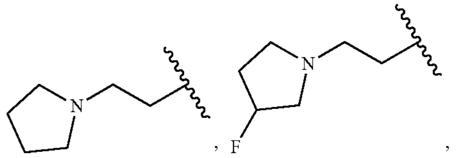
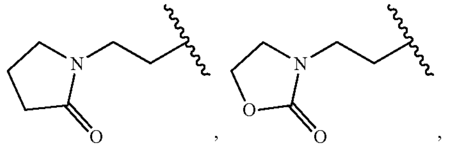
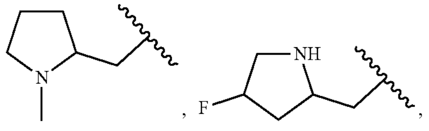
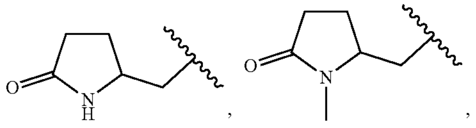
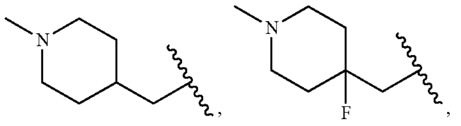

-continued
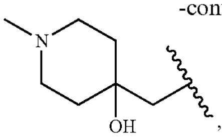,
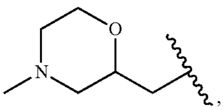,
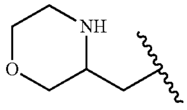,
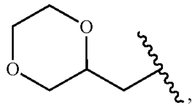,
-continued
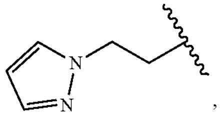,
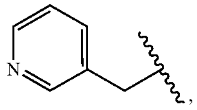, or
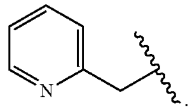.
25. A compound selected from the group consisting of:
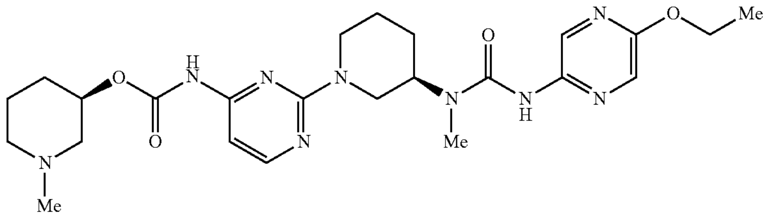
and
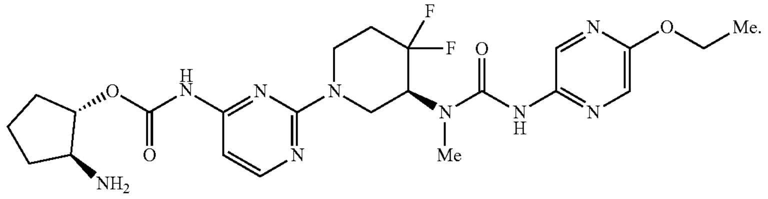
26. A compound selected from the group consisting of:
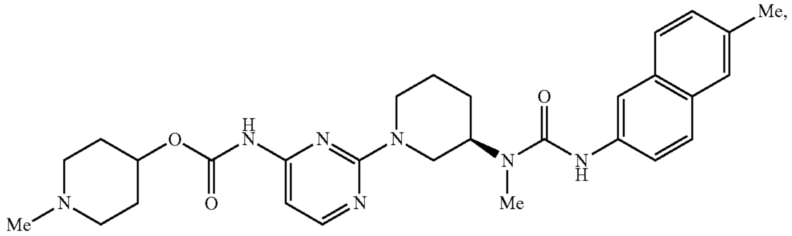
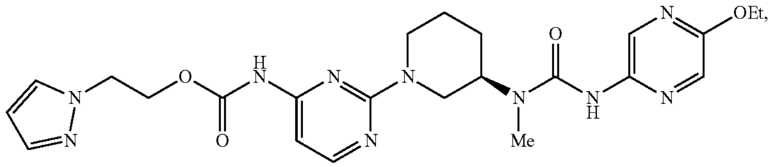
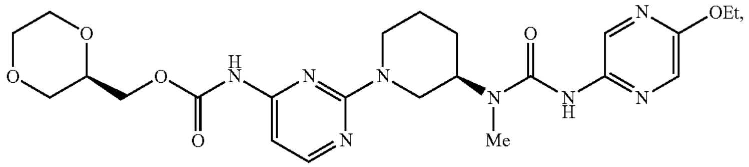
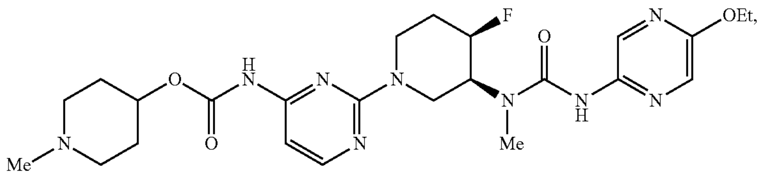

-continued
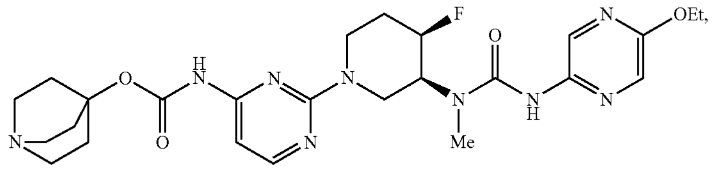
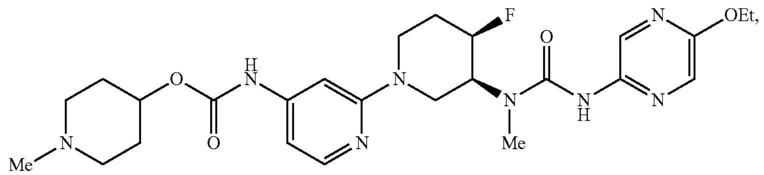
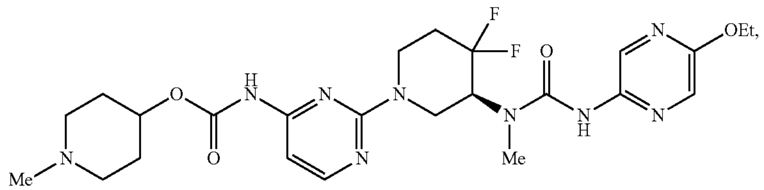
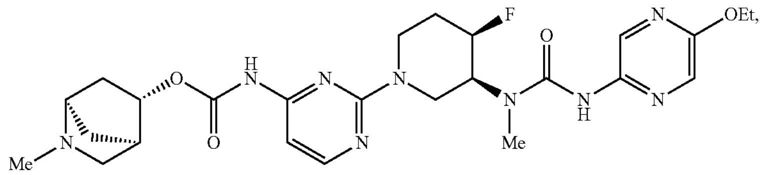
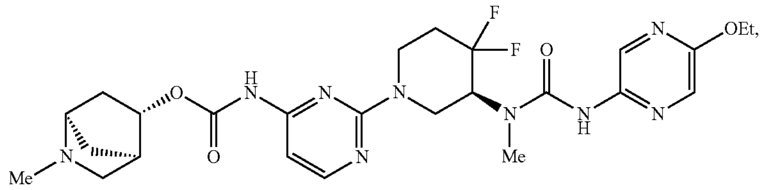
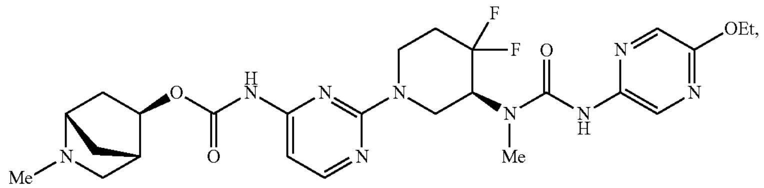
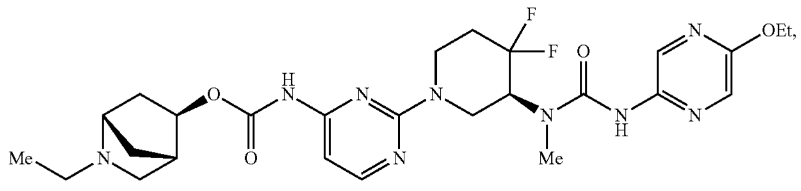
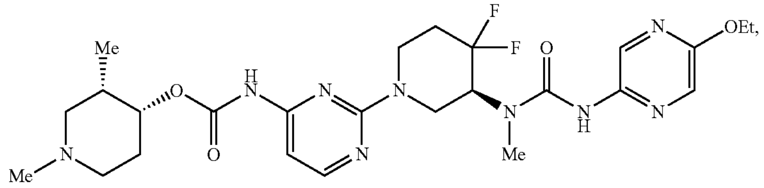
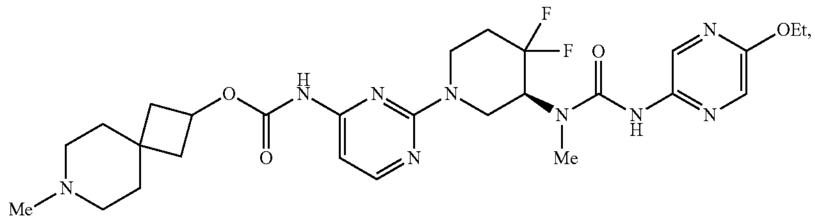

-continued
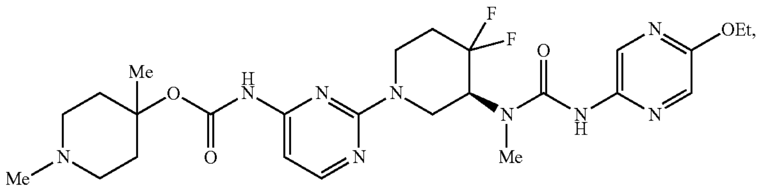
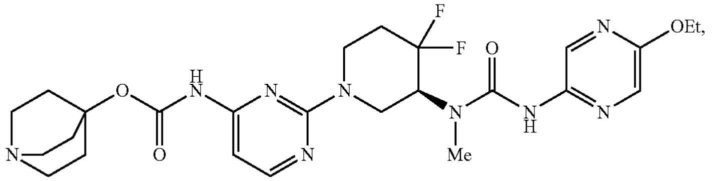
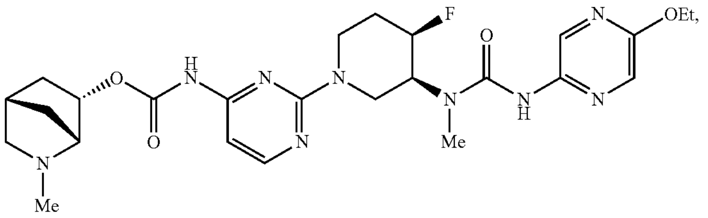
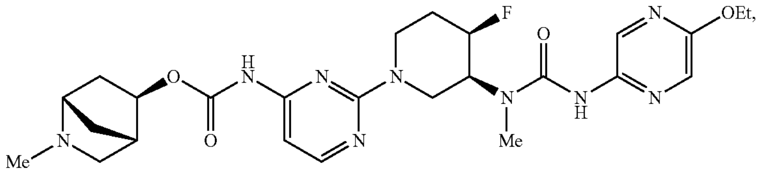
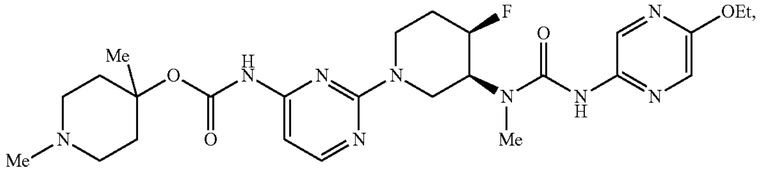
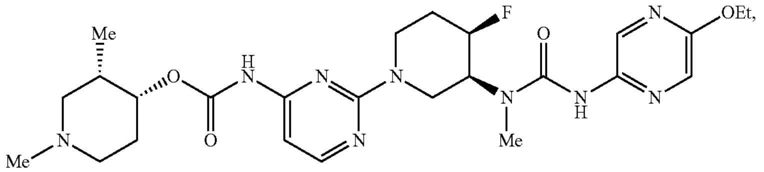
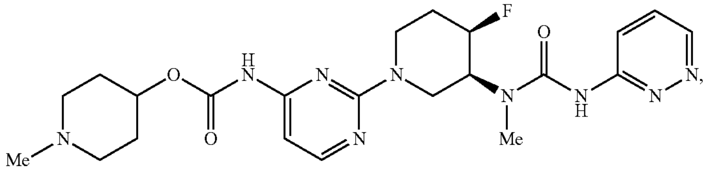
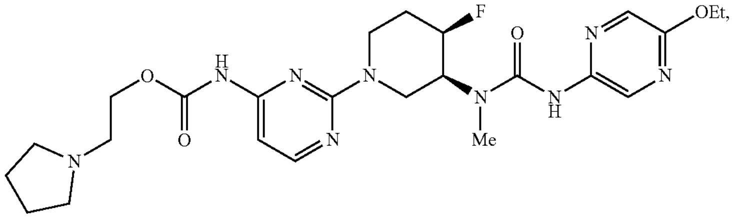
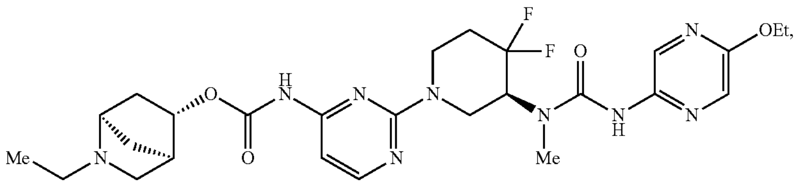

-continued
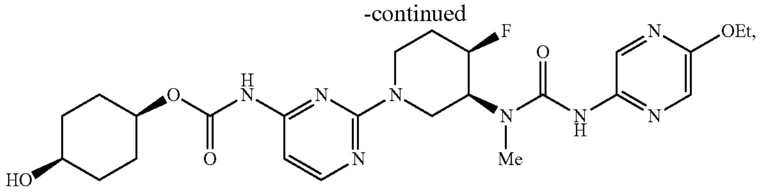
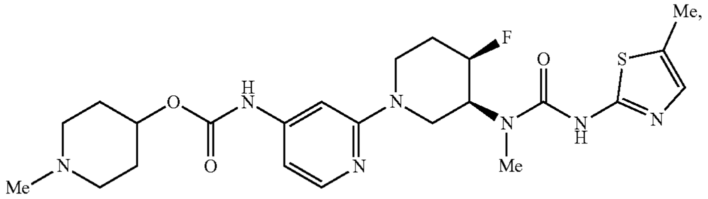
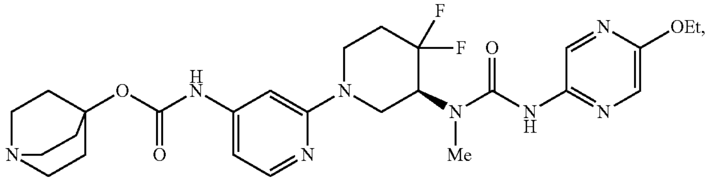
and
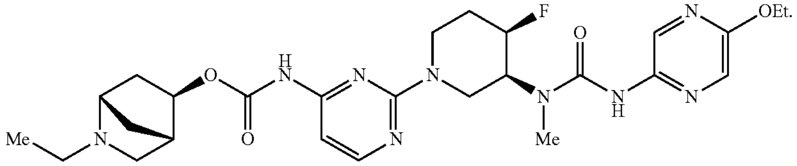 [SMILES: CCOc1cnc(NC(=O)N(C)[C@H]2CN(c3nccc(NC(=O)O[C@@H]4C[C@@H]5C[C@H]4CN5CC)n3)CC[C@H]2F)cn1]
27. A compound selected from the group consisting of:
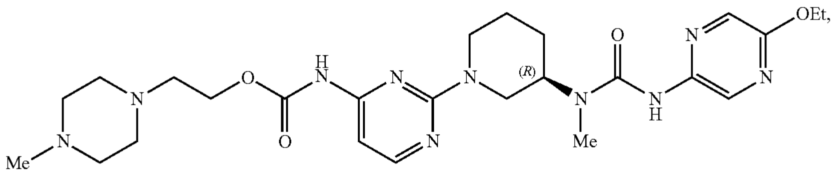
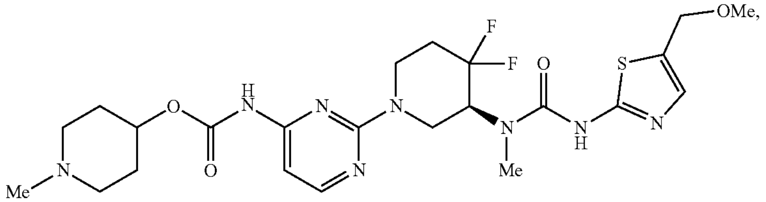
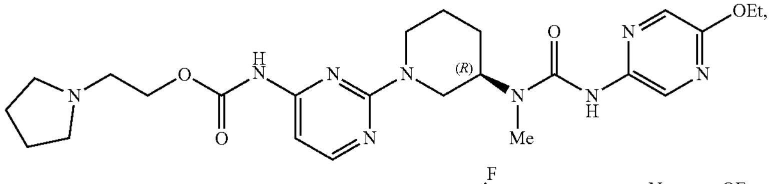
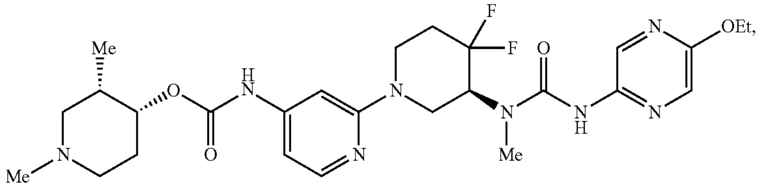
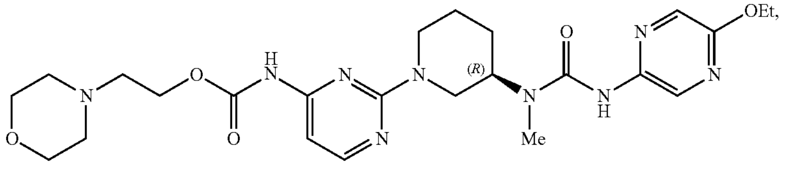

-continued
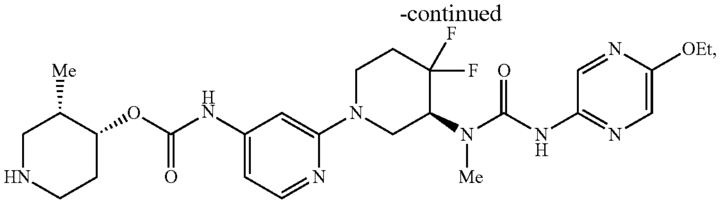
,
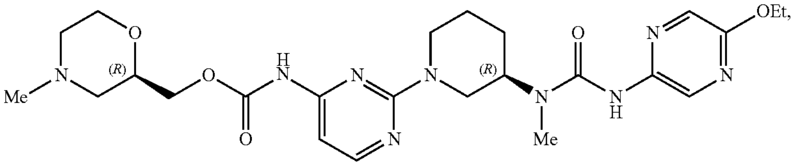
,
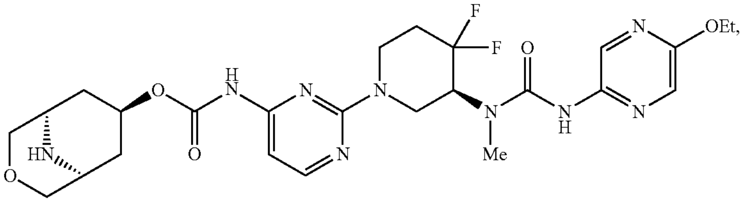
,
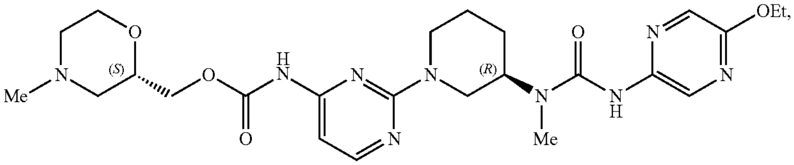
,
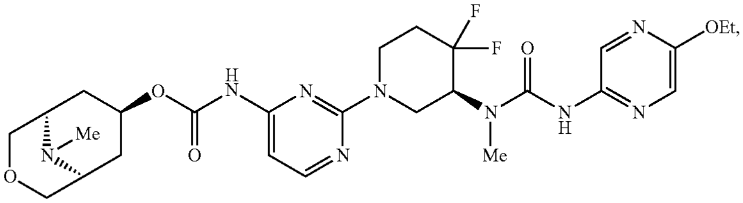
,
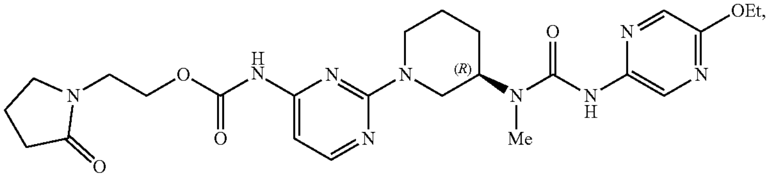
,
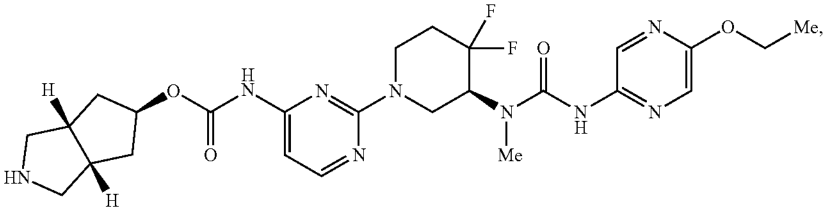
,
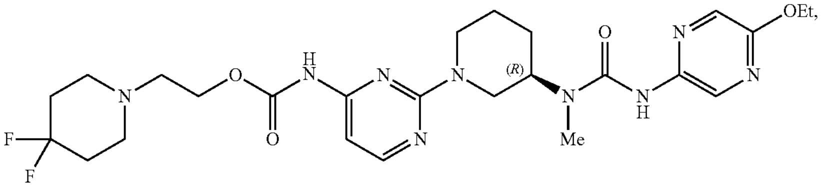
,
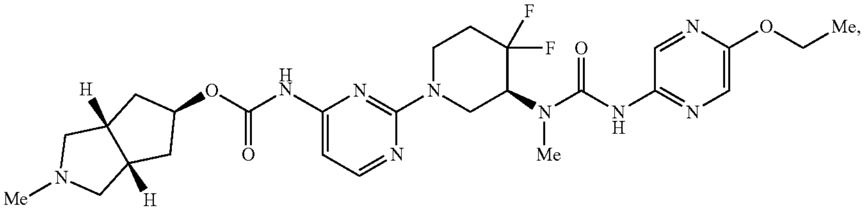
, -continued
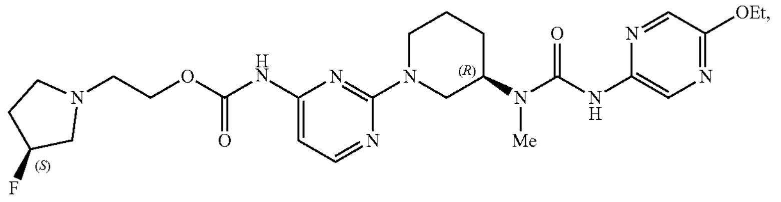
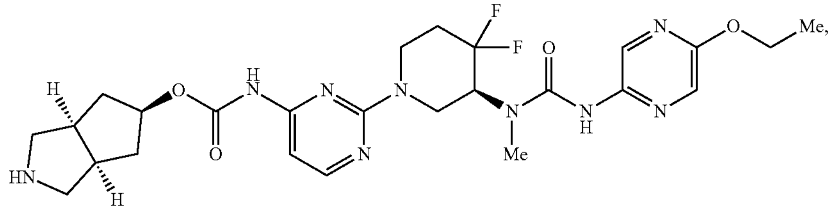
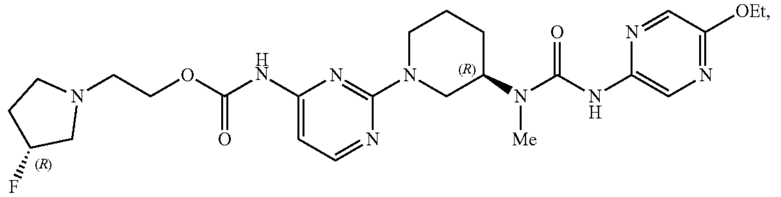
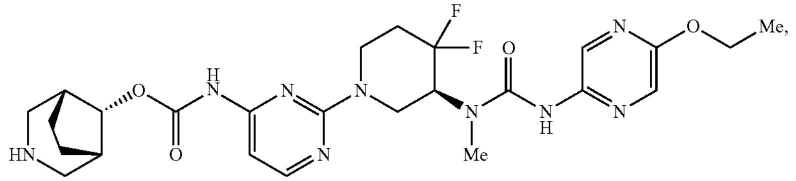
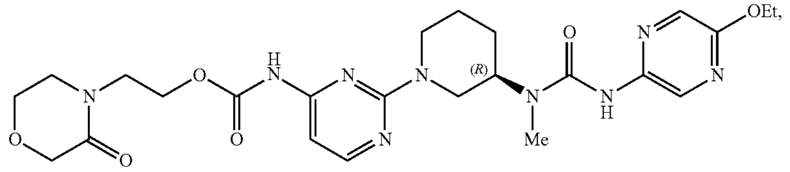
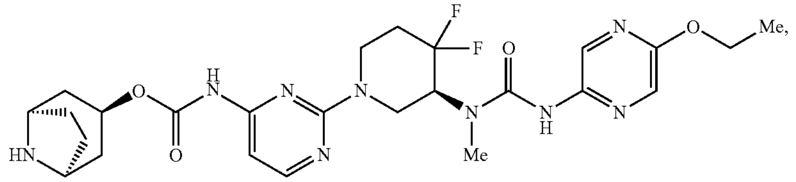
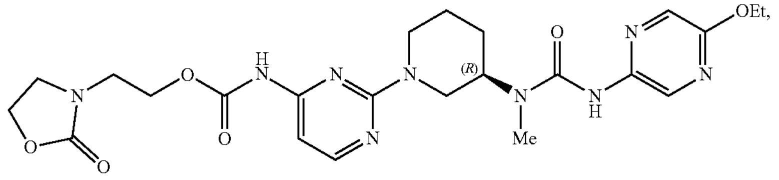
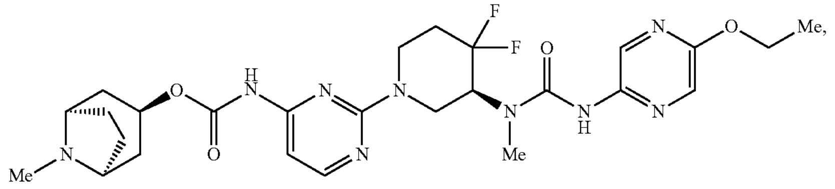
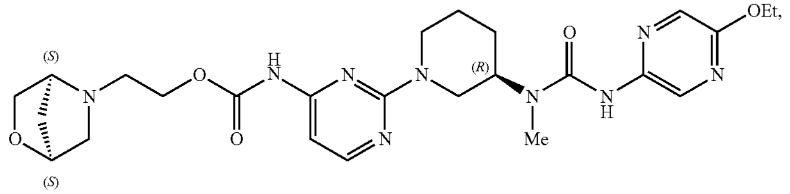

-continued
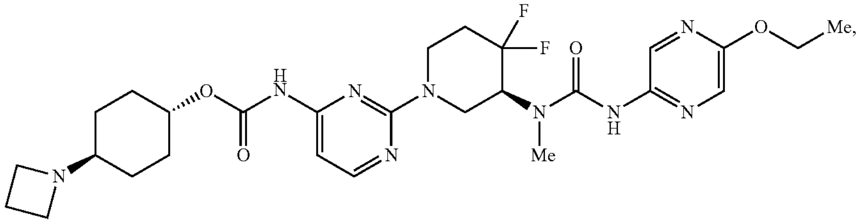
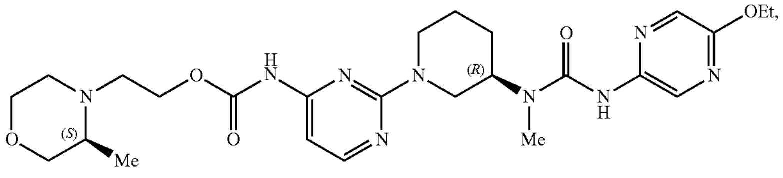
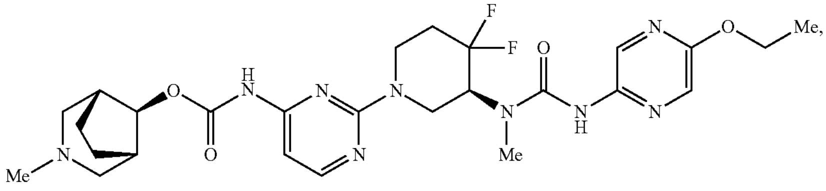
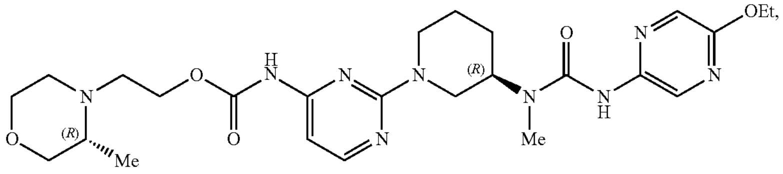
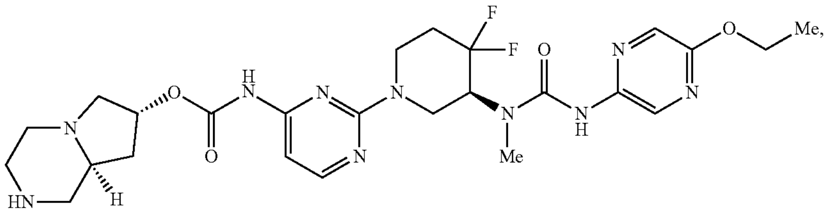
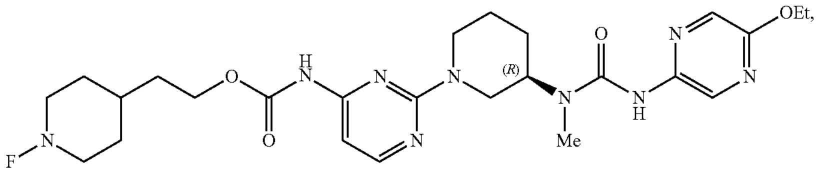
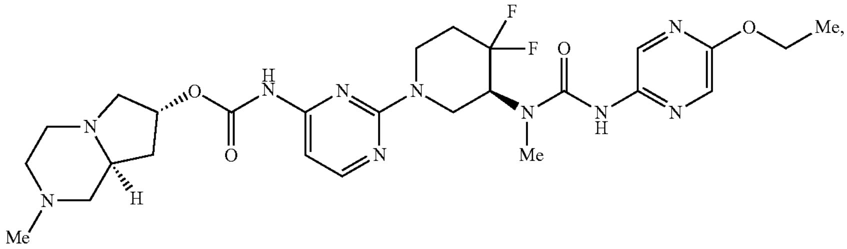
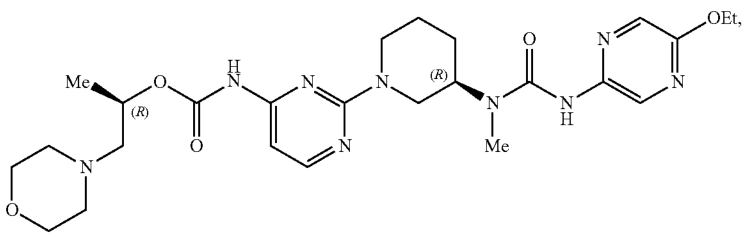

-continued
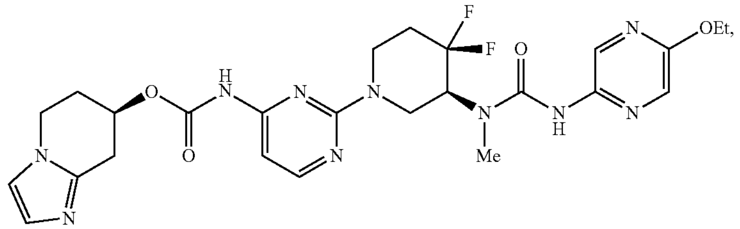
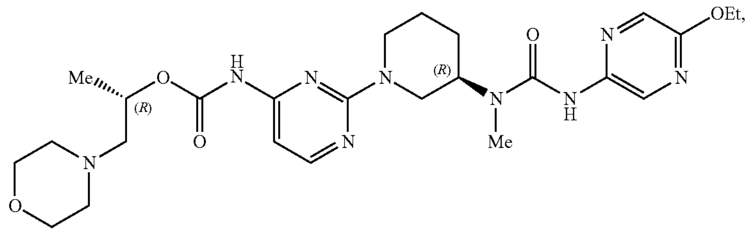
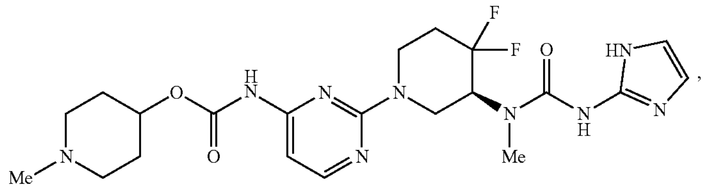
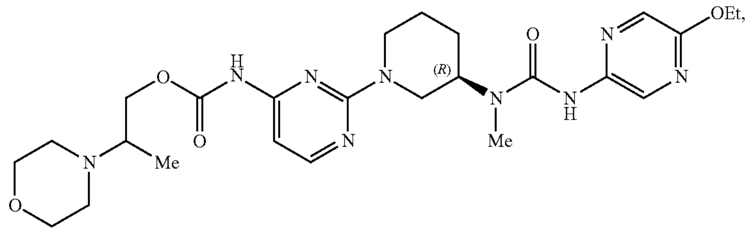
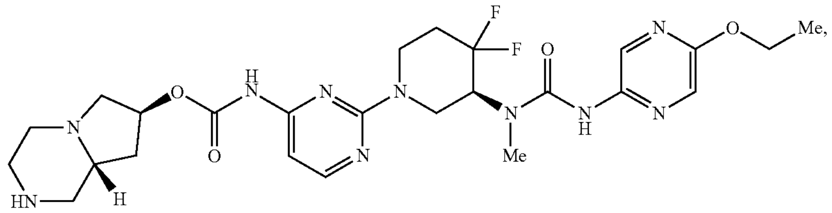
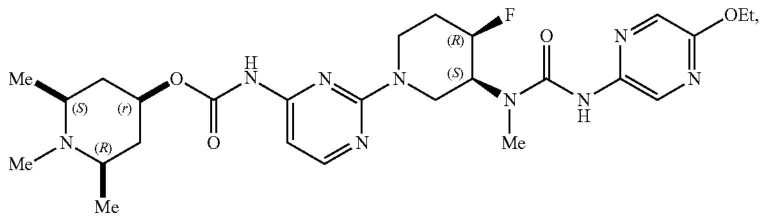
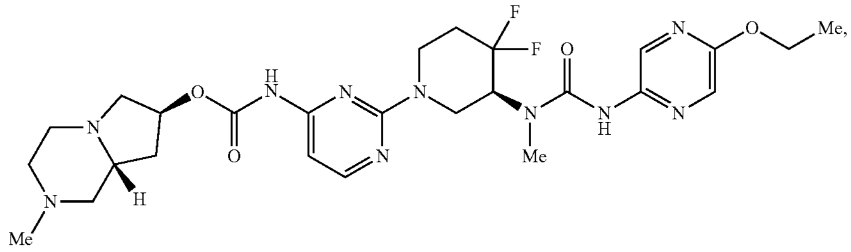

-continued
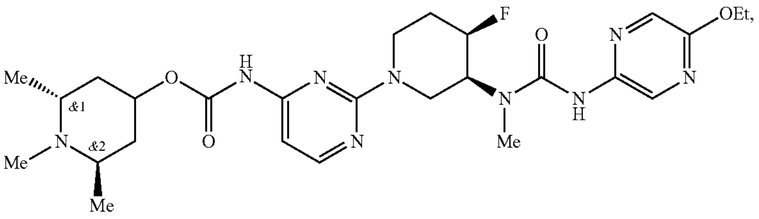
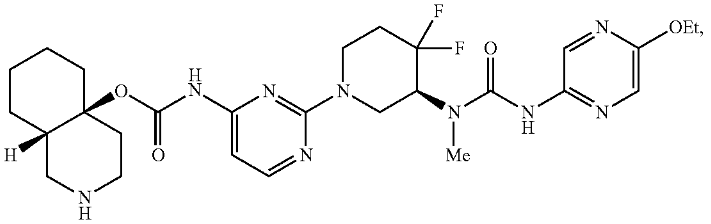
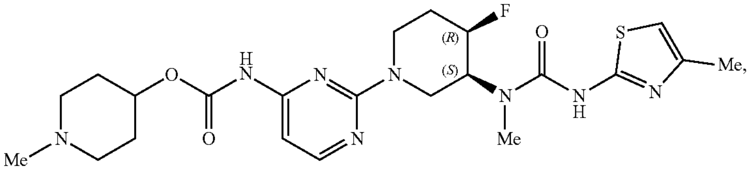
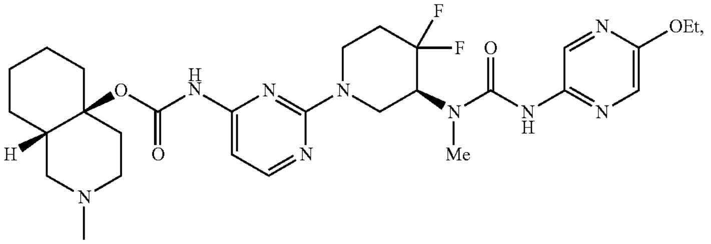
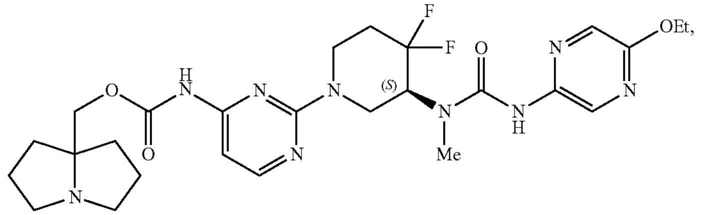
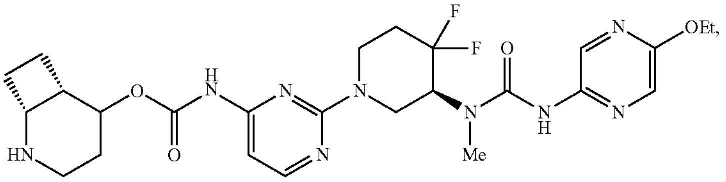
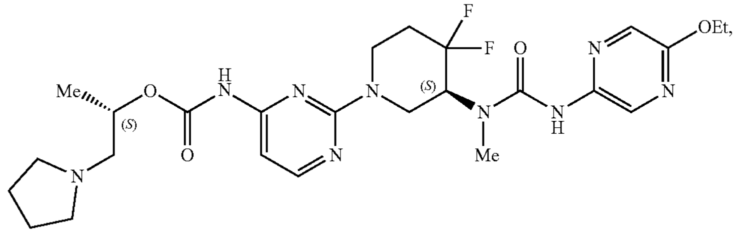
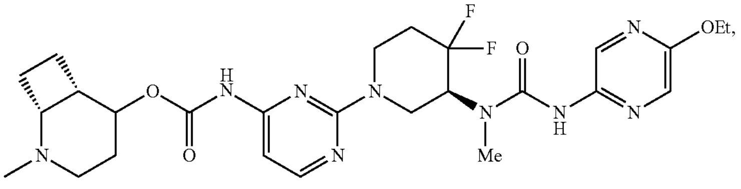

-continued
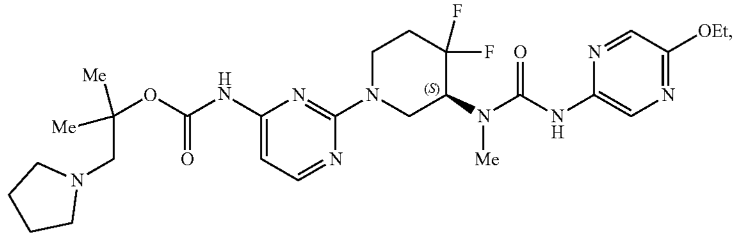
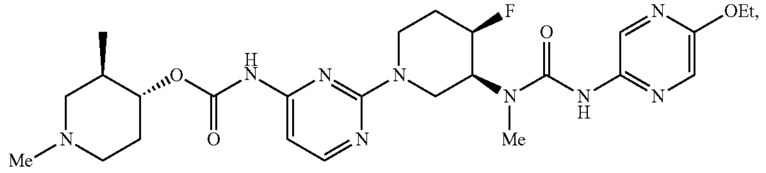
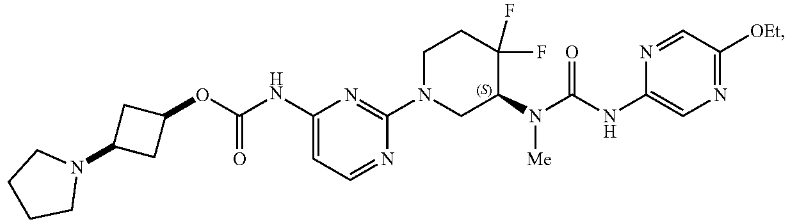
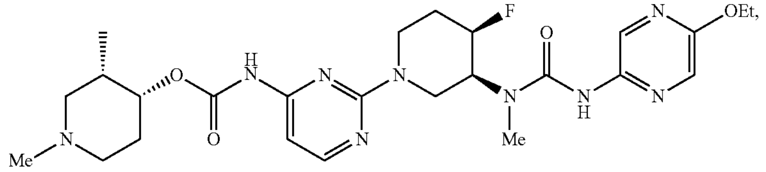
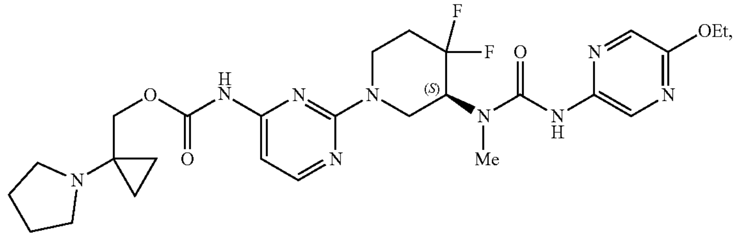
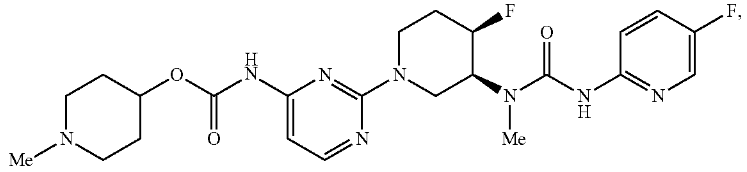
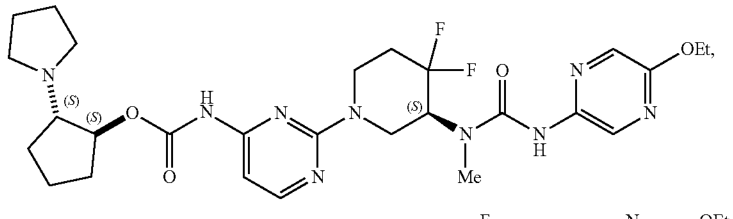
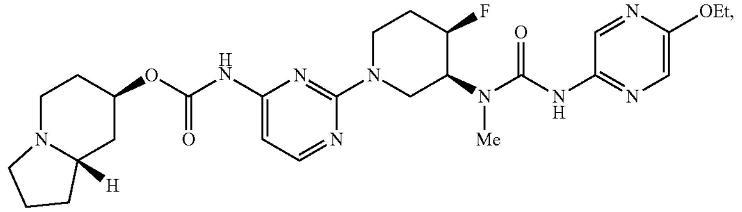

-continued
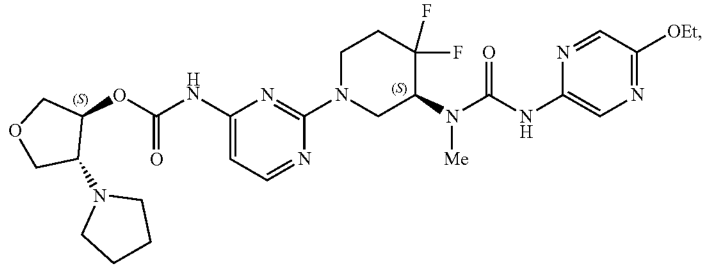
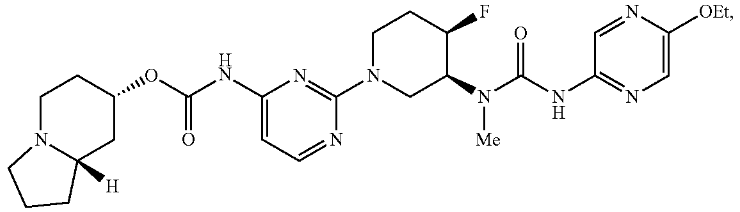
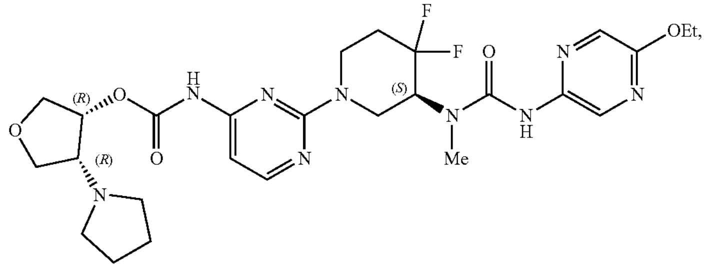
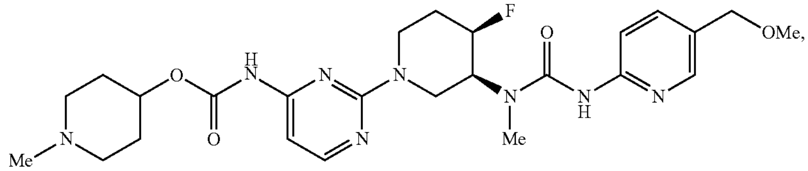
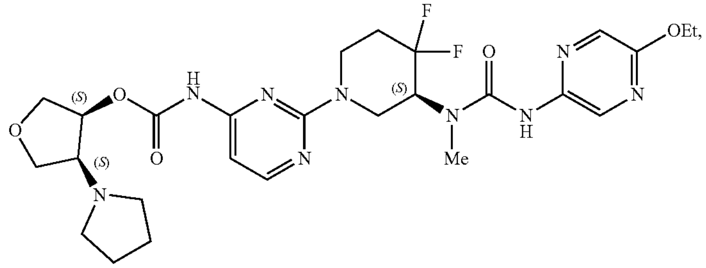
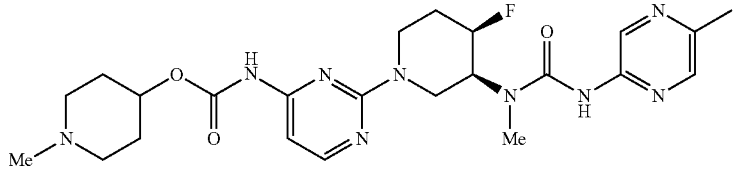
,
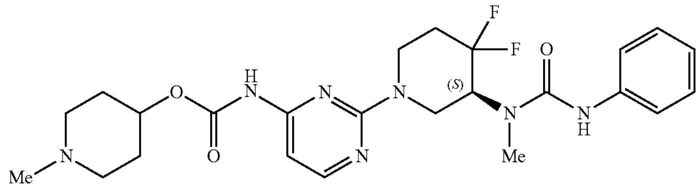
,
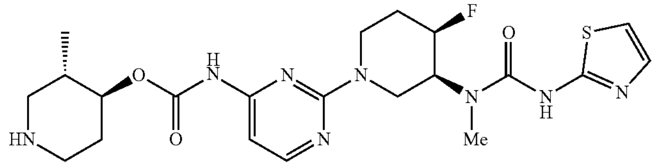
, -continued
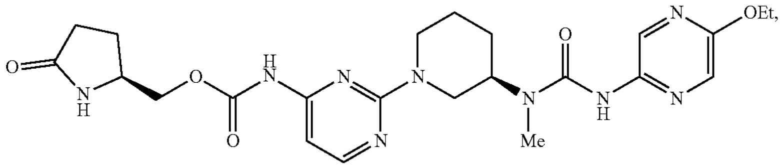
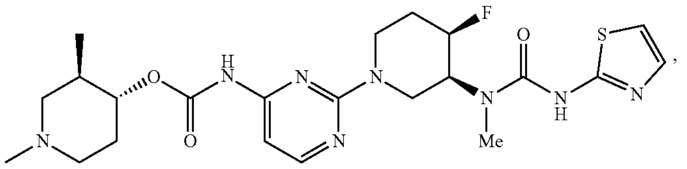
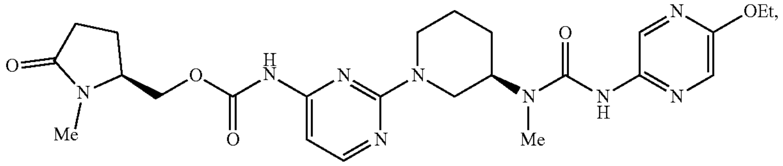
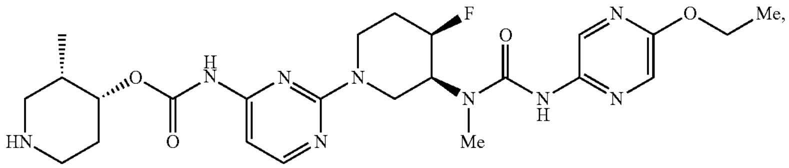
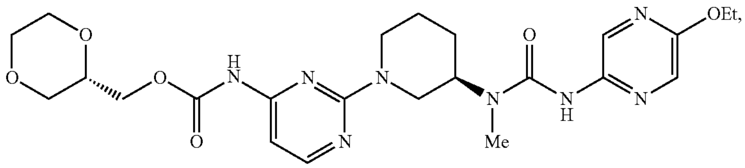
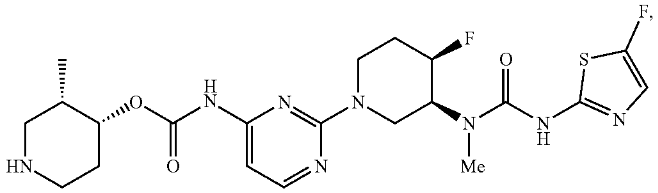
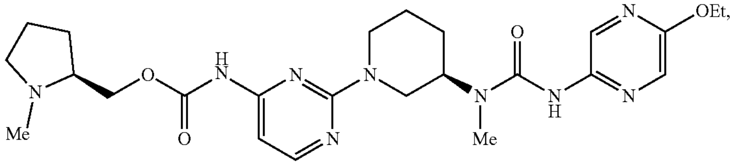
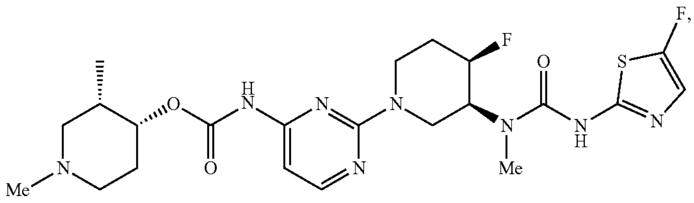
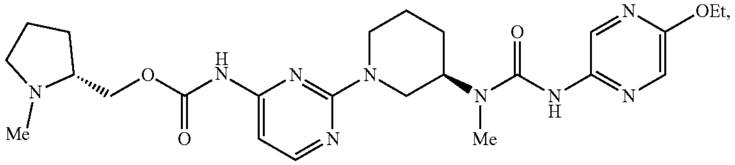

-continued
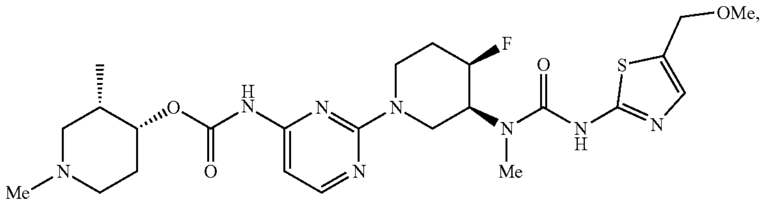
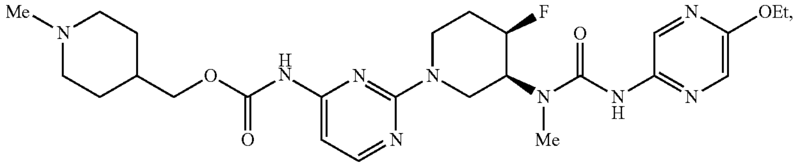
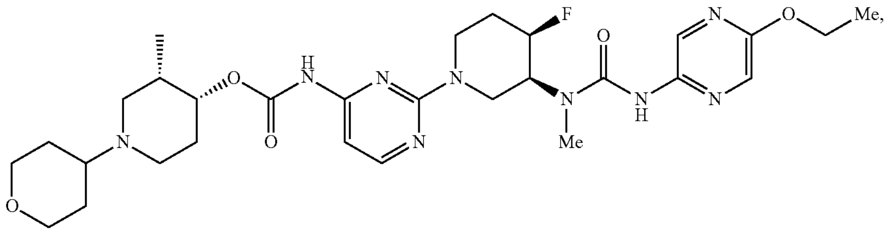
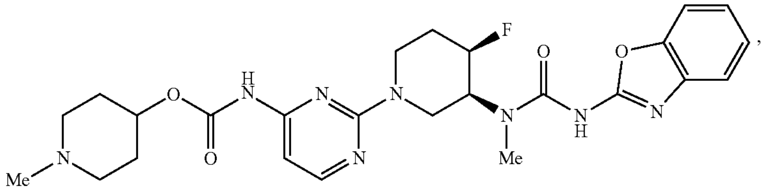
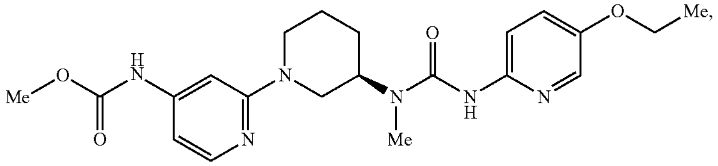
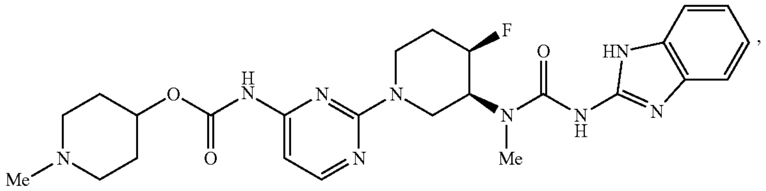
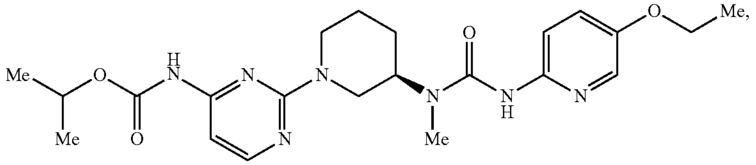
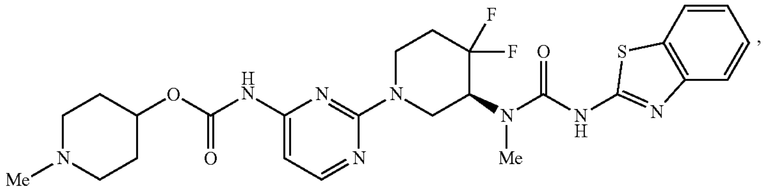
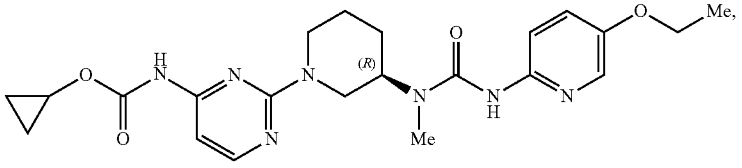

-continued
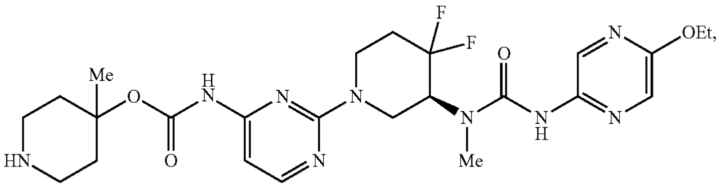
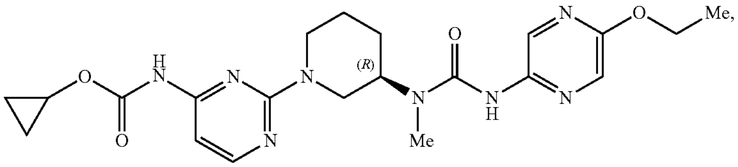
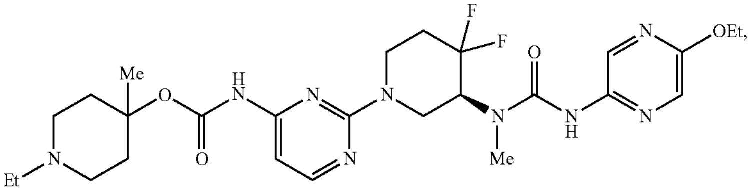
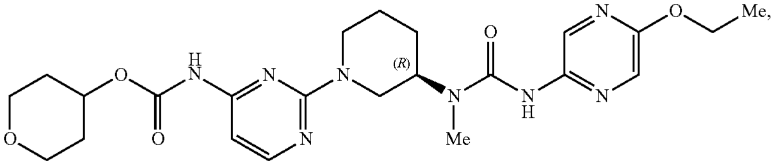
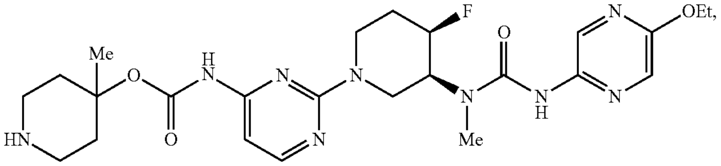
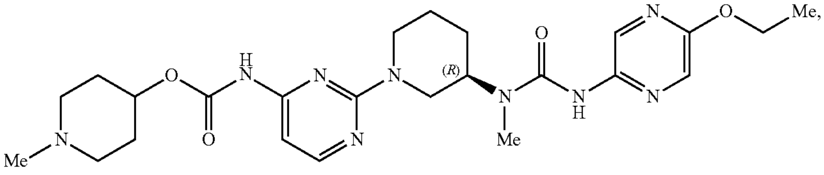
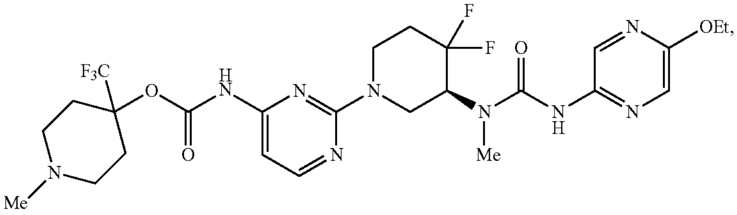
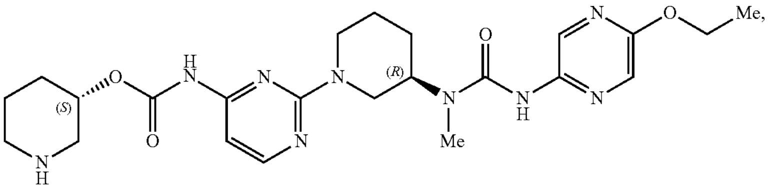
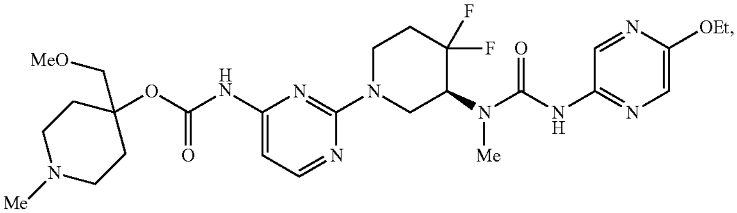

-continued
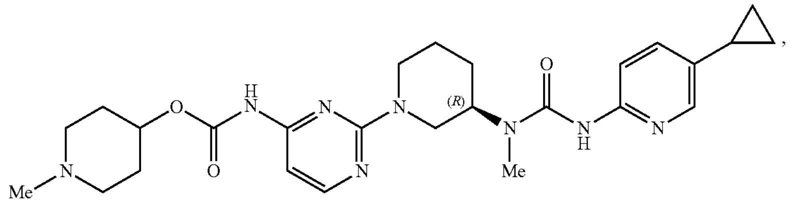
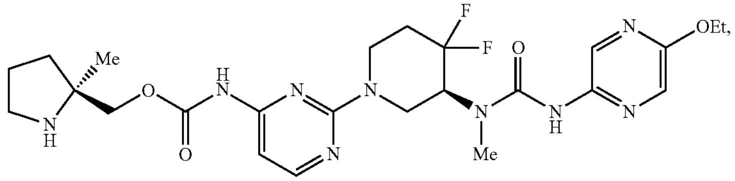
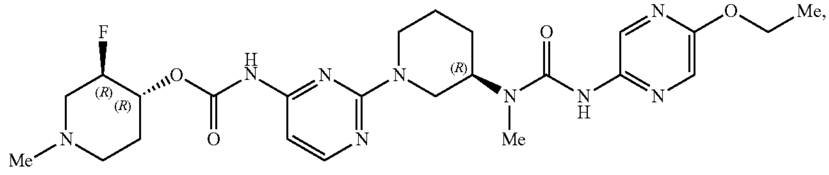
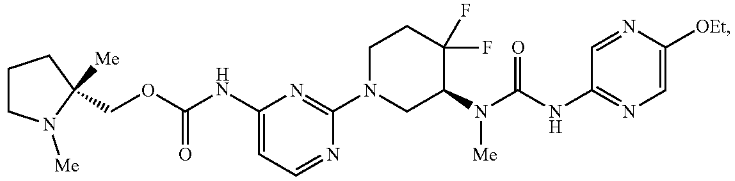
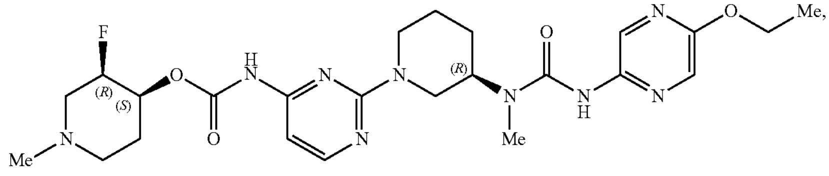
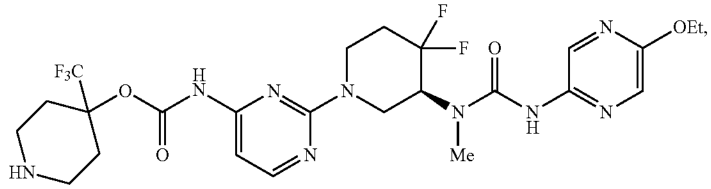
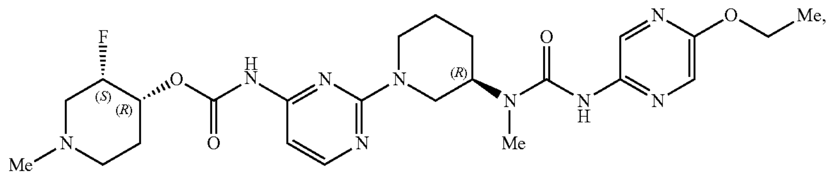
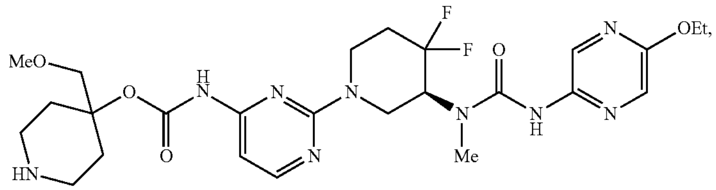
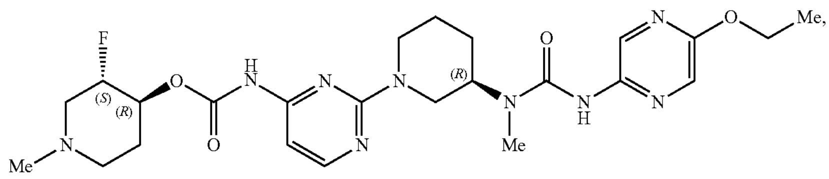

-continued
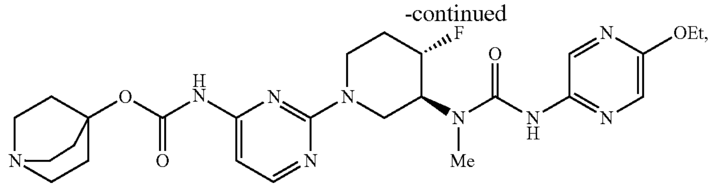
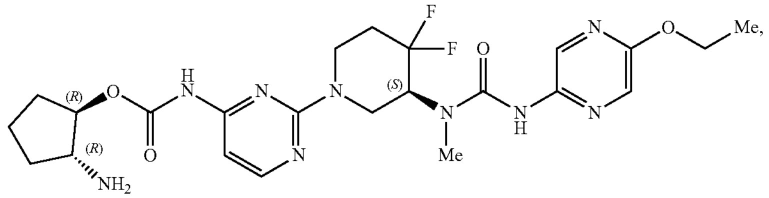
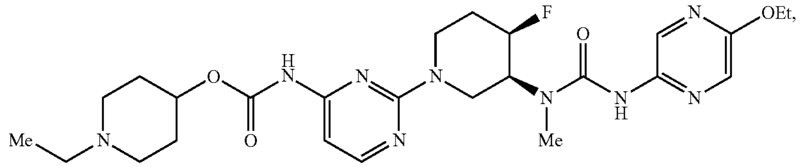
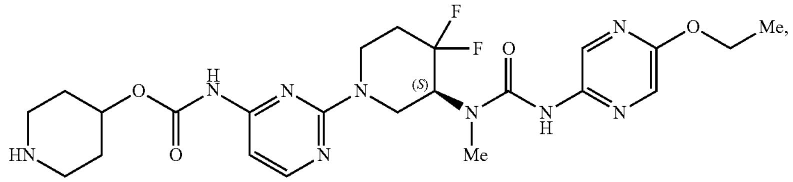
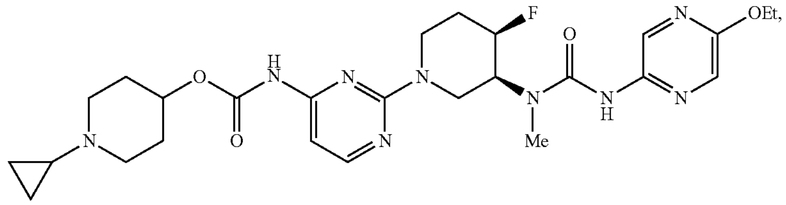
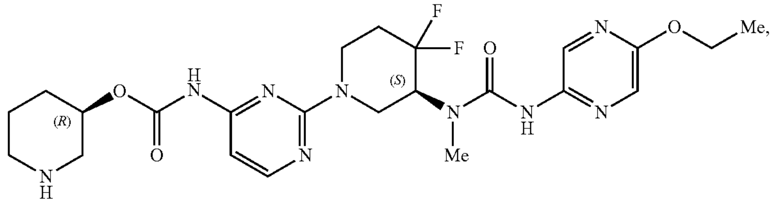
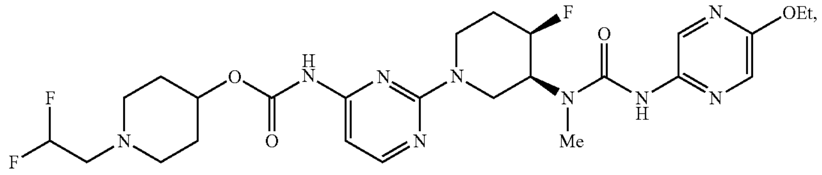
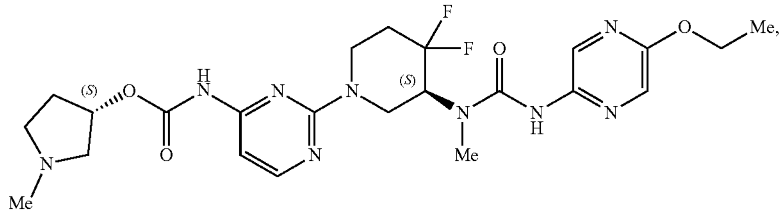

-continued
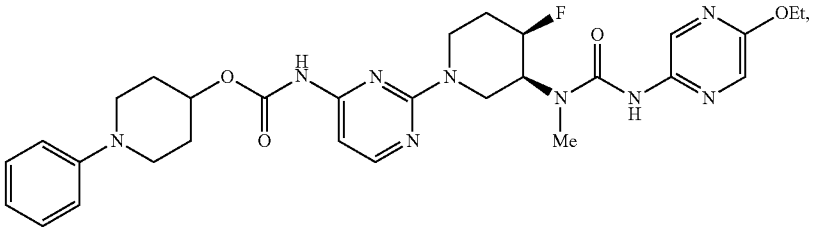
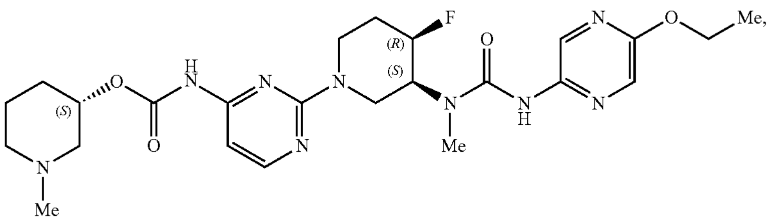
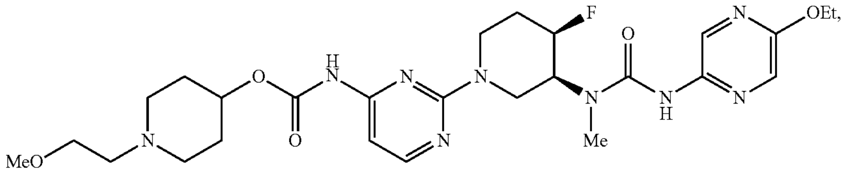
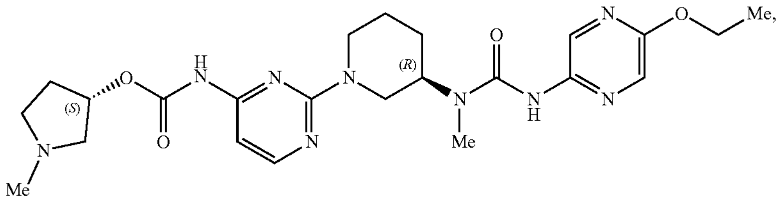
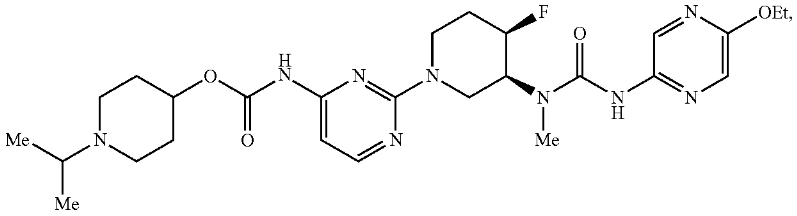
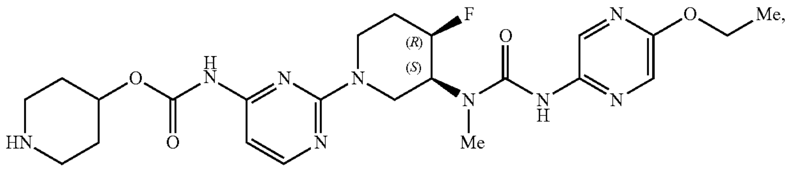
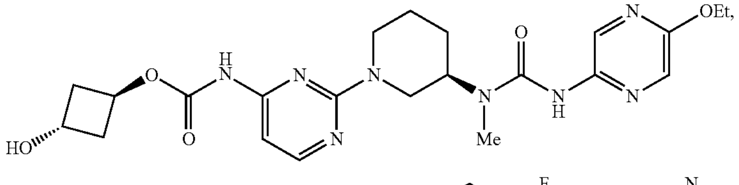
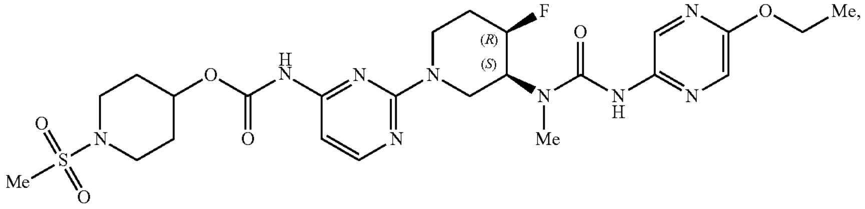

-continued
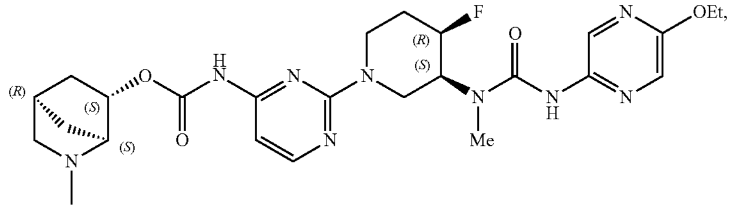
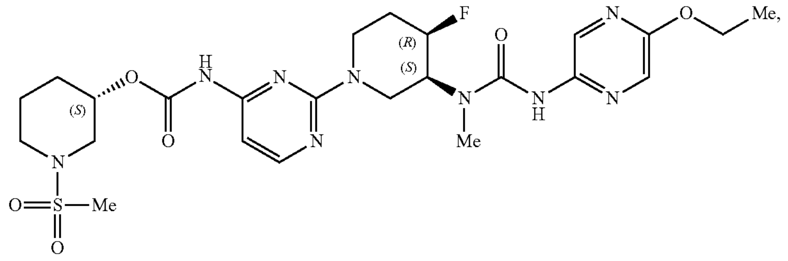
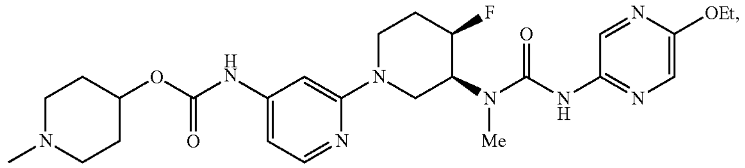
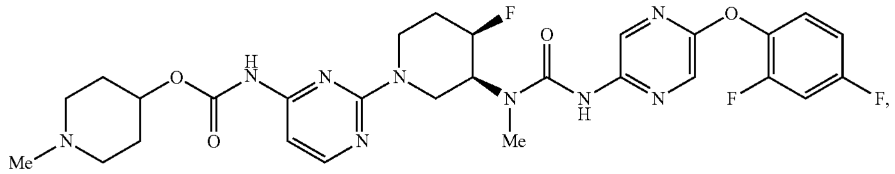
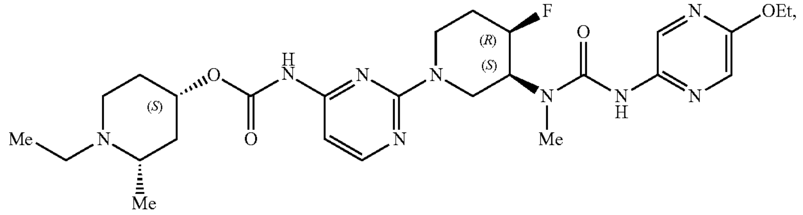
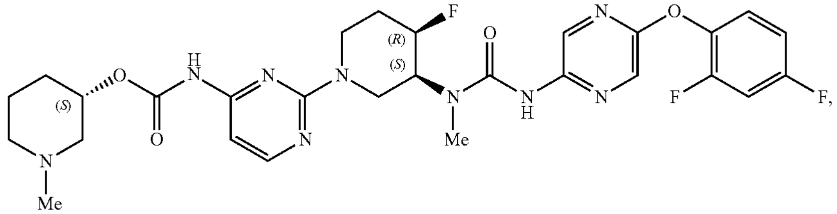
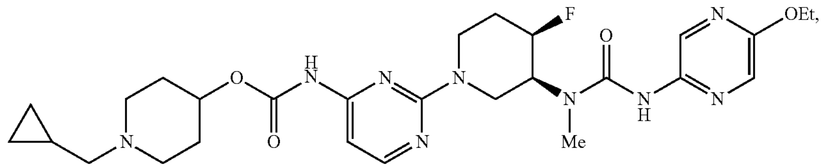
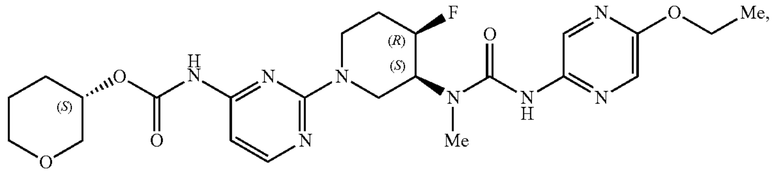
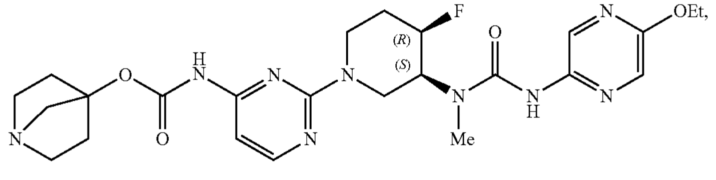

-continued
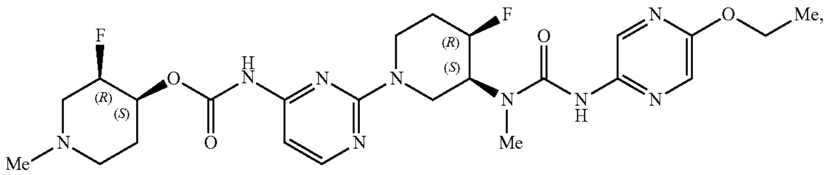
,
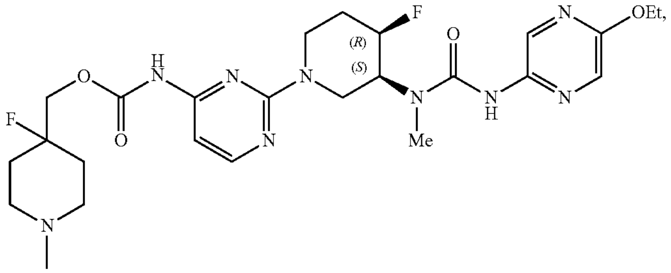
,
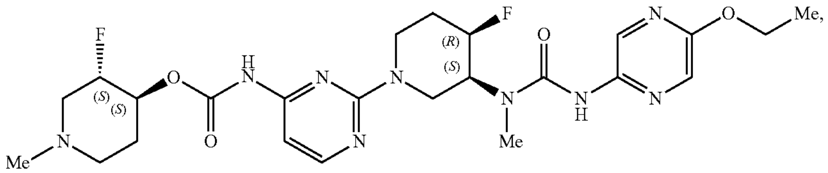
,
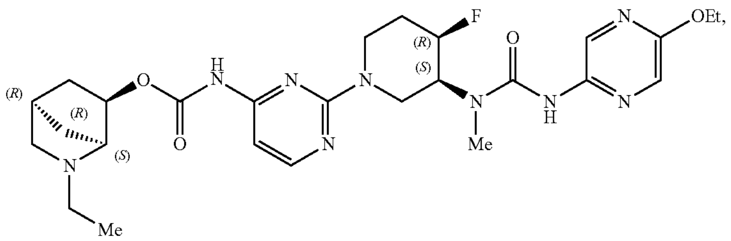
,
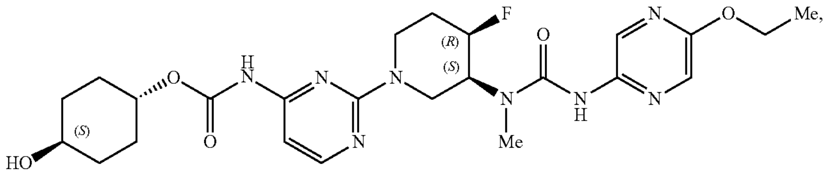
,
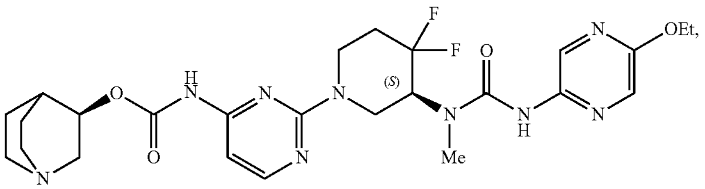
,
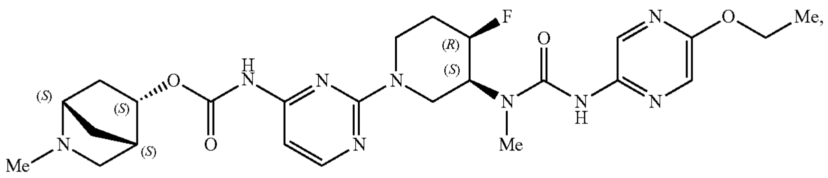
,
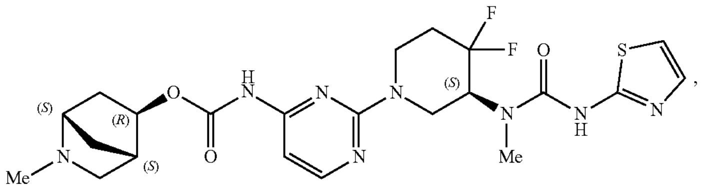
, -continued
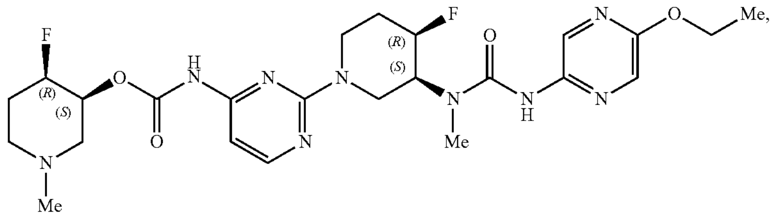
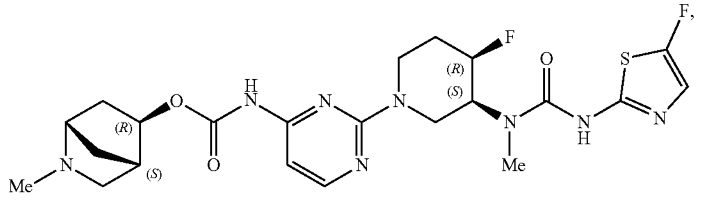
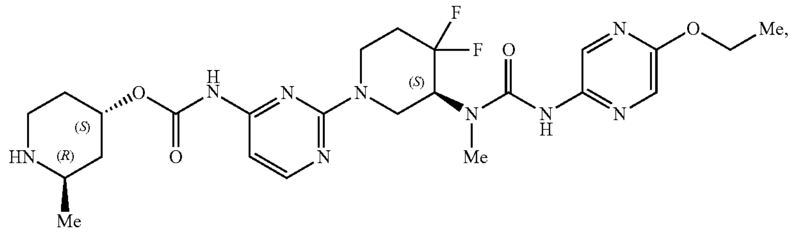
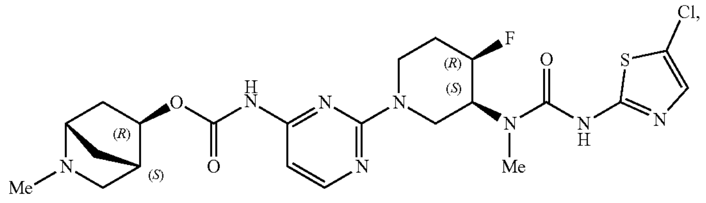
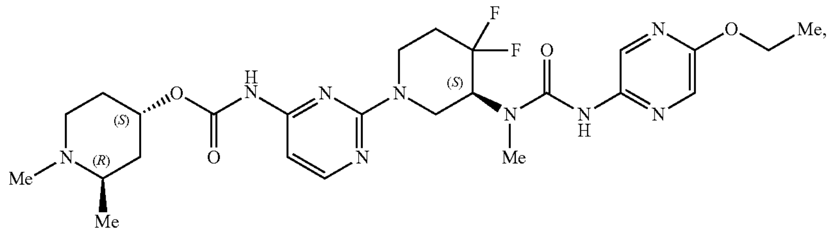
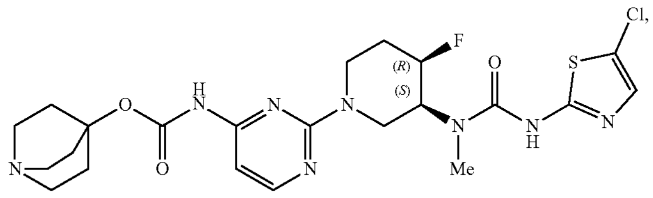
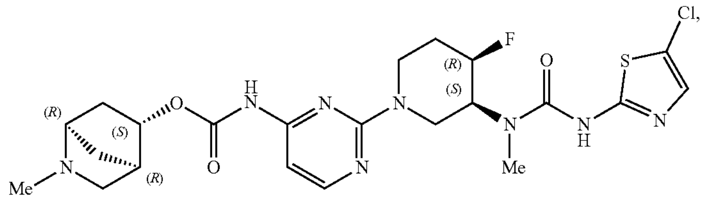
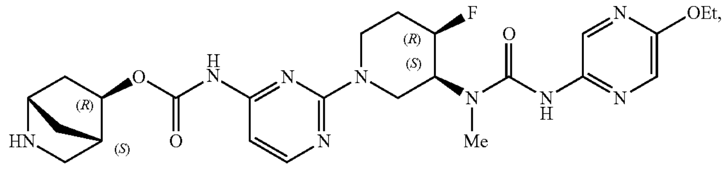

-continued
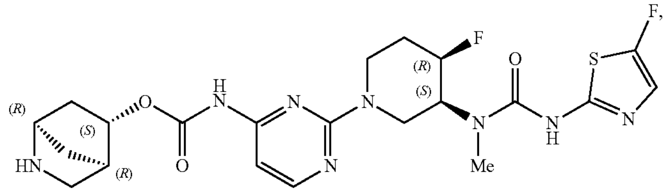
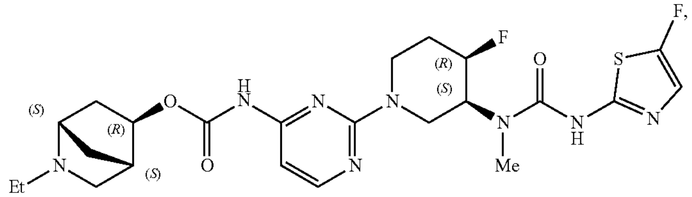
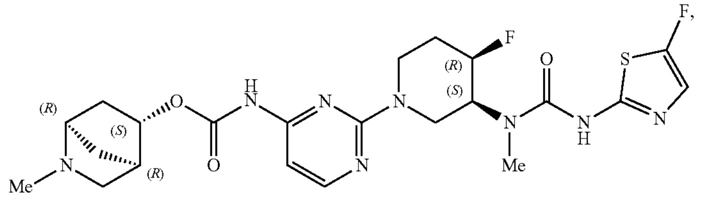
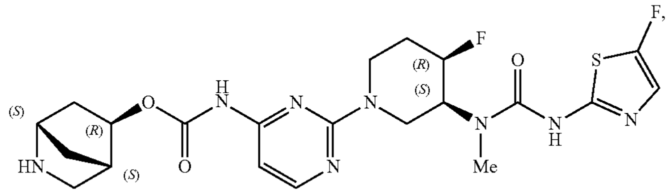
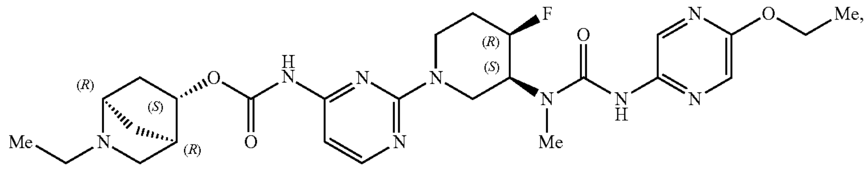
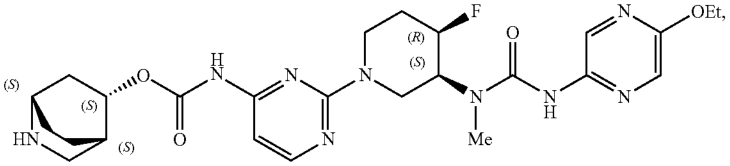
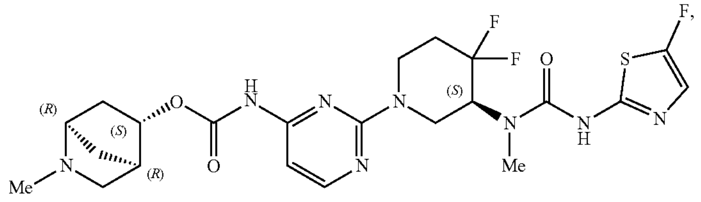
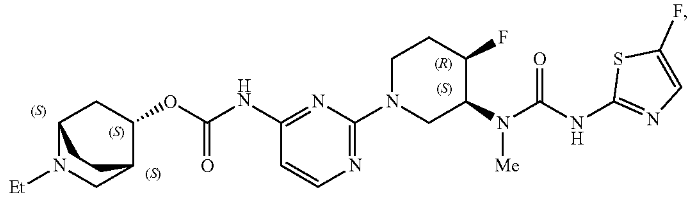
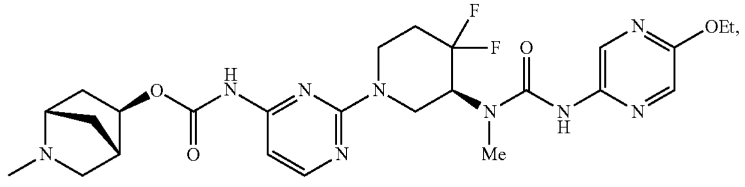

-continued
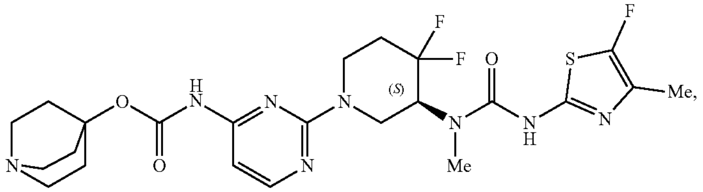
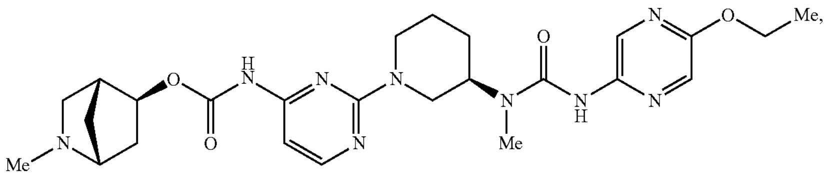
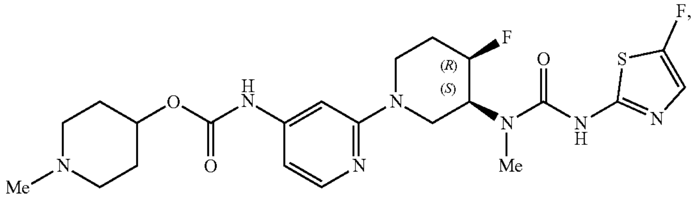
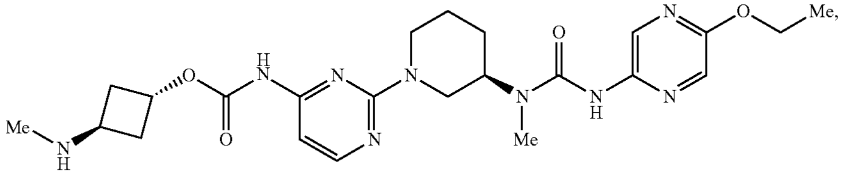
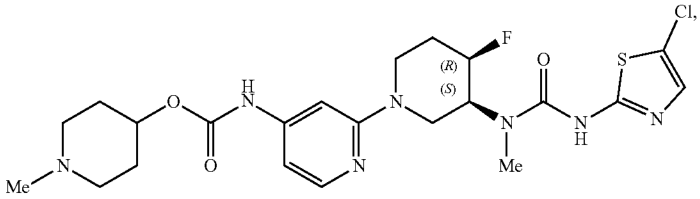
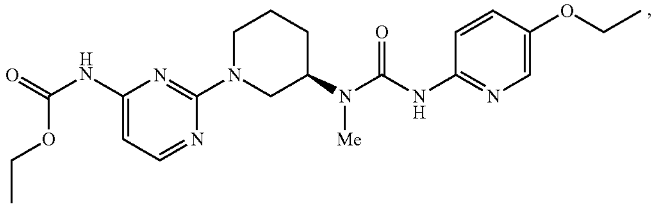
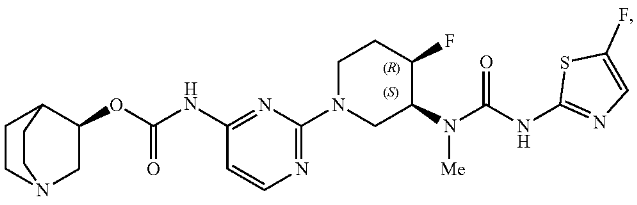
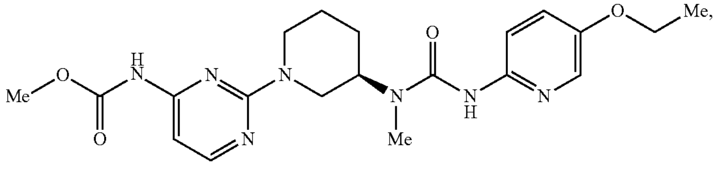
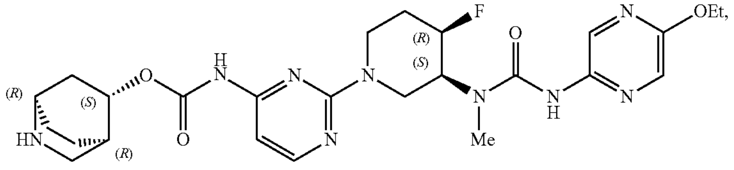

-continued
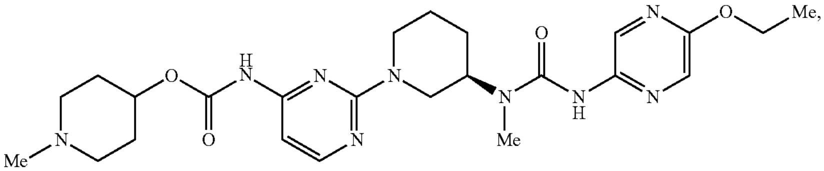
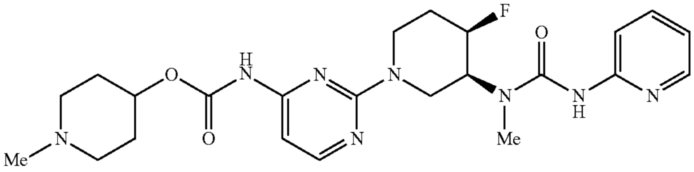
,
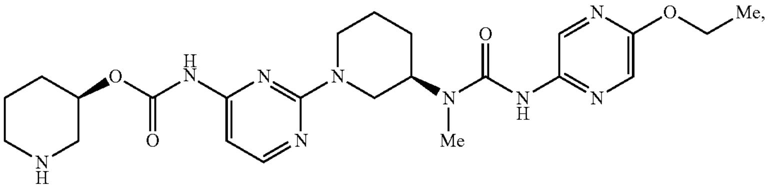
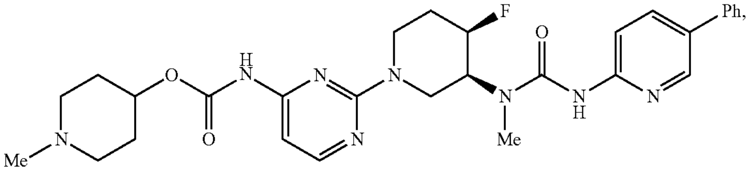
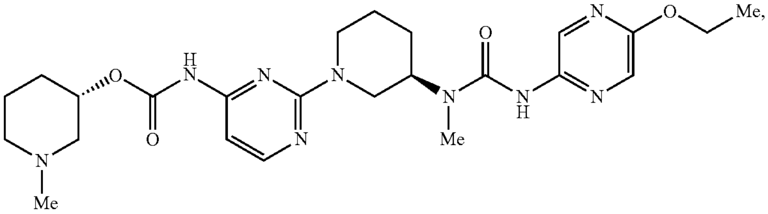
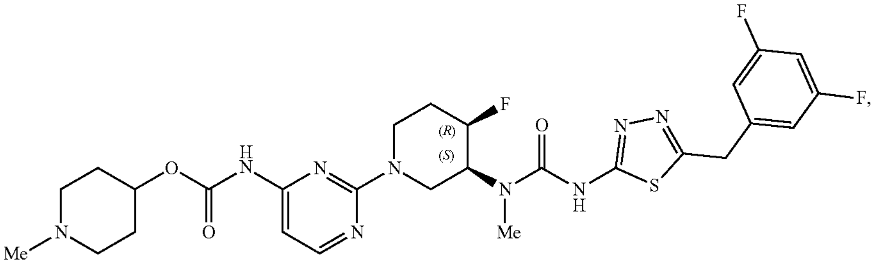
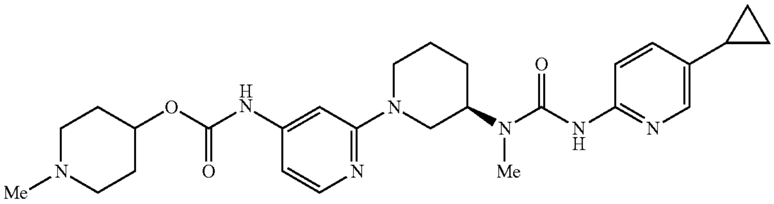
,
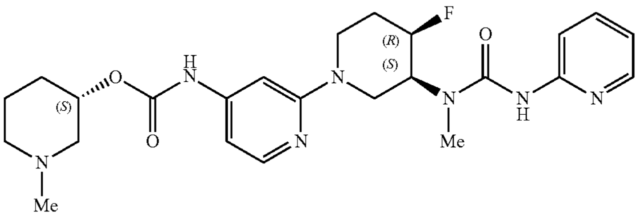
, -continued
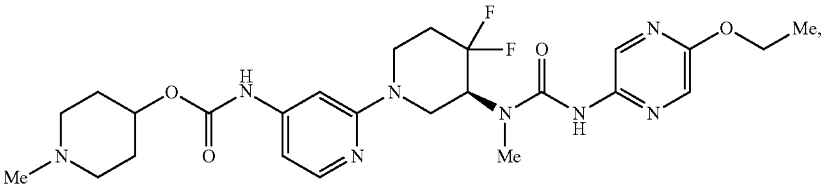
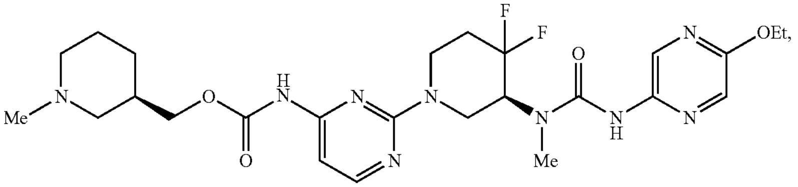
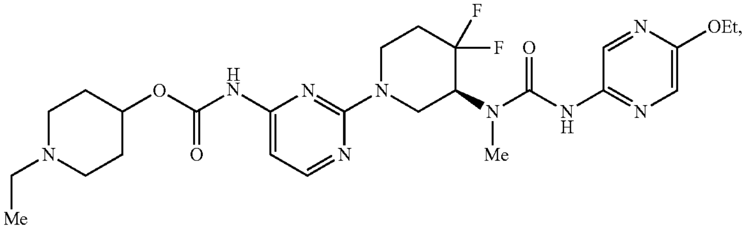
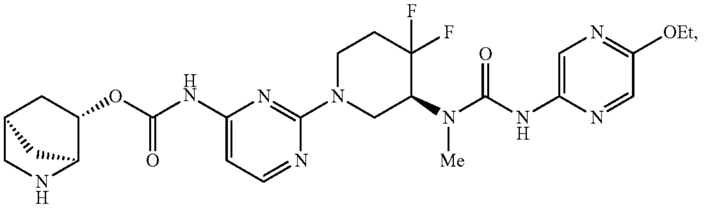
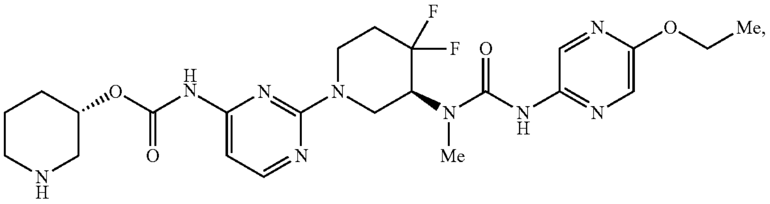
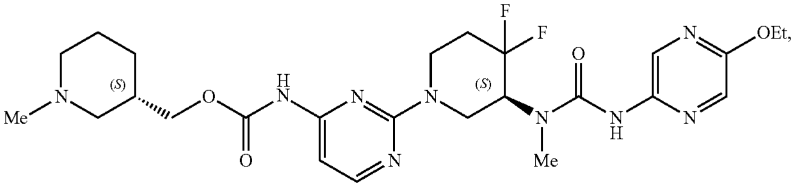
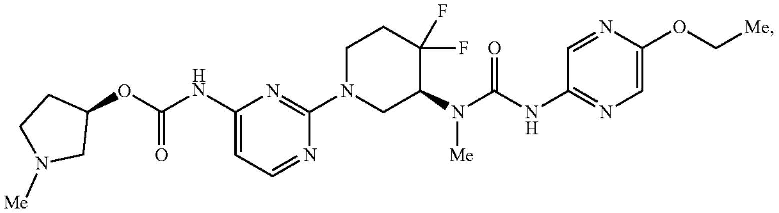
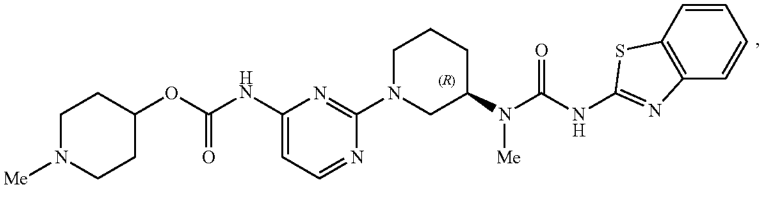

-continued
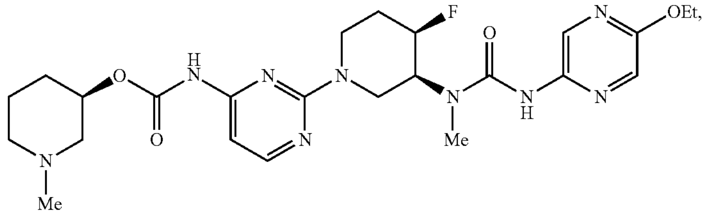
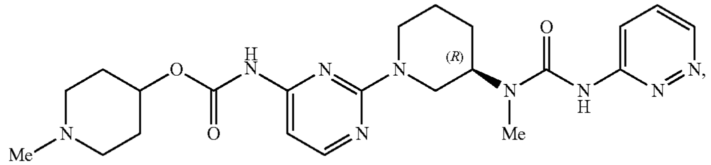
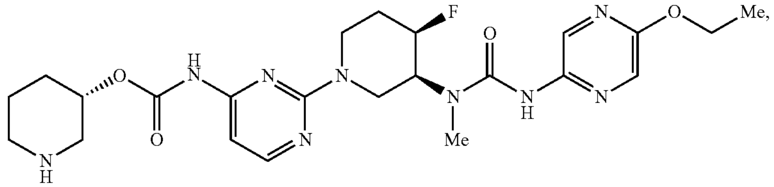
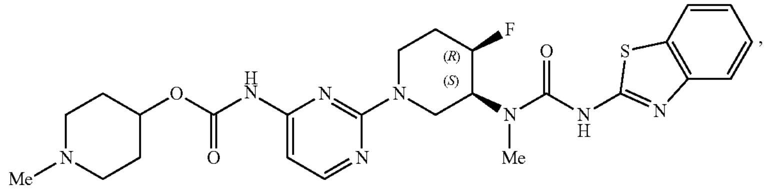
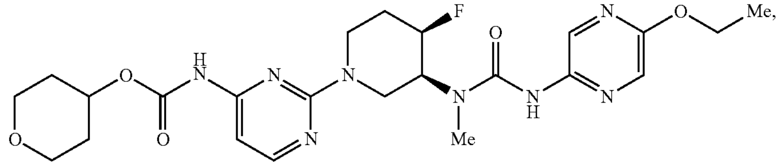
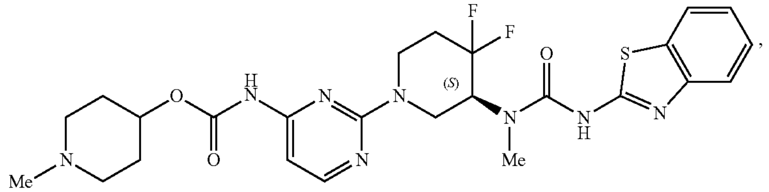
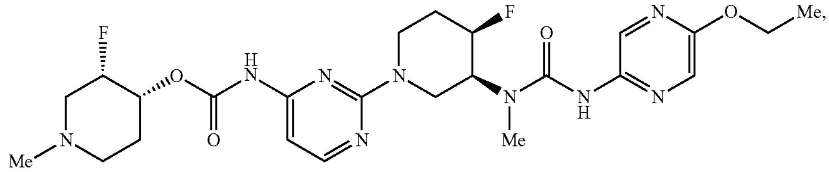
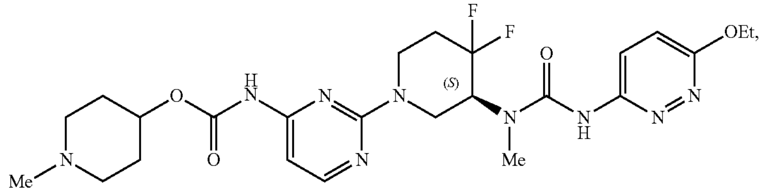
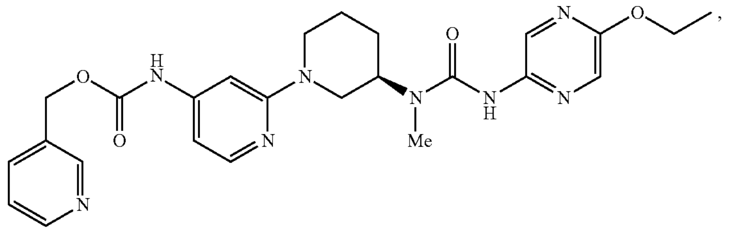

-continued
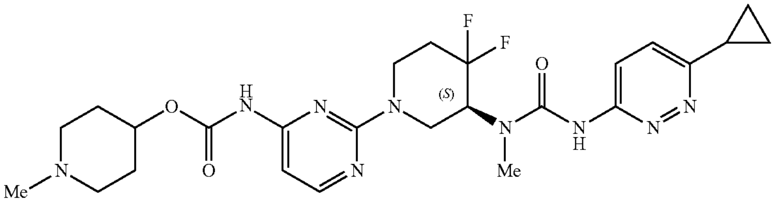
,
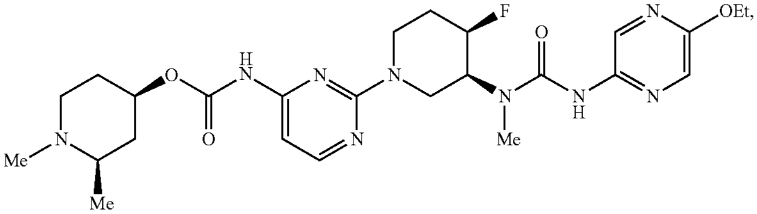
,
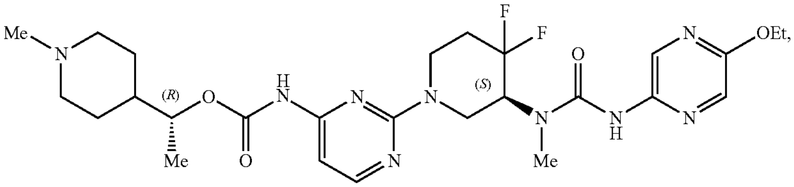
,
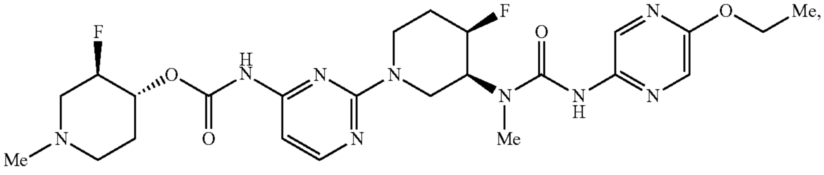
,
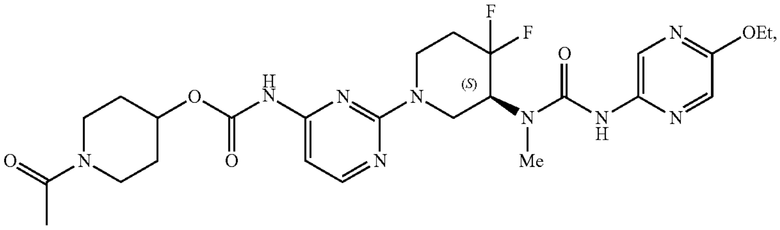
,
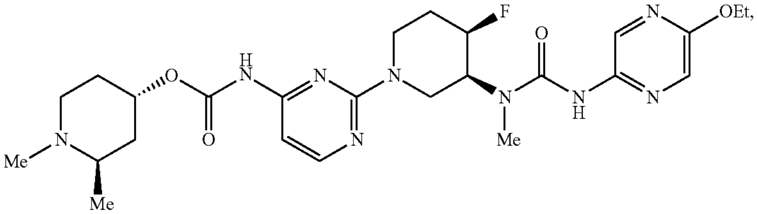
,
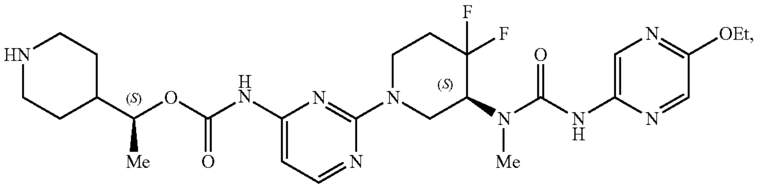
,
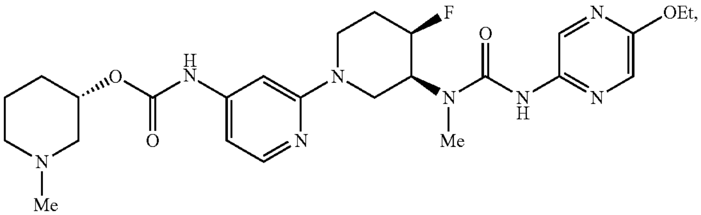
, -continued
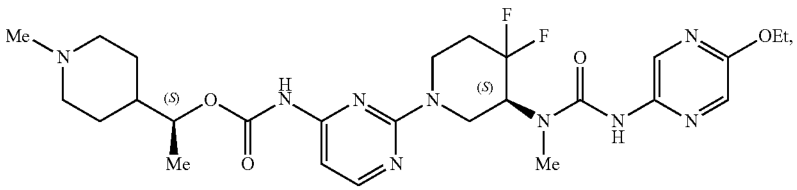
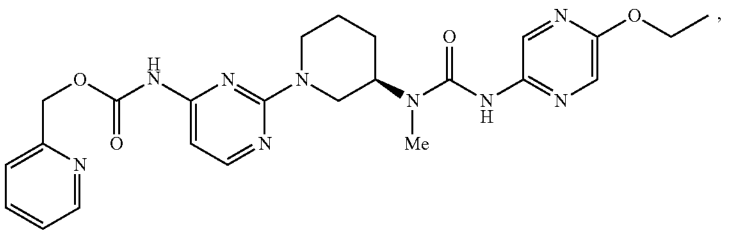
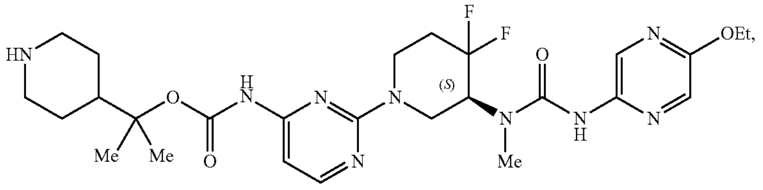
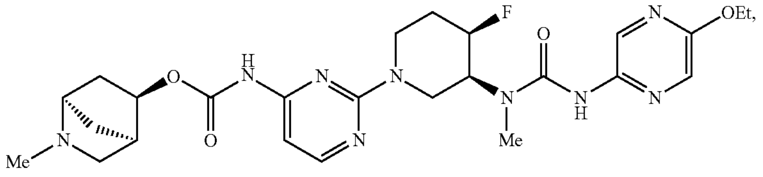
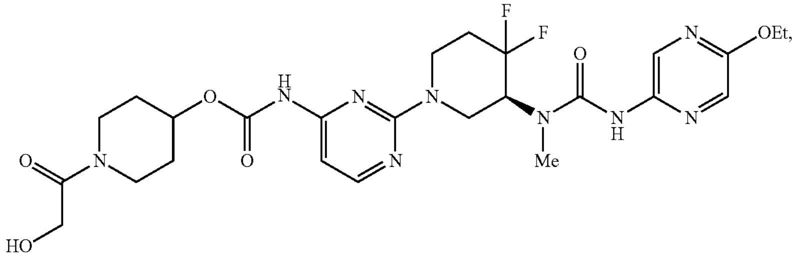
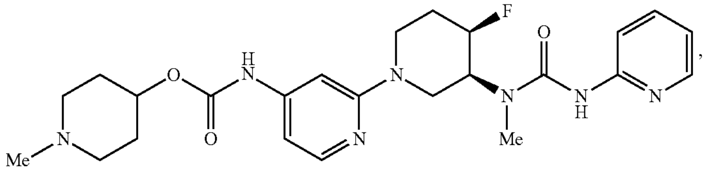
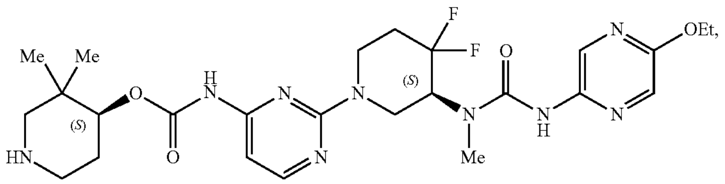
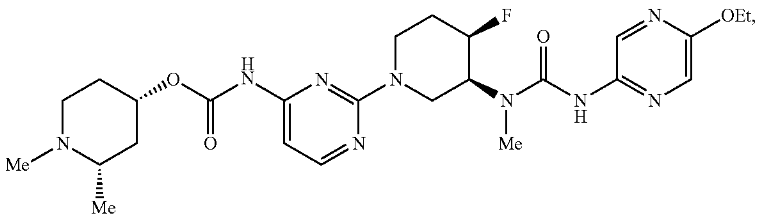

-continued
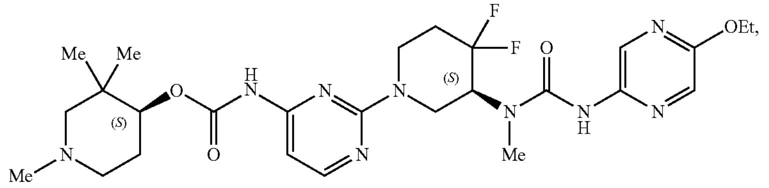
,
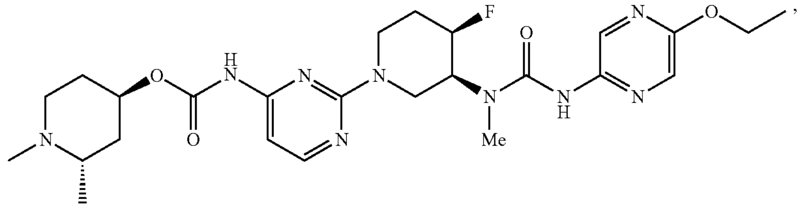
,
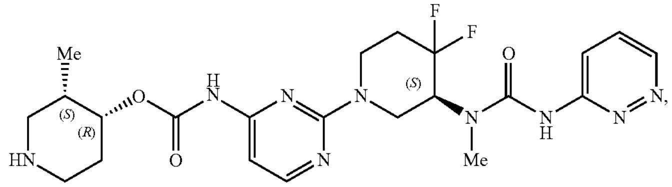
,
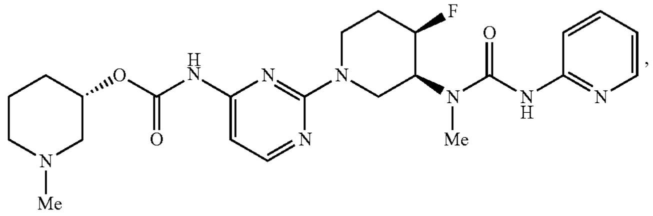
,
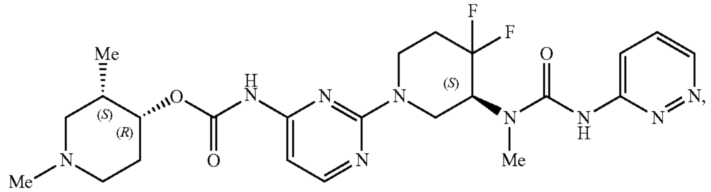
,
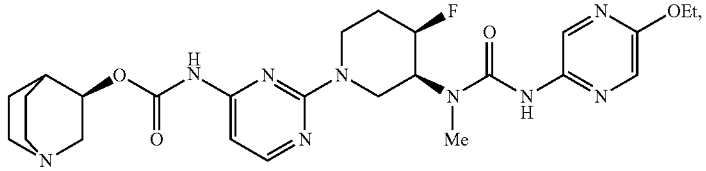
,
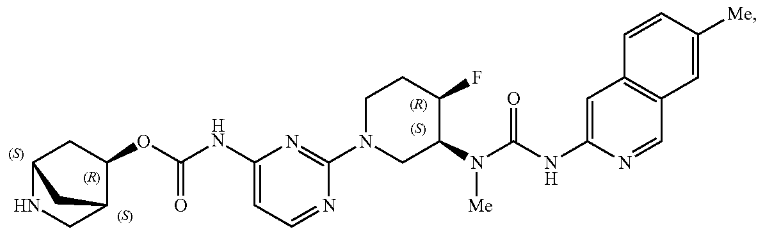
,
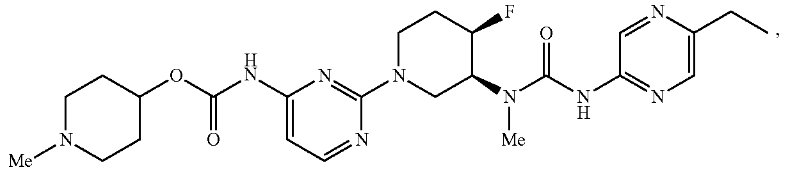
, -continued
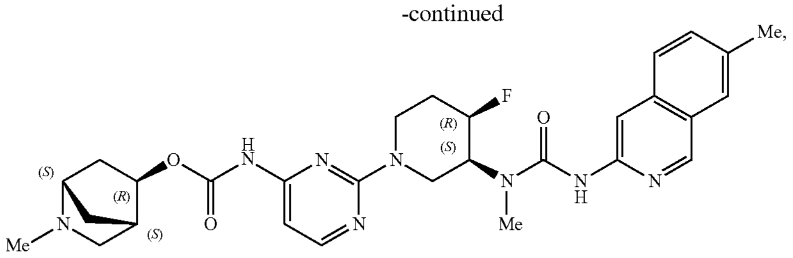
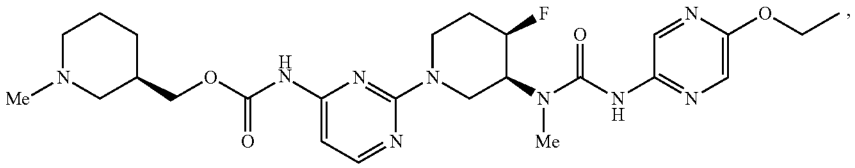
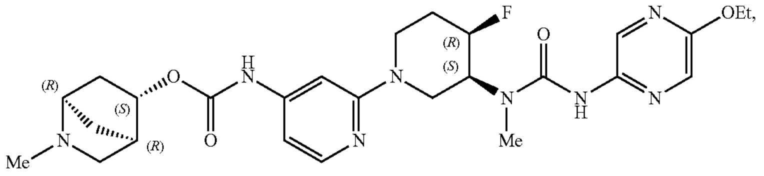
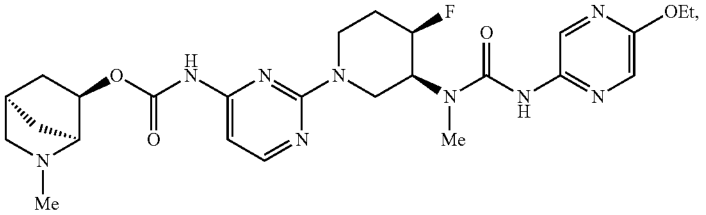
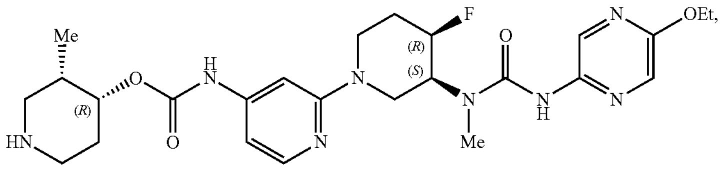
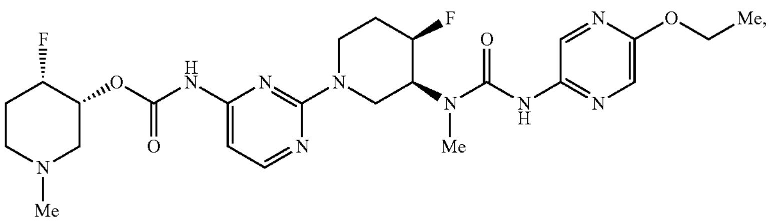
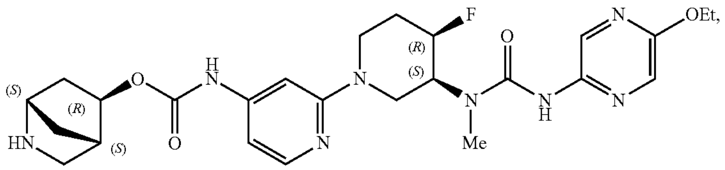
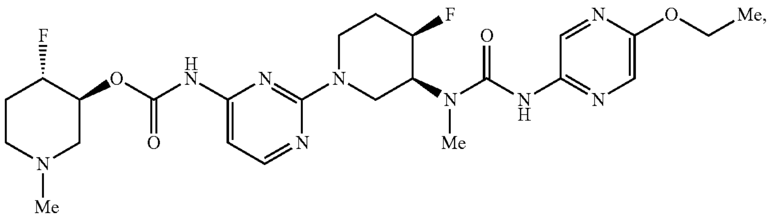

-continued
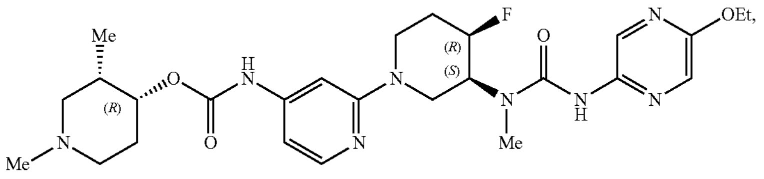
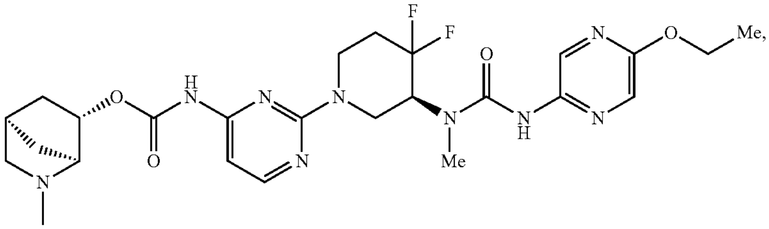
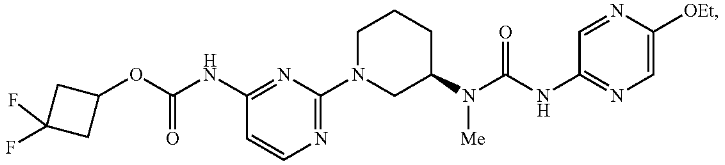
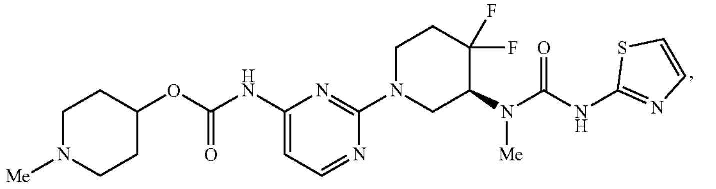
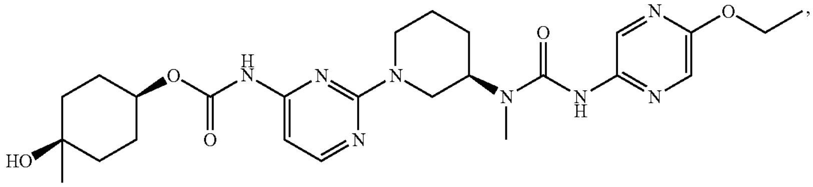
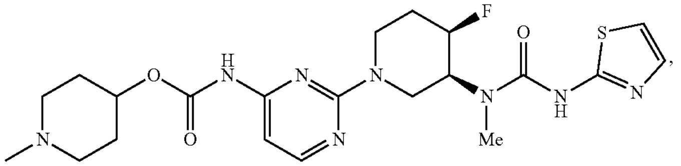
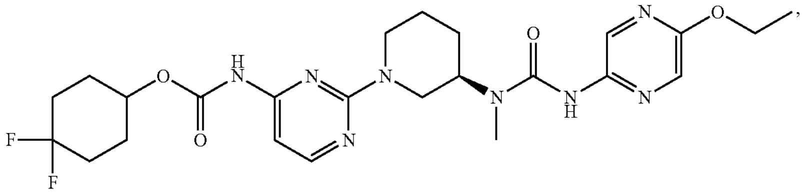
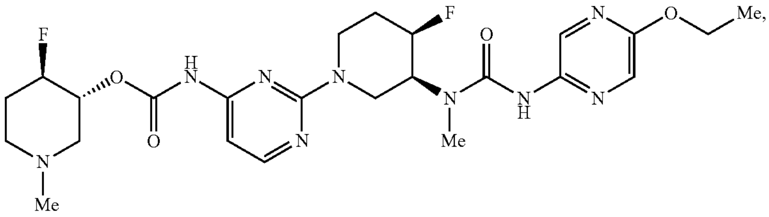
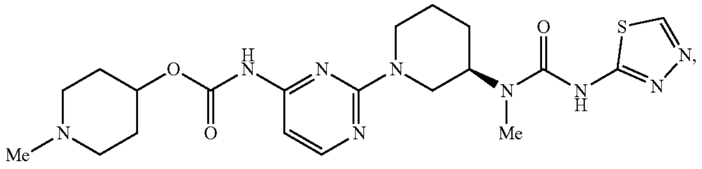

-continued
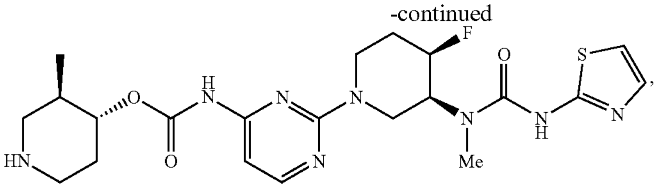
,
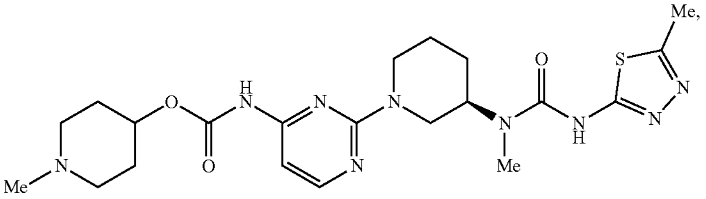
,
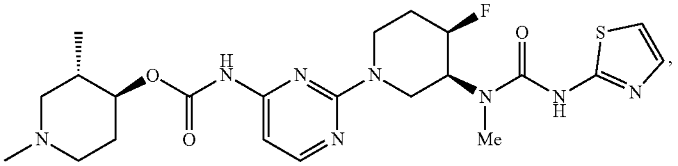
,
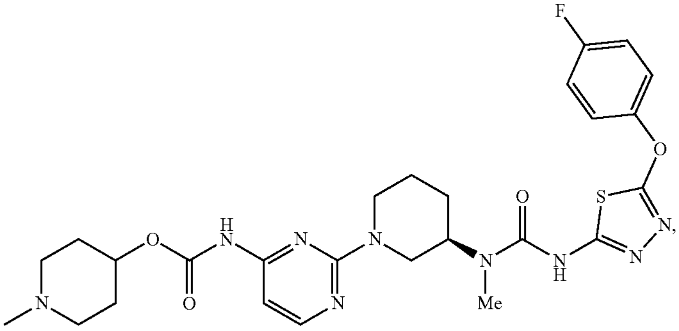
,
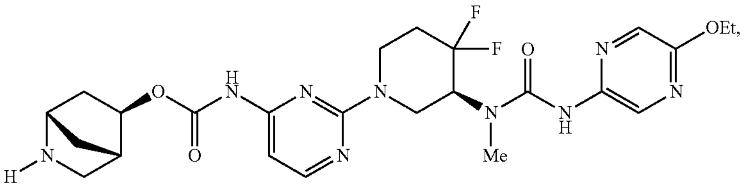
,
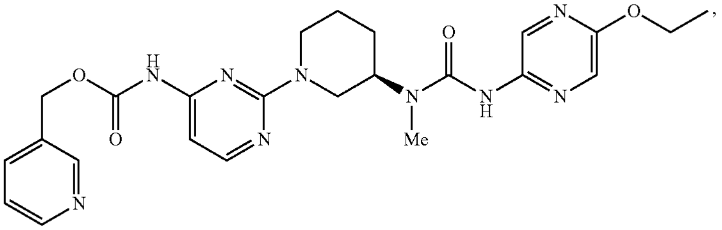
,
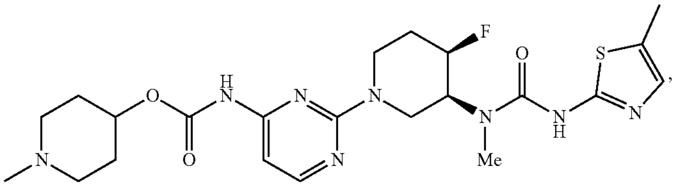
,
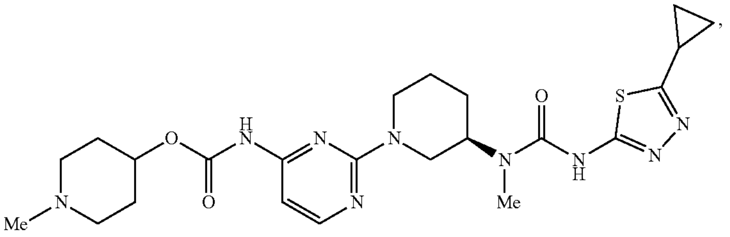
, -continued
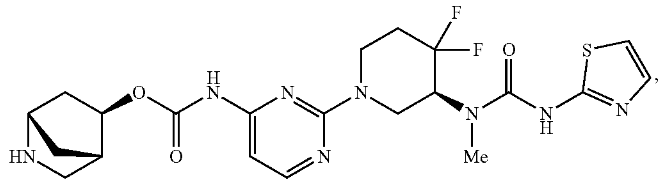,
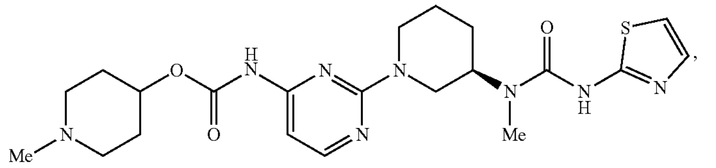,
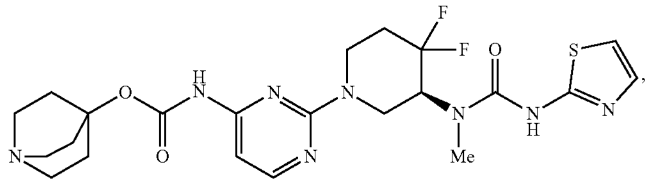,
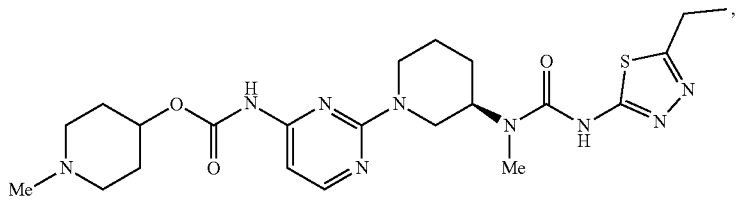,
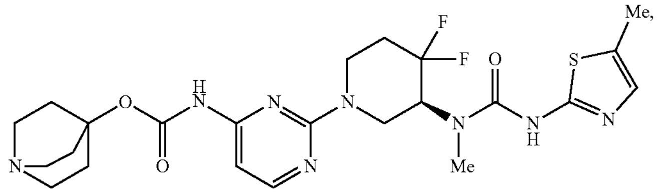,
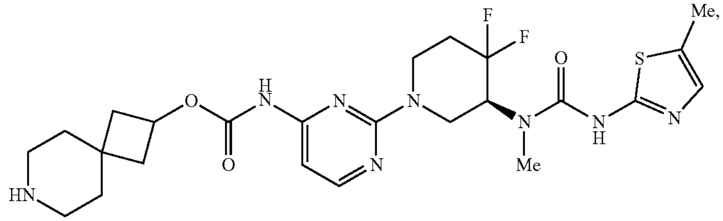,
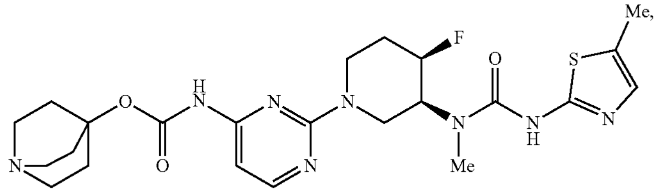,
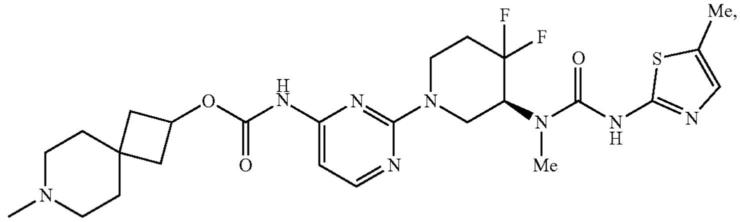, -continued
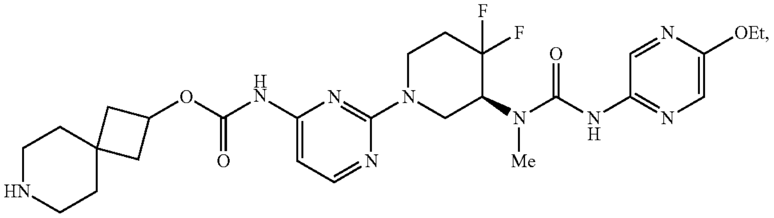
,
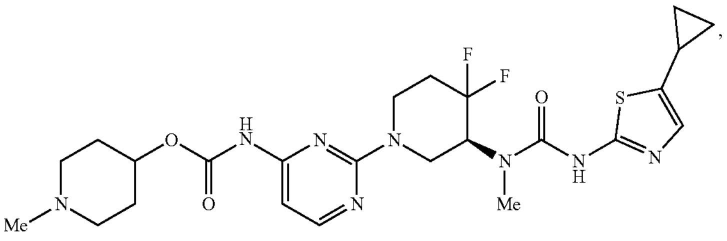
,
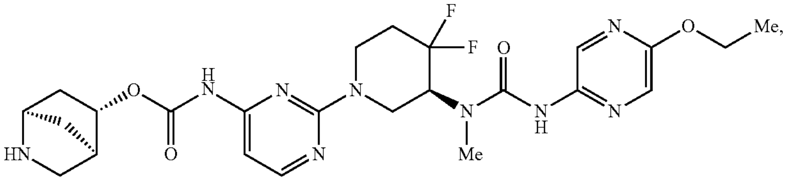
,
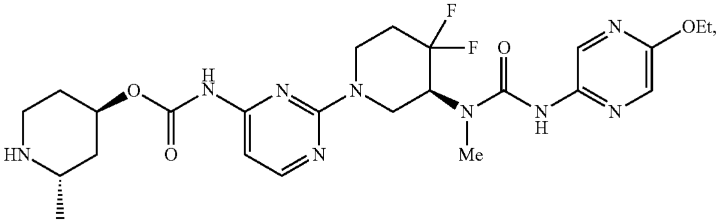
,
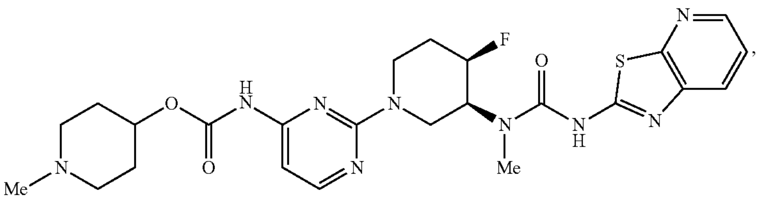
,
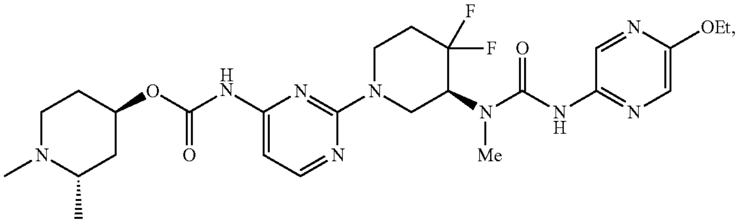
,
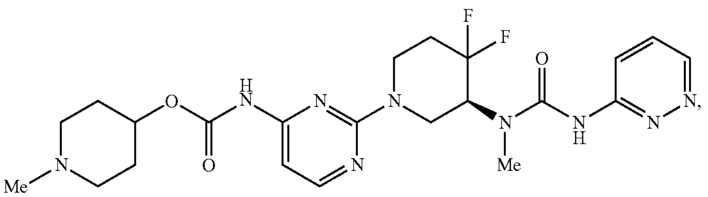
,
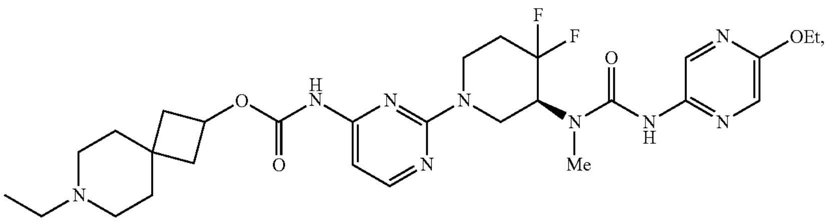
, -continued
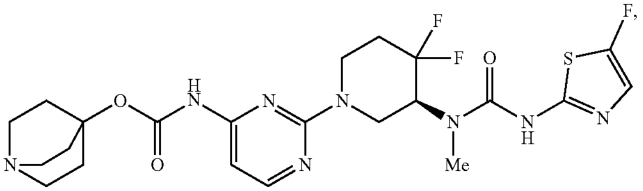
,
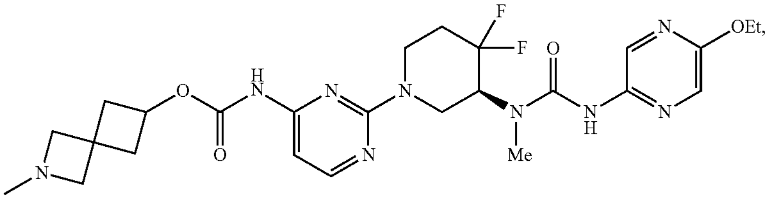
,
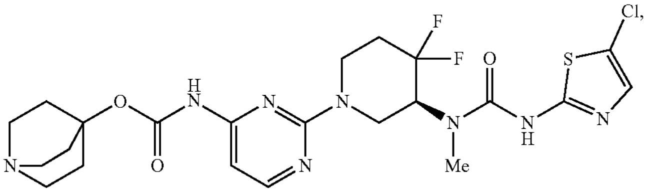
,
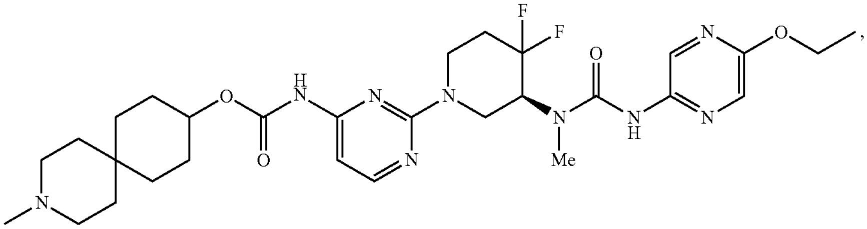
,
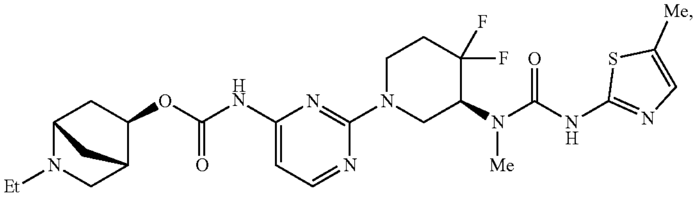
,
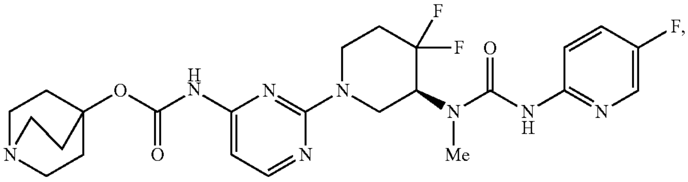
,
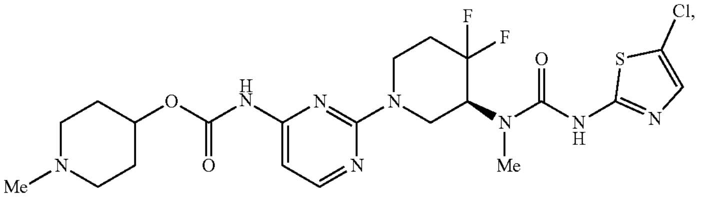
,
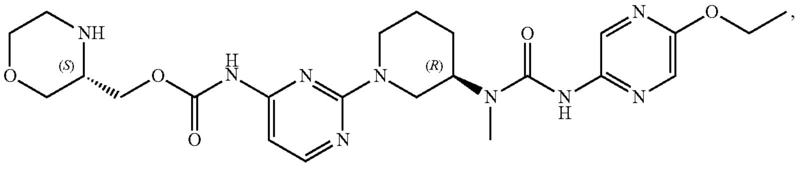
, -continued
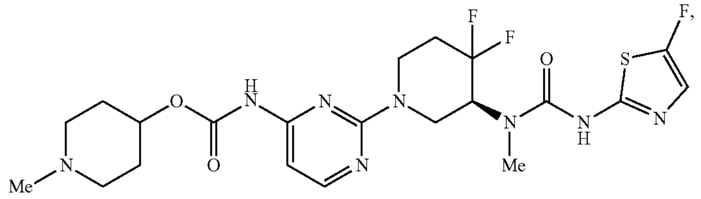
,
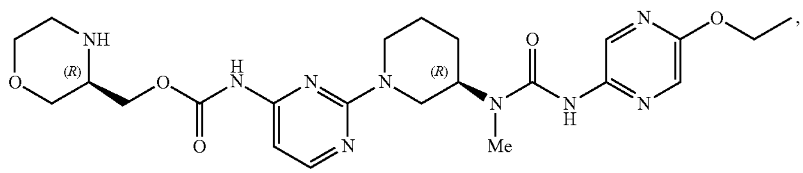
,
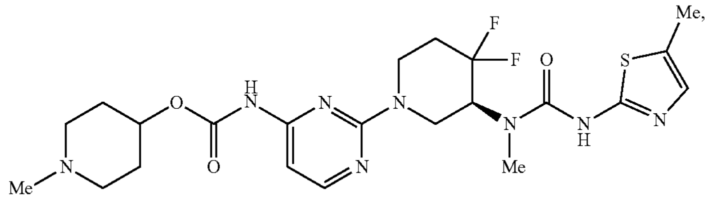
,
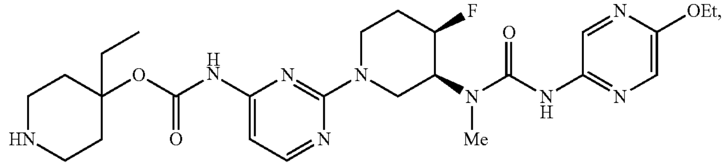
,
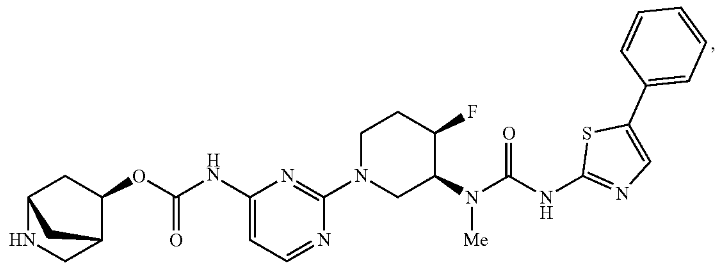
,
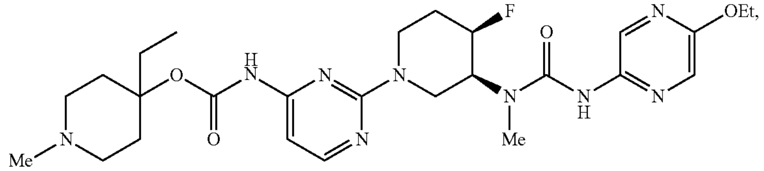
,
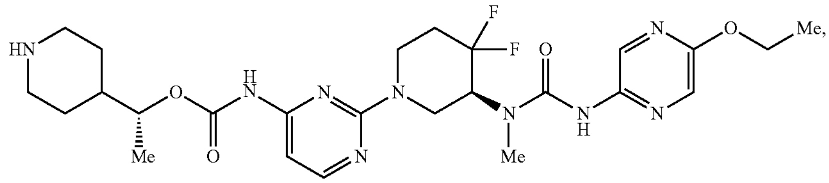
,
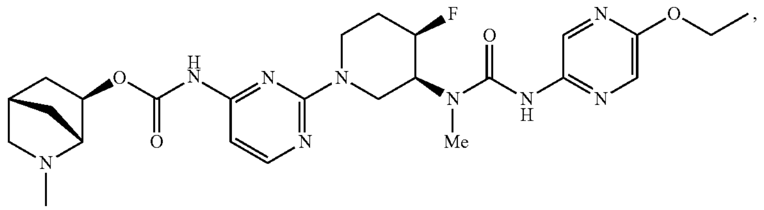
, -continued
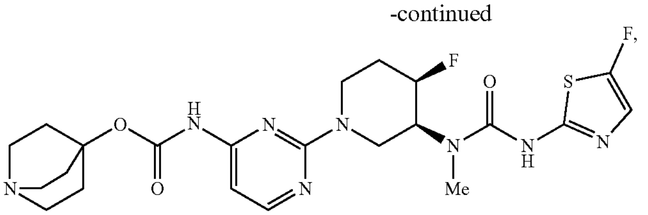
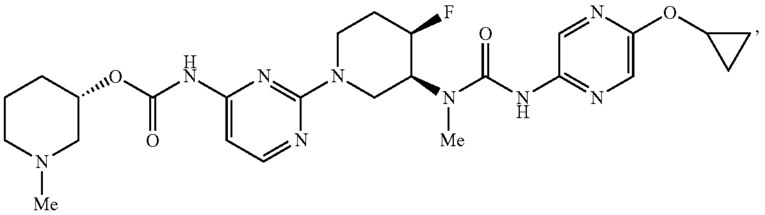
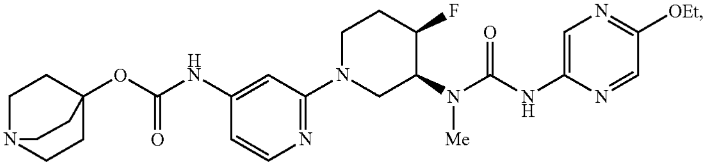
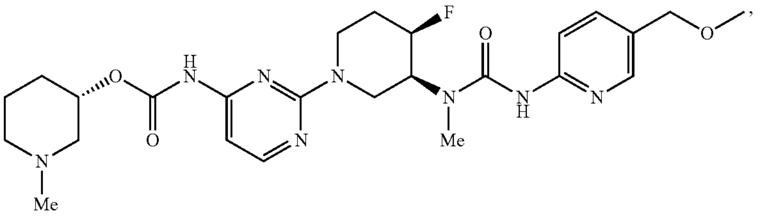
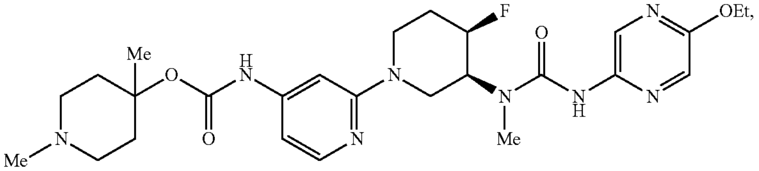
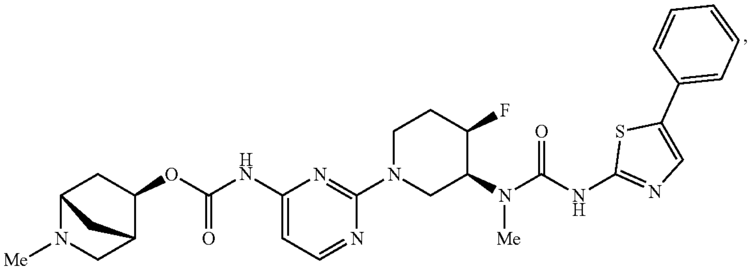
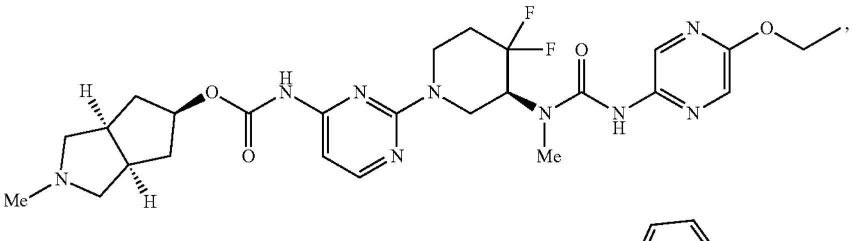
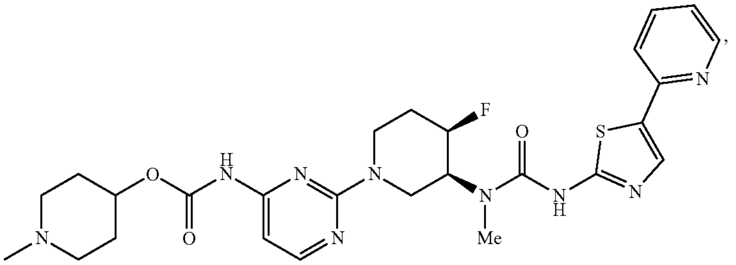

-continued
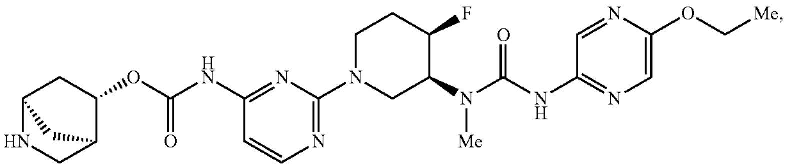
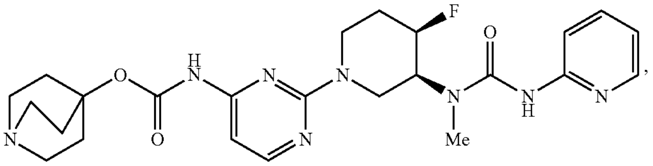
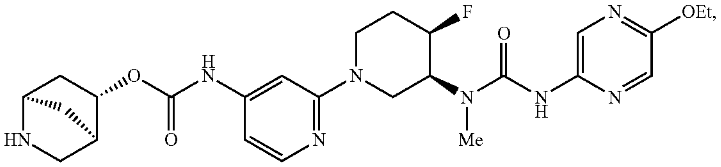
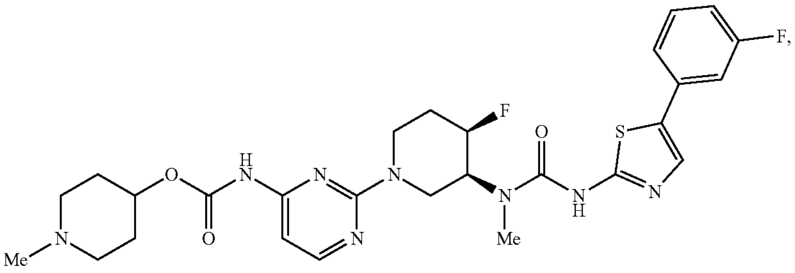
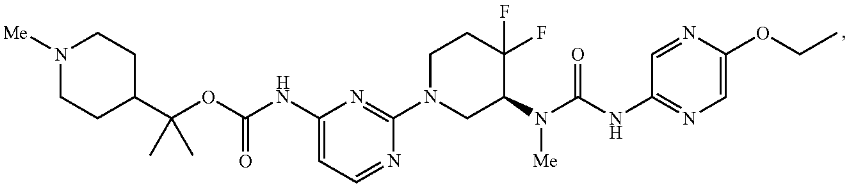
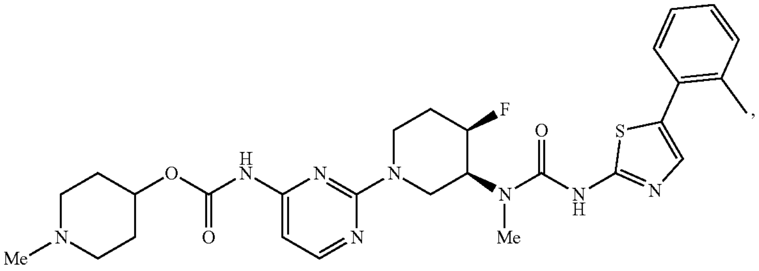
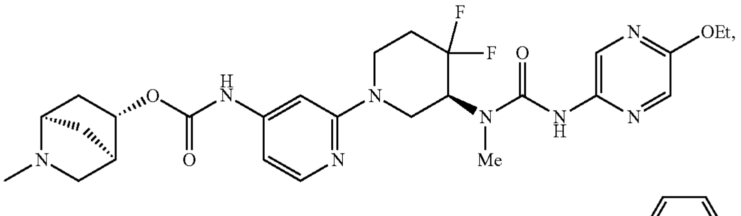
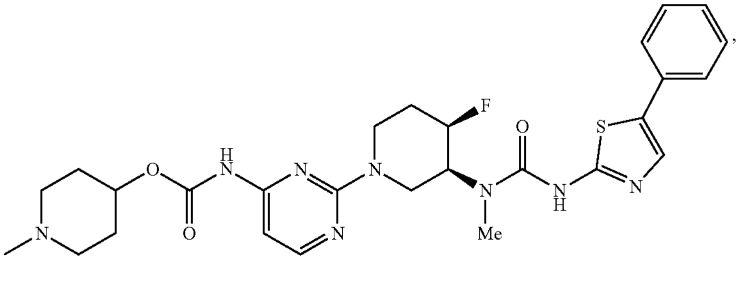

-continued
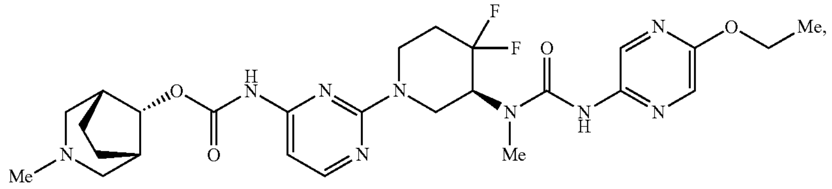
,
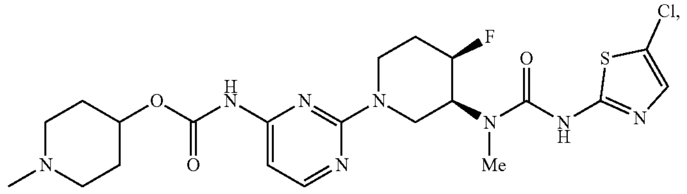
,
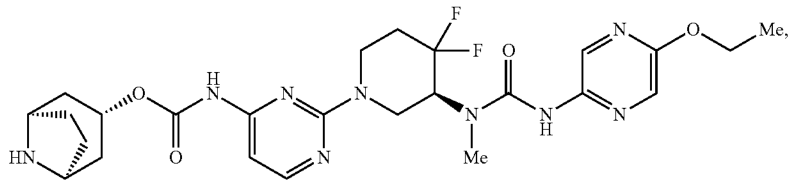
,
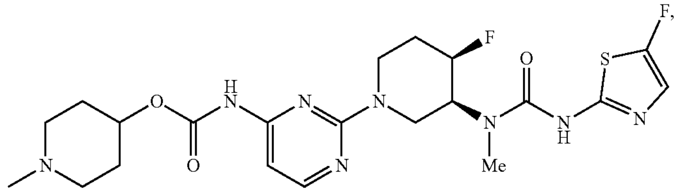
,
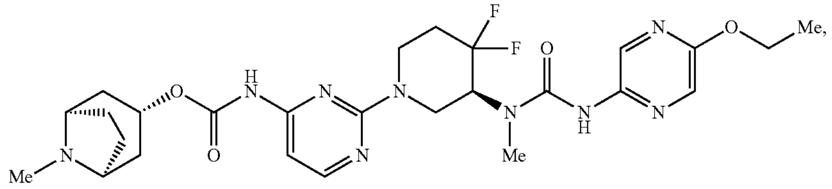
,
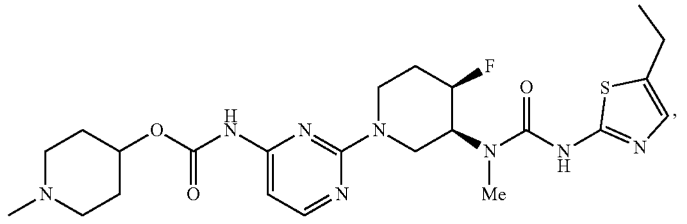
,
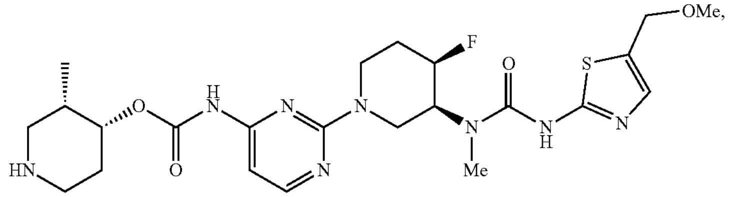
,
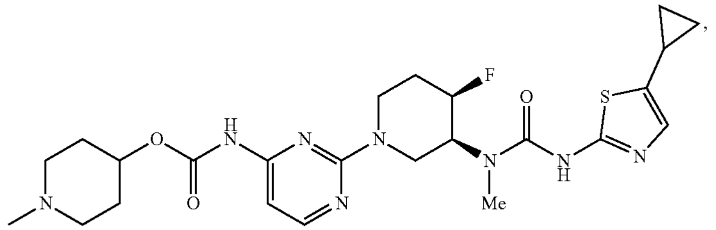
, -continued
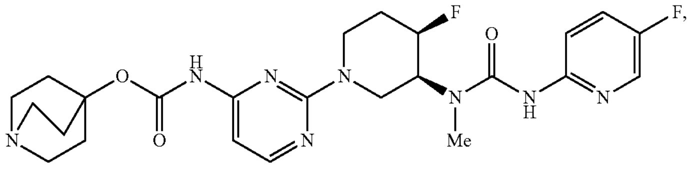
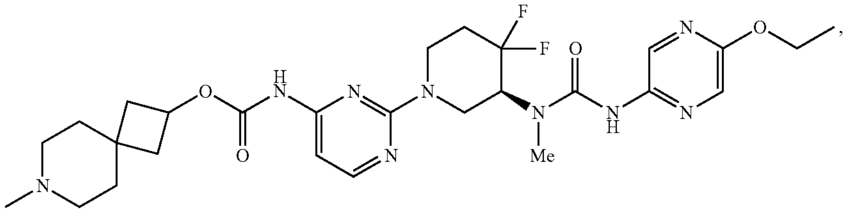
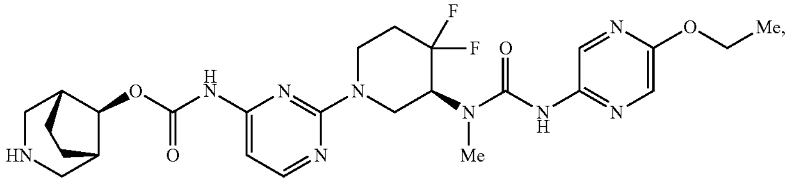
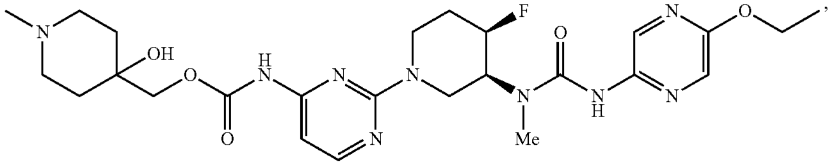
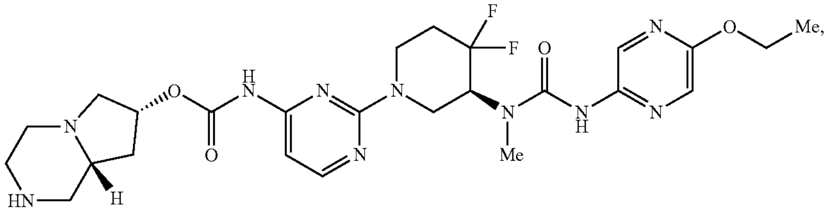
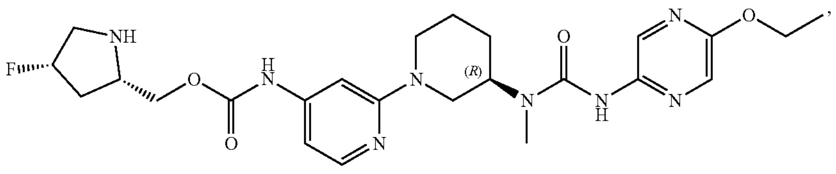
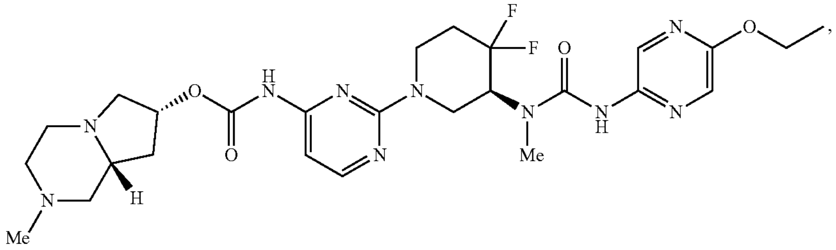
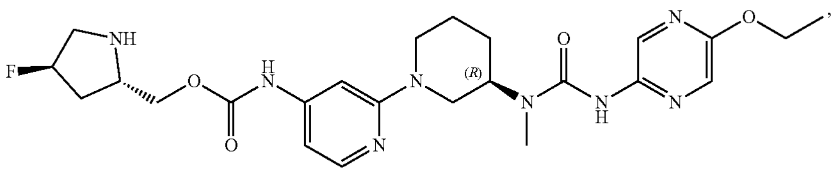

-continued
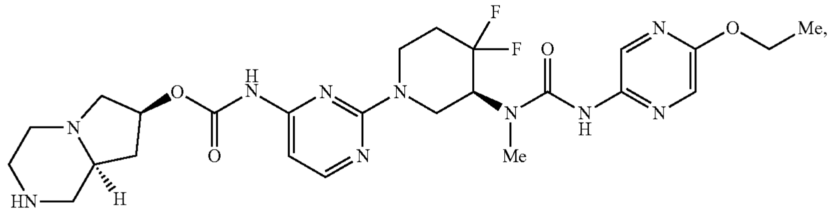
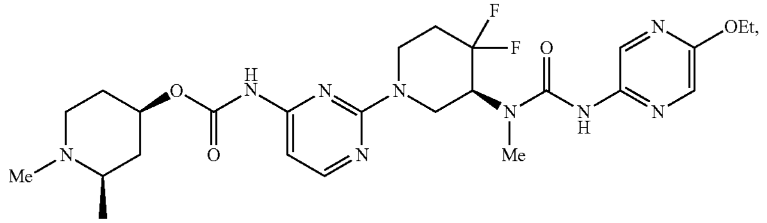
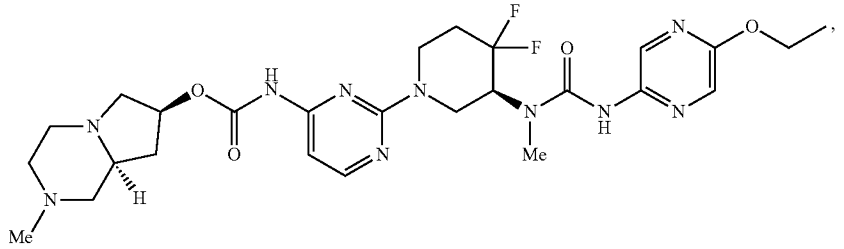
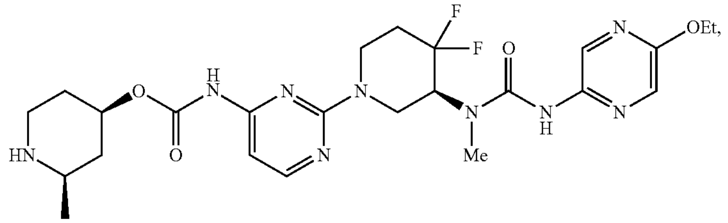
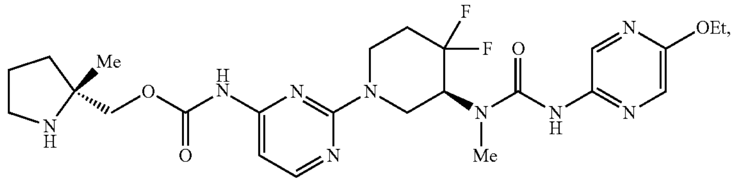
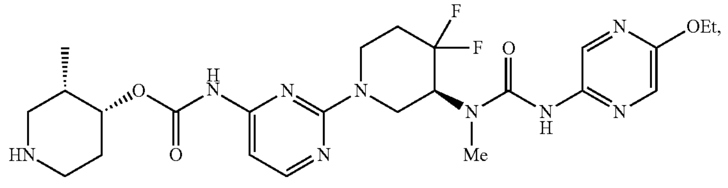
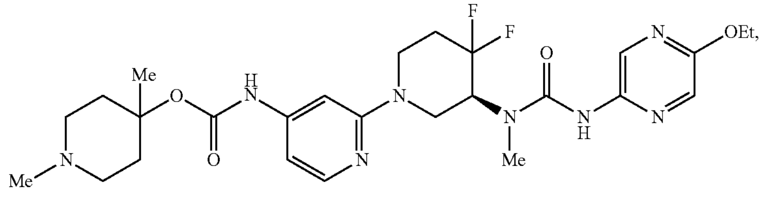
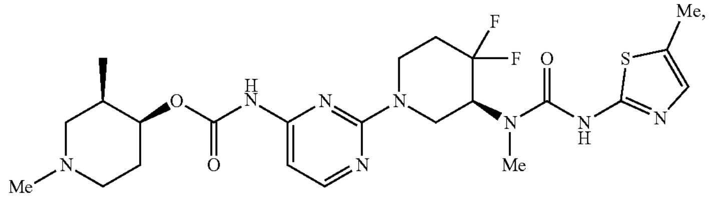

-continued
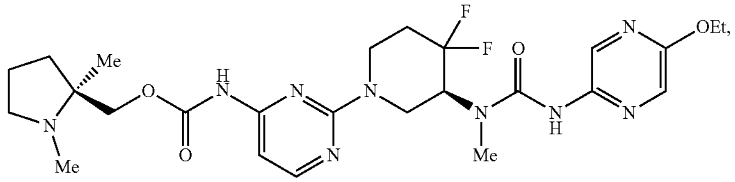
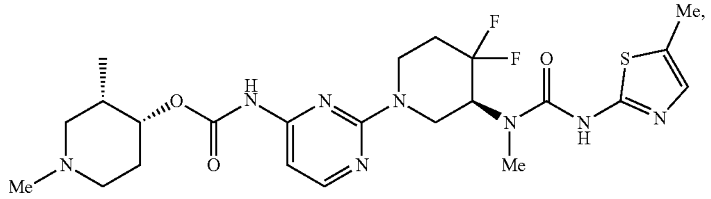
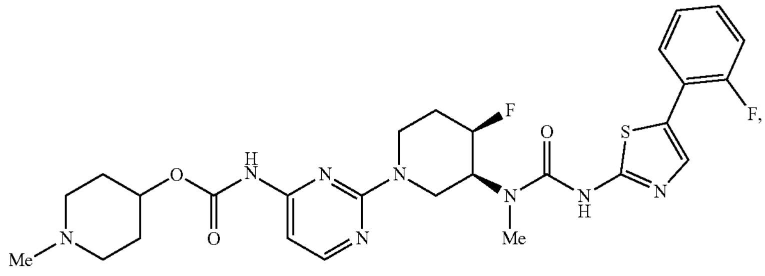
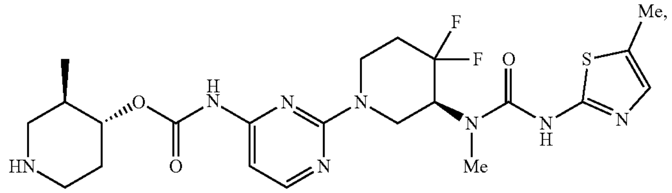
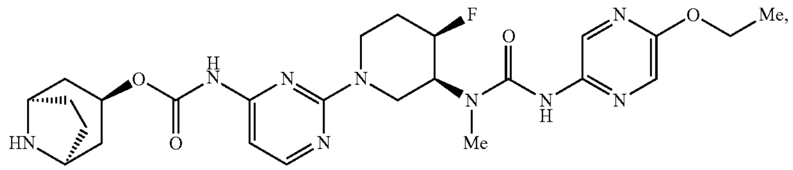
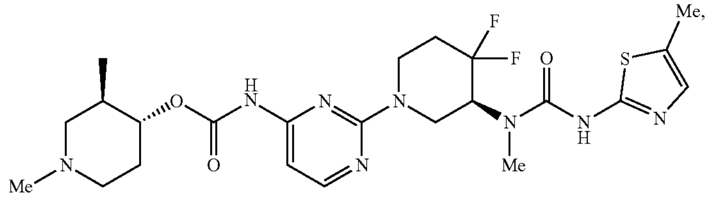
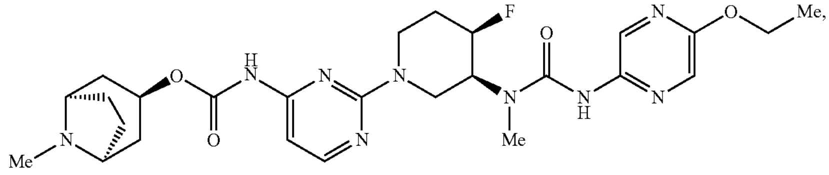
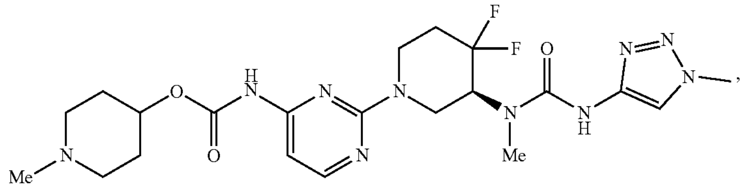

-continued
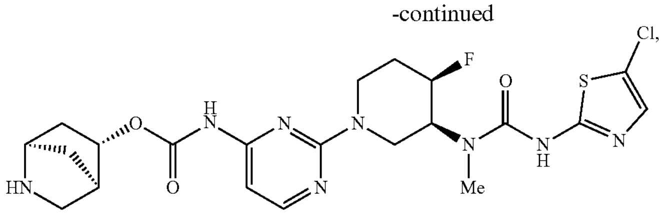
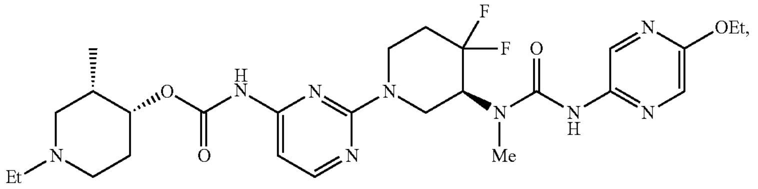
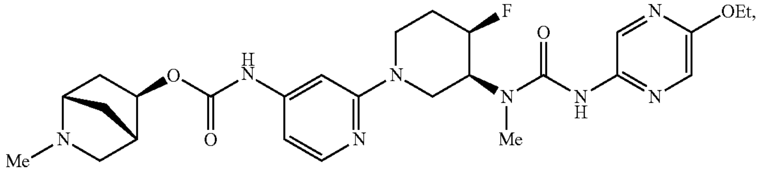
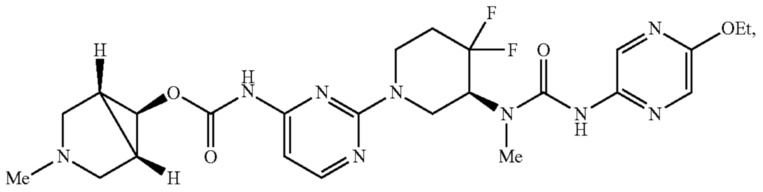
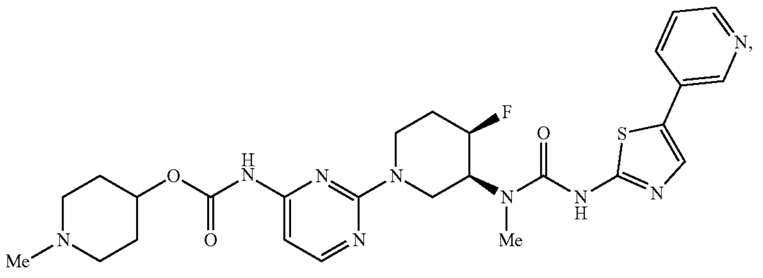
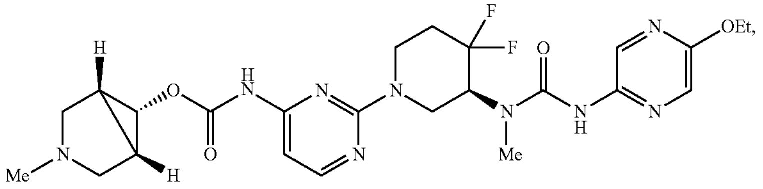
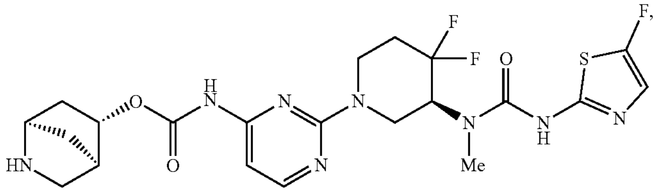
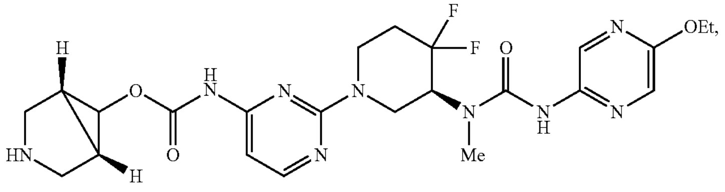

-continued
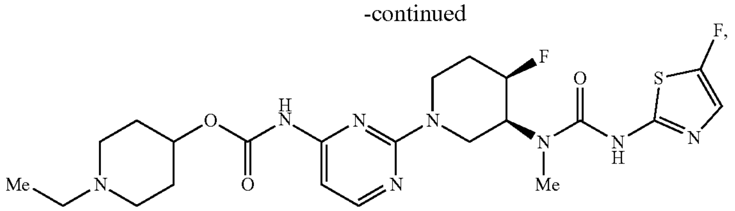
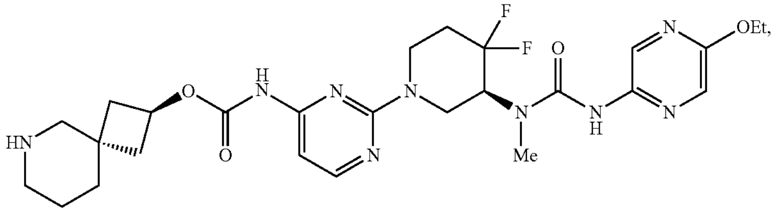
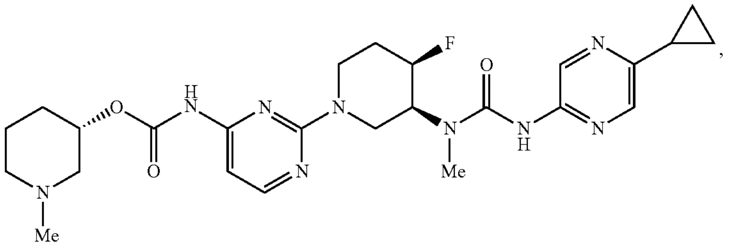
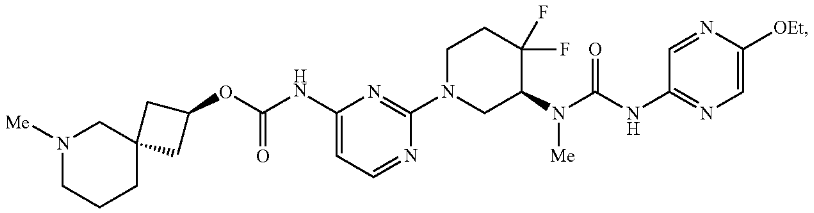
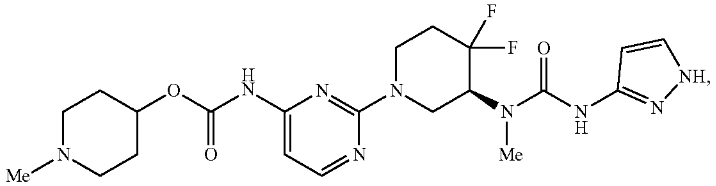
and
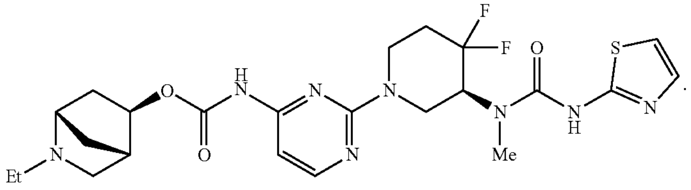
28. The compounnd of claim 1, wherein the compound is selected from the group consisting of:
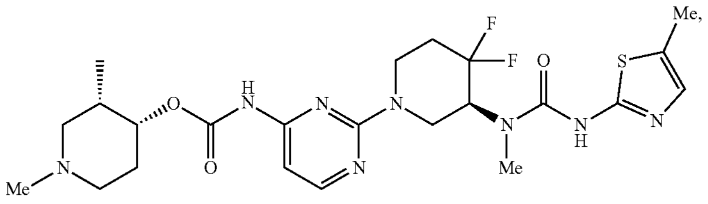

-continued
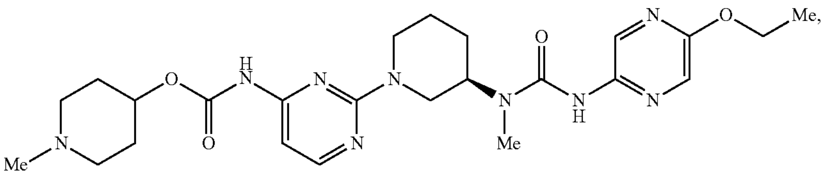
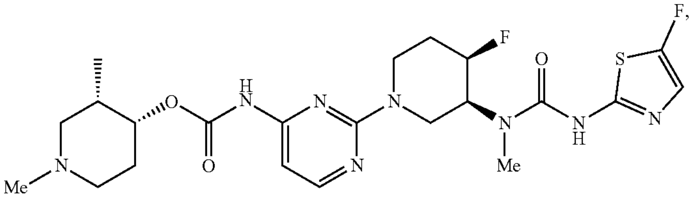
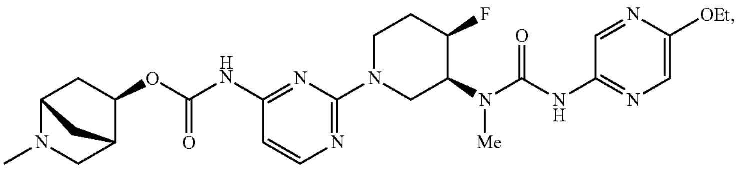
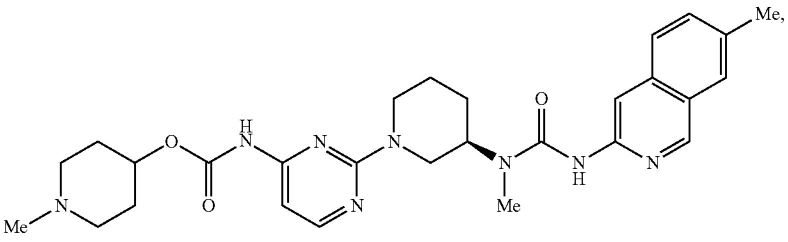
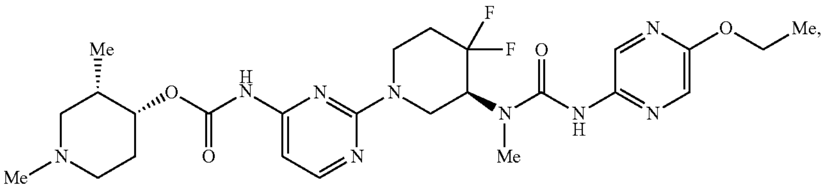
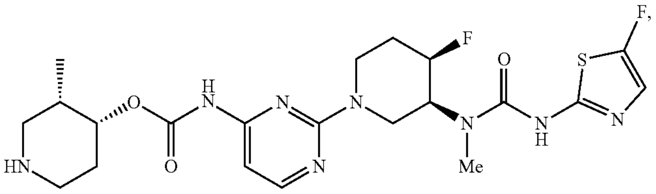

-continued
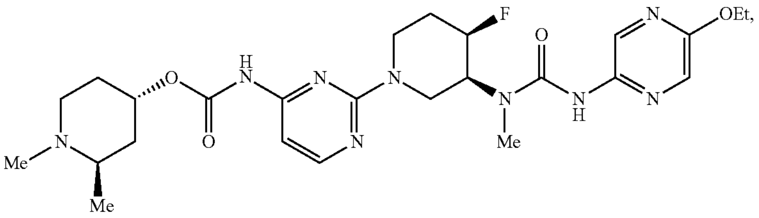
,
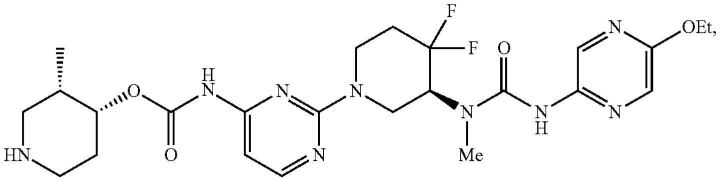
,
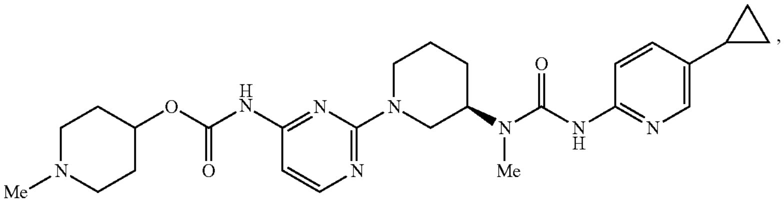
,
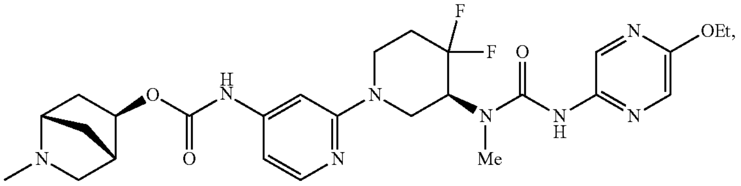
, and
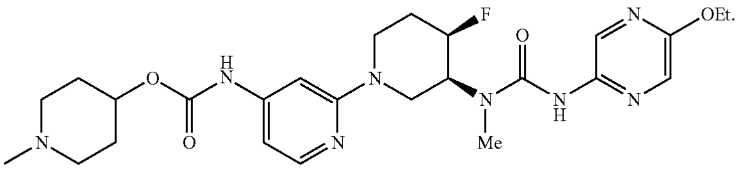
.

29. A pharmaceutical composition comprising a compound of claim 1, or a pharmaceutically acceptable salt thereof, and one or more pharmaceutically acceptable excipients.

* * * * *